(12) United States Patent
Canan Koch et al.

(10) Patent No.: US 7,179,918 B2
(45) Date of Patent: Feb. 20, 2007

(54) HIV PROTEASE INHIBITORS, COMPOSITIONS CONTAINING THE SAME, THEIR PHARMACEUTICAL USES AND MATERIALS FOR THEIR SYNTHESIS

(75) Inventors: Stacie S. Canan Koch, La Jolla, CA (US); Therese N. Alexander, San Diego, CA (US); Benjamin J. Burke, San Diego, CA (US); Tanya M. Jewell, Encinitas, CA (US); David J. Kucera, Del Mar, CA (US); Maria Angelica Linton, San Diego, CA (US); Lennert J. Mitchell, Jr., Chula Vista, CA (US); Siegfried H. Reich, Solana Beach, CA (US); Donald J. Skalitzky, San Diego, CA (US); John H. Tatlock, San Diego, CA (US); Michael D. Varney, Solana Beach, CA (US); Scott C. Virgil, San Diego, CA (US); Stephen E. Webber, San Diego, CA (US); Stephen T. Worland, Del Mar, CA (US); Mark Barvian, Ann Arbor, MI (US); Gary Bolton, Ann Arbor, MI (US); Frederick Earl Boyer, Jr., Canton Township, MI (US); Jeffrey J. Machak, Shelby Township, MI (US); Tod Holler, Ann Arbor, MI (US); Sean T. Murphy, Ypsilanti, MI (US); Michael Melnick, Ann Arbor, MI (US); Vara Prasad Josyula, Ann Arbor, MI (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/166,979

(22) Filed: Jun. 11, 2002

(65) Prior Publication Data
US 2003/0225071 A1 Dec. 4, 2003

Related U.S. Application Data

(60) Provisional application No. 60/297,460, filed on Jun. 11, 2001, provisional application No. 60/297,729, filed on Jun. 11, 2001.

(51) Int. Cl.
C07D 207/16 (2006.01)
C07D 221/02 (2006.01)

(52) U.S. Cl. ............... 546/112; 546/146; 548/540; 514/423

(58) Field of Classification Search ........... 548/540; 514/423; 546/146, 112
See application file for complete search history.

(56) References Cited

U.S. PATENT DOCUMENTS 5,629,406 A 5/1997 Higashida et al.
5,644,028 A 7/1997 Mimoto et al.
5,932,550 A 8/1999 Kato et al. ............... 514/19
5,962,640 A 10/1999 Kato et al. ............... 530/337
6,222,043 B1 4/2001 Kato et al.
6,313,094 B1 11/2001 Mimoto et al.
6,329,502 B1 12/2001 Mimoto et al.
2002/0049165 A1 4/2002 Mimoto et al.
2005/0124683 A1* 6/2005 Alegria et al. ............ 514/423
2005/0153903 A1* 7/2005 Kucera et al. ............ 514/19

FOREIGN PATENT DOCUMENTS

AU 705193 2/1997
CA 2179935 12/1996
EP 0498680 2/1992
EP 0574135 B1 12/1993

(Continued)

OTHER PUBLICATIONS

Takashiro et al., Bioorganic & Medicinal Chemistry 6 (1998) 595-604.*

(Continued)

Primary Examiner—Joseph K. McKane
Assistant Examiner—Rebecca Anderson
(74) Attorney, Agent, or Firm—Fitzpatrick, Cella, Harper & Scinto

(57) ABSTRACT

Compounds of the formula:

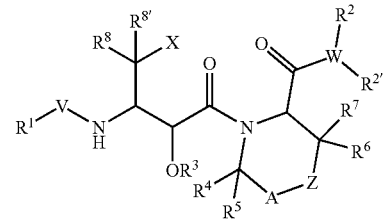

where the formula variables are as defined herein, are disclosed that advantageously inhibit or block the biological activity of the HIV protease. These compounds, as well as pharmaceutical compositions containing these compounds, are useful for treating patients or hosts infected with the HIV virus. Intermediates and synthetic methods for preparing such compounds are also described.

24 Claims, No Drawings

FOREIGN PATENT DOCUMENTS

| | | |
|---|---|---|
| EP | 0706794 | 4/1996 |
| EP | 0751145 A2 | 6/1996 |
| EP | 0490667 | 6/1999 |
| JP | 8259532 | 10/1996 |
| JP | 10-87489 | 4/1998 |
| JP | 10101654 | 4/1998 |
| JP | 10-182601 | 7/1998 |
| JP | 2003119137 | 4/2003 |
| WO | WO93/13066 | 7/1993 |
| WO | WO 95/09843 | 4/1995 |
| WO | WO 48/46582 | 10/1998 |
| WO | WO 00/48466 | 8/2000 |
| WO | WO 02/100844 | 12/2002 |
| WO | WO 2002 100845 | 12/2002 |
| WO | WO 03/035076 | 5/2003 |
| WO | WO 03/035650 | 5/2003 |
| WO | WO 03/049690 | 6/2003 |
| WO | WO 03/062204 | 7/2003 |
| WO | WO 03/062238 | 7/2003 |
| WO | WO 03/047564 | 12/2003 |

OTHER PUBLICATIONS

Database CAS ONLINE on STN, Chem. Abstr., Accession No. 1998:211105, JP 10087489 A2 (Sankyo Co., LTD.) Apr. 7, 1998, abstract.*
Charlesworth et al., "Phthalide Formation," *Can J. Chem.* 41:1071-1077 (1963).
Demange et al., "Practical Synthesis of Boc and Fmoc Protected 4-Fluoro and 4-Difluoroprolines from *Trans*-4-Hydrozyproline," *Tetrahedron Letters* 39:1169-1172 (1998).
Dondoni et al., "Total Synthesis of (+)-Galactostatin. An Illustration of the Utility of the Thiazole-Aldehyde Synthesis," *J. Org. Chem.* 60:4749-4754 (1995).
*Enantiomers, Racemates, and Resolutions* (1991).
Fujiwara et al., "Orientation in Nitration and Sulfonation of 2,5-Dimethylbenzoic Acid," *Can J. Chem.* 48:1346-1349 (1970).
Harada et al., "Synthesis and Resolution of -N-[1-methyl-4(3-methylbenzyl)hexahydro-1*H-1,4-diazepin-6-yl*]-1H-indazole-3-Carboxamide By Preferential Crystallization," *Tetrahedron Asymmetry* 8(14):2367-2374 (1997).
Holzgrabe, U., "Cer(IV)sulfat-Oxidationen: Intramolekulare Cyclisierung von N-Benzyl-β-Aminoketonen zu 4-Benzoyl-1,2,3,4-tetrahydro-isochinolinen," *Arch. Pharm.* 320:647-654 (1987).
Huang et al., "The Improved Preparation of 7,8-Dihydro-Quinoline-596H)-One And 6,7-Dihydro-5H-1-Pyrindin-5-One," *Synthetic Communications* 28(7): 1197-1200 (1998).
Hursthouse et al., "Reations of Ethyl 2-acetyl-2-azabicyclo[2.2.1]Hept-5-ene-3-Carboxylate and 4-acetylamino-2-oxabicyclo[3.3.0]oct-7-en-3-one With Some Electrophiles," *J. Chem. Soc.* 1:2419-2425 (1995).
Karanewsky et al., "Phosphinyloxy)acyl Amino Acid Inhibitors Of Angiotensin Converting Enzyme," *J. Med. Chem.* 33:1459-1469 (1990).
Ludeman et al. "Synthesis and Antitumor Activity of Cyclophosphamide Analogs. 1. Benzo Annnulated Cyclophosphamide and Related Systems," *Journal of Medicinal Chemistry* 18(12):1251 (1975).
Matayoshi et al., "Novel Fluorogenic Substrates For Assaying Retroviral Proteases By Resonance Energy Transfer," *Science* 247:954-958 (1990).
Miller, "Preparation of Crystalline Diphenyldiazomethane," *J. Org. Chem.* 24:560-561 (1958).
Mimoto et al., "Structure-Activity Relationship of Small-Sized HIV Protease Inhibitors Containing Allophenylnorstatine," *J. Med. Chem.* 42:1789-1802 (1999).
Nagasawa, et al., "β-Substituted Cysteines as Sequestering Agents for Ethanol-Derived Acetaldehyde in Vivo," *J. Med. Chem.* 30:1373 (1987).
Nussbaumer et al., "Synthesis and Structure-Activity Relationships of Benzo[b]thienylallylamine Antimycotics,". *Med. Chem.* 34:65-73 (1991).
O'Brien et al., "Inhibitors of Acyl-CoA:Choloesterol O-Acyl Transferase (ACAT) as Hypocholesterolemic Agents. Incorporation of Amide or Amine Functionalities into a Series of Disubstituted Ureas And Carbamates. Effects on ACAT Inhibition In Vitro and Efficacy In Vivo," *J. Med. Chem.* 37:1810-1822 (1994).
Onda et al., "Structure of Carzinophilin. II. A New Amino Acid and Its Derivative From Carzinophillin," *Chem. Pharm. Bull.* 19(10):2013-2019 (1971).
Pauwels et al., "Rapid and Automated Tetrazolium-Based Colorimetric Assay For The Detection Of Anti-HIV Compounds," *Journal of Virological Methods* 20:309-321 (1988).
Petropoulos et al., "A Novel Phenotypic Drug Susceptibility Assay for Human Immunodeficiency Virus Type 1," *Antimicrob Agents Chemother* 44(4):920-928 (2000).
*Protective Groups In Organic Synthesis* 3rd Edition (1999).
Weislow et al., "New Soluble-Formazan Assay For HIV-1 Cytopathic Effects: Application To High-Flux For AIDS-Antiviral Activity," *Journal of the National Cancer Institute* 81(8):577-586 (1989).
Wipf et al., "SN2'-Reactions of Peptide Aziridines. A Cuprate-Based Approach to (E)-Alkene Isosteres" *J. Org. Chem.* 59:4875-4886 (1994).
Yoshimura et al., "JE-2147: A Dipeptide Protease Inhibitor (PI) That Potently Inhibits Multi-PI-Resistant HIV-1," *Proc. Natl. Acad. Sci. USA* 96:8675-8680 (Jul. 1999).
Bell et al., "Developmetn of Orally Active Oxytocin Antagonists: Studies on 1-(1-{4-[1-(2-Methyl-1-oxidopyridin-3-ylmethyl)piperidin-4-yloxy]-2-methoxybenzoyl}peperidin-4-yl)-1,4-dihydrobenz[d][1,3]oxazin-2-one (L-372,662) and Related Pyridines," *J. Med. Chem.* 41:2146-2163 (1998).
Bobbitt et al., "Synthesis of Isoquinoline Alkaloids. II. The Synthesis and Reactions of 4-Methyl-3-pyridinecarboxaldehyde and Other 4-Methyl-3-substituted Pyridines," *J. Org. Chem.* 25:560 (1959).
Bundgaard, *Design of Prodrugs* (1985).
Carlsen et al., "Thermolysis of N-Allylic 1,2,4-Triazoles," *Institute of Organic Chemistry* 34:797-805 (1997).
Van-Duc Le, "Structure-Activity Studies of FIV and HIV Protease Inhibitors Containing Allophenylnorstatine", Biorg. Med. Chem., vol. 9, 2001, pp. 1185-1195.
Mimoto et al. "Structure- Activity Relationship of Orally Potent Tripeptide- Based HIV Protease Inhibitors Containing HydroxymethylCarbonyl Isotease", Chem & Pharm. Bulletin, Pharm Soc. Of Japan, vol. 48 (9), 2000, pp. 1310-1326.
Sodergren et al. "Allylic Alcohols Via Catalytic Asymmmetric Expoxide Rearrangement", J. AmChem. Soc., vol. 122 (28), 2000, pp. 6610-6618.
Falorni et al. "Optically Active 4-Oxaproline Derivatives: New Useful Chiral Synthons Derived From Serine and Threonine", Tetrahedron: Asymmetry, vol. 6(1), 1995, pp. 287-294.
Yoshiaki, Patent Abstracts of Japan, Publication No. 10182601, 1998, No. 12.
Sheha et al., Euro J. Med. Chem., vol. 35 (10), 2000, pp. 887-894.
Kitzaki et al., Chem & Pharm. Bulletin, Pharm. Soc. of Japan, vol. 42(12), 1994, pp. 2636-2640.
Slee, J.A.C.S., vol. 117(48), 1995, pp. 11867-11878.
Komai et al., Biorg. Med. Chem., vol. 4 (8), 1996, pp. 1356-1377.
Kiso et. al., Arch. Pharm., Pharm. Med. Chem., vol. 331, 1998, pp. 87-89.
Matsumoto et al., Biorg. Med. Chem., vol. 9(2), 2001, pp. 417-430.
Tam et al., J. Med. Chem., vol. 35, No. 7, 1992, pp. 1318-1320.
Andrés, "Stereoselective Cyanation Of Chiral α-Amino Aldehydes By Reaction With Nagata's Reagent: A Route To Enantiopure β-Amino-α-Hydroxy Acids," *Tetrahedron Asymm.*, 2001, pp. 347-353, vol. 12.
Blanco, M. et al., "Enantiospecific And Stereoselective Synthesis Of Polyhydroxylated Pyrrolidines And Indolizidnes From Trans-4-Hydroxy-L-Proline," *J. Org. Chem.* 1996, pp. 4748-4755, vol. 61.

Humphrey, J. et al., "Chemical Synthesis Of Natural Product Peptides: Coupling Methods For The Incorporation Of Noncoded Amino Acids Into Peptides," *Chemical Reviews*, 1997, 2243-2266 vol. 97.

Ikunaka, et al., "A Concise Synthesis of (2S,3S)-BocAHPBA and ©-BocDMTA, Chiral Building Blocks for Peptide-Mimetic HIV Protease Inhibitors," *Tetrahedron Asymmetry*, 2002, vol. 13, 1201.

Jacques, et al., Enantiomers, Racemates, and Resolutions, 1981, John Wiley & Sons, New York.

Larock, et al., Comprehensive Organic Transformations, 1989, Chapter 9, New York.

Sasai, H., et al., "Diastereoselective Catalytic Asymmetric Nitroaldol Reaction Utilizing Rare Earth-Li-(R)-BINOL Complex. A Highly Efficient Synthesis Of Norstatine," *Tetrahedron Letters*, 1994, pp. 6123-6126, vol. 35, No. 33.

Sharma, R. et al., "Regioselective Enolization And Alkylation Of 4-Oxo-N-(9-Phenylfluoren-9-yl)Proline: Synthesis Of Enantiopure Proline-Valine And Hydroxyproline-Valine Chimeras," *J. Org. Chem.* 1996, pp. 202-209, vol. 61.

Sustmann, et al., Comprehensive Organic Synthesis, 1991, vol. 6, 301-434, Trost.

Patick, et al., "Protease Inhibitors as Antiviral Agents", Clinical Microbio. Reviews, Oct. 1998, pp. 614-627.

Sakurai, et al., "Structure-Activity Relationships of HIV-I PR Inhibitors Containing AHPBA", Bioorg. & Med. Chem., vol. 2(8), pp. 807-825, 1994.

* cited by examiner

HIV PROTEASE INHIBITORS, COMPOSITIONS CONTAINING THE SAME, THEIR PHARMACEUTICAL USES AND MATERIALS FOR THEIR SYNTHESIS

This application claims the benefit of U.S. Provisional Application No. 60/297,460, filed on Jun. 11, 2001, and U.S. Provisional Application No. 60/297,729, filed on Jun. 11, 2001.

BACKGROUND OF THE INVENTION

1. Field of the Invention

This invention relates to novel compounds useful as HIV protease inhibitors and to the use of such compounds as antiviral agents for treatment of HIV infected individuals. This invention also relates to methods of preparation of these compounds and to intermediates that are useful in the preparation thereof.

2. Related Background Art

Acquired Immune Deficiency Syndrome (AIDS) causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell which plays a vital role in the body's immune system. HIV infection of these white blood cells depletes this white cell population. Eventually, the immune system is rendered inoperative and ineffective against various opportunistic diseases such as, among others, pneumocystic carini pneumonia, Kaposi's sarcoma, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-translational processing of polyproteins. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

Related inhibitors of HIV proteases have been described in, e.g., U.S. Pat. No. 5,962,640, U.S. Pat. No. 5,932,550, Australian Patent No. 705193, Canadian Patent Application No. 2,179,935, European Patent Application No. 0 751 145, and Japanese Patent Application No. 10087489. Other related HIV protease inhibitors have been described in K. Yoshimura, et al., *Proct. Natl. Acad. Sci. USA*, 96, 8675–8680 (1999) and T. Mimoto, et al., *J. Med. Chem.*, 42, 1789–1802 (1999).

On-going treatment of HIV-infected individuals with compounds that inhibit HIV protease has led to the development of mutant viruses that possess protesases that are resistant to the inhibitory effect of these compounds. Thus, to be effective, new HIV protease inhibitors must be effective not only against wild-type strains of HIV, but must also demonstrate efficacy against the newly emerging mutant strains that are resistant to the commercially available protease inhibitors. Accordingly, there continues to be a need for new inhibitors targeting the HIV protease in both wild type and mutant strains of HIV.

SUMMARY OF THE INVENTION

This invention relates to compounds useful for inhibiting the activity of HIV-protease of Formula I:

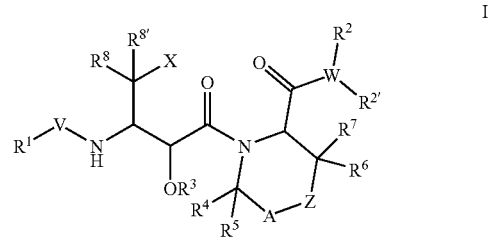

wherein:

$R^1$ is an aliphatic, carbocyclic or heterocyclic group, or a group having the formula: $OR^{1'}$, $SR^{1'}$, $NHR^{1'}$, $N(R^{1'})R^{1''}$ or $C(O)R^{1'}$, wherein $R^{1'}$ is an aliphatic, carbocyclic or heterocyclic group, and $R^{1''}$ is H or a $C_1$–$C_6$ aliphatic group or $R^{1'}$ and $R^{1''}$ together with the atom to which they are attached form a substituted or unsubstituted heterocyclic ring;

V is C=O, C=S or $SO_2$;

$R^2$ is an aliphatic group, a carbocyclic group, a carbocyclic-aliphatic group, a heterocyclic group, a heterocyclic-aliphatic group or $N(R^{2a})R^{2b}$, wherein $R^{2a}$ is an aliphatic, carbocyclic or heterocyclic group, and $R^{2b}$ is H or a $C_1$–$C_6$ aliphatic group;

W is N, O, C or CH;

when W is N, C or CH, $R^{2'}$ is H or a $C_1$–$C_6$ aliphatic group or $R^2$ and $R^{2'}$ taken together with the atom W to which they are attached form an unsubstituted or substituted carbocyclic or heterocyclic ring;

when W is O, $R^{2'}$ is absent;

X is

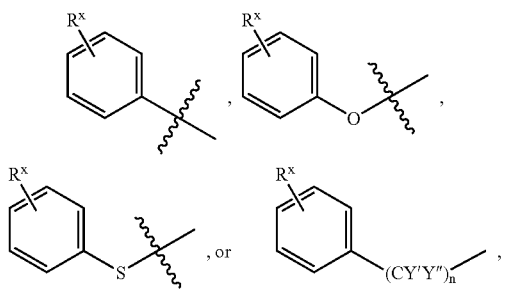

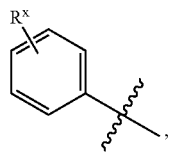

where Y' and Y'' are independently selected from H, halo, or a $C_1$–$C_6$ aliphatic group;

n is 0, 1 or 2;

$R^x$ is H or one or more substituents independently selected from $C_1$–$C_6$ alkyl, nitro, amino, cyano, halogen, $C_1$–$C_6$ haloalkyl, hydroxyl, $C_1$–$C_6$ alkoxy, alkylenedioxy, $C_1$–$C_6$ alkylcarbonyl, $C_1$–$C_6$ alkyloxycarbonyl, $C_1$–$C_6$ alkylcarbonyloxy, carboxyl, carbamoyl, formyl, $C_1$–$C_6$ alkylamino, dialkylamino, alkylaminocarbonyl, dialkylaminocarbonyl, alkylaminothiocarbonyl, di-$C_1$–$C_6$-alkylaminothiocarbonyl, $C_1$–$C_6$ alkylsulfonyl, $C_1$–$C_6$ alkylsulfenyl, $C_1$–$C_6$ alkylcarbonylamino, $C_1$–$C_6$ alkylthiocarbonylamino, $C_1$–$C_6$ alkylsulfonyloxy, $C_1$–$C_6$ alkylsulfonylamino, mercapto, and $C_1$–$C_6$ alkylthio;

$R^8$ and $R^{8'}$ are each independently H, halo or a $C_1$–$C_4$ aliphatic group;

A is $CH_2$, $CH(R^A)$ or is absent;

Z is S, O, SO, $SO_2$, $CH_2$, CHF, $CF_2$, CH(OH), CH(O—$R^Z$), CH(N—$R^Z R^{Z'}$), CH(S—$R^Z$), C(=O), or $CH(R^Z)$, where $R^Z$ is a $C_1$–$C_6$ aliphatic group or a carbocyclic or heterocyclic group and $R^{Z'}$ is H or a $C_1$–$C_6$ aliphatic group;

or $R^A$ and $R^Z$, taken together with A and Z form an unsubstituted or substituted 5 or 6 membered carbocyclic or heterocyclic ring;

$R^3$ is H or a $C_1$–$C_6$ aliphatic group;

$R^4$ and $R^5$ are independently selected from H, halo, a $C_1$–$C_6$ aliphatic group or a group having the formula $C(O)R^{4'}$, wherein $R^{4'}$ is an aliphatic, carbocyclic or heterocyclic group;

or $R^4$ and $R^5$, taken together with the atom to which they are bound, form an unsubstituted or substituted carbocyclic ring;

or $R^4$ and $R^6$ or $R^7$, together with the atoms to which they are bound, form an unsubstituted or substituted carbocyclic ring;

$R^6$ and $R^7$ are independently selected from H, halo or a $C_1$–$C_6$ aliphatic group;

or $R^6$ and $R^7$, taken together with the atom to which they are bound, form an unsubstituted or substituted carbocyclic or heterocyclic group;

wherein any of said aliphatic groups are saturated, partially unsaturated or fully unsaturated and unsubstituted or substituted by one or more suitable substituents; and wherein any of said carbocyclic or heterocyclic groups are unsubstituted or substituted by one or more suitable substituents; saturated, partially unsaturated or fully unsaturated; or mono-, bi- or tri-cyclic;

provided that $R^2$ is not an aliphatic group, a phenyl group or a phenyl-substituted aliphatic group when A is absent; Z is S, SO, $SO_2$, CHF, O or $CH_2$; V is C=O; W is N; $R^{2'}$, $R^3$, $R^8$ and $R^{8'}$ are H; $R^4$, $R^5$, $R^6$ and $R^7$ are H or a $C_1$–$C_6$ alkyl groups.

X is

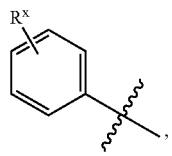

wherein $R^x$ is H; and $R^1$ is a substituted or unsubstituted 5 or 6-membered mono-cyclic carbocyclic or heterocyclic group;

or provided that $R^2$ is not t-butyl when $R^1$ is substituted or unsubstituted phenyloxymethylene, or quinolylmethyenecarbonylaminomethylene; A is absent; Z is S; V is C=O; W is N; $R^{2'}$, $R^3$, $R^4$, $R^5$, $R^8$ and $R^{8'}$ are H; $R^6$ and $R^7$ are H, methyl, ethyl or propyl; and X is wherein $R^x$ is H or methoxy.

The present invention relates to compounds of Formula I below, and prodrugs, pharmaceutically active metabolites, and pharmaceutically acceptable salts and solvates thereof that inhibit the protease encoded by human immunodeficiency virus (HIV) type 1 (HIV-1) or type 2 (HIV-2), as well as mutant strains thereof. These compounds are useful in the treatment of infection by HIV and the treatment of the acquired immune deficiency syndrome (AIDS). The compounds, their pharmaceutically acceptable salts, and the pharmaceutical compositions of the present invention can be used alone or in combination with other antivirals, immunomodulators, antibiotics or vaccines. Compounds of the present invention can also be converted to prodrugs, by derivatization, according to conventional techniques. Methods of treating AIDS, methods of treating HIV infection and methods of inhibiting HIV protease are disclosed.

DETAILED DESCRIPTION OF INVENTION AND PREFERRED EMBODIMENTS

In the compounds of this invention, the aliphatic groups are optionally substituted by one or more suitable substituents selected from aryl, cycloalkyl, heterocycloalkyl, heteroaryl, nitro, amino, cyano, halogen, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio, heteroarylthio, wherein any of the alkyl, alkylene, aryl, cycloalkyl, heterocycloalkyl, heteroaryl moieties present in the above substituents may be further substituted. The alkyl, alkylene, cycloalkyl, heterocycloalkyl, aryl, and heteroaryl moieties of any of the above substituents may be optionally substituted by one or more of alkyl (except for alkyl), haloalkyl, aryl, nitro, amino, alkylamino, dialkylamino, halogen, hydroxyl, alkoxy, haloalkoxy, aryloxy, mercapto, alkylthio or arylthio groups.

In the compounds of this invention the substituted carbocyclic or heterocyclic groups may be optionally substituted by one or more of the following: alkyl, alkenyl, alkynyl, aryl, cycloalkyl, cycloalkenyl, heterocycloalkyl, heterocycloalkenyl, heteroaryl, nitro, amino, cyano, halogen, hydroxyl, alkoxy, alkenyloxy, alkynyloxy, alkylenedioxy, aryloxy, cycloalkoxy, cycloalkenyloxy, heterocycloalkoxy, heterocycloalkenyloxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio, heteroarylthio, wherein any of the alkyl, alkylene, aryl, cycloalkyl, heterocycloalkyl, heteroaryl moieties present in the above substituents may be further substituted. Preferred "suitable substituents" include alkyl, alkenyl, alkynyl, aryl, cycloalkyl, heterocycloalkyl, heteroaryl, halogen, hydroxyl, alkoxy, alkylenedioxy, aryloxy, cycloalkoxy, heteroaryloxy, alkylthio, haloalkylthio and carboxyl. The alkyl, alkylene, cycloalkyl, heterocycloalkyl, aryl, and heteroaryl moieties of any of the above substituents may be optionally substituted by one or more of: alkyl, haloalkyl, nitro, amino, alkylamino, dialkylamino, halogen, hydroxyl, alkoxy, haloalkoxy, mercapto, alkylthio.

In accordance with a convention used in the art,

is used in structural formulas herein to depict the bond that is the point of attachment of the moiety or substituent to the core or backbone structure.

As used herein, the term "aliphatic" represents a saturated or unsaturated, straight- or branched-chain hydrocarbon, containing 1 to 10 carbon atoms which may be unsubstituted or substituted by one or more of the substituents described below. The term "aliphatic" is intended to encompass alkyl, alkenyl and alkynyl groups.

As used herein, the term "alkyl" represents a straight- or branched-chain saturated or unsaturated hydrocarbon, containing 1 to 10 carbon atoms which may be unsubstituted or substituted by one or more of the substituents described below. Exemplary alkyl substituents include, but are not limited to methyl (Me), ethyl (Et), propyl, isopropyl, butyl, isobutyl, t-butyl, and the like. The term "lower alkyl" refers to an alkyl group containing from 1 to 6 carbon atoms The term "alkenyl" represents a straight- or branched-chain hydrocarbon, containing one or more carbon-carbon double bonds and having 2 to 10 carbon atoms which may be unsubstituted or substituted by one or more of the substituents described below. Exemplary alkenyl substituents include, but are not limited to ethenyl, propenyl, butenyl, allyl, pentenyl and the like.

The term "alkynyl" represents a straight- or branched-chain hydrocarbon, containing one or more carbon-carbon triple bonds and having 2 to 10 carbon atoms which may be unsubstituted or substituted by one or more of the substituents described below. An alkynyl moiety may also contain one or more carbon-carbon double bonds. Exemplary alkynyl substituents include, but are not limited to ethynyl, butynyl, propynyl (propargyl) isopropynyl, pentynyl, hexynyl and the like.

The term "carbocyclic" represents a saturated, partially saturated, or fully unsaturated (aromatic) cyclic hydrocarbon group containing from 3 to 14 carbon atoms which may be unsubstituted or substituted by one or more of the substituents described herein below. The term "carbocyclic" is intended to encompass mono-, bi- and tri-cyclic saturated, partially saturated, or fully unsaturated hydrocarbon groups; for example, cycloalkyl, cycloalkenyl and aryl groups. The term "carbocyclic" is also intended to encompass bi- and tri-cyclic hydrocarbon groups which contain any combination of ring moieties that are saturated, partially saturated, or fully unsaturated (aromatic). Partially saturated carbocycles include, for example, dihydroarenes (e.g., indanyl) or tetrahydro-arenes (e.g. tetrahydronaphthalene), wherein any one or more points of saturation may occur in any ring moiety of the carbocycle. In addition, it is understood that bonding between any bi- or tri-cyclic carbocyclic group and any other substituent or variable group may be made at any suitable position of the carbocycle. The term "carbocyclic-aliphatic" group is intended to encompass aliphatic groups having a carbocyclic substituent (e.g., phenylmethyl-(benzyl), phenylethyl-, cyclopropylmethyl-, etc.), wherein the carbocyclic moiety and the aliphatic moiety thereof may be independently substituted by one or more suitable substituents.

"Cycloalkyl" represents a group comprising a non-aromatic monocyclic, bicyclic, or tricyclic hydrocarbon containing from 3 to 14 carbon atoms which may be unsubstituted or substituted by one or more of the substituents described below. Exemplary cycloalkyls include monocyclic rings having from 3–8 carbon atoms, such as cyclopropyl, cyclobutyl, cyclopentyl, cyclohexyl, cycloheptyl and the like. Illustrative examples of cycloalkyl groups include the following:

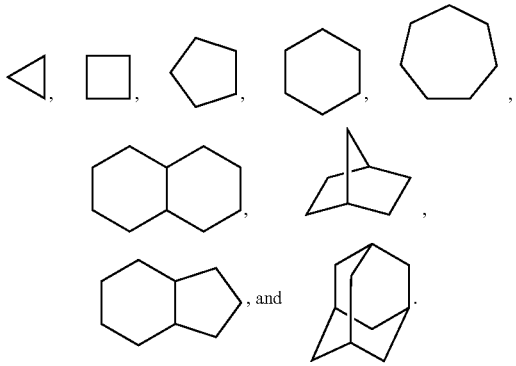

"Cycloalkenyl" represents a group comprising a non-aromatic monocyclic, bicyclic, or tricyclic hydrocarbon containing from 4 to 14 carbon atoms which may be unsubstituted or substituted by one or more of the substituents described below and contains at least one carbon-carbon double bond. Exemplary monocyclic cycloalkenyls include groups having from 4–8, preferably 5–6, carbon atoms, such as cyclopentenyl, cyclopentadienyl, cyclohexenyl, cycloheptenyl and the like. Illustrative examples of cycloalkenyl groups include the following:

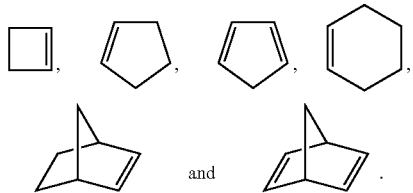

"Aryl" represents a group comprising an aromatic, monovalent monocyclic, bicyclic, or tricyclic radical containing from 6 to 18 carbon ring atoms, which may be unsubstituted or substituted by one or more of the substituents described below. Illustrative examples of aryl groups include the following:

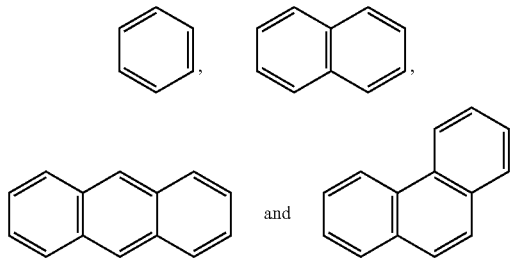

The term "carbocyclic" also to encompasses mixed bi- and tri-cyclic cycloalkyl/cycloalkenyl/aryl groups, which may be unsubstituted or substituted by one or more of the substituents described below. Illustrative examples of such mixed bi-and tri-cyclic groups include the following:

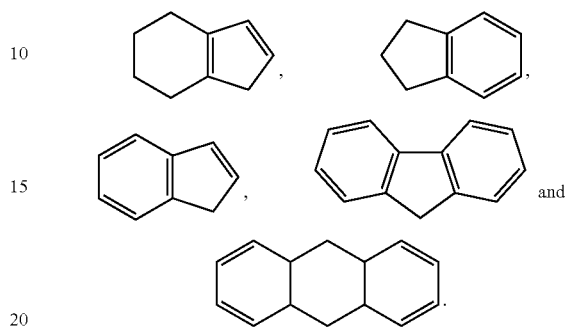

It is understood that bonding or substitution of any bi-cyclic or tri-cyclic carbocyclic or heterocyclic group described herein may be at any suitable position on any ring. Illustrative examples of such bonding in mixed bi-and tri-cyclic carbocyclic groups include the following:

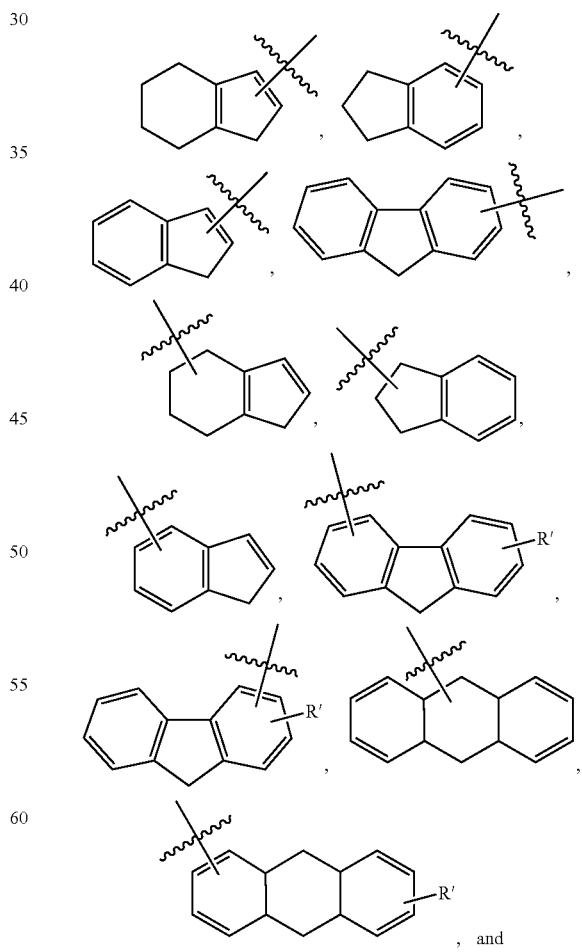

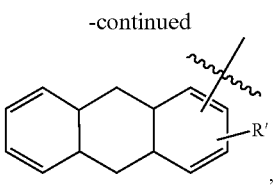

wherein R' is any suitable substituent.

The term "heterocyclic" represents a saturated, partially saturated, or fully unsaturated (aromatic) cyclic group containing from 3 to 18 ring atoms, which includes 1 to 5 heteroatoms selected from nitrogen, oxygen and sulfur, and which may be unsubstituted or substituted by one or more of the substituents described herein below. The term "heterocyclic" is intended to encompass mono-, bi- and tri-cyclic saturated, partially saturated, or fully unsaturated heteroatom-containing cyclic groups; for example, heterocycloalkyl, heterocycloalkenyl and heteroaryl groups. The term "heterocyclic" is also intended to encompass bi- and tri-cyclic groups which contain any combination of ring moieties that are saturated, partially saturated, or fully unsaturated (aromatic). Partially saturated heterocycles include, for example, dihydroheteroarenes (e.g., dihydroindole) or tetrahydro-heteroarenes (e.g. tetrahydroquinoline), wherein any one or more points of saturation may occur in any ring moiety of the heterocycle. In addition, it is understood that bonding between any bi- or tri-cyclic heterocyclic group and any other substituent or variable group may be made at any suitable position of the heterocycle (i.e., there is no restriction that a substituent or variable group must be bonded to the heteroatom-containing moiety of a bi- or tri-cyclic heterocyclic group). The term "heterocyclic-aliphatic" group is intended to encompass aliphatic groups having a heterocyclic substituent (e.g., pyridylmethyl-, thiazolylmethyl-, tetrahydrofuranylmethyl-, etc.) wherein the heterocyclic moiety and the aliphatic moiety thereof may be independently substituted by one or more suitable substituents.

"Heterocycloalkyl" represents a group comprising a saturated monovalent monocyclic, bicyclic, or tricyclic radical, containing 3 to 18 ring atoms, which includes 1 to 5 heteroatoms selected from nitrogen, oxygen and sulfur, and which may be unsubstituted or substituted by one or more of the substituents described below. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, tetrahydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like. Illustrative examples of heterocycloalkyl groups include the following:

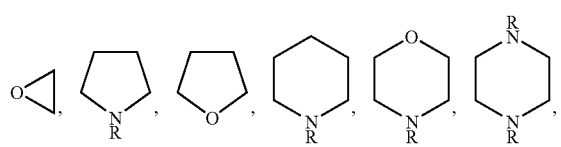

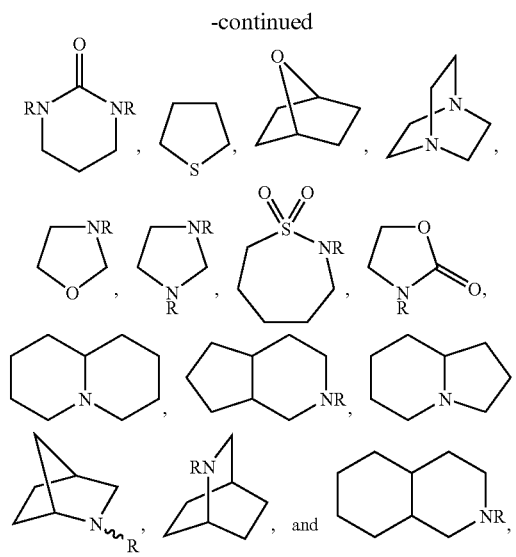

wherein R is H, alkyl, hydroxyl or represents a compound according to Formula I, and the bond depicted as "〰", represents bonding to either face of the bi-cyclic moiety (i.e., endo or exo).

The term "heterocycloalkenyl" is used herein to represent a non-aromatic, monovalent monocyclic, bicyclic, or tricyclic radical, containing 4 to 18 ring atoms, which may include from 1 to 5 heteroatoms selected from nitrogen, oxygen and sulfur, and which may be unsubstituted or substituted by one or more of the substituents described below and which contains at least one carbon-carbon or carbon-heteroatom double bond. Exemplary monocyclic heterocycloalkenyls include groups having from 4–8, preferably 5–6, ring atoms. Illustrative examples of heterocycloalkenyl groups include, but are not limited to, dihydrofuryl, dihydropyranyl, isoxazolinyl, dihydropyridyl, tetrahydropyridyl, and the like. Illustrative examples of heterocycloalkenyl groups include the following:

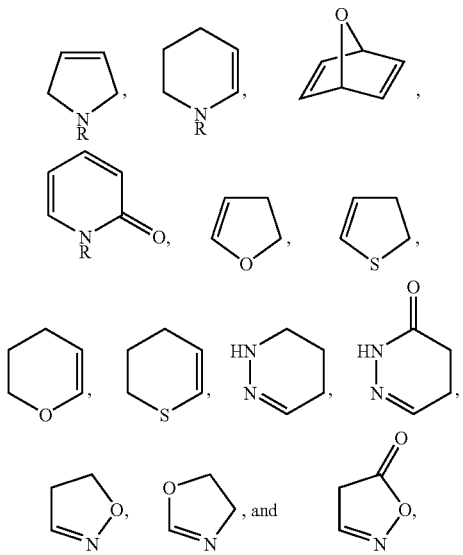

wherein R is H, alkyl, hydroxyl or represents a compound according to Formula I.

"Heteroaryl" represents a group comprising an aromatic monovalent monocyclic, bicyclic, or tricyclic radical, containing 5 to 18 ring atoms, including 1 to 5 heteroatoms selected from nitrogen, oxygen and sulfur, which may be unsubstituted or substituted by one or more of the substituents described below. As used herein, the term "heteroaryl" is also intended to encompass the N-oxide derivative (or N-oxide derivatives, if the heteroaryl group contains more than one nitrogen such that more than one N-oxide derivative may be formed) of the nitrogen-containing heteroaryl groups described herein. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Illustrative examples of N-oxide derivatives of heteroaryl groups include, but are not limited to, pyridyl N-oxide, pyrazinyl N-oxide, pyrimidinyl N-oxide, pyridazinyl N-oxide, triazinyl N-oxide, isoquinolyl N-oxide, and quinolyl N-oxide. Further examples of heteroaryl groups include the following moieties:

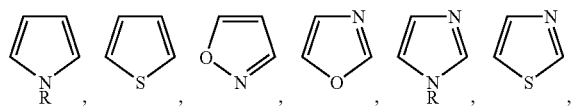

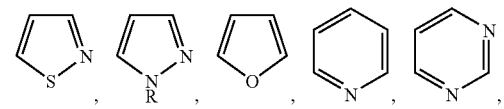

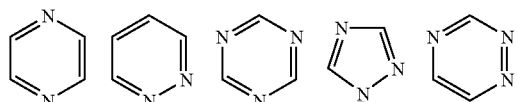

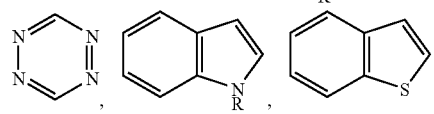

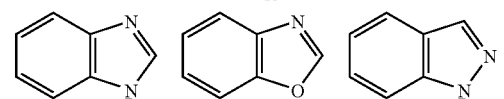

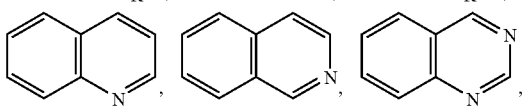

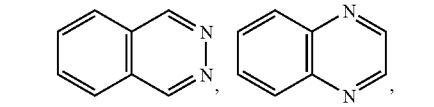

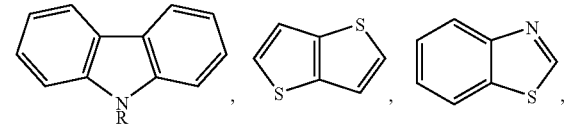

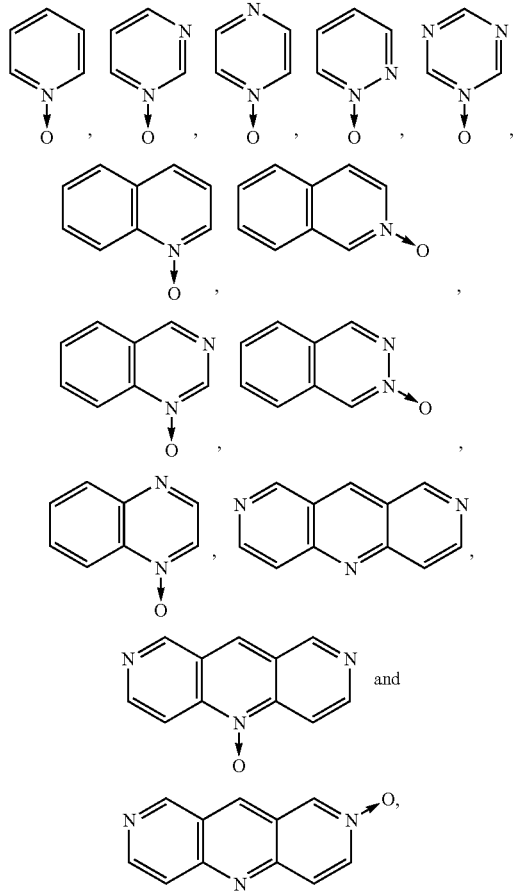

wherein R is H, alkyl, hydroxyl or represents a compound according to Formula I.

The term "heterocyclic" also to encompasses mixed bi- and tri-cyclic heterocycloalkyl/heterocycloalkenyl/heteroaryl groups, which may be unsubstituted or substituted by one or more of the substituents described below. Illustrative examples of such mixed bi-and tri-cyclic heterocyclic groups include the following:

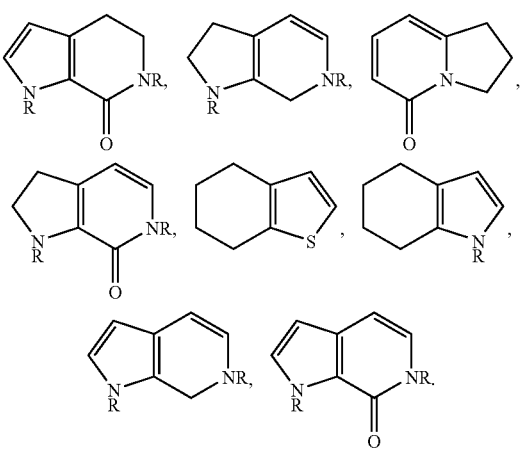

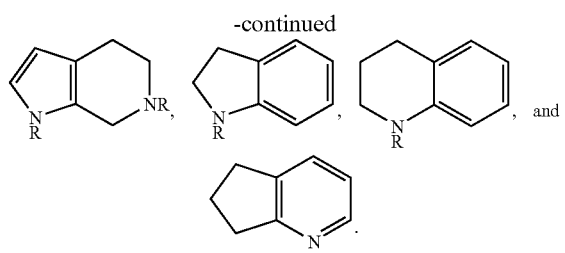

Illustrative examples of such bonding in mixed bi-and tri-cyclic heterocyclic groups include the following:

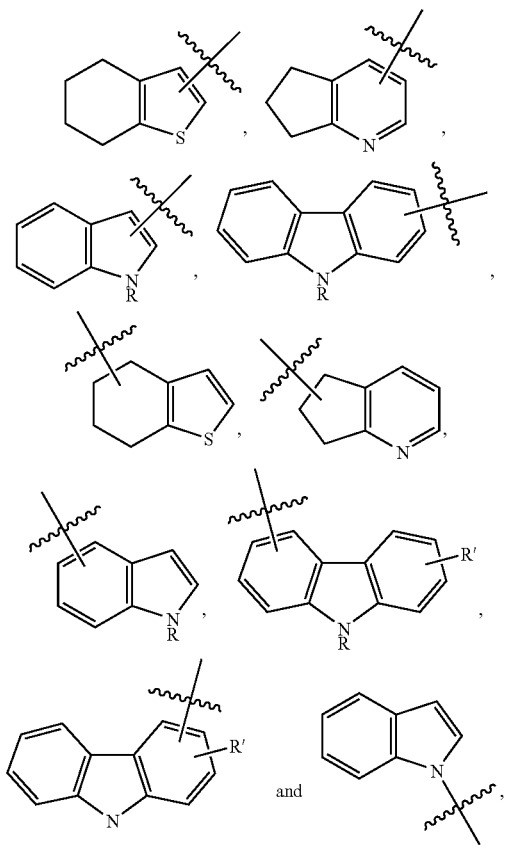

wherein R' is any suitable substituent.

Unless otherwise stated, exemplary "suitable substituents" that may be present on any of the above aliphatic, carbocyclic, heterocyclic, alkyl, alkenyl, alkynyl, aryl, cycloalkyl, cycloalkenyl, heterocycloalkyl, heterocycloalkenyl or heteroaryl groups, described herein, include alkyl (except for alkyl), aryl, cycloalkyl, heterocycloalkyl, heteroaryl, nitro, amino, cyano, halogen, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, heteroarylthio, wherein any of the alkyl, alkylene, aryl, cycloalkyl, heterocycloalkyl, heteroaryl moieties present in the above substituents may be further substituted. The alkyl, alkylene, cycloalkyl, heterocycloalkyl, aryl, and heteroaryl moieties of any of the above substituents may be optionally substituted by one or more of alkyl (except for alkyl), haloalkyl, aryl, nitro, amino, alkylamino, dialkylamino, halogen, hydroxyl, alkoxy, haloalkoxy, aryloxy, mercapto, alkylthio or arylthio groups.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3$^{rd}$ ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

In the compounds of this invention, $R^2$ and $R^{2'}$, independently or taken together, may be a suitable nitrogen protecting group. As indicated above, nitrogen protecting groups are well known in the art and any nitrogen protecting group that is useful in the methods of preparing the compounds of this invention or may be useful in the HIV protease inhibitory compounds of this invention may be used. Exemplary nitrogen protecting groups include alkyl, substituted alkyl, carbamate, urea, amide, imide, enamine, sulfenyl, sulfonyl, nitro, nitroso, oxide, phosphinyl, phosphoryl, silyl, organometallic, borinic acid and boronic acid groups. Examples of each of these groups, methods for protecting nitrogen moieties using these groups and methods for removing these groups from nitrogen moieties are disclosed in T. Greene and P. Wuts, supra. Preferably, when $R^2$ and/or $R^{2'}$ are independently suitable nitrogen protecting groups, suitable $R^2$ and $R^{2'}$ substituents include, but are not limited to, carbamate protecting groups such as alkyloxycarbonyl (e.g., Boc: t-butyloxycarbonyl) and aryloxycarbonyl (e.g., Cbz: benzyloxycarbonyl, or FMOC: fluorene-9-methyloxycarbonyl), alkyloxycarbonyls (e.g., methyloxycarbonyl), alkyl or arylcarbonyl, substituted alkyl, especially arylalkyl (e.g., trityl (triphenylmethyl), benzyl and substituted benzyl), and the like. When $R^2$ and $R^{2'}$ taken together are a suitable nitrogen protecting group, suitable R²/R²' substituents include phthalimido and a stabase (1,2-bis(dialkylsilyl)) ethylene).

The terms "halogen" and "halo" represent chloro, fluoro, bromo or iodo substituents. "Heterocycle" is intended to mean a heteroaryl or heterocycloalkyl group. "Acyl" is intended to mean a —C(O)—R radical, where R is a substituted or unsubstituted alkyl, cycloalkyl, aryl, heterocycloalkyl or heteroaryl group. "Acyloxy" is intended to mean an —OC(O)—R radical, where R is a substituted or unsubstituted alkyl, cycloalkyl, aryl, heterocycloalkyl or heteroaryl group. "Thioacyl" is intended to mean a —C(S)—R radical, where R is a substituted or unsubstituted alkyl, cycloalkyl, aryl, heterocycloalkyl or heteroaryl group. "Sulfonyl" is intended to mean an —SO₂— biradical. "Sulfenyl" is intended to mean an —SO— biradical. "Sulfo" is intended to mean an —SO₂H radical. "Hydroxy" is intended to mean the radical —OH. "Amine" or "amino" is intended to mean the radical —NH₂. "Alkylamino" is intended to mean the radical —NHR$_a$, where R$_a$ is an alkyl group. "Dialkylamino" is intended to mean the radical —NR$_a$R$_b$, where R$_a$ and R$_b$ are each independently an alkyl group, and is intended to include heterocycloalkyl groups, wherein R$_a$ and R$_b$, taken together, form a heterocyclic ring that includes the amine nitrogen. "Alkoxy" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons. "Alkoxycarbonyl" is intended to mean the radical —C(O)OR$_a$, where R$_a$ is an alkyl group. "Alkylsulfonyl" is intended to mean the radical —SO₂R$_a$, where R$_a$ is an alkyl group. "Alkylenedioxy" is intended to mean the divalent radical —OR$_a$O— which is bonded to adjacent atoms (e.g., adjacent atoms on a phenyl or naphthyl ring), wherein R$_a$ is a lower alkyl group. "Alkylaminocarbonyl" is intended to mean the radical —C(O)NHR$_a$, where R$_a$ is an alkyl group. "Dialkylaminocarbonyl" is intended to mean the radical —C(O)NR$_a$R$_b$, where R$_a$ and R$_b$ are each independently an alkyl group. "Mercapto" is intended to mean the radical —SH. "Alkylthio" is intended to mean the radical —SR$_a$, where R$_a$ is an alkyl group. "Carboxy" is intended to mean the radical —C(O)OH. "Keto" or "oxo" is intended to mean the diradical =O. "Thioketo" is intended to mean the diradical =S. "Carbamoyl" is intended to mean the radical —C(O)NH₂. "Cycloalkylalkyl" is intended to mean the radical -alkylcycloalkyl, wherein alkyl and cycloalkyl are defined as above, and is represented by the bonding arrangement present in the groups —CH₂-cyclohexane or —CH₂-cyclohexene. "Arylalkyl" is intended to mean the radical -alkylaryl, wherein alkyl and aryl are defined as above, and is represented by the bonding arrangement present in a benzyl group. "Aminocarbonylalkyl" is intended to mean the radical -alkylC(O)NH₂ and is represented by the bonding arrangement present in the group —CH₂CH₂C(O)NH₂. "Alkylaminocarbonylalkyl" is intended to mean the radical -alkylC(O)NHR$_a$, where R$_a$ is an alkyl group and is represented by the bonding arrangement present in the group —CH₂CH₂C(O)NHCH₃. "Alkylcarbonylaminoalkyl is intended to mean the radical -alkylNHC(O)-alkyl and is represented by the bonding arrangement present in the group —CH₂NHC(O)CH₃. "Dialkylaminocarbonylalkyl" is intended to mean the radical -alkylC(O)NR$_a$R$_b$, where R$_a$ and R$_b$ are each independently an alkyl group. "Aryloxy" is intended to mean the radical —OR$_c$, where R$_c$ is an aryl group. "Heteroaryloxy" is intended to mean the radical —OR$^d$, where R$^d$ is a heteroaryl group. "Arylthio" is intended to mean the radical —SR$_c$, where R$_c$ is an aryl group. "Heteroarylthio" is intended to mean the radical —SR$_d$, where R$^d$ is a heteroaryl group.

One embodiment of this invention comprises the compounds depicted by Formula I-A:

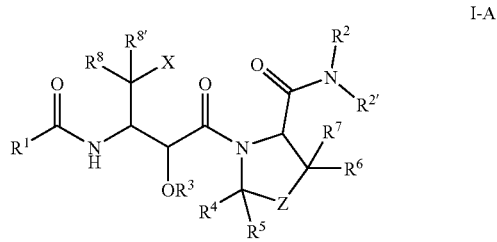

I-A wherein:

R¹ is an aliphatic group, a bi- or tri-cyclic carbocyclic or heterocyclic group or a group having the formula: OR¹', SR¹', NHR¹', N(R¹')R¹'' or C(O)R¹', wherein R¹' is an aliphatic, carbocyclic or heterocyclic group, and R¹'' is H or a C₁–C₆ aliphatic group or R¹' and R¹'' together with the atom to which they are attached form a substituted or unsubstituted heterocyclic ring;

R² is an aliphatic group, a carbocyclic group, a carbocyclic-aliphatic group, a heterocyclic group, or a heterocyclic-aliphatic group;

R²' is H or a C₁–C₆ alkyl group;

or R² and R²' taken together with the nitrogen atom to which they are attached form an unsubstituted or substituted carbocyclic or heterocyclic ring;

X is

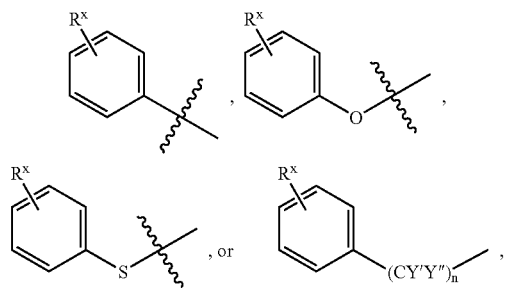

wherein Y' and Y'' are independently selected from H, halo, or a C₁–C₆ aliphatic group, wherein R$^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

n is 1 or 2;

R⁸ and R⁸' are each independently H, halo or a C₁–C₄ aliphatic group;

Z is S, O, SO, SO₂, CH₂, CHF, CF₂, CH(OH), CH(O—R$^Z$), CH(N—R$^Z$R$^{Z'}$), CH(S—R$^Z$), C(=O), or CH(R$^Z$), where R$^Z$ is a C₁–C₆ aliphatic group or a carbocyclic or heterocyclic group and R$^{Z'}$ is H or a C₁–C₆ aliphatic group;

$R^3$ is H or a $C_1$–$C_6$ aliphatic group;

$R^4$ and $R^5$ are independently selected from H, halo, a $C_1$–$C_6$ aliphatic group or a group having the formula $C(O)R^{4'}$, wherein $R^{4'}$ is an aliphatic, carbocyclic or heterocyclic group;

$R^6$ and $R^7$ are independently selected from H, halo or a $C_1$–$C_6$ aliphatic group;

wherein any of said aliphatic groups are unsubstituted or substituted by one or more suitable substituents and saturated, partially unsaturated or fully unsaturated; and wherein any of said carbocyclic or heterocyclic groups are mono-, bi- or tri-cyclic; saturated, partially unsaturated or fully unsaturated; or unsubstituted or substituted by one or more suitable substituents.

provided that $R^2$ is not an aliphatic group, a phenyl group or a phenyl-substituted aliphatic group, when A is absent; Z is S, SO, $SO_2$, CHF, O, or $CH_2$; V is C=O; W is N; $R^{2'}$, $R^3$, $R^8$ and $R^{8'}$ are H or a $C_1$–$C_4$ alkyl group; $R^4$, $R^5$, $R^6$ and $R^7$ are H or a $C_1$–$C_6$ alkyl group; X is

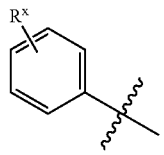

$R^1$ is a substituted or unsubstituted 5 or 6-membered mono-cyclic carbocyclic or heterocyclic group;

Another embodiment of this invention comprises the compounds depicted by Formula I-A, wherein:

$R^1$ is a 3-, 4-, or 7-membered mono-cyclic carbocyclic or heterocyclic group.

In another embodiment, the compounds of this invention are depicted by Formula I-A, wherein:

$R^1$ is a 5- or 6-membered monocyclic carbocyclic or heterocyclic group; and $R^2$ is cycloalkyl, cycloalkylalkyl, cycloalkenyl, cycloalkenylalkyl, a bi- or tri-cyclic carbocyclic group, a bi- or tri-cyclic carbocyclic-alkyl group, a bi- or tri-cyclic carbocyclic-alkenyl group, a bi- or tri-cyclic carbocyclic-alkynyl group, a heterocyclic group, a heterocyclic-alkyl group, a heterocyclic-alkenyl group or a heterocyclic-alkynyl group;

Another embodiment of this invention relates to compounds useful for inhibiting the activity of HIV-protease having Formula I-A, wherein:

$R^1$ is an aliphatic, carbocyclic or heterocyclic group, or a group having the formula: $OR^{1'}$, $SR^{1'}$, $NHR^{1'}$, $N(R^{1'})R^{1''}$ or $C(O)R^{1'}$, wherein $R^{1'}$ is an aliphatic, carbocyclic or heterocyclic group, and $R^{1''}$ is H or a $C_1$–$C_6$ aliphatic group or $R^{1'}$ and $R^{1''}$ together with the atom to which they are attached form a substituted or unsubstituted heterocyclic ring;

X is

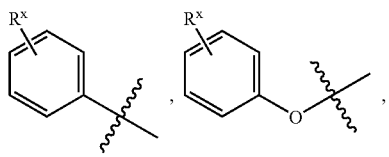

-continued

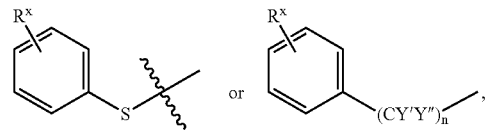

where Y' and Y" are independently selected from H, halo, or a $C_1$–$C_6$ aliphatic group, n is 0, 1 or 2 and $R^x$ is H or one or more suitable substituents independently selected from $C_1$–$C_6$ alkyl, nitro, amino, cyano, halogen, $C_1$–$C_6$ haloalkyl, hydroxyl, $C_1$–$C_6$ alkoxy, alkylenedioxy, $C_1$–$C_6$ alkylcarbonyl, $C_1$–$C_6$ alkyloxycarbonyl, $C_1$–$C_6$ alkylcarbonyloxy, carboxyl, carbamoyl, formyl, $C_1$–$C_6$ alkylamino, di-$C_1$–$C_6$ alkylamino, $C_1$–$C_6$ alkylaminocarbonyl, di-$C_1$–$C_4$ alkylaminocarbonyl, $C_1$–$C_6$ alkylaminothiocarbonyl, di-$C_1$–$C_6$-alkylaminothiocarbonyl, $C_1$–$C_6$ alkylsulfonyl, $C_1$–$C_6$ alkylsulfenyl, $C_1$–$C_6$ alkylcarbonylamino, $C_1$–$C_6$ alkylthiocarbonylamino, $C_1$–$C_6$ alkylsulfonyloxy, $C_1$–$C_6$ alkylsulfonylamino, mercapto, $C_1$–$C_6$ alkylthio and halo-$C_1$–$C_6$ alkylthio; and $R^8$ and $R^{8'}$ are each independently H, halo or a $C_1$–$C_4$ aliphatic group provided that $R^8$ and $R^{8'}$ are not both H when X is

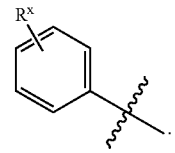

Another embodiment of this invention relates to compounds depicted by Formula I-A, wherein:

$R^1$ is a bi- or tri-cyclic carbocyclic or heterocyclic group, wherein said carbocyclic or heterocyclic group is saturated, partially unsaturated or fully unsaturated; and unsubstituted or substituted by one or more suitable substitutents.

A specific embodiment of a compound of Formula I-A of this invention, wherein Z is S and $R^{2'}$, $R^8$ and $R^{8'}$ are each H, may be represented as follows:

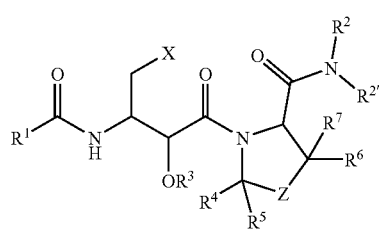

wherein the formula variables are as defined in Formula I-A, above.

Another embodiment of this invention comprises the compounds depicted by Formula I-B:

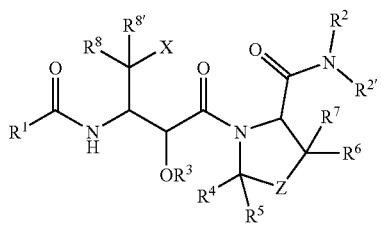

wherein

R¹ is an aliphatic, carbocyclic or heterocyclic group, or a group having the formula: OR¹', SR¹', NHR¹', N(R¹')R¹''' or C(O)R¹', wherein R¹' is an aliphatic, carbocyclic or heterocyclic group, and R¹''' is H or a $C_1$–$C_6$ aliphatic group or R¹' and R¹''' together with the atom to which they are attached form a substituted or unsubstituted heterocyclic ring;

R² is an aliphatic group, a carbocyclic group, a carbocyclic-aliphatic group, a heterocyclic group, or a heterocyclic-aliphatic group;

R²' is H or a $C_1$–$C_6$ aliphatic group;

X is

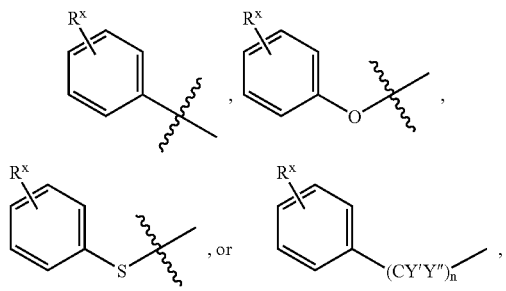

wherein Y' and Y'' are independently selected from H, halo, or a $C_1$–$C_6$ aliphatic group; n is 1 or 2; and $R^x$ is H or one or more suitable substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

R⁸ and R⁸' are each independently H, halo or a $C_1$–$C_4$ aliphatic group;

Z is S, O, SO, SO₂, CH₂, CHF, CF₂, CH(OH), CH(O—R^Z), CH(N—R^Z R^Z'), CH(S—R^Z), C(=O), or CH(R^Z), where R^Z is a $C_1$–$C_6$ aliphatic group or a carbocyclic or heterocyclic group and R^Z' is H or a $C_1$–$C_6$ aliphatic group;

R³ is H or a $C_1$–$C_6$ aliphatic group;

R⁴ and R⁵ are independently selected from H, halo, a $C_1$–$C_6$ aliphatic group or a group having the formula C(O)R⁴', wherein R⁴' is an aliphatic, carbocyclic or heterocyclic group;

R⁶ and R⁷ are independently selected from H, halo or a $C_1$–$C_6$ aliphatic group;

where any of said aliphatic groups are saturated, partially unsaturated or fully unsaturated and unsubstituted or substituted by one or more suitable substituents; and where any of said carbocyclic or heterocyclic groups are optionally unsubstituted, substituted by one or more suitable substituents; saturated, partially unsaturated or fully unsaturated; or mono-, bi- or tri-cyclic.

A specific embodiment of a compound of Formula I-B of this invention, wherein Z is S and R²', R⁸ and R⁸' are each H, may be represented as follows:

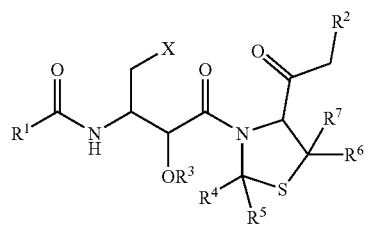

wherein the formula variables are as defined in Formula I-B, above.

In yet another embodiment, the compounds of this invention useful for inhibiting the activity of HIV-protease have the Formula I-C:

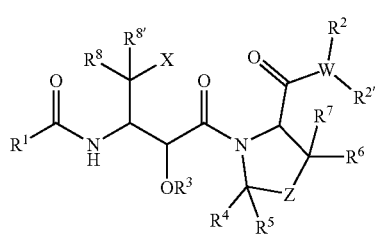

wherein

R¹ is an aliphatic, carbocyclic or heterocyclic group, or a group having the formula: OR¹', SR¹', NHR¹', N(R¹')R¹''' or C(O)R¹', wherein R¹' is an aliphatic, carbocyclic or heterocyclic group, and R¹''' is H or a $C_1$–$C_6$ aliphatic group or R¹' and R¹''' together with the atom to which they are attached form a substituted or unsubstituted heterocyclic ring;

R² is an aliphatic group, a carbocyclic group, a carbocyclic-aliphatic group, a heterocyclic group, or a heterocyclic-aliphatic group;

W is N, O or C;

when W is N or C, R²' is H or a $C_1$–$C_6$ alkyl group or R² and R²' taken together with the atom W to which they are attached form an unsubstituted or substituted carbocyclic or heterocyclic ring;

when W is O, R²' is absent;

X is

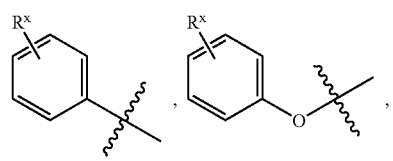

-continued

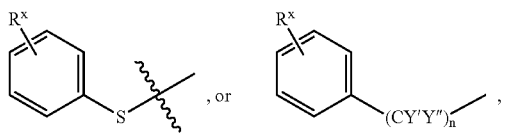

wherein Y' and Y" are independently selected from H, halo, or a $C_1$–$C_6$ aliphatic group; n is 1 or 2; and $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

$R^8$ and $R^{8'}$ are each independently H, halo or a $C_1$–$C_4$ aliphatic group;

Z is $CF_2$, CH(OH), CH(O—$R^Z$) or CH($R^Z$), where $R^Z$ is a $C_1$–$C_6$ aliphatic group or a carbocyclic or heterocyclic group;

$R^3$ is H or a $C_1$–$C_6$ aliphatic group;

$R^4$ and $R^5$ are independently selected from H, halo, a $C_1$–$C_6$ aliphatic group or a group having the formula C(O)$R^{4'}$, wherein $R^{4'}$ is an aliphatic, carbocyclic or heterocyclic group;

$R^6$ and $R^7$ are independently selected from H, halo or a $C_1$–$C_6$ aliphatic group;

where any of said aliphatic groups are saturated, partially unsaturated or fully unsaturated and unsubstituted or substituted by one or more suitable substituents; and where any of said carbocyclic or heterocyclic groups are unsubstituted or substituted by one or more suitable substituents; saturated, partially unsaturated or fully unsaturated; or mono-, bi- or tri-cyclic.

A specific embodiment of a compound of Formula I-C of this invention, wherein Z is $CF_2$ and $R^8$ and $R^{8'}$ are each H, may be represented as follows:

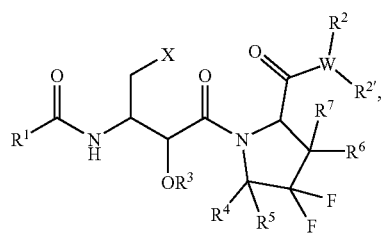

wherein the formula variables are as defined in Formula I-C, above.

Another embodiment of this invention comprises the compounds depicted by the Formula I-D, as follows:

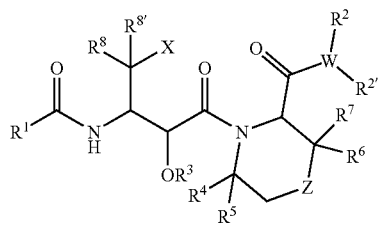

I-D wherein $R^1$ is an aliphatic, carbocyclic or heterocyclic group, or a group having the formula: $OR^{1'}$, $SR^{1'}$, $NHR^{1'}$, $N(R^{1'})R^{1''}$ or $C(O)R^{1'}$, wherein $R^{1'}$ is an aliphatic, carbocyclic or heterocyclic group, and $R^{1''}$ is H or a $C_1$–$C_6$ aliphatic group or $R^{1'}$ and $R^{1''}$ together with the atom to which they are attached form a substituted or unsubstituted heterocyclic ring;

$R^2$ is an aliphatic group, a carbocyclic group, a carbocyclic-aliphatic group, a heterocyclic group, or a heterocyclic-aliphatic group;

W is N, O or C;

when W is N or C, $R^{2'}$ is H or a $C_1$–$C_6$ alkyl group or $R^2$ and $R^{2'}$ taken together with the atom W to which they are attached form an unsubstituted or substituted carbocyclic or heterocyclic ring;

when W is O, $R^{2'}$ is absent;

X is

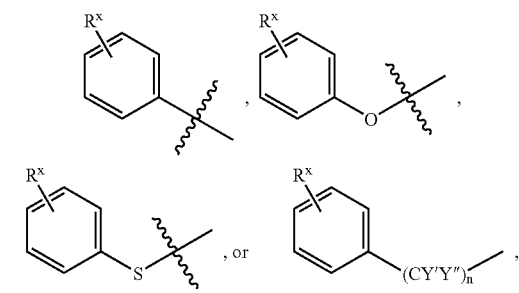

wherein Y' and Y" are independently selected from H, halo, or a $C_1$–$C_6$ aliphatic group; n is 1 or 2; and $R^x$ is H or one or more suitable substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

$R^8$ and $R^{8'}$ are each independently H, halo or a $C_1$–$C_4$ aliphatic group;

Z is S, O, SO, $SO_2$, CHF, $CH_2$, $CF_2$, CH(OH), CH(O—$R^Z$), CH(N—$R^Z R^{Z'}$), CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;

$R^3$ is H or a $C_1$–$C_6$ aliphatic group;

$R^4$ and $R^5$ are independently selected from H, halo, a $C_1$–$C_6$ aliphatic group or a group having the formula $C(O)R^{4'}$, wherein $R^{4'}$ is an aliphatic, carbocyclic or heterocyclic group;

$R^6$ and $R^7$ are independently selected from H, halo or a $C_1$–$C_6$ aliphatic group;

where any of said aliphatic groups are saturated, partially unsaturated or fully unsaturated and unsubstituted or substituted by one or more suitable substituents; and where any of said carbocyclic or heterocyclic groups are unsubstituted or substituted by one or more suitable substituents; saturated, partially unsaturated or fully unsaturated; or mono-, bi- or tri-cyclic.

Another embodiment of this invention comprises the compounds depicted by the Formula I-E, as follows:

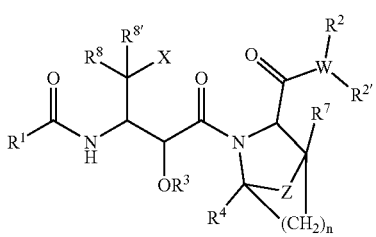

I-E wherein $R^1$ is an aliphatic, carbocyclic or heterocyclic group, or a group having the formula: $OR^{1'}$, $SR^{1'}$, $NHR^{1'}$, $N(R^{1'})R^{1''}$ or $C(O)R^{1'}$, wherein $R^{1'}$ is an aliphatic, carbocyclic or heterocyclic group, and $R^{1''}$ is H or a $C_1$–$C_6$ aliphatic group or $R^{1'}$ and $R^{1''}$ together with the atom to which they are attached form a substituted or unsubstituted heterocyclic ring;

$R^2$ is an aliphatic group, a carbocyclic group, a carbocyclic-aliphatic group, a heterocyclic group, or a heterocyclic-aliphatic group;

W is N, O or C;

when W is N or C, $R^{2'}$ is H or a $C_1$–$C_6$ alkyl group or $R^2$ and $R^{2'}$ taken together with the atom W to which they are attached form an unsubstituted or substituted carbocyclic or heterocyclic ring;

when W is O, $R^{2'}$ is absent;

X is

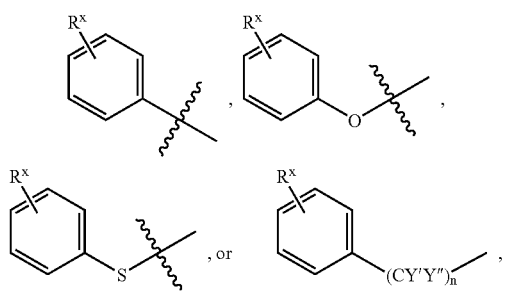

wherein Y' and Y'' are independently selected from H, halo, or a $C_1$–$C_6$ aliphatic group, wherein $R^x$ is H or one or more suitable substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, alkylthio;

$R^8$ and $R^{8'}$ are each independently H, halo or a $C_1$–$C_4$ aliphatic group;

Z is S, O, SO, $SO_2$, $CH_2$, CHF, $CF_2$, CH(OH), CH(O—$R^Z$), CH(N—$R^Z R^{Z'}$), CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;

n is 1 or 2;

$R^3$ is H or a $C_1$–$C_6$ aliphatic group;

$R^4$ is selected from H, halo, a $C_1$–$C_6$ aliphatic group or a group having the formula $C(O)R^{4'}$, wherein $R^{4'}$ is an aliphatic, carbocyclic or heterocyclic group;

$R^7$ is H, halo or a $C_1$–$C_6$ aliphatic group;

where any of said aliphatic groups are saturated, partially unsaturated or fully unsaturated and unsubstituted or substituted by one or more suitable substituents; and where any of said carbocyclic or heterocyclic groups are unsubstituted, substituted by one or more suitable substituents; saturated, partially unsaturated or fully unsaturated; or mono-, bi- or tri-cyclic.

A specific embodiment of s compound of Formula I-E, wherein n is 2 and $R^8$ and $R^{8'}$ are each H, may be represented as follows:

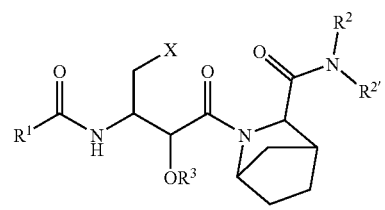

wherein the formula variables are as defined above.

Another embodiment of this invention comprises the compounds of Formula I, wherein A is CH($R^4$), Z is CH($R^Z$) and $R^4$ and $R^Z$ taken together form a 5 or 6-membered carbocyclic ring, depicted by the Formula I-F, as follows:

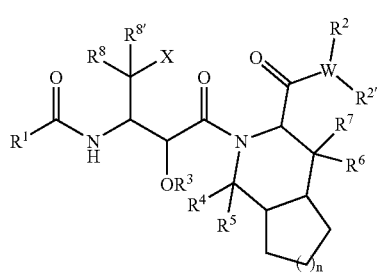

I-F wherein $R^1$ is an aliphatic, carbocyclic or heterocyclic group, or a group having the formula: $OR^{1'}$, $SR^{1'}$, $NHR^{1'}$, $N(R^{1'})R^{1''}$ or $C(O)R^{1'}$, wherein $R^{1'}$ is an aliphatic, carbocyclic or heterocyclic group, and $R^{1''}$ is H or a $C_1$–$C_6$ aliphatic group or $R^{1'}$ and $R^{1''}$ together with the atom to which they are attached form a substituted or unsubstituted heterocyclic ring;

$R^2$ is an aliphatic group, a carbocyclic group, a carbocyclic-aliphatic group, a heterocyclic group, or a heterocyclic-aliphatic group;

W is N, O or C;

when W is N or C, $R^{2'}$ is H or a $C_1$–$C_6$ alkyl group or $R^2$ and $R^{2'}$ taken together with the atom W to which they are attached form an unsubstituted or substituted carbocyclic or heterocyclic ring;

when W is O, $R^{2'}$ is absent;

X is

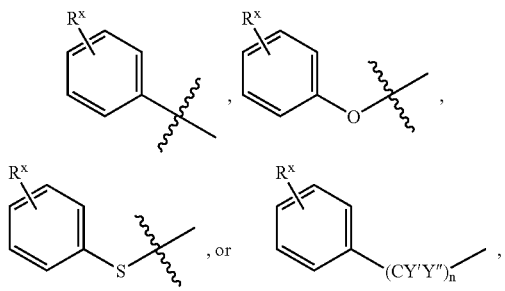

wherein Y' and Y" are independently selected from H, halo, or a $C_1$–$C_6$ aliphatic group, wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

n is 1 or 2;

$R^3$ is H or a $C_1$–$C_6$ aliphatic group;

$R^4$ and $R^5$ are independently selected from H, halo, a $C_1$–$C_6$ aliphatic group or a group having the formula $C(O)R^{4'}$, wherein $R^{4'}$ is an aliphatic, carbocyclic or heterocyclic group;

$R^6$ and $R^7$ are independently selected from H, halo or a $C_1$–$C_6$ aliphatic group;

$R^8$ and $R^{8'}$ are each independently H, halo or a $C_1$–$C_4$ aliphatic group;

where any of said aliphatic groups ar saturated, partially unsaturated or fully unsaturated and unsubstituted or substituted by one or more suitable substituents; and where any of said carbocyclic or heterocyclic groups are unsubstituted or substituted by one or more suitable substituents; saturated, partially unsaturated or fully unsaturated; or mono-, bi- or tri-cyclic.

A specific embodiment of a compound of Formula I-F, wherein n is 2 and $R^8$ and $R^{8'}$ are each H, may be represented as follows:

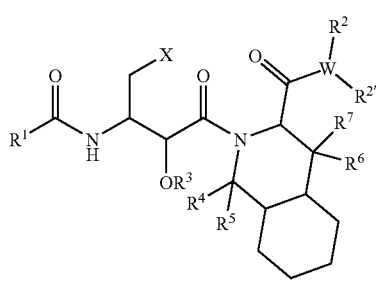

wherein the formula variables are as defined above.

In one embodiment, the compounds of Formula I-A of this invention, wherein $R^6$ and $R^7$, taken together with the atom to which they are bound, form a carbocyclic group, comprise spiro-fused bi-cyclic compounds having the Formula I-G:

I-G

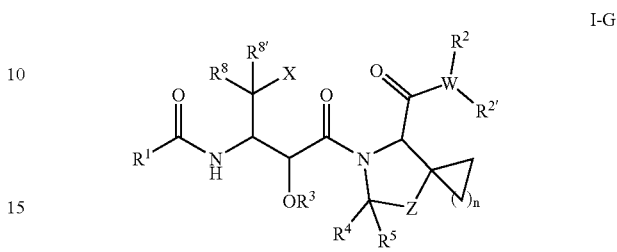

wherein $R^1$ is an aliphatic, carbocyclic or heterocyclic group, or a group having the formula: $OR^{1'}$, $SR^{1'}$, $NHR^{1'}$, $N(R^{1'})R^{1''}$ or $C(O)R^{1'}$, wherein $R^{1'}$ is an aliphatic, carbocyclic or heterocyclic group, and $R^{1'''}$ is H or a $C_1$–$C_6$ aliphatic group or $R^{1'}$ and $R^{1''}$ together with the atom to which they are attached form a substituted or unsubstituted heterocyclic ring;

$R^2$ is an aliphatic group, a carbocyclic group, a carbocyclic-aliphatic group, a heterocyclic group, or a heterocyclic-aliphatic group;

W is N, O or C;

when W is N or C, $R^{2'}$ is H or a $C_1$–$C_6$ alkyl group or $R^2$ and $R^{2'}$ taken together with the atom W to which they are attached form an unsubstituted or substituted carbocyclic or heterocyclic ring.

when W is O, $R^{2'}$ is absent;

X is

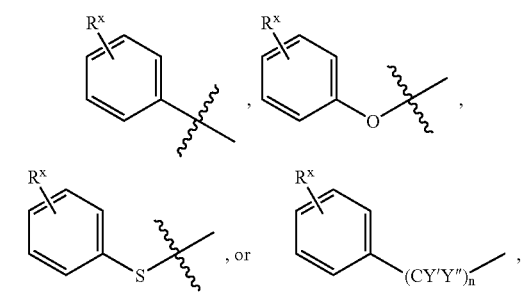

wherein Y' and Y" are independently selected from H, halo, or a $C_1$–$C_6$ aliphatic group, wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, alkylthio;

$R^8$ and $R^{8'}$ are each independently H, halo or a $C_1$–$C_4$ aliphatic group;

Z is S, O, SO, $SO_2$, CHF, $CH_2$, $CF_2$, CH(OH), CH(O—$R^Z$), CH(N—$R^Z R^{Z'}$), CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;

n is 1, 2, 3 or 4;

$R^3$ is H or a $C_1$–$C_6$ aliphatic group;

$R^4$ and $R^5$ are independently selected from H, halo, a $C_1$–$C_6$ aliphatic group or a group having the formula $C(O)R^{4'}$, wherein $R^{4'}$ is an aliphatic, carbocyclic or heterocyclic group;

where any of said aliphatic groups are saturated, partially unsaturated or fully unsaturated and unsubstituted or substituted by one or more suitable substituents; and where any of said carbocyclic or heterocyclic groups are unsubstituted, substituted by one or more suitable substituents; saturated, partially unsaturated or fully unsaturated; or mono-, bi- or tri-cyclic.

In the compounds of this inventions, $R^2$ may consist of a substituted aliphatic group; wherein $R^2$ may be represented as —$CH_2$—B, —$CH_2CH_2$—B, —$CH(CH_3)B$, and the like, wherein B is a carbocyclic or heterocyclic group as described herein, and wherein the B group may be unsubstituted or substituted with one or more substituents selected from $C_1$–$C_4$ alkyl, halo, haloalkyl, hydroxy, alkoxy, halo alkoxy, alkylthio, haloalkylthio, amino, dialkylamino, alkyl-$SO_2$, cyano, alkylcarbonylamino and cycloalkylalkyloxy.

Specific embodiments of the compounds of this invention comprise the compounds depicted by Formula I-A':

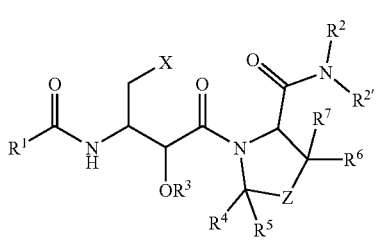

I-A' wherein:

$R^1$ is an alkyl, alkenyl, or alkynyl group, a bi- or tri-cyclic cycloalkyl, cycloalkenyl, aryl, heterocycloalkyl, heterocycloalkenyl or heteroaryl group or a group having the formula: $OR^{1'}$, $SR^{1'}$, $NHR^{1'}$, $N(R^{1'})R^{1''}$ or $C(O)R^{1'}$, wherein $R^{1'}$ is an alkyl, alkenyl, or alkynyl group, a bi- or tri-cyclic cycloalkyl, cycloalkenyl, aryl, heterocycloalkyl, heterocycloalkenyl or heteroaryl group, or a cycloalkylalkyl, cycloalkenylalkyl, arylalkyl, heterocycloalkylalkyl, heterocycloalkenylalkyl, heteroarylalkyl, cycloalkylalkenyl, cycloalkenylalkenyl, arylalkenyl, heterocycloalkylalkenyl, heterocycloalkenylalkenyl, heteroarylalkenyl, cycloalkylalkynyl, cycloalkenylalkynyl, arylalkynyl, heterocycloalkylalkynyl, heterocycloalkenylalkynyl, or heteroarylalkynyl group; and $R^{1'''}$ is H or a $C_1$–$C_6$ alkyl, alkenyl or alkynyl group or $R^{1'}$ and $R^{1'''}$ together with the atom to which they are attached form a substituted or unsubstituted heterocyclic ring;

$R^2$ is a cycloalkyl, cycloalkylalkyl, cycloalkenyl, or cycloalkenylalkyl group, a bi- or tri-cyclic aryl group, a bi- or tri-cyclic arylalkyl group, a bi- or tri-cyclic arylalkenyl group, a bi- or tri-cyclic arylalkynyl group, or a heterocycloalkyl, heterocycloalkylalkyl, heterocycloalkenyl, heterocycloalkenylalkyl, heteroaryl or heteroarylalkyl group;

$R^{2'}$ is H or a $C_1$–$C_6$ alkyl group;

or $R^2$ and $R^{2'}$ taken together with the nitrogen atom to which they are attached form a heterocycloalkyl or heterocycloalkenyl ring;

X is

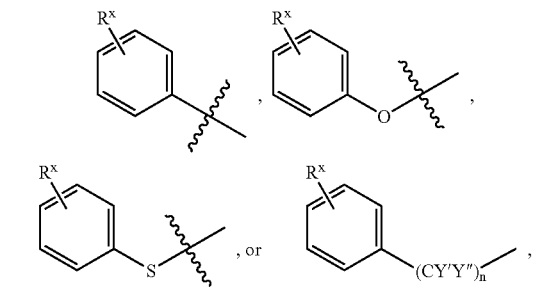

wherein Y' and Y" are independently selected from H, halo, or a $C_1$–$C_6$ aliphatic group, wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

Z is S, O, SO, $SO_2$, $CH_2$, CHF, $CF_2$, CH(OH), CH(O—$R^Z$), CH(N—$R^ZR^{Z'}$), CH(S—$R^Z$), C(=O), or $CH(R^Z)$, where $R^Z$ is a $C_1$–$C_6$ aliphatic group or a carbocyclic or heterocyclic group and $R^{Z'}$ is H or a $C_1$–$C_6$ aliphatic group;

$R^3$ is H or a $C_1$–$C_6$ aliphatic group;

$R^4$ and $R^5$ are independently selected from H, halo, and a $C_1$–$C_6$ aliphatic group;

$R^6$ and $R^7$ are independently selected from H, halo and a $C_1$–$C_6$ aliphatic group;

where any of the alkyl, alkenyl, alkynyl, cycloalkyl, cycloalkenyl, aryl, heterocycloalkyl, heterocycloalkenyl or heteroaryl groups or the alkyl, alkenyl, alkynyl, cycloalkyl, cycloalkenyl, aryl, heterocycloalkyl, heterocycloalkenyl or heteroaryl moieties of the cycloalkylalkyl, cycloalkenylalkyl, arylalkyl, heterocycloalkylalkyl, heterocycloalkenylalkyl, heteroarylalkyl, cycloalkylalkenyl, cycloalkenylalkenyl, arylalkenyl, heterocycloalkylalkenyl, heterocycloalkenylalkenyl, heteroarylalkenyl, cycloalkylalkynyl, cycloalkenylalkynyl, arylalkynyl, heterocycloalkylalkynyl, and heterocycloalkenylalkynyl, heteroarylalkynyl groups are unsubstituted or substituted by one or more suitable substituents; and where any of said carbocyclic or heterocyclic groups are optionally mono-, bi- or tri-cyclic; saturated, partially unsaturated or fully unsaturated; and unsubstituted or substituted by one or more suitable substituents.

provided that $R^2$ is not an aliphatic group, a phenyl group or a phenyl-substituted aliphatic group, when Z is S, SO, $SO_2$, CHF, O, or $CH_2$; $R^{2'}$, $R^3$, $R^8$ and $R^{8'}$ are H or a $C_1$–$C_4$ alkyl group; $R^4$, $R^5$, $R^6$ and $R^7$ are H or a $C_1$–$C_6$ alkyl group; X is

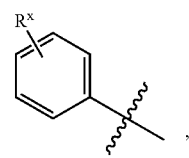

R[1] is a substituted or unsubstituted 5 or 6-membered monocyclic carbocyclic or heterocyclic group;

or provided that R[2] is not t-butyl when R[1] is substituted or unsubstituted phenyloxymethylene, or quinolylmethylenecarbonylaminomethylene; A is absent; Z is S; R[2'], R[3], R[4], and R[5], are H; R[6] and R[7] are H, methyl, ethyl or propyl; and X is

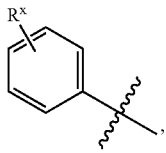

wherein R$^x$ is H or methoxy,

In another embodiment, the compounds of this invention are depicted by Formula I-A; wherein:

Z is $CF_2$, CH(OH), CH(O—R$^Z$), CH(NR$^Z$R$^{Z'}$), CH(S—R$^Z$), C=O or CH(R$^Z$), where R$^Z$ is a $C_1$–$C_6$ aliphatic group or a carbocyclic or heterocyclic group and R$^{Z'}$ is H or a $C_1$–$C_6$ aliphatic group.

Specific examples of the compounds of Formula I-B comprise compounds having the formula I-B'

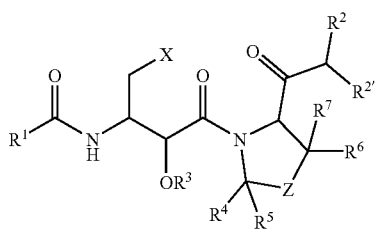

wherein

R[1] is an aliphatic, carbocyclic or heterocyclic group,

R[2] is an aliphatic group, a carbocyclic-aliphatic group, or a heterocyclic-aliphatic group;

R[2'] is H or a $C_1$–$C_6$ alkyl group;

or R[2] and R[2'] taken together with the carbon atom to which they are both attached form an unsubstituted or substituted carbocyclic ring;

X is

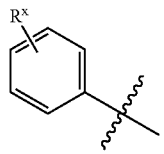 or 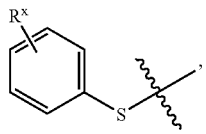

wherein R$^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

Z is S, O, SO, $SO_2$, CHF, $CH_2$, $CF_2$, C(=O), or CH(R$^Z$), where R$^Z$ is a $C_1$–$C_6$ aliphatic group or a carbocyclic or heterocyclic group;

R[3] is H or a $C_1$–$C_6$ aliphatic group;

R[4] and R[5] are independently selected from H, halo, or a $C_1$–$C_6$ aliphatic group;

R[6] and R[7] are independently selected from H, halo or a $C_1$–$C_6$ aliphatic group;

wherein any of said aliphatic groups are saturated, partially saturated or fully unsaturated and unsubstituted or substituted by one or more suitable substituents; and wherein any of said carbocyclic or heterocyclic groups are unsubstituted or substituted by one or more suitable substituents; saturated, partially unsaturated or fully unsaturated; or mono-, bi- or tri-cyclic.

More specific examples of the compounds of Formula I-B' comprise compounds wherein R[1] is a carbocyclic group, R[2] is a $C_1$–$C_6$ aliphatic group or a carbocyclic-$C_1$–$C_6$-aliphatic group;

Z is S, O, $CH_2$, $CF_2$;

R[3], R[4] and R[5] are each H; and

R[6] and R[7] are each a $C_1$–$C_6$ aliphatic group;

where any of said aliphatic groups are saturated, partially unsaturated or fully unsaturated and unsubstituted or substituted by one or more suitable substituents; and where any of said carbocyclic or heterocyclic groups are unsubstituted or substituted by one or more suitable substituents; saturated, partially unsaturated or fully unsaturated; or mono-, bi- or tri-cyclic.

Specific examples of the compounds of Formula I-B' comprise compounds wherein

R[1] is a phenyl group, unsubstituted or substituted with one or more substituents selected from alkyl, hydroxyl, halo, halo alkyl, haloalkoxy, methylene dioxy, and di-fluoromethylene dioxy;

R[2] is an alkenyl group, an aralkyl group or a straight or branched chain saturated alkyl;

X is

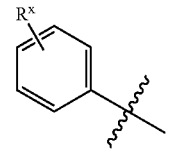

where R$^x$ is H;

Z is S;

R[3], R[4] and R[5] are each H; and

R[6] and R[7] are each methyl;

wherein any of said alkenyl, aralkyl, or alkyl groups are unsubstituted or substituted with one or more substituents, independently selected from methyl, halo, trifluoromethyl or methoxy.

Another specific emobdiment of the compounds of Formula I-B' comprise compounds wherein R[1] is a phenyl group, unsubstituted or substituted with one or more substituents selected from alkyl, hydroxyl, halo, halo alkyl, haloalkoxy, methylene dioxy, and di-fluoromethylene dioxy;

R[2] is an alkenyl group, an aralkyl group or a straight or branched chain saturated alkyl;

X is

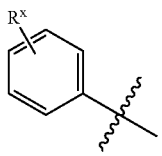

where $R^x$ is H;
Z is $CF_2$;
$R^3$, $R^4$ and $R^5$ are each H; and
$R^6$ and $R^7$ are each methyl;

Wherein any of said alkenyl, aralkyl, or alkyl groups are unsbstituted or substituted with one or more substitutents, independently selected from methyl, halo, trifluoromethyl or methoxy.

Other specific examples of this invention, comprise the compounds having the Formula I-C:

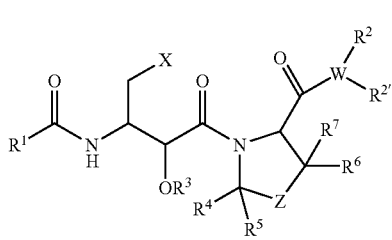

I-C' wherein
$R^1$ is an aliphatic, carbocyclic or heterocyclic group, or a group having the formula: $OR^{1'}$, wherein $R^{1'}$ is a carbocyclic or heterocyclic group;
$R^2$ is an aliphatic group, a carbocyclic group, a carbocyclic-aliphatic group, a heterocyclic group, or a heterocyclic-aliphatic group;
W is N;
$R^{2'}$ is H or a $C_1$–$C_6$ alkyl group;
X is

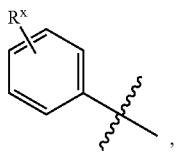

, wherein $R^x$ is H; dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, or alkylthio;
Z is $CF_2$, CH(OH) or C(=O);
$R^3$, $R^4$ and $R^5$ are each H; and
$R^6$ and $R^7$ are each methyl.

More specific examples of this invention, comprise the compounds having the Formula I-C', wherein:
$R^1$ is an aryl group, an aryloxyalkyl group, an alkynyloxy group, a heterocycloalkyloxy group or heteroaryl group;
$R^2$ is an alkyl, alkenyl, or alkynyl group, an arylalkyl group; a heteroarylalkyl group, an indanyl group, a chromanyl group, a tetrahydronaphthalene group, an aliphatic group, a carbocyclic group, a carbocyclic-aliphatic group, a heterocyclic group, or a heterocyclic-aliphatic group; and
$R^{2'}$ is H;
wherein the alkyl, alkenyl, alkynyl, arylalkyl; heteroarylalkyl, indanyl, chromanyl or tetrahydronaphthalene group is optionaaly unsubstituted or substitutee with one or more substituents independently selected from alkyl, hydroxy, halo, haloalkyl, cyano, alkoxy or methylenedioxy.

Specific examples of this invention, comprise the compounds having the Formula I-C', wherein:
$R^1$ is a phenyl group, a phenyoxymethyl group, a tetrahydrofuranyloxy group, a $C_1$–$C_4$ alkynyloxy group, or a isoxazolyl group, where the phenyl group, phenyoxymethyl group or isoxazolyl group is unsubstituted or substituted by hydroxyl or methyl;
$R^2$ is an $C_1$–$C_5$ alkyl, $C_1$–$C_6$ alkenyl, or $C_1$–$C_4$ alkynyl group, a benzyl group; a furanylmethyl group, a thienylmehtyl group, an indanyl group, a chromanyl group, a tetrahydronaphthalene group, or a cyclohexenyl group, where the alkyl groups is unsubstituted or substituted with one or more halogen; and the phenyl group is unsubstituted or substituted with halogen, hydroxyl, methoxy, methylenedioxy or methyl;
$R^{2'}$ is H;
X is

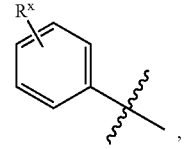

, wherein $R^x$ is H; and
Z is $CF_2$;

Other specific embodiments of this invention comprise the compounds depicted by the Formula I-D' or I-E', as follows:

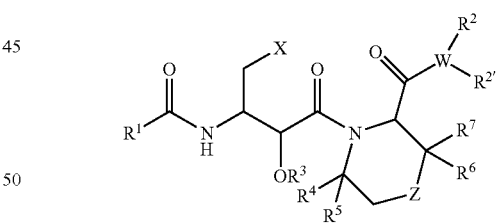

I-D'

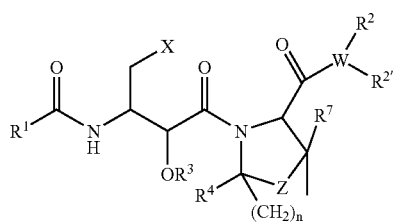

I-E' wherein
$R^1$ is a carbocyclic or heterocyclic group,
$R^2$ is an aliphatic group, a carbocyclic group, a carbocyclic-aliphatic group, a heterocyclic group, or a heterocyclic-aliphatic group;

W is N;

R² is H or a $C_1$–$C_6$ alkyl group;

X is

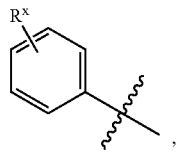

wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

Z is O, $CH_2$, CHF, $CF_2$, or $CH(R^Z)$, where $R^Z$ is a $C_1$–$C_6$ aliphatic group;

$R^3$, $R^4$, $R^5$, $R^6$ and $R^7$ are each H; and wherein any of said aliphatic groups are saturated, partially unsaturated or fully unsaturated and unsubstituted or substituted by one or more suitable substituents; and wherein any of said carbocyclic or heterocyclic groups are unsubstituted or substituted by one or more suitable substituents; saturated, partially unsaturated or fully unsaturated; or mono-, bi- or tri-cyclic.

More specifically, embodiments of this invention, comprise compounds according to Formula I-D' or I-E' wherein $R^1$ is a carbocyclic group;

$R^2$ is an arylalkyl group;

$R^{2'}$ is H;

X is

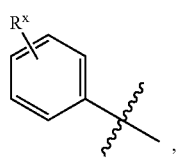

wherein $R^x$ is H; and

Z is $CH_2$;

wherein said carbocyclic group and arylalkyl group are unsubstituted or substituted with one or more substituents selected from methyl, halo, or hydroxy.

Another specific embodiment of this invention comprises compounds of Formula I-F', as follows:

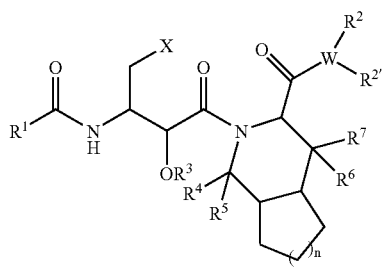

I-F wherein $R^1$ is a carbocyclic or heterocyclic group, $R^2$ is an aliphatic group, a carbocyclic group, a carbocyclic-aliphatic group, a heterocyclic group, or a heterocyclic-aliphatic group;

W is N;

$R^{2'}$ is H or a $C_1$–$C_6$ alkyl group;

X is

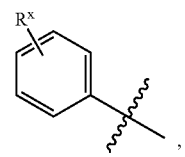

wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

n is 1 or 2;

$R^3$, $R^4$ and $R^5$ are each H; and $R^7$ is H;

wherein any of said aliphatic groups are saturated, partially unsaturated or fully unsaturated and unsubstituted or substituted by one or more suitable substituents; and wherein any of said carbocyclic or heterocyclic groups are unsubstituted or substituted by one or more suitable substituents; saturated, partially unsaturated or fully unsaturated; or mono-, bi- or tri-cyclic.

More specifically, embodiments of this invention, comprise compounds according to Formula I-F', wherein $R^1$ is a carbocyclic group;

$R^2$ is an arylalkyl group;

$R^{2'}$ is H;

X is

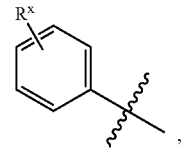

wherein $R^x$ is H;
wherein said carbocyclic group, and arylalkyl group unsubstituted or substituted with one or more substituents selected from methyl, halo, or hydroxy.

In one embodiment, the compounds of Formula I-A of this invention, wherein $R^6$ and $R^7$, taken together with the atom to which they are bound, form a carbocyclic group, comprise spiro-fused bi-cyclic compounds having the Formula I-G':

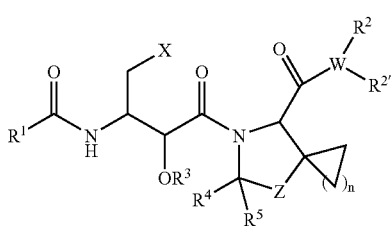

I-G' wherein
$R^1$ is a carbocyclic or heterocyclic group;
$R^2$ is an aliphatic group, a carbocyclic group, a carbocyclic-aliphatic group, a heterocyclic group, or a heterocyclic-aliphatic group;
W is N, C or CH;
$R^{2'}$ is H
X is

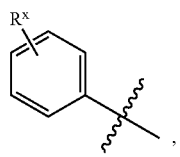

, wherein $R^x$ is H or one or more suitable substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;
Z is S, O, $CH_2$, CHF, $CF_2$, or $CH(R^Z)$, where $R^Z$ is a $C_1$-$C_6$ aliphatic group;
n is 2, 3 or 4;
$R^3$, $R^4$ and $R^5$ are each H;
wherein any of said aliphatic groups are saturated, partially unsaturated or fully unsaturated and unsubstituted or substituted by one or more suitable substituents; and
wherein any of said carbocyclic or heterocyclic groups are unsubstituted or substituted by one or more suitable substituents; saturated, partially unsaturated or fully unsaturated; or mono-, bi- or tri-cyclic.

More specific embodiments comprise the compounds of Formula I-G' wherein:
$R^1$ is a carbocyclic group;
$R^2$ is an arylalkyl group;
W is N;
$R^{2'}$ is H;
X is

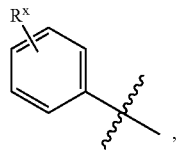

, wherein $R^x$ is H; and
Z is $CH_2$;
$R^3$, $R^4$, $R^5$ and $R^7$ are each H;
wherein said carbocyclic group and arylalkyl group unsubstituted or substituted with one or more substituents selected from methyl, halo, or hydroxy.

More specific embodiments comprise the compounds of Formula I-G' wherein:
$R^1$ is a carbocyclic group;
$R^2$ is an arylalkyl group;
W is N;
$R^{2'}$ is H;
X is

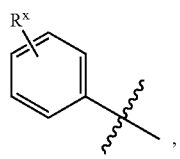

, wherein $R^x$ is H; and
Z is $CF_2$;
$R^3$, $R^4$, $R^5$ and $R^7$ are each H;
wherein said carbocyclic group and arylalkyl group unsubstituted or substituted with one or more substituents selected from methyl, halo, or hydroxy.

More specific embodiments comprise the compounds of Formula I-G' wherein:
$R^1$ is a carbocyclic group;
$R^2$ is an arylalkyl group;
W is N;
$R^{2'}$ is H;
X is

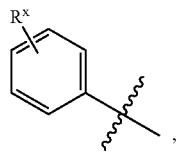

, wherein $R^x$ is H; and
Z is S;
$R^3$, $R^4$, $R^5$ and $R^7$ are each H;
wherein said carbocyclic group and arylalkyl group unsubstituted or substituted with one or more substituents selected from methyl, halo, or hydroxy.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

All compounds of this invention contain at least one chiral center and may exist as single stereoisomers (e.g., single enantiomers or single diastereomers), any mixture of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that contains at least 90% of a single stereoisomer of each chiral center present in the compounds. Where the stereochemistry of the chiral carbons present in the chemical structures illustrated herein is not specified, the chemical structure is intended to encompass compounds containing either stereoisomer of each chiral center present in the compound. Preferably, however, the inventive compounds are used in optically pure, that is, stereoisomerically pure, form or substantially optically pure (substantially stereoisomerically pure) form. As used herein, the term "stereoisomeric" purity (or "optical" purity) refers to the "enantiomeric" purity and/or "diastereomeric" purity of a compound. Compounds that are substantially enantiomerically pure contain at least 90% of a single isomer and preferably contain at least 95% of a single isomer of each chiral center present in the enantiomer. Compounds that are substantially diastereomerically pure contain at least 90% of a single isomer of each chiral center present in the diastereomer, and preferably contain at least 95% of a single isomer of each chiral center. More preferably, the substantially enantiomerically and diasteriomerically pure compounds in this invention contain at least 97.5% of a single isomer and most preferably contain at least 99% of a single isomer of each chiral center in the compound. The term "racemic" or "racemic mixture" refers to a mixture of equal amounts of enantiomeric compounds, which encompasses mixtures of enantiomers and mixtures of enantiomeric diastereomers. The compounds of this invention may be obtained in stereoisomerically pure (i.e., enantiomerically and/or diastereomerically pure) or substantially stereoisomerically pure (i.e., substantially enantiomerically and/or diastereomerically pure) form. Such compounds may be obtained synthetically, according to the procedures described herein using optically pure or substantially optically pure materials. Alternatively, these compounds may be obtained by resolution/separation of a mixture of stereoisomers, including racemic mixtures, using conventional procedures. Exemplary methods that may be useful for the resolution/separation of stereoisomeric mixtures include chromatography and crystallization/recrystallization. Other useful methods may be found in "*Enantiomers, Racemates, and Resolutions*," J. Jacques et al., 1981, John Wiley and Sons, New York, N.Y., the disclosure of which is incorporated herein by reference. Preferred stereoisomers of the compounds of this invention are described herein.

Especially preferred embodiments of this invention comprise compounds, wherein the stereogenic centers (chiral carbons) have the following designated stereochemistry:

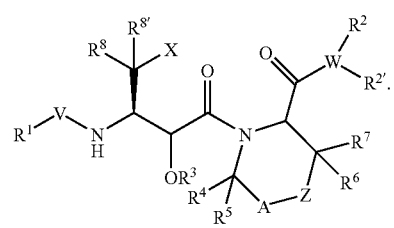

More preferably, at least two of the stereogenic centers have the following designated stereochemistry:

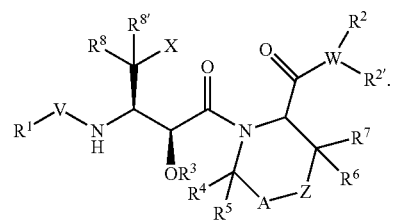

Even more preferably, at least three of the stereogenic centers have the following designated stereochemistry:

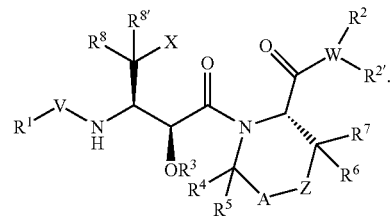

Exemplary compounds of this invention may be represented as follows:

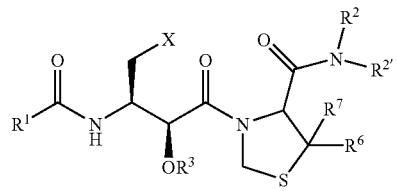

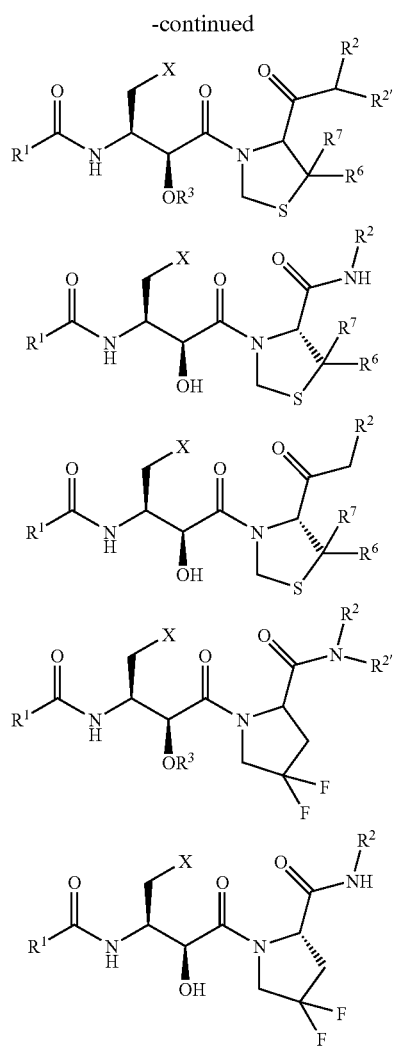
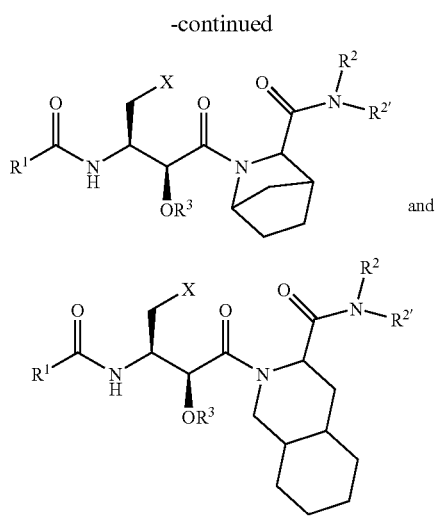
wherein each of the formula variables are as defined above.
Exemplary compounds of this invention include the following. The abbreviation "Bn" in some of the following structures indicates a "benzyl" substituent.
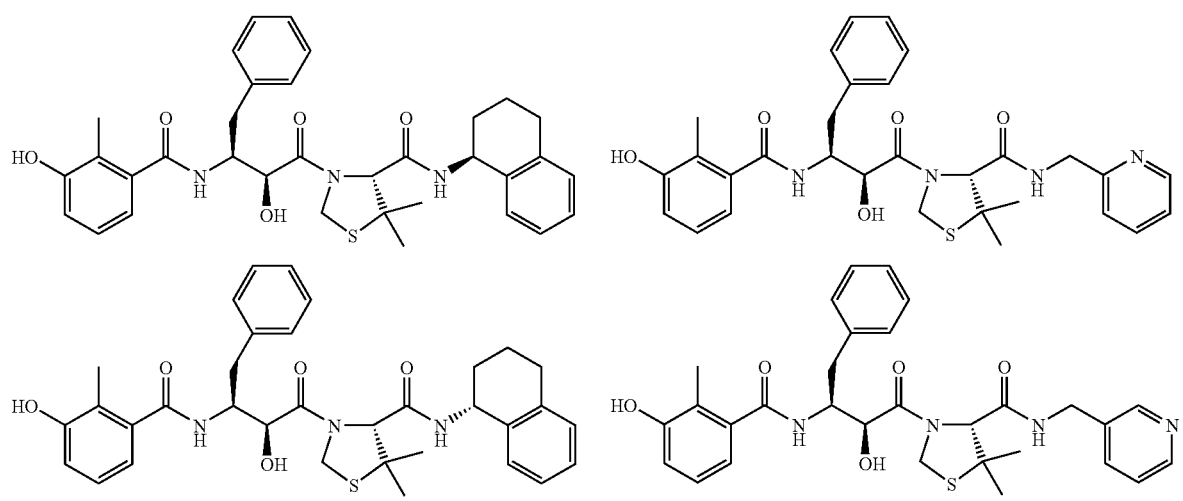

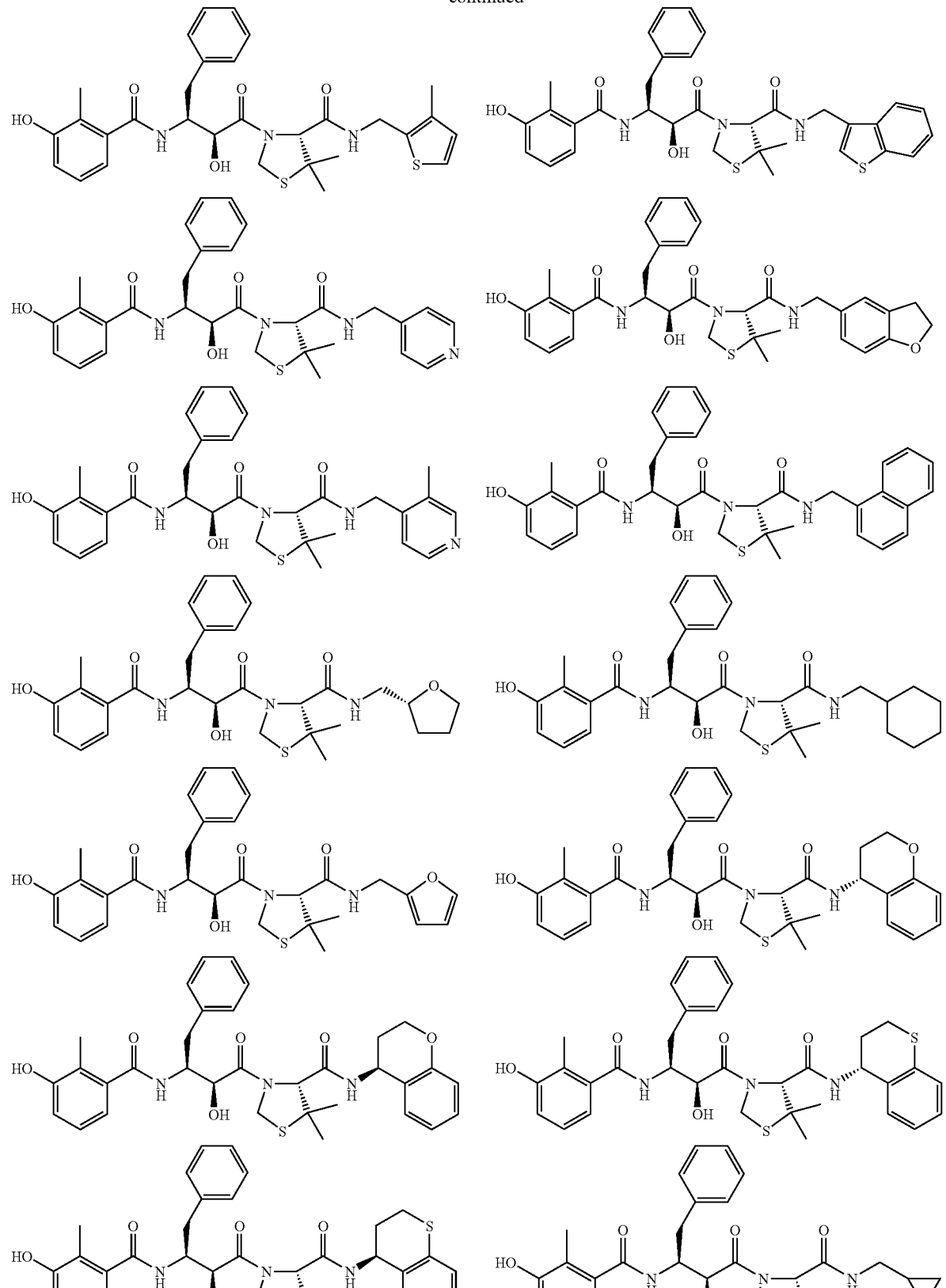

and the prodrugs, pharmaceutically active metabolites, and pharmaceutically acceptable salts and solvates thereof.

The invention is also directed to the intermediates of Formula II, which are useful in the synthesis of certain compounds of Formula I:

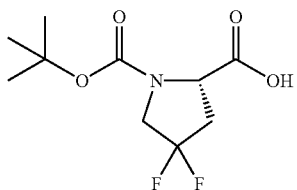
20a

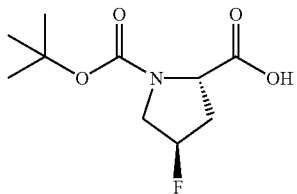
20b

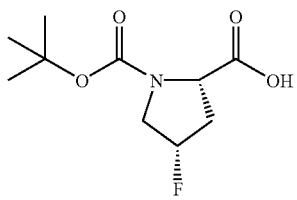
20c

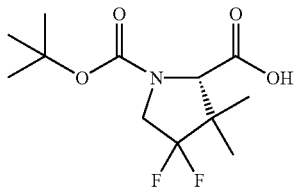
20d

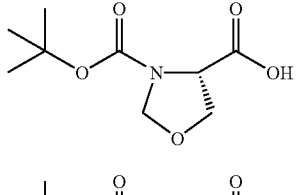
20e

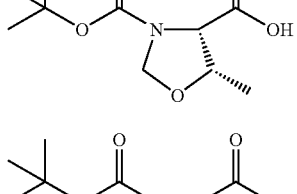
20f

20g

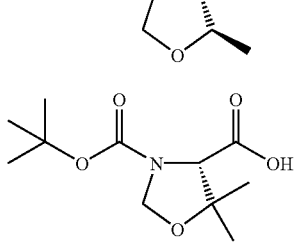
20h

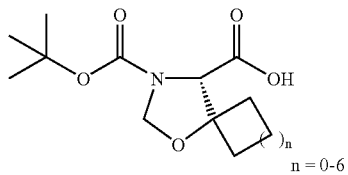
20i n = 0-6

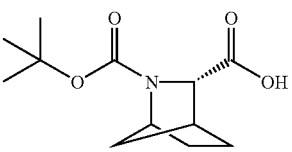
20j

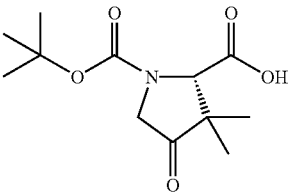
20k

The HIV protease inhibitor compounds of this invention include prodrugs, the pharmaceutically active metabolites, and the pharmaceutically acceptable salts and solvates thereof. In preferred embodiments, the compounds of Formula I, prodrugs, pharmaceutically acceptable salts, and pharmaceutically active metabolites and solvates thereof demonstrate an HIV-protease inhibitory activity, corresponding to $K_i$ of at least 100 nM, an $EC_{50}$ of at least 10 mM or an $IC_{50}$ of at least 10 mM. Preferably, the compounds of this invention demonstrate an HIV-protease inhibitory activity, corresponding to a $K_i$ of at least 10 nM, an $EC_{50}$ of at least 1 mM or an $IC_{50}$ of at least 1 mM. More preferably, the compounds of this invention demonstrate an HIV-protease inhibitory activity against mutant strains of HIV, corresponding to a $K_i$ of at least 100 nM, an $EC_{50}$ of at least 10 mM or an $IC_{50}$ of at least 10 mM. Even more preferably, the compounds of this invention demonstrate protease inhibitory activity against mutant strains corresponding to a $K_i$ of at least 10 nM, an $EC_{50}$ of at least 1 mM or an $IC_{50}$ of at least 1 mM.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, —$PO(OR)_2$ or —$C=NR$, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B.V., Amsterdam, The Netherlands. The following are examples of prodrugs that can be converted to the compounds of this invention under physiological conditions, by solvolysis or metabolically:

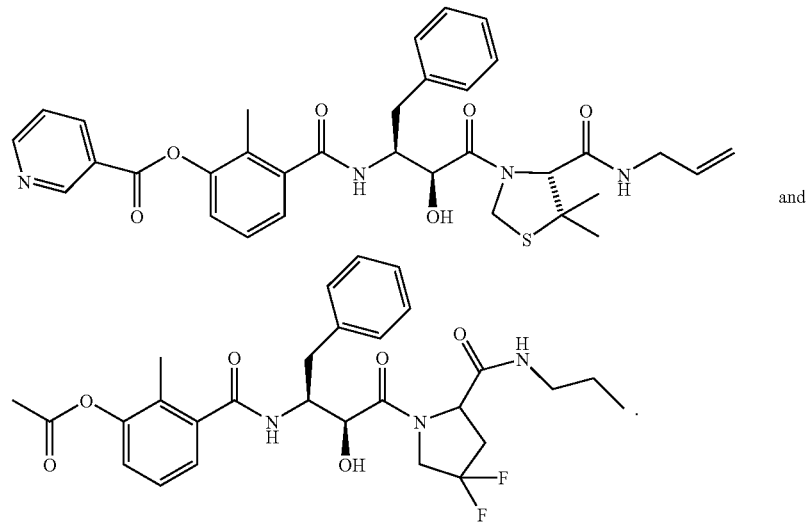

and

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates (mesylates), propanesulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, and solvates may exist in different crystal forms, all of which are intended to be within the scope of the present invention and specified formulas.

The present invention is also directed to a method of inhibiting HIV protease activity, comprising contacting the protease with an effective amount of a compound of Formula I, or a pharmaceutically acceptable salt, prodrug, pharmaceutically active metabolite, or solvate thereof. For example, HIV protease activity may be inhibited in mammalian tissue by administering a compound of Formula I or a pharmaceutically acceptable salt, prodrug, pharmaceutically active metabolite, or solvate thereof. More preferably, the present method is directed at inhibiting HIV-protease activity.

"Treating" or "treatment" is intended to mean at least the mitigation of a disease condition in a mammal, such as a human, that is alleviated by the inhibition of the activity of HIV proteases. The methods of treatment for mitigation of a disease condition include the use of the compounds in this invention in any conventionally acceptable manner, for example, as a prophylactic. The activity of the inventive compounds as inhibitors of HIV protease activity may be measured by any of the suitable methods known to those skilled in the art, including in vivo and in vitro assays. Examples of suitable assays for activity measurements are escribed herein. Administration of the compounds of the Formula I and their pharmaceutically acceptable prodrugs, salts, active metabolites, and solvates may be performed according to any of the generally accepted modes of administration available to those skilled in the art. Illustrative examples of suitable modes of administration include oral, nasal, parenteral, topical, transdermal, and rectal.

An inventive compound of Formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

The present invention includes pharmaceutical compositions useful for inhibiting HIV protease, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV protease, and a method of treating infection by HIV, or of treating AIDS or ARC. Additionally, the present invention is directed to a pharmaceutical composition comprising a therapeutically effective amount of a compound of the present invention in combination with a therapeutically effective amount of an HIV infection/AIDS treatment agent selected from:

1) an HIV/AIDS antiviral agent,
2) an anti-infective agent, and
3) an immunomodulator.

The present invention also includes the use of a compound of the present invention as described above in the preparation of a medicament for (a) inhibiting HIV protease, (b) preventing or treating infection by HIV, or (c) treating AIDS or ARC.

The present invention further includes the use of any of the HIV protease inhibiting compounds of the present invention as described above in combination with one or more HIV infection/AIDS treatment agents selected from an HIV/AIDS antiviral agent, an anti-infective agent, and an immunomodulator for the manufacture of a medicament for (a) inhibiting HIV protease, (b) preventing or treating infection by HIV, or (c) treating AIDS or ARC, said medicament comprising an effective amount of the HIV protease inhibitor compound and an effective amount of the one or more treatment agents.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension. A dose of the pharmaceutical composition contains at least a therapeutically effective amount of the active compound (i.e., a compound of Formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of HIV protease activity, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an inventive agent that, when administered to a mammal in need thereof, is sufficient to effect treatment for disease conditions alleviated by the inhibition of the activity of one or more variant of the HIV protease. The amount of a given compound of the invention that will be therapeutically effective will vary depending upon factors such as the particular compound, the disease condition and the severity thereof, the identity of the mammal in need thereof, which amount may be routinely determined by artisans.

The compounds of this invention are also useful in the preparation and execution of screening assays for antiviral compounds. For example, the compounds of this invention are useful for isolating enzyme mutants that are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

GENERAL SYNTHETIC METHODS

Preferably, the inventive compounds are prepared by the methods of the present invention, including the General Methods shown below. When stereochemistry is not specified in chemical structures, either stereocenter may be utilized. The following abbreviations also apply: Boc (tert-butoxycarbonyl), Ac (acetyl), Cbz (benzyloxycarbonyl), DMB (2,4-dimethoxybenzyl), TBS (tert-butyldimethylsilyl), TBDPS (tert-butyldiphenylsilyl), Ms (methanesulfonate), Ts (toluenesulfonate), Bn (benzyl), and Tr (triphenylmethyl)

All reactions were performed in septum-sealed flasks under a slight positive pressure of argon unless otherwise noted. All commercial reagents and solvents were used as received from their respective suppliers with the following exceptions: Tetrahydrofuran (THF) was distilled from sodium benzophenone ketyl prior to use. Dichloromethane ($CH_2Cl_2$) was distilled from calcium hydride prior to use. Flash chromatography was performed using silica gel 60 (Merck art. 9385). $^1$H NMR spectra were recorded at 300 MHz utilizing a Varian UNITYplus 300 spectrometer. Chemical shifts are reported in ppm (δ) downfield relative to internal tetramethylsilane, and coupling constants are given in Hertz. Infrared absorption spectra were recorded using a Perkin-Elmer 1600 series FTIR spectrometer. Elemental analyses were performed by Atlantic Microlab, Inc., Norcross, Ga. Melting points are uncorrected.

All P2' amine variants mentioned in General Methods A–E described hereinbelow were either purchased and used directly or synthesized as follows.

Method A: Representative Procedure for Reduction of Ketones to Alcohols.

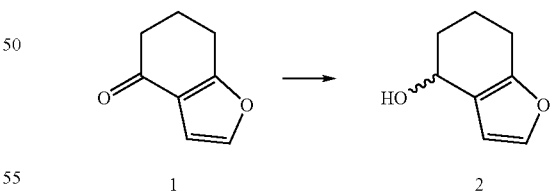

6,7-Dihydro-4-(5H)-benzofuranone (1) (1.00 g 7.34 mmol) was dissolved in methanol (55 mL). The mixture was cooled to 0° C. and $NaBH_4$ (0.31 g, 8.08 mmol) was added in portions. The reaction was stirred for 2 h at 0° C. at which time the methanol was evaporated. The residue was dissolved in EtOAc and poured into $NaHCO_3$ (saturated aqueous) and extracted with EtOAc (3×10 mL). The combined organic extracts were washed with brine (10 mL), passed over a short plug of $Na_2SO_4$, and concentrated in vacuo to give 2 (1.01 g, 99%, as a mixture of isomers) as a pale yellow, thick oil, which was of sufficient quality to be advanced to the next step without further purification. Rf (50% EtOAc/hexanes): 0.53.

Method B: Representative Procedure for Reduction of Acids to Alcohols.

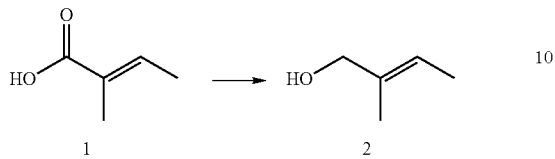

Tiglic acid (1) (20.0 g, 0.200 mol) was dissolved in ether (80 ml) and added dropwise over 30 min to a suspension of LiAlH$_4$ (15.0 g, 0.417 mol) in ether (80 ml) at 0° C. and the reaction mixture was allowed to warm to room temperature. After 3 h the mixture was re-cooled to 0° C. and quenched slowly by the addition of H$_2$O (15 ml), 15% NaOH (15 ml) and H$_2$O (15 ml). The reaction mixture was filtered to remove the granular precipitate and washed thoroughly with ether. The filtrate was washed successively with 1N HCl, NaHCO$_3$ (saturated aqueous), and brine. The combined organic layers were dried over MgSO$_4$ and concentrated in vacuo to give (E)-2-methyl-but-2-en-1-ol (2) as a clear oil (12.8 g, 74%).

Method C: Representative Procedure for Alkylation of Phenols Alcohols.

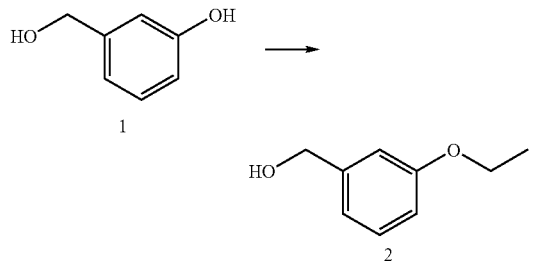

3-Hydroxybenzylalcohol (1) (0.500 g 4.03 mmol) was dissolved in DMF (2 mL) at ambient temperature. Ethyl bromide (0.900 mL, 12.1 mmol) and finely crushed K$_2$CO$_3$ (2.78 g, 20.1 mmol) were added and the reaction mixture was stirred for 5 h. The DMF was then removed in vacuo and the residue was partitioned between EtOAc and H$_2$O, and extracted with EtOAc (3×10 mL). The organic layers were washed with brine (10 mL) and passed over a short plug of Na$_2$SO$_4$. The solvents were removed in vacuo to give alcohol 2 (0.55 g, 90%) as a pale yellow, thick oil, which was of sufficient quality to be advanced to the next step without further purification. Rf (40% EtOAC/hexanes): 0.69.

Method D: Representative Procedure for Conversion of Alcohols to Amines.

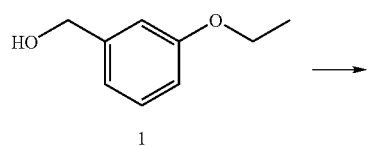

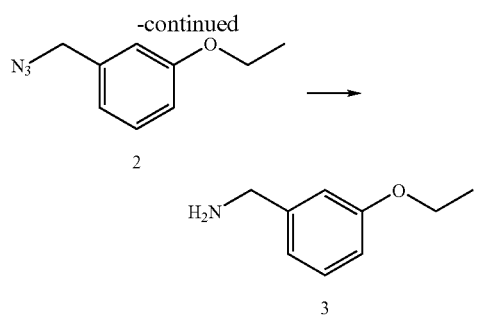

3-Ethoxy-phenyl-methanol (1) (1.23 g 8.08 mmol) was dissolved in CH$_2$Cl$_2$ (10 mL) at ambient temperature and diphenylphosphoryl azide (2.67 g, 9.70 mmol) and 1,8-diazabicyclo[5.4.0]undec-7-ene (1.45 mL, 9.70 mmol) were added. The mixture was stirred for 5 h at which time the CH$_2$Cl$_2$ was removed in vacuo and the crude residue was partitioned between EtOAc and H$_2$O and extracted with EtOAc (3×10 mL). The combined organic layers were washed with brine (10 mL), passed over a short plug of Na$_2$SO$_4$, and concentrated in vacuo to give a yellow oil that was loaded directly onto a flash silica gel column and was quickly eluted with 10% EtOAc/hexanes. The solvents were removed in vacuo to give azide 2 (1.43 g, 84%) as a colorless oil. Rf (30% EtOAc/hexanes): 0.79.

1-Azidomethyl-3-ethoxy-benzene (2) (1.19 g 6.71 mmol) was dissolved in MeOH (15 mL) and palladium 10% on activated carbon, wet (20% in weight) was added. The reaction was hydrogenated for 30 min at 40 PSI in a Parr Hydrogenator. The black suspension was then filtered through compacted celite and the methanol was removed in vacuo to give amine 3 (0.88 g, 88%) as a pale yellow, thick oil, which was of sufficient quality to be advanced to the coupling reactions without further purification.

Method E: Representative Procedure for Conversion of Alcohols to Bromides.

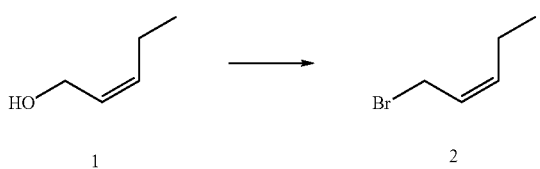

Cis-2-penten-1-ol (1) (1.00 g, 11.6 mmol) and carbon tetrabromide (3.85 g, 13.9 mmol) were dissolved in CH$_2$Cl$_2$ (75 mL). The mixture was cooled to 0° C. and triphenylphosphine (3.65 mL, 13.9 mmol) dissolved in CH$_2$Cl$_2$ (50 mL) was added dropwise. The mixture was allowed to warm to room temperature and was stirred overnight. The CH$_2$Cl$_2$ was removed in vacuo and the crude residue was loaded directly onto a flash silica gel column and eluted quickly with 20% EtOAc/hexanes. The solvents were removed in vacuo to give bromide 2 (1.53 g, 88%) as a colorless volatile oil. Rf (30% EtOAC/hexanes): 0.89.

Method F: Representative Procedure for Conversion of Bromides to Amines.

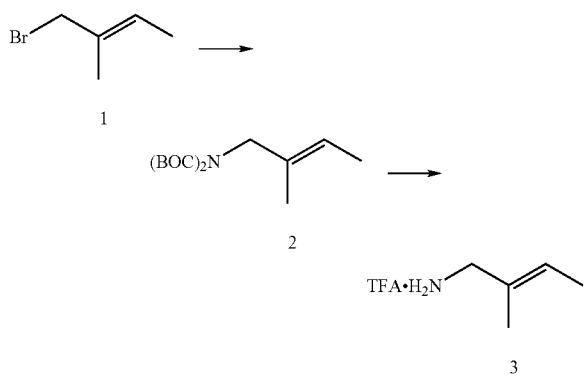

A mixture of bromide 1 (3.00 g, 20.1 mmol), di-tert-butyl-iminodicarboxylate (4.8 g, 22 mmol), and $K_2CO_3$ (3.10 g, 80.4 mmol) in DMF (30 ml) was stirred at ambient temperature overnight. The mixture was partitioned between 1N HCl and EtOAc. The organic layer was washed with $H_2O$ and brine, then dried over $NaSO_4$. Concentration in vacuo afford a yellow oil which upon purification by flash column chromatography (hexanes to 5% EtOAc/Hexane gradient) yielded protected amine 2 as a clear oil (2.0 g, 35%).

A mixture of the diBOC amine 2 (2.0 g, 7.0 mmol), trifluoroacetic acid (2.7 ml, 35 mmol) and $CH_2Cl_2$ (40 ml) was stirred at ambient temperature overnight. The reaction mixture was concentrated in vacuo to give the TFA salt of (E)-2-methyl-but-2-enylamine (3).

Method G: Representative Procedure for Reduction of Aromatic Nitro Groups by Hydrogenation.

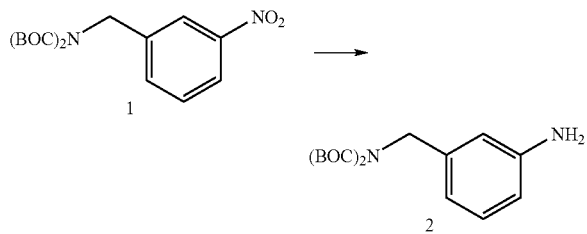

Compound 1 (2.04, 5.79 mmol) was dissolved in EtOAc (20 mL) and palladium 10% on activated carbon, wet (20% in weight) was added. The reaction was hydrogenated for 4 h at 45 PSI in a Parr Hydrogenator. The black suspension was then filtered through compacted celite and the methanol was removed in vacuo to give aniline 2 (1.65 g, 88%) as a pale yellow, thick oil, which was of sufficient quality to be advanced to the acetylation reaction without further purification.

Method H: Representative Procedure for Acetylation of Anilines.

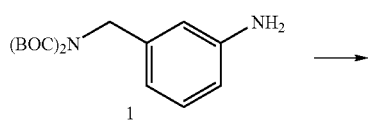

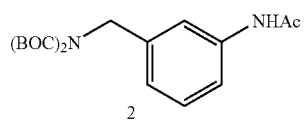

Aniline 1 (1.65 g, 5.12 mmol) was dissolved in $CH_2Cl_2$ (25 mL) at ambient temperature. Acetyl chloride (0.48 g, 6.14 mmol) and N,N-Diisopropylethylamine (0.79 g, 6.14 mmol) were added, and the reaction was stirred overnight. The $CH_2Cl_2$ was removed in vacuo and the crude residue was partitioned between EtOAc and 5% $KHSO_4$ and extracted with EtOAc (3×10 mL). The combined organic extracts were washed with $NaHCO_3$ (saturated aqueous, 10 mL), brine (10 mL), and dried over $Na_2SO_4$. The solvents were removed in vacuo to give an orange oil which was of sufficient quality to be advanced to the next step without further purification. Rf (50% EtOAC/hexanes): 0.42.

Method I: Representative Procedure for Reduction of Aldehydes to Amines.

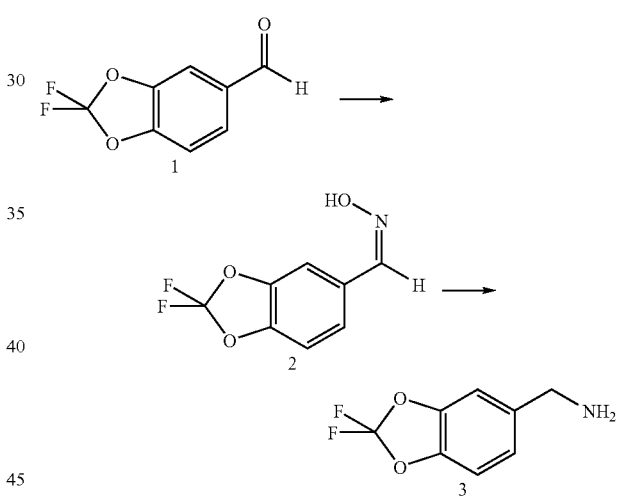

Hydroxyl amine hydrochloride (758 mg, 10.7 mmol) and pyridine (2.16 mL) was added to a solution of 2,2-difluoro-5-formyl benzodioxole (1) (2.00 g, 10.7 mmol) in MeOH (10 mL). After 18 hours the MeOH was removed in vacuo. The reaction mixture was diluted with EtOAc and was washed sequentially with $H_2O$, 10% w/v $CuSO_4$, and brine and then dried over $MgSO_4$. The solution was concentrated in vacuo. The hydroxy imine was purified by column chromatography using 20% EtOAc/Hexanes to give 1.37 g (64% yield) of a white solid. Imine was then subjected to LAH reduction as described above to provide amine 3.

Method J: Representative Procedure for the Hydroxylation of a Substituted Benzoic Acid

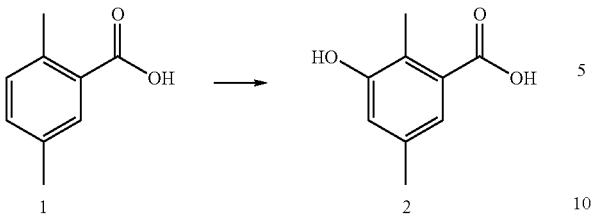

2,5-dimethyl-benzoic acid (1) (20 g, 133 mmol) was dissolved in concentrated $H_2SO_4$ (30 mL) and fuming $H_2SO_4$ (20% $SO_3$, 70 mL). The reaction mixture was heated to 110° C. for 2 hours. After cooling, the solution was poured carefully into a beaker of ice $H_2O$ (400 mL) and was then neutralized with 20% aqueous NaOH (400 mL). The $H_2O$ was partially removed in vacuo until a white salt mixture started to form. The solid was collected on a sintered-glass funnel and was then dried in a vacuum oven. The dried salt mixture was placed in a ceramic crucible with KOH (160 g) and was melted together using a butane torch for 0.5 h. After cooling, the fused solid was dissolved in $H_2O$ (300 mL) and acidified with concentrated HCl (300 mL). The product was extracted from the aqueous solution with EtOAc (3×200 mL). The combined organic layers were washed with brine (100 mL) and dried over $MgSO_4$. The solvents were removed in vacuo and the solid residue was recrystallized with 20% EtOAc/$CHCl_3$ four times to afford 3-hydroxy-2,5-dimethyl-benzoic acid (2) as a light brown solid (9.8 g, 44%)

$^1$H NMR (Acetone-$d_6$) δ 10.93 (br s, 1H), 8.34 (br s, 1H), 7.20 (s, 1H), 6.86 (s, 1H), 2.37 (s, 3H), 2.24 (s, 3H).

REFERENCES

Fujiwara, A. N.; Acton, E. M. *Can. J. Chem.* 1970, 48, 1346–1349.

Charlesworth, E. H.; Levene, L. *Can. J. Chem.* 1963, 41, 1071–1077.

The following amines were synthesized for the corresponding example numbers:

EXAMPLE A35 AND EXAMPLE A36

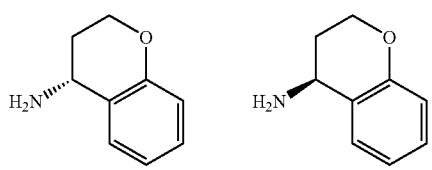

Amines were generated from reducing the corresponding ketone as described in method A above followed by conversion to the azide and reduction as described in method D above. The mixture of isomers was coupled to the chiral thiazolidine core and separated.

EXAMPLE A37 AND EXAMPLE A38

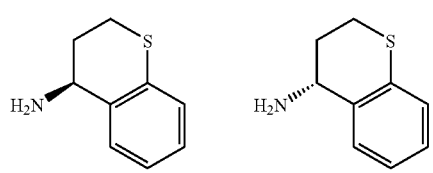

Amines were generated as described for Examples A35 and A36, separating the diastereomers at the thiazolidine stage.

EXAMPLE A84 AND EXAMPLE A85

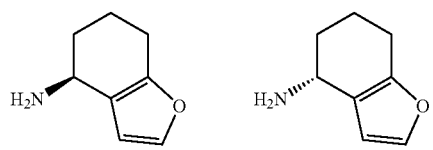

Amines were generated as described for Examples A35 and A36, separating the diastereomers at the thiazolidine stage.

EXAMPLE A86 AND EXAMPLE A87

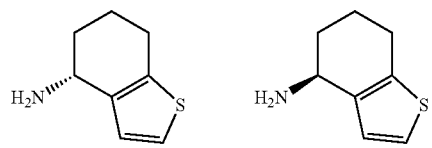

Amines were generated as described for Example A35 and A36, separating the diastereomers at the thiazolidine stage.

EXAMPLE A43

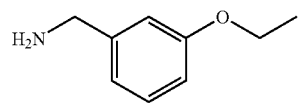

Amine was generated by alkylation of 3-hydroxybenzyl alcohol with ethyl bromide as describe in method C above followed by conversion of the alcohol to the amine as described in method D above provided desired amine.

EXAMPLE A44

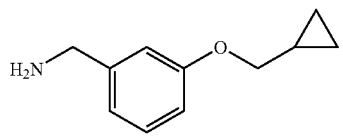

Amine was generated as described above for Example A43 using the cyclopropyl alkylating agent.

EXAMPLE A93

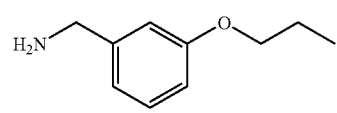

Amine was generated as described above for Example A43 using propylbromide as the alkylating agent.

EXAMPLE A67

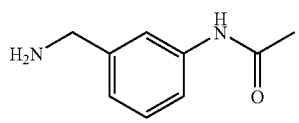

Amine was generated from displacement of bromide in 3-nitrobenzylbromide with di BOC amine as described in method F above. Reduction of the nitro moiety to the aniline (method G above) followed by acetylation (method H above) and BOC removal (method F above) provided desired amine.

EXAMPLE A72, EXAMPLE A73 AND EXAMPLE A80

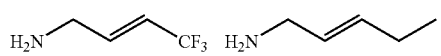

Amines were generated from conversion of the corresponding primary alcohols as described in method E above. Displacement of the bromide with di BOC amine and deprotection with TFA (method F above) provided the desired amines.

EXAMPLE A77

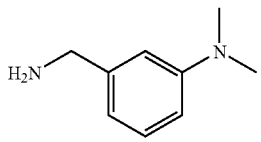

Amine was generated from 3-dimethylaminobenzyl alcohol as described in method D above.

EXAMPLE A48

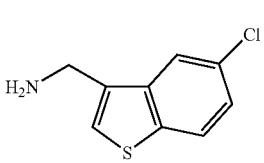

Amine was generated by bromination of the corresponding methyl compound (Nussbaumer, P., et. al. *J. Med Chem.*, 1991, 34, 65–73.). Conversion of the bromide to the amine was accomplished by azide displacement of the bromide followed by reduction as described in method D above.

EXAMPLE A69

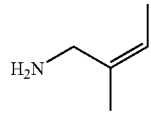

Amine was generated by reduction of the corresponding methyl ester to the primary alcohol (Wipf, *J. Org. Chem.* 1994, 59, 4875–86.). Conversion to the bromide (method E above) followed by displacement with diBOC amine and deprotection (method F above) provided desired amine.

EXAMPLE A70 AND EXAMPLE A71

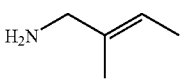

Amines were generated from the corresponding carboxylic acids. Reduction of the acid as described in method B above followed by bromide displacement as described in method E above gave the primary bromide. Conversion of the bromide to the primary amine followed the procedure described in method F above.

EXAMPLE A74

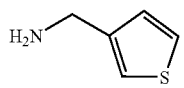

Amine was generated from the primary alcohol as described in method D above.

EXAMPLE A76

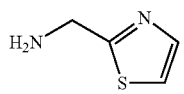

Amine was generated by first reduction of the corresponding aldehyde with sodium borohydride to the primary alcohol (Dondoni, *J. Org. Chem.* 1995, 60, 4749–54.). The alcohol was then converted to the amine as described in method D above.

EXAMPLE A82 AND EXAMPLE A83

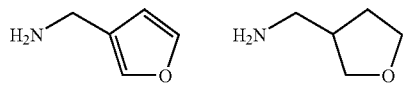

Amines were generated by conversion of the primary alcohol as described in method D above. Tetrahydrofuran amine (Example A83) was the byproduct of over-reduction of A82.

EXAMPLE A91

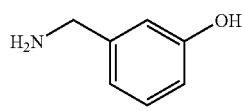

Amine was generated from the corresponding carboxylic acid. Reduction of the acid as described in method B above gave the primary alcohol. The alcohol was then converted to the amine using the procedure described in method D above.

EXAMPLE A92

Amine was generated from 3-benzyloxybenzyl alcohol. Conversion to the azide and reduction of both the azide and benzyl protecting group were accomplished using method D as described above with longer hydrogenation time.

EXAMPLE A94

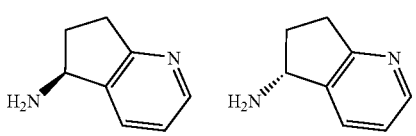

Amine was generated by LiAlH$_4$ reduction of 2-cyanophenol (Ludeman, S. M., et. al. *J. Med. Chem.* 1975, 18, 1252–3.).

EXAMPLE A88 AND EXAMPLE A89

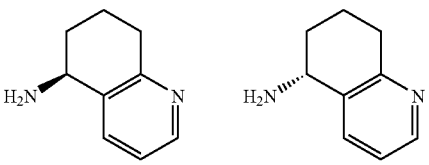

Amines were generated from the corresponding achiral ketone prepared by the method of Haunz (Huanz, et. al. *Synth. Commun.* 1998, 28, 1197–1200.). The ketone was reduced to the alcohol as a mixture of isomers using method A as described above. The mixture was converted to a mixture of amines by the procedure described in method D above. The amines were coupled to the thiazolidine core as a mixture and were then separated to provide Examples A88 and A89.

EXAMPLE A78 AND EXAMPLE A79

Amines were generated from the corresponding achiral ketone prepared by the method of Bell (Bell, et. al. *J. Med. Chem.* 1998, 41, 2146–63.). The ketone was reduced to the alcohol as a mixture of isomers using method A as described above. The mixture was converted to a mixture of amines by the procedure described in method D above. The amines were coupled to the thiazolidine core as a mixture and were then separated to provide Examples A78 and A79.

EXAMPLE A81

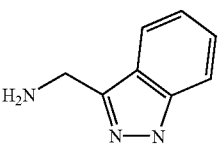

Amine was generated from the corresponding carboxylic acid. Reduction of the acid using the procedure described in method A above provided the primary alcohol which was converted to the bromide using the method of Onda (Onda, M. et. al. *Chem. Pharm. Bull.* 1971, 10, 2013–19.). The bromide was then converted to the amine using the procedure described in method F above.

EXAMPLE A110

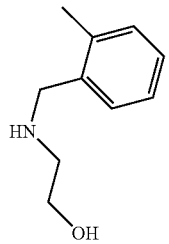

Amine was generated from the condensation of o-tolualdehyde with 2-aminoethanol followed by reduction with sodium borohydride (*Tetrahedron Assym.* 1997, 8, 2367–74.).

EXAMPLE A103

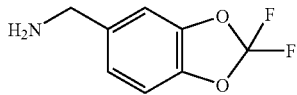

Amine was generated from the corresponding aldehyde by the reductive amination procedure described in method I above.

EXAMPLE A105

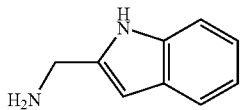

Amine was generated by reduction of the corresponding methyl ester to the primary alcohol (Wipf, *J. Org. Chem.* 1994, 59, 4875–86.). The alcohol was converted to the amine by the procedure described in method D above.

EXAMPLE A107

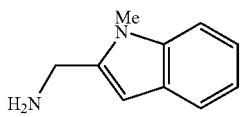

Amine was generated from reduction of the corresponding carboxylic acid to the primary alcohol as described in method A above. The alcohol was converted to the amine using the procedure described in method D above.

EXAMPLE A106 AND EXAMPLE A97

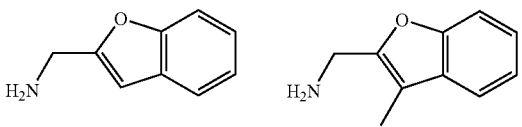

Amines were generated by the borane reduction of the corresponding carboxylic acids to the primary alcohols. The alcohols were converted to the amines using the procedure described in method D above.

EXAMPLE A46

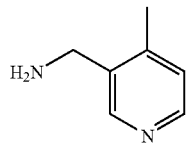

Amine was generated by the condensation of ethylacetoacetate with cyanoacetamide followed by reaction with phosphorus oxychloride to provide 3-cyano-2,5-dihydroxy-4-methylpyridine. Hydrogenation with palladium dichloride gave the 3-cyano-4-methylpyridine which was hydrogenated with Raney nickel in ammonia and ethanol to afford the desired amine (*J. Org. Chem.* 1959, 25, 560.).

EXAMPLE A10

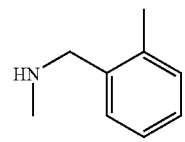

Amine was generated by a reductive amination with the corresponding aldehyde (*Arch. Pharm.* 1987, 320, 647–54.).

EXAMPLE A109

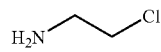

Amine was generated on the thiazolidine core as follows:

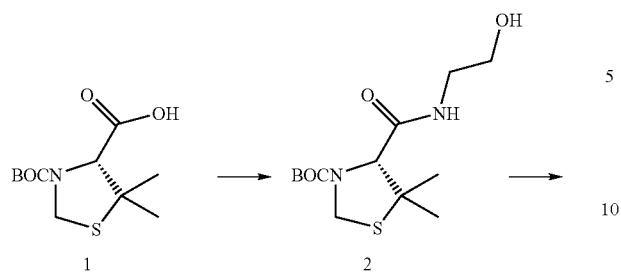

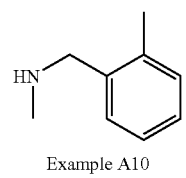

Example A10

EXAMPLE A10

The above amine was prepared according to Weinheim, G. *Arch. Pharm.* 1987, 320, 647–654.

General Method A

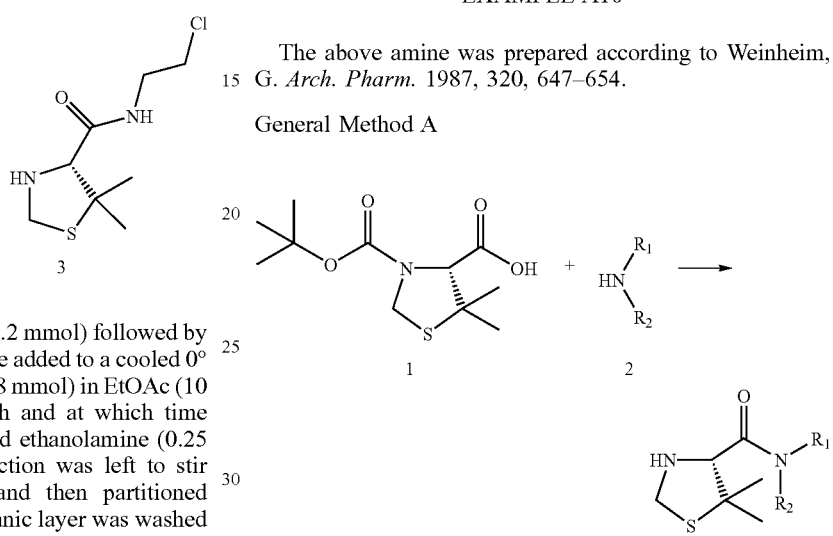

Diphenylchlorophosphate (1.0 ml, 4.2 mmol) followed by triethylamine (0.59 ml, 4.2 mmol) were added to a cooled 0° C. solution of BOC-DMTA 1 (1.0 g, 3.8 mmol) in EtOAc (10 ml). The mixture was stirred for 1 h and at which time triethylamine (0.59 ml, 4.2 mmol) and ethanolamine (0.25 ml, 4.2 mmol) were added. The reaction was left to stir overnight at ambient temperature and then partitioned between 1N HCl and EtOAc. The organic layer was washed with NaHCO$_3$(saturated aqueous) and brine. The organic layer was dried over Na$_2$SO$_4$ and concentrated in vacuo to a pale yellow oil 2. The oil was stirred with thionyl chloride (2 ml) for 45 min at room temperature. The mixture was concentrated in vacuo and the residual oil was partitioned between 1N NaOH and EtOAc. The organic layer was extracted with 1N HCl (2×20 ml). The combined aqueous layers were made basic with 1N NaOH and then extracted with EtOAc (3×60 ml). The organic layers were washed with brine, dried over Na$_2$SO$_4$ and concentrated in vacuo to give (R)-5,5-Dimethyl-thiazolidine-4-carboxylic acid (2-chloro-ethyl)-amide 3 as a clear oil (0.39 g, 55%).

The following amines were prepared as described:

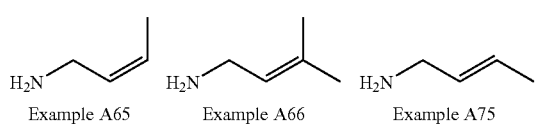

Example A65  Example A66  Example A75

The above amines were prepared according to Carlsen, H. J., *J. Heterocycle Chem.* 1997, 34, 797–806.

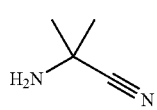

EXAMPLE A90

The above amine was prepared according to O'Brien, P. M., *J. Med. Chem.* 1994, 37, 1810–1822.

The synthesis of compounds with the general structure 5 is as follows. The boc-protected thiazolidine carboxylic acid 1 is coupled to the requisite amines 2 to yield amino amides 3 using a two step process. The process includes treatment of 1 with 2 in the presence of either diphenylchlophosphate or HATU, followed by exposure to methane sulfonic acid. Final compounds 5 are obtained by a DCC-mediated coupling of 3 and 4 followed by deprotection of the P2 phenol. Final compounds were purified either by flash chromatography or preparative HPLC.

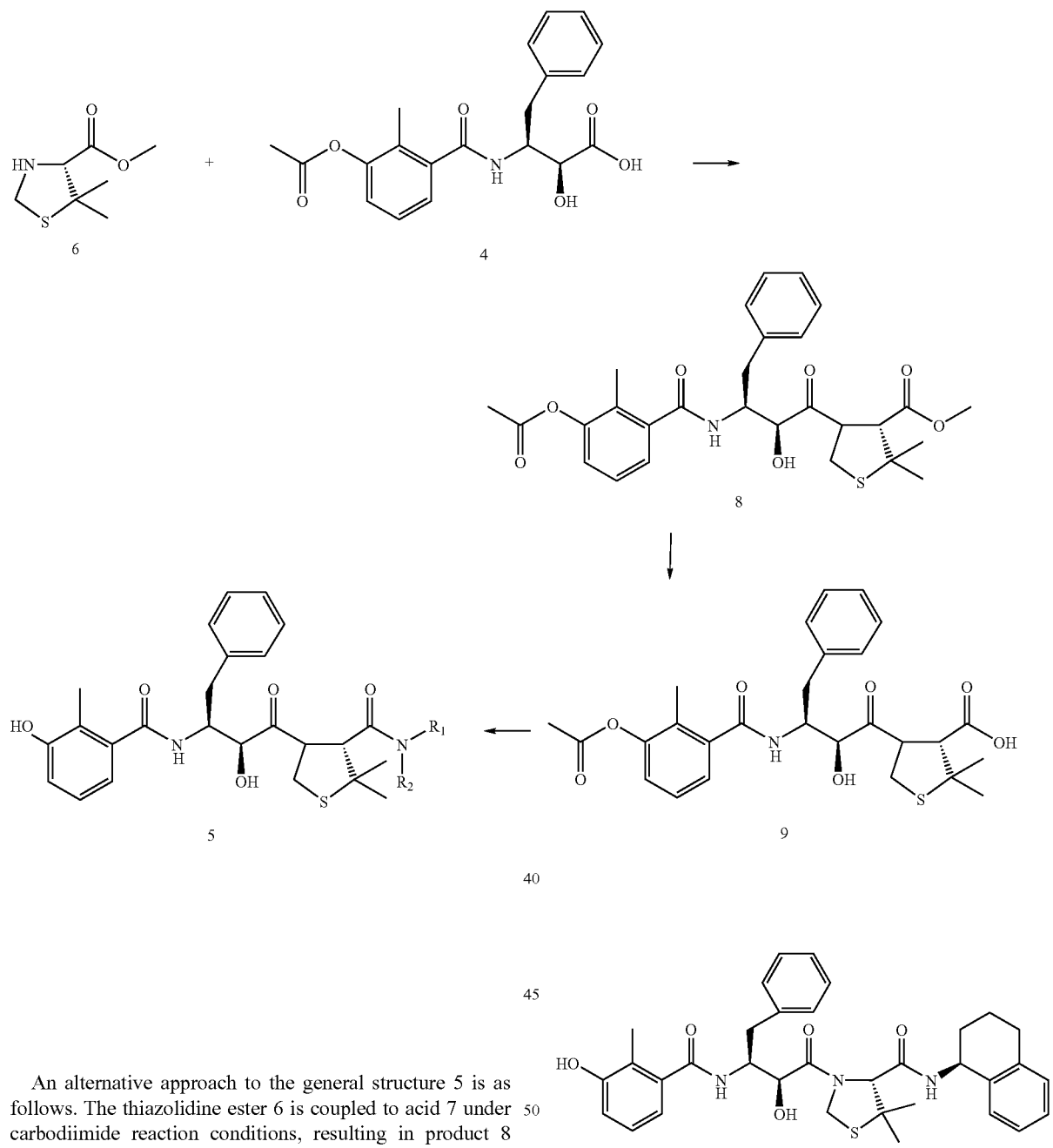

An alternative approach to the general structure 5 is as follows. The thiazolidine ester 6 is coupled to acid 7 under carbodiimide reaction conditions, resulting in product 8 which is converted to acid 9 by mild base hydrolysis. Acid 9 is combined with various amines, using diphenylphosphoryl azide, followed by cleavage of the P2 acetate to yield final compounds 5. The products were purified by either flash chromatography or preparative HPLC.

Specific Method A.

EXAMPLE A1

3-[2-Hydroxy-3-(3-hydroxy-2-methyl-benzoylamino)-4-phenyl-butyryl]-5,5-dimethyl-thiazolidine-4-carboxylic acid (1,2,3,4-tetrahydro-naphthalen-1-yl)-amide The title compound was prepared as follows. (R)-5,5-Dimethyl-thiazolidine-3,4-dicarboxylic acid 3-tert-butyl ester 1 (0.3 g, 1.15 mmol) was dissolved in EtOAc (3 mL) and cooled to 0° C. Diphenyl chlorophosphate (0.26 mL, 1.26 mmol) was added followed by TEA (0.18 mL, 1.26 mmol). The reaction was stirred at 0° C. for 1 h, and treated with (S)-1,2,3,4-Tetrahydro-1-naphthylamine (0.19 g, 1.26 mmol). The reaction mixture was stirred at room temperature overnight, then partitioned between 1N HCl (5 mL) and EtOAc (10 mL). The organic layer was washed with saturated NaHCO$_3$, brine, dried over Na$_2$SO$_4$ and concentrated to a light yellow oil. The resulting crude oil was dissolved in EtOAc (5 mL) and the cooled to 0° C. Methanesulfonic acid (0.36 mL, 5.32 mmol) was added and the solution was stirred at 0° C. for 15 minutes, then at room temperature for 1 h. The mixture was re-cooled to 0° C. and quenched with 5% Na₂CO₃ (5 mL) then extracted with EtOAc (10 mL). The organic layer was washed with brine, dried over Na₂SO₄ and concentrated in vacuo to give 3 as a yellow oil. The yellow oil 3 (0.34 g, 1.15 mmol) was dissolved in EtOAc (12 mL). AMB-AHPBA 4 (0.40 g, 1.09 mmol) was added followed by HOBt (0.15 g, 1.09 mmol). The mixture was stirred at room temperature 1 h, then cooled to 0° C. DCC (0.24 g, 1.15 mmol) was slowly added as solution in EtOAc (6 mL). The mixture was warmed to room temperature and stirred overnight. The mixture was filtered and the filtrate was washed with 1N HCl (10 mL), saturated NaHCO₃ (10 mL), brine (10 mL), dried over Na₂SO₄ and concentrated to give a crude white solid (contaminated with DCU). The DCU was removed by flash chromatography (30% to 50% EtOAc in hexanes) to provide a white solid, which was dissolved in MeOH (2 mL) and treated with 4N HCl in 1,4-dioxane (0.26 mL, 1.1 mmol). The reaction was stirred at room temperature overnight then partitioned between 1N HCl (10 mL) and EtOAc (10 mL). The organic layer was washed with saturated NaHCO₃, dried over Na₂SO₄ and concentrated to a residue which was purified by flash chromatography (60% EtOAc in hexanes) to provide the title compound as a white solid: mp=125–126° C.; IR (cm⁻¹) 3320, 2932, 1704, 1644, 1530, 1454, 1361, 1284; ¹H NMR (DMSO-d₆) δ 9.36 (s, 1H), 8.28 (d, J=8.6, 1H), 8.21 (d, J=8.8, 1H), 7.35–6.91 (m, 10H), 6.76 (d, J=8.0, 1H), 6.54 (d, J=7.5, 1H), 5.34 (d, J=6.0, 1H), 5.13 (d, J=9.0, 1H), 5.02 (d, J=9.0, 1H), 4.60–4.30 (m, 4H), 2.81–2.68 (m, 4H), 1.81 (s, 3H), 1.78–1.60 (m, 4H), 1.48 (s, 3H), 1.45 (s, 3H); Anal. Calcd for C₃₄H₃₉N₃O₅S.1.5H₂O: C, 64.95; H, 6.73; N, 6.68. Found: C, 64.88; H, 6.31; N, 6.18.

EXAMPLE A2

(R)-3-((2S,3R)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-methoxy-benzylamide

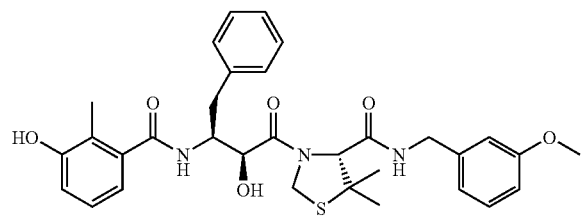

White solid: mp 108–110° C.; IR (neat, cm⁻¹) 3310, 2965, 1644, 1586, 1531, 1455, 1359, 1284; ¹H NMR (DMSO-d₆) δ 9.37 (s, 1H), 8.40 (t, J=6.0, 1H), 8.09 (d, J=8.1, 1H), 7.31–6.52 (m, 12H), 5.49 (d, J=6.0, 1H), 5.12 (d, J=9.3, 1H), 5.00 (d, J=9.3, 1H), 4.44–4.35 (m, 3H), 4.42 (s, 1H), 4.09 (dd, J=15.0, 6.0, 1H), 3.69 (s, 3H), 2.87–2.67 (m, 2H), 1.82 (s, 3H), 1.49 (s, 3H), 1.34 (s, 3H); Anal. Calcd for C₃₂H₃₇N₃O₆S.0.75H₂O: C, 63.50; H, 6.41; N, 6.94. Found: C, 63.60; H, 6.23; N, 6.80.

The following examples were prepared by the specific method outlined above using the requisite amine 2.

EXAMPLE A3

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (pyridin-2-ylmethyl)-amide

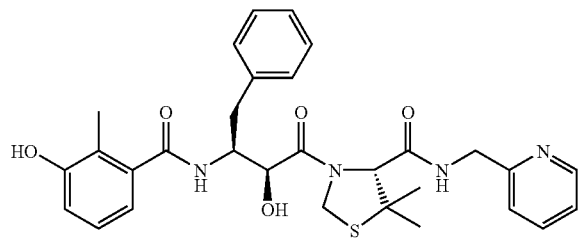

IR (neat cm⁻¹) 3315, 1642, 1529, 1437, 1372, 1284; ¹H NMR (DMSO-d₆) δ 9.38 (s, 1H), 8.59 (t, J=5.0, 1H), 8.45 (d, J=4.0, 1H), 8.15 (d, J=8.2, 1H), 7.65 (td, J=7.5, 1.8, 1H), 7.39 (d, J=7.9, 1H), 7.29–7.11 (m, 7H), 6.93 (t, J=7.7, 1H), 6.77 (d, J=8.1, 1H), 6.54 (d, J=7.0, 1H), 5.51 (d, J=6.6, 1H), 5.15 (d, J=9.2, 1H), 5.03 (d, J=9.2, 1H), 4.50–4.26 (m, 5H), 2.87–2.68 (m, 2H), 1.82 (s, 3H), 1.52 (s, 3H), 1.35 (s, 3H); HRMS (ESI) m/z calcd for C₃₀H₃₄N₄O₅SNa (M+Na)⁺ 585.2148, found 585.2141.

EXAMPLE A4

3-[2-Hydroxy-3-(3-hydroxy-2-methyl-benzoylamino)-4-phenyl-butyryl]-5,5-dimethyl-thiazolidine-4-carboxylic acid (1,2,3,4-tetrahydro-naphthalen-1-yl)-amide

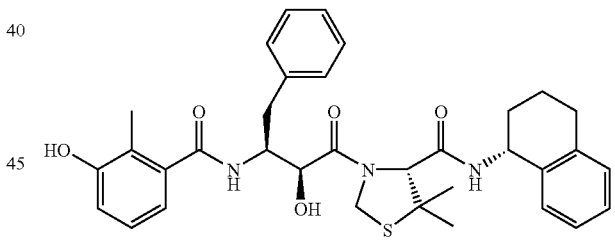

White solid: mp=123–125° C.; IR (cm⁻¹) 3314, 2932, 1704, 1644, 1584, 1530, 1454, 1360, 1284; ¹H NMR (DMSO-d₆) δ 9.36 (s, 1H), 8.42 (d, J=8.6, 1H), 8.23 (d, J=8.0, 1H), 7.38–6.90 (m, 10H), 6.77 (d, J=8.0, 1H), 6.45 (d, J=6.0, 1H), 5.45 (d, J=6.0, 1H,), 5.02 (d, J=9.0, 1H), 4.99 (d, J=9.0, 1H), 5.11–4.40 (m, 4H), 2.90–2.69 (m, 4H), 1.81 (s, 3H), 1.77–1.58 (m, 4H), 1.49 (s, 3H), 1.42 (s, 3H); Anal. Calcd for C₃₄H₃₉N₃O₅S.1.25H₂O: C, 65.42; H, 6.70; N, 6.73. Found: C, 65.41; H, 6.46; N, 6.60.

EXAMPLE A5

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (pyridin-3-ylmethyl)-amide

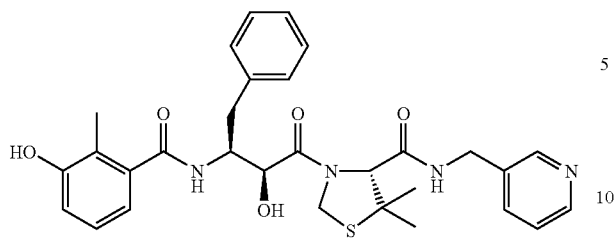

IR (neat cm$^{-1}$) 3310, 2931, 1642, 1537, 1455, 1373, 1279; $^1$H NMR (DMSO-d$_6$) δ 9.39 (s, 1H), 8.55–8.50 (m, 2H), 8.38 (s, 1H), 8.15 (d, J=8.2, 1H), 7.68 (d, J=8.1, 1H), 7.30–7.14 (m, 6H), 6.94 (t, J=7.5, 1H), 6.77 (d, J=8.1, 1H), 6.54 (d, J=7.7, 1H), 5.51 (d, J=6.6, 1H), 5.14 (d, J=9.2, 1H), 5.03 (d, J=9.2, 1H), 4.49–4.41 (m, 4H), 4.18 (dd, J=15.4, 5.5, 1H), 2.85–2.67 (m, 2H), 1.81 (s, 3H), 1.49 (s, 3H), 1.31 (s, 3H); HRMS (ESI) m/z calcd for C$_{30}$H$_{35}$N$_4$O$_5$S (M+H)$^+$ 563.2323, found 563.2337.

EXAMPLE A6

3-[2-Hydroxy-3-(3-hydroxy-2-methyl-benzoylamino)-4-phenyl-butyryl]-5,5-dimethyl-thiiazolidine-4-carboxylic acid methyl-(3-methyl-thiophen-2-ylmethyl)-amide

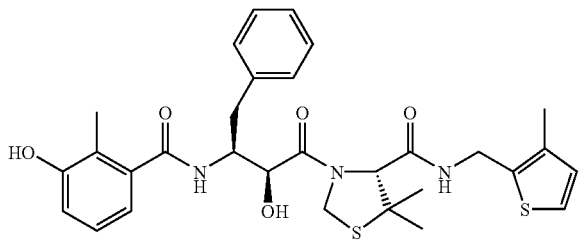

IR (neat or KBr cm$^{-1}$) 3150, 3000, 2942, 2187, 1712, 1600, 1567, 1505; $^1$H NMR (DMSO-d$_6$) δ 9.36 (s, 1H), 8.44 (t, J=7.98, 1H), 8.13–8.07 (m, 2H), 7.34–7.13 (m, 5H), 6.93 (t, J=7.9, 1H), 6.78 (d, J=7.7, 1H), 6.53 (d, J=7.1, 1H), 5.45 (d, J=7.0, 1H), 5.12 (dd, J=7.8, 8.2 1H), 4.51–4.31 (m, 4H), 2.86–2.67 (m, 2H), 2.19 (s, 3H), 1.81 (s, 3H), 1.51 (s, 3H), 1.34 (s, 3H); Anal. Calcd for C$_{30}$H$_{35}$N$_3$O$_5$S$_2$: calculated C, 61.94; H, 6.06; N, 7.22. Found C, 62.38; H, 6.23; N, 7.17.

EXAMPLE A7

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (benzo[b]thiophen-3-ylmethyl)-amide

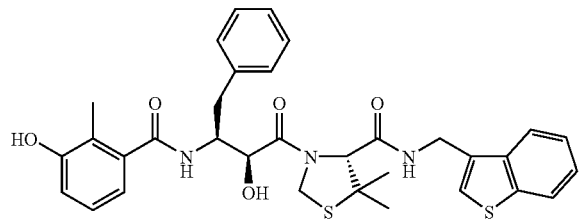

IR (neat cm$^{-1}$) 3401, 2931, 1637, 1531, 1455, 1367, 1284, 1108; $^1$H NMR (DMSO-d$_6$) δ 9.39 (s, 1H), 8.52 (t, J=5.7, 1H), 8.17 (d, J=8.2, 1H), 7.93 (d, J=6.4, 1H), 7.86 (d, J=6.9, 1H), 7.57 (s, 1H), 7.35–7.11 (m, 7H), 6.94 (t, J=7.9, 1H), 6.78 (d, J=7.9, 1H), 6.56 (d, J=7.5, 1H), 5.47 (d, J=5.0, 1H), 5.16 (d, J=9.2, 1H), 5.02 (d, J=9.2, 1H), 4.67 (dd, J=15.2, 5.9, 1H), 4.47–4.34 (m, 4H), 2.89–2.70 (m, 2H), 1.83 (s, 3H), 1.49 (s, 3H), 1.34 (s, 3H); HRMS (ESI) m/z calcd for C$_{33}$H$_{35}$N$_3$O$_5$S$_2$Na (M+Na)$^+$ 640.1910, found 640.1919; Anal. Calcd for C$_{33}$H$_{35}$N$_3$O$_5$S$_2$·H$_2$O: C, 62.34; H, 5.87; N, 6.61. Found: C, 62.93; H, 5.80; N, 6.57.

EXAMPLE A8

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (pyridin-4-ylmethyl)-amide

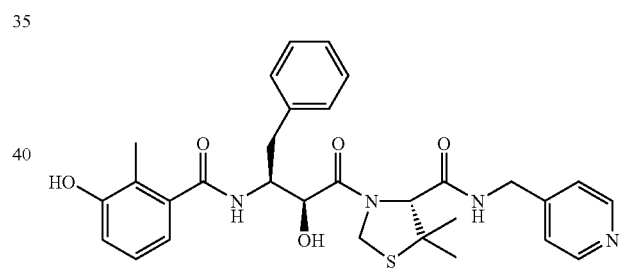

$^1$H NMR (DMSO-d$_6$) δ 9.38 (s, 1H), 8.55 (t, J=6.2, 1H), 8.42 (m, 1H), 8.13 (d, J=8.2, 1H), 7.30–7.19 (m, 7H), 6.94 (t, J=7.7, 1H), 6.77 (d, J=7.7, 1H), 6.54 (d, J=7.1, 1H), 5.54 (d, J=6.8, 1H), 5.15 (d, J=9.1, 1H), 5.02 (d, J=9.1, 1H), 4.48–4.13 (m, 5H), 2.87–2.68 (m, 2H), 1.81 (s, 3H), 1.52 (s, 3H), 1.35 (s, 3H); HRMS (ESI) m/z calcd for C$_{30}$H$_{34}$N$_4$O$_5$SNa (M+Na)$^+$ 585.2142, found 585.2153.

EXAMPLE A9

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2,3-dihydro-benzofuran-5-ylmethyl)-amide

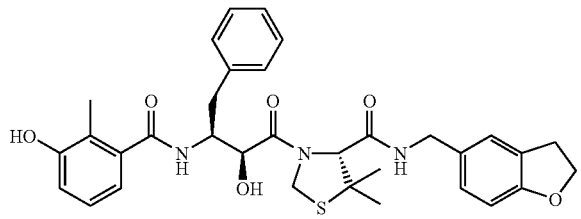

IR (neat, cm$^{-1}$) 3330, 2919, 1643, 1490, 1443, 11367, 1284; $^1$H NMR (DMSO-d$_6$) δ 9.37 (s, 1H), 8.35 (m, 1H), 8.12 (d, J=7.9, 1H), 7.32–7.09 (m, 6H), 6.99–6.91 (m, 2H), 6.77 (d, J=8.1, 1H), 6.68–6.53 (m, 2H), 5.45 (d, J=6.2, 1H), 5.12 (d, J=8.8, 1H), 5.00 (d, J=8.9, 1H), 4.50–4.39 (m, 6H), 4.29 (dd, J=14.5, 6.2, 1H), 4.14–4.04 (m, 2H), 3.15–2.99 (m, 2H), 1.81 (s, 3H), 1.48 (s, 3H), 1.33 (s, 3H); HRMS (ESI) m/z calcd for C$_{33}$H$_{37}$N$_3$O$_6$SNa (M+Na)$^+$ 626.2295, found 626.2283.

EXAMPLE A10

3-[2-Hydroxy-3-(3-hydroxy-2-methyl-benzoylamino)-4-phenyl-butyryl]-5,5-dimethyl-thiazolidine-4-carboxylic acid (3-methyl-pyridin-4-ylmethyl)-amide

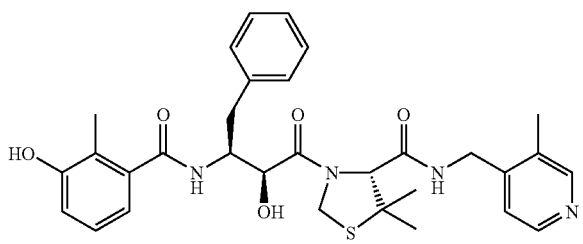

$^1$H NMR (DMSO-d$_6$) δ 9.34 (s, 1H), 8.47 (t, J=6.0, 1H), 8.29 (m, 2H), 8.11 (d, J=8.3, 1H), 7.32–7.14 (m, 6H), 6.94 (t, J=7.7, 1H), 6.78 (dd, J=7.7, 1.0, 1H), 6.55 (dd, J=7.7, 1.0, 1H), 5.49 (d, J=6.7, 1H), 5.16 (d, J=9.1, 1H), 5.03 (d, J=9.1, 1H), 4.51–4.38 (m, 3H), 4.49 (s, 1H), 4.13 (dd, J=16.4, 5.1, 1H), 2.88–2.69 (m, 2H), 2.25 (s, 3H), 1.83 (s, 3H), 1.53 (s, 3H), 1.37 (s, 3H); HRMS (ESI) m/z calcd for C$_{31}$H$_{37}$N$_4$O$_5$S (M+H)$^+$ 577.2485, found 577.2463; Anal. Calcd for C$_{31}$H$_{36}$N$_4$O$_5$S·0.3H$_2$O: C, 63.96; H, 6.34; N, 9.63; S, 5.51. Found: C, 63.95; H, 6.42; N, 9.51; S, 5.22.

EXAMPLE A11

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (naphthalen-1-ylmethyl)-amide

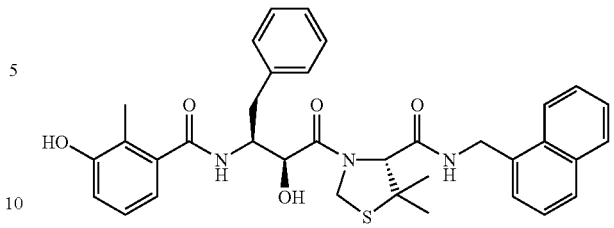

IR (neat, cm$^{-1}$) 3425, 1643, 1531, 1455, 1378, 1290, 1108; $^1$H NMR (DMSO-d$_6$) δ 9.39 (s, 1H), 8.50 (t, J=5.9, 1H), 8.15 (d, J=8.0, 2H), 8.07 (d, J=9.0, 1H), 7.90 (d, J=7.1, 1H), 7.81 (d, J=8.1, 1H), 7.54–7.12 (m, 9H), 6.95 (d, J=7.0, 1H), 6.78 (d, J=8.1, 1H), 6.56 (d, J=7.0, 1H), 5.15 (d, J=9.2, 1H), 5.01 (d, J=9.2, 1H), 4.95–4.86 (m, 1H), 4.76–4.48 (m, 4H), 2.90–2.71 (m, 2H), 1.84 (s, 3H), 1.47 (s, 3H), 1.34 (s, 3H); HRMS (ESI) m/z calcd for C$_{35}$H$_{37}$N$_3$O$_5$SNa (M+Na)$^+$ 634.2346, found 634.2332.

EXAMPLE A12

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid [(R)-1-(tetrahydro-furan-2-yl)methyl]-amide

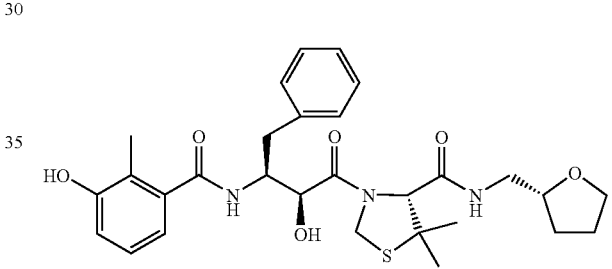

White solid: mp=105–107° C.; IR (cm$^{-1}$) 3339, 1644, 1537, 1454, 1372, 1285, 1079; $^1$H NMR (DMSO-d$_6$) δ 9.37 (s, 1H), 8.12 (d, J=8.8, 1H), 8.01 (t, J=5.0, 1H), 7.34–7.15 (m, 5H), 6.93 (t, J=7.5, 1H), 6.76 (d, J=7.5, 1H), 6.53 (d, J=7.5, 1H), 5.45 (d, J=5.5, 1H), 5.07 (d, J=9.3, 1H), 4.99 (d, J=9.3, 1H), 4.50–4.10 (m, 3H), 3.83–3.55 (m, 5H), 3.20–3.00 (m, 2H); 2.90–2.60 (m, 2H), 1.90–1.70 (m, 2H), 1.79 (s, 3H), 1.48 (s, 3H), 1.34 (s, 3H); Anal. Calcd for C$_{29}$H$_{37}$N$_3$O$_6$S·0.5H$_2$O: C, 61.68; H, 6.78; N, 7.44. Found: C, 61.46; H, 6.74; N, 7.47.

EXAMPLE A13

3-[2-Hydroxy-3-(3-hydroxy-2-methyl-benzoylamino)-4-phenyl-butyryl]-5,5-dimethyl-thiiazolidine-4-carboxylic acid cyclohexylmethyl-amide

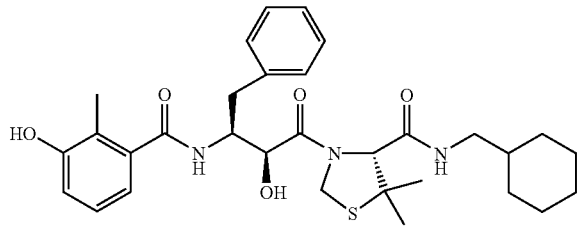

IR (neat or KBr cm⁻¹) 3743, 2924, 2360, 1868, 1844, 1771, 1699, 1646; ¹H NMR (DMSO-d$_6$) δ 9.36 (s, 1H), 8.13 (d, J=7.9 1H), 7.85 (t, J=7.2, 1H), 7.34–7.13 (m, 5H), 6.93 (t, J=7.9, 1H), 6.78 (d, J=7.7, 1H), 6.53 (d, J=7.1, 1H), 5.15 (d, J=7.0, 1H), 5.08 (d, J=7.8, 1H), 4.81 (s, 1H), 4.51 (d, J=6.2 1H), 4.46(s, 1H), 4.38 (d, J=6.32, 1H), 4.31 (s, 6H) 2.86–2.67 (m, 4H), 2.55 (s, 1H), 1.81 (s, 3H), 1.64–1.54 (m, 6H), 1.51 (s, 3H), 1.39 (s, 3H), 1.18–1.08 (m, 4H), 0.99–0.78 (m, 3H); Anal. Calcd for C$_{32}$H$_{47}$N$_3$O$_6$S.0.3TFA.0.75H$_2$O: C, 61.67; H, 7.01; N, 6.83. Found: C, 61.78; H, 6.66; N, 6.63.

EXAMPLE A14

3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (benzo[1,3]dioxol-5-ylmethyl)-amide

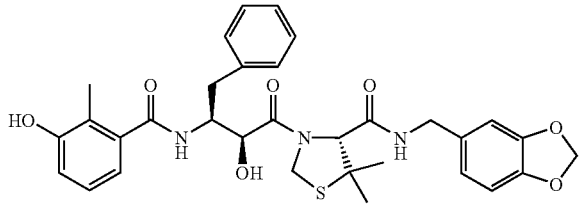

IR (neat or KBr cm⁻¹) 3302, 2922, 2351, 2333, 1768, 1750, 1646, 1537; ¹H NMR (DMSO-d$_6$) δ 9.36 (s, 1H), 8.44 (s, 1H), 8.13 (d, J=7.9 1H), 7.34–7.13 (m, 5H), 6.99–6.77 (m, 4H), 6.78 (d, J=7.7, 1H), 5.93 (d, J=7.1, 2H), 5.15 (d, J=7.0, 1H), 5.08 (d, J=7.8, 1H), 4.43 (d, J=9.32, 2H), 4.34 (m, 2H), 4.12 (d, J=6.18, 1H), 4.08 (d, J=6.08, 1H), 2.86–2.67 (m, 2H), 2.55 (s, 1H), 1.81 (s, 3H), 1.51 (s, 3H), 1.39 (s, 3H); Anal. Calcd C$_{32}$H$_{35}$N$_3$O$_7$S.0.65TFA.1.0H$_2$O: C, 57.31; H, 5.44; N, 6.02. Found: C, 57.58; H, 5.47; N, 5.85.

EXAMPLE A15

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (furan-2-ylmethyl)-amide

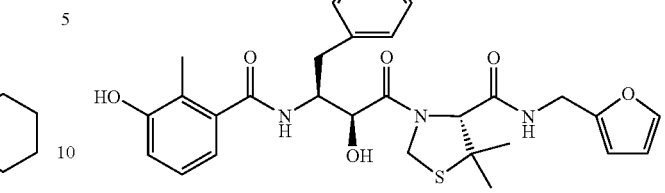

IR (neat or KBr cm⁻¹) 3311, 2931, 2360, 2333, 1732, 1718, 1695, 1646; ¹H NMR (DMSO-d$_6$) δ 9.36 (s, 1H), 8.44 (t, J=6.98, 1H), 8.13 (d, J=7.9 1H), 7.53 (s, 1H), 7.34–7.13 (m, 5H), 6.95 (t, J=7.8, 1H), 6.78 (d, J=7.7, 1H), 6.56 (d, J=7.4, 1H), 6.35 (d, J=7.1, 1H), 6.26 (d, J=7.12, 1H), 5.15 (d, J=7.0, 1H), 5.08 (d, J=7.8, 1H), 4.45 (d, J=7.5, 1H), 4.34–4.22 (m, 4H), 4.20 (m, 2H), 2.86–2.67 (m, 2H), 1.81 (s, 3H), 1.51 (s, 3H), 1.39 (s, 3H); Anal. Calcd C$_{29}$H$_{33}$N$_3$O$_6$S.0.2TFA.1.0H$_2$O: C, 59.60; H, 5.99; N, 7.09. Found C, 59.68; H, 5.73; N, 6.97.

EXAMPLE A16

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (R)-chroman-4-ylamide

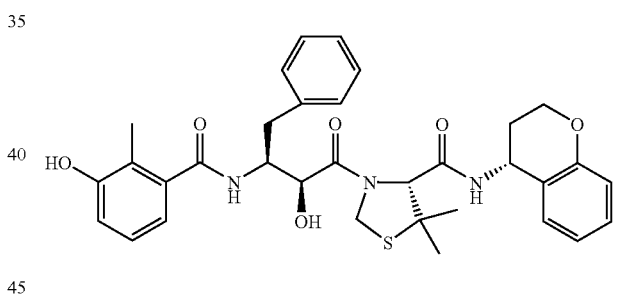

White solid: mp=135–136° C.; IR (cm⁻¹) 3312, 2928, 1644, 1584, 1520, 1489, 1454, 1283, 1105; ¹H NMR (DMSO-d$_6$) δ 9.37 (s, 1H), 8.55 (d, J=8.2, 1H), 8.20 (d, J=8.9, 1H), 7.36 (d, J=7.2, 2H,) 7.26–7.07 (m, 5H); 6.95–6.90 (m, 1H), 6.81–6.73 (m, 3H), 6.54 (d, J=7.2, 1H), 5.47 (d, J=6.9, 1H), 5.16 (d, J=8.9, 1H), 5.01 (d, J=8.9, 1H), 4.54–4.32 (m, 4H), 4.22–4.12 (m, 2H), 2.94–2.64 (m, 2H), 2.10–1.90 (m, 2H), 1.80 (s, 3H), 1.49 (s, 3H), 1.41 (s, 3H); Anal. Calcd for C$_{33}$H$_{37}$N$_3$O$_6$S.1.25H$_2$O: C, 63.29; H, 6.36; N, 6.71. Found: C, 63.22; H, 6.18; N, 6.51.

EXAMPLE A17

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (S)-chroman-4-ylamide

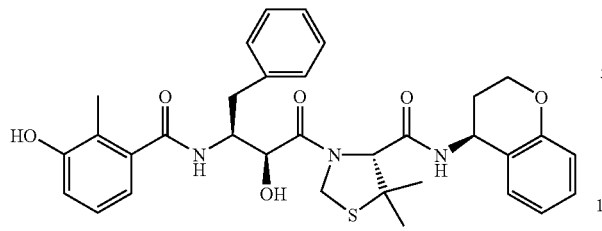

White solid: mp=135–136° C.; IR (cm$^{-1}$) 3311, 2928, 1644, 1584, 1520, 1489, 1454, 1283, 1105; $^1$H NMR (DMSO-d$_6$) δ 9.37 (s, 1H), 8.49 (d, J=8.2, 1H), 8.23 (d, J=8.4, 1H); 7.33–7.10 (m, 7H), 6.94–6.75 (m, 4H), 6.54 (d, J=7.7, 1H), 5.34 (d, J=7.2, 1H), 5.14 (d, J=8.9, 1H), 5.01 (d, J=8.9, 1H), 4.54–4.30 (m, 4H), 4.24–4.10 (m, 2H), 2.82–2.62 (m, 2H), 2.10–1.90 (m, 2H), 1.79 (s, 3H), 1.49 (s, 3H), 1.45 (s, 3H); Anal. Calcd for C$_{33}$H$_{37}$N$_3$O$_6$S.0.25H$_2$O: C, 65.17; H, 6.21; N, 6.91. Found: C, 65.24; H, 6.28; N, 6.95.

EXAMPLE A18

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (R)-thiochroman-4-ylamide

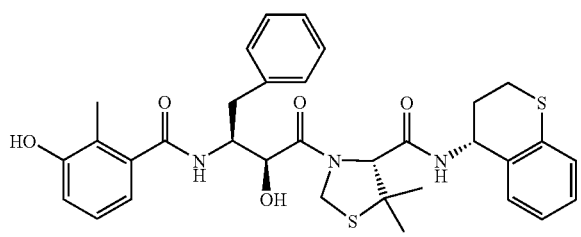

White solid: mp=125–127° C.; IR (cm$^{-1}$) 3313, 2926, 1644, 1585, 1520, 1455, 1285, 1081, 1048; $^1$H NMR (DMSO-d$_6$) δ 9.37 (s, 1H), 8.61 (d, J=8.3, 1H), 8.20 (d, J=8.6, 1H), 7.38–6.90 (m, 10H), 6.76 (d, J=8.1, 1H), 6.54 (d, J=7.9, 1H), 5.46 (d, J=6.6, 1H), 5.17 (d, J=9.0, 1H), 5.01 (d, J=9.0, 1H), 4.56–4.21 (m, 4H), 3.20–2.61 (m, 4H), 2.30–2.00 (m, 2H), 1.79 (s, 3H), 1.49 (s, 3H), 1.41 (s, 3H); Anal. Calcd for C$_{33}$H$_{37}$N$_3$O$_5$S$_2$.0.5H$_2$O: C, 63.03; H, 6.09; N, 6.68. Found: C, 62.84; H, 6.29; N, 6.38.

EXAMPLE A19

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (S)-thiochroman-4-ylamide

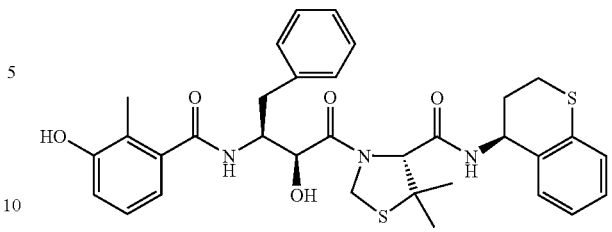

White solid: mp=125–127° C.; IR (cm$^{-1}$) 3312, 2927, 1644, 1585, 1520, 1455, 1372, 1285; $^1$H NMR (DMSO-d$_6$) δ 9.37 (s, 1H), 8.47 (d, J=7.5, 1H), 8.23 (d, J=7.7, 1H), 7.37–6.91 (m, 10H), 6.76 (d, J=8.6, 1H), 6.54 (d, J=7.5, 1H), 5.33 (d, J=6.8, 1H), 5.15 (d, J=9.0, 1H), 5.00 (d, J=9.0, 1H), 4.60–4.30 (m, 4H), 3.20–2.62 (m, 4H), 2.30–2.10 (m, 2H), 1.79 (s, 3H), 1.49 (s, 3H), 1.46 (s, 3H); Anal. Calcd for C$_{33}$H$_{37}$N$_3$O$_5$S$_2$.1.75H$_2$O: C, 60.86; H, 6.27; N, 6.45. Found: C, 60.57; H, 5.90; N, 6.32.

EXAMPLE A20

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cyclopropylmethyl-amide

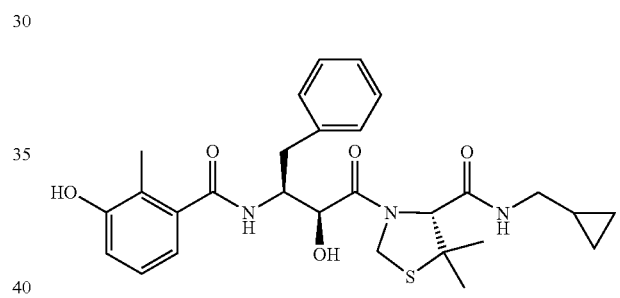

$^1$H NMR (DMSO-d$_6$) δ 9.32, (s, 1H), 8.08 (d, J=8.4, 1H), 7.98 (t, J=6.0, 1H), 7.33 (d, J=6.9, 2H), 7.24 (t, J=7.2, 2H), 7.16 (t, J=7.1, 1H), 6.94 (t, J=7.8, 1H), 6.88 (d, J=7.1, 1H), 6.55 (d, J=6.6, 1H), 5.09 (d, J=9.1, 1H), 5.00 (d, J=9.1, 1H), 4.46 (d, J=3.4, 1H), 4.41 (s, 1H), 4.40 (m, 1H), 2.95 (m, 2H), 2.87–2.65 (m, 2H), 1.82 (s, 3H), 1.50 (s, 3H), 1.38 (s, 3H), 0.89 (m, 1H), 0.38 (m, 2H), 0.16 (m, 2H); HRMS (ESI) m/z calcd for C$_{27}$H$_{35}$N$_3$O$_5$SNa (M+Na)$^+$ 548.2190, found 548.2180.

EXAMPLE A21

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cyclohexylamide

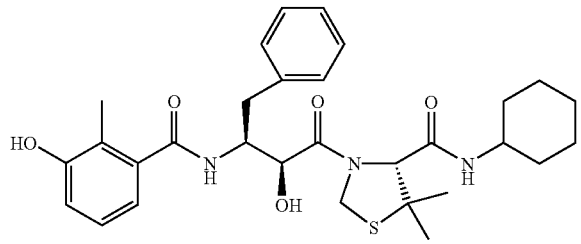

¹H NMR (DMSO-d₆) δ 9.33, (s, 1H), 8.18 (d, J=8.4, 1H), 7.79 (d, J=8.0, 1H), 7.35–7.12 (m, 5H), 6.92 (t, J=7.9, 1H), 6.75 (d, J=8.1, 1H), 6.53 (d, J=7.5, 1H), 5.29 (d, J=7.0, 1H), 5.09 (d, J=9.2, 1H), 5.00 (d, J=9.2, 1H), 4.56–4.37 (m, 2H), 3.61–3.49 (m, 2H), 2.89–2.65 (m, 2H), 1.80 (s, 3H), 1.79–1.58 (m, 5H), 1.48 (s, 3H), 1.36 (s, 3H), 1.35–1.02 (m, 5H); Anal. Calcd for C₃₀H₃₉N₃O₅S: C, 65.07; H, 7.10; N, 7.59. Found: C, 65.39; H, 6.92; N, 7.32.

EXAMPLE A22

3-(2-Hydroxy-3-{[1-(3-hydroxy-2-methyl-phenyl)-methanoyl]-amino}-4-phenyl-butanoyl)-5,5-dimethyl-thiazolidine-4-carboxylic acid-(4-methyl-pyridin-3-ylmethyl)amide

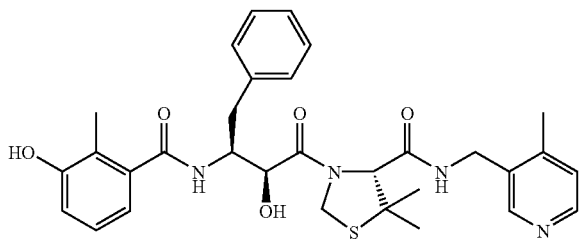

¹H NMR (DMSO-d₆) δ 9.33 (s, 1H), 8.43 (s, 1H), 8.39 (t, J=6.0, 1H), 8.29 (d, J=4.9, 1H), 8.11 (d, J=8.2, 1H), 7.31 (d, J=7.0, 2H), 7.24 (d, J=7.0, 2H), 7.17 (m, 2H), 6.95 (t, J=7.7, 1H), 6.78 (d, J=7.3, 1H), 6.55 (d, J=7.0, 1H), 5.42 (d, J=6.7, 1H), 5.14 (d, J=9.1, 1H), 5.01 (d, J=9.2, 1H), 4.54–4.40 (m, 4H), 4.17 (dd, J=5.1, 15.1, 1H), 2.82 (dd, J=3.0, 14.1, 1H), 2.72 (dd, J=10.1, 14.2, 1H), 2.30 (s, 3H), 1.82 (s, 3H), 1.49 (s, 3H), 1.32 (s, 3H); Anal. Calcd for C₃₁H₃₆N₄O₅S.2H₂O: C, 60.76; H, 6.58; N, 9.14; S, 5.23. Found: C, 60.89; N, 6.26; H, 8.90; S, 5.05.

EXAMPLE A23

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (thiophen-2-ylmethyl)-amide

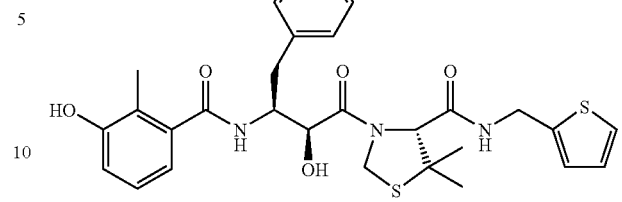

¹H NMR (DMSO-d₆) δ 9.35 (s, 1H), 8.51 (t, J=6.0, 1H), 8.08 (d, J=8.4, 1H), 7.40–7.12 (m, 6H), 7.04–6.88 (m, 3H), 6.80 (d, J=7.4, 1H), 6.57 (d, J=7.4, 1H), 5.12 (d, J=9.0, 1H), 5.02 (d, J=9.0, 1H), 4.58–4.30 (m, 5H), 2.97–2.67 (m, 2H), 1.84 (s, 3H), 1.50 (s, 3H), 1.35 (s, 3H); HRMS (ESI) m/z calcd for C₂₉H₃₃N₃O₅S₂Na (M+Na)⁺ 590.1754, found 590.1762; Anal. Calcd for C₂₉H₃₃N₃O₅S₂.0.5H₂O, 0.2 TFA: C, 58.90; H, 5.75; N, 7.01. Found: C, 58.85; N, 5.71; H, 6.95.

EXAMPLE A24

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (5-chloro-benzo[b]thiophen-3-ylmethyl)-amide

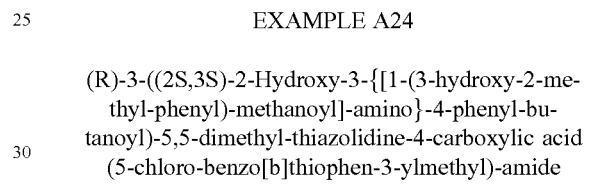

IR (neat, cm⁻¹) 3401, 1643, 1531, 1443, 1284, ¹H NMR (DMSO-d₆) δ 937 (s, 1H), 8.54 (t, J=5.7, 1H), 8.16 (d, J=8.4, 1H), 8.00–7.95 (m, 2H), 7.67 (s, 1H), 7.38 (dd, J=8.6, 2.0, 1H), 7.32–7.11 (m, 5H), 6.97 (t, J=7.7, 1H), 6.77 (d, J=7.9, 1H), 6.55 (d, J=7.1, 1H), 5.46 (s br, 1H), 5.14 (d, J=9.3, 1H), 5.02 (d, J=9.5, 1H), 4.62–4.40 (m, 5H), 2.87–2.67 (m, 2H), 1.82 (s, 3H), 1.47 (s, 3H), 1.30 (s, 3H); HRMS (ESI) m/z calcd for C₃₃H₃₄N₃O₅S₂ClNa (M+Na)⁺ 674.1521, found 674.1547; Anal. Calcd for C₃₃H₃₄ClN₃O₅S₂.H₂O: C, 59.13; H, 5.41; N, 6.27. Found: C, 59.19; H, 5.41; N, 6.08.

EXAMPLE A25

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cyclopropylamide

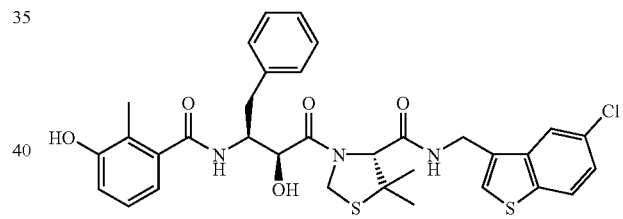

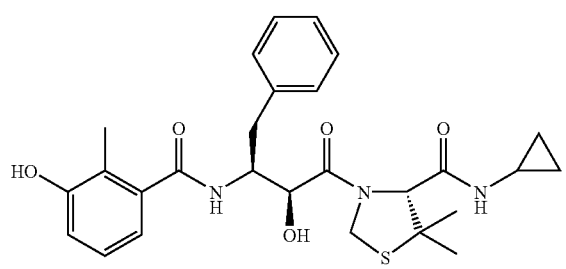

¹H NMR (DMSO-d₆) δ 9.32, (s, 1H), 8.20 (d, J=8.4, 1H), 7.80 (d, J=8.0, 1H), 7.36–7.10 (m, 5H), 6.90 (t, J=7.9, 1H), 6.75 (d, J=8.1, 1H), 6.55 (d, J=7.5, 1H), 5.35 (d, J=7.0, 1H), 5.15 (d, J=9.2, 1H), 5.02 (d, J=9.2, 1H), 4.59–4.30 (m, 3H), 2.89–2.65 (m, 3H), 1.82 (s, 3H), 1.48 (s, 3H), 1.36 (s, 3H), 0.73–0.59 (m, 2H) 0.57–0.33 (m, 2H); Anal. Calcd for $C_{27}H_{33}N_3O_5S$. C, 63.38; H, 6.50; N, 8.21. Found: C, 63.39; H, 6.82; N, 8.32.

EXAMPLE A26

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cyclobutylamide

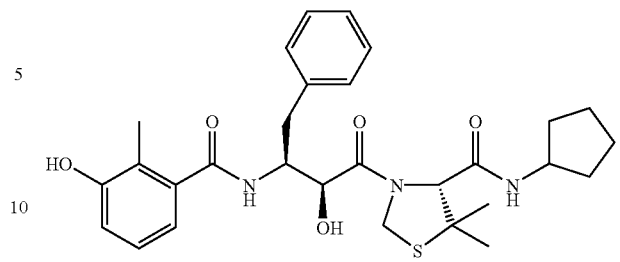

¹H NMR (DMSO-d₆) δ 9.33, (s, 1H), 8.15 (d, J=8.4, 1H), 7.80 (d, J=8.0, 1H), 7.38–7.11 (m, 5H), 6.88 (t, J=7.9, 1H), 6.75 (d, J=8.1, 1H), 6.52 (d, J=7.4, 1H), 5.30 (d, J=7.0, 1H), 5.12 (d, J=9.2, 1H), 4.99 (d, J=9.2, 1H), 4.63–4.42 (m, 3H), 2.96–2.67 (m, 3H), 1.81 (s, 3H), 1.78–1.57 (m, 4H), 1.50 (s, 3H), 1.36 (s, 3H) 1.34–1.02 (m, 4H); Anal. Calcd for $C_{29}H_{37}N_3O_5S$: C, 64.54; H, 6.91; N, 7.79. Found: C, 64.22; H, 6.78; N, 7.93.

EXAMPLE A28

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2-phenyl-cyclopropyl)-amide

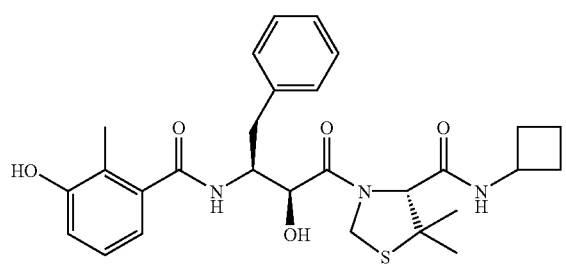

¹H NMR (DMSO-d₆) δ 9.33, (s, 1H), 8.18 (d, J=8.4, 1H), 7.79 (d, J=8.0, 1H), 7.40–7.12 (m, 5H), 6.90 (t, J=7.9, 1H), 6.75 (d, J=8.1, 1H), 6.47 (d, J=7.5, 1H), 5.34 (d, J=7.0, 1H), 5.14 (d, J=9.2, 1H), 4.99 (d, J=9.2, 1H), 4.55–4.32 (m, 3H), 2.90–2.65 (m, 3H), 1.81 (s, 3H), 1.49 (s, 3H), 1.36 (s, 3H) 1.34–1.02 (m, 6H); Anal. Calcd for $C_{28}H_{35}N_3O_5S$: C, 63.97; H, 6.71; N, 7.99. Found: C, 64.05; H, 6.55; N, 8.07.

EXAMPLE A27

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cyclopentylamide

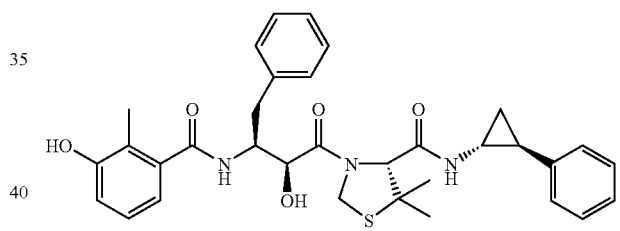

IR (neat, cm¹) 3425, 1637, 1525, 1455, 1278, ¹H NMR (DMSO-d₆) δ 9.37 (s, 1H), 8.26 (m, 1H), 8.17 (d, J=7.7, 1H), 7.36–7.05 (m, 10H), 6.93 (t, J=7.7, 1H), 6.77 (d, J=8.1, 1H), 6.54 (d, J=7.0, 1H), 5.38 (d, J=6.2, 1H), 5.12 (d, J=9.0, 1H), 5.01 (d, J=9.3, 1H), 4.49–4.36 (m, 3H), 2.84–2.68 (m, 2H), 1.92–1.82 (m, 2H), 1.81 (s, 3H), 1.50 (s, 3H), 1.37 (s, 3H), 1.22–1.09 (m, 2H); HRMS (ESI) m/z calcd for $C_{33}H_{37}N_3O_5SNa$ (M+Na)⁺ 610.2346, found 610.2335; Anal. Calcd for $C_{33}H_{37}N_3O_5S \cdot 0.8H_2O$: C, 65.82; H, 6.46; N, 6.98. Found: C, 65.77; H, 6.34; N, 6.84.

EXAMPLE A29

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (R)-indan-1-ylamide

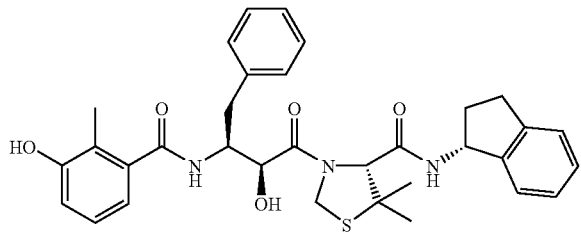

White solid: mp 128–130° C.; IR (neat, cm⁻¹) 3306, 1632, 1537, 1454, 1286; ¹H NMR (DMSO-$d_6$) δ 9.37 (s, 1H), 8.37 (d, J=8.1, 1H), 8.17 (d, J=8.4, 1H), 7.38–7.06 (m, 9H), 6.93 (t, J=7.5, 1H), 6.77 (d, J=7.5, 1H), 6.54 (d, J=7.5, 1H), 5.44 (d, J=6.9, 1H), 5.35 (dd, J=16.7, 8.1, 1H), 5.15 (d, J=8.8, 1H), 5.01 (d, J=8.8, 1H), 4.58–4.32 (m, 3H), 2.95–2.70 (m, 2H), 2.40–2.20 (m, 2H), 1.90–1.70 (m, 2H), 1.81 (s, 3H), 1.51 (s, 3H), 1.43 (s, 3H); Anal. Calcd for $C_{33}H_{37}N_3O_5S \cdot 0.75H_2O$: C, 65.92; H, 6.45; N, 6.99. Found: C, 65.57; H, 6.31; N, 6.82.

EXAMPLE A30

N-{(1S,2S)-1-Benzyl-3-[(R)-5,5-dimethyl-4-(1-morpholin-4-yl-methanoyl)-thiazolidin-3-yl]-2-hydroxy-3-oxo-propyl}-3-hydroxy-2-methyl-benzamide

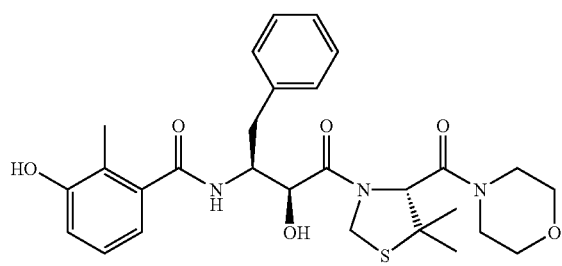

IR (neat, cm⁻¹) 3341, 2955, 1640, 1524, 1455, 1284, 1113, ¹H NMR (DMSO-$d_6$) δ 9.36 (s, 1H), 8.24 (d, J=8.6, 1H,), 7.36–7.13 (m, 5H), 6.94 (t, J=7.7, 1H), 6.78 (d, J=7.5, 1H), 6.53 (d, J=7.5, 1H), 5.34 (m, 1H), 5.12 (d, J=9.2, 1H), 5.04 (d, J=9.2, 1H), 4.50 (m, 1H), 4.33–4.30 (m, 2H), 3.78–3.51 (m, 8H), 2.81–2.62 (m, 2H), 1.80 (s, 3H), 1.56 (s, 3H), 1.38 (s, 3H); HRMS (ESI) m/z calcd for $NaC_{28}H_{35}N_3O_6S$ (M+Na)⁺ 564.2139, found 564.2116.

EXAMPLE A31

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cycloheptylamide

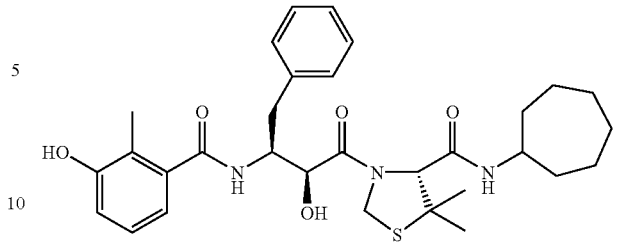

¹H NMR (DMSO-$d_6$) δ 9.32, (s, 1H), 8.20 (d, J=8.4, 1H), 7.78 (d, J=8.0, 1H), 7.40–7.12 (m, 5H), 6.92 (t, J=7.9, 1H), 6.73 (d, J=8.1, 1H), 6.50 (d, J=7.5, 1H), 5.29 (d, J=7.0, 1H), 5.19 (d, J=9.2, 1H), 5.03 (d, J=9.2, 1H), 4.62–4.37 (m, 3H), 2.92–2.67 (m, 3H), 1.80 (s, 3H), 1.79–1.01 (m, 18H); Anal. Calcd for $C_{31}H_{41}N_3O_5S$: C, 65.58; H, 7.28; N, 7.40. Found: C, 65.74; H, 7.07; N, 7.53.

EXAMPLE A32

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (S)-cyclohex-2-enylamide

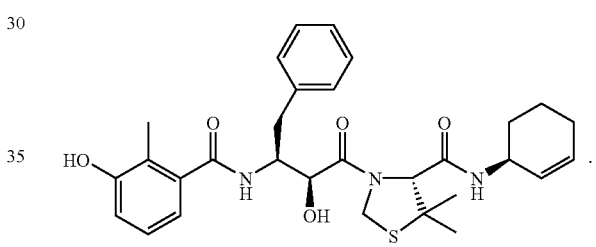

White solid: mp 177–179° C.; IR (neat, cm⁻¹) 3319, 2943, 1637, 1531, 1455, 1361, 1284; ¹H NMR (DMSO-$d_6$) δ 9.35 (s, 1H), 8.16 (d, J=7.6, 1H), 7.95 (d, J=7.7, 1H), 7.38–7.10 (m, 5H), 6.93 (t, J=7.6, 1H), 6.76 (d, J=7.6, 1H), 6.53 (d, J=7.6, 1H), 5.80–5.70 (m, 1H), 5.50–5.40 (m, 1H), 5.35 (d, J=6.9, 1H), 5.11 (d, J=9.2, 1H), 4.99 (d, J=9.2, 1H), 4.55–4.30 (m, 4H), 2.84–2.62 (m, 2H), 2.00–1.62 (m, 9H), 1.48 (s, 3H), 1.37 (s, 3H); Anal. Calcd for $C_{30}H_{37}N_3O_5S \cdot 0.5H_2O$: C, 64.26; H, 6.83; N, 7.49. Found: C, 64.21; H, 6.74; N, 7.36.

EXAMPLE A33

N-{(1S,2S)-1-Benzyl-3-[(R)-5,5-dimethyl-4-(1-thiomorpholin-4-yl-methanoyl)-thiazolidin-3-yl]-2-hydroxy-3-oxo-propyl}-3-hydroxy-2-methyl-benzamide

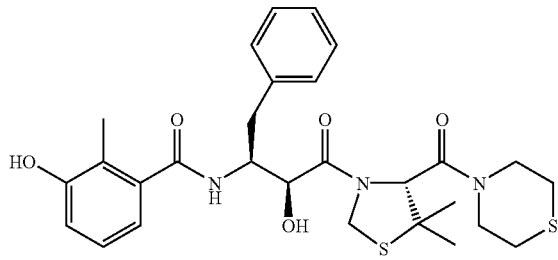

¹H NMR (DMSO-d₆) δ 9.40 (s, 1H), 8.30 (d, J=8.4, 1H), 7.40–7.16 (m, 5H), 6.97 (t, J=7.5, 1H), 6.80 (d, J=8.1, 1H), 6.57 (d, J=7.1, 1H), 5.40 (d, J=7.1, 1H), 5.18 (d, J=9.2, 1H), 5.06 (d, J=9.7, 1H), 4.54 (m, 1H), 4.35–4.19 (m, 2H), 3.68–3.59 (m, 2H), 3.28–3.10 (m, 2H), 2.87–2.44 (m, 6H), 1.83 (s, 3H), 1.60 (s, 3H), 1.37 (s, 3H); HRMS (ESI) m/z calcd for $C_{28}H_{35}N_3O_5S_2Na$ (M+Na)⁺ 580.1910, found 580.1922.

EXAMPLE A34

N-{(1S,2S)-1-Benzyl-3-[(R)-5,5-dimethyl-4-(1-piperidin-1-yl-methanoyl)-thiazolidin-3-yl]-2-hydroxy-3-oxo-propyl}-3-hydroxy-2-methyl-benzamide

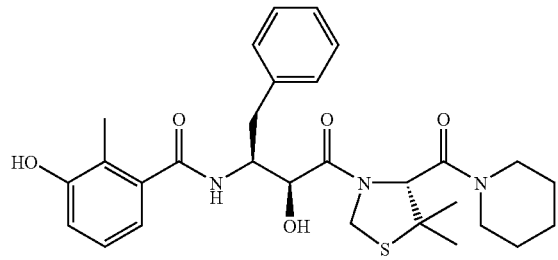

IR (neat, cm⁻¹) 3389, 2931, 1631, 1461, 1284, ¹H NMR (DMSO-d₆) δ 9.36 (s, 1H), 8.05 (d, J=8.1, 1H), 7.38–7.12 (m, 5H), 6.94 (t, J=7.7, 1H), 6.77 (d, J=7.3), 1H), 6.53 (d, J=7.3, 1H), 5.29 (d, J=7.1, 1H), 5.14–5.01 (m, 2H), 4.50 (m, 1H), 4.32–4.19 (m, 2H), 3.78–3.67 (m, 2H), 3.42–3.09 (m, 2H), 2.81–2.62 (m, 2H), 1.80 (s, 3H), 1.75–1.35 (m, 6H), 1.57 (s, 3H), 1.36 (s, 3H); HRMS (ESI) m/z calcd for $C_{29}H_{37}N_3O_5SNa$ (M+Na)⁺ 562.2346, found 562.2327; Anal. Calcd for $C_{29}H_{37}N_3O_5S·0.8H_2O$: C, 62.86; H, 7.02; N, 7.58. Found: C, 62.83; H, 6.95; N, 7.38.

EXAMPLE A35

(R)-3-((2S,3S)-2-Hydroxy-3-{[1-(3-hydroxy-2-methyl-phenyl)-methanoyl]-amino}-4-phenyl-butanoyl)-5,5-dimethyl-thiazoline-4-carboxylic acid (S)-indan-1-ylamide

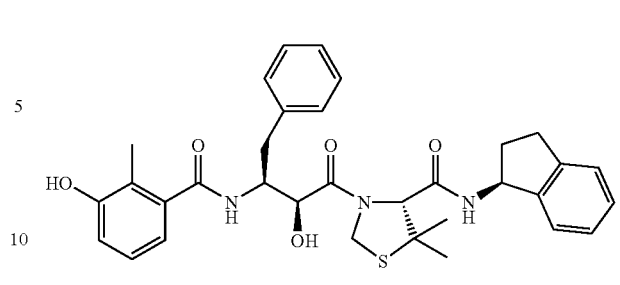

White solid: mp 204–206° C.; IR (neat, cm⁻¹) 3307, 1633, 1537, 1454, 1287; ¹H NMR (DMSO-d₆) δ 9.37 (s, 1H), 8.37 (d, J=8.1, 1H), 8.17 (d, J=8.4, 1H), 7.38–7.06 (m, 9H), 6.93 (t, J=7.5, 1H), 6.77 (d, J=7.5, 1H), 6.54 (d, J=7.5, 1H), 5.44 (d, J=6.9, 1H), 5.35 (dd, J=16.7, 8.1, 1H), 5.13 (d, J=8.8, 1H), 5.04 (d, J=8.8, 1H), 4.58–4.32 (m, 3H), 2.95–2.70 (m, 2H), 2.40–2.20 (m, 2H), 1.90–1.70 (m, 2H), 1.81 (s, 3H), 1.51 (s, 3H), 1.43 (s, 3H); Anal. Calcd for $C_{33}H_{37}N_3O_5S$: C, 67.44; H, 6.35; N, 7.15. Found: C, 67.10; H, 6.43; N, 7.02.

EXAMPLE A36

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (4-methyl-cyclohexyl)-amide

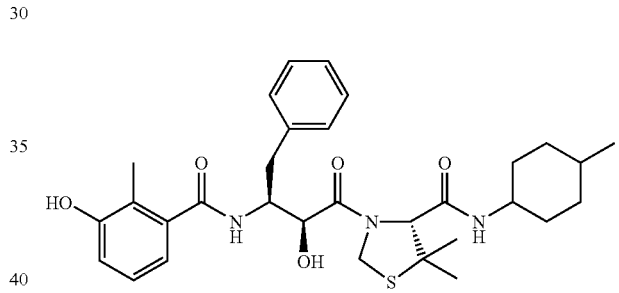

White solid: mp 192–194° C.; IR (neat, cm⁻¹) 3298, 2955, 1638, 1531, 1449, 1349, 1284, 1099; ¹H NMR (DMSO-d₆) δ 9.35 (s, 1H), 8.22–8.21 (m, 1H), 7.82–7.70 (m, 1H), 7.34–7.14 (m, 5H), 6.95–6.90 (m, 1H), 6.76 (d, J=8.1, 1H), 6.53 (d, J=7.3, 1H), 5.33 (d, J=5.9, 1H), 5.13–4.94 (m, 2H), 4.60–4.30 (m, 3H), 3.80–3.40 (m, 1H), 2.81–2.68 (m, 2H), 1.79 (s, 3H), 1.80–1.13 (m, 15H), 0.89–0.82 (m, 3H); Anal. Calcd for $C_{31}H_{41}N_3O_5S·1H_2O$: C, 63.57; H, 7.40; N, 7.17. Found: C, 63.73; H, 7.36; N, 6.91.

EXAMPLE A37

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (tetrahydro-furan-2-ylmethyl)-amide

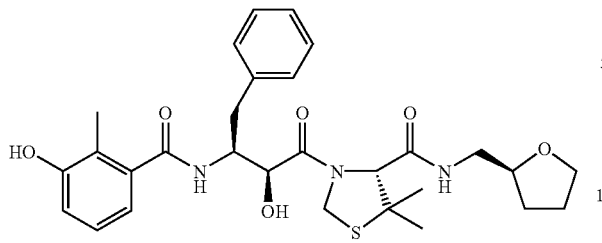

¹H NMR (DMSO-d₆) δ 9.36 (s, 1H), 8.14 (d, J=8.8, 1H), 8.03 (t, J=5.0, 1H), 7.32–7.15 (m, 5H), 6.94 (t, J=7.5, 1H), 6.79 (d, J=7.5, 1H), 6.57 (d, J=7.5, 1H), 5.49 (d, J=5.5, 1H), 5.12 (d, J=9.3, 1H), 5.02 (d, J=9.3, 1H), 4.52–4.12 (m, 3H), 3.79–3.53 (m, 5H), 3.31–3.20 (m, 2H); 2.92–2.62 (m, 2H), 1.90–1.71 (m, 2H), 1.69 (s, 3H), 1.48 (s, 3H), 1.34 (s, 3H); Anal. Calcd for $C_{29}H_{37}N_3O_6S \cdot 0.5H_2O$: C, 61.68; H, 6.78; N, 7.44. Found: C, 61.52; H, 6.62; N, 7.53.

EXAMPLE A38

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (R)-cyclohex-2-enylamide

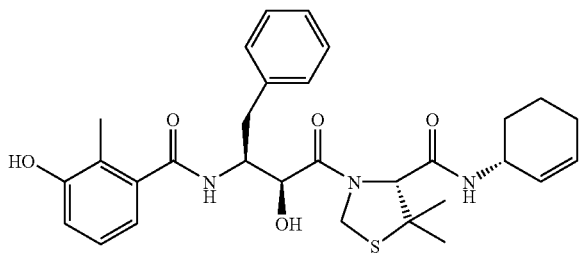

White solid: mp=193–195° C.; IR (neat, cm⁻¹) 3316, 2931, 1637, 1584, 1519, 1449, 1349, 1279, 1085; ¹H NMR (DMSO-d₆) δ 9.34 (s, 1H), 8.14 (d, J=8.4, 1H), 8.03 (d, J=8.1, 1H), 7.35–7.12 (m, 5H), 6.93 (t, J=7.2, 1H), 6.77 (d, J=7.2, 1H), 6.53 (d, J=7.2, 1H), 5.79 (d, J=9.9, 1H), 5.52 (d, J=9.9, 1H), 5.36 (d, J=6.8, 1H), 5.10 (d, J=9.2, 1H), 4.99 (d, J=9.2, 1H), 4.48–4.20 (m, 4H), 2.84–2.62 (m, 2H), 2.00–1.85 (m, 2H), 1.80 (s, 3H), 1.80–1.40 (m, 4H), 1.48 (s, 3H), 1.37 (s, 3H); Anal. Calcd for $C_{30}H_{37}N_3O_5S \cdot 0.25H_2O$: C, 64.60; H, 6.78; N, 7.53. Found: C, 64.83; H, 6.72; N, 7.44.

EXAMPLE A39

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (cyclopent-1-enylmethyl)-amide

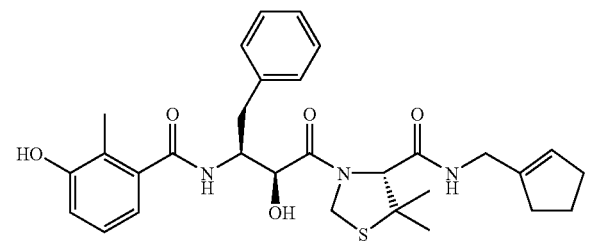

¹H NMR (DMSO-d₆) δ 9.37 (s, 1H), 8.11 (d, J=7.9, 1H), 8.06 (t, J=5.7, 1H), 7.33–7.13 (m, 5H), 6.94 (t, J=7.7, 1H), 6.77 (d, J=8.1, 1H), 6.53 (d, J=7.5, 1H), 5.50 (s, 1H), 5.45 (d, J=6.6, 1H), 5.11 (d, J=9.0, 1H), 4.98 (d, J=9.2, 1H), 4.47–4.38 (m, 3H), 3.81 (dd, J=15.8, 6.4, 1H), 3.61 (dd, J=15.9, 5.3, 1H), 2.84–2.67 (m, 2H), 2.20–2.15 (m, 4H), 1.83–1.73 (m, 2H), 1.80 (s, 3H), 1.49 (s, 3H), 1.35 (s, 3H); HRMS (ESI) m/z calcd for $C_{30}H_{37}N_3O_5SNa$ (M+Na)⁺ 574.2346, found 574.2354.

EXAMPLE A40

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (thiophen-3-ylmethyl)-amide

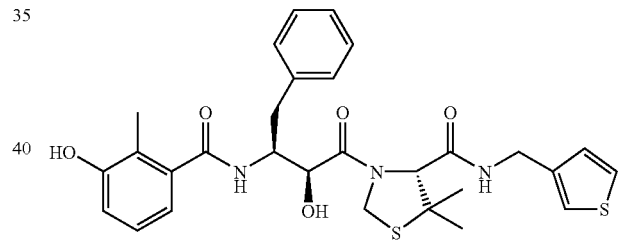

¹H NMR (DMSO-d₆) δ 9.40 (s, 1H), 8.44 (t, J=5.7, 1H), 8.16 (d, J=8.1, 1H), 7.45 (m, 1H), 7.35–7.15 (m, 6H), 7.05 (d, J=6.0, 1H), 6.97 (t, J=7.7, 1H), 6.80 (d, J=8.1, 1H), 6.57 (d, J=7.3, 1H), 5.52 (d, J=6.4, 1H), 5.15 (d, J=9.3, 1H), 5.03 (d, J=9.2, 1H), 5.12–4.37 (m, 4H), 2.86–2.67 (m, 2H), 4.18 (dd, J=15.2, 5.1, 1H), 2.89–2.70 (m, 2H), 1.84 (s, 3H), 1.52 (s, 3H), 1.36 (s, 3H); HRMS (ESI) m/z calcd for $C_{29}H_{33}N_3O_5S_2Na$ (M+Na)⁺ 590.1754, found 590.1734; Anal. Calcd for $C_{29}H_{33}N_3O_5S_2 \cdot 0.6H_2O$: C, 60.20; H, 5.96; N, 7.26. Found: C, 60.26; H, 6.02; N, 7.08.

EXAMPLE A41

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (thiazol-2-ylmethyl)-amide

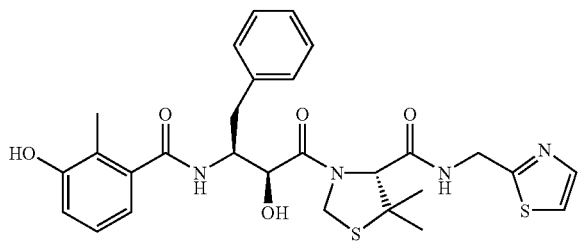

¹H NMR (DMSO-d₆) δ 9.38 (s, 1H), 8.82 (t, J=5.9, 1H), 8.11 (d, J=8.2, 1H), 7.68 (d, J=3.3, 1H), 7.57 (d, J=3.1, 1H), 7.33–7.13 (m, 5H), 6.94 (t, J=7.7, 1H), 6.77 (d, J=7.3, 1H), 6.54 (d, J=6.6, 1H), 5.49 (d, J=6.4, 1H), 5.11 (d, J=9.3, 1H), 5.02 (d, J=9.3, 1H), 4.64–4.38 (m, 5H), 2.88–2.68 (m, 2H), 1.82 (s, 3H), 1.51 (s, 3H), 1.36 (s, 3H); HRMS (ESI) m/z calcd for $C_{28}H_{32}N_4O_5S_2Na$ (M+Na)⁺ 591.1706, found 591.1710.

EXAMPLE A42

3-[2-Hydroxy-3-(3-hydroxy-2-methyl-benzoylamino)-4-phenyl-butyryl]-5,5-dimethyl-thiazolidine-4-carboxylic acid (5,6,7,8-tetrahydro-quinolin-5-yl)-amide

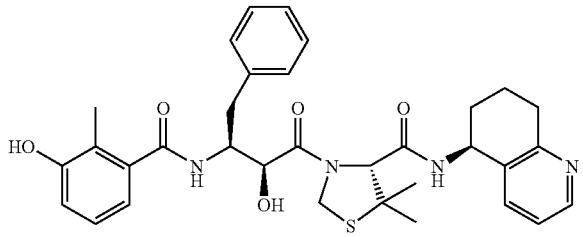

Purified by Prep HPLC using 15% CH₃CN/H₂O (0.1% TFA) to 95% CH₃CN at 254 nm. White foam; IR (cm⁻¹) 3298, 2943, 1637, 1584, 1531, 1447, 1366; ¹H NMR (DMSO-d₆) δ 9.36 (s, 1H), 8.34–8.28 (m, 2H), 8.20 (d, J=8.6, 1H), 7.55 (d, J=6.9, 1H), 7.27–6.90 (m, 7H), 6.76 (d, J=8.1, 1H), 6.53 (d, J=7.5, 1H), 5.37 (d, J=6.7, 1H), 5.10–5.00 (m, 1H), 5.14 (d, J=9.3, 1H), 5.01 (d, J=9.3, 1H), 4.58–4.40 (m, 2H),), 4.40 (s, 1H), 2.90–2.60 (m, 2H), 2.00–1.80 (m, 6H), 1.79 (s, 3H), 1.49 (s, 3H), 1.42 (s, 3H); Anal. Calcd for $C_{33}H_{38}N_4O_5S.0.5TFA.0.6H_2O$: C, 60.90; H, 5.97; N, 8.36. Found: C, 60.87; H, 6.28; N, 8.44.

EXAMPLE A43

3-[2-Hydroxy-3-(3-hydroxy-2-methyl-benzoylamino)-4-phenyl-butyryl]-5,5-dimethyl-thiazolidine-4-carboxylic acid (5,6,7,8-tetrahydro-quinolin-5-yl)-amide

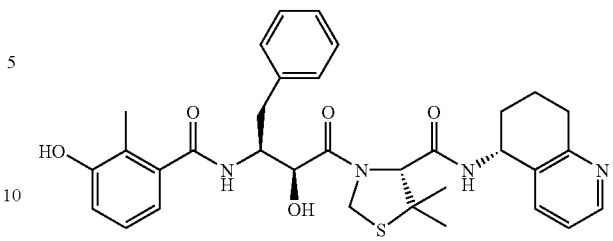

Purified by Prep HPLC using 15% CH₃CN/H₂O (0.1% TFA) to 95% CH₃CN at 254 mm. White foam; IR (cm⁻¹) 3298, 2942, 1637, 1584, 1531, 1447, 1366, 1208, 1091; ¹H NMR (DMSO-d₆) δ 9.36 (s, 1H), 8.47 (d, J=8.8, 1H), 8.30 (dd, J=4.8, 1.2, 1H), 8.18 (d, J=8.4, 1H), 7.63 (d, J=7.2, 1H), 7.37–6.90 (m, 7H), 6.76 (d, J=8.1, 1H), 6.55 (d, J=7.5, 1H), 5.45 (d, J=6.9, 1H), 5.50–5.05 (m, 1H), 5.16 (d, J=8.9, 1H), 5.01 (d, J=8.9, 1H), 4.52–4.49 (m, 2H),), 4.42 (s, 1H), 3.00–2.65 (m, 2H), 2.00–1.60 (m, 6H), 1.80 (s, 3H), 1.50 (s, 3H), 1.42 (s, 3H); Anal. Calcd for $C_{33}H_{38}N_4O_5S.0.5TFA.0.6H_2O$: C, 60.90; H, 5.97; N, 8.36. Found: C, 60.87; H, 6.28; N, 8.44.

EXAMPLE A44

3-(2-Hydroxy-3-{[1-(3-hydroxy-2-methyl-phenyl)-methanoyl]-amino}-4-phenyl-butanoyl)-5,5-dimethyl-thiazolidine-4-carboxylic acid (1H-indazol-3-ylmethyl)-amide

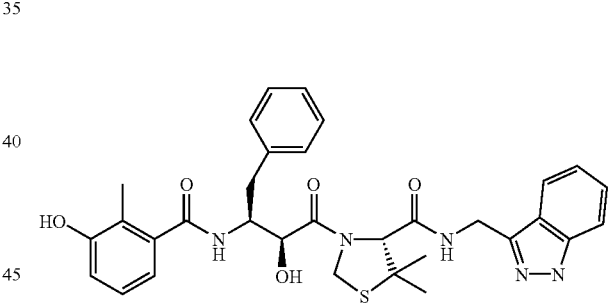

¹H NMR (DMSO-d₆) δ 12.81 (s, 1H), 9.34 (s, 1H), 8.51 (t, J=5.5, 1H), 8.14 (d, J=8.2, 1H) 7.86–6.56 (m, 12H), 5.35 (d, J=6.6, 1H), 5.12 (d, J=9.1, 1H), 5.03 (d, J=9.1, 1H), 4.74–4.41 (m, 5H), 4.49 (s, 1H), 2.91–2.69 (m, 2H), 1.84 (s, 3H), 1.47 (s, 3H), 1.30 (s, 3H); Anal. Calcd for $C_{32}H_{35}N_5O_5S.0.5EtOAc$: C, 63.23; H, 6.09; N, 10.85; S, 4.97. Found: C, 63.12; H, 6.27; N, 10.78; S, 4.86.

EXAMPLE A45

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (furan-3-ylmethyl)-amide

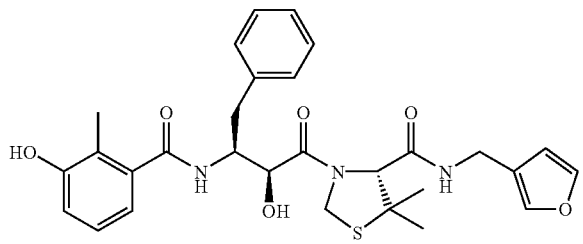

¹H NMR (DMSO-d₆) δ 9.40 (s, 1H), 8.34 (t, J=5.7, 1H), 8.18 (d, J=8.4, 1H), 7.57 (m, 2H), 7.36–7.15 (m, 5H), 6.97 (t, J=7.7, 1H), 6.80 (d, J=7.9, 1H), 6.57 (d, J=7.3, 1H), 6.41 (s, 1H), 5.47 (d, J=6.2, 1H), 5.12 (d, J=9.2, 1H), 5.00 (d, J=9.2, 1H), 4.46–4.39 (m, 3H), 4.22–3.98 (m, 2H), 2.85–2.67 (m, 2H), 1.81 (s, 3H), 1.48 (s, 3H), 1.32 (s, 3H); HRMS (ESI) m/z calcd for $C_{29}H_{34}N_3O_6S$ (M+H)⁺ 552.2168, found 551.2173; Anal. Calcd for $C_{29}H_{33}N_3O_6S$: C, 61.63; H, 6.15; N, 7.43. Found: C, 61.76; H, 6.10; N, 7.24.

EXAMPLE A46

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (tetrahydro-furan-3-ylmethyl)-amide

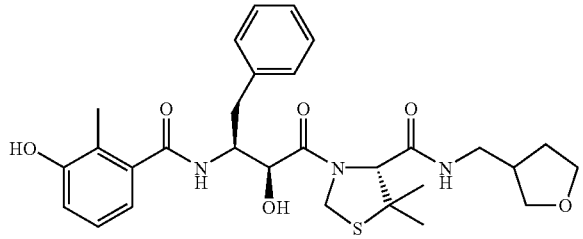

¹H NMR (DMSO-d₆) δ 9.36 (s, 1H), 8.14–8.03 (m, 2H), 7.34–7.13 (m, 5H), 6.93 (t, J=7.9, 1H), 6.76 (d, J=8.1, 1H), 6.52 (d, J=7.5, 1H), 5.43 (m, 1H), 5.10 (d, J=9.3, 1H), 4.99 (d, J=9.2, 1H), 4.46–4.35 (m, 3H), 3.69–3.50 (m, 4H), 3.40–3.22 (m, 1H), 3.12–2.95 (m, 2H), 2.84–2.66 (m, 2H), 2.36–2.27 (m, 1H), 1.87–1.76 (m, 1H), 1.80 (s, 3H), 1.49 (s, 3H), 1.34 (s, 3H); HRMS (ESI) m/z calcd for $C_{29}H_{37}N_3O_6SNa$ (M+Na)⁺ 556.2470, found 556.2481; Anal. Calcd for $C_{29}H_{37}N_3O_6S \cdot 0.75H_2O$: C, 61.19; H, 6.72; N, 7.38. Found: C, 61.24; H, 6.59; N, 7.01.

EXAMPLE A47

3-[2-Hydroxy-3-(3-hydroxy-2-methyl-benzoylamino)-4-phenyl-butyryl]-5,5-dimethyl-thiazolidine-4-carboxylic acid (4,5,6,7-tetrahydro-benzofuran-4-yl)-amide

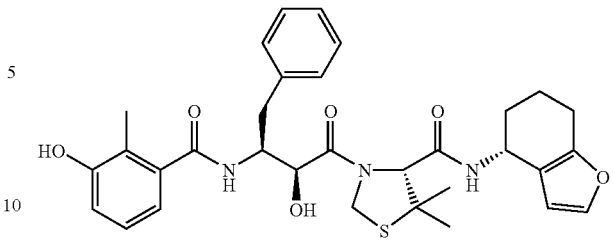

White foam; IR (cm⁻¹) 3331, 2943, 1643, 1590, 1522, 1445, 1364, 1282; ¹H NMR (DMSO-d₆) δ 9.35 (s, 1H), 8.21–8.16 (m, 2H), 7.42–7.14 (m, 6H), 6.96–6.90 (m, 1H), 6.76 (d, J=8.2, 1H), 6.54 (d, J=7.2, 1H), 6.28 (d, J=1.8, 1H), 5.39 (d, J=6.9, 1H), 5.13 (d, J=9.0, 1H), 5.02 (d, J=9.0, 1H), 4.90–4.70 (m, 1H), 4.55–4.30 (m, 3H), 2.89–2.68 (m, 2H), 1.81 (s, 3H), 2.00–1.50 (m, 6H), 1.48 (s, 3H), 1.39 (s, 3H); Anal. Calcd for $C_{32}H_{37}N_3O_6S \cdot 0.5H_2O$: C, 63.98; H, 6.38; N, 6.99. Found: C, 63.93; H, 6.44; N, 6.68.

EXAMPLE A48

3-[2-Hydroxy-3-(3-hydroxy-2-methyl-benzoylamino)-4-phenyl-butyryl]-5,5-dimethyl-thiazolidine-4-carboxylic acid (4,5,6,7-tetrahydro-benzofuran-4-yl)-amide

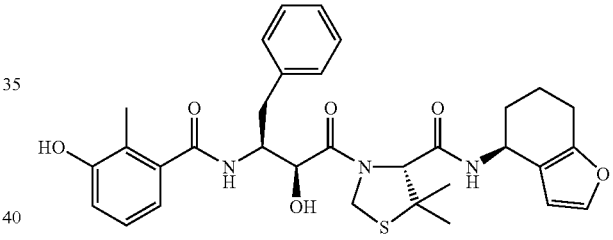

White foam; IR (cm⁻¹) 3316, 2935, 1754, 1657, 1642, 1584, 1530, 1454, 1357, 1284, 1209; ¹H NMR (DMSO-d₆) δ 9.35 (s, 1H), 8.19 (d, J=8.8, 1H), 8.14 (d, J=8.1, 1H), 7.43–7.14 (m, 6H), 6.96–6.91 (m, 1H), 6.77 (d, J=7.9, 1H), 6.54 (d, J=7.5, 1H), 6.38 (d, J=1.9, 1H), 5.32 (d, J=6.9, 1H), 5.13 (d, J=9.0, 1H), 5.00 (d, J=9.0, 1H), 4.83–4.50 (m, 1H), 4.52–4.12 (m, 3H), 2.82–2.62 (m, 2H), 1.79 (s, 3H), 2.00–1.50 (m, 6H), 1.47 (s, 3H), 1.41 (s, 3H); Anal. Calcd for $C_{32}H_{37}N_3O_6S \cdot 0.5H_2O$: C, 63.98; H, 6.38; N, 6.99. Found: C, 64.03; H, 6.37; N, 6.66.

EXAMPLE A49

3-[2-Hydroxy-3-(3-hydroxy-2-methyl-benzoylamino)-4-phenyl-butyryl]-5,5-dimethyl-thiazolidine-4-carboxylic acid (4,5,6,7-tetrahydro-benzo[b]thiophen-4-yl)-amide

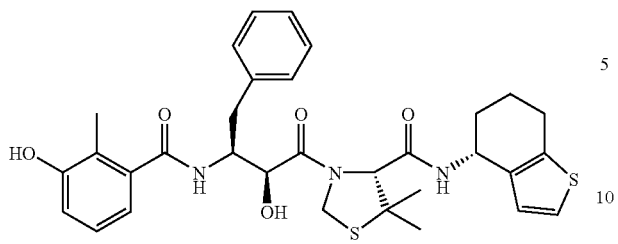

White foam; IR (cm⁻¹) 3317, 2943, 1643, 1525, 1455, 1367, 1256; ¹H NMR (DMSO-$d_6$) δ 9.36 (s, 1H), 8.36 (d, J=8.6, 1H), 8.18 (d, J=8.2, 1H), 7.37 (d, J=7.2, 1H), 7.28–6.75 (m, 8H), 6.54 (d, J=7.2, 1H), 5.41 (d, J=6.9, 1H), 5.14 (d, J=8.8, 1H), 4.99 (d, J=8.8, 1H), 5.00–4.56 (m, 1H),), 4.52–4.30 (m, 3H), 2.80–2.60 (m, 2H), 1.81 (s, 3H), 2.00–1.60 (m, 6H), 1.49 (s, 3H), 1.41 (s, H); Anal. Calcd for $C_{32}H_{37}N_3O_5S_2 \cdot 0.5H_2O$: C, 62.31; H, 6.21; N, 6.81. Found: C, 62.30; H, 6.17; N, 6.60.

EXAMPLE A50

3-[2-Hydroxy-3-(3-hydroxy-2-methyl-benzoylamino)-4-phenyl-butyryl]-5,5-dimethyl-thiazolidine-4-carboxylic acid (4,5,6,7-tetrahydro-benzo[b]thiophen-4-yl)-amide

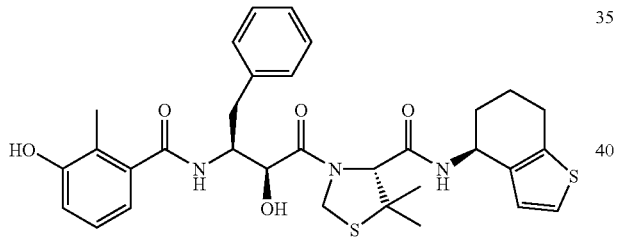

White foam; IR (cm⁻¹) 3321, 2935, 1642, 1585, 1530, 1372, 1283, 1045; ¹H NMR (DMSO-$d_6$) δ 9.35 (s, 1H), 8.24 (d, J=8.8, 1H), 8.20 (d, J=8.4, 1H), 7.31 (d, J=7.2, 1H), 7.23–6.70 (m, 8H), 6.54 (d, J=7.2, 1H), 5.32 (d, J=6.4, 1H), 5.13 (d, J=9.2, 1H), 5.01 (d, J=9.2, 1H), 5.00–4.60 (m, 1H), 4.60–4.30 (m, 3H), 2.80–2.60 (m, 2H), 1.80 (s, 3H), 2.00–1.60 (m, 6H), 1.47 (s, 3H), 1.42 (s, 3H); Anal. Calcd for $C_{32}H_{37}N_3O_5S_2$: C, 63.24; H, 6.14; N, 6.91. Found: C, 63.59; H, 6.20; N, 6.68.

EXAMPLE A51

3-[2-Hydroxy-3-(3-hydroxy-2-methyl-benzoylamino)-4-phenyl-butyryl]-5,5-dimethyl-thiazolidine-4-carboxylic acid (6,7-dihydro-5H-[1]pyrindin-5-yl)-amide

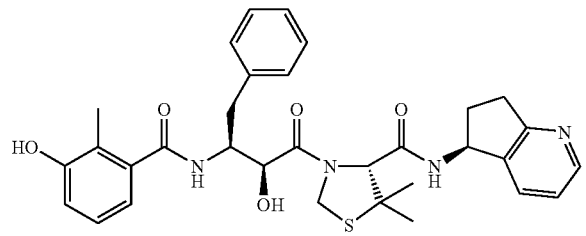

Purified by Prep HPLC using 15% $CH_3CN/H_2O$ (0.1% TFA) to 95% $CH_3CN$ at 254 nm. White foam; IR (cm⁻¹) 3296, 2966, 1644, 1538, 1554, 1373, 1284, 1046; ¹H NMR (DMSO-$d_6$) δ 9.36 (s, 1H), 8.41 (d, J=7.3, 1H), 8.33 (d, J=4.4, 1H), 8.19 (d, J=9.2, 1H), 7.55 (d, J=7.2, 1H), 7.36 (d, J=7.2, 1H), 7.28–6.90 (m, 6H), 6.76 (d, J=7.9, 1H), 6.53 (d, J=6.6, 1H), 5.39 (d, J=7.2, 1H), 5.32 (dd, J=14.9, 7.3, 1H), 5.15 (d, J=9.0, 1H), 5.02 (d, J=9.0, 1H), 4.54–4.34 (m, 3H), 3.00–2.60 (m, 4H), 2.44–2.30 (m, 1H), 1.98–1.81 (m, 1H), 1.79 (s, 3H), 1.48 (s, 3H), 1.40 (s, 3H); Anal. Calcd for $C_{32}H_{36}N_4O_5S \cdot 0.25TFA \cdot 0.5H_2O$: C, 62.33; H, 6.00; N, 8.95. Found: C, 62.58; H, 6.15; N, 8.95.

EXAMPLE A52

3-[2-Hydroxy-3-(3-hydroxy-2-methyl-benzoylamino)-4-phenyl-butyryl]-5,5-dimethyl-thiazolidine-4-carboxylic acid (6,7-dihydro-5H-[1]pyrindin-5-yl)-amide

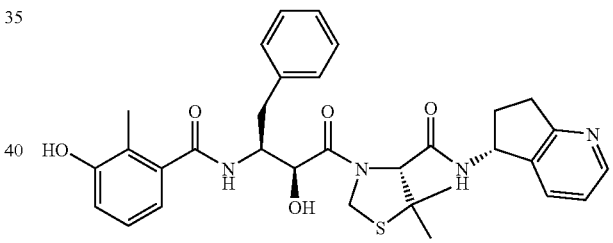

Purified by Prep HPLC using 15% $CH_3CN/H_2O$ (0.1% TFA) to 95% $CH_3CN$ at 254 nm. White foam; IR (cm⁻¹) 3296, 2966, 1643, 1539, 1554, 1373, 1284, 1045; ¹H NMR (DMSO-$d_6$) δ 9.35 (s, 1H), 8.59 (d, J=8.0, 1H), 8.32 (d, J=4.0, 1H), 8.16 (d, J=8.4, 1H), 7.57 (d, J=7.7, 1H), 7.36 (d, J=7.7, 1H), 7.25–6.90 (m, 6H), 6.76 (d, J=8.0, 1H), 6.54 (d, J=7.7, 1H), 5.43 (d, J=6.9, 1H), 5.36 (dd, J=16.0, 8.0, 1H), 5.14 (d, J=9.0, 1H), 5.01 (d, J=9.0, 1H), 4.54–4.36 (m, 3H), 2.90–2.70 (m, 4H), 2.44–2.30 (m, 1H), 1.84–1.70 (m, 1H), 1.80 (s, 3H), 1.51 (s, 3H), 1.42 (s, 3H); Anal. Calcd for $C_{32}H_{36}N_4O_5S \cdot 0.25TFA \cdot 0.5H_2O$: C, 62.33; H, 6.00; N, 8.95. Found: C, 62.41; H, 6.38; N, 8.81.

EXAMPLE A53

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2-methyl-furan-3-ylmethyl)-amide

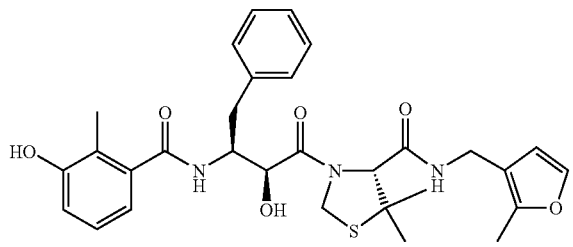

¹H NMR (DMSO-d₆) δ 9.37 (s, 1H), 8.20 (m, 1H), 8.14 (d, J=7.9, 1H), 7.35–7.13 (m, 6H), 6.94 (t, J=7.7, 1H), 6.75 (d, J=8.0, 1H), 6.53 (d, J=7.5, 1H), 6.28 (s, 1H), 5.42 (d, J=6.6, 1H), 5.11 (d, J=9.0, 1H), 4.99 (d, J=9.1, 1H), 4.46–4.38 (m, 3H), 4.12–3.92 (m, 2H), 2.84–2.66 (m, 2H), 2.20 (s, 3H), 1.80 (s, 3H), 1.46 (s, 3H), 1.30 (s, 3H); HRMS (ESI) m/z calcd for C₃₀H₃₆N₃O₆S (M+H)⁺ 566.2332, found 566.2325; Anal. Calcd for C₃₀H₃₅N₃O₆S·0.5H₂O: C, 62.70; H, 6.31; N, 7.31. Found: C, 62.82; H, 6.19; N, 7.09.

EXAMPLE A54

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (3-methyl-benzofuran-2-ylmethyl)-amide

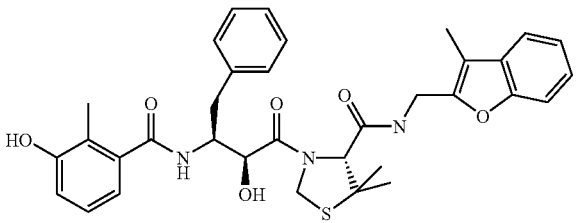

¹H NMR (DMSO-d₆) δ 9.37 (s, 1H), 8.55 (t, J=5.5, 1H), 8.15 (d, J=8.3, 1H), 7.52 (d, J=6.9, 1H, 7.51–7.36 (m, 3H), 7.28–7.18 (m, 5H), 6.96 (t, J=7.8, 1H), 6.78 (d, J=8.0, 1H), 6.55 (d, J=7.4, 1H), 5.42 (br s, 1H), 5.12 (d, J=9.1, 1H), 5.00 (d, J=9.1, 1H), 4.48–4.39 (m, 5H), 2.83 (m, 1H), 2.72 (dd, J=13.5, 10.7, 1H), 2.20 (s, 3H), 1.99 (s, 3H), 1.46 (s, 3H), 1.27 (s, 3H); HRMS (ESI) m/z calcd for C₃₄H₃₈N₃O₆S (M+H)⁺ 616.2481, found 616.2464; Anal. Calcd for C₃₄H₃₇N₃O₆S: C, 66.32; H, 6.06; N, 6.82. Found: C, 60.06; H, 6.04; N, 6.71.

EXAMPLE A55

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((S)-6,8-difluoro-chroman-4-yl)-amide

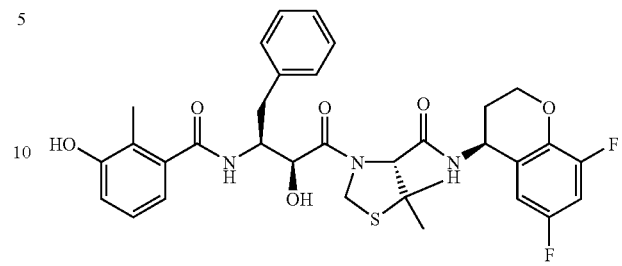

White solid: ¹H NMR (DMSO) δ 9.36 (s, 1H), 8.49 (d, J=8.1, 1H), 8.21 (d, J=8.6, 1H), 7.30–6.50 (m, 10H), 5.34 (d, J=6.2, 1H), 5.16 (d, J=9.3, 1H), 5.10–4.90 (m, 2H), 4.55–4.20 (m, 3H), 2.80–2.60 (m, 2H), 2.10–1.95 (m, 2H), 1.78 (s, 3H), 1.50 (s, 3H), 1.43 (s, 3H), 1.40–1.35 (m, 1H), 1.30–1.20 (m, 1H); HRMS (ESI) m/z calcd for C₃₃H₃₆N₃O₆F₂S (M+H)⁺ 640.2293, found 640.2284.

EXAMPLE A56

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((S)-5-fluoro-indan-1-yl)-amide

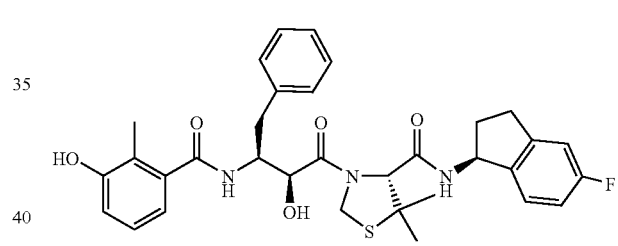

White solid: ¹H NMR (DMSO) δ 9.36 (s, 1H), 8.33 (d, J=7.8, 1H), 8.20 (d, J=8.6, 1H), 7.30–6.50 (m, 1H), 5.37 (d, J=6.9, 1H), 5.30–5.20 (m, 1H), 5.14 (d, J=8.9, 1H), 5.02 (d, J=8.9, 1H), 4.60–4.30 (m, 3H), 3.00–2.60 (m, 4H), 2.50–2.30 (m, 1H), 2.00–1.80 (m, 1H), 1.19 (s, 3H), 1.48 (s, 3H), 1.41 (s, 3H).; HRMS (ESI) m/z calcd for C₃₃H₃₇N₃O₅FS (M+H)⁺ 606.2438, found 606.2441.

EXAMPLE A57

N-{(1S,2S)-1-Benzyl-3-[(R)-5,5-dimethyl-4-(N'-methyl-N'-phenyl-hydrazinocarbonyl)-thiazolidin-3-yl]-2-hydroxy-3-oxo-propyl}-3-hydroxy-2-methyl-benzamide

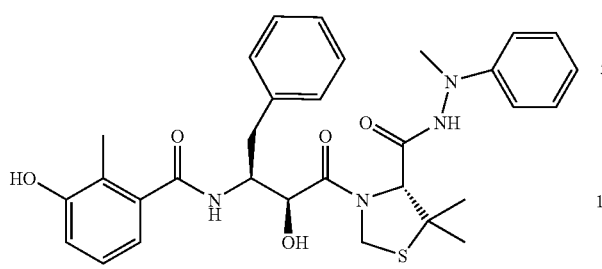

¹H NMR (DMSO-d₆) δ 10.12 (s, 1H), 9.37 (s, 1H), 8.18 (d, 1H, J=8.2), 7.26–7.11 (m, 7H), 6.96–6.87 (m, 3H), 6.77 (d, 1H, J=7.3), 6.68 (t, 1H, J=7.1), 6.54 (d, 1H, J=7.5), 5.55 (d, 1H, J=6.6), 5.16 (d, 1H, J=9.3), 5.04 (d, 1H, J=9.2), 4.48 (d, 1H, J=4.5), 4.42–4.32 (m, 1H), 4.40 (s, 1H), 3.05 (s, 3H), 2.86–2.68 (m, 2H), 1.81 (s, 3H), 1.55 (s, 3H), 1.47 (s, 3H). Exact mass calculated for $C_{31}H_{37}N_4O_5S$ (M+H)⁺ 577.2485, found 577.2469.

EXAMPLE A58

3-[2-Hydroxy-3-(3-hydroxy-2-methyl-benzoylamino)-4-phenyl-butyryl]-5,5-dimethyl-thiiazolidine-4-carboxylic acid (ethyl-morpholino)-amide

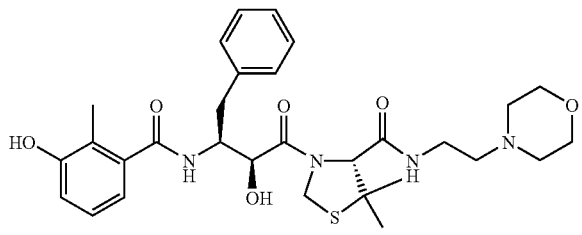

White solid: ¹H NMR (DMSO-d₆) δ 9.81, (s 1H), 9.40 (s, 1H), 8.18 (s, 1H), 7.41–6.91 (m, 10H), 6.62 (d, J=7.7, 1H), 5.12 (q, J=9.3, 1H), 4.44–4.35 (m, 3H), 4.08–2.78 (m, 12H), 2.81–2.67 (m, 2H), 1.88 (s, 3H), 1.49 (s, 3H), 1.34 (s, 3H); Anal. ($C_{30}H_{40}N_4O_6S \cdot 1.0H_2O \cdot 0.5TFA$) calculated C, (56.13); H, (6.45); N, (8.42). found C, (56.31); H, (6.55); N, (7.83). HRMS (ESI) m/z calcd for 585.2740, found 585.2747.

EXAMPLE A59

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2,2-difluoro-benzo[1,3]dioxol-5-ylmethyl)-amide

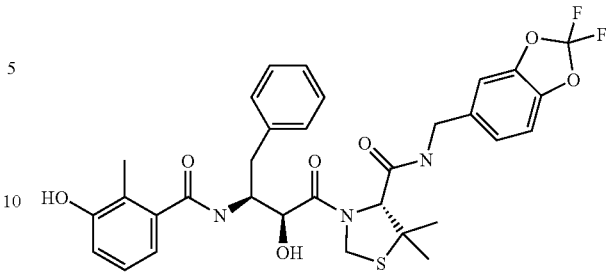

¹H NMR (DMSO-d₆) δ 9.36 (s, 1H), 8.55 (t, J=5.8, 1H), 8.14 (d, J=8.4, 1H), 7.29–7.11 (m, 8H), 6.94 (t, J=7.8, 1H), 6.77 (d, J=7.9, 1H), 6.54 (d, J=7.4, 1H), 5.58 (d, J=8.2, 1H), 5.17 (d, J=9.2, 1H), 5.02 (d, J=9.2, 1H), 4.49–4.39 (m, 3H), 4.43 (s, 1H), 4.21 (dd, J=5.4, 15.3, 1H), 2.83 (m, 1H), 2.71 (dd, J=13.5, 10.7, 1H), 2.20 (s, 3H), 1.51 (s, 3H), 1.34 (s, 3H); HRMS (ESI) m/z calcd for $C_{32}H_{34}F_2N_3O_7S$ (M+H)⁺ 642.2086, found 642.2099; Anal. Calcd for $C_{32}H_{33}F_2N_3O_7S$: C, 59.90; H, 5.18; N, 6.55. Found: C, 60.01; H, 5.27; N, 6.29.

EXAMPLE A60

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (1H-benzoimidazol-2-ylmethyl)-amide

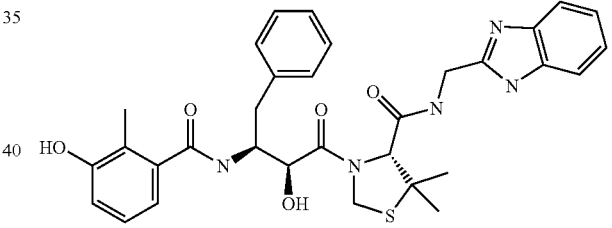

¹H NMR (DMSO-d₆) δ 9.37 (s, 1H), 8.72 (t, J=5.5, 1H), 8.18 (d, J=8.3, 1H), 7.33–7.11 (m, 10H), 6.95 (t, J=7.9, 1H), 6.79 (d, J=8.1, 1H), 6.57 (d, J=7.1, 1H), 5.54 (d, J=6.6, 1H), 5.14 (d, J=9.3, 1H), 5.05 (d, J=9.3, 1H), 4.75 (m, 1H), 4.55–4.28 (m, 3H), 4.09 (dd, J=10.4, 5.2, 1H), 2.86 (m, 1H), 2.72 (dd, J=13.5, 10.7, 1H), 1.82 (s, 3H), 1.53 (s, 3H), 1.36 (s, 3H); HRMS (ESI) m/z calcd for $C_{32}H_{36}N_5O_5S$ (M+H)⁺ 602.2437, found 602.2424; Anal. Calcd for $C_{32}H_{35}N_5O_5S \cdot 0.4H_2O$: C, 63.12; H, 5.93; N, 11.50. Found: C, 63.02; H, 5.99; N, 11.49.

EXAMPLE A61

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (1H-indol-2-ylmethyl)-amide

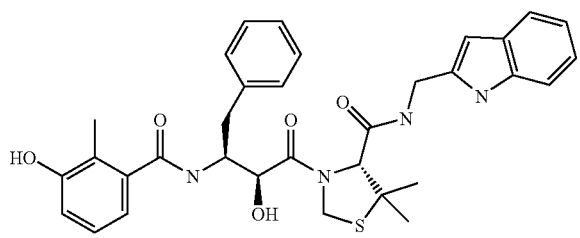

¹H NMR (DMSO-d₆) δ 10.74 (s, 1H), 9.39 (s, 1H), 8.46 (t, J=4.9, 1H), 8.17 (d, J=8.3, 1H), 7.45 (d, J=7.7, 1H), 7.37 (t, J=7.9, 2H), 7.26 (t, J=7.1, 2H), 7.18 (d, J=7.2, 1H), 7.10 (t, J=7.2, 1H), 6.99 (d, J=7.6, 1H), 6.95 (d, J=7.5, 1H), 6.79 (d, J=7.7, 1H), 6.57 (d, J=7.1, 1H), 6.41 (s, 1H), 5.49 (br s, 1H), 5.15 (d, J=9.1, 1H), 5.02 (d, J=9.2, 1H), 4.69–4.39 (m, 4H), 2.86 (m, 1H), 2.74 (dd, J=13.5, 10.6, 1H), 1.83 (s, 3H), 1.50 (s, 3H), 1.38 (s, 3H); HRMS (ESI) m/z calcd for $C_{33}H_{37}N_4O_5S$ (M+H)⁺ 601.2485, found 605.2460.

EXAMPLE A62

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (benzofuran-2-ylmethyl)-amide

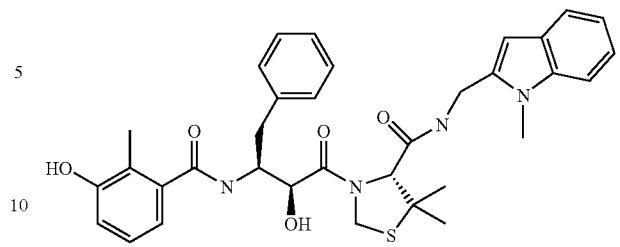

¹H NMR (DMSO-d₆) δ 9.39 (s, 1H), 8.46 (t, J=4.9, 1H), 8.17 (d, J=8.3, 1H), 7.45 J=7.7, 1H), 7.37 (t, J=7.9, 2H), 7.26 (t, J=7.1, 2H), 7.18 (d, J=7.2, 1H), 7.10 (t, J=7.2, 1H), 6.99 (d, J=7.6, 1H), 6.95 (d, J=7.5, 1H), 6.79 (d, J=7.7, 1H), 6.57 (d, J=7.1, 1H), 6.41 (s, 1H), 5.49 (br s, 1H), 5.15 (d, J=9.1, 1H), 5.02 (d, J=9.2, 1H), 4.66 (dd, J=15.5, 6.4, 1H), 4.49 (s, 1H), 4.44 (m, 1H), 4.34 (dd, J=15.5, 4.2, 1H), 3.67 (s, 3H), 2.86 (m, 1H), 2.74 (dd, J=13.5, 10.6, 1H), 1.83 (s, 3H), 1.50 (s, 3H), 1.38 (s, 3H); HRMS (ESI) m/z calcd for $C_{34}H_{39}N_4O_5S$ (M+H)⁺ 615.2641, found 615.2628; Anal. Calcd for $C_{34}H_{38}N_4O_5S\cdot 0.3H_2O$: C, 65.85; H, 6.27; N, 9.03. Found: C, 65.80; H, 6.23; N, 8.91.

EXAMPLE A64

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (3-methyl-benzofuran-2-ylmethyl)-amide

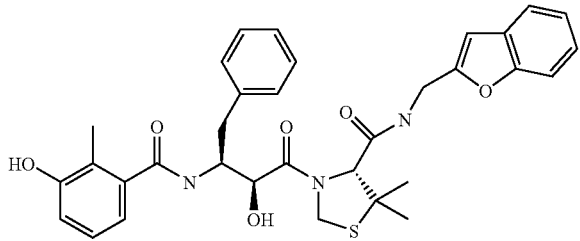

¹H NMR (DMSO-d₆) δ 9.37 (s, 1H), 8.55 (t, J=5.5, 1H), 8.15 (d, J=8.3, 1H), 7.52 (d, J=6.9, 1H), 7.51–7.36 (m, 3H), 7.28–7.18 (m, 5H), 6.96 (t, J=7.8, 1H), 6.78 (d, J=8.0, 1H), 6.61 (s, 1H), 6.55 (d, J=7.4, 1H), 5.42 (br s, 1H), 5.12 (d, J=9.1, 1H), 5.00 (d, J=9.1, 1H), 4.48–4.39 (m, 5H), 2.83 (m, 1H), 2.72 (dd, J=13.5, 10.7, 1H), 1.99 (s, 3H), 1.46 (s, 3H), 1.27 (s, 3H); HRMS (ESI) m/z calcd for $C_{33}H_{36}N_3O_6S$ (M+H)⁺ 602.2325, found 602.2326.

EXAMPLE A63

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (1-methyl-1H-indol-2-ylmethyl)-amide

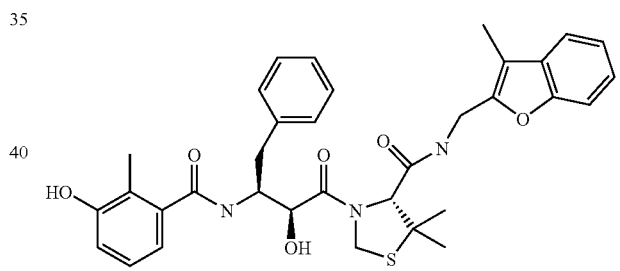

¹H NMR (DMSO-d₆) δ 9.37 (s, 1H), 8.55 (t, J=5.5, 1H), 8.15 (d, J=8.3, 1H), 7.52 (d, J=6.9, 1H, 7.51–7.36 (m, 3H), 7.28–7.18 (m, 5H), 6.96 (t, J=7.8, 1H), 6.78 (d, J=8.0, 1H), 6.55 (d, J=7.4, 1H), 5.42 (br s, 1H), 5.12 (d, J=9.1, 1H), 5.00 (d, J=9.1, 1H), 4.48–4.39 (m, 5H), 2.83 (m, 1H), 2.72 (dd, J=13.5, 10.7, 1H), 2.20 (s, 3H), 1.99 (s, 3H), 1.46 (s, 3H), 1.27 (s, 3H); HRMS (ESI) m/z calcd for $C_{34}H_{38}N_3O_6S$ (M+H)⁺ 616.2481, found 616.2464; Anal. Calcd for $C_{34}H_{37}N_3O_6S$: C, 66.32; H, 6.06; N, 6.82. Found: C, 60.06; H, 6.04; N, 6.71.

EXAMPLE A64

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (3-methyl-benzofuran-2-ylmethyl)-amide

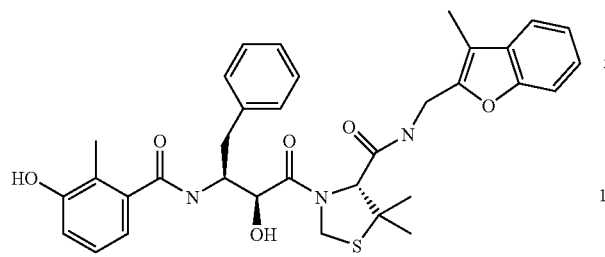

<sup>1</sup>H NMR (DMSO-d$_6$) δ 9.37 (s, 1H), 8.55 (t, J=5.5, 1H), 8.15 (d, J=8.3, 1H), 7.52 (d, J=6.9, 1H, 7.51–7.36 (m, 3H), 7.28–7.18 (m, 5H), 6.96 (t, J=7.8, 1H), 6.78 (d, J=8.0, 1H), 6.55 (d, J=7.4, 1H), 5.42 (br s, 1H), 5.12 (d, J=9.1, 1H), 5.00 (d, J=9.1, 1H), 4.48–4.39 (m, 5H), 2.83 (m, 1H), 2.72 (dd, J=13.5, 10.7, 1H), 2.20 (s, 3H), 1.99 (s, 3H),

EXAMPLE A65

3-[2-Hydroxy-3-(3-hydroxy-2-methyl-benzoylamino)-4-phenyl-butyryl]-5,5-dimethyl-thiiazolidine-4-carboxylic acid (propyl-morpholino)-amide

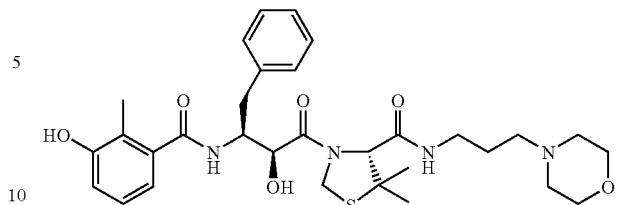

White solid: <sup>1</sup>H NMR (DMSO-d$_6$) δ 9.81, (s 1H), 9.40 (s, 1H), 8.18 (s, 1H), 7.41–6.91 (m, 10H), 6.62 (d, J=7.7, 1H), 5.12 (dd, J=9.3, 1H), 4.44–4.35 (m, 3H), 4.08–2.78 (m, 13H), 2.81–2.67 (m, 2H), 1.88 (s, 3H), 1.49 (s, 3H), 1.34 (s, 3H); Anal. (C$_{31}$H$_{42}$N$_4$O$_6$S.0.18H$_2$O) calculated C, (51.56); H, (5.53); N, (9.36). found C, (52.05); H, (5.95); N, (6.51). HRMS (ESI) m/z calcd for 599.2902, found 599.2903.

General Method B

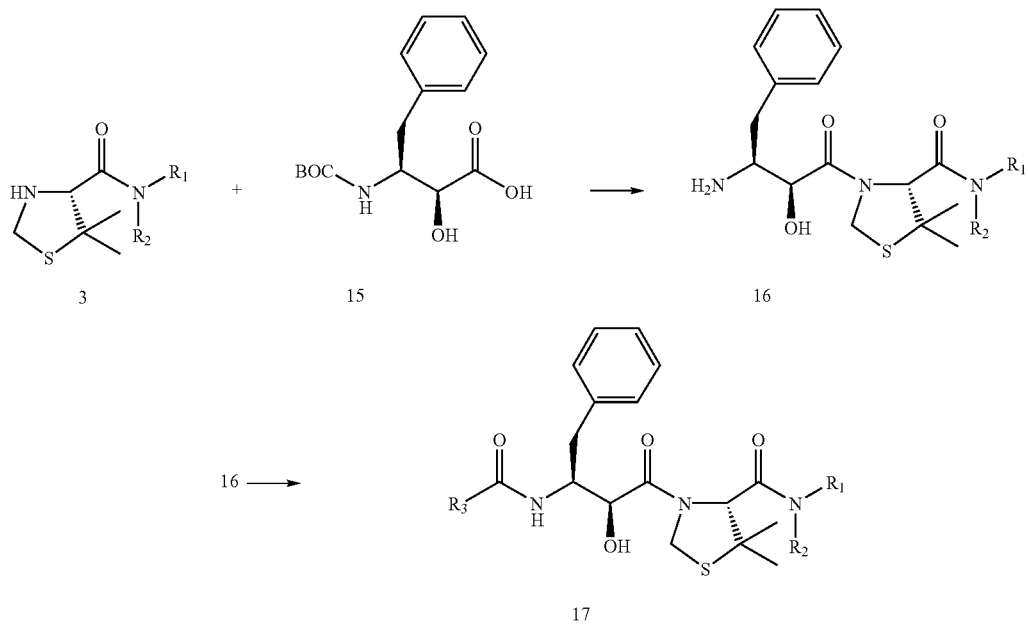

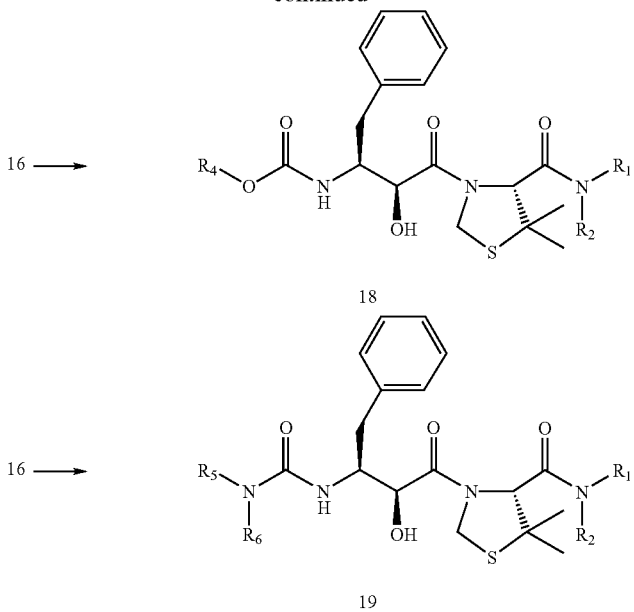

Amides of the general structure 3 (synthesized in the same manor as in the Methods A section) are coupled to boc-protected acid 15, and exposed to methane sulfonic acid to yield amines 16. Subjecting amines 16 to the reaction conditions depicted yielded a series of amides 17, carbamates 18, and ureas 19.

Synthesis of Amines of the General Type 16.

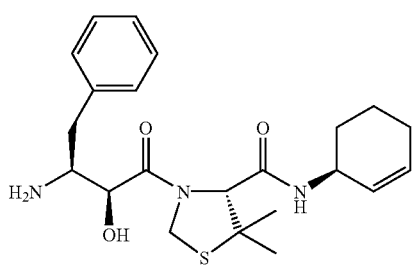

The title compound was prepared as follows. (R)-5,5-Dimethyl-thiazolidine-3,4-dicarboxylic acid 3-tert-butyl ester 1 (1.95 g, 7.47 mmol) was dissolved in EtOAc (25 mL) and cooled to 0° C. Diphenyl chlorophosphate (1.71 mL, 8.23 mmol) was added followed by TEA (1.14 mL, 8.23 mmol). The reaction was stirred at 0° C. for 1 h, and treated with (S)-Cyclohex-2-enylamine (0.8 g, 8.23 mmol). The reaction mixture was stirred at room temperature overnight, then partitioned between 1N HCl (25 mL) and EtOAc (30 mL). The organic layer was washed with saturated NaHCO$_3$, brine, dried over Na$_2$SO$_4$ and concentrated to a yellow oil. The resulting oil (2.54 g, 7.47 mmol) was dissolved in EtOAc (30 mL) and then cooled to 0° C. Methanesulfonic acid (2.27 mL, 33.62 mmol) was added and the solution was stirred at 0° C. for 15 minutes, then at room temperature for 4 h. The mixture was re-cooled to 0° C. and quenched with 10% Na$_2$CO$_3$ (30 mL) then extracted with EtOAc (30 mL). Organic layer was washed with brine, dried over Na$_2$SO$_4$ and concentrated in vacuo to give a yellow oil 3. The resulting yellow oil (1.86 g, 7.74 mmol) was dissolved in EtOAc (77 mL). BOC-AHPBA 4 (2.29 g, 7.74 mmol) was added followed by HOBt (1.05 g, 7.74 mmol). The mixture was stirred at room temperature 1 h, then cooled to 0° C. DCC (1.60 g, 7.74 mmol) was slowly added as solution in EtOAc (30 mL). The mixture was allowed to gradually warm to room temperature and stirred overnight. The mixture was filtered and the filtrate was washed with 1N HCl (40 mL), saturated NaHCO$_3$ (40 mL), brine (40 mL), dried over Na$_2$SO$_4$ and concentrated to give a crude white solid (contaminated with DCU). The DCU was removed by flash chromatography (30% to 50% EtOAc in hexanes) to provide a white solid (4 g, 7.73 mmol), which was dissolved in EtOAc (30 mL) and then cooled to 0° C. Methanesulfonic acid (2.35 mL, 34.76 mmol) was added and the solution was stirred at 0° C. for 15 minutes, then at room temperature for 3 h. The mixture was re-cooled to 0° C. and quenched with 10% Na$_2$CO$_3$ (35 mL) then extracted with EtOAc (30 mL). Organic layer was washed with brine, dried over Na$_2$SO$_4$ and concentrated in vacuo to give a material which was recrystalized from 60% EtOAc in hexanes to provide B1 (2.41 g, 80%) as a white solid. $^1$H NMR (DMSO-d$_6$) δ 8.21 (d, J=8.1, 1H), 7.31–7.17 (m, 5H), 5.80 (d, J=5.6, 1H), 5.52–5.48 (m, 2H), 5.30–5.25 (m, 2H), 4.89 (s, 2H), 4.26 (s, 1H), 4.21–4.00 (m, 3H), 3.15–2.70 (m, 2H), 2.50–2.00 (m, 2H), 2.00–1.00 (m, 4H), 1.49 (s, 3H), 1.31 (s, 3H); Anal. Calcd for C$_{22}$H$_{31}$N$_3$O$_3$S: C, 63.28; H, 7.48; N, 10.06. Found: C, 63.40; H, 7.20; N, 9.98.

The following amines 16b–k were prepared by the specific method outlined above using the requisite amine.

101

16b

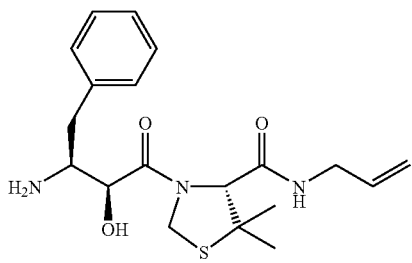

¹H NMR (DMSO-d₆) δ 8.36 (t, J=6.0, 1H), 7.36–7.14 (m, 5H), 5.70 (m, 1H), 5.34 (s br, 1H), 5.12 (d, J=17.0, 1H), 4.96–4.88 (m, 3H), 4.34 (s, 1H), 4.10 (d, J=7.0, 1H), 3.80–3.55 (m, 2H), 3.06 (d, J=13.0, 1H), 2.87 (t, J=9.0, 1H), 20.38 (dd, J=13.0, 10.0, 1H), 1.52 (s, 3H), 1.33 (s, 3H).

16c

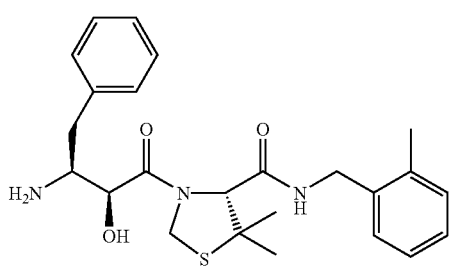

¹H NMR (DMSO-d₆) δ 8.69 (t, J=5.3, 1H), 7.34–7.14 (m, 5H), 5.34 (s br, 1H), 4.90 (s, 2H), 4.29 (s, 1H), 4.08 (d, J=7.0, 1H), 3.90–3.70 (m, 2H), 3.07 (dd, J=13.4, 2.5, 1H), 2.96 (t, J=2.6, 1H), 2.88, (ddd, J=9.8, 8.0, 2.8, 1H), 2.37 (dd, J=13.2, 9.9, 1H), 1.50 (s, 3H), 1.32 (s, 3H).

16e

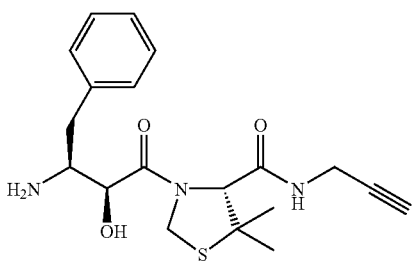

102

¹H NMR (DMSO-d₆) δ 8.74 (t, J=5.4, 1H), 7.36 (m, 1H), 7.34–7.14 (m, 5H), 6.24 (m, 1H), 6.16 (d, J=3.3, 1H), 5.32 (s br, 1H), 4.90 (s, 2H), 4.32 (s, 1H), 4.30–4.10 (m, 2H), 4.07 (d, J=9.0, 1H), 3.09 (dd, J=13.1, 2.6, 1H), 2.80 (ddd, J=10.0, 8.0, 2.7, 1H), 2.33 (dd, J=13.1, 10.0, 1H), 1.50 (s, 3H), 1.28 (s, 3H).

16f

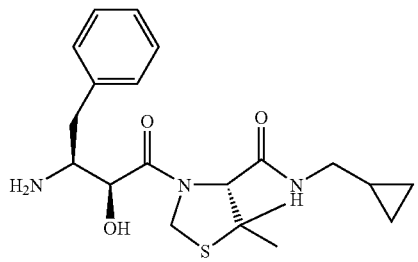

¹H NMR (DMSO-d₆) δ 8.36 (t, J=5.4, 1H), 7.33–7.15 (m, 5H), 5.30 (s br, 1H), 4.90 (s, 2H), 4.30 (s, 1H), 4.09 (d, J=7.9, 1H), 3.06 (dd, J=13.2, 2.0, 1H), 3.02–2.77 (m, 3H), 2.47 (dd, J=13.4, 10.1, 1H), 1.50 (s, 3H), 1.34 (s, 3H), 0.80 (m, 1H), 0.28 (m, 2H), 0.06 (m, 2H).

16g

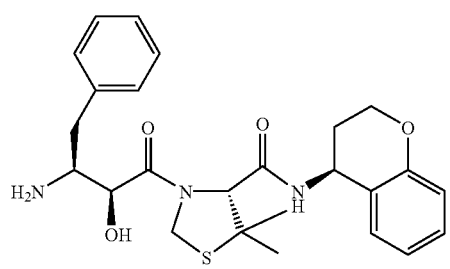

¹H NMR (DMSO-d₆) δ 8.59 (d, J=7.3, 1H), 7.29–7.20 (m, 5H), 7.04 (d, J=6.8, 1H), 6.89 (d, J=7.2, 1H), 6.76–6.72 (m, 1H), 6.53–6.46 (m, 1H), 5.32 (d, J=5.9, 1H), 4.89 (s, 2H), 4.89–4.80 (m, 1H), 4.24 (s, 1H), 4.17–3.90 (m, 2H), 3.08–3.04 (m, 2H), 2.20–1.70 (m, 4H), 1.52 (s, 3H), 1.35 (s, 3H); Anal. Calcd for C₂₅H₃₁N₃O₄S: C, 63.94; H, 6.65; N, 8.95. Found: C, 63.76; H, 6.60; N, 8.98.

16h

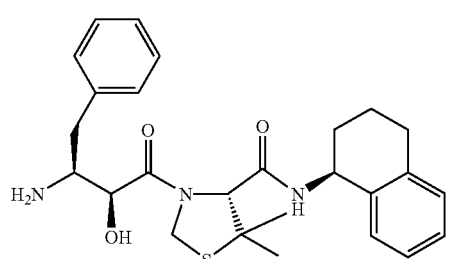

¹H NMR (DMSO-d₆) δ 8.37 (d, J=7.3, 1H), 7.30–6.66 (m, 9H), 5.29 (d, J=8.2, 1H), 4.86 (s, 2H), 4.86–4.80, (m, 1H), 4.23 (s, 1H), 4.05–3.97 (m, 1H), 3.08–3.04 (m, 1H), 2.70–2.40 (m, 4H), 2.20–2.00 (m, 2H), 1.70–1.55 (m, 4H), 1.52 (s, 3H), 1.36 (s, 3H); Anal. Calcd for C₂₆H₃₃N₃O₃S: C, 66.78; H, 7.11; N, 8.99. Found: C, 66.90; H, 7.01; N, 8.98.

16d

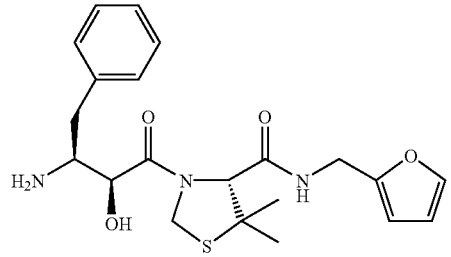

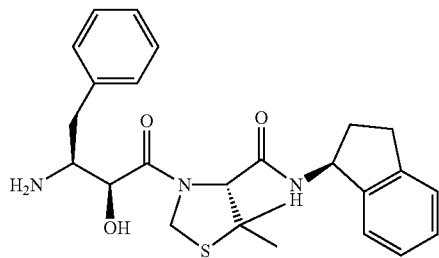
16i
¹H NMR (DMSO-d₆) δ 8.47 (d, J=8.6, 1H), 7.28–6.82 (m, 9H), 5.33 (d, J=5.9, 1H), 5.25–5.19 (m, 1H), 4.91 (d, J=9.2, 1H), 4.85 (d, J=9.2, 1H), 4.29 (s, 1H), 4.03 (d, J=8.1, 1H), 3.08–3.05 (m, 1H), 2.77–2.60 (m, 2H), 2.30–2.10 (m, 2H), 1.70–1.50 (m, 2H), 1.52 (s, 3H), 1.36 (s, 3H); Anal. Calcd for $C_{25}H_{31}N_3O_3S$: C, 66.20; H, 6.89; N, 9.26. Found: C, 66.35; H, 7.01; N, 8.98.
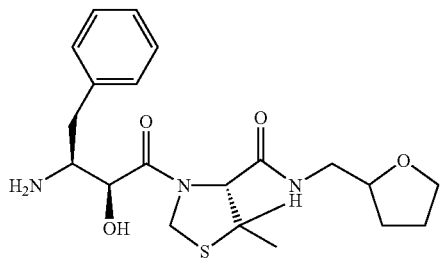
16j
¹H NMR (DMSO-d₆) δ 8.35 (t, J=5.7, 1H), 7.31–7.16 (m, 5H), 5.24 (d, J=8.1, 1H), 4.92 (d, J=9.2, 1H), 4.88 (d, J=9.2, 1H), 4.31 (s, 1H), 4.09 (m, 1H), 3.83–3.51 (m, 2H), 3.42–3.31 (m, 1H), 3.23–3.07 (m, 2H), 2.99–2.91 (m, 1H), 2.86–2.79 (m, 1H), 2.34 (dd, J=13.0, 10.1, 1H), 1.80–1.42 (m, 6H), 1.50 (s, 3H), 1.31 (s, 3H).
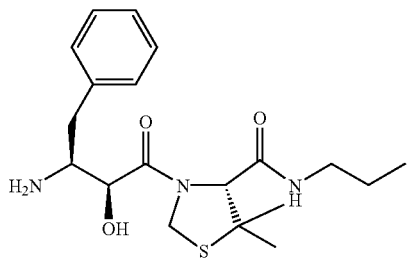
16k
¹H NMR (DMSO-d₆) δ 8.13 (t, J=5.4, 1H), 7.35–7.15 (m, 5H), 5.28 (d, J=8.1, 1H), 4.79 (m, 2H), 4.27 (s, 1H), 4.07 (t, J=7.1, 1H), 3.10–2.71 (m, 4H), 2.37 (dd, J=13.2, 9.9, 1H), 1.49 (s, 3H), 1.34 (m, 2H), 1.33 (s, 3H), 0.77 (t, J=7.4, 3H).
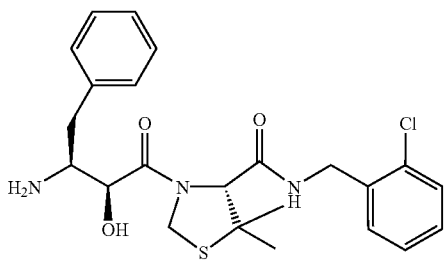
16l
Isolated yield: 84%; MS (APCI, m/z): 461, 463 (M+H)
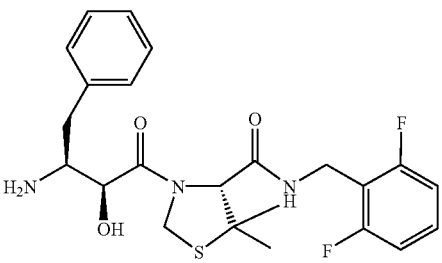
16m
Isolated yield: 93%; MS (APCI, m/z): 464 (M+H).
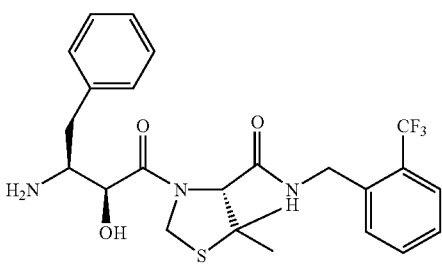
16n
Isolated yield: 86%; MS (APCI, m/z): 496 (M+H).
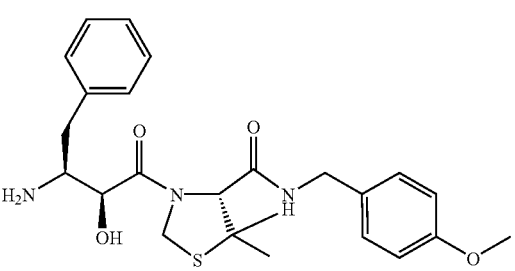
16o
Isolated yield: 87%. MS-APCI (m/z+): 458.

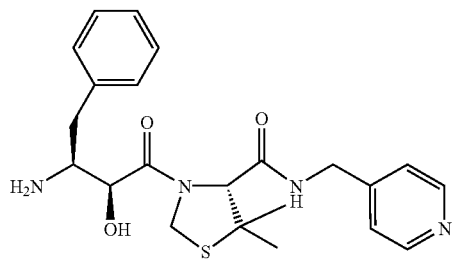

Isolated yield: 45%. MS-APCI (m/z+): 341, 429.

Synthesis of Final Products of the General Type 17, 18 and 19 from 16a–k, General Methods:

Carbamate formation #1—The corresponding amine, of general structure 16, triethylamine (2 eq.) and chloroformate (1.1–1.2 eq.) were taken in dichloromethane and stirred at room temperature under nitrogen. (1.5 hr to overnight). The solvent was then removed in vacuo and the resulting residue subjected to flash silica gel chromatography or preparative HPLC to afford the desired product.

Carbamate formation #2—The corresponding alcohol was treated with phosgene (1.7 eq.) in toluene followed by diisopropylethylamine (1.1 eq.) and the amine of general structure 16. The solvent was then removed in vacuo and the resulting residue subjected to flash silica gel chromatography or preparative HPLC to afford the desired product.

Amide formation—To a solution of acid, amine 16 and HOBT in $CH_2Cl_2$ was added EDC and the solution stirred overnight at room temperature. The solution was concentrated in vacuo and the residue dissolved in ethyl acetate and a small portion of water. The solution was washed with saturated $NH_4Cl$ or 0.5N HCl (2×), saturated $NaHCO_3$ (2×), brine (1×), dried with $MgSO_4$ and concentrated in vacuo. The resulting residue subjected to flash silica gel chromatography or preparative HPLC to afford the desired product.

Urea formation #1—The corresponding amine and isocyanate (1.1–1.2 eq.) were taken in dichloromethane and stirred at room temperature under nitrogen. (1.5 hr to overnight). The solvent was then removed in vacuo and the resulting residue subjected to flash silica gel chromatography or preparative HPLC to afford the desired product.

Urea formation #2—The corresponding amine was dissolved in $CH_2Cl_2$ and treated with diisopropylethylamine (1.5 eq.) and phosgene (1 eq., 20% soln. in toluene) at −78° C. The resulting solution was warmed to room temperature and treated with the amine of general structure 16. The resulting residue subjected to flash silica gel chromatography or preparative HPLC to afford the desired product.

Specific Carbamate Synthesis

EXAMPLE B1

{1-Benzyl-3-[5,5-dimethyl-4-(2-methyl-benzylcarbamoyl)-thiazolidin-3-yl]-2-hydroxy-3-oxo-propyl}-carbamic acid tetrahydropfuran-3-yl-ester

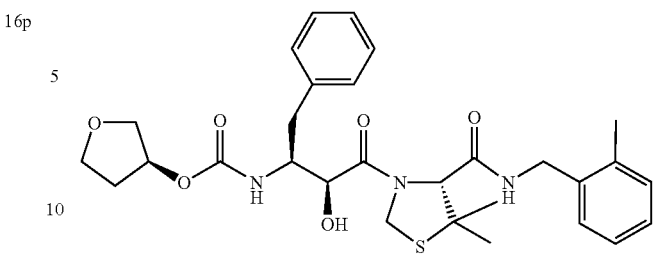

(S)-(+)-3-Hydroxytetrahydrofuran (0.11 mL, 1.37 mmol) was dissolved in toluene (1 mL) and cooled to 0° C. with magnetic stirring. To this was added Phosgene as a 20% solution in toluene (1.2 mL, 2.34 mmol). The resulting solution was stirred for 24 h at 23° C. then concentrated. The residue was dissolved in dry THF (3 mL) and treated with Diisopropylethylamine (0.25 mL, 1.40 mmol). 16c was added as a slurry in THF (0.3 g, 0.73 mmol) and resulting amber solution was stirred at 23° C. for 3 h. The solution was diluted with EtOAc (10 mL) and washed with 10% citric acid (25 mL) dried over $Na_2SO_4$, filtered, and concentrated to a white solid.

$^1$H NMR ($CDCl_3$) δ 7.23–7.09 (m, 9H), 6.79 (s br, 1H), 5.90 (s br, 1H), 5.16–3.63 (m, 17H), 1.55 (s, 3H), 1.50 (s, 3H), 1.45 (s, 3H); HRMS (ESI) m/z calcd for $C_{29}H_{37}N_3O_6SNa$ (M+Na)$^+$ 578.2301, found 578.2288; Anal. Calcd for $C_{29}H_{37}N_3O_6S\cdot 1H_2O$: C, 60.71; H, 6.85; N, 7.32. Found: C, 60.97; H, 6.47; N, 6.91.

Specific Amide Synthesis

EXAMPLE B2

1,2,3,4-Tetrahydro-quinoline-5-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

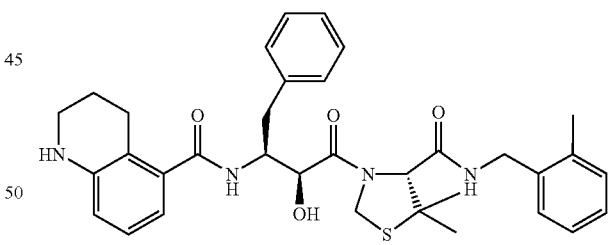

The amine 16c (0.21 g, 0.48 mmol) and 1,2,3,4-Tetrahydroquinoline-5-carboxylic acid (0.085 g, 0.48 mmol) were dissolved in dry $CH_2Cl_2$ (5 mL) at 23° C. with magnetic stirring. The solution was treated sequentially with EDC (0.18 g, 0.96 mmol), HOBt (0.13 g, 0.96 mmol), and Triethylamine (0.14 mL, 0.96 mmol). The result was stirred for 24 h and then poured into $H_2O$ (25 mL). The mixture was extracted with EtOAc (2×25 mL). The combined organics were washed sequentially with saturated $NaHCO_3$ (1×50 mL), 0.5N HCl (1×50 mL), and $H_2O$ (1×50 mL). The result was dried over $Na_2SO_4$, filtered, and concentrated. The residue was purified by flash column chromatography (40%–60% EtOAc in hexanes) to yield the title compound as a pale yellow solid (0.21 g, 72%).

$^1$H NMR (DMSO-d$_6$) δ 8.32 (t, J=5.1, 1H,), 8.04 (d, J=8.4, 1H,), 7.33–7.10 (m, 9H), 6.79 (t, J=7.7, 1H,), 6.41 (d, J=8.1, 1H), 6.22 (d, J=7.3, 1H), 5.71 (s br, 1H), 5.46 (d, J=6.8, 1H), 5.14 (d, J=9.2, 1H), 5.01 (d, J=9.2, 1H), 4.48–4.37 (m, 4H), 4.11 (dd, J=15.0, 4.8, 1H), 3.07 (m, 2H), 2.84–2.67 (m, 2H), 2.32–2.26 (m, 2H), 2.26 (s, 3H), 1.59 (m, 2H), 1.49 (s, 3H), 1.35 (s, 3H); HRMS (ESI) m/z calcd for C$_{34}$H$_{40}$N$_4$O$_4$SNa (M+Na)$^+$ 623.2662, found 623.2669; Anal. Calcd for C$_{34}$H$_{40}$N$_4$O$_4$S: C, 66.97; H, 6.78; N, 9.18. Found: C, 66.97; H, 6.73; N, 9.12.

Specific Urea Synthesis

EXAMPLE B3

3-(2-hydroxy-3-{[1-(3-hydroxy-pyrrolidin-yl)-methanoyl]-amino}-4-phenyl-butanoyl)-5,5-dimethyl-thiazolidine-4-carboxylic acid-2-methyl-benzylamide

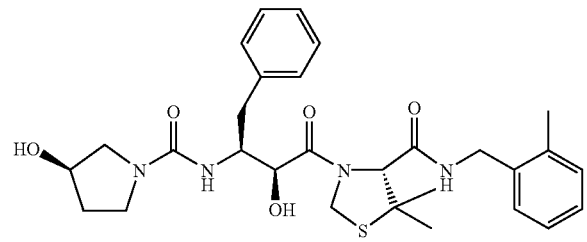

(R)-Pyrrolidin-3-ol (0.21 g, 2.40 mmol) was dissolved in dry CH$_2$Cl$_2$ (15 mL) and cooled to –78° C. under argon with magnetic stirring. To this solution was added Diisopropylethylamine (0.63 mL, 3.63 mmol) followed by Phosgene as a 20% solution in toluene (1.2 mL, 2.40 mmol). The resulting yellow solution was stirred for 20 min at –78° C. then allowed to warm to room temperature. The solution was concentrated and re-dissolved in dry CH$_2$Cl$_2$ (5 mL) and THF (5 mL). To this was added Diisopropylethylamine (0.31 mL, 1.81 mmol) followed by 16c. The result was stirred for 16 h at 23° C. then diluted with EtOAc (50 mL). The mixture was washed sequentially with 10% citric acid (1×50 mL), saturated NaHCO$_3$ (1×50 mL), H$_2$O (1×50 mL). The organics were dried over Na$_2$SO$_4$, filtered, and concentrated. The residue was purified by flash column chromatography (5% MeOH in EtOAc) to yield the title compound (0.12 g, 18%) as a white foam.

$^1$H NMR (DMSO-d$_6$) δ 8.38 (t, J=5.7, 1H), 7.34–7.09 (m, 10H), 5.99 (d, J=8.3, 1H), 5.04 (d, J=9.5, 1H), 4.96 (d, J=9.5, 1H), 4.49 (s, 1H), 4.48–4.38 (m, 3H), 4.22–3.83 (m, 4H), 3.29–3.04 (m, 3H), 2.77–2.70 (m, 2H), 2.28 (s, 3H), 1.52 (s, 3H), 1.32 (s, 3H), 1.82–1.69 (m, 2H); HRMS (ESI) m/z calcd for C$_{29}$H$_{38}$N$_4$O$_5$SNa (M+Na)$^+$ 577.2455, found 577.2440; Anal. Calcd for C$_{29}$H$_{38}$N$_4$O$_5$S.2H$_2$O: C, 58.96; H, 7.17; N, 9.48; S, 5.43. Found: C, 58.90; H, 6.40; N, 9.23; S, 5.24.

The following examples were prepared by the corresponding specific method outlined above using the requisite P2 fragment.

EXAMPLE B4

3-{2-Hydroxy-4-phenyl-3-[2-(2H-[1,2,4t]triazol-3-ylsufanyl)-ethanoylamino]-butanoyl}5,5-dimethyl-thiazolidine-4-carboxylic acid-2-methyl-benzylamide

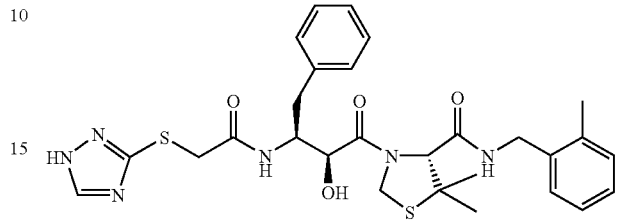

$^1$H NMR (DMSO-d$_6$) δ 14.00 (s br, 1H), 8.54 (s br, 1H), 8.35 (t, J=5.7, 1H), 8.30 (s br, 1H), 7.32–7.06 (m, 10H), 4.98 (d, J=9.2, 1H), 4.92 (d, J=9.2, 1H), 4.50 (s, 1H), 4.43–4.36 (m, 2H), 4.12 (m, 2H), 3.77 (s br, 2H), 2.76–2.58 (m, 2H), 2.26 (s, 3H), 1.50 (s, 3H), 1.32 (s, 3H); HRMS (ESI) m/z calcd for C$_{28}$H$_{34}$N$_6$O$_4$S$_2$Na (M+Na)$^+$ 605.1975, found 605.1988; Anal. Calcd for C$_{28}$H$_{34}$N$_6$O$_4$S$_2$.0.25H$_2$O: C, 57.27; H, 5.92; N, 14.31; S, 10.92. Found: C, 57.21; H, 5.97; N, 14.10; S, 10.71.

EXAMPLE B5

{(1S,2S)-1-Benzyl-3-[(R)-5,5-dimethyl-4-(2-methyl-benzylcarbamoyl)-thiazolidin-3-yl]-2-hydroxy-3-oxo-propyl}-carbamic acid (R)-2-isopropyl-tetrahydro-thiophen-3-yl ester

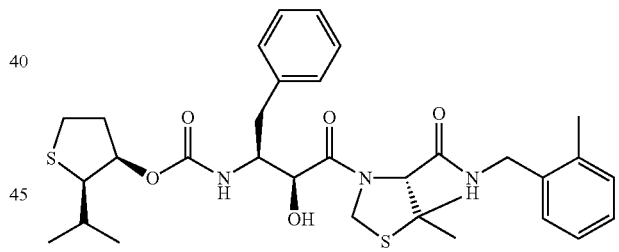

$^1$H NMR (DMSO-d$_6$) δ 8.38 (s br, 2H), 7.42–7.09 (m, 9H), 5.12 (s, 1H), 4.99 (s, 2H), 4.52–3.80 (m, 5H), 3.19–2.79 (m, 6H), 2.29 (s, 3H), 1.99–1.71 (m, 3H), 1.51 (s, 3H), 1.39 (s, 3H), 0.99 (m, 6H); Anal. Calcd for C$_{32}$H$_{43}$N$_3$O$_5$S$_2$: C, 62.61; H, 7.06; N, 6.85. Found: C, 62.45; H, 6.84; N, 7.04.

EXAMPLE B6

2,3-Dihydro-1H-indole-4-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

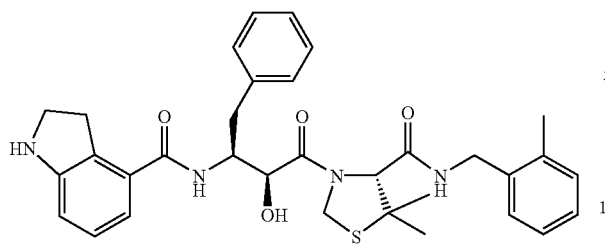

Pale yellow solid; IR (neat, cm$^{-1}$) 3417, 1644, 1529, 1453, 1114; $^1$H NMR (DMSO-d$_6$) δ 8.35 (t, J=5.1, 1H), 8.06 (d, J=8.6, 1H), 7.34–7.11 (m, 9H), 6.91 (t, J=7.7, 1H), 6.78 (d, J=5.5, 1H), 6.70 (d, J=7.5, 1H), 6.53 (d, J=7.7, 1H), 5.58 (s, 1H), 5.10 (d, J=9.2, 1H), 5.00 (d, J=9.2, 1H), 4.51–4.36 (m, 4H), 4.13 (dd, J=15.0, 4.6, 1H), 3.34–3.29 (m, 2H), 2.80–2.00 (m, 4H), 2.25 (s, 3H), 1.50 (s, 3H), 1.35 (s, 3H); HRMS (ESI) m/z calcd for C$_{33}$H$_{38}$N$_4$O$_4$SNa (M+Na)$^+$ 609.2506, found 609.2485.

EXAMPLE B7

(R)-3-{(2S,3S)-3-[2-(2,6-Dimethylphenoxy)-ethanoylamino]-2-hydroxy-4-phenyl-butanoyl}-5,5-dimethylthiazolidine-4-carboxylic acid 2-methyl-benzylamide

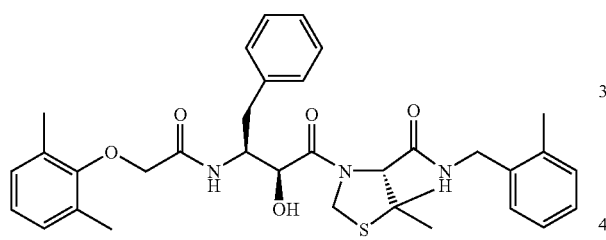

EXAMPLE B8

1H-Indole-4-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

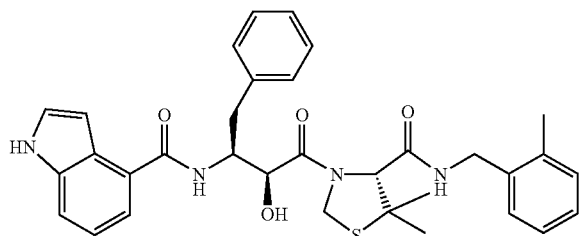

White solid; IR (neat, cm$^{-1}$) 3422, 1642, 1520, 1349, 1114; $^1$H NMR (DMSO-d$_6$) δ 11.24 (s, 1H), 8.36 (t, J=6.1, 1H), 8.18 (d, J=8.2, 1H), 7.50 (d, J=8.1, 1H), 7.51–7.06 (m, 12H), 6.71 (s, 1H), 5.48 (d, J=6.4, 1H), 5.11 (d, J=9.3, 1H), 5.04 (d, J=9.3, 1H), 4.58–4.49 (m, 3H), 4.39 (dd, J=15.2, 6.6, 1H), 4.14 (dd, J=15.2, 4.9, 1H), 2.86 (m, 2H), 2.25 (s, 3H), 1.51 (s, 3H), 1.35 (s, 3H); HRMS (ESI) m/z calcd for C$_{33}$H$_{36}$N$_4$O$_4$SNa (M+Na)$^+$ 607.2349, found 607.2350.

EXAMPLE B9

1H-Indazle-4-carboxylic acid {1-benzyl-3-[5,5-dimethyl-4-(2-methyl-benzyl carbamoyl)-thiazolidin-3-yl]-2-hydroxy-3-oxo-propyl}-amide

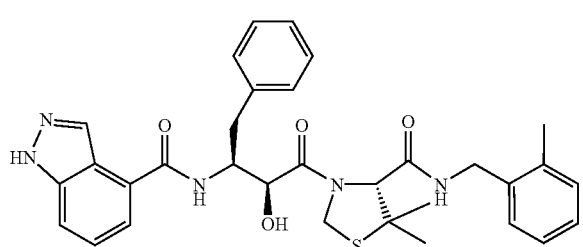

$^1$H NMR (DMSO-d$_6$) δ 13.18 (s, 1H), 8.46 (d, J=8.2, 1H), 8.35 (t, J=5.6, 1H), 8.20 (s, 1H), 7.68–7.06 (m, 12H), 5.53 (d, J=6.6, 1H), 5.13 (d, J=9.1, 1H), 5.06 (d, J=9.1, 1H), 4.61–4.54 (m, 2H), 4.51 (s, 1H), 4.40 (dd, J=14.9, 6.2, 1H), 4.16 (dd, J=14.9, 4.7, 1H), 2.91–2.89 (m, 2H), 2.51 (s, 3H), 1.53 (s, 1), 1.31 (s, 3H); HRMS (ESI) m/z calcd for C$_{32}$H$_{35}$N$_5$O$_4$SNa (M+Na)$^+$ 608.2302, found 608.2273; Anal. Calcd for C$_{32}$H$_{35}$N$_5$O$_4$S.0.35H$_2$O: C, 64.92; H, 6.08; N, 11.83; S, 5.42. Found: C, 65.15; H, 6.21; N, 11.44; S, 5.13.

EXAMPLE B10

{(1S,2S)-1-Benzyl-3-[(R)-5,5-dimethyl-4-(2-methyl-benzylcarbamoyl)-thiazolidin-3-yl]-2-hydroxy-3-oxo-propyl}-carbamic acid prop-2-ynyl ester

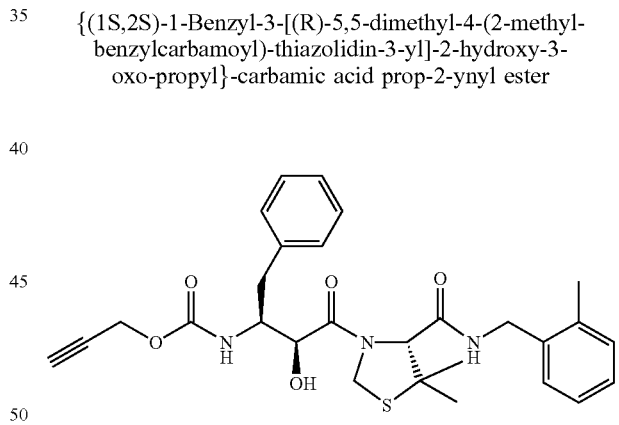

Isolated yield: 83%; 1H-NMR (400 MHz, dmso-d$_6$): δ 8.30 (t, 1H), 7.48 (d, 1H), 7.0–7.3 (m, 10H), 5.35 (d, 1H), 4.96 (q, 2H), 4.48–4.31 (m, 5H), 4.14 (dd, 1H), 3.87 (m, 1H), 3.44 (s, 1H), 2.7 (dd, 1H), 2.61 (t, 1H), 2.26 (s, 3H), 1.48 (s, 3H), 1.35 (s, 3H); IR (KBr in cm-1): 3302, 1711, 1643, 1528, 1237, 1047; MS (APCI, m/z): 524 (M+H): C28H33N3O5S1.0.21H2O Calculated: C, 63.76; H, 6.39; N, 7.97, Observed: C, 64.22; H, 6.35; N, 8.02. HPLC: Rf (min.) 20.177; Purity: 99%.

EXAMPLE B11

{(1S,2S)-1-Benzyl-3-[(R)-5,5-dimethyl-4-(2-methyl-benzylcarbamoyl)-thiazolidin-3-yl]-2-hydroxy-3-oxo-propyl}-carbamic acid allyl ester

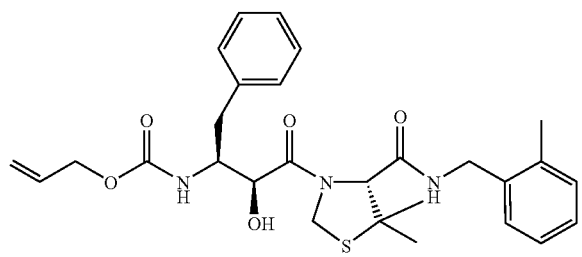

Isolated yield: 83%; 1H-NMR (400 MHz, dmso-d$_6$): δ 8.30 (t, 1H), 7.04–7.35 (m, 10H), 5.7–5.83 (m, 1H), 5.3 (d, 1H), 5.09 (d, 1H), 5.14 (d, 1H), 4.96 (q, 2H), 4.3 (s, 1H), 4.3–4.43 (m, 4H), 4.13 (dd, 1H), 3.87 (m, 1H) 2.74 (dd, 1H), 2.61 (dd, 1H), 2.26 (s, 3H), 1.48 (s, 3H), 1.30 (s, 3H); IR (KBr in cm−1): 3324, 1691, 1645, 1530, 1238, 1041; MS (APCI, m/z): 526 (M+H), 468; C28H35N3O5S1.0.35H2O Calculated: C, 63.22; H, 6.76; N, 7.90. Observed: C, 663.98; H, 6.71; N, 7.99. HPLC: Rf (min.) 20.97; Purity: 98%.

EXAMPLE B12

(R)-3-[(2S,3S)-2-Hydroxy-3-(2-methyl-butyrylamino)-4-phenyl-butyryl]-5,5-dimethyl-thiazolidine-4-carboxylic acid 2-methyl-benzylamide

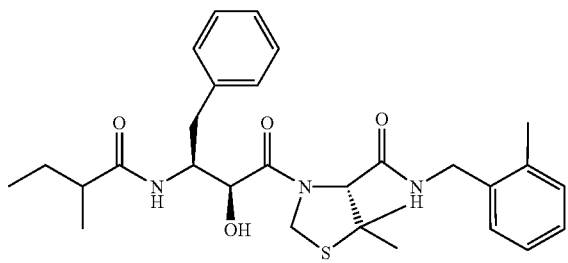

Isolated yield: 75%; 1H-NMR (400 MHz, dmso-d$_6$): δ 8.37 (q, 1H), 7.71 (d, 1H), 7.04–7.37 (m, 9H), 5.24 (brd, 1H), 5.11 (t, 1H), 5.04 (dd, 1H), 4.5–4.28 (m, 3H), 4.15 (m, 2H), 2.75–2.54 (m, 2H), 2.28 (s, 3H), 2.11 (m, 1H), 1.5 (s, 3H), 1.27 (s, 3H). 1.02–1.24 (m, 2H), 0.93 (d) +0.7 (m) +0.41 (t) 6H; IR (KBr in cm−1): 3311, 2966, 1642, 1530; MS (APCI, m/z): 526 (M+H), 480, 265; C29H39N3O4S1.0.38H2O Calculated: C, 65.41; H, 7.53; N, 7.89. Observed: C, 66.26; H, 7.48; N, 7.99. HPLC: R$_f$(min.) 20.68; Purity: 100%.

EXAMPLE B13

(R)-3-[(2S,3S)-3-(3-Allyl-ureido)-2-hydroxy-4-phenyl-butyryl]-5,5-dimethyl-thiazolidine-4-carboxylic acid 2-methyl-benzylamide

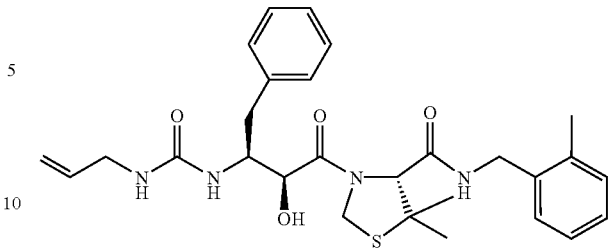

Isolated yield: 65%; 1H-NMR (400 MHz, dmso-d$_6$): δ 8.35 (t, 1H), 7.35–7.04 (m, 10H), 6.13 (d, 1H), 5.96 (t, 1H), 5.70 (m, 1H), 5.13–4.87 (m, 5H), 4.5–4.35 (m, 2H), 4.17 (dd, 1H), 4.04 (t, 1H), 3.52 (m, 2H), 2.22 (s, 3H), 1.48 (s, 3H), 1.32 (s, 3H); MS (APCI, m/z): 541 (M+H), 442, 396, 277; HPLC: Rf (min.) 21.05; Purity: >95%.

EXAMPLE B14

{(1S,2S)-1-Benzyl-3-[(R)-5,5-dimethyl-4-(2-methyl-benzylcarbamoyl)-thiazolidin-3-yl]-2-hydroxy-3-oxo-propyl}-carbamic acid but-3-enyl ester

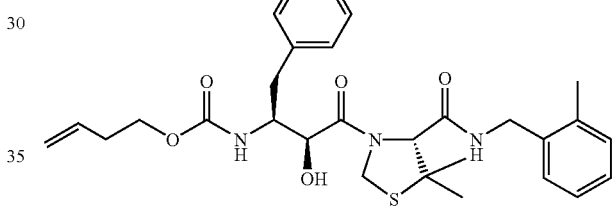

Isolated yield: 81%; 1H-NMR (400 MHz, dmso-d$_6$): δ 8.26 (t, 1H), 7.0–7.27 (m, 10H) 5.7–5.56 (m, 1H), 5.27 (d, 1H), 4.83–5.04 (m, 4H), 4.4 (s, 1H), 4.35 (m, 2H), 4.13 (dd, 1H), 3.65–3.87 (m, 2H), 2.65 (d, 1H), 2.52 (m, 1H), 2.22 (s, 3H), 2.17 (m, 2H), 1.44 (s, 3H), 1.26 (s, 3H); MS (APCI, m/z): 540 (M+H), 468; HPLC: Rf (min.) 21.31; Purity: 96%.

EXAMPLE B15

3-[(S)-3-(Cyclopropanecarbonyl-amino)-2-hydroxy-4-phenyl-butyryl]-5,5-dimethyl-thiazolidine-4-carboxylic acid 2-methyl-benzylamide

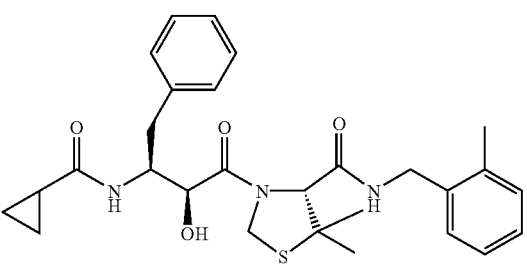

Isolated yield: 78%; 1H-NMR (400 MHz, dmso-d$_6$): δ 8.35 (t, 1H), 8.26 (d, 1H), 7.0–7.26 (m, 10H), 5.174 (d, 1H), 5.0 (d, 1H), 4.87 (d, 1H), 4.44 (s, 1H), 4.3–4.44 (m, 2H), 4.17–4.04 (m, 2H), 2.30–2.70 (m, 2H), 1.52 (m, 1H), 1.44 (s, 3H), 1.30 (s, 3H), 0.52 (m, 2H), 0.44 (m, 2H); MS (APCI, m/z): 510 (M+H), 265; HPLC: Rf (min.) 19.857; Purity: 94%.

EXAMPLE B16

{(S)-1-Benzyl-3-[5,5-dimethyl-4-(2-methyl-benzyl-carbamoyl)-thiazolidin-3-yl]-2-hydroxy-3-oxo-propyl}-carbamic acid isopropyl ester

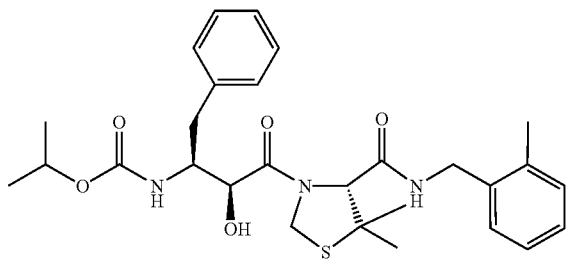

Isolated yield: 81%; 1H-NMR (400 MHz, dmso-d$_6$): δ 8.26 (t, 1H), 7.0–7.30 (m, 10H), 5.26 (brs, 1H), 4.91 (q, 2H), 4.35–4.13 (m, 2H), 4.13 (dd, 1H), 4.83 (t, 1H), 3.7 (q, 1H), 2.66 (dd, 1H), 2.52 (t, 1H), 2.2 (s, 3H), 1.44 (s, 3H), 1.26 (s, 3H), 0.74 (t, 6H); MS (APCI, m/z): 528 (M+H), 468; HPLC: Rf (min.) 21.127; Purity: 98%.

EXAMPLE B17

3-[(S)-2-Hydroxy-3-(3-isopropyl-ureido)-4-phenyl-butyryl]-5,5-dimethyl-thiazolidine-4-carboxylic acid 2-methyl-benzylamide

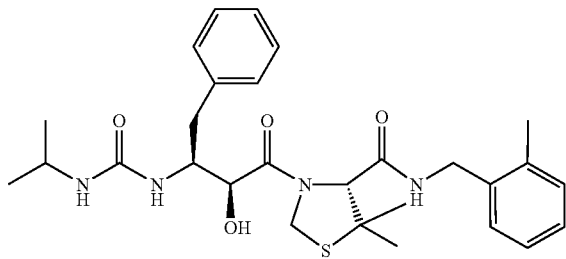

Isolated yield: 81%; 1H-NMR (400 MHz, dmso-d$_6$): δ 8.35 (t, 1H), 7.0–7.32 (m, 10H), 5.87 (d, 1H), 5.7 (d, 1H), 5.17 (d, 1H), 5.03 (d, 1H), 4.91 (d, 1H), 4.48–4.3 (m, 2H), 4.44 (s, 1H), 4.17 (dd, 1H), 4.0 (m, 1H), 3.52 (m, 1H), 2.65 (dd, 1H), 2.22 (s, 3H), 1.48 (s, 3H), 1.35 (s, 3H), 0.91 (d, 3H), 0.83 (d, 3H); MS (APCI, m/z): 527 (M+H), 442, 396, 263; HPLC: Rf (min.) 19.94; Purity: 95%.

EXAMPLE B18

(R)-3-((2S,3S)-2-Hydroxy-3-pent-4-ynoylamino-4-phenyl-butyryl)-5,5-dimethyl-thiazolidine-4-carboxylic acid 2-methyl-benzylamide

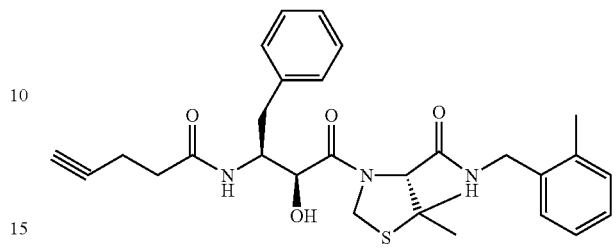

Isolated yield: 79%; 1H-NMR (400 MHz, dmso-d$_6$): δ 8.35 (t, 1H), 8.08 (d, 1H), 7.35–7.0 (m, 10H), 5.26 (d, 1H), 5.04 (d, 1H), 5.87 (d, 1H), 4.48 (s, 1H), 4.38 (m, 2H), 4.15 (m, 2H), 2.74–2.52 (m, 2H), 2.22 (s, 3H), 2.17 (m, 4H), 1.48 (s, 3H), 1.30 (s, 3H); IR (KBr in cm−1): 3294, 1642, 1530, 744; MS (APCI, m/z): 522 (M+H), 476, 265; C30H36N4O4S1.2.44H2O Calculated: C, 60.80; H, 6.95; N, 9.45. Observed: C, 65.67; H, 6.61; N, 10.21. HPLC: Rf (min.) 19.787; Purity: 100%.

EXAMPLE B19

(R)-3-[(2S,3S)-2-Hydroxy-4-phenyl-3-(3,3,3-trifluoropropionylamino)-butyryl]-5,5-dimethyl-thiazolidine-4-carboxylic acid 2-methyl-benzylamide

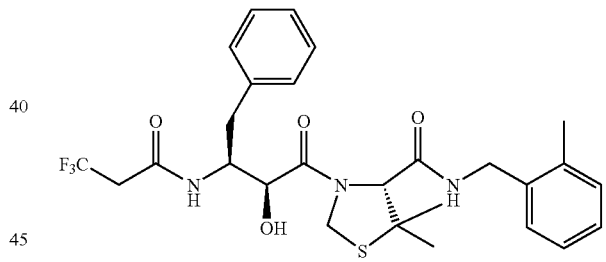

Isolated yield: 72%; 1H-NMR (400 MHz, dmso-d$_6$): δ 8.48 (d, 1H), 8.38 (t, 1H), 7.35–7.04 (m, 10H), 5.35 (d, 1H), 5.0 (d, 1H), 4.92 (d, 1H), 4.48 (s, 1H), 4.38 (m, 2H), 4.17 (m, 2H), 3.14 (m, 2H), 2.7 (d, 1H), 2.6 (t, 1H), 2.26 (s, 3H), 1.48 (s, 3H), 1.35 (s, 3H); IR (KBr in cm−1): 3305, 1649, 1534, 1239, 1110, 743; MS (APCI, m/z): 552 (M+H), 431, 265; C27H32N3O4S1F3.0.41H2O Calculated: C, 58.01; H, 5.92; N, 7.52. Observed: C, 58.79; H, 5.85; N, 7.62. HPLC: Rf (min.) 20.319; Purity: 100%.

EXAMPLE B20

(R)-3-((2S,3S)-3-Butyrylamino-2-hydroxy-4-phenyl-butyryl)-5,5-dimethyl-thiazolidine-4-carboxylic acid 2-methyl-benzylamide

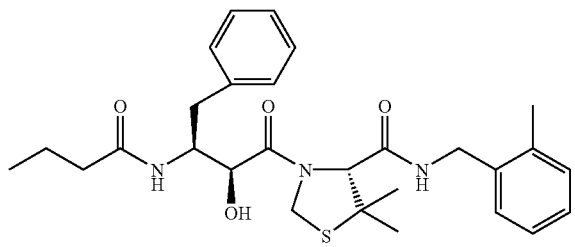

Isolated yield: 72%; 1H-NMR (400 MHz, dmso-d$_6$): δ 8.35 (t, 1H), 7.96 (d, 1H), 7.35–7.04 (m, 10H), 5.22 (d, 1H), 5.09 (d, 1H), 4.91 (d, 1H), 4.48 (s, 1H), 4.38 (m, 2H), 4.17 (m, 2H), 2.67 (d, 1H), 2.56 (t, 1H), 2.26 (s, 3H), 1.91 (t, 2H), 1.48 (s, 3H), 1.30 (s+m, 5H), 0.65 (t, 3H); IR (KBr in cm−1): 3308, 2967, 1641, 1534, 743; MS (APCI, m/z): 512 (M+H), 466, 265; C28H35N3O4S1.0.48H2O Calculated: C, 65.16; H, 7.03; N, 7.71. Observed: C, 65.16; H, 7.09; N, 8.44. HPLC: Rf (min.) 20.070; Purity: 95%.

EXAMPLE B21

2,3-Dihydro-1H-indole-4-carboxylic acid [(1S,2S)-3-((R)-4-allylcarbamoyl-5,5-dimethyl-thiazolidin-3-yl)-1-benzyl-2-hydroxy-3-oxo-propyl]-amide

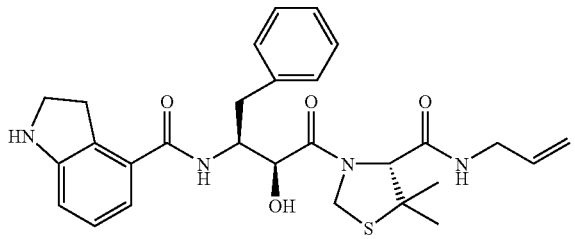

Beige solid; $^1$H NMR (DMSO-d$_6$) δ 8.09 (t, J=5.7, 1H), 8.00 (d, J=8.6, 1H), 7.70 (d, J=7.7, 1H), 7.34–7.11 (m, 6H), 6.91 (t, J=7.9, 1H), 6.68 (d, J=8.1, 1H), 5.80–5.71 (m, 1H), 5.58 (s, 1H), 5.44 (d, J=7.0, 1H), 5.23–5.01 (m, 4H), 4.47–4.39 (m, 4H), 3.73–3.61 (m, 2H), 2.99–2.81 (m, 4H), 1.50 (s, 3H), 1.35 (s, 3H); HRMS (ESI) m/z calcd for C$_{28}$H$_{34}$N$_4$O$_4$SNa (M+Na)$^+$ 545.219, found 545.2205.

EXAMPLE B22

[(1S,2S)-3-((R)-4-Allylcarbamoyl-5,5-dimethyl-thiazolidin-3-yl)-1-benzyl-2-hydroxy-3-oxo-propyl]-carbamic acid (S)-(tetrahydro-furan-3-yl) ester

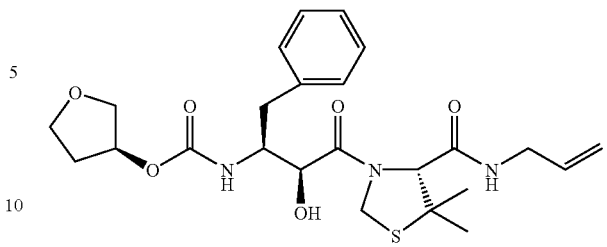

White solid; $^1$H NMR (DMSO-d$_6$) δ 8.06 (t, J=5.9, 1H), 7.27–7.12 (m, 6), 5.76 (m, 1H), 5.39 (d, J=7.1, 1H), 5.19 (dd, J=17.2, 1.7, 1H), 5.03–4.90 (m, 4H), 4.39–4.35 (m, 2H), 3.88 (m, 1H), 3.76–3.58 (m, 5H), 3.42 (d, J=10.4, 1H), 2.75–2.55 (m, 2H), 2.03 (m, 1H), 1.80 (m, 1H), 1.49 (s, 3H), 1.34 (s, 3H); HRMS (ESI) m/z calcd for C$_{24}$H$_{33}$N$_3$O$_6$SNa (M+Na)$^+$ 514.1982, found 514.1967.

EXAMPLE B23

(R)-3-{(2S,3S)-3-[2-(2,6-Dimethyl-phenoxy)-ethanoylamino]-2-hydroxy-4-phenyl-butanoyl}-5,5-dimethyl-thiazolidine-4-carboxylic acid allylamide

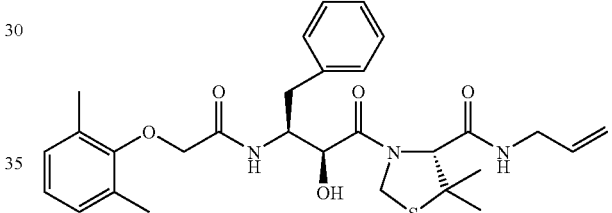

White solid; IR (neat, cm$^{-1}$) 3418, 1651, 1532, 1454, 1372, 1264, 1195; $^1$H NMR (DMSO-d$_6$) δ 8.15 (t, J=5.7, 1H), 8.10 (d, J=8.8, 1H), 7.32–7.13 (m, 5H), 7.00–6.89 (m, 3H), 5.83–5.71 (m, 1H), 5.48 (d, J=6.8, 1H), 5.21 (dd, J=17.2, 1.8, 1H), 5.03–4.91 (m, 3H), 4.49–4.36 (m, 3H), 4.16 (d, J=14.1, 1H), 3.98 (d, J=14.1, 1H), 3.72 (m, 2H), 2.79–2.76 (m, 2H), 2.13 (s, 6H), 1.50 (s, 3H), 1.36 (s, 3H); HRMS (ESI) m/z calcd for C$_{29}$H$_{37}$N$_3$O$_5$SNa (M+Na)$^+$ 562.2346, found 562.2324.

EXAMPLE B24

1-H-indazole-4-carboxylic acid [3-(4-allylcarbamoyl-5,5-dimethyl-thiazolidin-3-yl)-1-benzyl-2-hydroxy-3-oxo-propyl]-amide

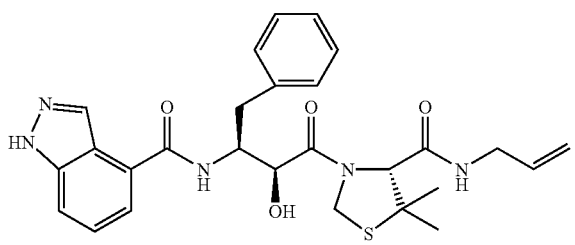

$^1$H NMR (DMSO-$d_6$) δ 13.18 (s, 1H), 8.42 (d, J=8.2, 1H), 8.19 (s, 1H), 8.10 (t, J=5.7, 1H), 7.68–7.11 (m, 8H), 5.81–5.72 (m, 1H), 5.52 (d, J=6.8, 1H), 5.24–4.83 (m, 4H), 4.57 (m, 2H), 4.42 (s, 1H), 3.74–3.66 (m, 2H), 2.90 (m, 2H), 1.53 (s, 3H), 1.37 (s, 3H); Anal. Calcd for $C_{27}H_{31}N_5O_4S \cdot 0.25H_2O$: C, 61.63; H, 6.04; N, 13.31; S, 6.09. Found: C, 61.63; H, 6.09; N, 12.95; S, 5.95.

EXAMPLE B25

(R)-3-{(2S,3S)-2-Hydroxy-4-phenyl-3-[2-(1H-[1,2,4]triazol-3-ylsulfanyl)-ethanoylamino]-butanoyl}-5,5-dimethyl-thiazolidine-4-carboxylic acid allylamide

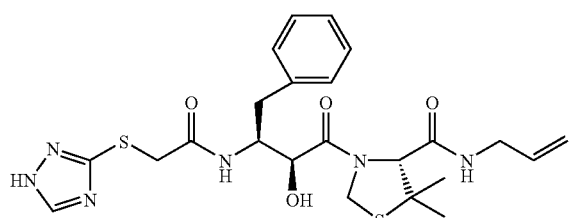

EXAMPLE B26

{(1S,2S)-1-Benzyl-3-[(R)-4-(cyclopropylmethyl-carbamoyl)-5,5-dimethyl-thiazolidin-3-yl]-2-hydroxy-3-oxo-propyl}-carbamic acid (S)-(tetrahydrofuran-3-yl) ester

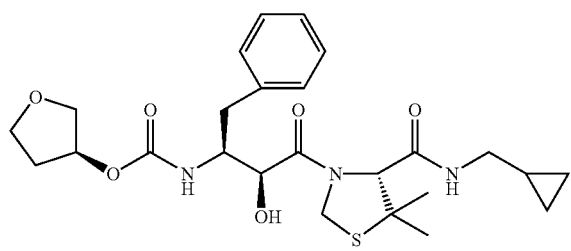

White solid; $^1$H NMR (DMSO-$d_6$) δ 7.99 (t, J=5.7, 1H), 7.28–7.07 (m, 6H), 5.32 (d, J=7.3, 1H), 4.96–4.92 (m, 3H), 4.38 (s, 1H), 3.90 (m, 1H), 3.76–3.54 (m, 4H), 3.41 (d, J=10.4, 1H), 3.04–2.92 (m, 2H), 2.73–2.54 (m, 2H), 2.03 (m, 1H), 1.83 (m, 1H), 1.49 (s, 3H), 1.36 (s, 3H), 0.88 (m, 1H), 0.35 (m, 2H), 0.15 (m, 2H); HRMS (ESI) m/z calcd for $C_{25}H_{35}N_3O_6SNa$ (M+Na)$^+$ 528.2139, found 528.2121.

EXAMPLE B27

(R)-3-{(2S,3S)-3-[2-(2,6-Dimethyl-phenoxy)-ethanoylamino]-2-hydroxy-4-phenyl-butanoyl}-5,5-dimethyl-thiazolidine-4-carboxylic acid cyclopropylmethyl-amide

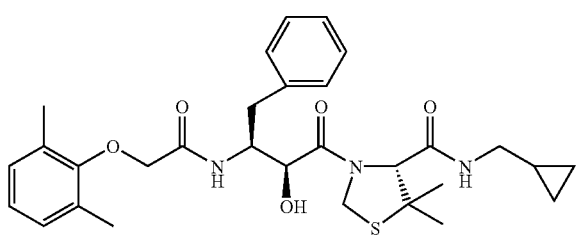

White solid; IR (neat, cm$^{-1}$) 3413, 1648, 1531, 1443, 1390, 1196; $^1$H NMR (DMSO-$d_6$) δ 8.12 (d, J=9.0, 1H), 8.06 (t, J=5.7, 1H), 7.33–7.13 (m, 5H), 7.01–6.89 (m, 3H), 5.44 (d, J=6.8, 1H), 4.97 (d, J=9.0, 1H), 4.91 (d, J=9.0, 1H), 4.47–4.36 (m, 2H), 4.41 (s, 1H), 4.16 (d, J=14.2, 1H), 3.98 (d, J=14.2, 1H), 3.10–2.76 (m, 4H), 2.13 (s, 6H), 1.51 (s, 3H), 1.38 (s, 3H), 0.88 (m, 1H), 0.36 (m, 2H), 0.15 (m, 2H); HRMS (ESI) m/z calcd for $C_{30}H_{39}N_3O_5SNa$ (M+Na)$^+$ 576.2503, found 576.2503.

EXAMPLE 28

2,3-Dihydro-1H-indole-4-carboxylic acid {(1S,2S)-1-benzyl-3-[(R)-4-(cyclopropylmethyl-carbamoyl)-5,5-dimethyl-thiazolidin-3-yl]-2-hydroxy-3-oxo-propyl}-amide

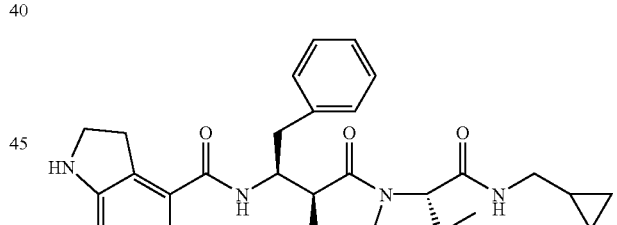

Off white solid; $^1$H NMR (DMSO-$d_6$) δ 8.03–8.01 (m, 2H), 7.35–7.11 (m, 5H), 6.91 (t, J=7.7, 1H), 6.69 (d, J=7.9, 1H), 6.52 (d, J=7.7, 1H), 5.58 (s br, 1H), 5.39 (d, J=6.8, 1H), 5.06 (d, J=9.2, 1H), 4.99 (d, J=9.2, 1H), 4.48–4.39 (m, 4H), 2.98–2.79 (m, 6H), 1.51 (s, 3H), 1.37 (s, 3H), 0.87 (m, 1H), 0.35 (m, 2H), 0.14 (m, 2H); HRMS (ESI) m/z calcd for $C_{29}H_{36}N_4O_4SNa$ (M+Na)$^+$ 559.2349, found 559.2353.

EXAMPLE B29

2,3-Dihydro-1H-indole-4-carboxylic acid {(1S,2S)-1-benzyl-3-[(R)-4-((S)-chroman-4-ylcarbamoyl)-5,5-dimethyl-thiazolidin-3-yl]-2-hydroxy-3-oxo-propyl}-amide

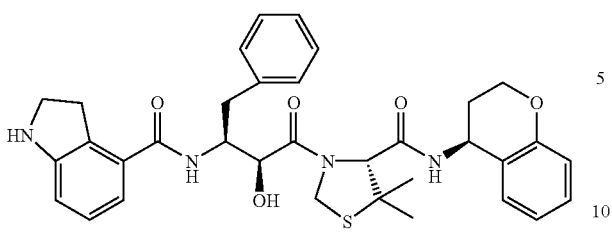

Beige solid; $^1$H NMR (DMSO-d$_6$) δ 8.52 (d, J=8.1, 1H), 8.21 (d, J=8.4, 1H), 7.54–6.72 (m, 13H), 5.40 (d, J=5.9, 1H), 5.20–4.90 (m, 3H), 4.70–4.12 (m, 3H), 3.10–2.80 (m, 4H), 2.20–1.90 (m, 6H), 1.51 (s, 3H), 1.49 (s, 3H); HRMS (ESI) m/z calcd for C$_{34}$H$_{38}$N$_4$O$_5$SNa (M+Na)$^+$ 685.2303, found 685.2319; Anal. Calcd for C$_{34}$H$_{38}$N$_4$O$_5$S·0.5H$_2$O: C, 65.47; H, 6.30; N, 8.98. Found: C, 65.34; H, 6.02; N, 8.75.

EXAMPLE B30

(R)-3-{(2S,3S)-3-[2-(2,6-Dimethyl-phenoxy)-ethanoylamino]-2-hydroxy-4-phenyl-butanoyl}-5,5-dimethyl-thiazolidine-4-carboxylic acid (S)-chroman-4-ylamide

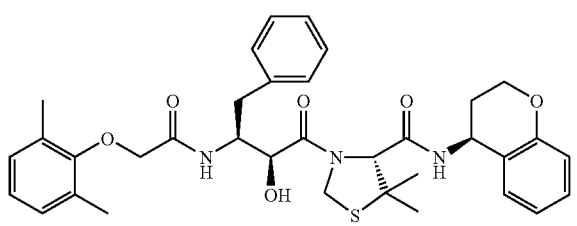

White solid: mp=105–107° C.; $^1$H NMR (DMSO-d$_6$) δ 8.49 (d, J=7.7, 1H), 8.14 (d, J=8.6, 1H), 7.40–6.65 (m, 12H), 5.44 (d, J=7.3, 1H), 4.96 (d, J=8.6, 1H), 4.94 (d, J=8.6, 1H), 4.44–3.94 (m, 8H), 2.82–2.70 (m, 2H), 2.15 (s, 6H), 2.10–1.90 (m, 2H), 1.49 (s, 3H), 1.45 (s, 3H); HRMS (ESI) m/z calcd for C$_{35}$H$_{41}$N$_3$O$_6$SNa (M+Na)$^+$ 654.2608, found 654.2622; Anal. Calcd for C$_{35}$H$_{41}$N$_3$O$_6$S: C, 66.54; H, 6.54; N, 6.65. Found: C, 66.54; H, 6.68; N, 6.69.

EXAMPLE B31

(R)-3-{(2S,3S)-2-Hydroxy-4-phenyl-3-[2-(1H-[1,2,4]triazol-3-ylsulfanyl)-ethanoylamino]-butanoyl}-5,5-dimethyl-thiazolidine-4-carboxylic acid (S)-chroman-4-ylamide

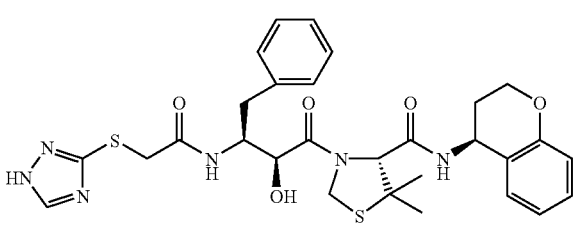

$^1$H NMR (DMSO-d$_6$) δ 8.47 (d, J=8.2, 1H), 8.37 (d, J=8.6, 1H), 8.23 (s br, 1H), 7.20–7.08 (m, 7H), 6.85–6.74 (m, 2H), 5.26 (d, J=6.6, 1H), 4.98–4.89 (m, 3H), 4.41 (s, 1H), 4.30–4.20 (m, 4H), 3.75 (dd, J=22.2, 14.5, 2H), 2.75–2.50 (m, 2H), 2.20–1.90 (m, 2H), 1.48 (s, 3H), 1.44 (s, 3H); HRMS (ESI) m/z calcd for C$_{29}$H$_{34}$N$_6$O$_5$S$_2$Na (M+Na)$^+$ 633.1924, found 633.1930.

EXAMPLE B32

((1S,2S)-1-Benzyl-3-{(R)-5,5-dimethyl-4-[(S)-(1,2,3,4-tetrahydro-naphthalen-1-yl)carbamoyl]-thiazolidin-3-yl}-2-hydroxy-3-oxo-propyl)-carbamic acid 2,6-dimethyl-benzyl ester

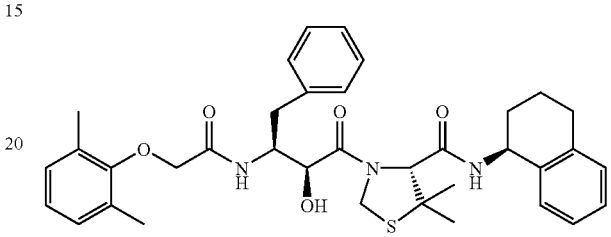

White solid: mp=88–90° C.; $^1$H NMR (DMSO-d$_6$) δ 8.30 (d, J=8.9, 1H), 8.15 (d, J=9.3, 1H), 7.35–6.85 (m, 12H), 5.45 (d, J=6.0, 1H), 5.20–4.90 (m, 2H), 4.45–3.90 (m, 6H), 2.80–2.62 (m, 2H), 2.14 (s, 6H), 1.90–1.60 (m, 6H), 1.49 (s, 3H), 1.45 (s, 3H); HRMS (ESI) m/z calcd for C$_{36}$H$_{43}$N$_3$O$_5$SNa (M+Na)$^+$ 652.2816, found 652.2836; Anal. Calcd for C$_{36}$H$_{43}$N$_3$O$_5$S: C, 68.65; H, 6.88; N, 6.67. Found: C, 68.45; H, 6.98; N, 6.58.

EXAMPLE B33

((1S,2S)-1-Benzyl-3-{(R)-5,5-dimethyl-4-[(S)-(1,2,3,4-tetrahydro-naphthalen-1-yl)carbamoyl]-thiazolidin-3-yl}-2-hydroxy-3-oxo-propyl)-carbamic acid (S)-(tetrahydro-furan-3-yl) ester

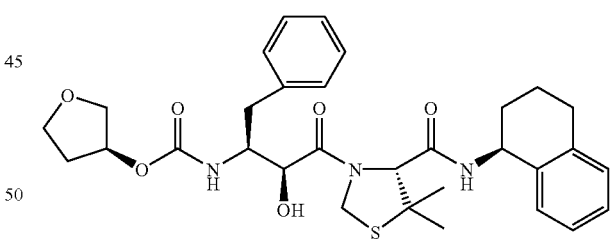

White solid: mp=103–105° C.; $^1$H NMR (DMSO-d$_6$) δ 8.26 (d, J=7.9, 1H), 7.30–7.08 (m, 10H), 5.50 (d, J=7.9, 1H), 5.00–4.90 (m, 3H), 4.42–4.38 (m, 3H), 4.00–3.30 (m, 5H), 3.00–2.40 (m, 4H), 1.90–1.60 (m, 4H), 1.47 (s, 3H), 1.43 (s, 3H), 1.40–1.38 (m, 2H); HRMS (ESI) m/z calcd for C$_{31}$H$_{39}$N$_3$O$_6$SNa (M+Na)$^+$ 604.2452, found 604.2430; Anal. Calcd for C$_{31}$H$_{39}$N$_3$O$_6$S·0.25H$_2$O: C, 63.51; H, 6.79; N, 7.17. Found: C, 63.40; H, 6.73; N, 7.08.

EXAMPLE B34

2,3-Dihydro-1H-indole-4-carboxylic acid [(1S,2S)-1-benzyl-3-((R)-5,5-dimethyl-4-prop-2-ynylcarbamoyl-thiazolidin-3-yl)-2-hydroxy-3-oxo-propyl]-

121 amide

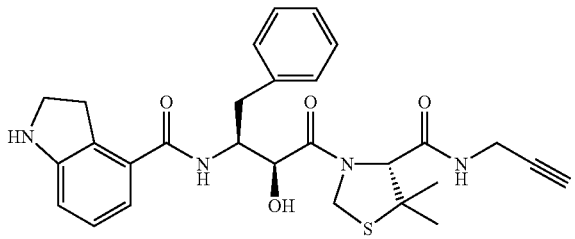

Orange solid; $^1$H NMR (DMSO-$d_6$) δ 8.41 (t, J=5.0, 1H), 8.01 (d, J=8.3, 1H), 7.34–7.11 (m, 5H), 6.91 (t, J=7.7, 1H), 6.68 (d, J=7.5, 1H), 6.52 (d, J=7.9, 1H), 5.58 (s br, 1H), 5.45 (d, J=6.8, 1H), 5.06 (d, J=9.3, 1H), 4.99 (d, J=9.5, 1H), 4.48–4.37 (m, 4H), 3.84 (m, 2H), 3.09 (m, 1H), 2.98–2.81 (m, 4H), 1.50 (s, 3H), 1.35 (s, 3H); HRMS (ESI) m/z calcd for $C_{28}H_{32}N_4O_4SNa$ (M+Na)$^+$ 543.2036, found 543.2039.

EXAMPLE B35

1-H-indazole-4-carboxylic acid [1-benzyl-3-(5,5-dimethyl-4-prop-2-ynylcarbamoyl-thiazolidin-3-yl)-2-hydroxy-3-oxo-propyl]-amide

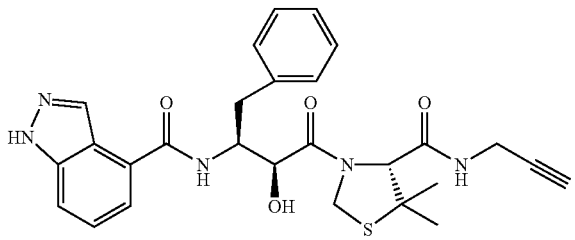

$^1$H NMR (DMSO-$d_6$) δ 13.18 (s, 1H), 8.42 (m, 2H), 8.19 (s, 1H), 7.68–7.12 (m, 8H), 5.54 (d, J=5.6, 1H), 5.10 (d, J=9.3, 1H), 5.08 (d, J=9.3, 1H), 4.54 (m, 2H), 4.41 (s, 1H), 3.87 (m, 2H), 3.03 (t, J=2.5, 1H), 2.89 (m, 2H), 1.53 (s, 3H), 1.38 (s, 3H); HRMS (ESI) m/z calcd for $C_{27}H_{29}N_5O_4SNa$ (M+Na)$^+$ 542.1832, found 542.1855; Anal. Calcd for $C_{27}H_{29}N_5O_4S\cdot0.25H_2O$: C, 61.87; H, 5.67; N, 13.36; S, 6.12. Found: C, 61.85; H, 5.64; N, 13.19; S, 6.08.

EXAMPLE B36

(R)-3-{(2S,3S)-3-[2-(2,6-Dimethyl-phenoxy)-ethanoylamino]-2-hydroxy-4-phenyl-butanoyl}-5,5-dimethyl-thiazolidine-4-carboxylic acid prop-2-ynylamide

122

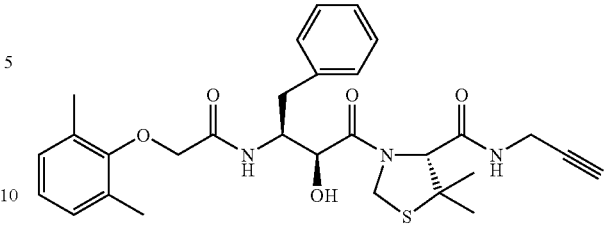

White solid; IR (neat, cm$^{-1}$) 3418, 1658, 1530, 1378, 1196; $^1$H NMR (DMSO-$d_6$) δ 8.46 (t, J=5.1, 1H), 8.10 (d, J=9.0, 1H), 7.33–7.14 (m, 5H), 7.01–6.89 (m, 3H), 5.49 (d, J=6.8, 1H), 4.97 (d, J=9.2, 1H), 4.92 (d, J=9.0, 1H), 4.48–4.35 (m, 2H), 4.40 (s, 1H), 4.15 (d, J=14.3, 1H), 3.99 (d, J=14.1, 1H), 3.93–3.86 (m, 2H), 3.10 (s, 1H), 2.77 (m, 2H), 1.50 (s, 3H), 1.37 (s, 3H), 2.13 (s, 6H); HRMS (ESI) m/z calcd for $C_{29}H_{35}N_3O_5SNa$ (M+Na)$^+$ 560.2190, found 560.2168.

EXAMPLE B37

1-H-indazole-4-carboxylic acid (1-benzyl-3-{4[(furan-2-ylmethyl)-carbamoyl]-5,5-dimethyl-thiazolidin-3-yl}-2-hydroxy-3-oxo-propyl)-amide

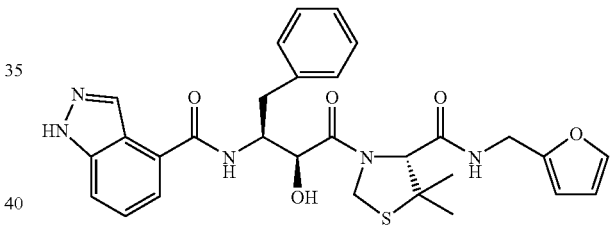

$^1$H NMR (DMSO-$d_6$) δ 13.18 (s, 1H), 8.44 (m, 2H), 8.19 (s, 1H), 7.68–7.12 (m, 9H), 6.34 (m, 1H), 6.26 (m, 1H), 5.54 (d, J=6.6, 1H), 5.10 (d, J=9.2, 1H), 5.06 (d, J=9.2, 1H), 4.55 (m, 2H), 4.44 (s, 1H), 4.29 (m, 2H), 2.90 (m, 2H), 1.51 (s, 3H), 1.30 (s, 3H); HRMS (ESI) m/z calcd for $C_{29}H_{31}N_5O_5SNa$ (M+Na)$^+$ 584.1938, found 584.1922; Anal. Calcd for $C_{29}H_{31}N_5O_5S\cdot0.5H_2O$: C, 61.03; H, 5.65; N, 12.27; S, 5.62. Found: C, 61.14; H, 5.60; N, 12.17; S, 5.60.

EXAMPLE B38

(R)-3-{(2S,3S)-3-[2-(2,6-Dimethyl-phenoxy)-ethanoylamino]-2-hydroxy-4-phenyl-butanoyl}-5,5-dimethyl-thiazolidine-4-carboxylic acid (furan-2-ylmethyl)-amide

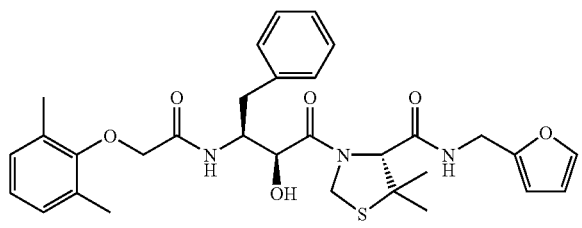

White solid; IR (neat, cm$^{-1}$) 3409, 1657, 1530, 1452, 1371, 1195; $^1$H NMR (DMSO-d$_6$) δ 8.47 (t, J=5.7, 1H), 8.12 (d, J=8.8, 1H), 7.52 (s, 1H), 7.32–7.14 (m, 5H), 7.01–6.89 (m, 3H), 6.33 (m, 1H), 6.26 (m, 1H), 5.50 (d, J=7.0, 1H), 4.97 (d, J=9.0, 1H), 4.92 (d, J=9.0, 1H), 4.46–4.27 (m, 5H), 4.15 (d, J=14.3, 1H), 4.00 (d, J=14.3, 1H), 2.79 (m, 2H), 2.14 (s, 6H), 1.48 (s, 3H), 1.31 (s, 3H); HRMS (ESI) m/z calcd for C$_{31}$H$_{37}$N$_3$O$_6$SNa (M+Na)$^+$ 602.2295, found 602.2310.

EXAMPLE B39

2,3-Dihydro-1H-indole-4-carboxylic acid ((1S,2S)-1-benzyl-3-{(R)-4-[(furan-2-ylmethyl)-carbamoyl]-5,5-dimethyl-thiazolidin-3-yl}-2-hydroxy-3-oxo-propyl)-amide

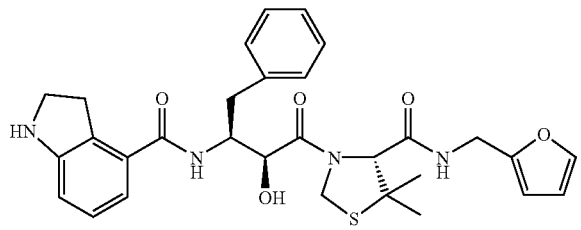

Pale pink solid; $^1$H NMR (DMSO-d$_6$) δ 8.42 (t, J=5.3, 1H), 8.02 (d, J=8.2, 1H), 7.53 (s, 1H), 7.34–7.11 (m, 6H), 6.91 (t, J=7.7, 1H), 6.69 (d, J=7.7, 1H), 6.52 (d, J=7.7, 1H), 6.34 (m, 1H), 6.25 (m, 1H), 5.58 (s br, 1H), 5.46 (d, J=6.6, 1H), 5.06 (d, J=9.2, 1H), 4.99 (d, J=9.2, 1H), 4.48–4.18 (m, 5H), 4.40 (s, 1H), 3.00–2.79 (m, 4H), 1.48 (s, 3H), 1.30 (s, 3H).

EXAMPLE B40

(R)-3-{(2S,3S)-2-Hydroxy-4-phenyl-3-[((S)-1-tetrahydro-furan-2-yl-methanoyl)-amino]-butanoyl}-5,5-dimethyl-thiazolidine-4-carboxylic acid (furan-2-ylmethyl)-amide

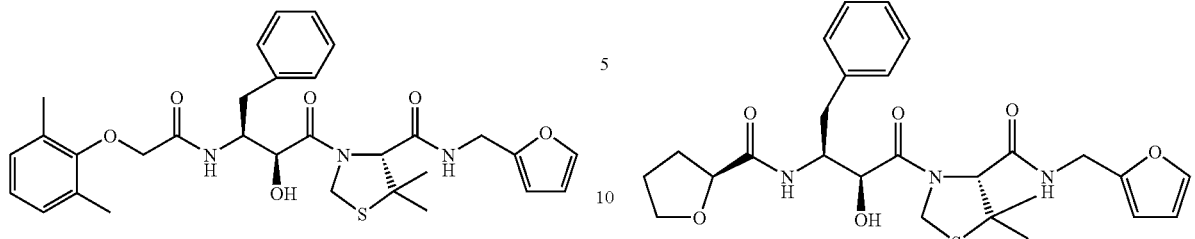

Off white solid; $^1$H NMR (DMSO-d$_6$) δ 8.44 (t, J=5.3, 1H), 7.57 (d, J=9.0, 1H), 7.53 (s, 1H), 7.23–7.15 (m, 5H), 6.34 (m, 1H), 6.26 (m, 1H), 5.45 (d, J=6.8, 1H), 4.94 (s, 2H), 4.39 (s, 2H), 4.28 (m, 3H), 4.10 (m, 1H), 3.79–3.64 (m, 2H), 2.79–2.64 (m, 2H), 1.98–1.87 (m, 2H), 1.65–1.33 (m, 2H), 1.47 (s, 3H), 1.30 (s, 3H); HRMS (ESI) m/z calcd for C$_{26}$H$_{33}$N$_3$O$_6$SNa (M+Na)$^+$ 538.1982, found 538.1997.

EXAMPLE B41

2,3-Dihydro-1H-indole-4-carboxylic acid {(1S,2S)-1-benzyl-3-[(R)-4-((S)-cyclohex-2-enylcarbamoyl)-5,5-dimethyl-thiazolidin-3-yl]-2-hydroxy-3-oxo-propyl}-amide

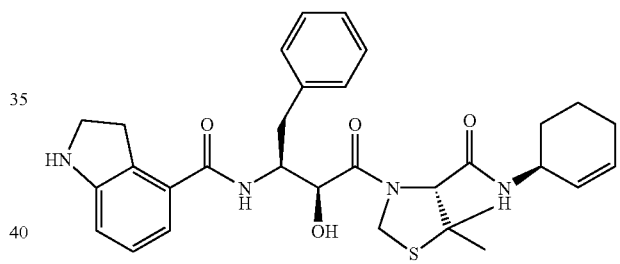

$^1$H NMR (DMSO-d$_6$) δ 8.01 (d, J=8.2, 1H), 7.94 (d, J=7.7, 1H), 7.36–7.06 (m, 5H), 6.90 (t, J=7.6, 1H), 6.69 (d, J=7.6, 1H), 6.52 (d, J=7.6, 1H), 5.80–5.68 (m, 1H), 5.35 (d, J=6.7, 1H), 5.07 (d, J=9.2, 1H), 4.98 (d, J=9.2, 1H), 4.49–4.32 (m, 3H), 4.32–4.20 (m, 1H), 3.00–2.71 (m, 6H), 2.00–1.60 (m, 6H), 1.49 (s, 3H), 1.37 (s, 3H); HRMS (ESI) m/z calcd for C$_{31}$H$_{38}$N$_4$O$_4$SNa (M+Na)$^+$ 585.2506, found 585.2500; Anal. Calcd for C$_{31}$H$_{38}$N$_4$O$_4$S.1H$_2$O: C, 64.11; H, 6.94; N, 9.65. Found: C, 64.38; H, 6.72; N, 9.54.

EXAMPLE B42

2,3-Dihydro-1H-indole-4-carboxylic acid {(1S,2S)-1-benzyl-2-hydroxy-3-[(R)-4-((S)-indan-1-ylcarbamoyl)-5,5-dimethyl-thiazolidin-3-yl]-3-oxo-propyl}-amide

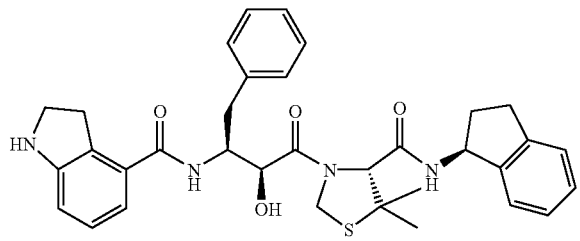

¹H NMR (DMSO-d₆) δ 8.32 (d, J=8.1, 1H), 8.06 (d, J=8.6, 1H), 7.33–7.11 (m, 9H), 6.91 (t, J=7.6, 1H), 6.71 (d, J=7.6, 1H), 6.53 (d, J=7.6, 1H), 5.36–5.25 (m, 2H), 5.09 (d, J=9.2, 1H), 5.01 (d, J=9.2, 1H), 4.50 (d, J=3.6, 1H), 4.44 (s, 1H), 4.42–4.32 (m, 1H), 2.97–2.71 (m, 6H), 2.39–2.34 (m, 2H), 1.87–1.80 (m, 2H), 1.50 (s, 3H), 1.44 (s, 3H); HRMS (ESI) m/z calcd for $C_{34}H_{38}N_4O_4SNa$ (M+Na)⁺ 621.2506, found 621.2519; Anal. Calcd for $C_{34}H_{38}N_4O_4S \cdot 0.25H_2O$: C, 67.69; H, 6.43; N, 9.29. Found: C, 67.73; H, 6.26; N, 8.98.

EXAMPLE B43

(R)-3-((2S,3S)-2-Hydroxy-3-{[1-(3-hydroxy-2,4-dimethyl-phenyl)-methanoyl]-amino}-4-phenyl-butanoyl)-5,5-dimethyl-thiazolidine-4-carboxylic acid (S)-indan-1-ylamide

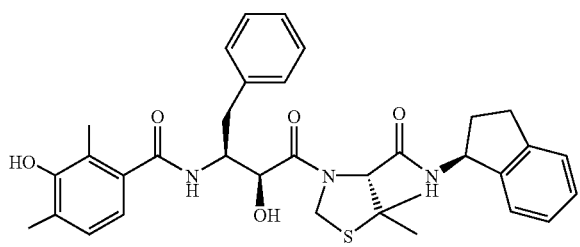

¹H NMR (DMSO-d₆) δ 8.33 (d, J=7.7, 1H), 8.24 (s, 1H), 8.14 (d, J=8.4, 1H), 7.32–7.12 (m, 9H), 6.86 (d, J=7.7, 1H), 6.53 (d, J=7.7, 1H), 5.38–5.26 (m, 2H), 5.14 (d, J=9.2, 1H), 5.03 (d, J=9.2, 1H), 4.60–4.30 (m, 4H), 2.95–2.64 (m, 3H), 2.42–2.30 (m, 1H), 1.90–1.80 (m, 1H), 2.12 (s, 3H), 1.85 (s, 3H), 1.49 (s, 3H), 1.44 (s, 3H); HRMS (ESI) m/z calcd for $C_{34}H_{39}N_3O_5SNa$ (M+Na)⁺ 624.2503, found 624.2509; Anal. Calcd for $C_{34}H_{39}N_3O_5S$: C, 67.86; H, 6.53; N, 6.98. Found: C, 67.77; H, 6.50; N, 6.79.

EXAMPLE B44

2,3-Dihydro-1H-indole-4-carboxylic acid [(1S,2S)-1-benzyl-3-((R)-5,5-dimethyl-{[(R)-1-(tetrahydro-furan-2-yl)methyl]-carbamoyl}-thiazolidin-3-yl)-2-hydroxy-3-oxo-propyl]-amide White solid; IR (neat, cm⁻¹) 3401, 2978, 2861, 1643, 1531, 1455, 1372, 1279, 1073; ¹H NMR (DMSO-d₆) δ 8.04 (m, 2H), 7.35–7.11 (m, 6H), 6.90 (t, J=7.7, 1H), 6.68 (d, J=7.7, 1H), 6.52 (d, J=7.7, 1H), 5.58 (s br, 1H), 5.39 (d, J=6.8, 1H), 5.06 (d, J=9.2, 1H), 4.97 (d, J=9.3, 1H), 4.49–4.36 (m, 3H), 3.83–3.56 (m, 4H), 3.15 (m, 2H), 2.99–2.78 (m, 4H), 1.78 (m, 4H), 1.50 (s, 3H), 1.36 (s, 3H); HRMS (ESI) m/z calcd for $C_{30}H_{38}N_4O_5SNa$ (M+Na)⁺ 589.2455, found 589.2440.

EXAMPLE B45

2,3-Dihydro-1H-indole-4-carboxylic acid [(1S,2S)-1-benzyl-3-((R)-5,5-dimethyl-4-propylcarbamoyl-thiazolidin-3-yl)-2-hydroxy-3-oxo-propyl]-amide

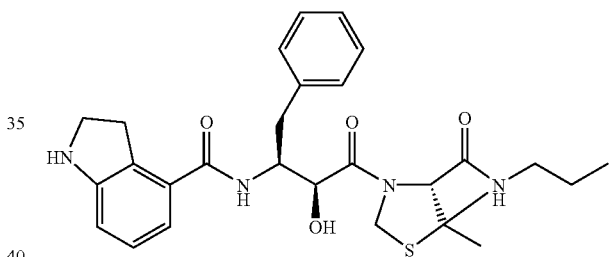

Pink solid; ¹H NMR (DMSO-d₆) δ 8.01 (d, J=8.2, 1H), 7.89 (t, J=5.3, 1H), 7.35–7.10 (m, 5H), 6.90 (t, J=7.8, 1H), 6.68 (d, J=7.8, 1H), 6.52 (d, J=7.8, 1H), 5.57 (s, 1H), 5.39 (d, J=6.9, 1H), 5.05 (d, J=9.2, 1H), 4.98 (d, J=9.2, 1H), 4.49–4.40 (m, 2H), 4.35 (s, 1H), 3.04–2.78 (m, 8H), 1.49 (s, 3H), 1.34 (s, 3H), 1.43–1.30 (m, 2H), 0.82 (t, J=7.5, 3H); HRMS (ESI) m/z calcd for $C_{28}H_{36}N_4O_4SNa$ (M+Na)⁺ 547.2349, found 547.2323; Anal. Calcd for $C_{28}H_{36}N_4O_54S \cdot 0.25H_2O$: C, 63.55; H, 6.95; N, 10.59. Found: C, 63.33; H, 6.60; N, 10.46.

EXAMPLE B46

3-{(2S,3S)-3-[3-(2-Chloro-benzyl)-ureido]-2-hydroxy-4-phenyl-butyryl}-5,5-dimethyl-thiazolidine-4-carboxylic acid 2-chloro-benzylamide

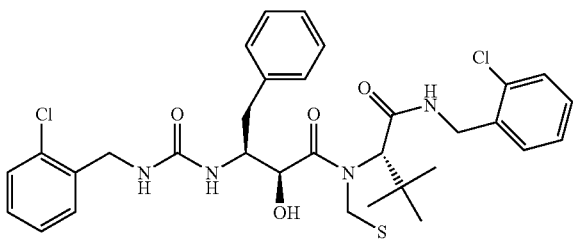

1H-NMR (400 MHz, dmso-d⁶): 7.00–7.40 (m, 13H), 4.00–4.80 (m, 9H), 2.60 (m, 2H), 1.50, 1.40 (s, 3H), 1.26, 1.22 (s, 3H); MS (APCI, m/z): 628, 630; $C_{31}H_{34}Cl_2N_4O_4S$ Calculated: C, 58.14; H, 5.44; N, 8.90, Observed: C, 58.54; H, 5.41; N, 8.71.

EXAMPLE B47

{(1S,2S)-1-Benzyl-3-[(R)-4-(2-chloro-benzylcarbamoyl)-5,5-dimethyl-thiazolidin-3-yl]-2-hydroxy-3-oxo-propyl}-carbamic acid allyl ester

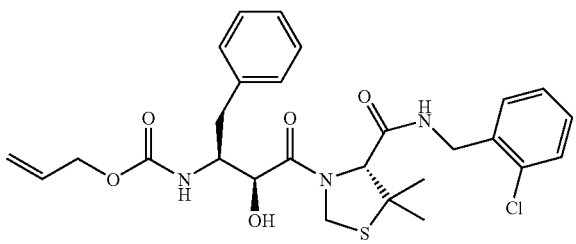

Isolated yield: 68%; 1H-NMR (400 MHz, dmso-d⁶): 7.00–7.40 (m, 9H), 6.60 (m, 1H), 5.80 (m, 1H), 5.32 (m, 1H), 5.19 (m, 1H), 4.00–5.00 (m, 9H), 2.75 (m, 2H), 1.56, 1.51 (s, 3H), 1.36, 1.33 (s, 3H);

MS (APCI, m/z): 548 (M+H); $C_{27}H_{32}ClN_3O_5S \cdot 0.89H_2O$ Calculated: C, 57.69; H, 6.06; N, 7.22. Observed: C, 57.30; H, 5.70; N, 7.22.

EXAMPLE B48

{1-Benzyl-3-[4-(2-chloro-benzylcarbamoyl)-5,5-dimethyl-thiazolidin-3-yl]-2-hydroxy-3-oxo-propyl}-carbamic acid prop-2-ynyl ester

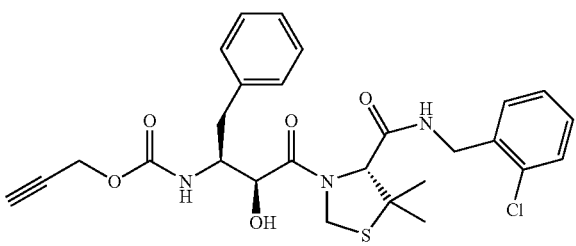

Isolated yield: 45%; 1H-NMR (400 MHz, dmso-d⁶): 6.88–7.62 (m, 9H), 4.20–5.00 (m, 9H), 2.70–2.90 (m, 2H), 2.42 (t, J=2.5 Hz, 1H), 1.56, 1.50 (s, 3H), 1.37, 1.32 (s, 3H); MS (APCI, m/z): 545 (M+H); $C_{27}H_{30}ClN_3O_5S \cdot 0.65H_2O$ Calculated: C, 58.35; H, 5.68; N, 7.56. Observed: C, 57.96; H, 5.48; N, 7.37.

EXAMPLE B49

3-{(2S,3S)-3-[3-(2,6-Difluoro-benzyl)-ureido]-2-hydroxy-4-phenyl-butyryl}-5,5-dimethyl-thiazolidine-4-carboxylic acid 2,6-difluoro-benzylamidea)

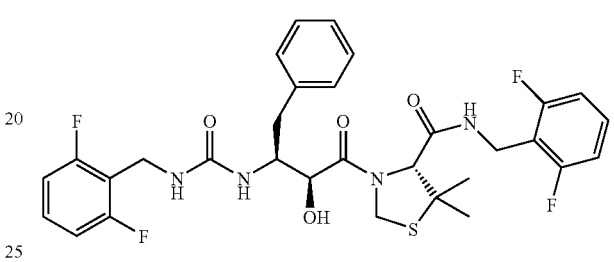

Isolated yield: 42%; 1H-NMR (400 MHz, dmso-d⁶): 6.60–7.40 (m, 11H), 4.00–4.80 (m, 9H), 2.60 (m, 2H), 1.50, 1.37 (s, 3H), 1.30, 1.13 (s, 3H); MS (APCI, m/z): 633; $C_{31}H_{32}F_4N_4O_4S$ Calculated: C, 58.85; H, 5.10; N, 8.86. Observed: C, 58.54; H, 5.00; N, 8.71.

EXAMPLE B50

{(1S,2S)-1-Benzyl-3-[(R)-4-(2,6-difluoro-benzylcarbamoyl)-5,5-dimethyl-thiazolidin-3-yl]-2-hydroxy-3-oxo-propyl}-carbamic acid allyl ester

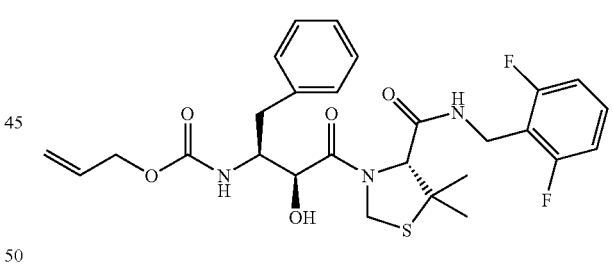

Isolated yield: 71%; 1H-NMR (400 MHz, dmso-d⁶): 6.60–7.40 (m, 8H), 5.80 (m, 1H), 5.05–5.35 (m, 2H), 4.00–5.00 (m, 9H), 2.75 (m, 2H), 1.56, 1.52 (s, 3H), 1.37, 1.35 (s, 3H); MS (APCI, m/z): 548 (M+H); $C_{27}H_{32}ClN_3O_5S \cdot 0.13H_2O$ Calculated: C, 58.97; H, 5.73; N, 7.64. Observed: C, 58.58; H, 5.61; N, 7.53.

EXAMPLE B51

{1-Benzyl-3-[4-(2,6-difluoro-benzylcarbamoyl)-5,5-dimethyl-thiazolidin-3-yl]-2-hydroxy-3-oxo-propyl}-carbamic acid prop-2-ynyl

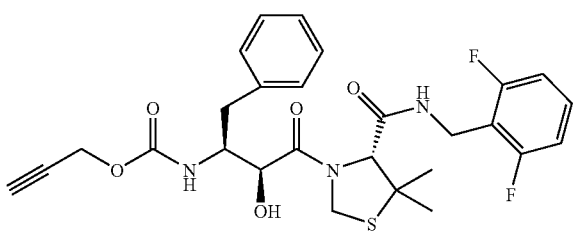

Isolated yield: 73%; 1H-NMR (400 MHz, dmso-d$^6$): 6.60–7.40 (m, 8H), 4.20–5.00 (m, 9H), 2.70–2.90 (m, 2H), 2.42 (m, 1H), 1.56, 1.50 (s, 3H), 1.38, 1.34 (s, 3H); MS (APCI, m/z): 546 (M+H); $C_{27}H_{30}ClN_3O_5S$ Calculated: C, 59.44; H, 5.36; N, 7.70. Observed: C, 59.33; H, 5.39; N, 7.56.

EXAMPLE B52

3-{(2S,3S)-2-Hydroxy-4-phenyl-3-[3-(2-trifluoromethyl-benzyl)-ureido]-butyryl}-5,5-dimethyl-thiazolidine-4-carboxylic acid 2-trifluoromethyl-benzylamide

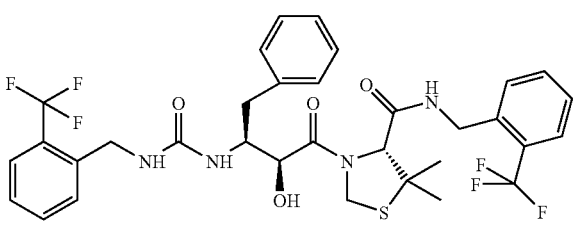

Isolated yield: 82%; 1H-NMR (400 MHz, dmso-d$^6$): 7.00–7.57 (m, 13H), 4.00–4.80 (m, 9H), 2.60 (m, 2H), 1.46, 1.40 (s, 3H), 1.25, 1.22 (s, 3H); MS (APCI, m/z): 697 (M+H); $C_{33}H_{34}F_6N_4O_4S$ Calculated: C, 56.89; H, 4.92; N, 8.04, Observed: C, 56.33; H, 4.78; N, 7.94.

EXAMPLE B53

{(1S,2S)-1-Benzyl-3-[5,5-dimethyl-4-(2-trifluoromethyl-benzylcarbamoyl)-thiazolidin-3-yl]-2-hydroxy-3-oxo-propyl}-carbamic acid allyl ester

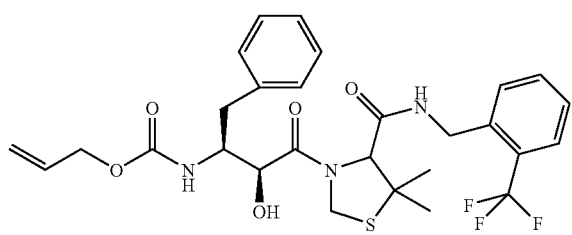

Isolated yield: 80%; 1H-NMR (400 MHz, dmso-d$^6$): 7.00–7.70 (m, 9H), 5.80 (m, 1H), 5.20 (m, 2H), 4.00–5.00 (m, 9H), 2.75 (m, 2H), 1.56, 1.50 (s, 3H), 1.40, 1.29 (s, 3H); MS (APCI, m/z): 580 (M+H); $C_{28}H_{32}F_3N_3O_5S\cdot0.56H_2O$ Calculated: C, 57.70; H, 5.60; N, 7.21. Observed: C, 57.31; H, 5.31; N, 6.83.

EXAMPLE B54

{1-Benzyl-3-[5,5-dimethyl-4-(2-trifluoromethyl-benzylcarbamoyl)-thiazolidin-3-yl]-2-hydroxy-3-oxo-propyl}-carbamic acid prop-2-ynyl ester

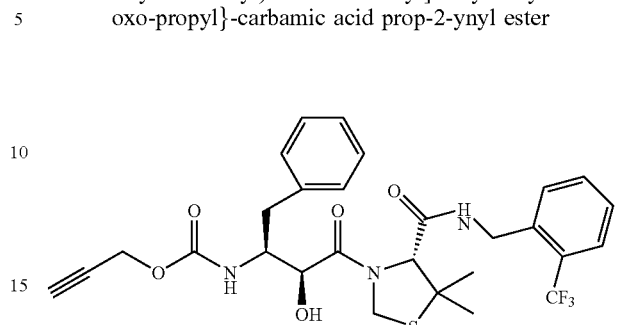

Isolated yield: 61%; 1H-NMR (400 MHz, dmso-d$^6$): 6.90–7.60 (m, 9H), 4.20–5.00 (m, 9H), 2.60–2.80 (m, 2H), 2.42 (m, 1H), 1.55, 1.48 (s, 3H), 1.40, 1.28 (s, 3H); MS (APCI, m/z): 578 (M+H); $C_{28}H_{30}F_3N_3O_5S$ Calculated: C, 58.17; H, 5.24; N, 7.27. Observed: C, 57.78; H, 5.25; N, 6.94.

EXAMPLE B55

3-{(2S,3S)-3-[3-(3-Fluoro-phenyl)-ureido]-2-hydroxy-4-phenyl-butyryl}-5,5-dimethyl-thiazolidine-4-carboxylic acid 2-methyl-benzylamide

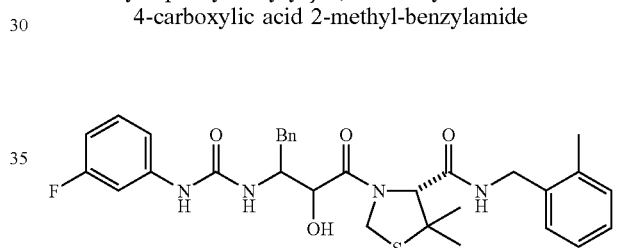

Isolated yield: 40%. $^1$H NMR (400 MHz, DMSO-d$_6$): δ 8.73 (s, 1H), 8.39 (t, 1H), 7.36–7.10 (m, 1H), 6.91 (d, 1H), 6.65 (t, 1H), 6.45 (d, 1H), 5.33 (br s, 1H), 4.98 (s, 2H), 4.49 (s, 2H), 4.38 (dd, 1H), 4.22–4.12 (m, 2H), 2.58 (d, 2H), 2.55 (m, 1H), 2.24 (s, 3H), 1.49 (s, 3H), 1.35 (s, 3H); MS-APCI (m/z+): 315, 579 (M+H).

EXAMPLE B56

N-[(1S,2S)-3-(4-Allylcarbamoyl-5,5-dimethyl-thiazolidin-3-yl)-1-benzyl-2-hydroxy-3-oxo-propyl]-nicotinamide

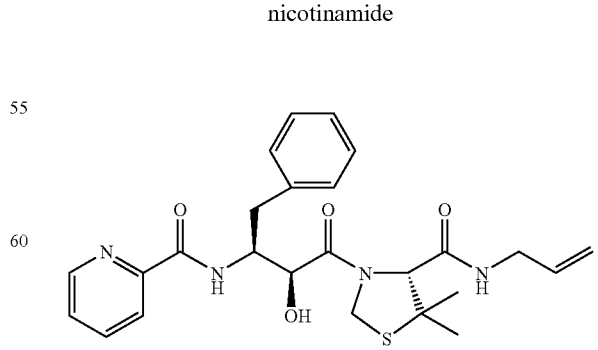

White solid: $^1$H NMR (DMSO-d$_6$) δ 8.81 (d, J=8.6, 1), 8.77 (d, J=6.2, 1H), 8.12 (m, 1H), 7.99 (m, 1H), 7.63 (m, 1H), 7.32–7.12 (m, 7H), 5.78 (m, 1H), 5.18 (m, 2H), 4.56 (m, 3H), 4.40 (m, 4H), 2.87–2.67 (m, 2H), 1.49 (s, 3H), 1.34 (s, 3H); Anal. (C$_{26}$H$_{32}$N$_4$O$_4$S.0.5H$_2$O.0.5TFA) calculated C, (57.65); H, (6.36); N, (10.19). found C, (57.73); H, (5.91); N, (10.15). HRMS (ESI) m/z calcd for 483.2075, found 497.2066.

EXAMPLE B57

3-[(2S,3S)-3-(5-Bromo-thiophene-2-sulfonylamino)-2-hydroxy-4-phenyl-butyryl]-5,5-dimethyl-thiazolidine-4-carboxylic acid 2-methyl-benzylamide

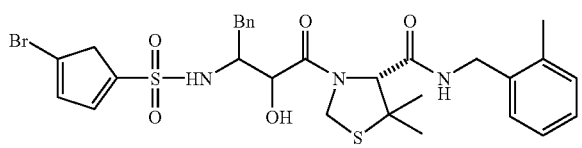

Isolated yield: 33%. MS-APCI (m/z+): 667 (M+H); HPLC: Rf (min) 20.98; Purity: 97%.

EXAMPLE B58

3-[(2S,3S)-3-(4-Cyano-benzenesulfonylamino)-2-hydroxy-4-phenyl-butyryl]-5,5-dimethyl-thiazolidine-4-carboxylic acid 2-methyl-benzylamide

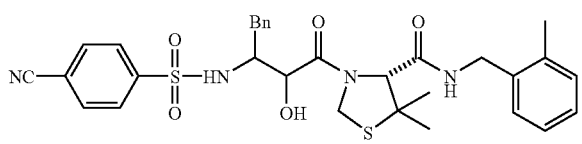

Isolated yield: 25%. MS-APCI (m/z+): 607 (M+H); HPLC: Rf (min) 20.71; Purity: 96%.

EXAMPLE B59

3-[(2S,3S)-3-(3-Benzyl-ureido)-2-hydroxy-4-phenyl-butyryl]-5,5-dimethyl-thiazolidine-4-carboxylic acid 2-methyl-benzylamide

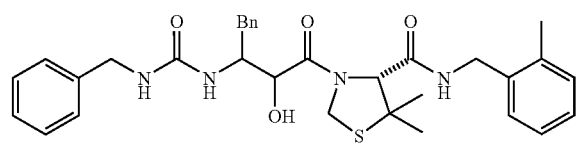

Isolated yield: 69%. $^1$H NMR (400 MHz, DMSO-d$_6$): δ 8.35 (t, 1H), 7.29 (d, 1H), 7.25–7.6 (m, 13H), 6.31 (t, 1H), 6.18 (d, 1H), 5.11 (d, 1H), 5.01 (d, 1H), 4.95 (d, 1H), 4.48–4.45 (s, 2H), 4.37 (dd, 1H), 4.19–4.03 (m, 4H), 2.70 (d, 1H), 2.53–2.46 (m, partially obscured by DMSO, 1H), 2.24 (s, 3H), 1.49 (s, 3H), 1.33 (s, 3H); MS-APCI (m/z+): 575 (M+H); HPLC: Rf(min.) 20.66; Purity: 97%, C$_{32}$H$_{38}$N$_4$O$_4$S.0.4H$_2$O calculated: 66.05, 6.72, 9.63; found: 66.18, 6.70, 9.61.

EXAMPLE B60

3-{(S)-2-Hydroxy-3-[3-(4-methoxy-benzyl)-ureido]-4-phenyl-butyryl}-5,5-dimethyl-thiazolidine-4-carboxylic acid 2-methyl-benzylamide

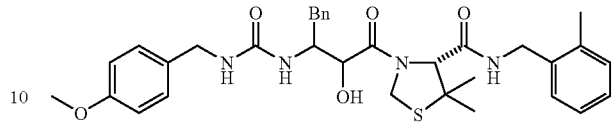

Isolated yield: 41%. $^1$H NMR (400 MHz, DMSO-d$_6$): δ 8.36 (t, 1H), 7.30–7.05 (m, 11H), 7.00 (d, 1H), 6.79 (d 1H), 6.23 (t, 1H), 6.12 (d, 1H), 5.10 (d, 1H), 5.02 (d, 1H), 4.94 (d, 1H), 4.48–4.44 (m, 2H), 4.38 (dd, 1H), 4.14 (dd, 1H), 4.08–3.96 (m, 4H), 3.69 (s, 3H), 2.68 (d, 1H), 2.24 (s, 3H), 1.49 (s, 3H), 1.33 (s, 3H); MS-APCI (m/z+): 605 (M+H).

EXAMPLE B61

3-[(2S,3S)-3-(3-Benzyl-ureido)-2-hydroxy-4-phenyl-butyryl]-5,5-dimethyl-thiazolidine-4-carboxylic acid benzylamide

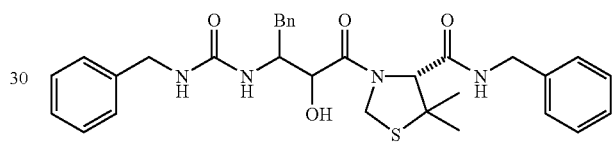

Isolated yield: 53%. $^1$H NMR (400 MHz, DMSO-d$_6$): δ 8.48 (t, 1H), 7.29–7.16 (m, 13H), 7.06 (d, 2H), 6.31–6.25 (m, 2H), 6.17 (d, 1H), 5.14 (d, 1H), 5.00 (d, 1H), 4.95 (d, 1H), 4.47–4.34 (m, 2H), 4.25–4.03 (m, 4H), 2.72 (d, 1H), 1.48 (s, 3H), 1.31 (s, 3H); MS-APCI (m/z+): 561; C$_{31}$H$_{36}$N$_4$O$_4$S.0.3H$_2$O calculated: C, 65.77; H, 6.52; N, 9.90, found: C, 65.70; H, 6.50; N, 9.90.

EXAMPLE B62

3-{(2S,3S)-2-Hydroxy-3-[3-(2-methyl-benzyl)-ureido]-4-phenyl-butyryl}-5,5-dimethyl-thiazolidine-4-carboxylic acid 2-methyl-benzylamide

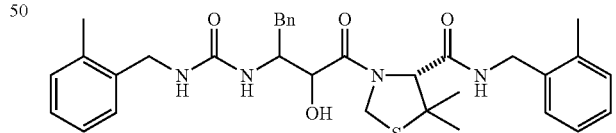

Isolated yield: 84%. $^1$H NMR (400 MHz, DMSO-d$_6$): δ 8.36 (t, 1H), 7.30–7.04 (m, 12H), 6.97 (d, 1H), 6.21–6.15 (m, 2H), 5.11 (d, 1H), 5.02 (d, 1H), 4.93 (d, 1H), 4.48–4.44 (m, 2H), 4.39 (dd, 1H), 4.19–4.04 (m, 4H), 2.67 (d, 2H), 2.24 (s, 3H), 2.14 (s, 3H), 1.48 (s, 3H), 1.33 (s, 3H); MS-APCI (m/z+): 589; HPLC: Rf (min) 21.25; Purity: 100%.

EXAMPLE B63

33-{(2S,3S)-2-Hydroxy-3-[3-(4-methoxy-benzyl)- ureido]-4-phenyl-butanoyl}-5,5-dimethyl-thiazolidine-4-carboxylic acid 4-methoxy-benzylamide

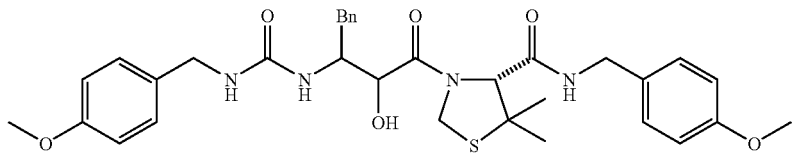

Isolated yield: 59%. ¹H NMR (400 MHz, DMSO-$d_6$): δ 8.41 (t, 1H), 7.22–7.14 (m, 8H), 7.00 (d, 2H), 6.83–6.77 (m, 3H), 6.23–6.21 (m, 2H), 6.11 (d, 1H), 5.11 (d, 1H), 5.00 (d, 1H), 4.94 (d, 1H), 4.46–4.41 (m, 2H), 4.29–3.96 (m, 4H), 3.69 (s, 3H), 3.65 (s, 3H), 2.68 (d, 1H), 1.47 (s, 3H), 1.28 (s, 3H); MS-APCI (m/z+): 121, 621; HPLC: Rf (min) 20.68; Purity: 98%.

EXAMPLE B64

{(1S,2S)-1-Benzyl-2-hydroxy-3-[4-(4-methoxy-benzylcarbamoyl)-5,5-dimethyl-thiazolidin-3-yl]-3-oxo-propyl}-carbamic acid prop-2-ynyl ester

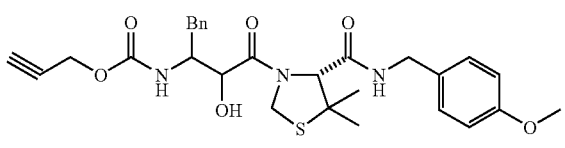

Isolated yield: 64%. ¹H NMR (400 MHz, DMSO-$d_6$): δ 8.39 (t, 1H), 7.46 (d, 1H), 7.27–7.13 (m, 8H), 6.79 (d, 2H), 5.34 (d, 1H), 4.93 (dd, 2H), 4.50 (s, 2H), 4.40 (s, 2H), 4.29 (dd, 1H), 4.14 (dd, 1H), 3.97–3.88 (m, 1H), 3.67 (s, 3H), 2.72–2.58 (m, 2H), 1.48 (s, 3H), 1.27 (s, 3H); MS-APCI (m/z+): 540; HPLC: Rf (min) 19.07; Purity: 100%; $C_{28}H_{33}N_3O_6S \cdot 0.4H_2O$: calcd: C, 61.50; H, 6.23; N, 7.68. found: C, 61.54; H, 6.37; N, 7.63.

EXAMPLE B65

3-[(2S,3S)-2-Hydroxy-3-((S)-2-methyl-butyrylamino)-4-phenyl-butyryl]-5,5-dimethyl-thiazolidine-4-carboxylic acid 2-methyl-benzylamide

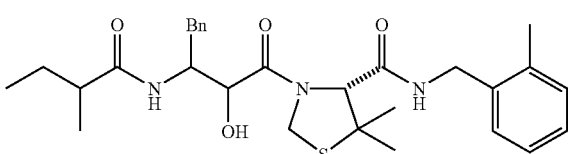

Isolated yield: 98%. ¹H NMR (400 MHz, DMSO-$d_6$): δ 8.36 (t, 1H), 7.92 (d, 1H), 7.31–7.26 (m, 3H), 7.18–7.08 (m, 6H), 5.19 (d, 1H), 5.10 (d, 1H), 4.92 (d, 1H), 4.48 (s, 1H), 4.40 (dd, 1H), 4.19–4.14 (m, 2H), 2.69–2.57 (m, 2H), 2.26 (s, 3H), 2.13–2.08 (m, 1H), 1.48 (s, 3H), 1.44–1.36 (m, 1H), 1.33 (s, 3H); 1.20–1.14 (m, 1H), 0.75–0.65 (m, 6H); MS-APCI (m/z+): 265, 526 (M+H); $C_{29}H_{39}N_3O_4S$: calcd: C, 66.26; H, 7.48; N, 7.99. found: C, 65.93; H, 7.59; N, 7.83.

EXAMPLE B66

3-{(2S,3S)-2-Hydroxy-3-[3-(2-methyl-benzyl)-ureido]-4-phenyl-butyryl}-5,5-dimethyl-thiazolidine-4-carboxylic acid (pyridin-4-ylmethyl)-amide

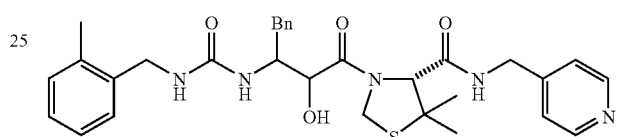

Isolated yield: 41%. MS-APCI (m/z+): 225, 576; HPLC: Rf (min) 17.93; Purity: 98%; $C_{31}H_{37}N_5O_4S \cdot 0.6H_2O$: calcd: C, 63.48; H, 6.56; N, 11.94; found: C, 63.41; H, 6.44; N, 11.87.

EXAMPLE B67

((1S,2S)-1-Benzyl-3-{5,5-dimethyl-4-[(pyridin-4-ylmethyl)-carbamoyl]-thiazolidin-3-yl}-2-hydroxy-3-oxo-propyl)-carbamic acid prop-2-ynyl ester

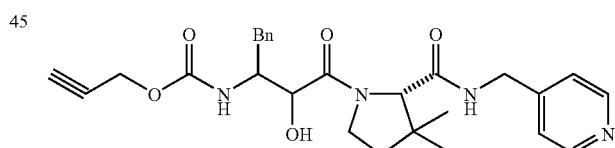

Isolated yield: 22%. ¹H NMR (400 MHz, DMSO-$d_6$): δ 8.55 (t, 1H), 8.49 (d, 2H), 7.46 (d, 1H), 7.28 (d, 2H), 7.26–7.09 (m, 6H), 5.42 (d, 1H), 4.97 (d, 1H), 4.47–4.38 (m, 5H), 4.93 (d, 1H), 4.23 (dd, 1H), 3.92–3.88 (m, 1H), 2.72–2.56 (m, 2H), 1.51 (s, 3H), 1.33 (s, 3H); MS-APCI (m/z+): 455, 511; HPLC: Rf (min) 16.76; Purity: 100%.

EXAMPLE B68

3-{(2S,3S)-2-Hydroxy-3-[(1-methyl-1H-pyrrole-3-carbonyl)-amino]-4-phenyl-butyryl}-5,5-dimethyl-thiazolidine-4-carboxylic acid (pyridin-4-ylmethyl)-amide

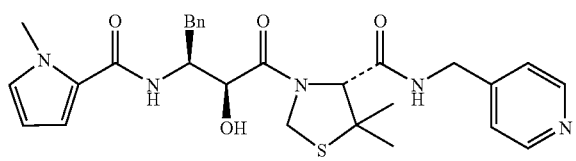

Isolated yield: 21%. ¹H NMR (400 MHz, DMSO-d₆): δ 8.57 (t, 1H), 8.41 (d 2H), 7.90 (d, 1H), 7.30 (d, 2H), 7.25 (d, 2H), 7.21–7.19 (m, 1H), 7.14 (t, 1H), 7.07 (t, 1H), 6.81–6,78 (m, 2H), 5.95–5.92 (m, 1H), 5.45 (d, 1H), 5.12 (d, 1H), 5.00 (d, 1H), 4.49–4.34 (m, 3H), 4.32–4.29 (m, 1H), 4.22 (dd, 1H), 3.68 (s, 3H), 2.81–2.76 (m, 2H), 1.52 (s, 3H), 1.34 (s, 3H); MS-APCI (m/z+): 536; HPLC: Rf (min) 17.58; Purity: 96%.

EXAMPLE B69

3-{3-[3-(2,4-Dimethyl-benzyl)-ureido]-2-hydroxy-4-phenyl-butyryl}-5,5-dimethyl-thiazolidine-4-carboxylic acid 2-methyl-benzylamide

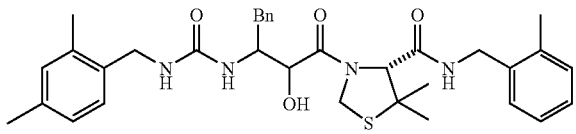

Isolated yield: 17%; MS-APCI (m/z+): 603; HPLC: Rf (min) 21.96; Purity: 97%.

EXAMPLE B70

3-{2-Hydroxy-3-[3-(2-methoxy-benzyl)-ureido]-4-phenyl-butyryl}-5,5-dimethyl-thiazolidine-4-carboxylic acid 2-methyl-benzylamide

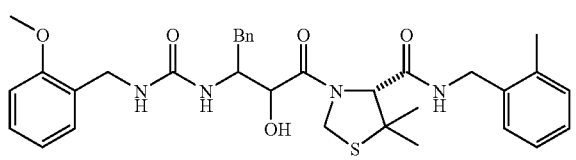

Isolated yield: 18%; MS-APCI (m/z+): 605; HPLC: Rf (min) 21.72; Purity: 94%.

EXAMPLE B71

3-{3-[3-(2,4-Difluoro-benzyl)-ureido]-2-hydroxy-4-phenyl-butyryl}-5,5-dimethyl-thiazolidine-4-carboxylic acid 2-methyl-benzylamide

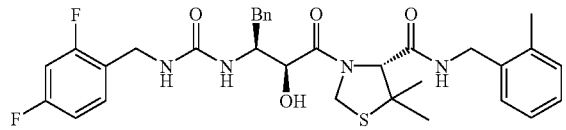

Isolated yield: 12%; MS-APCI (m/z+): 611; HPLC: Rf (min) 21.00; Purity: 86%.

EXAMPLE B72

3-{3-[3-(2-Bromo-benzyl)-ureido]-2-hydroxy-4-phenyl-butyryl}-5,5-dimethyl-thiazolidine-4-carboxylic acid 2-methyl-benzylamide

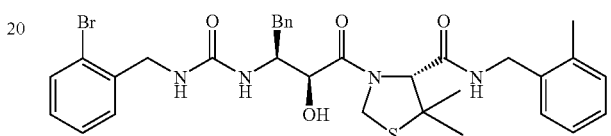

Isolated yield: 16%; MS-APCI (m/z+): 442, 468, 655; HPLC: Rf (min) 21.59; Purity: 94%.

EXAMPLE B73

3-{3-[3-(4-Bromo-benzyl)-ureido]-2-hydroxy-4-phenyl-butyryl}-5,5-dimethyl-thiazolidine-4-carboxylic acid 2-methyl-benzylamide

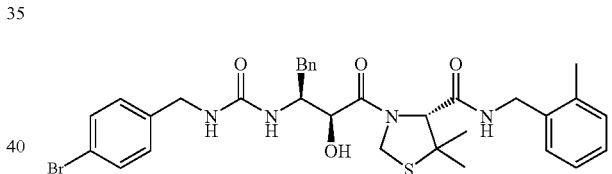

Isolated yield: 5%; MS-APCI: 652 (M–H); HPLC: Rf (min) 22.12; Purity: 95%.

EXAMPLE B74

(R)-3-{(2S,3S)-3-[3-(3,4-Dimethoxy-benzyl)-ureido]-2-hydroxy-4-phenyl-butyryl}-5,5-dimethyl-thiazolidine-4-carboxylic acid 2-methyl-benzylamide

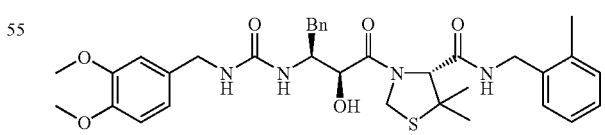

Isolated yield: 24%; MS-APCI (m/z+): 635; HPLC: Rf (min) 19.44; Purity: 88%.

EXAMPLE B75

(R)-3-{(2S,3S)-2-Hydroxy-4-phenyl-3-[3-(3-trifluoromethyl-benzyl)-ureido]-butyryl}-5,5-dimethyl-thiazolidine-4-carboxylic acid 2-methyl-benzylamide

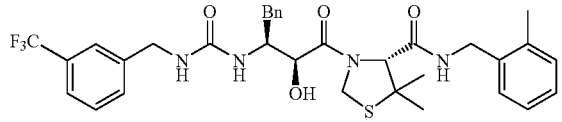

Isolated yield: 19%; MS-APCI (m/z+): 643; HPLC: Rf (min) 21.87; Purity: 95%.

EXAMPLE B76

(R)-3-{(2S,3S)-2-Hydroxy-3-[3-(3-methoxy-benzyl)-ureido]-4-phenyl-butyryl}-5,5-dimethyl-thiazolidine-4-carboxylic acid 2-methyl-benzylamide

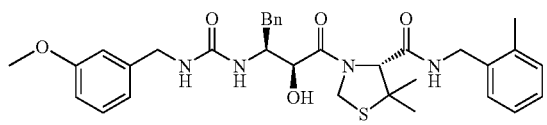

Isolated yield: 35% MS-APCI (m/z+): 605; HPLC: Rf (min) 20.63; Purity: 95%.

EXAMPLE B77

(R)-3-{(2S,3S)-3-[2-(2,6-Dichloro-phenoxy)-acetylamino]-2-hydroxy-4-phenyl-butyryl}-5,5-dimethyl-thiazolidine-4-carboxylic acid 2-methyl-benzylamide

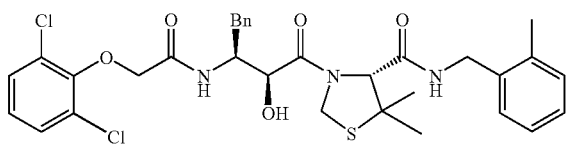

Isolated yield: 75%. $^1$H NMR (400 MHz, DMSO-$d_6$): δ 8.36 (t, 1H), 8.12 (d, 1H), 7.47 (d, 2H), 7.30–7.22 (m, 3H), 7.20–7.06 (m, 7H), 5.49 (d, 1H), 4.96 (d, 1H), 4.94 (d, 1H), 4.48–4.45 (m, 2H), 4.40–4.33 (m, 3H), 4.23–4.14 (m, 2H), 2.78–2.69 (m, 2H), 2.24 (s, 3H), 1.49 (s, 3H), 1.334 (s, 3H); MS-APCI (m/z+): 644, 646. HPLC: Rf (min) 22.23; Purity: 98%.

EXAMPLE B78

(R)-3-{(2S,3S)-2-Hydroxy-4-phenyl-3-[(1-o-tolylmethanoyl)-amino]-butanoyl}-5,5-dimethyl-thiazolidine-4-carboxylic acid (S)-indan-1-ylamide

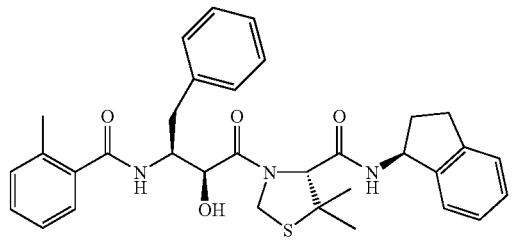

IR (neat, cm$^{-1}$) 3311, 3026, 2966, 1655, 1538, 1454, 1222, $^1$H NMR (DMSO) δ 8.40–8.25 (m, 2H), 7.40–7.10 (m, 13H), 5.43 (d, J=6.9, 1H), 5.30 (dd, J=15.0, 7.6, 1H), 5.14 (d, J=9.3, 1H), 5.04 (d, J=9.3, 1H), 4.54–4.30 (m, 3H), 3.00–2.60 (m, 4H), 2.42–2.30 (m, 1H), 2.02 (s, 3H), 1.90–1.80 (m, 1H), 1.49 (s, 3H), 1.44 (s, 3H) HRMS (ESI) m/z calcd for $C_{33}H_{38}N_3O_4S$ (M+H)$^+$ 572.2581, found 572.2583.

EXAMPLE B79

(R)-3-{(2S,3S)-2-Hydroxy-4-phenyl-3-[(1-o-tolylmethanoyl)-amino]-butanoyl}-5,5-dimethyl-thiazolidine-4-carboxylic acid (thiophen-2-ylmethyl)-amide

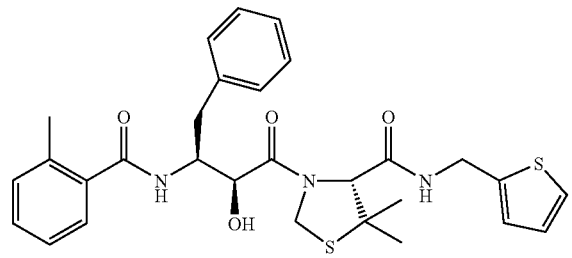

IR (neat, cm$^{-1}$) 3306, 3062, 2966, 1651, 1538, 1454, 1369, 1222, 1110, 700, $^1$H NMR (DMSO) δ 8.54 (t, J=6.0, 1H), 8.21 (d, J=7.9, 1H), 7.40–7.10 (m, 1H), 6.90 (dd, J=5.0, 3.5, 1H), 5.51 (d, J=6.6, 1H), 5.10 (d, J=9.3, 1H), 5.01 (d, J=9.3, 1H), 4.60–4.30 (m, 5H), 2.92–2.62 (m, 2H), 2.04 (s, 3H), 1.48 (s, 3H), 1.32 (s, 3H) HRMS (ESI) m/z calcd for $C_{29}H_{34}N_3O_4S_2$ (M+H)$^+$ 552.1989, found 552.1991.

EXAMPLE B80

(R)-3-{(2S,3S)-2-Hydroxy-4-phenyl-3-[(1-o-tolylmethanoyl)-amino]-butanoyl}-5,5-dimethyl-thiazolidine-4-carboxylic acid (S)-cyclohex-2-enylamide

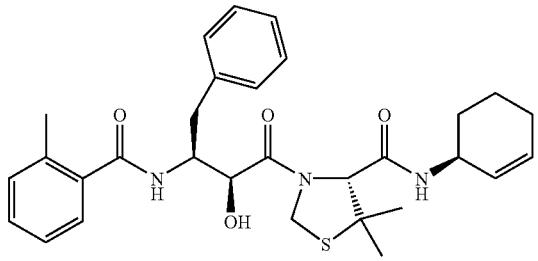

IR (neat, cm$^{-1}$) 3316, 2932, 1632, 1530, 1452, 1242, 1109, $^1$H NMR (DMSO) δ 8.25 (d, J=8.2, 1H), 7.95 (d, J=7.9, 1H), 7.40–7.05 (m, 9H), 5.80–5.70 (m, 2H), 5.50–5.40 (m, 1H), 5.39 (d, J=6.9, 1H), 5.12 (d, J=9.2, 1H), 5.00 (d, J=9.2, 1H), 4.54–4.20 (m, 3H), 2.90–2.62 (m, 2H), 2.02 (s, 3H), 2.00–1.60 (m, 6H), 1.48 (s, 3H), 1.37 (s, 3H); HRMS (ESI) m/z calcd for $C_{30}H_{38}N_3O_4S$ (M+H)$^+$ 536.2568, found 536.2583.

EXAMPLE B81

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic acid (S)-cyclohex-2-enylamide

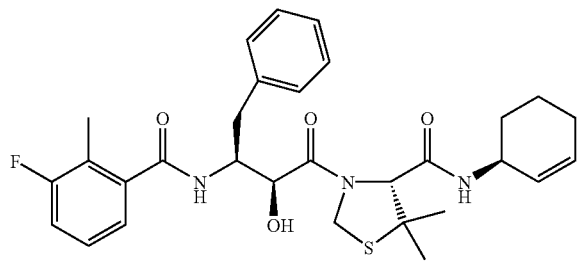

White solid: $^1$H NMR (DMSO) δ 8.37 (d, J=8.8, 1H), 7.95 (d, J=7.7, 1H), 7.40–6.90 (m, 8H), 5.80–5.70 (m, 2H), 5.50–5.40 (m, 2H), 5.10 (d, J=8.9, 1H), 5.00 (d, J=8.9, 1H), 4.60–4.20 (m, 3H), 2.90–2.60 (m, 2H), 2.00–1.89 (m, 2H), 1.88 (s, 3H), 1.80–1.60 (m, 4H), 1.48 (s, 3H), 1.37 (s, 3H); HRMS (ESI) m/z calcd for $C_{30}H_{37}N_3O_4SF$ (M+H)$^+$ 554.2502, found 554.2489.

EXAMPLE B82

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic acid (S)-indan-1-ylamide

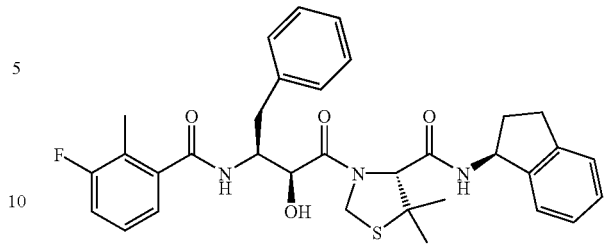

White solid: $^1$H NMR (DMSO) δ 8.43 (d, J=8.8, 1H), 8.34 (d, J=7.9, 1H), 7.40–7.10 (m, 11H), 6.95 (d, J=7.2, 1H), 5.47 (d, J=6.8, 1H), 5.30 (dd, J=15.6, 7.9, 1H), 5.13 (d, J=9.2, 1H), 5.04 (d, J=9.2, 1H), 4.50–4.30 (m, 3H), 3.00–2.60 (m, 4H), 2.42–2.30 (m, 1H), 1.89 (s, 3H), 1.90–1.79 (m, 1H), 1.49 (s, 3H), 1.41 (s, 3H); HRMS (ESI) m/z calcd for $C_{33}H_{37}N_3O_4FS$ (M+H)$^+$ 590.2489, found 590.2486.

EXAMPLE B83

(R)-3-((2S,3S)-2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid (S)-indan-1-ylamide

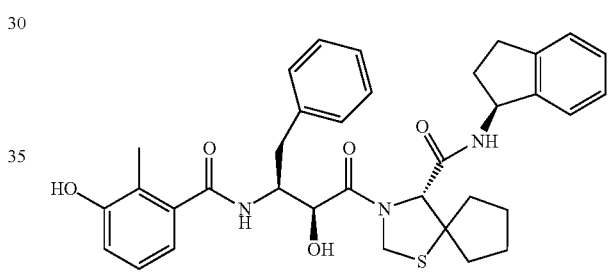

$^1$H NMR (DMSO-d$_6$) δ 9.37 (s, 1H), 8.33 (d, 1H, J=8.1), 8.20 (d, 1H, J=8.4), 7.30–7.13 (m, 9H), 6.94 (t, 1H, J=8.24), 6.76 (d, 1H, J=7.9), 6.54 (d, 1H, J=7.9), 5.40 (d, 1H, J=6.4), 5.29 (m, 1H), 5.13 (d, 1H, J=9.3), 4.98 (d, 1H, J=9.3), 4.60 (s, 1H), 4.51 (m, 1H), 4.40 (m, 1H), 2.96–2.63 (m, 4H), 2.54–2.26 (m, 2H), 2.04–1.68 (m, 8H), 1.79 (s, 3H). Exact mass calculated for $C_{35}H_{40}N_3O_5S$ (M+H)$^+$ 614.2689, found 614.2678.

EXAMPLE B84

(R)-3-((2S,3S)-2-Hydroxy-3-{[1-(3-hydroxy-2-methyl-phenyl)-methanoyl]-amino}-4-phenyl-butanoyl)-1-thia-3-aza-spiro[4.5]decane-4-carboxylic acid (S)-cyclohex-2-enylamide

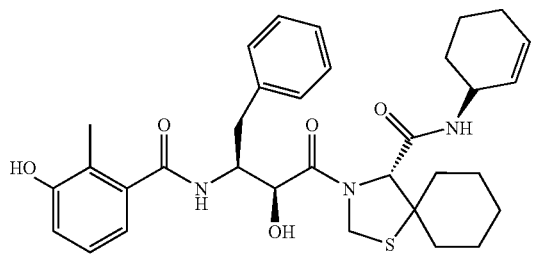

¹H NMR (DMSO-d₆) δ 9.35 (s, 1H), 8.14 (d, 1H, J=8.6), 8.01 (d, 1H, J=7.9), 7.34–7.13 (m, 5H), 6.90 (t, 1H, J=7.9), 6.78 (d, 1H, J=5.3), 6.52 (d, 1H, J=7.3), 5.57–5.72 (m, 1H), 5.48–5.44 (m, 1H), 5.36 (d, 1H, J=7.0), 5.05 (d, 1H, J=9.0), 4.91 (d, 1H, J=9.0), 4.55 (s, 1H), 4.49–4.46 (m, 1H), 4.42–4.28 (m, 2H), 2.79–2.69 (m, 2H), 1.93 (m, 2H), 1.79 (s, 3H), 1.77–1.45 (m, 14H). Exact mass calculated for $C_{33}H_{42}N_3O_5S$ (M+H)⁺ 592.2845, found 592.2842.

EXAMPLE B85

(R)-3-[(2S,3S)-2-Hydroxy-3-(4-hydroxy-butyrylamino)-4-phenyl-butyryl]-5,5-dimethyl-thiazolidine-4-carboxylic acid 2-methyl-benzylamide

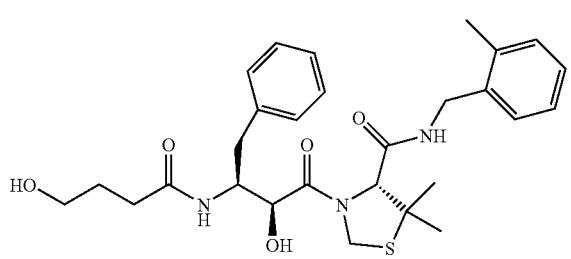

¹H NMR (DMSO-d₆) δ 8.36 (t, 1H, J=5.9), 7.97 (d, 1H, J=8.2), 7.31–7.09 (m, 9H), 5.23 (d, 1H, J=7.2), 5.05 (d, 1H, J=9.2), 4.92 (d, 1H, J=9.2), 4.48 (s, 1H), 4.44–4.34 (m, 2H), 4.19–4.13 (m, 2H), 3.26–3.20 (m, 2H), 2.72–2.54 (m, 2H), 2.25 (s, 3H), 2.04–1.98 (m, 2H), 1.49 (s, 3H), 1.47–1.38 (m, 2H), 1.34 (s, 3H). (no peak for primary OH) Exact mass calculated for $C_{28}H_{38}N_3O_5S$ (M+H)⁺ 528.2532, found 528.2540. Anal. Calcd for $C_{28}H_{37}N_3O_5S \cdot 0.3H_2O$: C, 63.08; H, 7.11; N, 7.88. Found: C, 62.95; H, 6.88; N, 7.56.

General Methods C

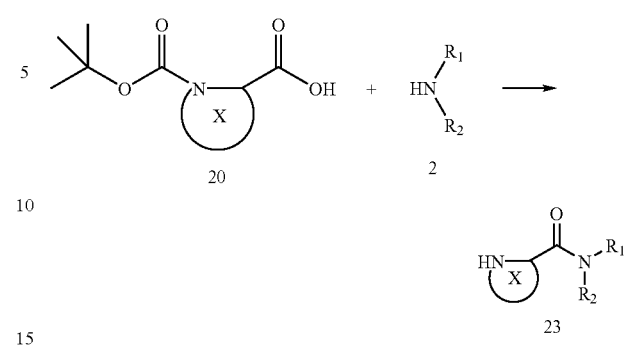

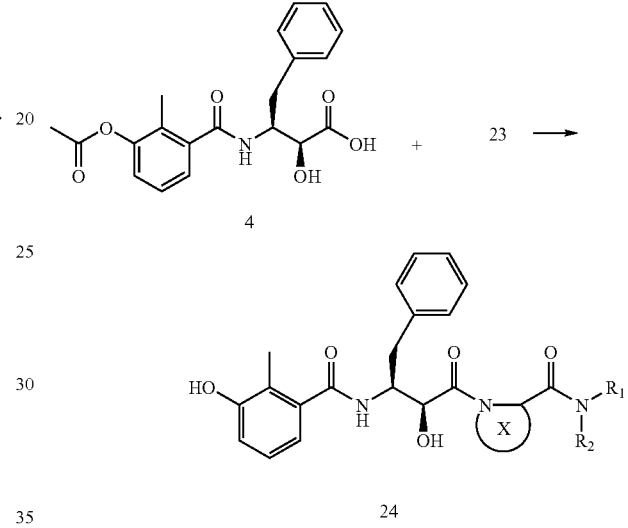

The synthesis of compounds with the general structure 24 is as follows. The boc-protected carboxylic acids 20a–j are coupled to the requisite amines 2 to yield amino amides 23 using a two step process. The process includes treatment of 20 with 2 in the presence of either diphenyl chlorophosphate or EDCI, followed by exposure to HCl or methane sulfonic acid. Final compounds 24 are obtained by a DCC-mediated coupling of 23 and 4 followed by deprotection of the P2 phenol. Final compounds were purified either by flash chromatography or preventive HPLC.

Additional General Method C

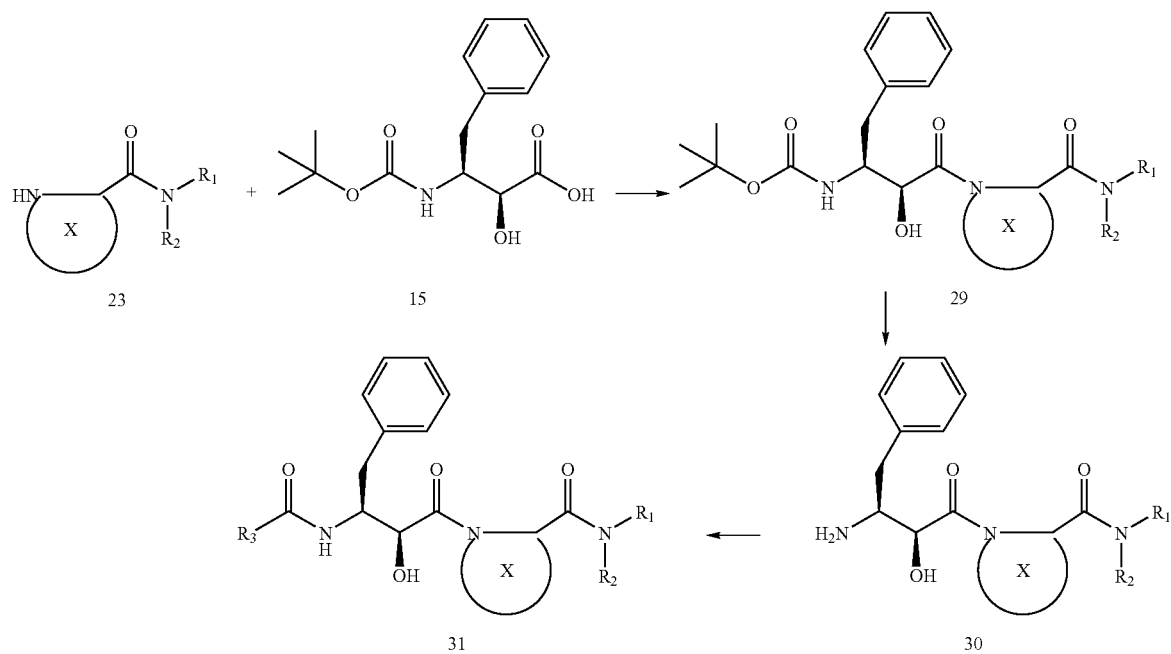

The synthesis of compounds of the general structure 31 (where P2 is not 2-methyl-3-hydroxy benzamide) is as follows. Amino amides of the general structure 23 were coupled to the Boc-acid intermediate 15 using DCC coupling conditions. The resulting intermediate 29 was deprotected under acidic conditions to yield amine of the general structure 30. Final compounds were obtained by modification of amine 30 by methods described in General Methods B section to give P2 amides, ureas, and carbamates.

Methods used for Synthesis of Compounds with P1 Variations.

EDCI coupling—To a solution of acid, amine and HOBT in $CH_2Cl_2$ was added EDCI and the solution stirred overnight at room temperature. The solution was concentrated in vacuo and the residue dissolved in ethyl acetate and a small portion of water. The solution was washed with saturated $NH_4Cl$ (2×), saturated $NaHCO_3$ (2×), brine (1×), dried with $MgSO_4$ and concentrated in vacuo. The crude used without further purification unless otherwise noted.

DCC coupling—A solution of acid, amine and HOBT was prepared in ethyl acetate. To the solution was then added DCC in an EtOAc solution at 0° C. and the mixture was stirred overnight at room temperature. The mixture was filtered and the filtrate was concentrated in vacuo. The residue dissolved in ethyl acetate washed with saturated $NH_4Cl$ (1×), saturated $NaHCO_3$ (1×), brine (1×), dried over $Na_2SO_4$ and concentrated in vacuo. The crude was used without further purification unless otherwise noted.

4N HCl Boc deprotection—To a solution of Boc-amine in dioxane was added 4N HCl solution in dioxane and the solution stirred overnight at room temperature. The solution was poured into saturated $NaHCO_3$ and the product was extracted into ethyl acetate. The organic solution was washed with brine, dried over $Na_2SO_4$ and concentrated in vacuo. The crude was used without further purification unless otherwise noted.

$MeSO_3H$ Boc deprotection—To a solution of Boc-amine in ethyl acetate at 0° C. was added methane sulfonic acid and the solution stirred 3–6 h at room temperature. The solution was cooled to 0° C. and sufficient saturated $NaHCO_3$ was added to quench the acid. The solution was diluted with ethyl acetate, washed with saturated $NaHCO_3$ and brine, dried over $Na_2SO_4$ and concentrated in vacuo. The crude used without further purification unless otherwise noted.

KCN Phenolic acetate deprotection—A solution of phenolic acetate and KCN in ethanol was heated at 50° C. overnight. The solution was concentrated in vacuo. The residue was purified by flash chromatography eluted with 0 to 5% methanol in $CH_2Cl_2$ unless otherwise noted.

NaOMe/MeOH Phenolic acetate deprotection—0.5 N $NaOCH_3$/MeOH Phenolic acetate deprotection—A solution of phenolic acetate in EtOAc and methanol was cooled to 0° C. in an ice bath. 0.5 N $NaOCH_3$/MeOH was then added dropwise and then stirred at 0° C. for 1.5–2 hrs following addition. Additional EtOAc was then added, the 0.15 N HCl (4.5 eq.) added dropwise. The phases were separated and organic phase washed with 2.5% $Na_2CO_3$ aqueous solution, then with 0.1 N HCl/brine (2:1), followed with brine, dried with $MgSO_4$ and concentrated in vacuo. The resulting residue subjected to flash silica gel chromatography to afford the desired product unless otherwise noted.

HCl/MeOH Phenolic acetate deprotection—To a solution of phenolic acetate in methanol was added 4N HCl in dioxane and the solution stirred at room temperature ca. 4 h. The solution was concentrated in vacuo. The residue was purified by flash chromatography eluted with 0 to 5% methanol in $CH_2Cl_2$ unless otherwise noted.

Fragments of the General Structure 20.

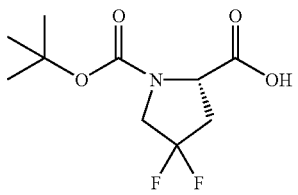
20a
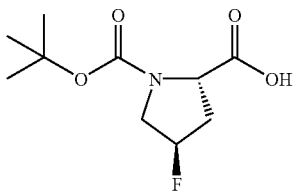
20b
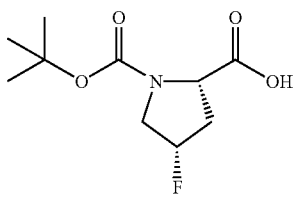
20c
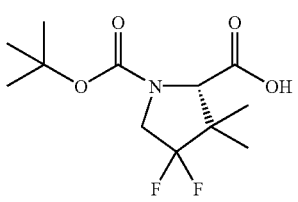
20d
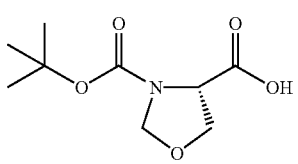
20e
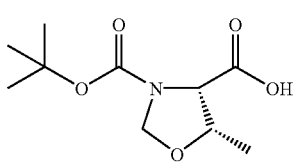
20f
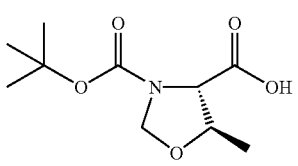
20g
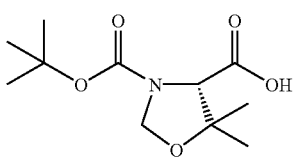
20h
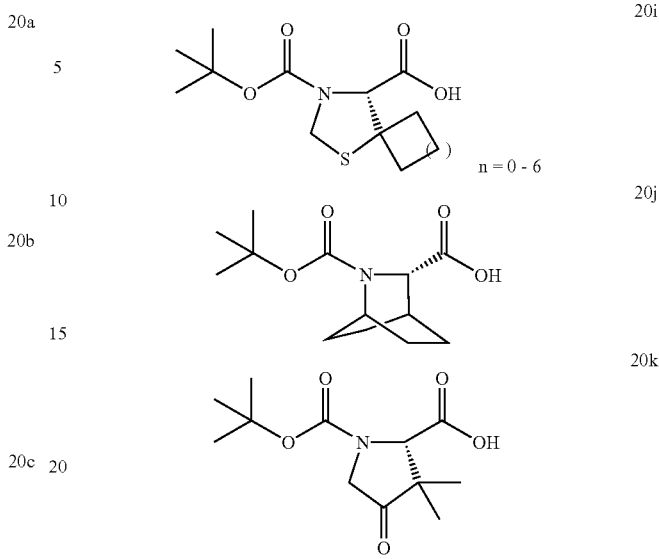
20i, 20j, 20k
Source of Boc-carboxylic Acids 20a–j
Boc-acids 20a, 20b and 20c were prepared following the procedure of Demange, L.; Ménez, A.; Dugave, C. *Tet. Lett.* 1998, 39, 1169.
Boc-acid 20d was prepared in the following way.
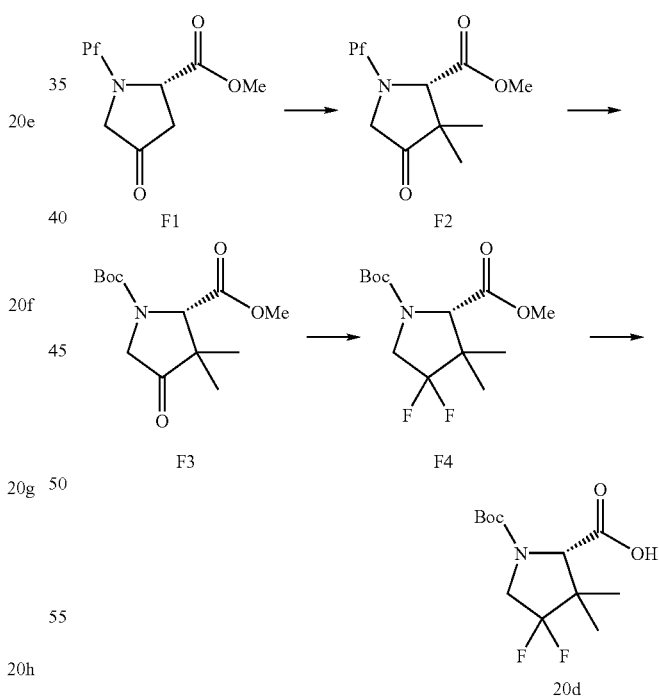
(2S)-3,3-Dimethyl-4-oxo-N-(9-phenylfluorenyl)proline methyl ester (F2):
The known ketone F1 (Blanco, M.-J.; Sardina, F. J. *J. Org. Chem.* 1996, 61, 4748)(14.2 g, 37 mmol) was dimethylated following the procedure of Sharma and Lubell (Sharma, R.; Lubell, W. D. *J. Org. Chem.* 1996, 61, 202) for the benzyl ester analog. The crude was purified by flash chromatography eluted with 0 to 10% ethyl acetate in hexanes. Isolated yield: 7.86 g (52%). $^1$H NMR (400 MHz, CDCl$_3$): δ 7.74 (d, 1H), 7.67 (d, 1H), 7.43–7.23 (m, 11H), 3.97 (d, 1H), 3.75 (d, 1H), 3.43 (s, 1H), 2.95 (s, 3H), 1.38 (s, 3H), 0.84 (s, 3H); MS-APCI (m/z+): 412, 241.

(2S)-3,3-Dimethyl-4-oxo-N-(Boc)proline methyl ester (F3):

To a solution of 9-phenylfluorene-protected amine F2 (300 mg, 0.73 mmol) and di-tert-butyl dicarbonate (320 mg, 1.5 mmol) in tetrahydrofuran (50 mL) was added 20 wt % palladium on carbon (100 mg), and the slurry was treated with 50 psi hydrogen gas for 40 h. The solution was filtered and concentrated in vacuo. The crude was purified by chromatography eluted with hexane, 10% ethyl acetate/hexane, and 25% ethyl acetate/hexane. Isolated yield: 182 mg (92%). $^1$H NMR (400 MHz, CDCl$_3$): δ 4.42 (s) +4.31 (s) (1H), 4.05 (d) +4.01 (d) (1H), 3.96 (d) +3.94 (d) (1H), 3.72 (s, 3H), 1.48 (s) +1.45 (s) (9H), 1.29 (s) +1.27 (s) (3H), 1.07 (s) +1.06 (s) (3H); MS-APCI (m/z+): 172.

(2S)-4,4-Difluoro-3,3-dimethyl-N-(Boc)proline methyl ester (F4):

A solution of ketone F3 (1.1 g, 4.1 mmol) and diethylaminosulfur trifluoride (4.3 mL, 32 mmol) in anhydrous dichloroethane (40 mL) was heated at 70° C. for 11 h. The solution was then cooled to ambient temperature and poured slowly into ice-cooled satd. NaHCO$_3$ soln (75 mL). The solution was diluted with ethyl acetate (100 mL) and washed with the NaHCO$_3$ soln, water (1×100 mL) and brine (1×100 mL), dried with magnesium sulfate and concentrated in vacuo. The crude was purified by flash chromatography eluted with 0 to 10% ethyl acetate in hexanes. Isolated yield: 0.75 g (63%). $^1$H NMR (400 MHz, DMSO-d$_6$): δ 4.15 (s) +4.07 (s) (1H), 3.88–3.77 (m, 2H), 3.76 (s) +3.75 (s) (3H), 1.47 (s) +1.41 (s) (9H), 1.27 (s, 3H), 1.06 (s, 3H); $^{19}$F NMR (376 MHz, DMSO-d$_6$): δ −112.8 (dt, J=230, 13 Hz) +−114.2 (dt, J=230, 15 Hz) (1F), −114.2 (dt, J=230, 14 Hz) +−115.1 (dt, J=230, 11 Hz) (1F); MS-APCI (m/z+): 194.

(2S)-4,4-Difluoro-3,3-dimethyl-N-(Boc)proline (20d):

To a solution of methyl ester F4 (4.7 g, 16 mmol) in methanol (100 mL) was added a solution of LiOH (6.8 g, 160 mmol) in water (50 mL) and the solution was heated at 50° C. for 14 h. The methanol was removed in vacuo and the remaining solution was diluted with water (200 mL). The aqueous solution was extracted with ether (2×200 mL), acidified with 1N HCl (200 mL) and extracted again with ether (2×200 mL). The combined organics were washed with brine (1×200 mL), dried with magnesium sulfate and concentrated in vacuo. The while solid was dried overnight at 40° C. under vacuum. Isolated yield: 4.3 g (95%). $^1$H NMR (400 MHz, DMSO-d$_6$): δ 12.95 (bs, 1H), 3.93 (s, 1H), 3.84–3.74 (m, 2H), 1.38 (s) +1.33 (s) (9H), 1.19 (s, 3H), 1.01 (s, 3H); $^{19}$F NMR (376 MHz, DMSO-d$_6$): δ −111.4 (dt, J=227, 13 Hz) +−112.4 (dt, J=227, 13 Hz) (1F), −113.5 (dt, J=227, 14 Hz) +−113.9 (dt, J=227, 15 Hz) (1F); MS-APCI (m/z+): 180.1, (m/z−): 278.

Boc-acids 20e, 20f, 20g and 20h were prepared following the procedure of Karanewsky, D.; et al. *J. Med. Chem.* 1990, 33, 1459.

Boc-acids of the general structure 20i were prepared by the following method.

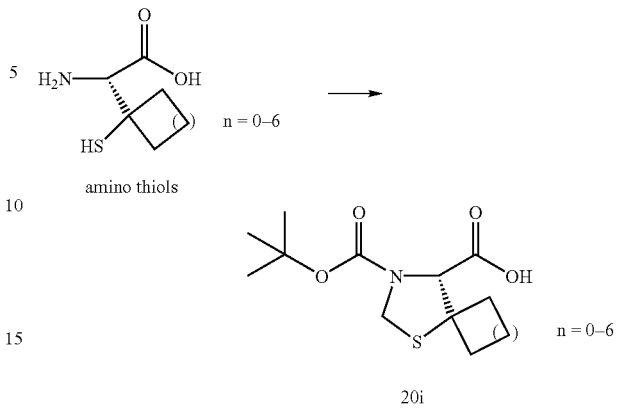

Example for n=2:

The known amino thiol (n=2) (Nagasawa, H. T.; et al. *J. Med. Chem.* 1987, 30, 1373.) (0.78 g, 3.7 mmol) was stirred in H$_2$O (10 mL) at room temp. The mixture was treated with 37% aqueous formaldehyde (0.36 mL, 4.8 mmol) and the result was stirred overnight at room temp. Next, Boc anhydride (0.96 g, 4.4 mmol) was added as a soln. in THF (5 mL). The result was stirred overnight at room temp. The desired product was isolated and purified by acid-base extraction. (2N HCl, sat. bicarb, and EtOAc).

The result 20i (n=2) was a white solid. Yield: (92%). $^1$H NMR (CDCl$_3$): δ 4.82–4.35 (m, 3H), 2.21–1.79 (m, 8H), 1.54 (s, 9H).

Boc-acid 20j was prepared following the procedure of Hursthouse, M. B., et al. *J. Chem. Soc. Perkin Trans. 1*, 1995, 2419–2425.

Boc-acid 20k was obtained by mild base hydrolysis of intermediate F3 from the preparation of Boc-acid 20d.

Specific Method C

EXAMPLE C1

(S)-4,4-Difluoro-1-[(2S,3S)-2-hydroxy-3-(3-hydroxy-2-methyl-benzoylamino)-4-phenyl-butyryl]-pyrrolidine-2-carboxylic acid 2-methyl-benzylamide

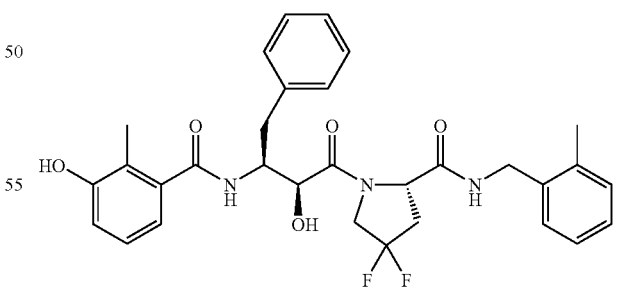

The title compound was prepared according to general methods using carboxylic acid 20a (0.96 g, 3.8 mmol), o-methylbenzyl amine (0.57 mL, 4.6 mmol), HOBT (0.62 g, 4.6 mmol), EDCI (0.88 g, 4.6 mmol), CH$_2$Cl$_2$ (50 mL). To give the crude Boc-amide (MS-APCI (m/z+): 355, 255) (1.35 g, 3.8 mmol). The Boc was removed using the general 4N HCl Boc deprotection. 4N HCl in 1,4-dioxane (5 mL), 1,4-dioxane (5 mL). The result was amino amide of general structure 23. Isolated yield: 0.79 g (71%, 2 steps). $^1$H NMR (400 MHz, DMSO-$d_6$): δ 9.02 (t, 1H), 7.24–7.14 (m, 4H), 4.55 (t, 1H), 4.35 (dd, 1H), 4.30 (dd, 1H), 3.73 (m, 2H), 2.94 (m, 2H), 2.52 (m, 1H), 2.27 (s, 3H); $^{19}$F NMR (376 MHz, DMSO-$d_6$): δ −95.3 (dq, J=235, 15 Hz, 1F), −96.5 (dq, J=235, 12 Hz, 1F); MS-APCI (m/z+): 255.

Amino amide 23 (100 mg, 0.34 mmol) was coupled to carboxylic acid 4 (140 mg, 0.38 mmol) using the general DCC coupling method outlined above. HOBT (51 mg, 0.38 mmol), DCC (78 mg, 0.38 mmol), TEA (50 µL, 0.36 mmol), CH$_2$Cl$_2$ (10 mL). The crude was purified by chromatography eluted with 10% acetone in CH$_2$Cl$_2$. Isolated yield: 0.13 g (63%). MS-APCI (m/z+): 608. This material was subjected to the general KCN phenolic acetate deprotection conditions (130 mg, 0.21 mmol), KCN (1 mg, 15 mmol), ethanol (10 mL). The crude was precipitated from diethyl ether and ethyl acetate with hexanes at −78° C. Isolated yield: 0.10 g (84%). $^1$H NMR (400 MHz, DMSO-$d_6$): δ 9.37 (s, 1H), 8.36 (t, 1H), 8.16 (d, 1H), 7.32–7.09 (m, 9H), 6.93 (t, 1H), 6.76 (d, 1H), 6.54 (d, 1H), 5.49 (d, 1H), 4.66 (dd, 1H), 4.34–4.15 (m, 6H), 2.85–2.67 (m, 3H), 2.40 (m, 1H), 2.22 (s, 3H), 1.79 (s, 3H); $^{19}$F NMR (376 MHz, DMSO-$d_6$): δ −98.7 (m, 2F); MS-APCI (m/z+): 566; HPLC Purity: 100%; Rf (min.) 19.01; Anal. $C_{31}H_{33}N_3O_5F_2$.0.3H$_2$O C, H, N calcd: C, 65.21; H, 5.93; N, 7.36. found: C, 65.11; H, 5.90; N, 7.17.

EXAMPLE C2

(S)-4,4-Difluoro-1-((2S,3S)-2-hydroxy-3-{[1-(3-hydroxy-2-methyl-phenyl)-methanoyl]-amino}-4-phenyl-butanoyl)-pyrrolidine-2-carboxylic acid (S)-indan-1-ylamide

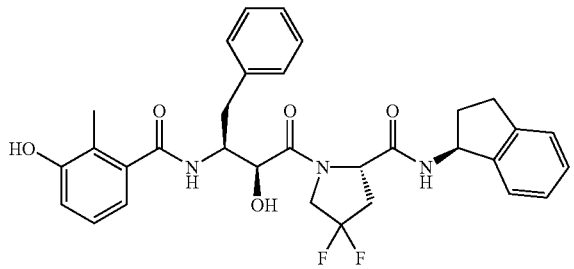

White solid; IR (neat, cm$^{-1}$) 3308, 3070, 2962, 1651, 1585, 1538, 1372, 1259, 1098; $^1$H NMR (DMSO-$d_6$) δ 9.34 (s, 1H), 8.36 (d, J=8.2, 1H), 8.21 (d, J=7.9, 1H), 7.33–7.14 (m, 9H), 6.96–6.91 (m, 1H), 6.77 (d, J=8.2, 1H), 6.55 (d, J=7.7, 1H), 5.41 (d, J=6.6, 1H), 5.28 (dd, J=15.0, 7.9, 1H), 4.68 (d, J=5.5, 1H), 4.63 (d, J=5.5, 1H), 4.40–4.20 (m, 3H), 3.00–2.62 (m, 4H), 2.50–2.30 (m, 4H), 1.79 (s, 3H); HRMS (ESI) m/z calcd for $C_{32}H_{34}N_3O_5F_2$ (M+H)$^+$ 578.2467, found 578.2476; Anal. Calcd for $C_{32}H_{33}N_3O_5F_2$: C, 66.54; H, 5.76; N, 7.27. Found: C, 66.35; H, 5.70; N, 7.20.

EXAMPLE C3

(S)-4,4-Difluoro-1-((2S,3S)-2-hydroxy-3-{[-(3-hydroxy-2-methyl-phenyl)-methanoyl]-amino}-4-phenyl-butanoyl)-pyrrolidine-2-carboxylic acid (1,2,3,4-tetrahydro-naphthalen-1-yl)-amide

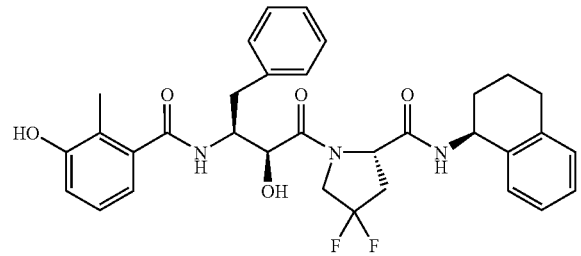

IR (neat, cm$^{-1}$) 3300, 2934, 1651, 1520, 1455, 1368, 1284; $^1$H NMR (DMSO-$d_6$) δ 9.35 (s, 1H), 8.35 (d, J=8.2, 1H), 8.21 (d, J=8.2, 1H), 7.34–7.10 (m, 9H), 6.96–6.91 (m, 1H), 6.77 (d, J=8.1, 1H), 6.55 (d, J=7.5, 1H), 5.40 (d, J=6.4, 1H), 5.00–4.90 (m, 1H), 4.65 (d, J=6.2, 1H), 4.63 (d, J=6.2, 1H), 4.40–4.20 (m, 3H), 3.00–2.60 (m, 4H), 2.50–2.40 (m, 2H), 1.90–1.60 (m, 4H), 1.79 (s, 3H); HRMS (ESI) m/z calcd for $C_{33}H_{36}N_3O_5F_2$ (M+H)$^+$ 592.2623, found 592.2610; Anal. Calcd for $C_{33}H_{35}N_3O_5F_2$.1H$_2$O: C, 65.01; H, 6.12; N, 6.89. Found: C, 65.07; H, 5.99; N, 6.75.

EXAMPLE C4

(S)-4,4-Difluoro-1-((2S,3S)-2-hydroxy-3-{[1-(3-hydroxy-2-methyl-phenyl)-methanoyl]-amino}-4-phenyl-butanoyl)-pyrrolidine-2-carboxylic acid (S)-cyclohex-2-enylamide

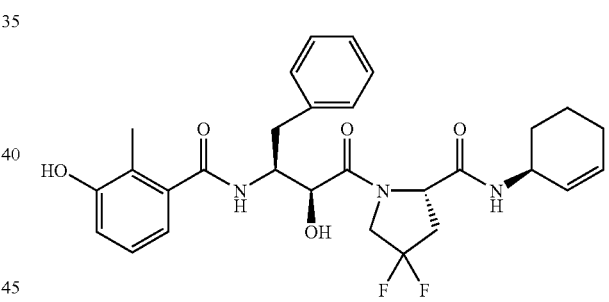

White solid; IR (neat, cm$^{-1}$) 3002, 2944, 1650, 1535, 1456, 1371, 1282, 1100; $^1$H NMR (DMSO-$d_6$) δ 9.35 (s, 1H), 8.18 (d, J=8.2, 1H), 8.01 (d, J=8.2, 1H), 7.35–7.13 (m, 5H), 6.96–6.91 (m, 1H), 6.76 (d, J=8.1, 1H), 6.54 (d, J=7.5, 1H), 5.77–5.73 (m, 1H), 5.49–5.45 (m, 1H), 5.39 (d, J=6.7, 1H), 4.60 (d, J=5.9, 1H), 4.56 (d, J=5.9, 1H), 4.40–4.10 (m, 4H), 2.90–2.60 (m, 4H), 2.50–2.30 (m, 2H), 1.79 (s, 3H), 1.78–1.60 (m, 2H), 1.60–1.38 (m, 2H); HRMS (ESI) m/z calcd for $C_{29}H_{34}N_3O_5F_2$ (M+H)$^+$ 542.2467, found 542.2460; Anal. Calcd for $C_{29}H_{33}N_3O_5F_2$.0.75H$_2$O: C, 62.75; H, 6.26; N, 7.57. Found: C, 62.77; H, 6.14; N, 7.37.

EXAMPLE C5

(S)-4,4-Difluoro-1-((2S,3S)-2-hydroxy-3-{[1-(3-hydroxy-2-methyl-phenyl)-methanoyl]-amino}-4-phenyl-butanoyl)-pyrrolidine-2-carboxylic acid 3-fluoro-2-methyl-benzylamide

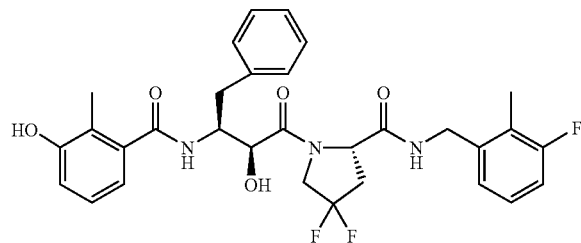

White solid; IR (neat, cm⁻¹) 3310, 1648, 1584, 1531, 1467, 1361, 1284, 1101; $^1$H NMR (DMSO-$d_6$) δ 9.36 (s, 1H), 8.43 (t, J=5.5, 1H), 8.16 (d, J=7.5, 1H), 7.31–6.90 (m, 9H), 6.76 (d, J=8.2, 1H), 6.54 (d, J=7.3, 1H), 5.33 (d, J=8.9, 1H), 4.67 (d, J=5.7, 1H), 4.64 (d, J=5.7, 1H), 4.38–4.17 (m, 5H), 2.90–2.60 (m, 4H), 2.14 (s, 3H), 1.79 (s, 3H); HRMS (ESI) m/z calcd for $C_{31}H_{33}N_3O_5F_3$ (M+H)⁺ 584.2372, found 584.2397; Anal. Calcd for $C_{31}H_{32}N_3O_5F_3·1H_2O$: C, 62.83; H, 5.61; N, 7.09. Found: C, 62.52; H, 5.63; N, 6.76.

EXAMPLE C6

(S)-4,4-Difluoro-1-((2S,3S)-2-hydroxy-3-{[1-(3-hydroxy-2-methyl-phenyl)-methanoyl]-amino}-4-phenyl-butanoyl)-pyrrolidine-2-carboxylic acid 5-fluoro-2-methyl-benzylamide

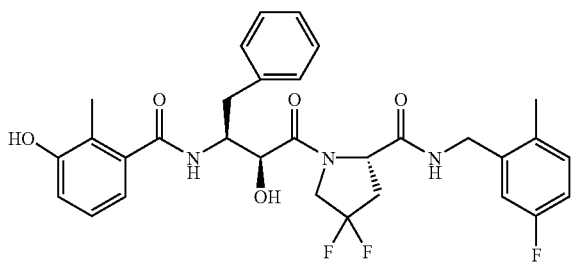

White solid; IR (neat, cm⁻¹) 3310, 1651, 1585, 1531, 1455, 1372, 1283, 1099; $^1$H NMR (DMSO-$d_6$) δ 9.36 (s, 1H), 8.45 (t, J=5.5, 1H), 8.15 (d, J=7.5, 1H), 7.30–6.90 (m, 9H), 6.76 (d, J=8.2, 1H), 6.55 (d, J=7.7, 1H), 5.54 (d, J=6.2, 1H), 4.68 (d, J=5.6, 1H), 4.65 (d, J=5.6, 1H), 4.40–4.00 (m, 5H), 3.00–2.60 (m, 4H), 2.19 (s, 3H), 1.79 (s, 3H); HRMS (ESI) m/z calcd for $C_{31}H_{33}N_3O_5F_3$ (M+H)⁺ 584.2372, found 584.2391; Anal. Calcd for $C_{31}H_{32}N_3O_5F_3·1H_2O$: C, 62.83; H, 5.61; N, 7.09. Found: C, 62.73; H, 5.65; N, 6.77.

EXAMPLE C7

4,4-Difluoro-1-[2-hydroxy-3-(3-hydroxy-2-methyl-benzoylamino)-4-phenyl-butyryl]-pyrrolidine-2-carboxylic acid propylamide

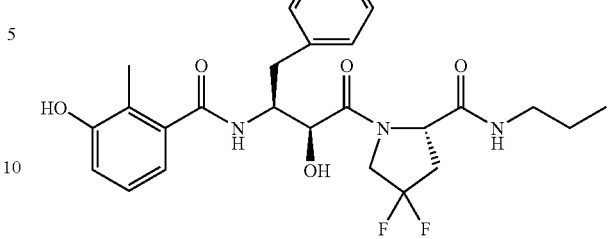

$^1$H-NMR (400 MHz, dmso-$d^6$): δ 9.30 (s, 1H), 8.13 (d, 1H), 7.87 (t, 1H), 7.35–7.08 (m, 5H), 6.91 (t, 1H), 6.74 (d, 1H), 6.52 (d, 1H), 5.44 (d, 1H), 4.57 (m, 1H), 4.35–4.09 (m, 3H), 2.96 (m, 2H), 2.83 (d, 1H), 2.7 (m, 2H), 2.35 (m, 1H), 1.8 (s, 3H), 1.35 (q, 2H), 0.78 (t, 3H); IR (KBr in cm−1): 3301, 1641, 1524, 1284; MS (APCI, m/z): 504 (M+H), 486, 312, 179.

EXAMPLE C8

(S)-4,4-Difluoro-1-((2S,3S)-2-hydroxy-3-{[1-(3-hydroxy-2-methyl-phenyl)-methanoyl]-amino}-4-phenyl-butanoyl)-pyrrolidine-2-carboxylic acid ((E)-2-methyl-but-2-enyl)-amide

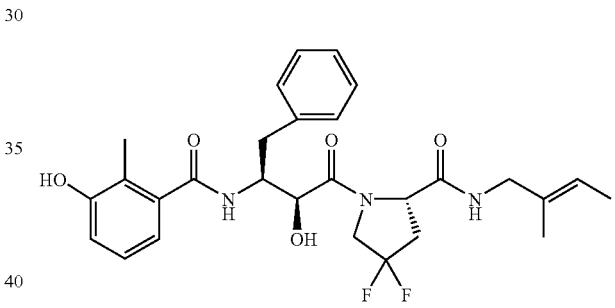

White solid; $^1$H NMR (DMSO-$d_6$) δ 9.36 (s, 1H), 8.13 (d, J=7.9, 1H), 8.02 (t, J=6.0, 1H), 7.33–7.13 (m, 5H), 6.93 (t, J=7.9, 1H), 6.76 (d, J=8.1, 1H), 6.54 (d, J=7.5, 1H), 5.49 (d, J=6.0, 1H), 5.29 (m, 1H), 4.60 (dd, J=9.3, 5.5, 1H), 4.33–4.16 (m, 4H), 3.66 (dd, J=15.2, 5.5, 1H), 3.52 (dd, J=15.2, 5.5, 1H), 2.86–2.66 (m, 3H), 2.37 (dd, J=14.5, 5.5, 1H), 1.79 (s, 3H), 1.50 (s, 6H); HRMS (ESI) m/z calcd for $C_{28}H_{34}N_3O_5F_2$ (M+H)⁺ 530.2467, found 530.2464.

EXAMPLE C9

(S)-4,4-Difluoro-1-((2S,3S)-2-hydroxy-3-{[1-(3-hydroxy-2-methyl-phenyl)-methanoyl]-amino}-4-phenyl-butanoyl)-pyrrolidine-2-carboxylic acid (3-methyl-but-2-enyl)-amide

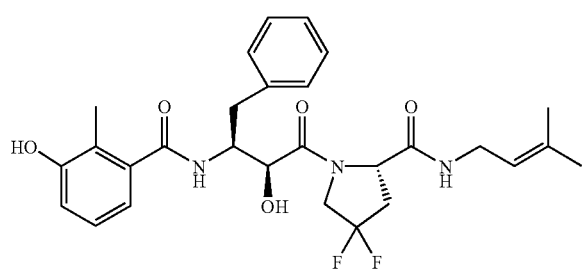

White solid; $^1$H NMR (DMSO-$d_6$) δ 9.36 (s, 1H), 8.15 (d, J=8.2, 1H), 7.97 (t, J=5.5, 1H), 7.35–7.14 (m, 5H), 6.94 (t, J=7.7, 1H), 6.76 (d, J=8.2, 1H), 6.53 (d, J=6.8, 1H), 5.47 (d, J=6.6, 1H), 5.07 (m, 1H), 4.57 (dd, J=9.2, 5.3, 1H), 4.32–4.15 (m, 4H), 3.70–3.60 (m, 2H), 2.86–2.64 (m, 3H), 2.38 (dd, J=14.1, 5.1, 1H), 1.79 (s, 3H), 1.62 (s, 3H), 1.58 (s, 3H); HRMS (ESI) m/z calcd for $C_{28}H_{34}N_3O_5F_2$ (M+H)$^+$ 530.2467, found 530.2463.

EXAMPLE C10

4,4-Difluoro-1-[2-hydroxy-3-(3-hydroxy-2-methyl-benzoylamino)-4-phenyl-butyryl]-pyrrolidine-2-carboxylic acid 2-chloro-benzylamide

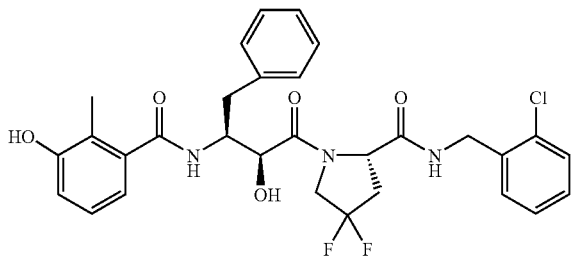

$^1$H-NMR (400 MHz, dmso-d$^6$): 9.35 (s, 1H), 9.3 (d, 1H), 8.52 (t, 1H), 8.13 (d, 1H), 7.44–7.09 (m, 9H), 6.91 (t, 1H), 6.74 (d, 1H), 6.48 (d, 1H), 5.35 (d, 1H), 4.65 (m, 1H), 4.44–4.17 (m, 5H), 2.96–2.57 (m, 3H), 2.41 (m, 1H), 1.74 (s, 3H); IR (KBr, cm$^{-1}$): 3300, 1640, 1522, 1283; MS (APCI, m/z): 586, 588 (M+H), 445, 330, 284.

EXAMPLE C11

4,4-Difluoro-1-[2-hydroxy-3-(3-hydroxy-2-methyl-benzoylamino)-4-phenyl-butyryl]-pyrrolidine-2-carboxylic acid (benzo[1,3]dioxol-5-ylmethyl)-amide

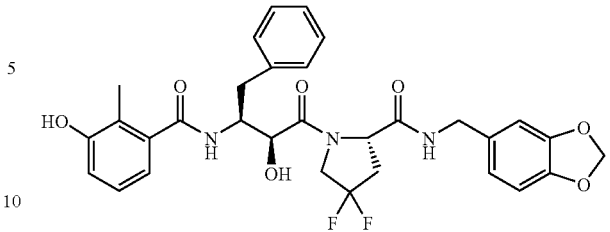

$^1$H-NMR (400 MHz, dmso-d$^6$): δ 9.35 (s, 1H), 8.38 (t, 1H), 8.13 (d, 1H), 7.35–7.09 (m, 5H), 6.91 (t, 1H), 6.74 (m, 4H), 6.52 (d, 1H), 5.91 (d, 2H), 5.52 (d, 1H), 4.61 (m, 1H), 4.17–4.38 (m, 4H), 4.09 (dd, 1H), 2.87 (d, 1H), 2.70 (q, 2H), 2.38 (dd, 1H), 0.78 (s, 3H); IR (KBr, cm$^{-1}$): 3299, 1643, 1492, 1445, 1237, 1038; MS (APCI, m/z): 531 (M+H), 340, 225, 180; HPLC: R$_f$ (min.) 18.226; Purity: 95%.

EXAMPLE C12

(S)-4,4-Difluoro-1-[(2S,3S)-2-hydroxy-3-(3-hydroxy-2-methyl-benzoylamino)-4-phenyl-butryl]-pyrrolidine-2-carboxylic acid 3-methoxy-benzylamide

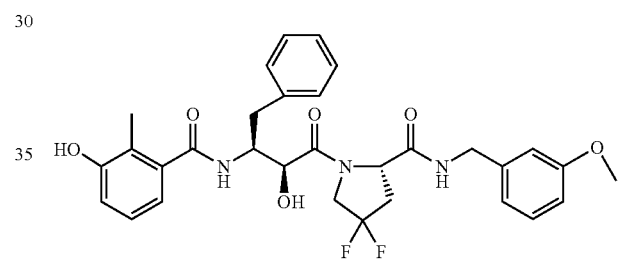

Isolated material was subjected to flash silica gel chromatography, eluting with 30% EtOAc/hexanes then with EtOAc/hexanes (4:1) to afford the title compound. Isolated yield: 89%. $^1$H NMR (400 MHz, DMSO-$d_6$): δ 9.36 (s, 1H), 8.45 (t, 1H), 8.13 (d, 1H), 7.29 (d, 2H), 7.24–7.19 (m, 3H), 7.17–7.14 (m, 2H), 6.92 (t, 1H), 6.82–6.80 (m, 2H), 6.76–6.73 (m, 1H), 6.54 (d, 1H), 5.60–5.50 (m, 1H), 4.64 (dd, 1H), 4.37–4.13 (m, 6H), 3.69 (s, 3H), 2.88–2.67 (m, 3H), 2.41 (dd, 1H), 1.79 (s, 3H); MS-APCI (m/z+): 582. Anal. $C_{31}H_{33}N_3O_6F_2 \cdot 0.2H_2O$ calcd: 63.62, 5.75, 7.18; found: 63.62, 5.93, 6.92.

EXAMPLE C13

(S)-4,4-Difluoro-1-[(2S,3S)-2-hydroxy-3-(3-hydroxy-2-methyl-benzoylamino)-4-phenyl-butyryl]-pyrrolidine-2-carboxylic acid 4-methoxy-benzylamide

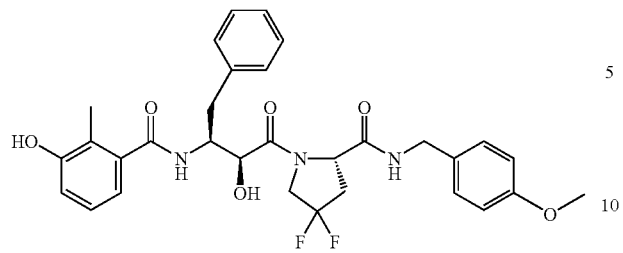

Isolated material was subjected to flash silica gel chromatography, eluting with EtOAc/hexanes (1:1) then with EtOAc/hexanes (4:1) to afford the title compound. Isolated yield: 91%. $^1$H NMR (400 MHz, DMSO-$d_6$): δ 9.36 (s, 1H), 8.40 (t, 1H), 8.14 (d, 1H), 7.30 (d, 2H), 7.21 (d, 2H), 7.17–7.14 (m, 3H), 6.92 (t, 1H), 6.82–6.80 (m, 2H), 6.76–6.73 (m, 1H), 6.54 (d, 1H), 5.60–5.50 (m, 1H), 4.64 (dd, 1H), 4.37–4.13 (m, 6H), 3.69 (s, 3H), 2.88–2.67 (m, 3H), 2.41 (dd, 1H), 1.79 (s, 3H); MS-APCI (m/z+): 582. HPLC: Rf(min.) 18.53; Purity: 100%.

EXAMPLE C14

(S)-4,4-Difluoro-1-[(2S,3S)-2-hydroxy-3-(3-hydroxy-2-methyl-benzoylamino)-4-phenyl-butyryl]-pyrrolidine-2-carboxylic acid 2-chloro-6-fluoro-benzylamide

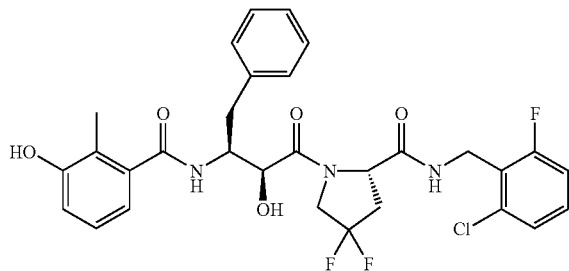

Isolated material was subjected to flash silica gel chromatography, eluting with EtOAc/hexanes gradient then with 2% MeOH/CH$_2$Cl$_2$ to afford the title compound. Isolated yield: 49%. $^1$H NMR (400 MHz, DMSO-$d_6$): δ 9.38 (s, 1H), 8.38 (t, 1H), 8.36 (d, 1H), 7.38–7.29 (m, 3H), 7.25–7.13 (m, 5H), 6.93 (t, 1H), 6.75 (d, 1H), 6.53 (d, 1H), 5.37 (d, 1H), 4.62 (dd, 1H), 4.47–4.18 (m, 6H), 2.90–2.64 (m, 3H), 2.35–2.26 (m, 1H), 1.78 (s, 3H); MS-APCI (m/z+): 312, 604. HPLC: Rf(min.) 19.02; Purity: 94%; Anal. C$_{30}$H$_{29}$N$_3$O$_5$F$_2$Cl.0.2H$_2$O calcd: 59.30, 4.88, 6.92, found: 59.27, 4.74, 6.69.

EXAMPLE C15

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid 2-methyl-benzylamide

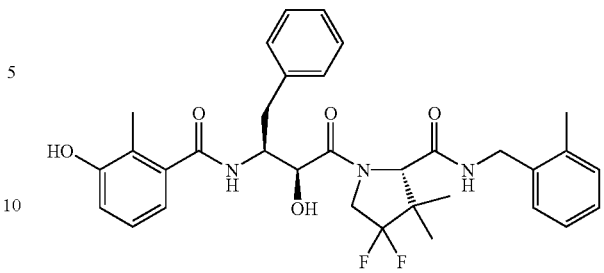

$^1$H NMR (400 MHz, DMSO-$d_6$): δ 9.36 (s, 1H), 8.30 (t, 1H), 8.17 (d, 1H), 7.33–7.10 (m, 9H), 6.93 (t, 1H), 6.76 (d, 1H), 6.53 (d, 1H), 5.51 (d, 1H), 4.50–4.25 (m, 6H), 4.15 (dd, 1H), 2.86 (d, 1H), 2.68 (t, 1H), 2.26 (s, 3H), 1.79 (s, 3H), 1.18 (s, 3H), 1.01 (s, 3H); $^{19}$F NMR (376 MHz, DMSO-$d_6$): δ –107.5 (dt, 1F), –114.2 (d, 1F); MS-APCI (m/z+): 594; HPLC Purity: 97%.: Rf(min.) 19.47; Anal. C$_{33}$H$_{37}$N$_3$O$_5$F$_2$.0.2H$_2$O calcd: C, 66.36; H, 6.31; N, 7.04. found: C, 66.30; H, 6.38; N, 6.75.

EXAMPLE C16

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid (S)-indan-1-ylamide

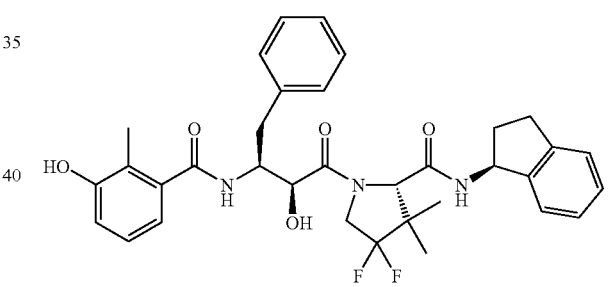

$^1$H NMR (400 MHz, DMSO-$d_6$): δ 9.36 (s, 1H), 8.30 (d, 1H), 8.20 (d, 1H), 7.32 (d, 2H), 7.24–7.12 (m, 7H), 6.93 (t, 1H), 6.76 (d, 1H), 6.53 (d, 1H), 5.45 (d, 1H), 5.29 (dd, 1H), 4.46 (dd, 1H), 4.38–4.20 (m, 4H), 2.98–2.74 (m, 3H), 2.67 (t, 1H), 2.42–2.32 (m, 1H), 1.86–1.80 (m, 1H), 1.78 (s, 3H), 1.18 (s, 3H), 1.10 (s, 3H); $^{19}$F NMR (376 MHz, DMSO-$d_6$): δ –109.1 (d, 1F), –113.5 (d, 1F); MS-APCI (m/z+): 606; HPLC Purity: 95%, Rf(min.) 21.30; Anal. C$_{34}$H$_{37}$N$_3$O$_5$F$_2$.0.4H$_2$O calcd: C, 66.63; H, 6.22; N, 6.86. found: C, 66.62; H, 6.19; N, 6.79.

EXAMPLE C17

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid prop-2-ynylamide

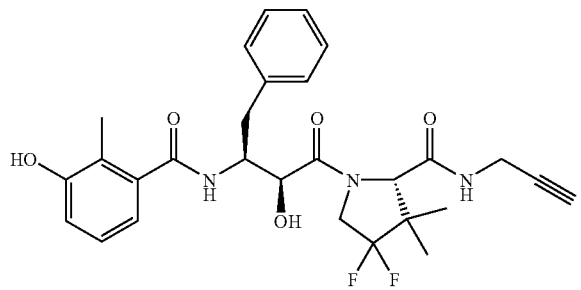

The title compound was purified by flash chromatography eluting with 0 to 5% MeOH/CH$_2$Cl$_2$, another column was run which was eluted with 50 to 100% ethyl acetate/hexanes. $^1$H NMR (400 MHz, DMSO-d$_6$): δ 9.35 (s, 1H), 8.40 (t, 1H), 8.13 (d, 1H), 7.32 (d, 2H), 7.24 (t, 2H), 7.15 (t, 1H), 6.93 (t, 1H), 6.75 (d, 1H), 6.51 (d, 1H), 5.54 (d, 1H), 4.43 (dd, 1H), 4.36–4.22 (m, 3H), 4.20 (s, 1H), 3.86 (m, 2H), 3.11 (s, 1H), 2.85 (d, 1H), 2.67 (t, 1H), 1.77 (s, 3H), 1.18 (s, 3H), 1.02 (s, 3H); $^{19}$F NMR (376 MHz, DMSO-d$_6$): δ −108.0 (d, 1F), −114.5 (d, 1F); MS-APCI (m/z+): 528, 312; HPLC: Rf(min.) 18.00; Purity: 97%. Anal. C$_{28}$H$_{31}$N$_3$O$_5$F$_2$ C, H, N calcd: C, 63.75; H, 5.92; N, 7.96. found: C, 63.67; H, 6.21; N, 7.85.

EXAMPLE C18

(S)-4,4-Difluoro-1-((2S,3S)-2-hydroxy-3-{[1-(3-hydroxy-2-methyl-phenyl)-methanoyl]-amino}-4-phenyl-butanoyl)-3,3-dimethyl-pyrrolidine-2-carboxylic acid 2-chloro-4-fluoro-benzylamide

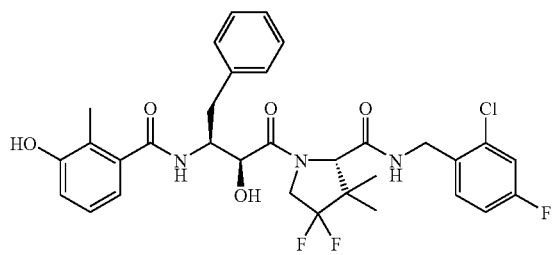

Isolated material was subjected preparative HPLC purification, eluting with EtOAc/hexanes to afford the title compound. $^1$H NMR (400 MHz, DMSO-d$_6$): δ 9.36 (s, 1H), 8.52 (t, 1H), 8.16 (d, 1H), 7.49 (dd, 1H), 7.40 (d, 1H), 7.28 (d, 2H), 7.24–7.19 (m, 3H), 7.15–7.10 (m, 2H), 6.92 (t, 1H), 6.75 (d, 1H), 6.52 (d, 1H), 5.55 (d, 1H), 4.46 (dd, 1H), 4.39–4.24 (m, 5H), 2.84 (d, 1H), 2.69–2.64 (m, 1H), 1.78 (s, 3H), 1.19 (s, 3H), 1.00 (s, 3H); MS-APCI (m/z+): 312, 632. HPLC: Rf(min.) 16.83; Purity: 93%.

EXAMPLE C19

(S)-4,4-Difluoro-1-((2S,3S)-2-hydroxy-3-{[1-(3-hydroxy-2-methyl-phenyl)-methanoyl]-amino}-4-phenyl-butanoyl)-3,3-dimethyl-pyrrolidine-2-carboxylic acid propylamide

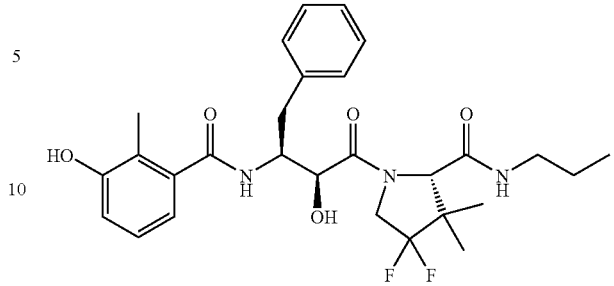

$^1$H NMR (400 MHz, DMSO-d$_6$): δ 9.35 (s, 1H), 8.13 (d, 1H), 7.89 (bs, 1H), 7.32 (d, 2H), 7.23 (t, 2H), 7.15 (t, 1H), 6.92 (t, 1H), 6.75 (d, 1H), 6.51 (d, 1H), 5.48 (d, 1H), 4.40 (dd, 1H), 4.34–4.14 (m, 4H), 3.01 (m, 2H), 2.84 (d, 1H), 2.67 (t, 1H), 1.78 (s, 3H), 1.39 (m, 2H), 1.17 (s, 3H), 1.01 (s, 3H), 0.83 (t, 3H); $^{19}$F NMR (376 MHz, DMSO-d$_6$): δ −108.3 (d, 1F), −114.0 (d, 1F); MS-APCI (m/z+): 532, 312; HPLC Purity: 100%, Rf(min.) 18.22; Anal. C$_{28}$H$_{35}$N$_3$O$_5$F$_2$.0.2H$_2$O calcd, C, 62.84; H, 6.67; N, 7.85. found: C, 62.71; H, 6.65; N, 7.64.

EXAMPLE C20

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid (furan-2-ylmethyl)-amide

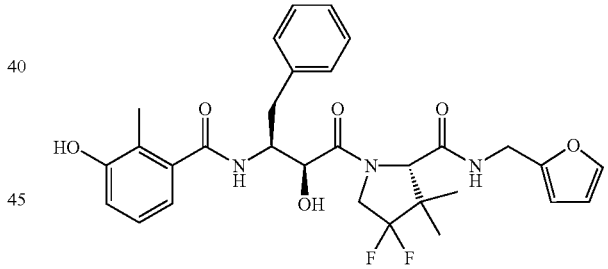

$^1$H NMR (400 MHz, DMSO-d$_6$): δ 9.35 (s, 1H), 8.40 (t, 1H), 8.13(d, 1H), 7.54 (s, 1H), 7.32 (d, 2H), 7.24 (t, 2H), 7.15 (t, 1H), 6.93 (t, 1H), 6.75 (d, 1H), 6.52 (d, 1H), 6.36 (s, 1H), 6.25 (s, 1H), 5.53 (d, 1H), 4.42 (dd, 1H), 4.36–4.24 (m, 6H), 2.85 (d, 1H), 2.68 (t, 1H), 1.79 (s, 3H), 1.16 (s, 3H), 0.97 (s, 3H); $^{19}$F NMR (376 MHz, DMSO-d$_6$): δ −108.2 (d, 1F), −114.3 (d, 1F); MS-APCI (m/z+): 570; HPLC: Rf(min.) 18.73; Purity: 100%. Anal. C$_{30}$H$_{33}$N$_3$O$_6$F$_2$ calcd: C, 63.26; H, 5.84; N, 7.38, found: C, 63.35; H, 5.71; N, 7.20.

EXAMPLE C21

4,4-Difluoro-1-[2-hydroxy-3-(3-hydroxy-2-methyl-benzoylamino)-4-phenyl-butyryl]-3,3-dimethyl-pyrrolidine-2-carboxylic acid isobutyl-amide

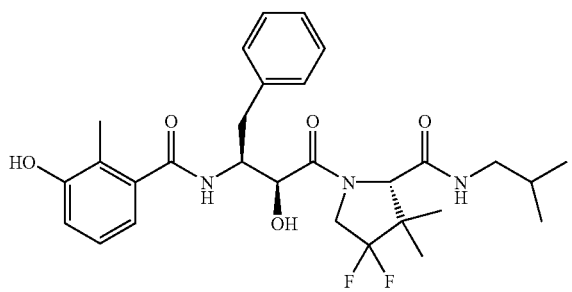

$^{1}$H NMR (400 MHz, DMSO-d$_6$): δ 9.35 (s, 1H), 8.14 (d, 1H), 7.90 (t, 1H), 7.33 (d, 2H), 7.23 (t, 2H), 7.15 (t, 1H), 6.93 (t, 1H), 6.76 (d, 1H), 6.52 (d, 1H), 5.46 (d, 1H), 4.41 (dd, 1H), 4.34–4.20 (m, 4H), 2.92–2.80 (m, 3H), 2.67 (t, 1H), 1.78 (s, 3H), 1.67 (m, 1H), 1.18 (s, 3H), 1.02 (s, 3H), 0.83 (d, 6H); $^{19}$F NMR (376 MHz, DMSO-d$_6$): δ –108.2 (dt, 1F), –113.9 (d, 1F); MS-APCI (m/z+): 546; HPLC Purity: 100%, Rf(min.) 18.81; Anal. C$_{29}$H$_{37}$N$_3$O$_5$F$_2$·0.2H$_2$O calcd: C, 63.42; H, 6.85; N, 7.65. found: C, 63.29; H, 6.77; N, 7.49.

EXAMPLE C22

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid (thiophen-2-ylmethyl)-amide

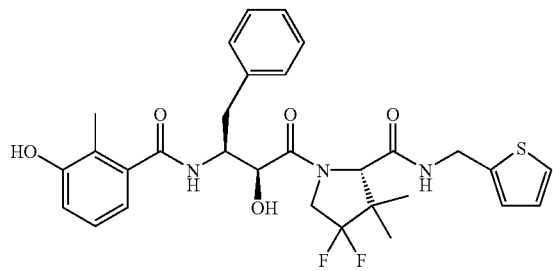

$^{1}$H NMR (400 MHz, DMSO-d$_6$): δ 9.36 (s, 1H), 8.53 (t, 1H), 8.13 (d, 1H), 7.36 (dd, 1H), 7.33 (d, 2H), 7.24 (t, 2H), 7.15 (t, 1H), 6.97 (t, 1H), 6.92 (m, 2H), 6.76 (d, 1H), 6.53 (d, 1H), 5.53 (d, 1H), 4.49–4.26 (m, 6H), 4.23 (s, 1H), 2.88 (d, 1H), 2.69 (dd, 1H), 1.79 (s, 3H), 1.17 (s, 3H), 1.00 (s, 3H); $^{19}$F NMR (376 MHz, DMSO-d$_6$): δ –108.6 (dt, 1F), –114.2 (d, 1F); MS-APCI (m/z+): 586; HPLC Purity: 100%, Rf(min.) 19.07; Anal. C$_{30}$H$_{33}$N$_3$O$_5$F$_2$S calcd: C, 61.52; H, 5.68; N, 7.17, found: C, 61.23; H, 5.64; N, 6.90.

EXAMPLE C23

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid (2,2,2-trifluoro-ethyl)-amide

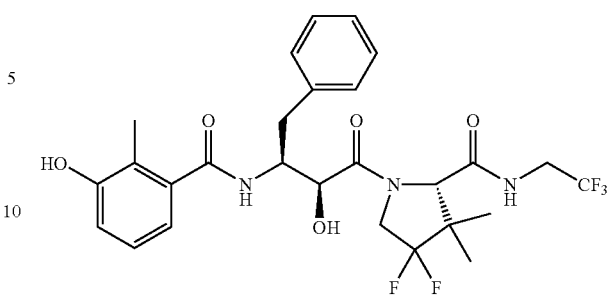

$^{1}$H NMR (400 MHz, DMSO-d$_6$): δ 9.35 (s, 1H), 8.66 (t, 1H), 8.14 (d, 1H), 7.31 (d, 2H), 7.24 (t, 2H), 7.15 (t, 1H), 6.93 (t, 1H), 6.75 (d, 1H), 6.51 (d, 1H), 5.56 (d, 1H), 4.45 (dd, 1H), 4.38–4.25 (m, 4H), 4.04–3.94 (m, 1H), 3.90–3.80 (m, 1H), 2.85 (d, 1H), 2.66 (dd, 1H), 1.77 (s, 3H), 1.19 (s, 3H), 1.01 (s, 3H); $^{19}$F NMR (376 MHz, DMSO-d$_6$): δ –71.0 (t, J=10 Hz, 3F), –108.0 (dm, J=227 Hz, 1F), –114.6 (d, J=227 Hz, 1F); MS-APCI (m/z+): 572, 312; HPLC Purity: 100%, Rf(min.) 18.98; Anal. C$_{27}$H$_{30}$N$_3$O$_5$F$_5$ calcd: C, 56.74; H, 5.29; N, 7.35. found: C, 56.56; H, 5.43; N, 7.15.

EXAMPLE C24

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid (S)-1-benzopyran-4-y

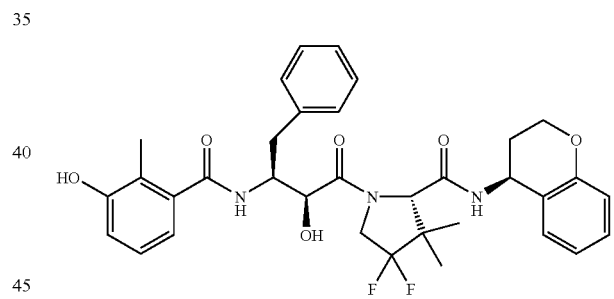

Isolated material was subjected to flash silica gel chromatography, eluting with 45% EtOAc/hexanes to afford the title compound. $^{1}$H NMR (400 MHz, DMSO-d$_6$): δ 9.35 (s, 1H), 8.47 (d, 1H), 8.20 (d, 1H), 7.33 (d, 2H), 7.23 (t, 2H), 7.17–7.12 (m, 3H), 6.93 (t, 1H), 6.87 (t, 1H), 6.79 (t, 2H), 6.53 (d, 1H), 5.40 (d, 1H), 4.96 (dd, 1H), 4.47 (dd, 1H), 4.34–4.14 (m, 6H), 2.82 (d, 1H), 2.67 (t, 1H), 2.03–1.98 (m, 1H), 1.93–1.89 (m, 1H), 1.79 (s, 3H), 1.17 (s, 3H), 1.12 (s, 3H); MS-APCI (m/z+): 622. HPLC: Rf(min.) 19.65; Purity: 94%; C$_{34}$H$_{37}$N$_3$O$_6$F$_2$·0.5H$_2$O calcd: 64.75, 6.07, 6.66, found: 64.77, 6.24, 6.54.

EXAMPLE C25

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid 4-methoxy-benzylamide

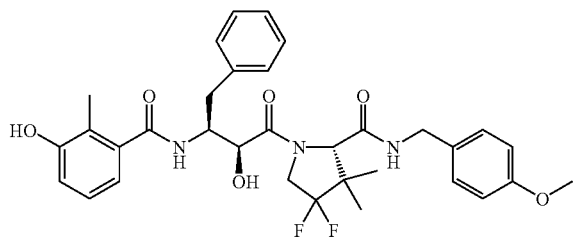

Isolated material was subjected to flash silica gel chromatography, eluting with 45% EtOAc/hexanes to afford the title compound. $^1$H NMR (400 MHz, DMSO-$d_6$): δ 9.36 (s, 1H), 8.34 (t, 1H), 8.13 (d, 1H), 7.31 (d, 2H), 7.25–7.13 (m, 5H), 6.93 (t, 1H), 6.83 (d, 2H), 6.76 (d, 1H), 6.53 (d, 1H), 5.54 (d, 1H), 4.43 (dd, 1H), 4.34–4.25 (m, 5H), 4.13 (dd, 1H), 3.68 (s, 3H), 2.88 (d, 1H), 2.68 (dd, 1H), 1.79 (s, 3H), 1.17 (s, 3H), 0.99 (s, 3H); MS-APCI (m/z+): 610; $C_{33}H_{37}N_3O_6F_2 \cdot 0.4H_2O$ calcd: 64.25, 6.18, 6.81, found: 64.19, 6.13, 6.73.

EXAMPLE C26

(S)-4,4-Difluoro-1-[(2S,3S)-2-hydroxy-3-(3-hydroxy-2-methyl-benzoylamino)-4-phenyl-butyryl]-3,3-dimethyl-pyrrolidine-2-carboxylic acid (1,3-benzodioxol-5-ylmethyl)-amide

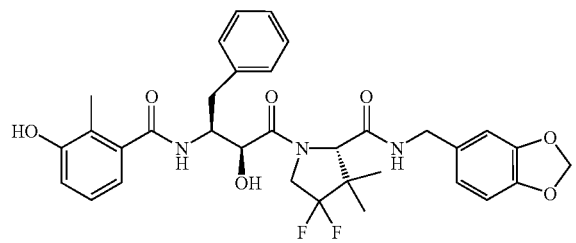

Isolated material was subjected to flash silica gel chromatography, eluting with 45% EtOAc/hexanes to afford the title compound. $^1$H NMR (400 MHz, DMSO-$d_6$): δ 9.33 (s, 1H), 8.35 (t, 1H), 8.12 (d, 1H), 7.29 (d, 2H), 7.21 (t, 2H), 7.12 (t, 1H), 6.91 (t, 1H), 6.81–6.71 (m, 4H), 6.51 (d, 1H), 5.91 (d, 2H), 5.53 (d, 1H), 4.43 (dd, 1H), 4.30–4.23 (m, 5H), 4.07 (dd, 1H), 2.86 (d, 1H), 2.66 (t, 1H), 1.77 (s, 3H), 1.16 (s, 3H), 0.98 (s, 3H); MS-APCI (m/z+): 135, 312, 624. HPLC: Rf(min.) 19.00; Purity: 97%; $C_{33}H_{35}N_3O_7F_2 \cdot 0.6H_2O$ calcd: 62.47, 5.75, 6.62, found, 62.41, 5.65, 6.36.

EXAMPLE C27

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic acid (S)-indan-1-ylamide

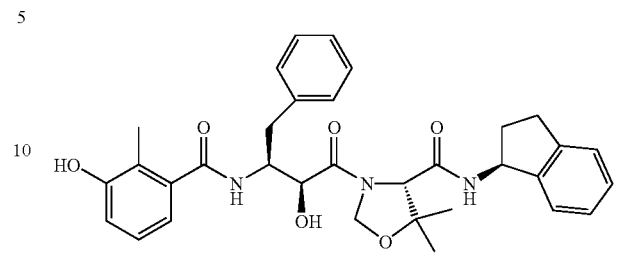

$^1$H NMR (DMSO-$d_6$) δ 9.35 (s, 1H), 8.31 (d, J=8.1, 1H), 8.13 (d, J=9.0, 1H), 7.30–7.13 (m, 9H), 6.94 (t, J=7.9, 1H), 6.76 (d, J=7.9, 1H), 6.55 (d, J=7.5, 1H), 5.72 (d, J=6.2, 1H), 5.46 (d, J=4.0, 1H), 5.31 (dd, J=15.6, 7.7, 1H), 5.24 (d, J=3.9, 1H), 4.36 (m, 1H), 4.19 (m, 1H), 4.16 (s, 1H), 2.94–2.64 (m, 4H), 2.41–2.34 (m, 1H), 1.86–1.77 (m, 1H), 1.77 (s, 3H), 1.29 (s, 3H), 1.27 (s, 3H); HRMS (ESI) m/z calcd for $C_{33}H_{38}N_3O_6$ (M+H)$^+$ 572.2761, found 572.2768.

EXAMPLE C28

(4S,5S)-3-((2S,3S)-2-Hydroxy-3-{[1-(3-hydroxy-2-methyl-phenyl)-methanoyl]-amino}-4-phenyl-butanoyl)-5-methyl-oxazolidine-4-carboxylic acid (S)-cyclohex-2-enylamide

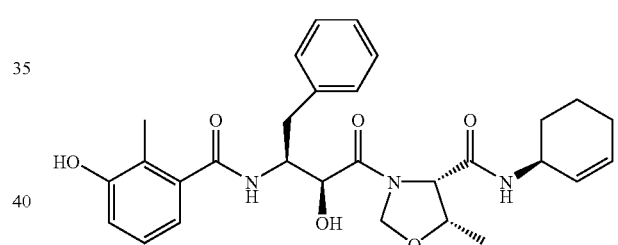

$^1$H NMR (DMSO-$d_6$) δ 9.36 (s, 1H), 8.12 (d, J=8.2, 1H), 7.92 (d, J=8.2, 1H), 7.31–7.13 (m, 5H), 6.94 (t, J=7.9, 1H), 6.76 (d, J=7.9, 1H), 6.56 (d, J=7.3, 1H), 5.77–5.73 (m, 1H), 5.66 (d, J=6.4, 1H), 5.51 (d, J=3.7, 1H), 5.50–5.44 (m, 1H), 5.06 (d, J=3.7, 1H), 4.40–4.15 (m, 5H), 2.97–2.65 (m, 2H), 1.94 (m, 2H), 1.79–1.67 (m, 2H), 1.77 (s, 3H), 1.57–1.44 (m, 2H), 1.20 (d, J=6.2, 3H); HRMS (ESI) m/z calcd for $C_{29}H_{36}N_3O_6$ (M+H)$^+$ 522.2604, found 522.2623.

EXAMPLE C29

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic acid (S)-cyclohex-2-enylamide

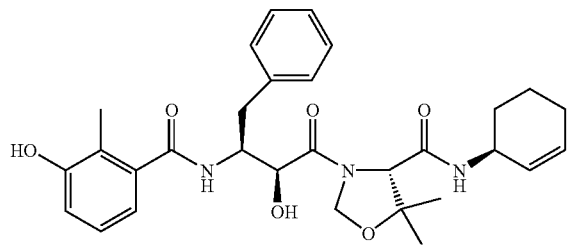

<sup>1</sup>H NMR (DMSO-d<sub>6</sub>) δ 9.36 (s br, 1H), 8.11 (d, J=8.6, 1H), 7.97 (d, J=7.9, 1H), 7.32–7.15 (m, 5H), 6.93 (t, J=7.7, 1H), 6.76 (d, J=8.1, 1H), 6.54 (d, J=7.3 1H), 5.76 (m, 1H), 5.67 (d, J=6.4, 1H), 5.54–5.41 (m, 1H), 5.43 (d, J=3.8, 1H), 5.21 (d, J=3.8, 1H), 4.40–4.28 (m, 2H), 4.19–4.14 (m, 2H), 2.88 (m, 1H), 2.70 (m, 1H), 1.95 (m, 2H), 1.78 (s, 3H), 1.82–1.68 (m, 2H), 1.58–1.45 (m, 2H), 1.28 (s, 3H), 1.22 (s, 3H); HRMS (ESI) m/z calcd for $C_{30}H_{38}N_3O_6$ (M+H)<sup>+</sup> 536.2761, found 536.2751; Anal. Calcd for $C_{30}H_{37}N_3O_6$: C, 67.27; H, 6.96; N, 7.85. Found: C, 67.07; H, 7.00; N, 7.71.

EXAMPLE C30

3-(2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid 2-methyl-benzamide

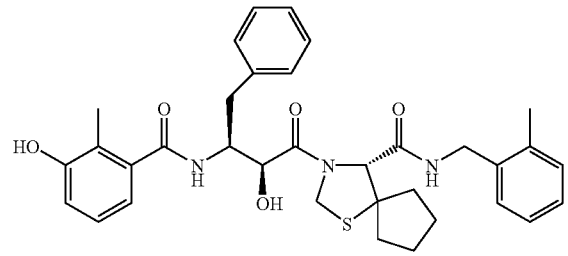

White solid; <sup>1</sup>H NMR (DMSO-d<sub>6</sub>) δ 9.37 (s, 1H), 8.38 (t, J=5.5, 1H), 8.26 (d, J=8.1, 1H), 7.31–6.85 (m, 10H), 6.76 (d, J=8.1, 1H), 6.53 (d, J=7.7, 1H), 5.54 (d, J=6.4, 1H), 5.12 (d, J=9.2, 1H), 4.95 (d, J=9.2, 1H), 4.55 (s, 1H), 4.50–4.10 (m, 3H), 4.01 (m, 1H), 2.90–2.60 (m, 2H), 2.20 (s, 3H), 2.10–1.85 (m, 4H), 1.81 (s, 3H), 1.80–1.50 (m, 4H); Anal. Calcd for $C_{34}H_{39}N_3O_5S$: C, 67.86; H, 6.53; N, 6.98. Found: C, 67.50; H, 6.23; N, 6.70.

EXAMPLE C31

3-(2-Hydroxy-3-{[1-(2-methyl-3-hydroxy-phenyl)-methanoyl]-amino}-4-phenyl-butanoyl)-1-thia-3-aza-spiro[4.5]decane-4-carboxylic acid 2-methyl-benzamide

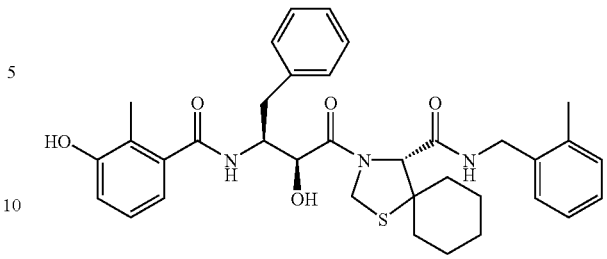

White solid; <sup>1</sup>H NMR (DMSO-d<sub>6</sub>) δ 9.37 (s, 1H), 8.36 (t, J=5.5, 1H), 8.28 (d, J=8.1, 1H), 7.34–6.83 (m, 10H), 6.74 (d, J=8.1, 1H), 6.60 (d, J=7.7, 1H), 5.57 (d, J=6.4, 1H), 5.09 (d, J=9.2, 1H), 4.97 (d, J=9.2, 1H), 4.65 (s, 1H), 4.55–4.06 (m, 3H), 4.01 (m, 1H), 2.91–2.50 (m, 2H), 2.22 (s, 3H), 2.10–1.83 (m, 5H), 1.80 (s, 3H), 1.78–1.50 (m, 5H); Anal. Calcd for $C_{35}H_{41}N_3O_5S$: C, 68.26; H, 6.71; N, 6.82. Found: C, 68.44; H, 6.53; N, 6.73.

EXAMPLE C32

7-(2-Hydroxy-3-{[1-(3-hydroxy-2-methyl-phenyl)-methanoyl]-amino}-4-phenyl-butanoyl)-5-thia-7-aza-spiro[3.4]octane-8-carboxylic acid-2-methyl benzylamide

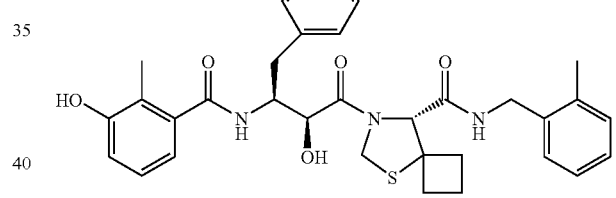

White solid; <sup>1</sup>H NMR (DMSO-d<sub>6</sub>) δ 9.37 (s, 1H), 8.40 (t, J=5.5, 1H), 8.33 (d, J=8.1, 1H), 7.34–6.92 (m, 10H), 6.81 (d, J=8.1, 1H), 6.51 (d, J=7.7, 1H), 5.48 (d, J=6.4, 1H), 5.09 (d, J=9.2, 1H), 4.87 (d, J=9.2, 1H), 4.63 (s, 1H), 4.58–4.17 (m, 3H), 4.05 (m, 1H), 2.89–2.62 (m, 2H), 2.26 (s, 3H), 2.13–1.86 (m, 3H), 1.80 (s, 3H), 1.79–1.50 (m, 3H); Anal. Calcd for $C_{33}H_{37}N_3O_5S$: C, 67.44; H, 6.35; N, 7.15. Found: C, 67.57; H, 6.13; N, 7.22.

EXAMPLE C33

(R)-3-((2S,3S)-2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid propylamide

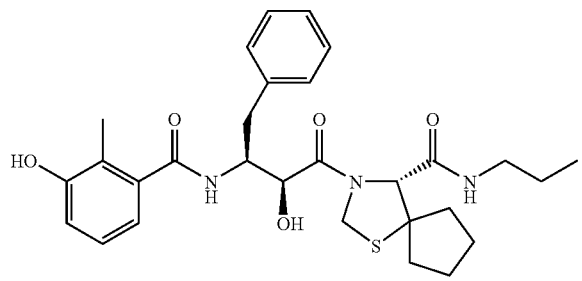

¹H NMR (DMSO-d₆) δ 9.36 (s, 1H), 8.11 (d, J=8.4, 1H), 7.86 (t, J=5.5, 1H), 7.34–7.13 (m, 5H), 6.93 (t, J=7.7, 1H), 6.80 (d, J=8.1, 1H), 6.52 (d, J=7.3, 1H), 5.44 (d, J=7.0, 1H), 5.08 (d, J=9.0, 1H), 4.95 (d, J=9.3, 1H), 4.47 (s, 1H), 4.44 (m, 2H), 3.04–2.95 (m, 2H), 2.85–2.70 (m, 2H), 1.93 (m, 2H), 1.81–1.61 (m, 6H), 1.80 (s, 3H), 1.31 (m, 2H), 0.82 (t, J=7.3, 3H); HRMS (ESI) m/z calcd for $C_{29}H_{38}N_3O_5S$ (M+H)⁺ 540.2532, found 540.2531.

EXAMPLE C34

(R)-3-((2S,3S)-2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid ((E)-2-methyl-but-2-enyl)-amide

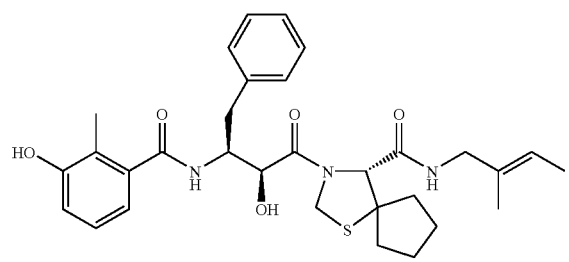

¹H NMR (DMSO-d₆) δ 9.37 (s, 1H), 8.08 (d, J=8.1, 1H), 7.92 (t, J=5.7, 1H), 7.33–7.15 (m, 5H), 6.93 (t, J=7.7, 1H), 6.77 (d, J=8.1, 1H), 6.53 (d, J=7.3, 1H), 5.48 (d, J=6.2, 1H), 5.32 (m, 1H), 5.08 (d, J=9.3, 1H), 4.92 (d, J=9.2, 1H), 4.49 (s, 1H), 4.43 (m, 2H), 3.74–3.67 (m, 1H), 3.42 (m, 1H), 2.85–2.72 (m, 2H), 1.98–1.90 (m, 2H), 1.82–1.62 (m, 6H), 1.81 (s, 3H), 1.49 (s, 6H); HRMS (ESI) m/z calcd for $C_{31}H_{40}N_3O_5S$ (M+H)⁺ 566.2689, found 566.2685.

EXAMPLE C35

(S)-3-((2S,3S)-2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid (S)-cyclohex-2-enylamide

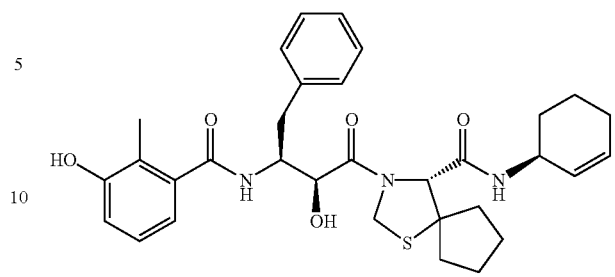

¹H NMR (DMSO-d₆) δ 9.35 (s, 1H), 8.15 (d, J=8.4, 1H), 7.91 (d, J=7.9, 1H), 7.34–7.12 (m, 5H), 6.96–6.91 (m, 1H), 6.76 (d, J=8.1, 1H), 6.53 (d, J=7.5, 1H), 5.80–5.65 (m, 1H), 5.48–5.40 (m, 1H), 5.36 (d, J=7.2, 1H), 5.10 (d, J=9.2, 1H), 4.94 (d, J=9.2, 1H), 4.54 (s, 1H), 4.50–4.20 (m, 3H), 2.90–2.60 (m, 2H), 2.10–1.82 (m, 4H), 1.79 (s, 3H), 1.78–1.40 (m, 10H); Anal. Calcd for $C_{32}H_{39}N_3O_5S$: C, 66.53; H, 6.80; N, 7.27. Found: C, 66.34; H, 6.62; N, 6.96.

EXAMPLE C36

(R)-3-((2S,3S)-2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid 5-fluoro-2-methyl-benzylamide

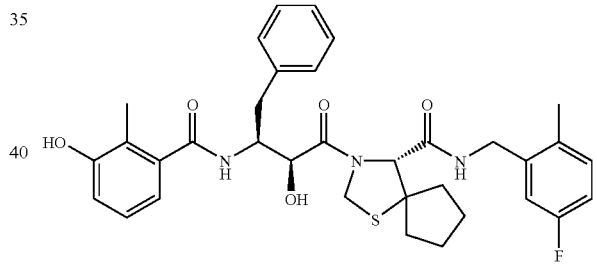

White solid; ¹H NMR (DMSO-d₆) δ 9.37 (s, 1H), 8.38 (t, J=5.5, 1H), 8.26 (d, J=8.1, 1H), 7.31–6.85 (m, 9H), 6.76 (d, J=8.1, 1H), 6.53 (d, J=7.7, 1H), 5.54 (d, J=6.4, 1H), 5.12 (d, J=9.2, 1H), 4.95 (d, J=9.2, 1H), 4.55 (s, 1H), 4.50–4.10 (m, 3H), 4.01 (dd, J=16.0, 5.5, 1H), 2.90–2.60 (m, 2H), 2.20 (s, 3H), 2.10–1.85 (m, 4H), 1.81 (s, 3H), 1.80–1.50 (m, 4H); Anal. Calcd for $C_{34}H_{38}N_3O_5SF$: C, 65.51; H, 6.21; N, 6.74. Found: C, 65.50; H, 6.23; N, 6.70.

EXAMPLE C37

(R)-3-((2S,3S)-2-Hydroxy-3-{[1-(3-hydroxy-2-methyl-phenyl)-methanoyl]-amino}-4-phenyl-butanoyl)-1-thia-3-aza-spiro[4.4]nonane-4-carboxylic acid (1,2,3,4-tetrahydro-naphthalen-1-yl)-amide

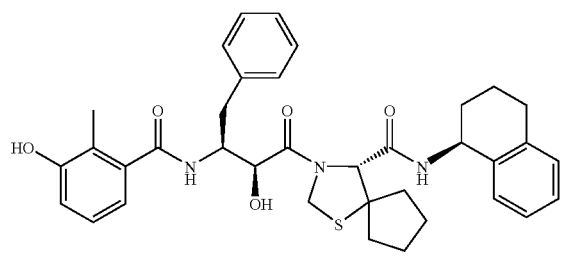

White solid; ¹H NMR (DMSO-d₆) δ 9.36 (s, 1H), 8.26 (d, J=8.4, 1H), 8.20 (d, J=8.4, 1H), 7.30–6.89 (m, 10H), 6.76 (d, J=8.1, 1H), 6.54 (d, J=7.3, 1H), 5.36 (d, J=6.8, 1H), 5.12 (d, J=9.2, 1H), 4.98–4.90 (m, 2H), 4.60–4.30 (m, 3H), 2.90–2.60 (m, 4H), 2.07 (s, 3H), 2.05–1.50 (m, 12H); Anal. Calcd for $C_{36}H_{41}N_3O_5S$: C, 68.87; H, 6.58; N, 6.69. Found: C, 68.80; H, 6.41; N, 6.60.

EXAMPLE C38

(R)-7-((2S,3S)-2-Hydroxy-3-{[1-(3-hydroxy-2-methyl-phenyl)-methanoyl]-amino}-4-phenyl-butanoyl)-5-thia-7-aza-spiro[3.4]octane-8-carboxylic acid propylamide

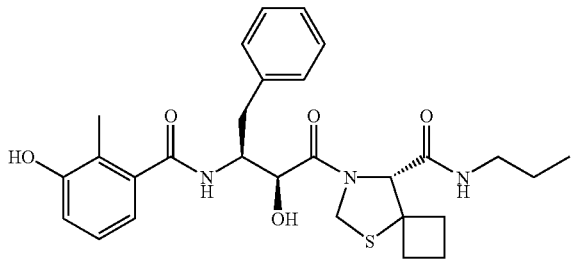

¹H NMR (DMSO-d₆) δ 9.36 (s, 1H), 8.11 (d, J=8.4, 1H), 7.96 (t, J=5.9, 1H), 7.33–7.13 (m, 5H), 6.93 (t, J=7.9, 1H), 6.76 (d, J=7.3, 1H), 6.53 (d, J=7.5, 1H), 5.41 (d, J=6.9, 1H), 4.96 (d, J=9.3, 1H), 4.92 (d, J=9.5, 1H), 4.50 (s, 1H), 4.45 (d, J=5.1, 1H), 4.37 (m, 1H), 3.03 (m, 2H), 2.82–2.66 (m, 2H), 2.56–2.42 (m, 2H), 2.16–1.80 (m, 4H), 1.80 (s, 3H), 1.39 (m, 2H), 0.82 (t, J=7.5, 3H); HRMS (ESI) m/z calcd for $C_{28}H_{36}N_3O_5S$ (M+H)⁺ 526.2376, found 526.2375.

EXAMPLE C39

(R)-7-((2S,3S)-2-Hydroxy-3-{[1-(3-hydroxy-2-methyl-phenyl)-methanoyl]-amino}-4-phenyl-butanoyl)-5-thia-7-aza-spiro[3.4]octane-8-carboxylic acid (S)-cyclohex-2-enylamide

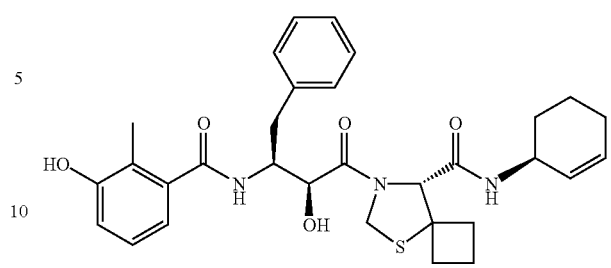

White solid; ¹H NMR (DMSO-d₆) δ 9.38 (s, 1H), 8.18 (d, J=8.2, 1H), 8.07 (d, J=8.1, 1H), 7.36–7.18 (m, 5H), 6.96 (t, J=8.2, 1H), 6.79 (d, J=8.3, 1H), 6.56 (d, J=7.1, 1H), 5.77 (m, 1H), 5.56–5.47 (m, 1H), 5.36 (d, J=7.0, 1H), 5.02 (d, J=9.3, 1H), 4.95 (d, J=9.3, 1H), 4.58 (s, 1H), 4.51 (m, 1H), 4.39–4.31 (m, 2H), 2.75–2.70 (m, 2H), 2.60–2.44 (m, 2H), 2.15 (m, 1H), 2.04–1.88 (m, 5H), 1.82 (s, 3H), 1.80–1.64 (m, 2H), 1.55–1.46 (m, 2H); HRMS (ESI) m/z calcd for $C_{31}H_{38}N_3O_5S$ (M+H)⁺ 564.2532, found 564.2523.

EXAMPLE C40

1-{3-[2-(2,6-Dimethyl-phenoxy)-acetylamino]-2-hydroxy-4-phenyl-butyryl}-4,4-difluoro-pyrrolidine-2-carboxylic acid 2-methyl-benzylamide

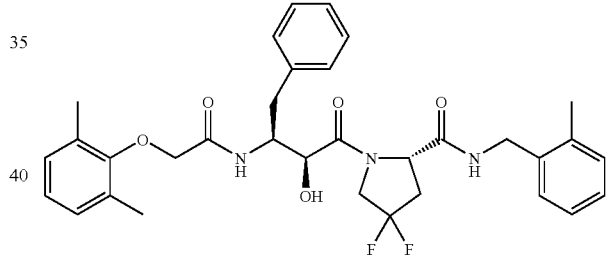

¹H NMR (400 MHz, DMSO-d₆): δ 8.36 (t, 1H), 8.13 (d, 1H), 7.29 (d, 2H), 7.25–7.08 (m, 7H), 6.99 (d, 2H), 6.91 (dd, 1H), 5.53 (d, 1H), 4.66 (dd, 1H), 4.33–4.10 (m, 7H), 3.94 (d, 1H), 2.86–2.73 (m, 4H), 2.46–2.38 (m, 1H), 2.22 (s, 3H), 2.12 (s, 6H); ¹⁹F NMR (376 MHz, DMSO-d₆): δ −98.1 (dq, 1F), −100.0 (dq, 1F); MS-APCI (m/z+): 594; HPLC Purity: 100%, Rf(min.) 21.97; Anal. $C_{33}H_{37}N_3O_5F_2 \cdot 0.3H_2O$ calcd: C, 66.16; H, 6.33; N, 7.01. found: C, 66.23; H, 6.57; N, 7.12.

EXAMPLE C41

{(1S,2S)-1-Benzyl-3-[(S)-4,4-difluoro-2-(2-methyl-benzylcarbamoyl)-pyrrolidin-1-yl]-2-hydroxy-3-oxo-propyl}-carbamic acid (S)-(tetrahydro-furan-3-yl) ester

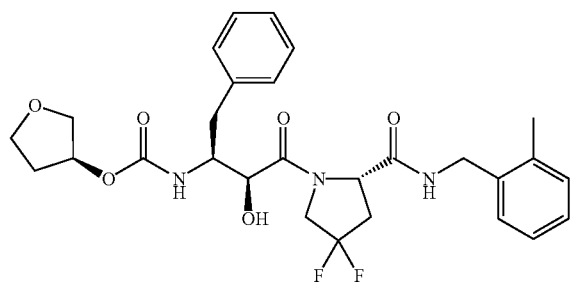

White solid; $^1$H NMR (DMSO-d$_6$) δ 8.34 (t, J=5.5, 1H), 7.31–7.09 (m, 10H), 5.40 (d, J=7.0, 1H), 4.95 (m, 1H), 4.65 (dd, J=9.2, 5.7, 1H), 4.35–4.09 (m, 5H), 3.81 (m, 1H), 3.75–3.56 (m, 3H), 3.40 (d, J=10.0, 1H), 2.80–2.36 (m, 4H), 2.23 (s, 3H), 2.05–1.95 (m, 1H), 1.81 (m, 1H); HRMS (ESI) m/z calcd for $C_{28}H_{34}N_3O_6F_2$ (M+H)$^+$ 546.2416, found 546.2418.

EXAMPLE C42

(S)-4,4-Difluoro-1-((2S,3S)-2-hydroxy-3-{[1-(3-hydroxy-2,4-dimethyl-phenyl)-methanoyl]-amino}-4-phenyl-butanoyl)-pyrrolidine-2-carboxylic acid 2-methyl-benzylamide

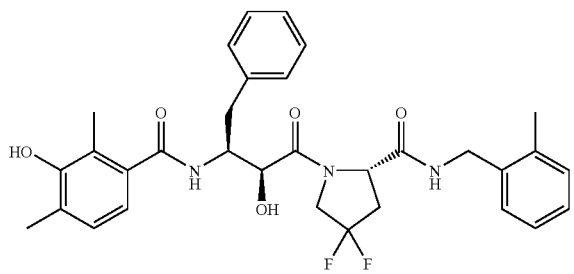

White solid; $^1$H NMR (DMSO-d$_6$) δ 8.35 (t, J=5.7, 1H), 8.25 (s br, 1H), 8.09 (d, J=7.9, 1H), 7.33–7.08 (m, 9H), 6.85 (d, J=7.7, 1H), 6.53 (d, J=7.5, 1H), 5.49 (d, J=6.2, 1H), 4.67 (dd, J=9.3, 5.5, 1H), 4.35–4.14 (m, 6H), 2.86–2.67 (m, 4H), 2.23 (s, 3H), 2.13 (s, 3H), 1.85 (s, 3H); HRMS (ESI) m/z calcd for $C_{32}H_{36}N_3O_5F_2$ (M+H)$^+$ 580.2623, found 580.2650.

EXAMPLE C43

3,5-Dimethyl-isoxazole-4-carboxylic acid {1-benzyl-3-[4,4-difluoro-2-(2-methyl-benzylcarbamoyl)-pyrrolidin-1-yl]-2-hydroxy-3-oxo-propyl}-amide

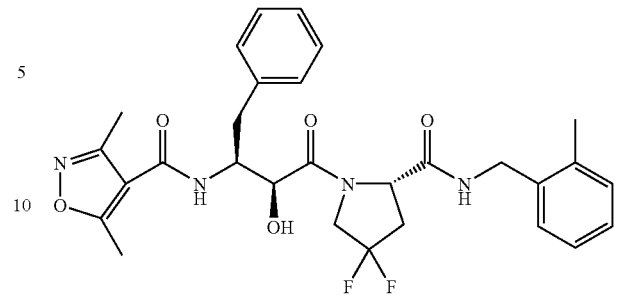

The crude was purified by chromatography eluted with 10% and 20% acetone in CH$_2$Cl$_2$. $^1$H NMR (400 MHz, DMSO-d$_6$): δ 8.41 (t, 1H), 8.13 (d, 1H), 7.29 (d, 2H), 7.24–7.09 (m, 7H), 5.54 (d, 1H), 4.66 (dd, 1H), 4.40 (dd, 1H), 4.34–4.28 (m, 3H), 4.25–4.18 (m, 2H), 2.87–2.68 (m, 3H), 2.43–2.36 (m, 1H), 2.25 (s, 3H), 2.22 (s, 3H), 2.07 (s, 3H); $^{19}$F NMR (376 MHz, DMSO-d$_6$): δ –98.0 (dq, 1F), –99.9 (dq, 1F); MS-APCI (m/z+): 555; HPLC Purity: 100%, Rf(min.) 19.63; Anal. $C_{29}H_{32}N_4O_5F_2$·0.3H$_2$O calcd: C, 62.20; H, 5.87; N, 10.00; found: C, 62.25; H, 6.00; N, 9.65.

EXAMPLE C44

{1-Benzyl-3-[4,4-difluoro-2-(2-methyl-benzylcarbamoyl)-pyrrolidin-1-yl]-2-hydroxy-3-oxo-propyl}-carbamic acid prop-2-ynyl ester

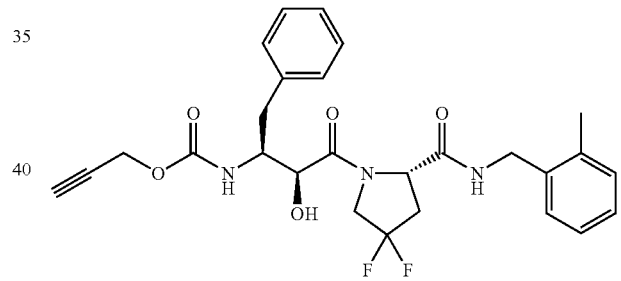

The crude was purified by chromatography eluted with 10% acetone in CH$_2$Cl$_2$. $^1$H NMR (400 MHz, DMSO-d$_6$): δ 8.37 (t, 1H), 7.53 (d, 1H), 7.28 (d, 2H), 7.24–7.10 (m, 7H), 5.36 (d, 1H), 4.65 (dd, 1H), 4.54–4.42 (m, 2H), 4.35–4.18 (m, 4H), 4.11 (dd, 1H), 3.8 (m, 1H), 3.43 (t, 1H), 2.79–2.69 (m, 2H), 2.59 (dd, 1H), 2.42–2.34 (m, 1H); $^{19}$F NMR (376 MHz, DMSO-d$_6$): δ –98.2 (dq, 1F), –99.7 (dq, 1F); MS-APCI (m/z+): 514; HPLC Purity: 92%, Rf(min.) 19.80; Anal. $C_{27}H_{29}N_3O_5F_2$ calcd: C, 63.15; H, 5.69; N, 8.18. found: C, 63.00; H, 6.02; N, 8.02.

EXAMPLE C45

1-{3-[2-(2,6-Dimethyl-phenoxy)-acetylamino]-2-hydroxy-4-phenyl-butyryl}-4,4-difluoro-pyrrolidine-2-carboxylic acid propylamide

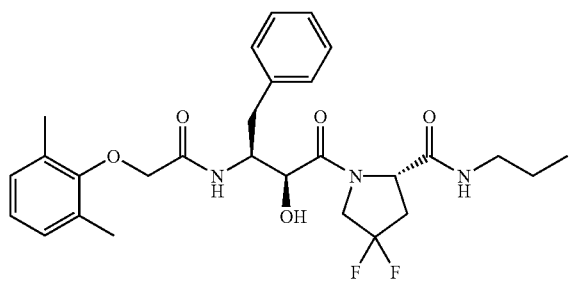

¹H-NMR (400 MHz, dmso-d⁶): 8.09 (d, 1H), 7.91 (t, 1H), 6.8–7.35 (m, 8H), 5.48 (d, 1H), 4.6 (m, 1H), 3.87–4.4 (m, 5H), 3.04 (d, 2H), 2.61–2.87 (m, 3H), 2.35 (m, 1H), 2.35 (s, 3H), 2.13 (s, 6H), 1.4 (q, 2H), 0.8 (t, 3H); IR (KBr in cm−1): 3278, 2931, 1657, 1534, 1449, 1194; MS (APCI, m/z): 531 (M+H), 340, 225, 180; HPLC: Rf(min.) 20.57; Purity: 95%.

EXAMPLE C46

(S)-1-{(2S,3S)-3-[2-(2,6-Dimethyl-phenoxy)-acetylamino]-2-hydroxy-4-phenyl-butyryl}-4,4-difluoro-3,3-dimethyl-pyrrolidine-2-carboxylic acid 2-methyl-benzylamide

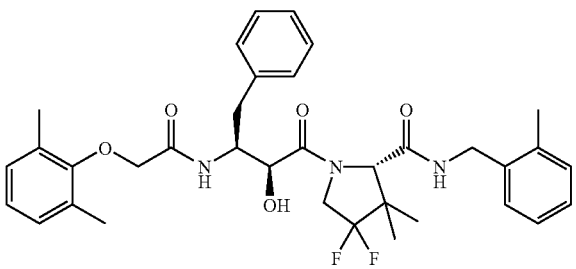

¹H NMR (400 MHz, DMSO-d₆): δ 8.33 (t, 1H), 8.14 (d, 1H), 7.33–7.28 (m, 3H), 7.22 (t, 2H), 7.16 (d, 1H), 7.14–7.06 (m, 3H), 7.02–6.86 (m, 2H), 6.91 (t, 1H), 5.50 (d, 1H), 4.36 (dd, 1H), 4.34–4.18 (m, 6H), 4.14 (d, 1H), 3.98 (d, 1H), 2.84–2.70 (m, 2H), 2.25 (s, 3H), 2.13 (s, 6H), 1.19 (s, 3H), 1.02 (s, 3H); ¹⁹F NMR (376 MHz, DMSO-d₆): δ −109.1 (dt, 1F), −113.3 (dt, 1F); MS-APCI (m/z+): 622; HPLC Purity: 94%, Rf(min.) 23.90; Anal. $C_{35}H_{41}N_3O_5F_2$ calcd: C, 67.62; H, 6.65; N, 6.76. found: C, 67.54; H, 7.02; N, 7.09.

EXAMPLE C47

{(1S,2S)-1-Benzyl-3-[(S)-5,5-dimethyl-4-(2-methyl-benzylcarbamoyl)-oxazolidin-3-yl]-2-hydroxy-3-oxo-propyl}-carbamic acid (S)-(tetrahydro-furan-3-yl) ester

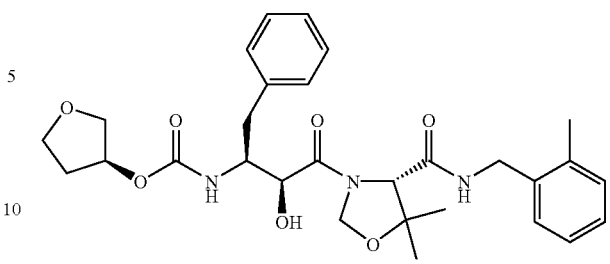

¹H NMR (DMSO-d₆) δ 8.29 (t, J=8.7, 1H), 7.25–7.13 (m, 10H), 5.60 (d, J=6.8, 1H), 5.31 (d, J=4.0, 1H), 5.16 (d, J=4.0, 1H), 4.88 (m, 1H), 4.47–4.05 (m, 5H), 3.86 (m, 1H), 3.72–3.54 (m, 3H), 2.80 (m, 1H), 2.60 (m, 1H), 2.26 (s, 3H), 2.04–1.94 (m, 1H), 1.81–1.76 (m, 1H), 1.29 (s, 3H), 1.16 (s, 3H) HRMS (ESI) m/z calcd for $C_{29}H_{38}N_3O_7$ (M+H)⁺ 540.2710, found 540.2706.

EXAMPLE C48

1-[2-Hydroxy-3-(3-hydroxy-2-methyl-benzoylamino)-4-phenyl-butyryl]-3,3-dimethyl-4-oxo-pyrrolidine-2-carboxylic acid 2-methyl-benzylamide

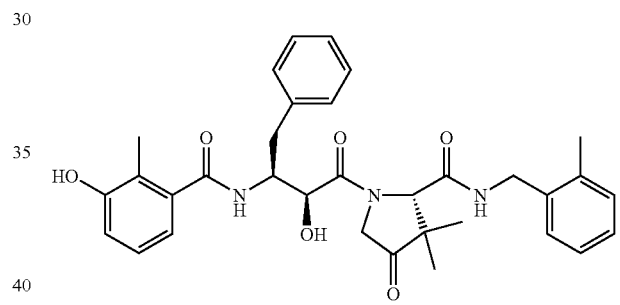

The product was recrystallized from ethyl acetate, ethyl ether and hexanes. ¹H NMR (400 MHz, DMSO-d₆): δ 9.34 (s, 1H), 8.73 (t, 1H), 8.18 (d, 1H), 7.26–7.05 (m, 9H), 6.92 (t, 1H), 6.75 (d, 1H), 6.51 (d, 1H), 5.56 (d, 1H), 4.75 (s, 1H), 4.55 (d, 1H), 4.40–4.32 (m, 4H), 4.14 (dd, 1H), 2.85 (d, 1H), 2.66 (dd, 1H), 2.23 (s, 3H), 1.75 (s, 3H), 1.11 (s, 3H), 0.94 (s, 3H); MS-APCI (m/z+): 572; HPLC Purity: 100%, Rf(min.) 19.31.

EXAMPLE C49

(3S,4aS,8aS)-2-((2S,3S)-2-Hydroxy-3-{[1-(3-hydroxy-2-methyl-phenyl)-methanoyl]-amino}-4-phenyl-butanoyl)-decahydro-isoquinoline-3-carboxylic acid 2-methyl-benzylamide

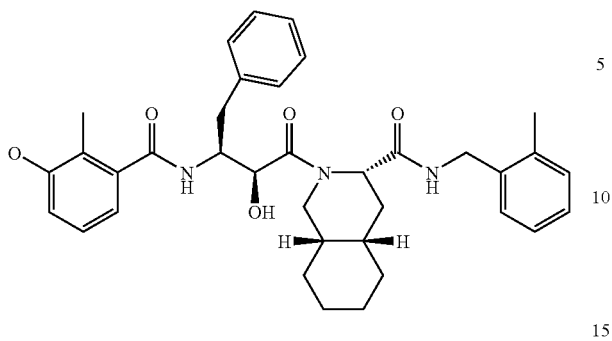

White solid: $^1$H NMR (DMSO) δ 9.38 (s, 1H), 8.45–8.15 (m, 2H), 7.40–6.40 (m, 12H), 5.18 (d, J=7.0, 1H), 5.00–3.35 (m, 5H), 3.00–1.00 (m, 22H); Anal. Calcd for $C_{36}H_{43}N_3O_5 \cdot 0.25H_2O$: C, 71.80; H, 7.28; N, 6.98. Found: C, 71.83; H, 7.40; N, 7.13.

EXAMPLE C50

2-(2-Hydroxy-3-{[1-(-hydroxy-2-methyl-phenyl)-methanoyl]-amino}-4-phenyl-butanoyl)-2-aza-bicyclo[2.2.1]-heptane-3-carboxylic acid-2-methyl-benzylamide

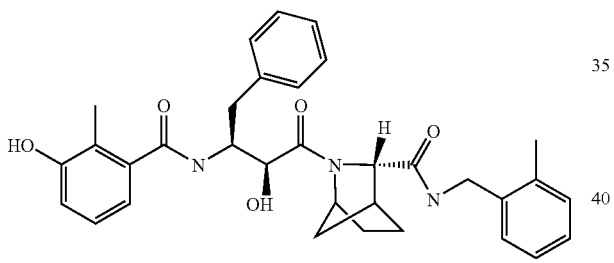

$^1$H NMR (DMSO) δ 9.34 (s, 1H), 8.25–8.17 (m, 2H), 7.40–7.16 (m, 9H), 6.96 (q, J=7.7, 1H), 6.80 (d, J=7.7, 1H), 6.58 (d, J=7.7, 1H), 4.91 (d, J=5.7, 1H), 4.74 (s, 1H), 4.46–4.00 (m, 5H), 2.85–2.66 (m, 3H), 2.28 (s, 3H), 1.88 (s, 3H), 1.85–1.50 (m, 6H); HRMS (ESI) m/z calcd for $C_{33}H_{37}N_3O_5Na$ (M+Na)$^+$ 578.2625, found 578.2604.

General Methods D

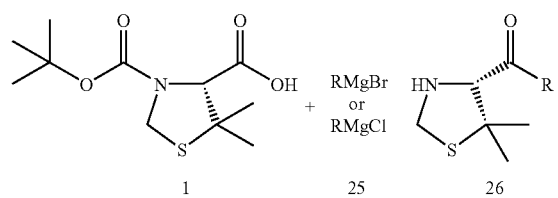

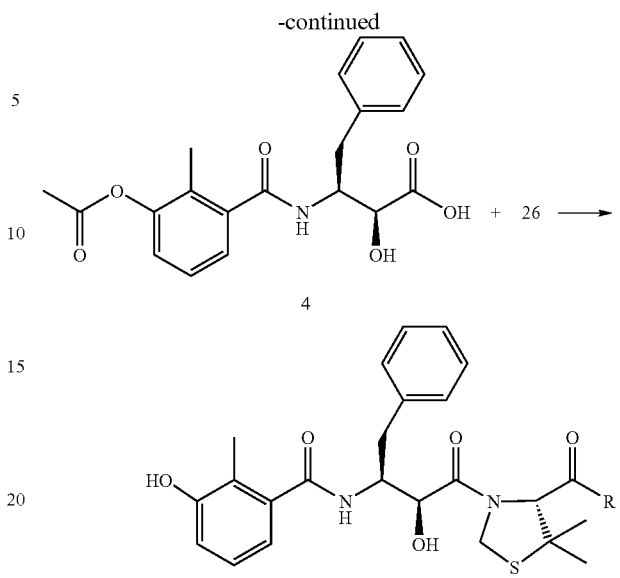

The synthesis of compounds with the general structure 27 is as follows. The boc-protected thiazolidine carboxylic acid 1 is converted to amino-ketones 26 with requisite grignard reagents 25 in the presence of oxalyl chloride. Final compounds 27 are obtained by a DCC-mediated coupling of 26 and 4 followed by deprotection of the P2 phenol. Final compounds were purified either by flash chromatography or preparative HPLC.

Specific Method D

EXAMPLE D1

N-[(1S,2S)-1-Benzyl-3-((R)-5,5-dimethyl-4-pent-4-enoyl-thiazolidin-3-yl)-2-hydroxy-3-oxo-propyl]-3-hydroxy-2-methyl-benzamide

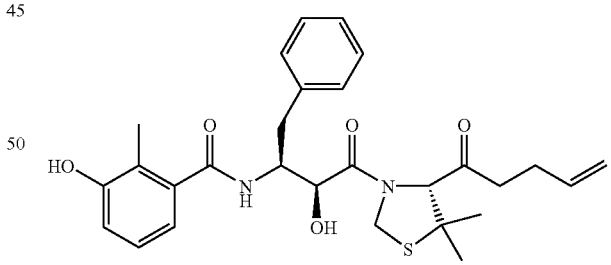

The title compound was prepared as follows. (R)-5,5-Dimethyl-thiazolidine-3,4-dicarboxylic acid 3-tert-butyl ester 1 (1.0 g, 3.80 mmol) was dissolved in benzene (10 mL) and cooled to 0° C. with magnetic stirring. Two drops of DMF were added followed by a drop wise addition of oxalyl chloride (0.33 mL, 3.80 mmol). When gas evolution ceased, the solution was concentrated to a yellow/red residue. The material was dissolved in dry THF (10 mL) and cooled to −78° C. with magnetic stirring. The grignard reagent, 3-butenylmagnesium bromide (7.7 mL, 3.80 mmol) was added dropwise over 10 min. The result was stirred at −78° C. for 1 h then at −55° C. for 30 min. The reaction was quenched at −55° C. with sat NH$_4$Cl soln.(3 mL) and then poured into H$_2$O (50 mL). The mixture was extracted with EtOAc (2×50 mL). The combined organics were washed with brine (1×100 mL), dried over Na$_2$SO$_4$, filtered, and concentrated. The result was the amino ketone 26 that was sufficiently pure to use in the subsequent step. The clear oil 26 (0.24 g, 1.15 mmol) was dissolved in EtOAc (10 mL). AMB-AHPBA 4 (0.40 g, 1.09 mmol) was added followed by HOBt (0.15 g, 1.09 mmol). The mixture was stirred at room temperature 1 h, then cooled to 0° C. DCC (0.24 g, 1.15 mmol) was slowly added as solution in EtOAc (6 mL). The mixture was warmed to room temperature and stirred overnight. The mixture was filtered and the filtrate was washed with 1N HCl (10 mL), saturated NaHCO$_3$ (10 mL), brine (10 mL), dried over Na$_2$SO$_4$ and concentrated to give a crude white solid (contaminated with DCU). The DCU was removed by flash chromatography (30% to 50% EtOAc in hexanes) to provide a white solid, which was dissolved in MeOH (2 mL) and treated with 4N HCl in 1,4-dioxane (0.26 mL, 1.1 mmol). The reaction was stirred at room temperature overnight then partitioned between 1N HCl (10 mL) and EtOAc (10 mL). The organic layer was washed with saturated sat. NaHCO$_3$ (1×25 mL) dried over Na$_2$SO$_4$, filtered, and concentrated to a residue which was purified by flash chromatography (60% EtOAc in hexanes) to provide the title compound as a white amorphous solid: $^1$H NMR (DMSO-d$_6$) δ 9.36 (s, 1H), 8.23 (d, J=8.1, 1H), 7.35–7.14 (m, 5H), 6.96 (t, J=7.5, 1H), 6.78 (d, J=8.2, 1H), 6.52 (d, J=7.5, 1H), 5.81–5.69 (m. 2H), 5.32 (d, J=9.7, 1H), 5.11–5.91 (m, 3H), 4.40 (m, 3H), 2.89–2.61 (m, 4H), 2.37–2.14 (m, 2H), 1.81 (s, 3H), 1.55 (s, 3H), 1.30 (s, 3H); Anal. Calcd for C$_{28}$H$_{34}$N$_2$O$_5$S: C, 65.86; H, 6.71; N, 5.49. Found: C, 65.52; H, 6.55; N, 5.81.

The following examples were synthesized using the specific method outlined above using the appropriate grignard reagent for the desired compound.

EXAMPLE D2

(R)-3-((2S,3R)-4,4-Difluoro-1-[4-(3-fluoro-phenyl)-2-hydroxy-3-(3-hydroxy-2-methyl-benzoylamino)-butyryl])-3,3-dimethyl-pyrrolidine-2-carboxylic acid allylamide

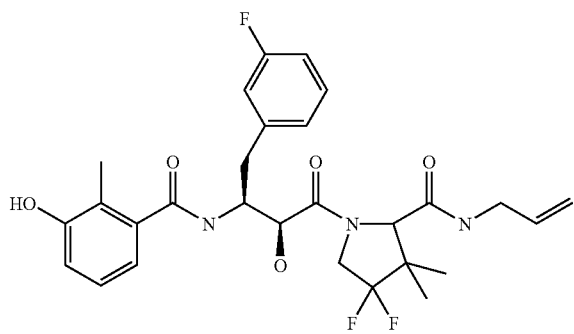

The following represents synthesis of key intermediates for the synthesis of the title compound.

L-2-tert-Butoxycarbonylamino-3-(3-fluoro-phenyl)-propionic acid.

A mixture of L-2-amino-3-(3-fluoro-phenyl)-propionic acid (20.0 g, 110 mmol, 1 eq) in H$_2$O (100 mL) was treated with Na$_2$CO$_3$ (16.2 g, 153 mmol, 1.4 eq) in H$_2$O (40 mL) followed by 1,4-dioxane (100 mL) and cooled to 0 C. The BOC$_2$O was added and the reaction mixture was stirred at ambient temperature for 5 h after which the dioxane was evaporated. H$_2$O (125 mL) was then added and the mixture then washed with Et$_2$O (2×100 mL). The aqueous phase was acidified with 10% citric acid followed by extraction with EtOAc (2×300 mL). The combined EtOAc layers were washed with H$_2$O (2×150 mL), brine (150 mL), dried (Na$_2$SO$_4$) and concentrated to give the acid as a colorless, viscous oil which slowly solidified upon standing (31 g, quant). $^1$H NMR (CDCl$_3$) 7.33–7.26 (m, 1H), 7.00–6.91 (m, 3H), 4.96 (s, 1H), 4.62 (bs, 1H), 3.23 (dd, J=14, 5.3, 2H), 1.44 (s, 9H); Anal Calcd for C$_{14}$H$_{18}$NO$_4$F: C, 59.36; H, 6.40; N, 4.94. Found: C, 59.29; H, 6.34; N, 4.90.

L-[2-(3-Fluoro-phenyl)-1-(methoxy-methyl-carbamoyl)-ethyl]-carbamic acid-tert-butyl ester.

To a solution of L-2-tert-butoxycarbonylamino-3-(3-fluoro-phenyl)-propionic acid (30.9 g, 109 mmol) in THF (180 mL) was added carbonyldiimidazole (21.2 g, 131 mmol, 1.2 eq). After stirring the solution at ambient temperature for 45 min was added DMF (64 mL), N,O-dimethylhydroxylamine hydrochloride (11.7 g, 120 mmol, 1.1 eq) and diisopropylethylamine (20 mL, 113 mmol, 1.04 eq). After stirring for a total time of 2 h, the solvents were evaporated in vacuo and the oily residue dissolved in EtOAc (300 mL). The organic phase was washed with H$_2$O (500 mL), 10% citric acid (2×150 mL), H$_2$O (500 mL), sat'd Na$_2$CO$_3$ (200 mL), brine (200 mL), dried (Na$_2$SO$_4$) and concentrated to give the product suitable for further use (31.6 g, 89%). $^1$H NMR (CDCl$_3$) 7.29–7.22 (m, 1H), 6.98–6.89 (m, 3H), 5.20 (bs, 1H), 4.96 (bs, 1H), 3.72 (s, 3H), 3.19 (s, 3H), 3.07 (dd, J=13.6, 5.9, 2H), 1.41 (s, 9H). Anal Calcd for C$_{16}$H$_{23}$N$_2$O$_4$F: C, 58.88; H, 7.10; N, 8.58. Found: C, 58.89; H, 7.19; N, 8.71.

L-[1-(3-Fluoro-benzyl)-2-oxo-ethyl]-carbamic acid tert-butyl ester.

To a 3-neck flask which purged with argon was added a 1 M solution of LAH in Et$_2$O (106 mL, 1.1 eq) and cooled to 0 C. A solution of L-[2-(3-fluoro-phenyl)-1-(methoxy-methyl-carbamoyl)-ethyl]-carbamic acid-tert-butyl ester (31.6 g, 97 mmol, 1 eq) in THF (150 mL) was added over a period of 1 h such that the temperature remained below 5 C. After stirring for an additional 30 min the reaction was quenched with EtOAc (60 mL) followed by 5% KHSO$_4$ (100 mL). EtOAc (500 mL) was added and the organic phase was washed with 1N HCl (3×100 mL), H$_2$O (500 mL), brine (200 mL), dried (Na$_2$SO$_4$) and concentrated to a white solid which was filtered and washed with heptane (200 mL). The aldehyde was suitable for further use (17.6 g, 68%). $^1$H NMR (CDCl$_3$) 9.65 (s, 1H), 7.33–7.26 (m, 1H), 7.01–6.89 (m, 3H), 5.06 (bs, 1H), 4.43 (broad m, 2H), 1.45 (s, 9H). Anal Calcd for C$_{14}$H$_{18}$NO$_3$F: C, 62.91; H, 6.79; N, 5.24. Found: C, 62.73; H, 6.66; N, 5.21.

3-tert-Butoxycarbonylamino-4-(3-fluoro-phenyl)-2-hydroxy-butyric acid (diastereomeric).

A solution of L-[1-(3-fluoro-benzyl)-2-oxo-ethyl]-carbamic acid tert-butyl ester (17.6 g, 66 mmol, 1 eq) in MeOH (104 mL) was cooled to 0 C. A solution of sodium bisulfite in H$_2$O (104 mL) was added and the mixture stirred for 5 h at 0 C after which it was placed in a freezer for 7 h. The reaction mixture was then charged with a solution of NaCN (3.87 g, 79 mmol, 1.2 eq) in H$_2$O (104 mL) followed by EtOAc (280 mL) and stirred at room temperature for 11 h after which the organic layer was separated, dried (Na$_2$SO$_4$) and concentrated to give the crude cyanohydrin as a waxy solid. This material was dissolved in 1,4 dioxane (265 mL), charged with anisole (11 mL) and cooled to 0 C. Concentrated HCl (265 mL) was added, with vigorous stirring, to the reaction mixture followed by heating at reflux for 1 h. The dioxane plus most of the water was evaporated in vacuo. The remaining residue was basified with 2N NaOH and washed with Et$_2$O (3×200 mL). The aqueous phase was then charged with 1,4 dioxane (120 mL) followed by BOC$_2$O (15.8 g, 1.1 eq). After stirring at ambient temperature for 3 h the dioxane was removed in vacuo and the remaining mixture acidified with 10% citric acid followed by extraction with EtOAc (2×300 ml). The combined organic layers were washed with H$_2$O (300 mL), brine (200 mL), dried (Na$_2$SO$_4$) and concentrated to give the acid as diastereomeric mixture (ca 1:1) and orange solid (10.56 g, 51%) $^1$H NMR (DMSO) 7.35–7.25 (m, 2H), 7.06–6.96 (m, 6H), 6.76 (d, J=9.0, 1H), 6.43 (d, J=9.6, 1H), 4.02–3.89 (m, 4H), 3.57 (m, 2H), 2.83 (dd, J=13.4, 6.1, 2H), 1.28 (s, 9H), 1.26 (s, 9H).

(2S,3R)-3-tert-Butoxycarbonylamino-4-(3-fluoro-phenyl)-2-hydroxy-butyric acid methyl ester.

To a solution of 3-tert-butoxycarbonylamino-4-(3-fluoro-phenyl)-2-hydroxy-butyric acid (diastereomeric) (10.56 g, 33.8 mmol., 1 eq) in DMF (130 mL) was suspended K$_2$CO$_3$ (6.07 g, 43 mmol, 1.3 eq) followed by CH$_3$I (4.2 mL, 68 mmol, 2 eq). After stirring for 2 h at ambient temperature the DMF was evaporated in vacuo. The remaining residue was dissolved in EtOAc (300 mL) and washed with H$_2$O (2×100 mL), sodium thiosulfate solution (100 mL), brine (200 mL) dried (Na$_2$SO$_4$) and concentrated to give a crude orange solid (9.55 g). Purification by column chromatography (1:1 EtOAc/hexanes) afforded 6.96 g total (63%); of which 3.28 g being the desired diastereomer (2S,3R)-3-tert-Butoxycarbonylamino-4-(3-fluoro-phenyl)-2-hydroxy-butyric acid methyl ester (cream colored solid), and 3.68 g being the undesired product (2R,3R)-3-tert-butoxycarbonylamino-4-(3-fluoro-phenyl)-2-hydroxy-butyric acid methyl ester. (2S, 3R) product: $^1$H NMR (CDCl$_3$) 7.30–7.22 (m, 1H), 7.01–6.90 (m, 3H), 4.88 (d, J=8.2, 1H), 4.32 (m, 2H), 3.67 (s, 3H), 2.79 (t, J=6.9, 2H), 1.40 (s, 9H). (2R,3R) product: $^1$H NMR (CDCl$_3$) 7.32–7.25 (m, 1H), 7.09–6.91 (m, 3H), 4.82 (d, J=9.8, 1H), 4.27 (dd, J=16.9, 7.6, 1H), 4.08 (d, J=3.2, 1H), 3.78 (s, 3H), 3.17 (d, J=4.5, 1H), 2.93(d, J=4.5, 1H), 1.40 (s, 9H).

(2S,3R)-3-tert-Butoxycarbonylamino-4-(3-fluoro-phenyl)-2-hydroxy-butyric acid.

A mixture of (2S,3R)-3-tert-Butoxycarbonylamino-4-(3-fluoro-phenyl)-2-hydroxy-butyric acid methyl ester (3.28 g, 10.05 mmol, 1 eq), 4N NaOH (4 mL, 16 mmol, 1.6 eq), MeOH (42 mL) and 1,4-dioxane (63 mL) was stirred at ambient temperature for 1.5 h after which the solvents were evaporated. To the residue was added 10% citric acid (100 mL) followed by extraction with EtOAc (100 mL). The organic layer was washed with H$_2$O (100 mL), brine (50 mL), dried (Na$_2$SO$_4$) and concentrated to give the desired product as a cream colored solid (3.06 g, 97%). $^1$H NMR (DMSO) 7.33–7.26 (m, 1H), 7.02–6.97 (m, 3H), 6.78 (d, J=5.2, 1H), 3.98 (d, J=5.5, 1H), 3.99–3.86 (m, 2H), 2.77–2.82 (m, 2H), 1.27 (s, 9H).

Conversion of Undesired (2R,3R) diastereomer-methylester to (2S,3R)-3-tert-butoxycarbonylamino-4-(3-fluoro-phenyl)-2-hydroxy-butyric acid.

(2S,3R)-3-tert-Butoxycarbonylamino-2-(2-chloro-acetoxy)-4-(3-fluoro-phenyl)-butyric acid methyl ester.

A solution of of the (2R,3R)-3-tert-butoxycarbonylamino-4-(3-fluoro-phenyl)-2-hydroxy-butyric acid methyl ester (8 g, 24.5 mmol, 1 eq), chloroacetic acid (5.79 g, 61.3 mmol, 2.5 eq), and PPh$_3$ (16 g, 61.3 mmol, 2.5 eq) in benzene (340 mL) was cooled to 0 C followed by the addition of diethylazodicarboxylate (9.7 mL, 61.3 mmol, 2.5 eq) over a 20 min period. After the addition, the reaction mixture was stirred at ambient temperature for 2 h after which the reaction mixture was concentrated and the residue purified by column chromatography with 30% EtOAc/hexanes as eluant. Appropriate fractions were combined and concentrated to give a yellow solid which was shaken with heptane and filtered to remove the yellow DEAD residues. The product was thus obtained as a white solid (4.25 g, 43%) $^1$H NMR (CDCl$_3$) 7.32 (m, 1H), 7.03–6.96 (m, 3H), 5.34 (d, J=3.5, 1H), 4.26 (s, 2H), 4.75–4.5 (series of m, 2H), 3.77 (s, 3H), 2.92 (bd, J=7, 2H), 1.43 (s, 9H).

(2S,3R)-3-tert-butoxycarbonylamino-4-(3-fluoro-phenyl)-2-hydroxy-butyric acid.

A mixture of (2S,3R)-3-tert-butoxycarbonylamino-2-(2-chloro-acetoxy)-4-(3-fluoro-phenyl)-butyric acid methyl ester (4.56 g, 11.3 mmol, 1 eq), 4N NaOH (6.5 mL, 25.9 mmol, 2.3 eq), MeOH (48 mL) and 1.4-dioxane (72 mL) was stirred at ambient temperature for 4 h after which the solvents were removed in vacuo and the residue was charged with H$_2$O (50 mL) and washed with Et$_2$O (100 mL). The aqueous layer was made acidic with 10% citric acid and extracted with EtOAc (2×75 mL). The combined EtOAc layers were washed with H$_2$O (3×50 mL) brine (50 mL), dried (Na$_2$SO$_4$), concentrated, shaken with heptane and filtered to give the desired acid as a white solid (3.3 g, 94%).

$^1$H NMR (DMSO) 9.42 (s, 1H),8.26 (d, J=8.1, 1H), 8.17 (t, J=5.9, 1H), 7.32 (m, 1H), 7.18 (m, 2H), 7.00 (m, 2H), 6.79 (d, J=8.1, 1H), 6.56 (d, J=7.5, 1H), 5.79 (m, 1H), 5.51 (d, J=6.4, 1H), 5.24 (d, J=15.4, 1H),5.06 (d, J=10.4, 1H), 4.49–4.28 (series of m, 5H), 3.74 (broad m, 2H), 2.89–2.67 (m, 2H), 1.81 (s, 3H), 1.22 (s, 3H), 1.05 (s, 3H). Anal Calcd for C$_{28}$H$_{32}$N$_3$O$_5$F$_3$x0.25H$_2$O: C, 60.91; H, 5.93; N, 7.61. Found: C, 60.96; H, 6.05; N, 7.20.

EXAMPLE D3

(S)-4,4-Difluoro-1-[(2S,3S)-4-(3-fluoro-phenyl)-2-hydroxy-3-(3-hydroxy-2-methyl-benzoylamino)-butyryl]-3,3-dimethyl-pyrrolidine-2-carboxylic acid isobutyl-amide

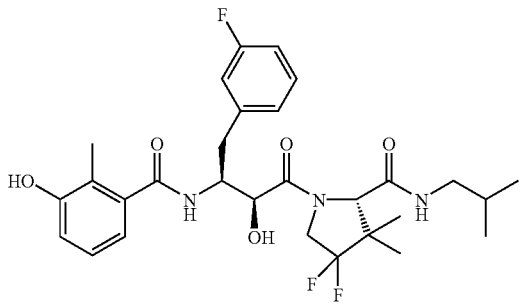

White solid: $^1$H NMR (DMSO-$d_6$) □9.14 (s, 1H), 8.03 (d, 1H, J=8.3), 7.76 (t, 1H, J=5.8), 7.09 (dd, 1H, J=7.4, 14.4), 6.99 (d, 2H, J=7.6), 6.81–6.73 (m, 2H), 6.58 (d, 1H, J=8.1), 6.34 (d, 1H, J=6.8), 5.23 (d, 1H, J=6.6), 4.25 (dd, 1H, J=12.2, 25.0), 4.15–4.08 (m, 3H), 2.77–2.46 (m, 4H), 1.59 (s, 3H), 1.52–1.43 (m, 1H), 1.00 (s, 3H), 0.83 (s, 3H), 0.65 (d, 6H, J=6.4); HRMS (ESI) m/z calcd for $C_{30}H_{37}F_3N_3O_5$ (M+H)$^+$ 564.6130, found: 564.2674; Anal. Calcd for $C_{30}H_{36}F_3N_3O_5$: C, 61.80; H, 6.44; N, 7.46. Found: C, 61.58; H, 6.45; N, 7.34.

EXAMPLE D4

(S)-4,4-Difluoro-1-[(2S,3S)-2-hydroxy-3-(3-hydroxy-2,5-dimethyl-benzoylamino)-4-phenyl-butyryl]-3,3-dimethyl-pyrrolidine-2-carboxylic acid propylamide

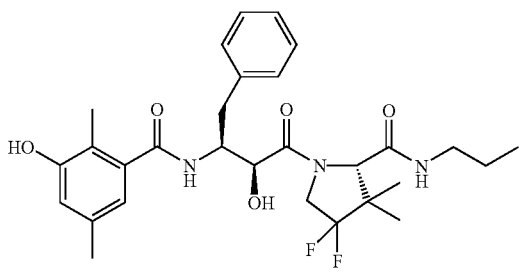

White solid: $^1$H NMR (DMSO-$d_6$) □9.17 (s, 1H), 8.04 (d, 1H, J=8.1), 7.85 (t, 1H, J=5.1), 7.29–7.09 (m, 5H), 6.53 (s, 1H), 6.30 (s, 1H), 5.38 (d, 1H, J=6.1), 4.40–4.24 (m, 3H), 4.14 (s, 1H), 3.04–2.90 (m, 2H), 2.77 (d, 1H, J=2.2), 2.65–2.59 (m, 1H), 2.09 (s, 3H), 1.67 (3, 3H), 1.39–1.31 (m, 2H), 1.13 (s, 3H), 0.97 (s, 3H), 0.78 (s, 3H). HRMS (ESI) m/z calcd for $C_{29}H_{38}F_2N_3O_5$ (M+H)$^+$ 546.6230, found 546.2780; Anal. Calcd for $C_{29}H_{37}F_2N_3O_5$: C, 63.84; H, 6.84; N, 7.70. Found: C, 63.44; H, 6.82; N, 7.52.

EXAMPLE D5

(S)-4,4-Difluoro-1-[(2S,3S)-2-hydroxy-3-(3-hydroxy-2,5-dimethyl-benzoylamino)-4-phenyl-butyryl]-3,3-dimethyl-pyrrolidine-2-carboxylic acid isobutyl-amide

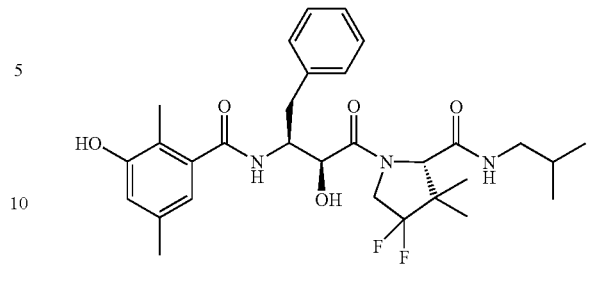

White solid: $^1$H NMR (DMSO-$d_6$) □9.24 (s, 1H), 8.11 (d, 1H, J=8.3), 7.94 (t, 1H, J=5.8), 7.37–7.16 (m, 5H), 6.60 (s, 1H), 6.38 (s, 1H), 5.44 (d, 1H, J=6.3), 4.48–4.29 (m, 3H), 4.25 (s, 1H), 2.94–2.83 (m, 3H), 2.73–2.64 (m, 1H), 2.16 (s, 3H), 1.75 (s, 3H), 1.74–1.65 (m, 1H), 1.21 (s, 3H), 1.05 (s, 3H), 0.86 (d, 6H, J=6.6); HRMS (ESI) m/z calcd for $C_{30}H_{40}F_2N_3O_5$ (M+H)$^+$ 560.6500, found: 560.2928; Anal. Calcd for $C_{30}H_{39}F_2N_3O_5$: C, 64.38; H, 7.02; N, 7.51. Found: C, 64.09; H, 7.05; N, 7.29.

EXAMPLE D6

(S)-4,4-Difluoro-1-[(2S,3S)-2-hydroxy-3-(3-hydroxy-2,5-dimethyl-benzoylamino)-4-phenyl-butyryl]-3,3-dimethyl-pyrrolidine-2-carboxylic acid (2,2,2-trifluoro-ethyl)-amide

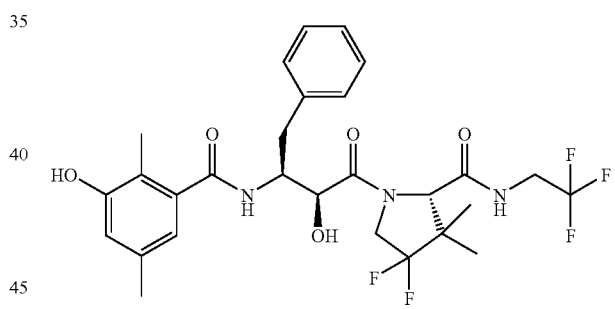

(S)-4,4-Difluoro-1-[(2S,3S)-2-hydroxy-3-(3-hydroxy-2,5-dimethyl-benzoylamino)-4-phenyl-butyryl]-3,3-dimethyl-pyrrolidine-2-carboxylic acid (2,2,2-trifluoro-ethyl)-amide White solid: $^1$H NMR (DMSO-$d_6$) □9.27 (s, 1H), 8.72 (t, 1H, J=6.2), 8.15 (d, 1H, J=8.1), 7.37–7.19 (m, 5H), 6.63 (s, 1H), 6.39 (s, 1H), 5.57 (d, 1H, J=6.3), 4.52–4.33 (m, 4H), 4.10–3.94 (m, 1H), 3.93–3.88 (m, 1H), 2.87 (d, 1H, J=7.3), 2.75–2.69 (m, 1H), 2.19 (s, 3H), 1.77 (s, 3H), 1.25 (s, 3H), 1.06 (s, 3H); HRMS (ESI) m/z calcd for $C_{28}H_{33}F_3N_3O_5$ (M+H)$^+$ 586.5670, found 586.2340; Anal. Calcd for $C_{28}H_{32}F_3N_3O_5 \cdot 0.4H_2O$: C, 56.73; H, 5.58; N, 7.09. Found: C, 56.64; H, 5.41; N, 6.94.

Combinatorial Chemistry Approach to HIV Protease P2' Inhibitors

General Method E

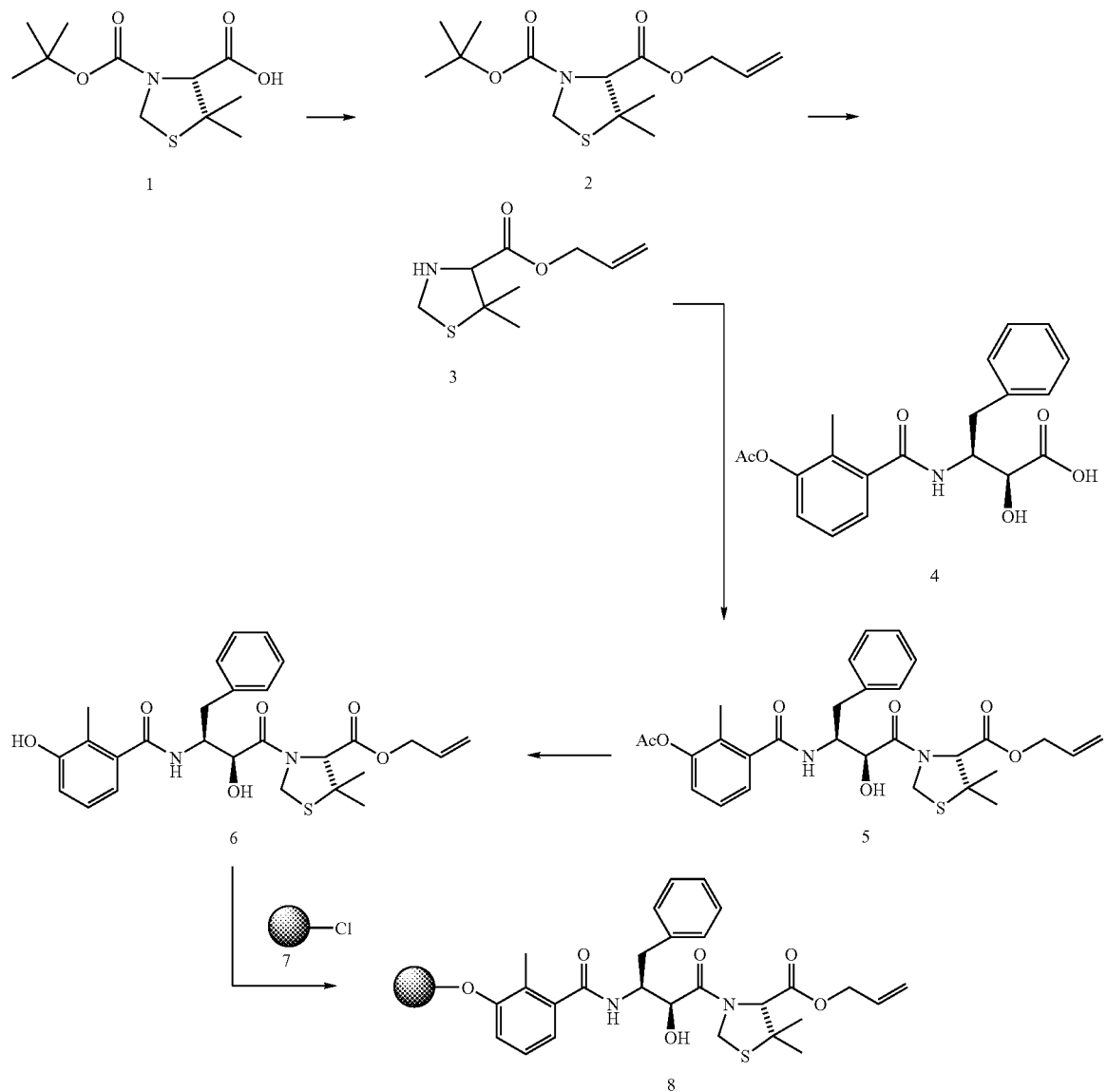

The combinatorial building block, 8, is prepared using the following method. The boc-protected thiazolidine carboxylic acid, 1, is treated with allyl bromide in the presence of NaNCO₃ to yield the boc-protected thiazolidine allyl ester, 2. Deprotection of boc-protected allyl ester, 2, with HCl (g) in EtOAc gives the HCl salt of the thiazolidine allyl ester amine, 3, which is treated with TEA and coupled to 4 in the presence of HOBT and DCC to give the building block precursor, 5. Deprotection of the building block, 5, with 4N HCl yields the phenol, 6. Loading the building block, 6, on to activated cross-linked trityl chloride polystyrene beads, 7, was accomplished in the following manner. The polystyrene cross-linked trityl alcohol was activated to the trityl chloride, 7, by treatment with 20% acetyl chloride in anhydrous CH₂Cl₂ at room temperature. The trityl chloride beads were combined with the phenol 6 in the presence of Hunig's base in anhydrous CH₂Cl₂ to yield the substrate loaded polystyrene beads 8. Intermediates were purified either by flash chromatography or preparative HPLC.

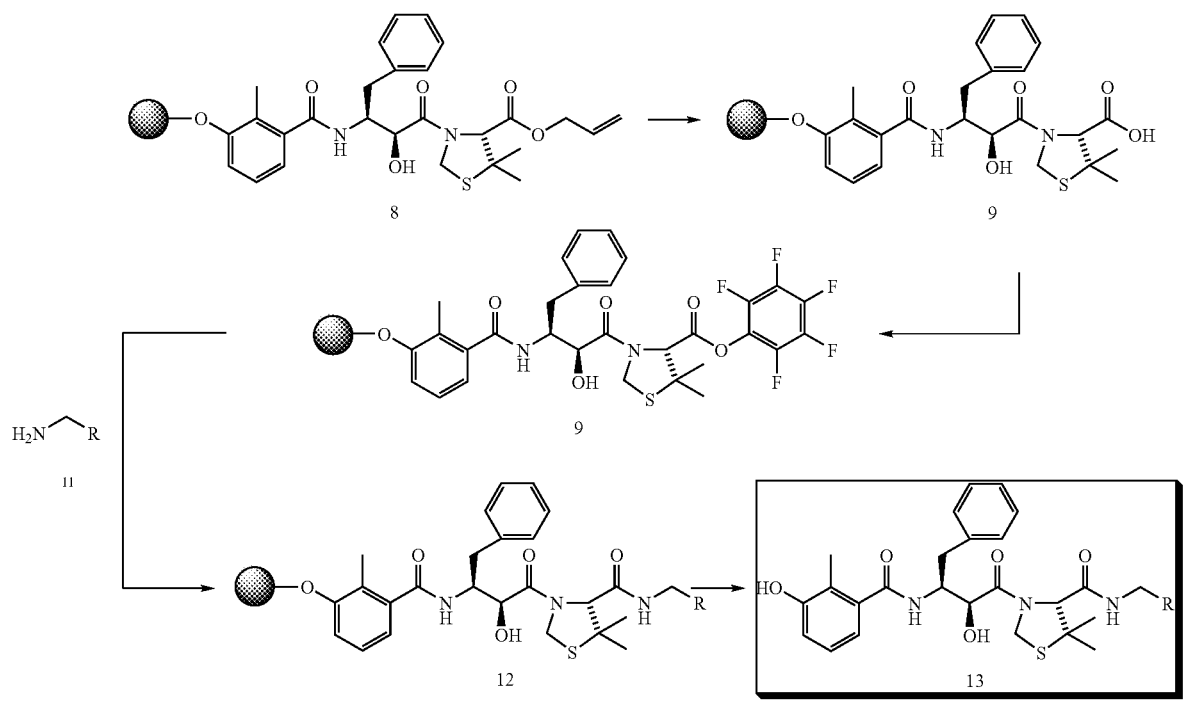

The synthesis of the HIV protease combinatorial library was carried out in the following fashion. The allyl ester was removed by treatment with Pd[PPh$_3$]$_4$ and NMM in anhydrous THF to give carboxylate 9, which was treated with pentafluorophenol, pentafluorophenol trifluoromethyl acetate and pyridine in DMF to yield the pentafluoro ester, 10. The pentafluoro ester 10 was treated with various primary amines in a 96-well plate format to give amides 12. The final products were cleaved from the polystyrene crowns with TFA to give products 13. Each product was analyzed by LCMS and HPLC. The following table typifies compounds synthesized by this combinatorial method.

TABLE 1

| P2' | Expected Mass (LCMS) | Observed Mass | % Inhibition |
|---|---|---|---|
| H$_2$N–CH$_2$CH$_2$–(N-methylpyrrolidinyl) | 582 | 583(MH$^+$) | 5 |
| H$_2$N–CH$_2$CH$_2$–piperidinyl | 582 | 583(MH$^+$) | 5 |
| HO–CH$_2$–CH(CH$_3$)–NH$_2$ | 529 | 552(Na$^+$) | 38 |
| H$_2$N–CH$_2$CH$_2$–N(CH$_3$)H | 528 | 529(MH$^+$) | 4 |

TABLE 1-continued

| P2' | Expected Mass (LCMS) | Observed Mass | % Inhibition |
|---|---|---|---|
| H$_2$N–CH$_2$CH$_2$–C$_6$H$_4$–OH | 591 | 614(Na$^+$) | 18 |
| (CH$_3$)$_3$C–CH$_2$CH$_2$–NH$_2$ | 555 | 578(Na$^+$) | 19 |
| H$_2$N–(CH$_2$)$_3$–N-methylpiperazinyl | 611 | 612(MH$^+$) | 1 |
| H$_2$N–(CH$_2$)$_3$–(5-methylpyrazol-4-yl) | 593 | 594(MH$^+$) | 6 |
| H$_2$N–CH$_2$CH$_2$–(2-pyridyl) | 576 | 577(MH$^+$) | 6 |

TABLE 1-continued

| P2' | Expected Mass (LCMS) | Observed Mass | % Inhibition |
|---|---|---|---|
| (2-(3,4-di-O-methyl/OH phenyl)ethylamine deriv.) | 635 | 658(Na+) | 5 |
| 4-(2-aminoethyl)benzoic acid | 656 | 656(MH+) | 8 |
| 2-methylbenzylamine | 575 | 598(Na+) | 86 |
| cyclopropylmethylamine | 525 | 548(Na+) | 56 |

TABLE 1-continued

| P2' | Expected Mass (LCMS) | Observed Mass | % Inhibition |
|---|---|---|---|
| neopentylamine | 541 | 564(Na+) | 63 |
| 3-aminopropanol | 529 | 552(Na+) | 49 |
| (5-methylfuran-2-yl)methylamine | 565 | 588(Na+) | 42 |
| 1-aminoindane | 587 | 610(Na+) | 54 |

Scheme 3: Solid Phase Synthesis Of HIV Protease Inhibitors

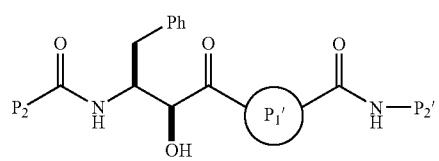

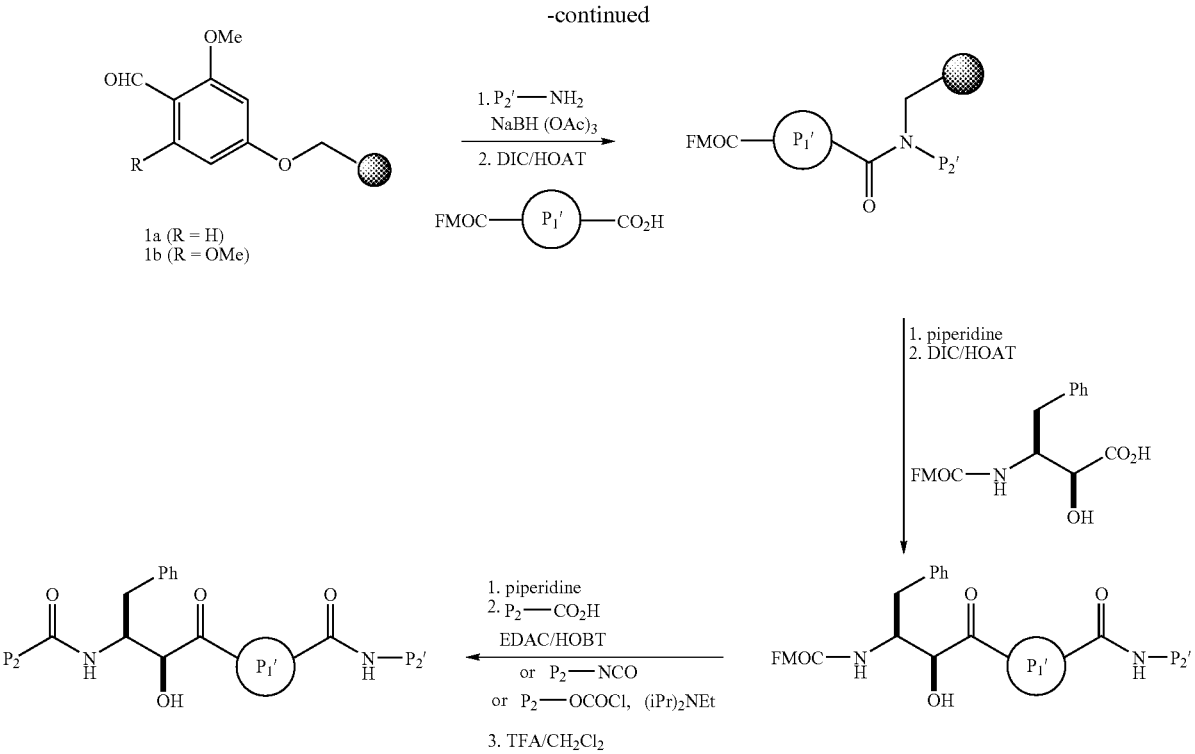

The solid phase combinatorial synthesis of HIV protease inhibitors was performed using the IRORI Directed Sorting Technology. Commercial 4-formyl-3-methoxyphenoxymethyl polystyrene resin 1a (PS-MB-CHO, Argonaut Technologies) or 4-formyl-3,5-dimethoxyphenoxymethyl polystyrene resin 1b (PL-FDMP resin, Polymer Laboratories) was loaded into individual Minikans.

Step A. Reductive Amination with $P_2'$ Amines

To separate flasks containing sorted MiniKans was added DCM (3 mL/MiniKan). The appropriate primary $P_2'$ amine (3 eq), sodium triacetoxyborohydride (5 eq), and acetic acid (3 eq) were added, and the mixtures were placed under argon, agitated with periodic venting at room temperature for 1–2 hours, and allowed to react overnight. For resin 1a, the filtrates were poured off and the MiniKans were washed with DCM, MeOH (2×), DCM (2×), Et$_3$N/DCM (1:3, 3×), DCM (2×), MeOH (3×), and DCM (4×). For resin 1b, a washing sequence of DCM, MeOH (2×), DCM (2×), Et$_3$N/DCM (1:3, 3×), DCM (2×), DMF, 1M NaOH/DMF (1:5, 3×), DMF (3×), MeOH (3×), and DCM (3×) was used. The MiniKans were dried under vacuum and taken on in Step B.

Step B. Peptide Coupling with $P_1'$ Amino Acids

To separate flasks containing the sorted MiniKans was added DMF (3 mL/MiniKan). The appropriate FMOC-protected amino acid (2.5 eq) and 1-hydroxy-7-azabenzotriazole (HOAT) (3 eq) were added and mixed until dissolved, and 1,3-diisopropylcarbodiimide (DIC) (3 eq) was added. The containers were placed under argon and agitated at room temperature overnight. The filtrates were poured off, and the MiniKans were washed with DMF (3×), MeOH (3×), DCM (2×), and DMF (2×). The MiniKans were taken directly on to Step C.

Step C. FMOC Deprotection

A container of MiniKans in DMF and piperidine (25%) with a total reaction volume of 3 mL/MiniKan was agitated under argon at room temperature for 45 minutes. The filtrate was removed, and the reaction procedure was repeated. The MiniKans were filtered and washed with DMF (3×), MeOH (2×), DCM (3×), and DMF, and taken directly on to Step D.

Step D. Peptide Coupling with FMOC-APNS

FMOC-Allophenylnorstatine (APNS) (3 eq) was added to the flask of MiniKans in DMF (3 mL/MiniKan). After dissolution, HOAT (3.5 eq) and DIC (3.5 eq) were added. The mixture was placed under argon and agitated at room temperature overnight. The reaction was filtered and the MiniKans were washed with DMF (3×), MeOH (3×), DCM (3×), and DMF. FMOC deprotection was carried out as in Step C, and the MiniKans were washed with DMF (3×), MeOH (2×), DCM (3×), dried under vacuum and taken on to Step E or F.

Step E. Peptide Coupling with $P_2$ acids

To separate flasks containing the sorted MiniKans in DMF (3 mL/MiniKan) was added the appropriate $P_2$ acid (3 eq), HOBT hydrate (4 eq), and (3-(dimethylamino)propyl)ethylcarbodiimide hydrochloride (EDAC) (3.5 eq). The reaction was agitated under argon at room temperature for 3 hours. After filtration, the MiniKans were washed with DMF (3×), MeOH (3×), and DCM (3×), dried under vacuum, and taken on to Step G.

Step F. Reaction with $P_2$ Isocyanates and Chloroformates

To separate flasks containing the sorted MiniKans in DCM (3 mL/MiniKan) was added the $P_2$ isocyanate (3 eq) or $P_2$ chloroformate (5 eq) and diisopropylethylamine (10 eq). The containers were agitated under argon at room temperature for 2–4 hours. After filtration, the MiniKans were washed with DCM (3×), MeOH (3×), and DCM (3×), dried under vacuum, and taken on to Step G.

Step G. Cleavage and Processing of the HIV Analogs
The individual MinKans were sorted into cleavage racks and a solution of 25% TFA in DCM (3 mL/MinKan) was added. The racks were agitated for 1.5 hours. The individual filtrates and DCM rinses were collected, concentrated, and purified by HPLC to provide the final compounds.
TABLE 2
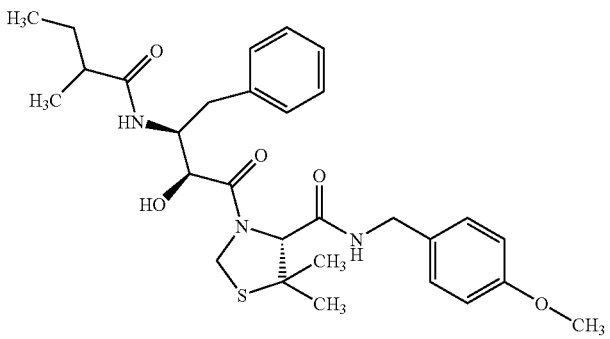
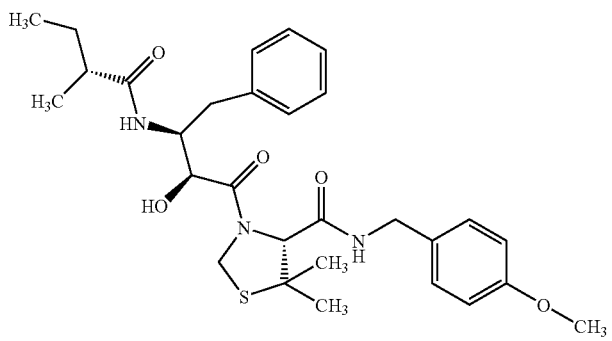
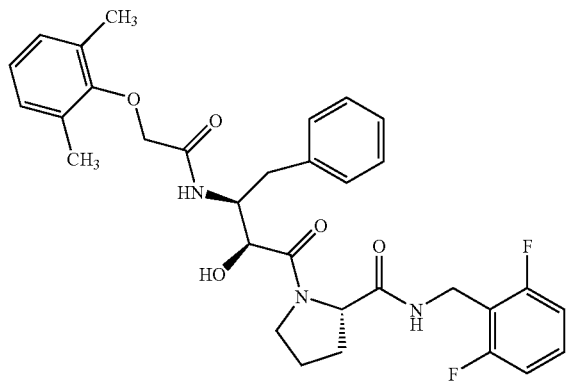
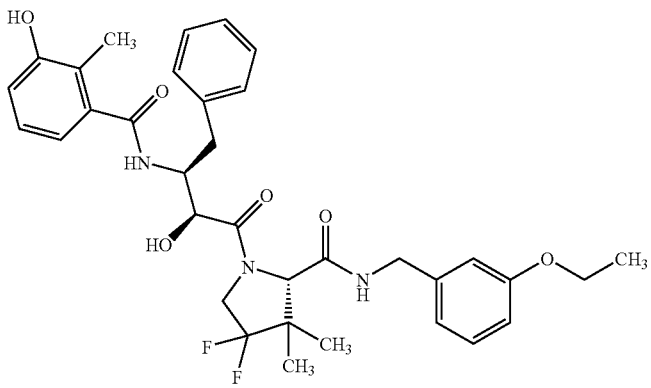

TABLE 2-continued
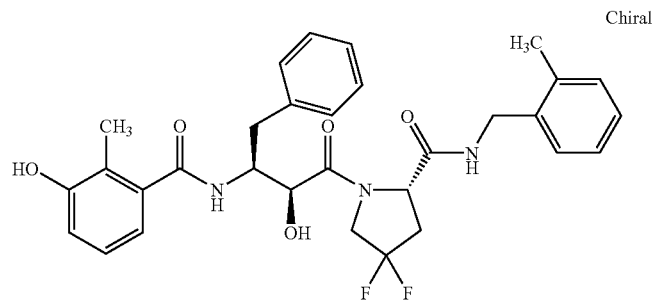
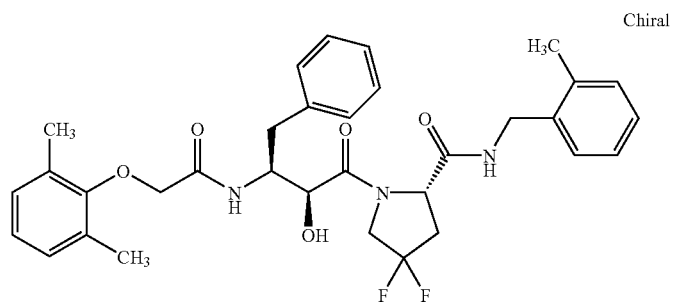
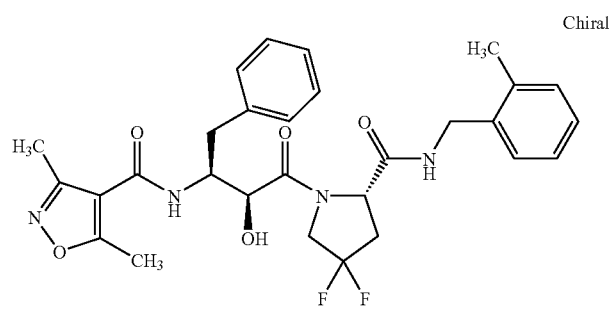
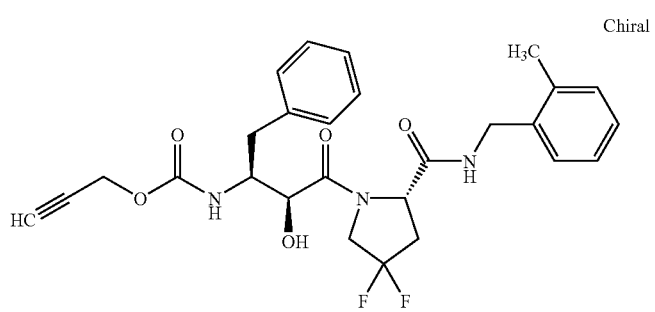
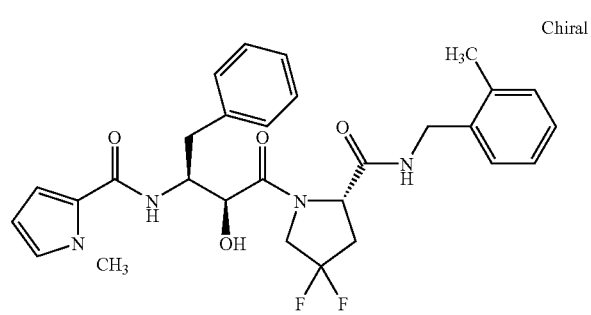

TABLE 2-continued
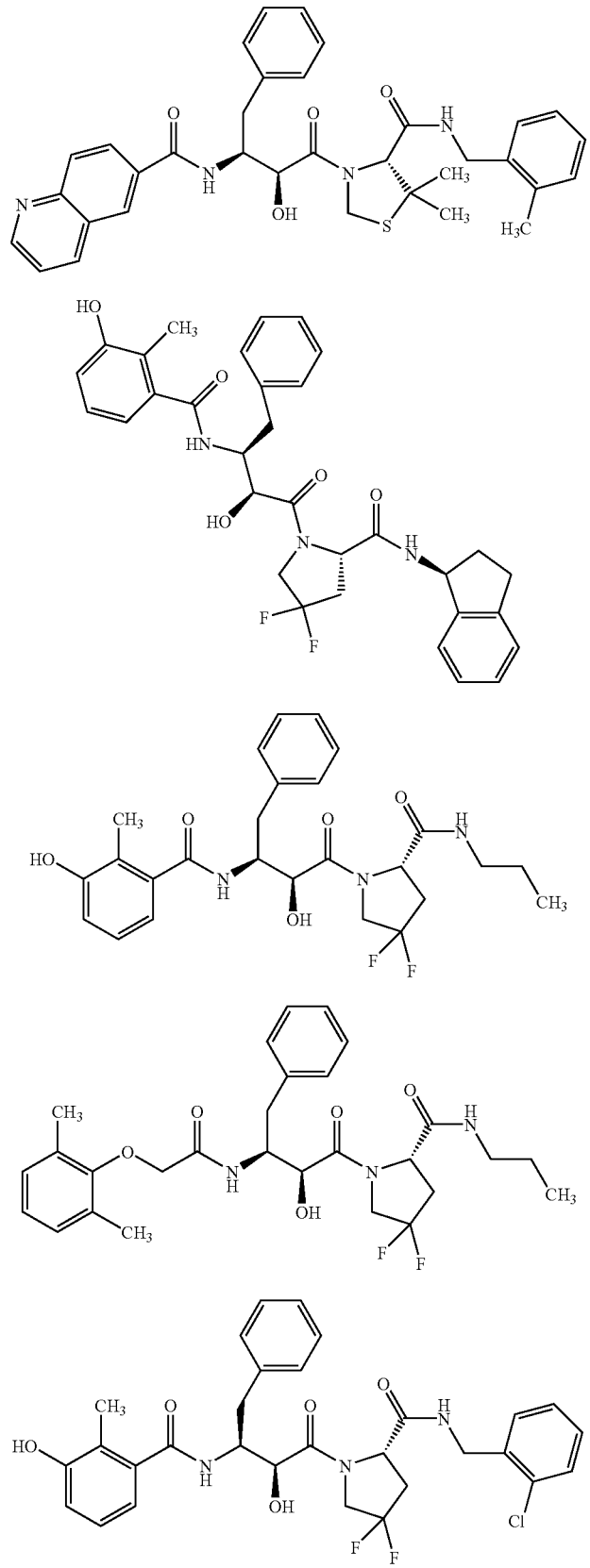

TABLE 2-continued
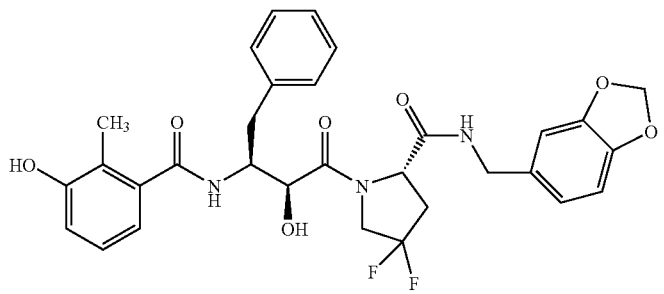
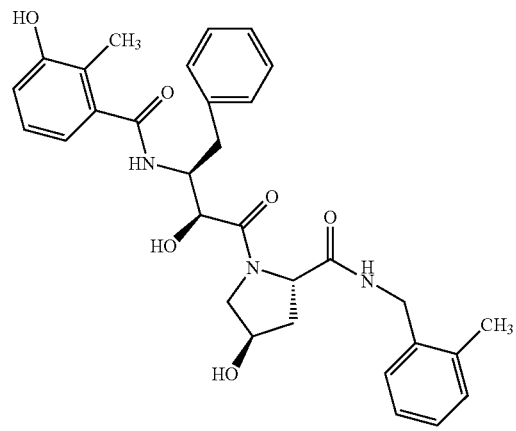
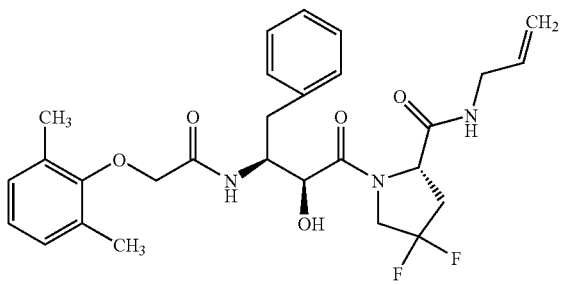
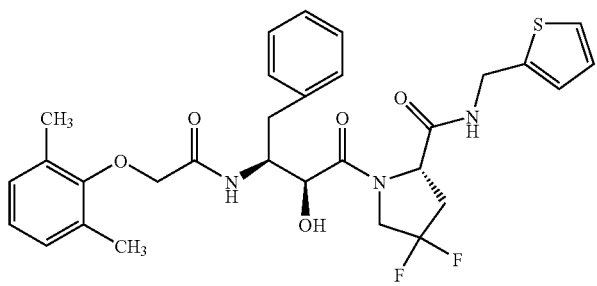
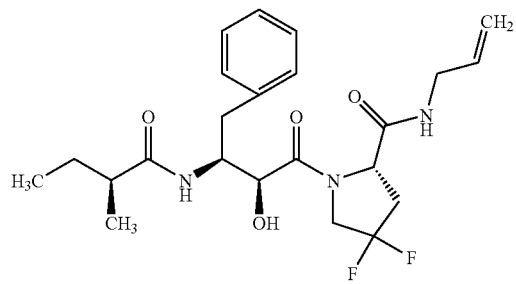

TABLE 2-continued
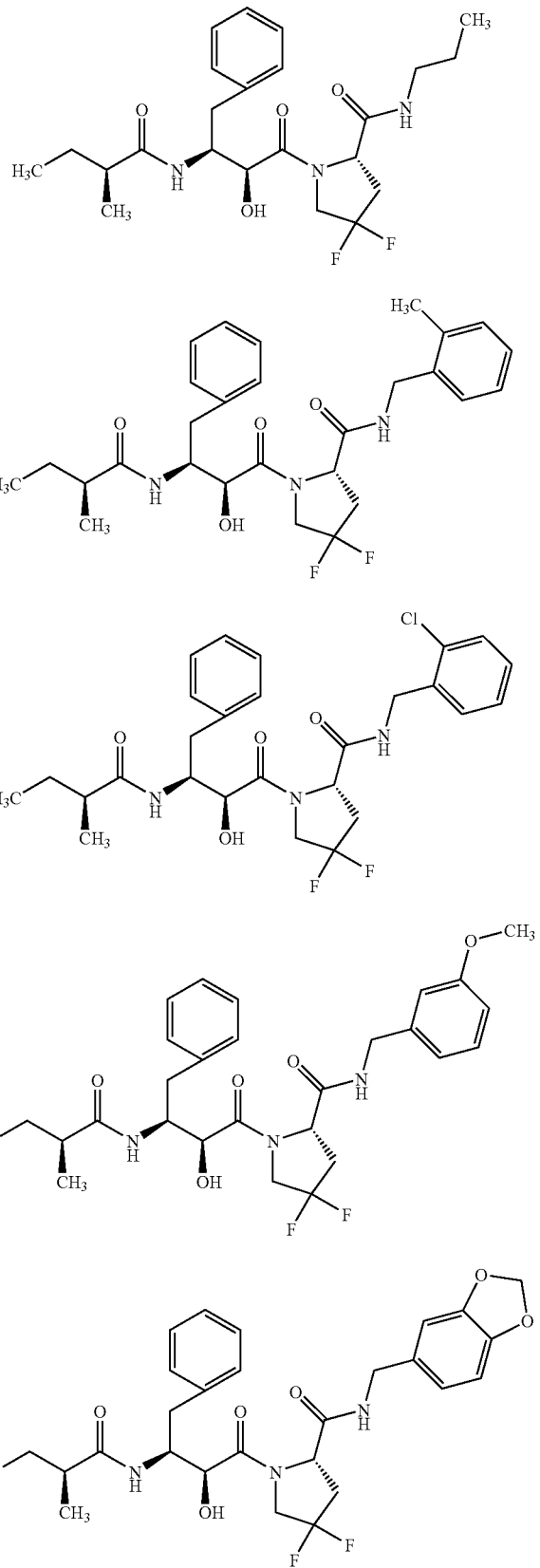

TABLE 2-continued
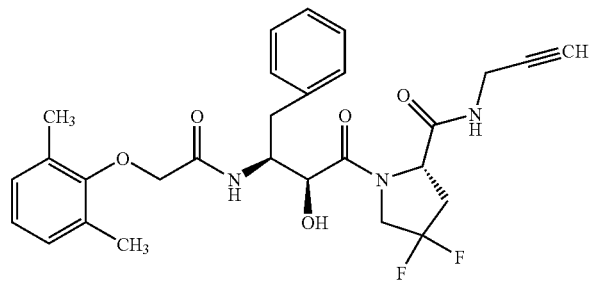
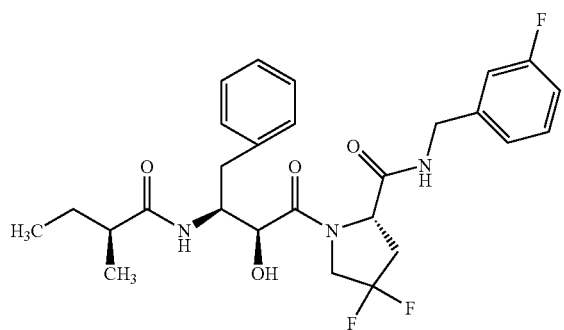
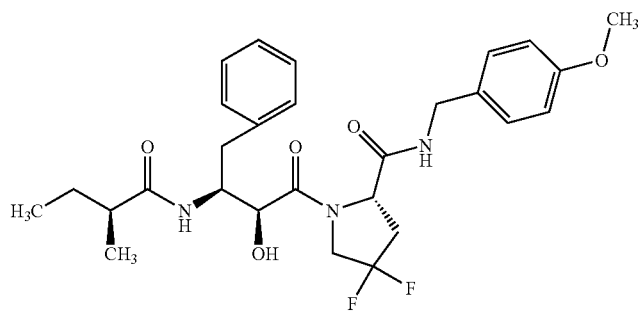
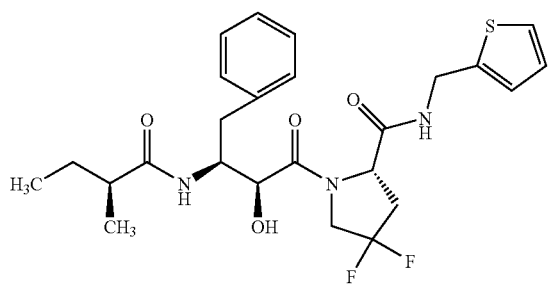
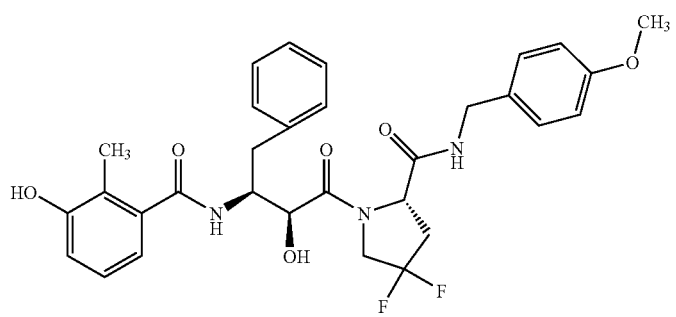

TABLE 2-continued
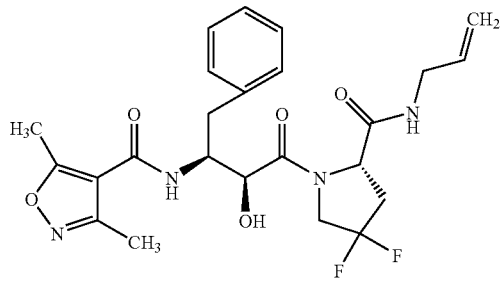
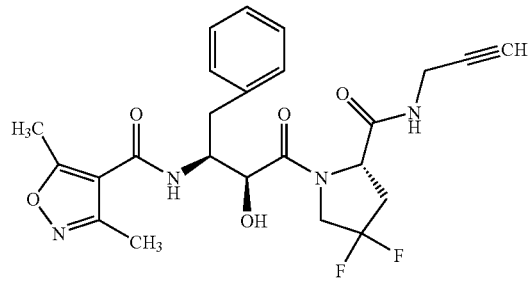
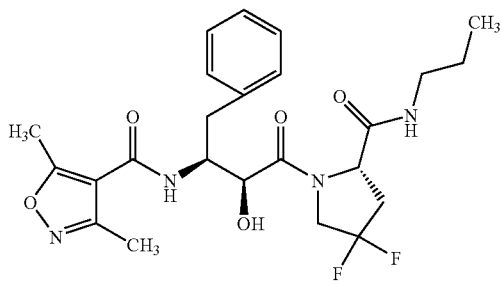
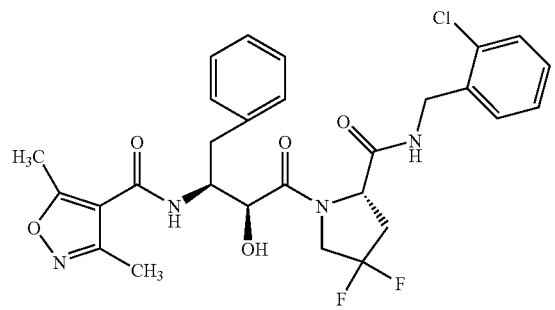
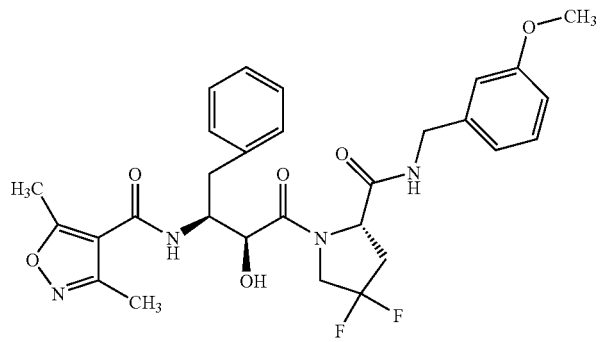

TABLE 2-continued
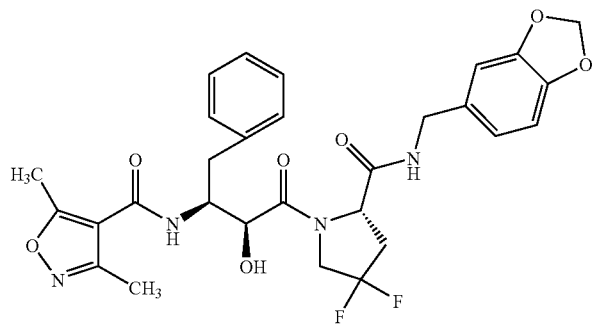
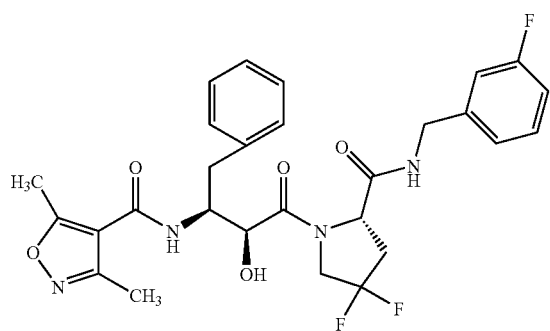
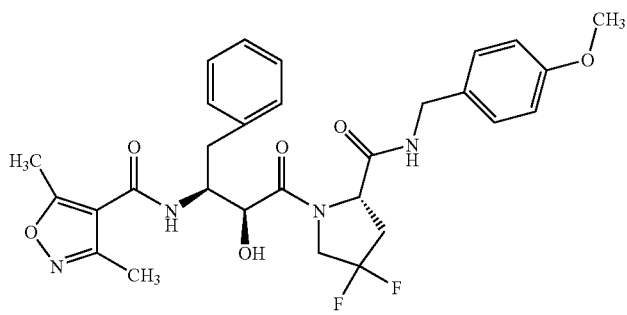
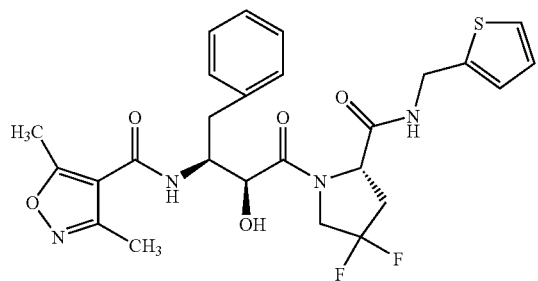
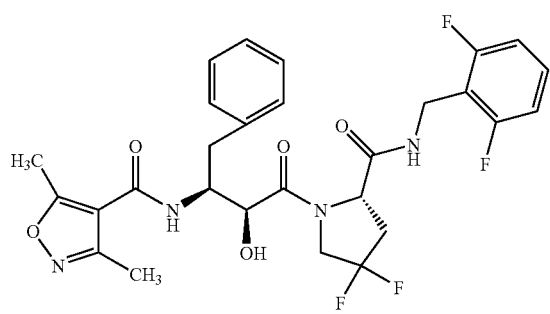

TABLE 2-continued
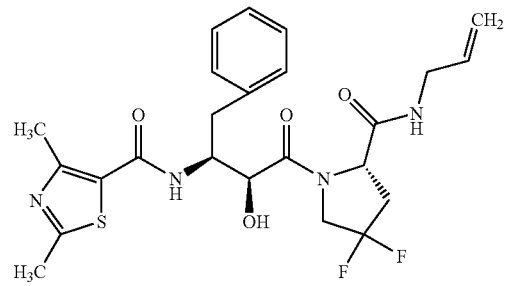
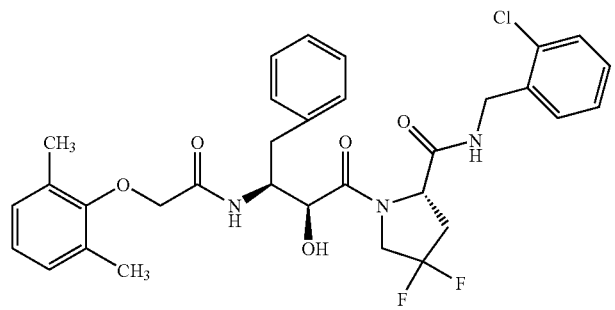
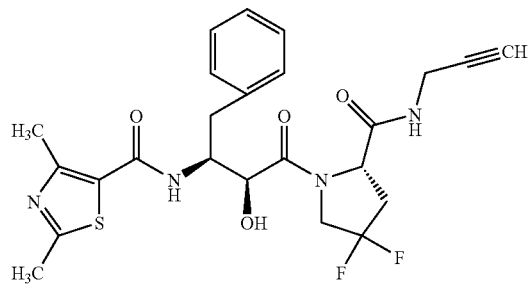
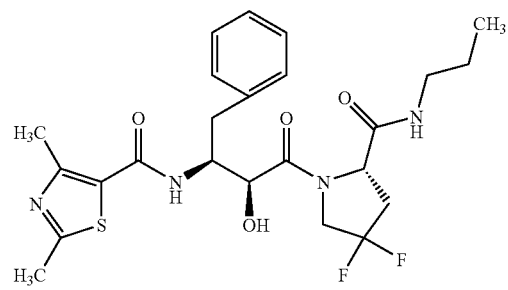
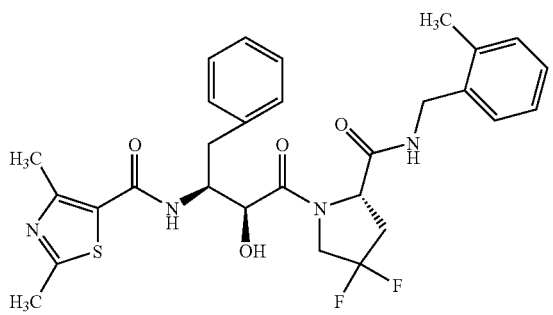

TABLE 2-continued
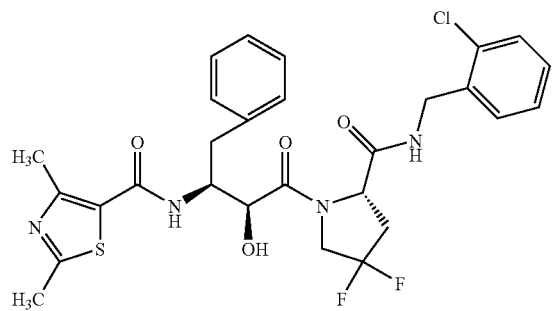
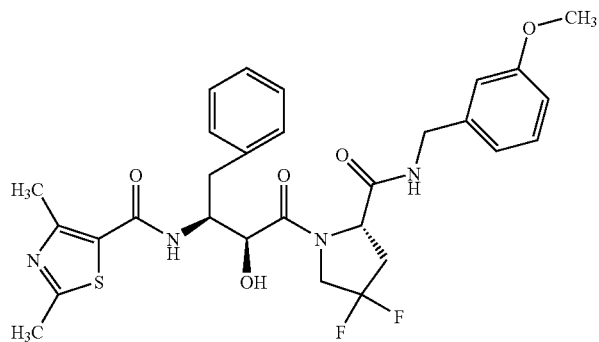
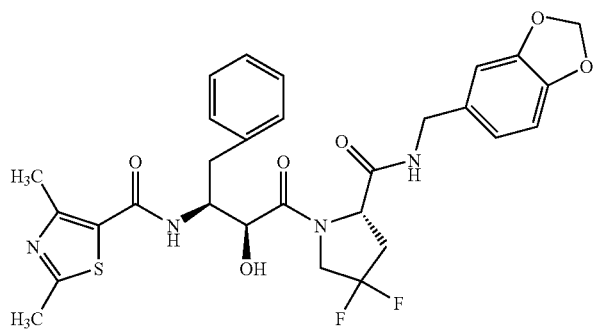
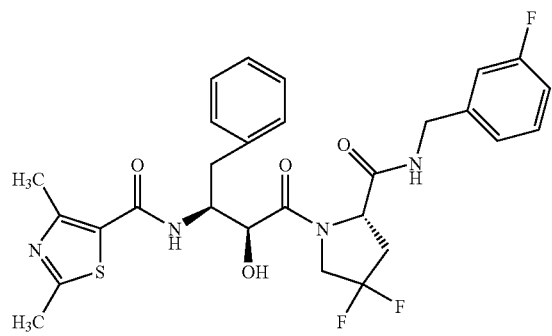

TABLE 2-continued
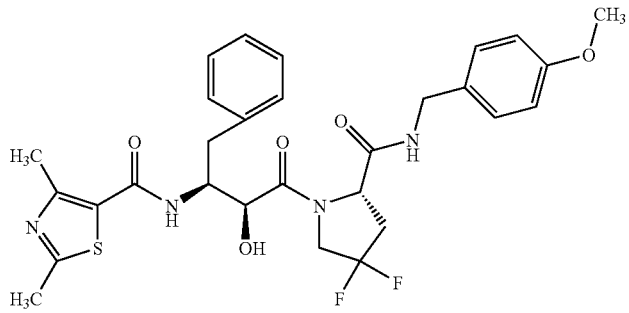
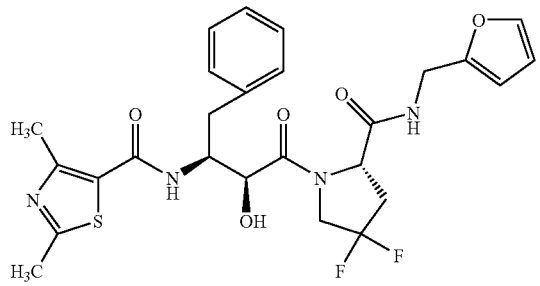
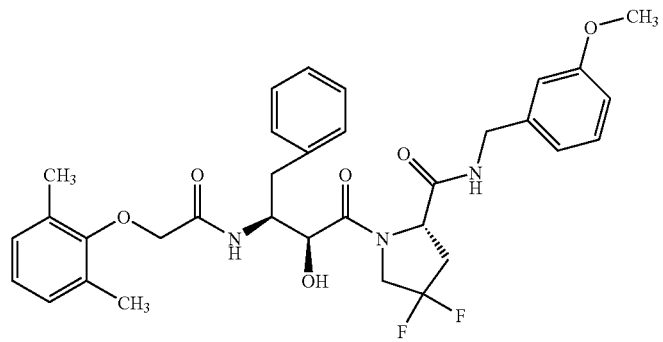
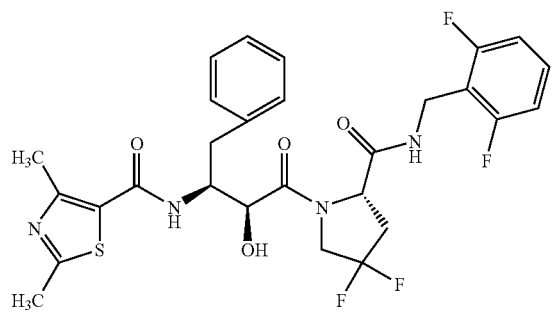
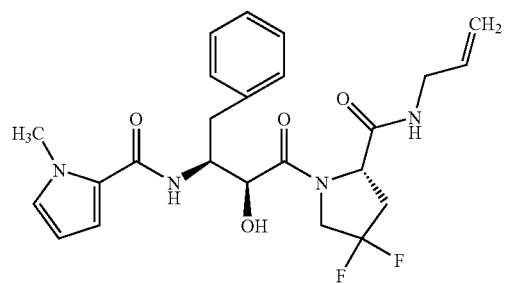

TABLE 2-continued
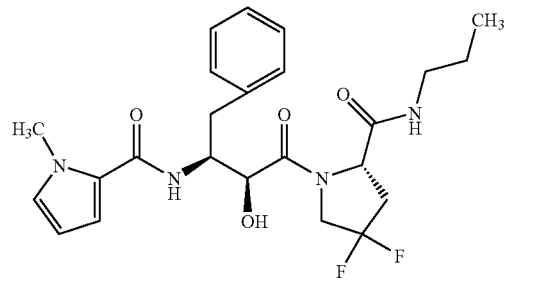
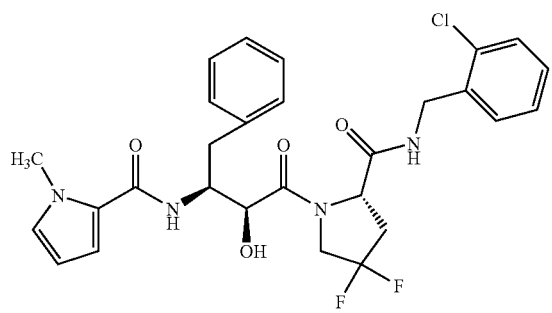
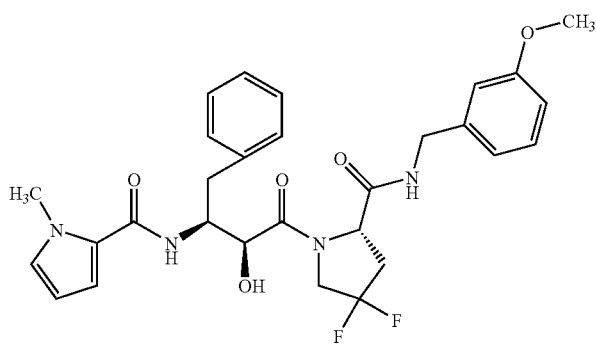
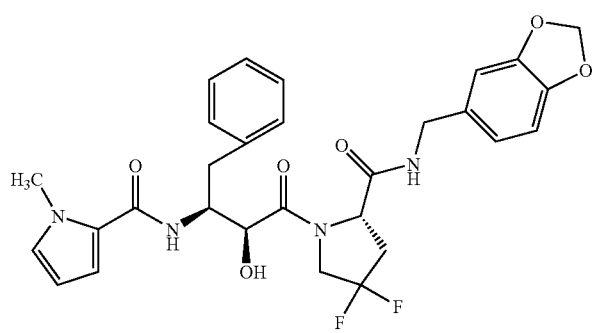
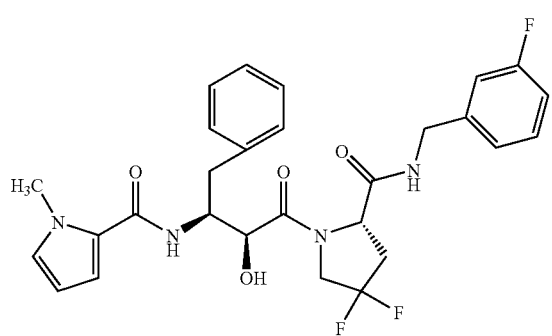

TABLE 2-continued
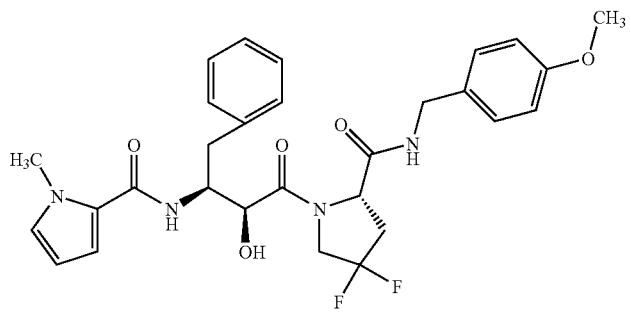
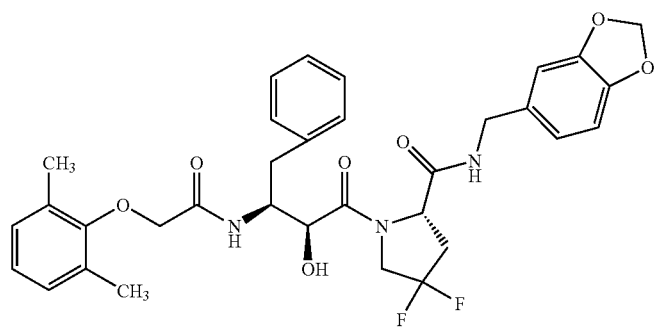
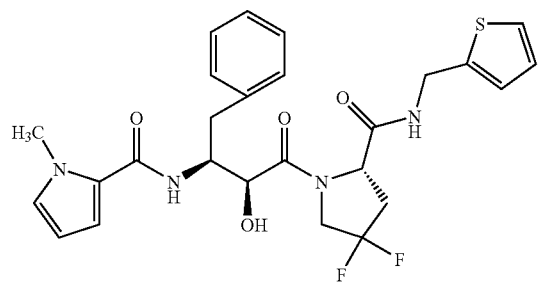
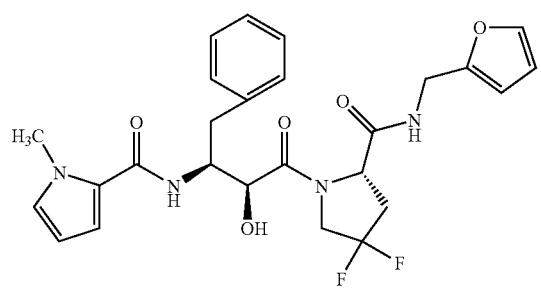
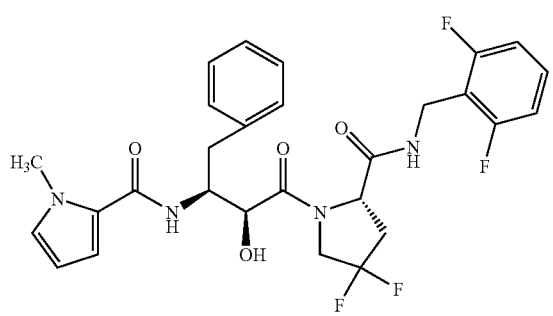

TABLE 2-continued
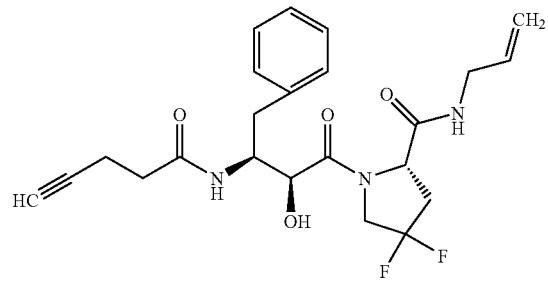
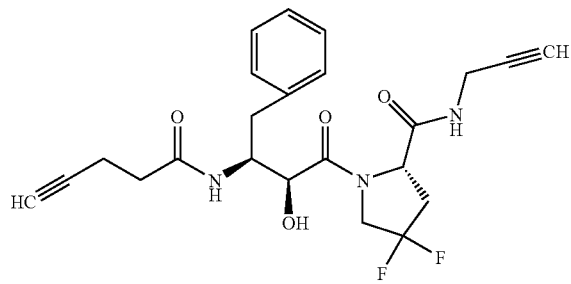
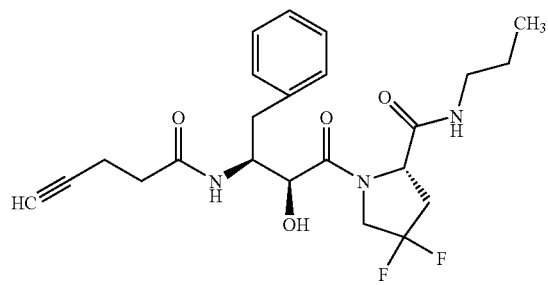
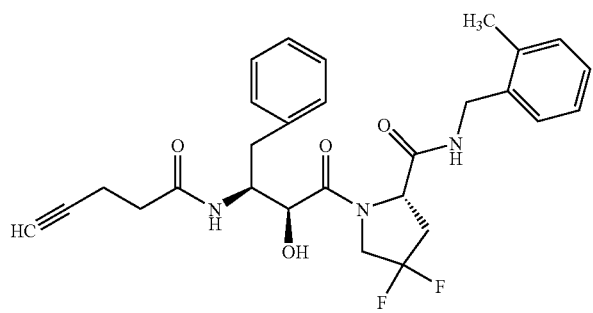
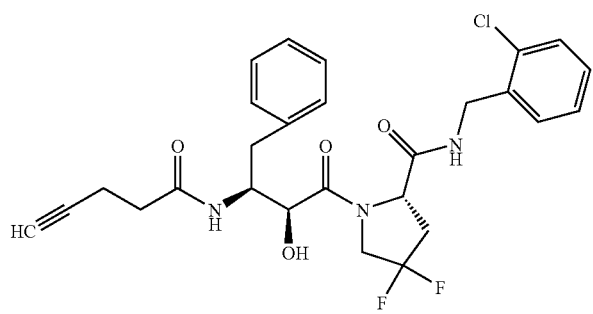

TABLE 2-continued
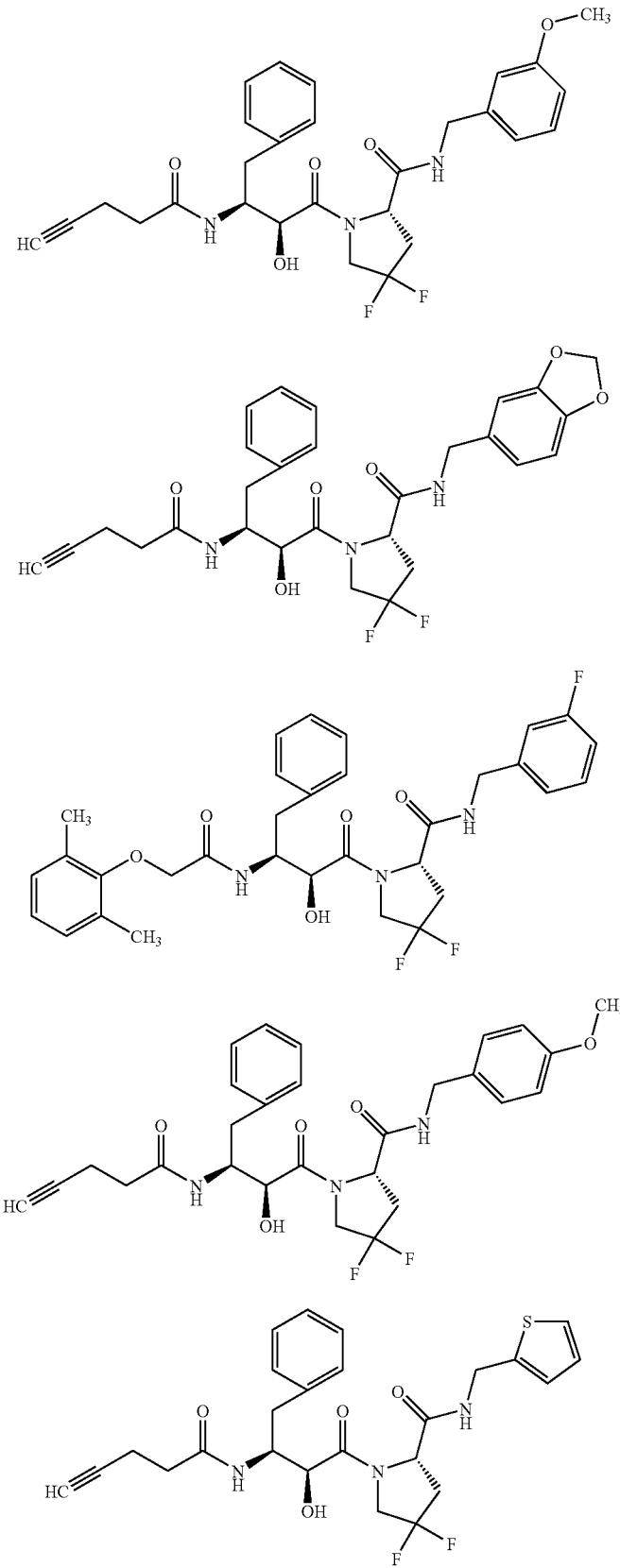

TABLE 2-continued
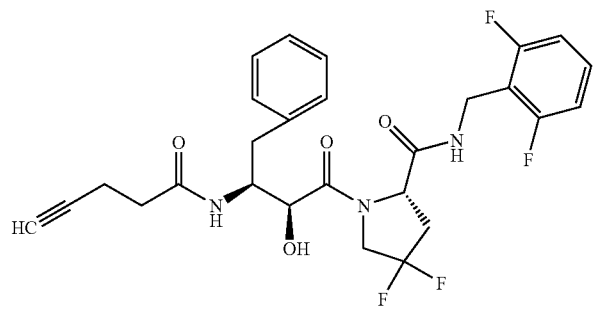
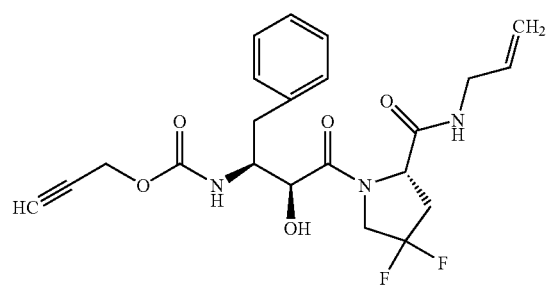
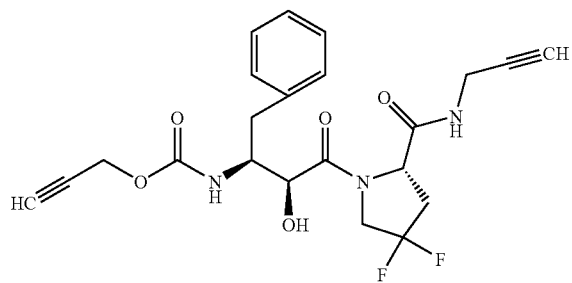
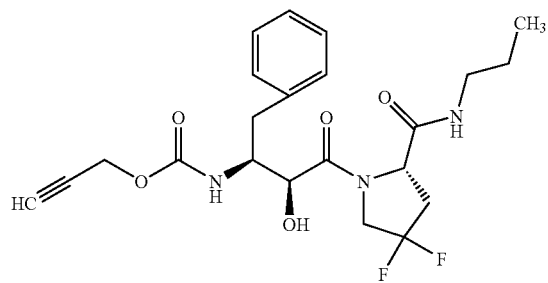
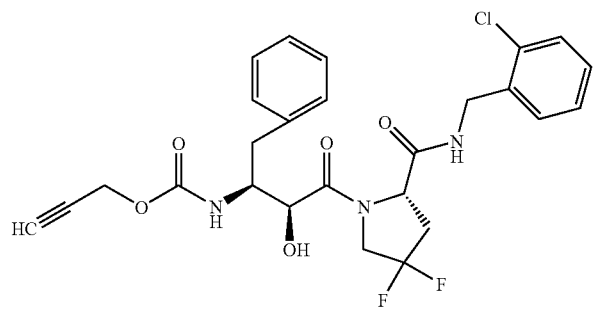

TABLE 2-continued
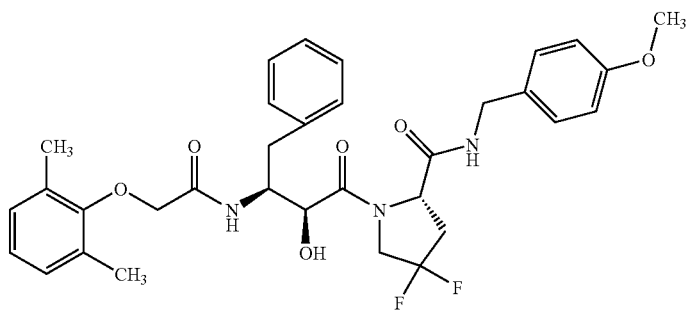
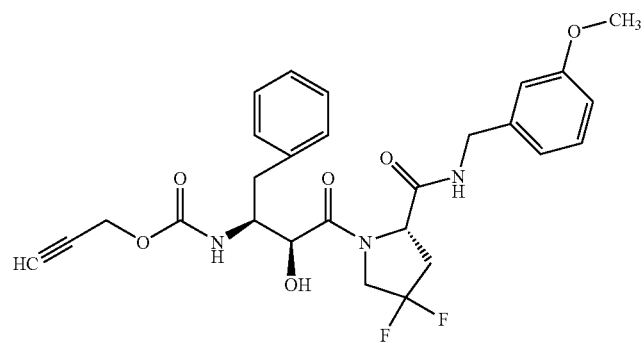
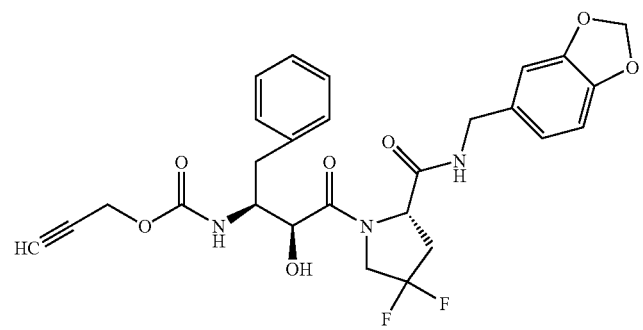
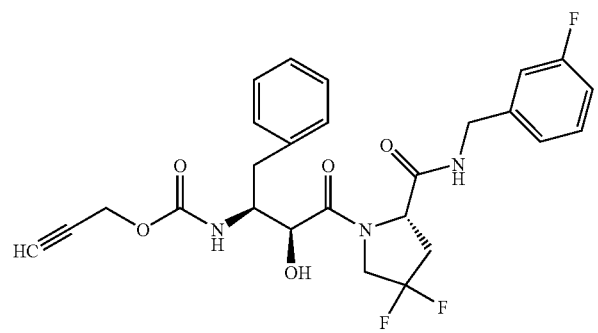

TABLE 2-continued
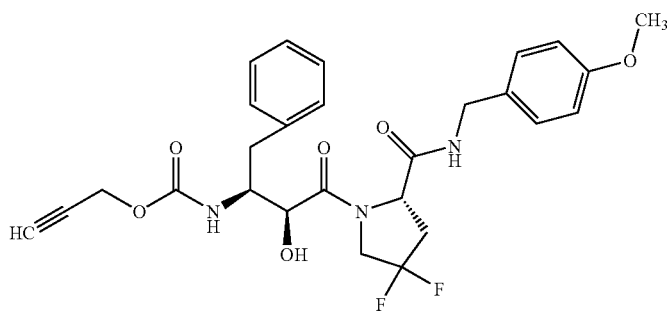
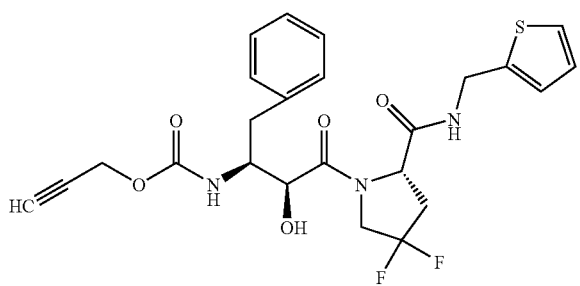
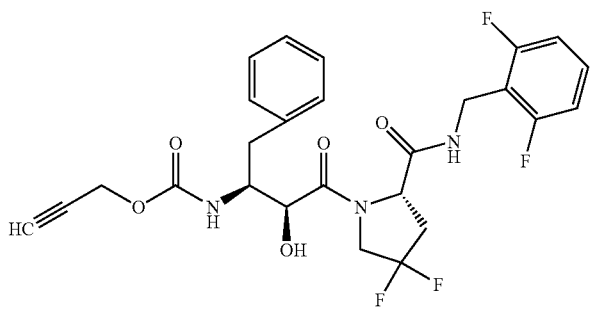
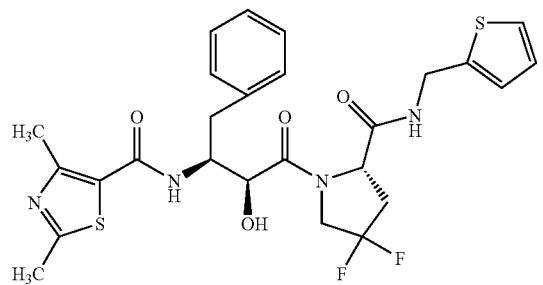
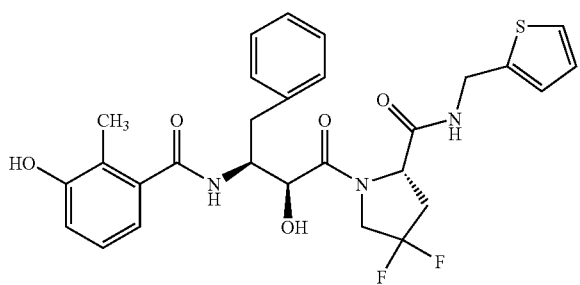

TABLE 2-continued
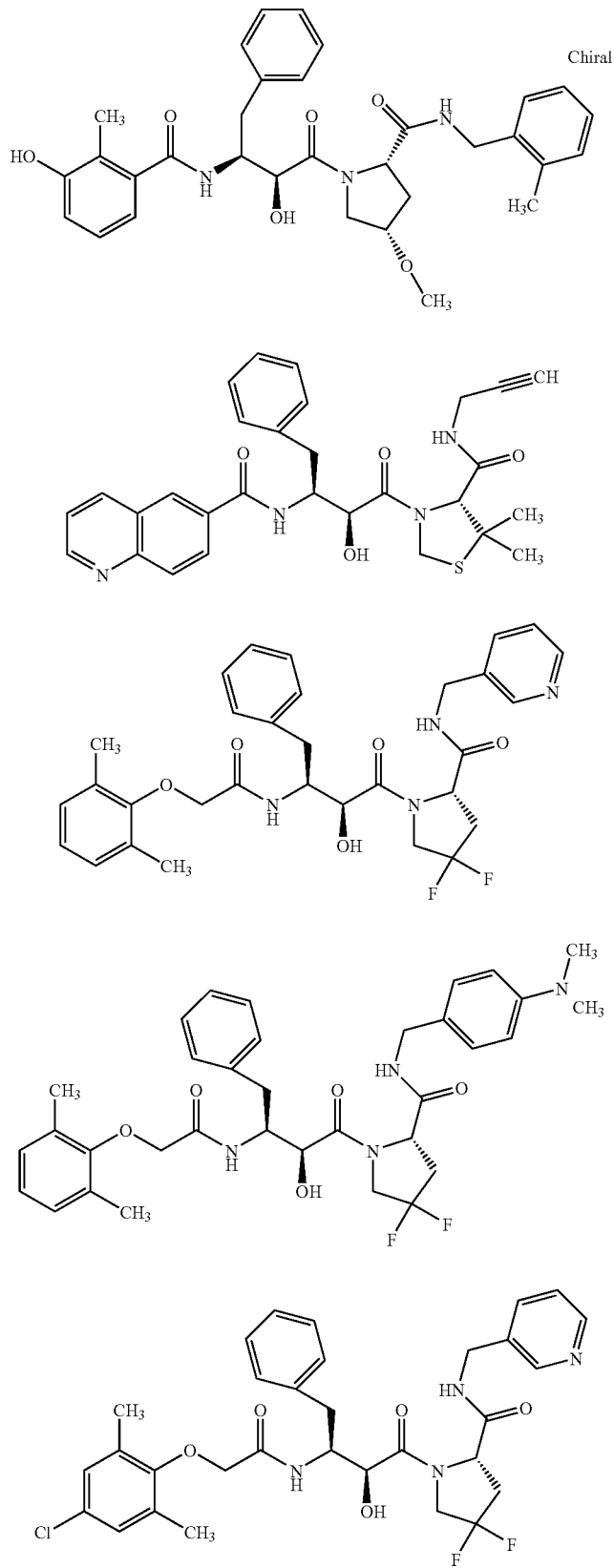

TABLE 2-continued
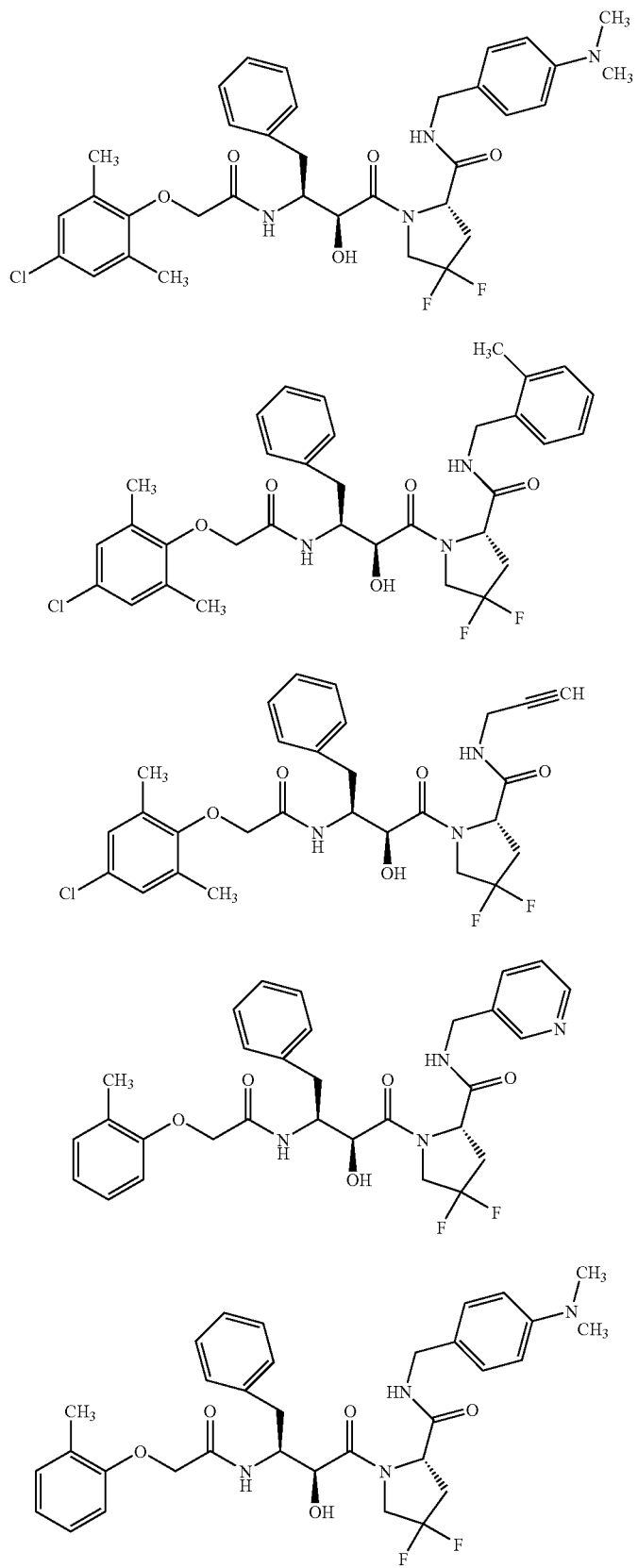

TABLE 2-continued
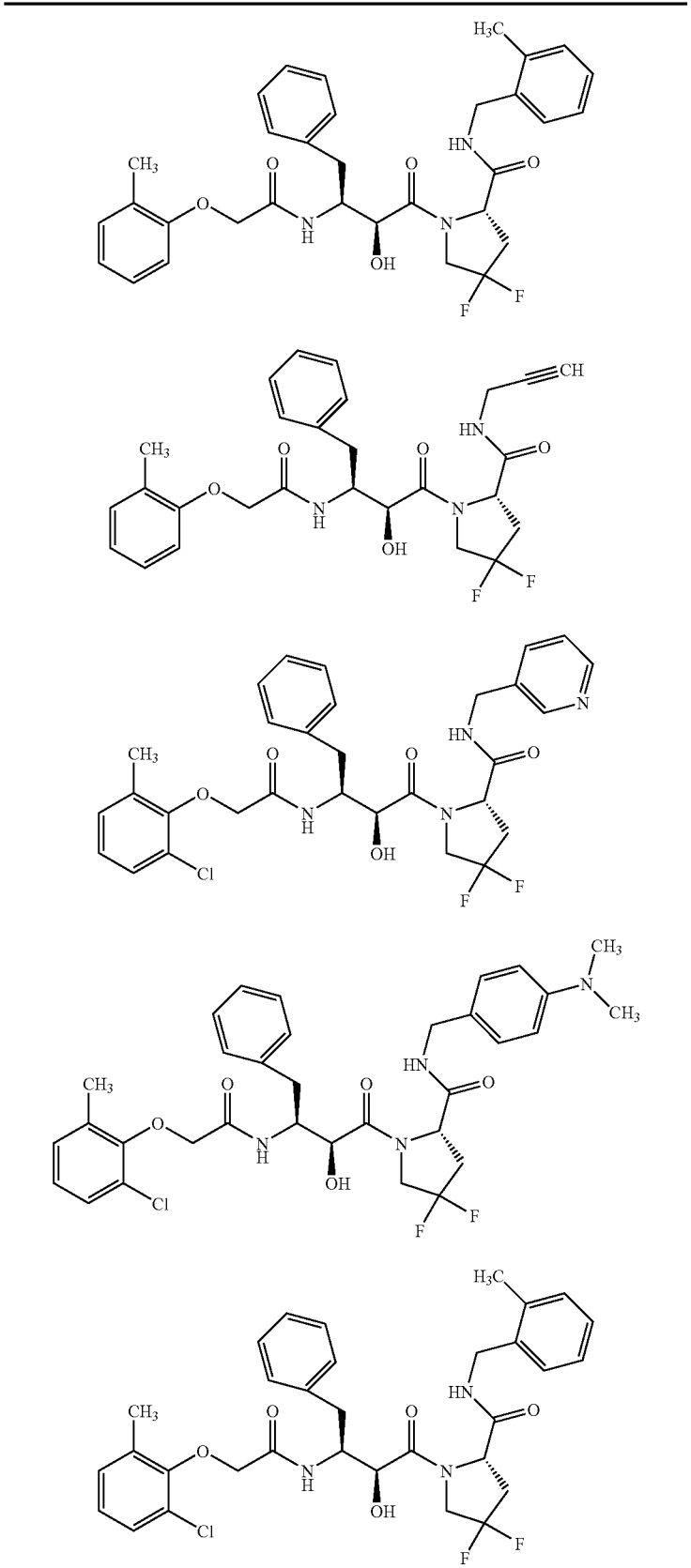

TABLE 2-continued
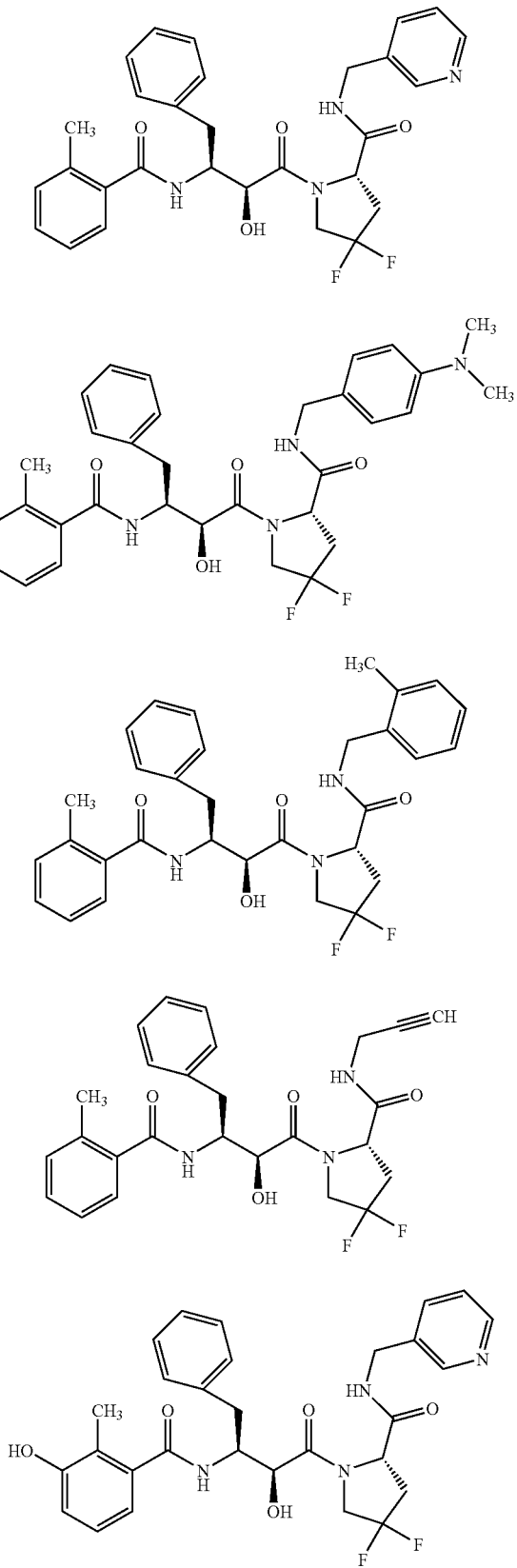

TABLE 2-continued
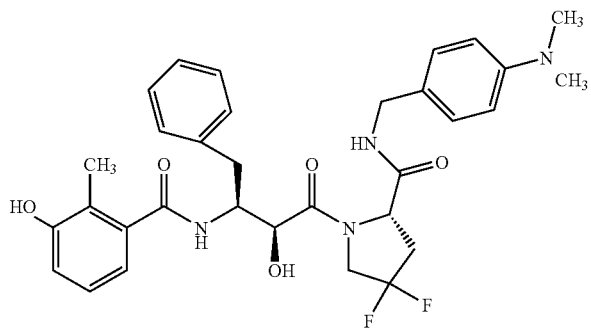
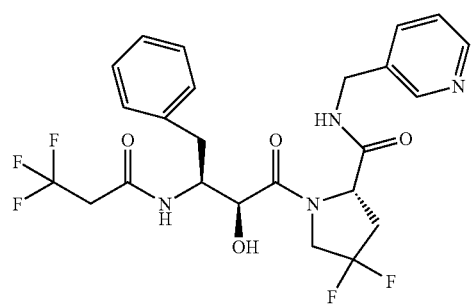
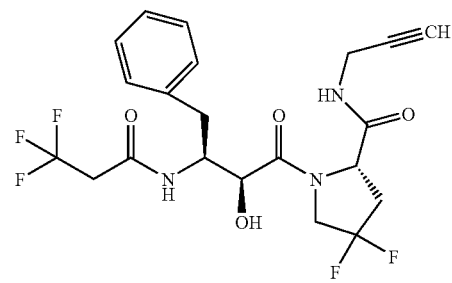
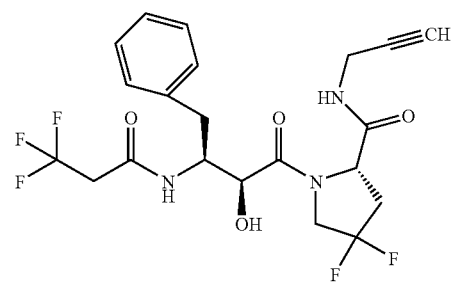
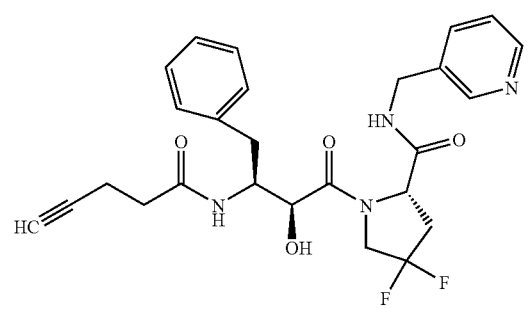

TABLE 2-continued
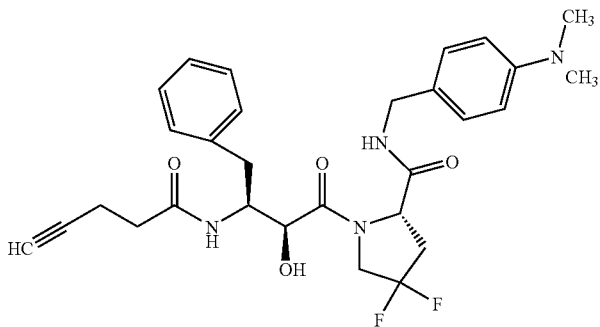
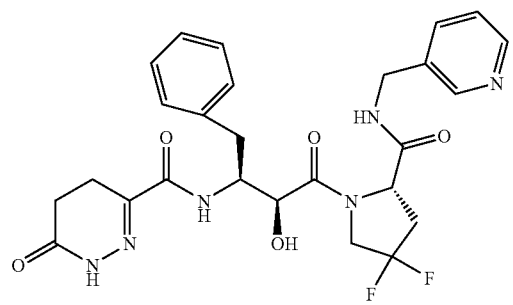
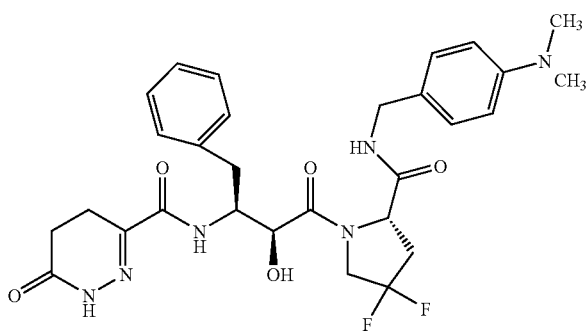
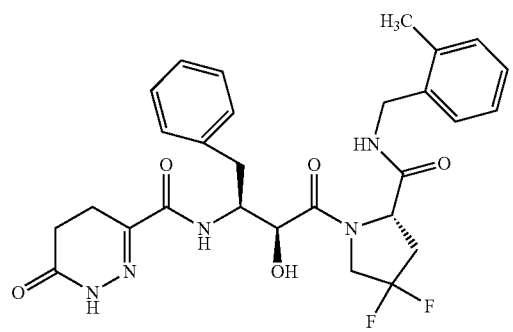
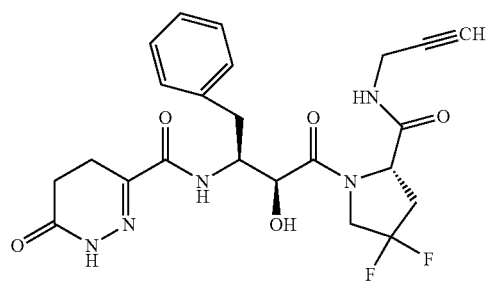

TABLE 2-continued
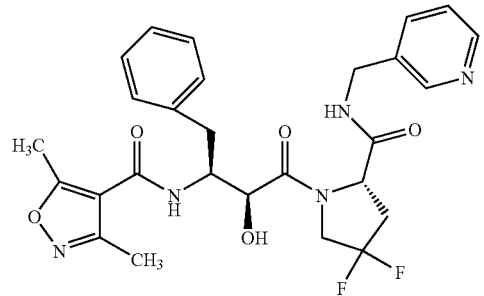
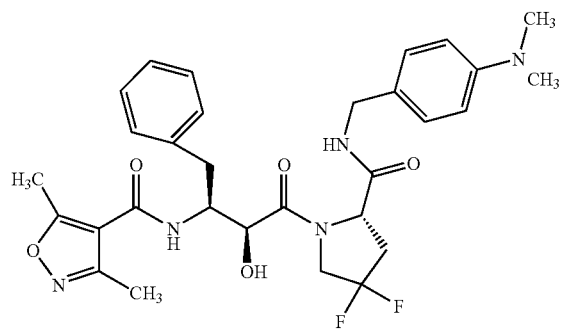
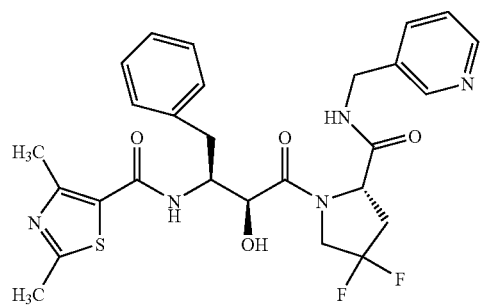
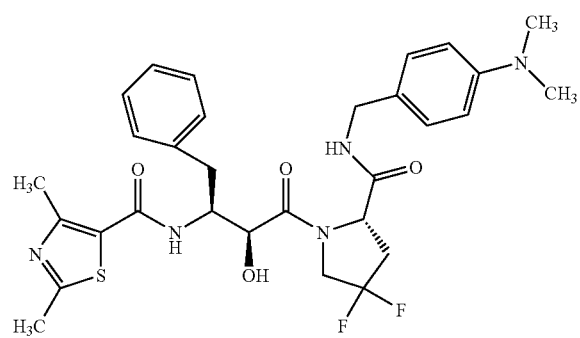
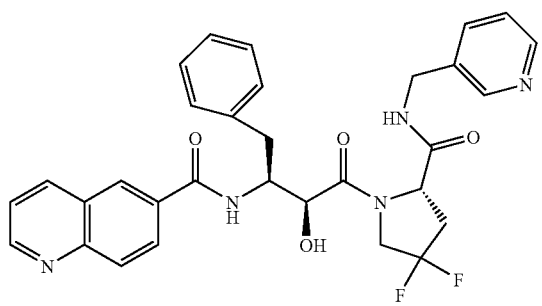

TABLE 2-continued
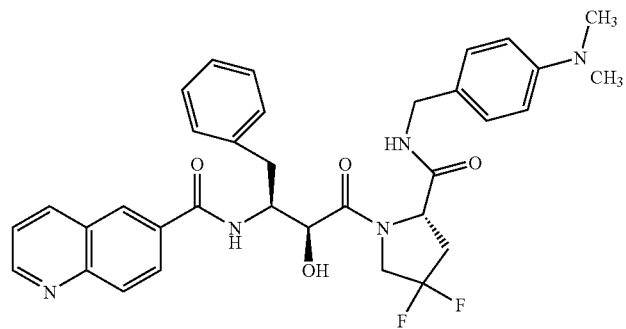
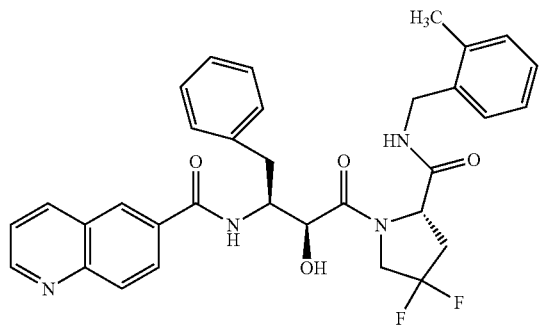
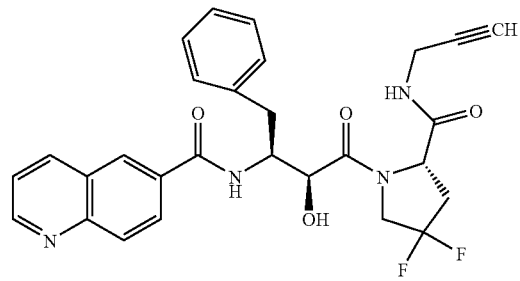
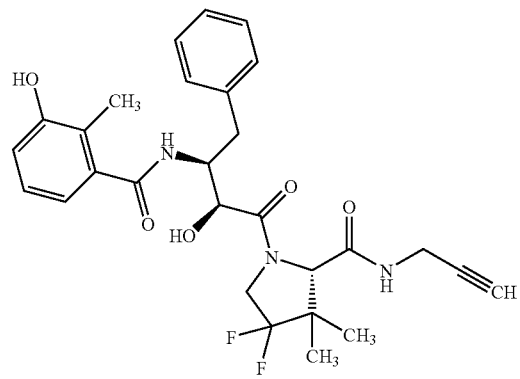

TABLE 2-continued
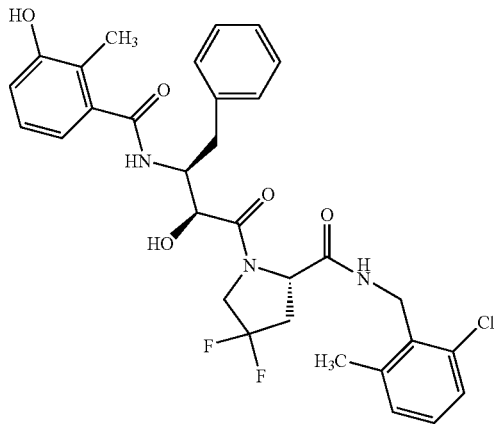
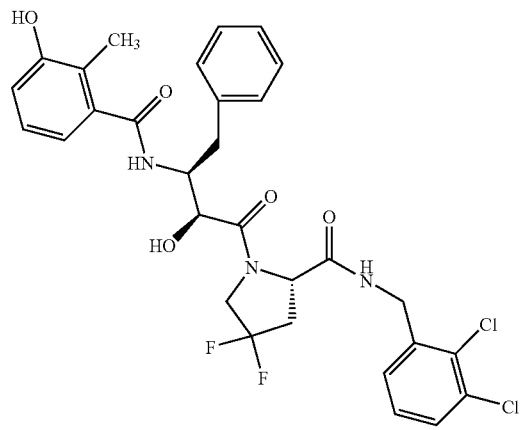
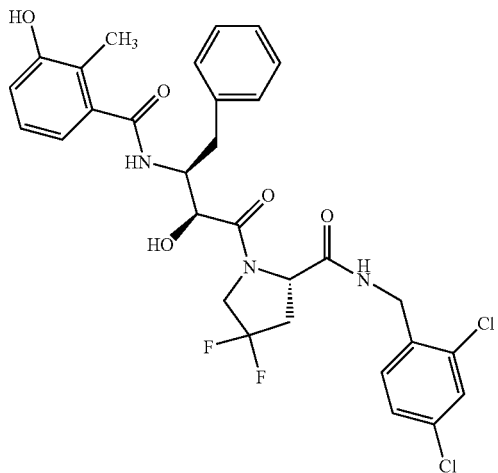

TABLE 2-continued
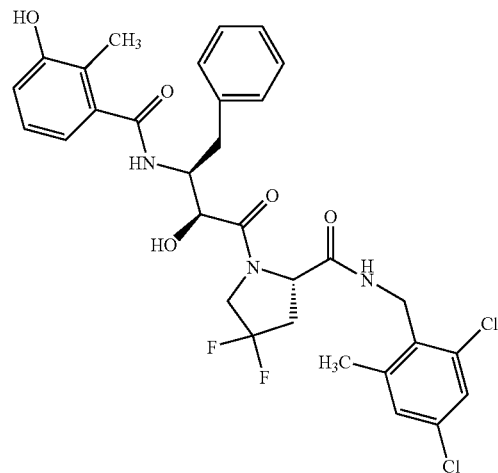
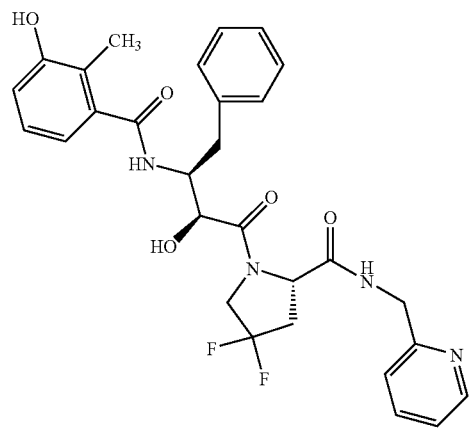
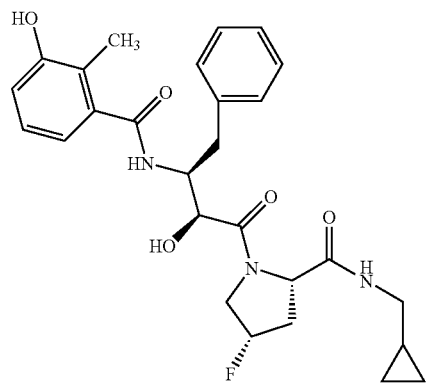

TABLE 2-continued
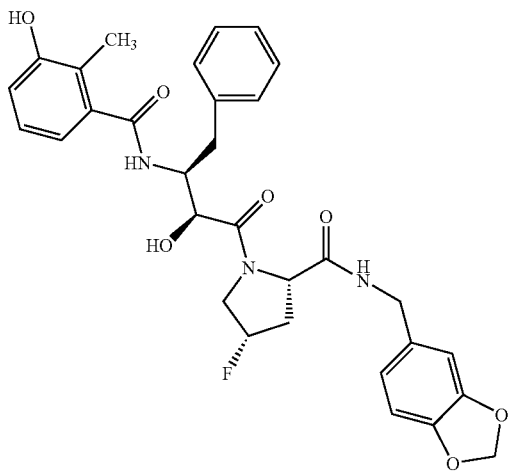
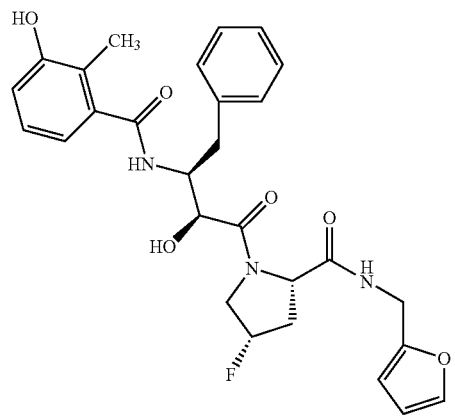
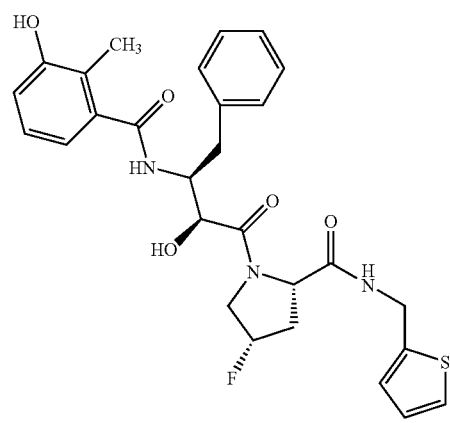

TABLE 2-continued
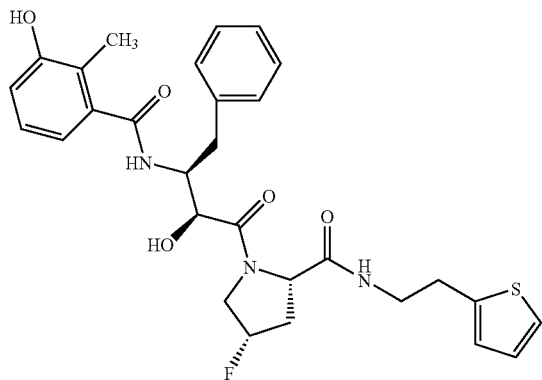
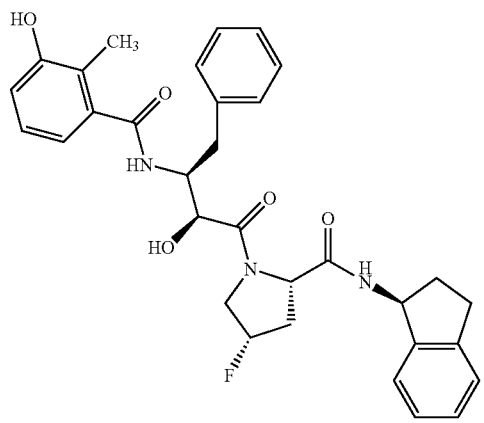
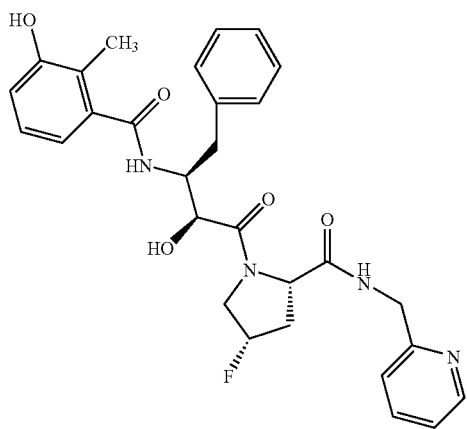

TABLE 2-continued
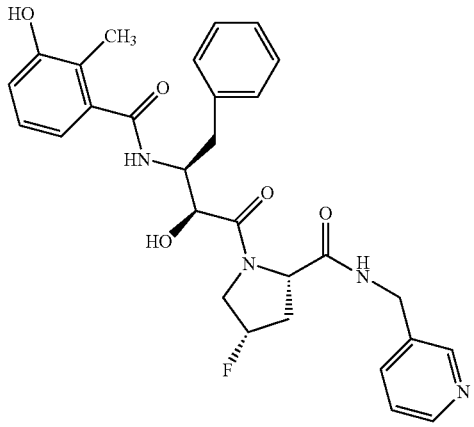
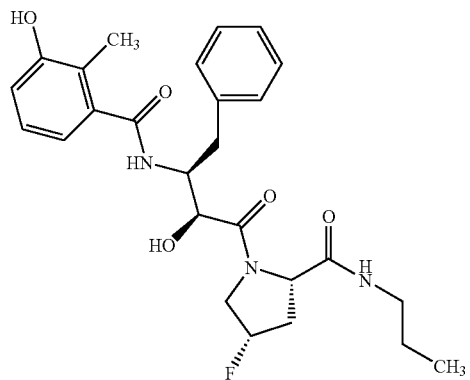
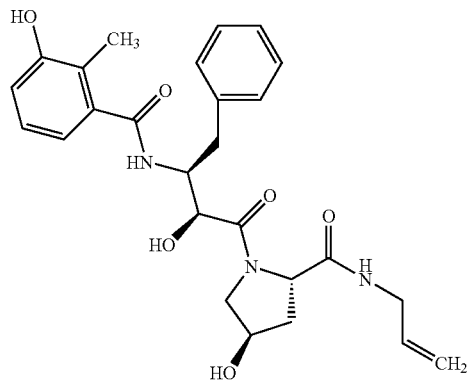
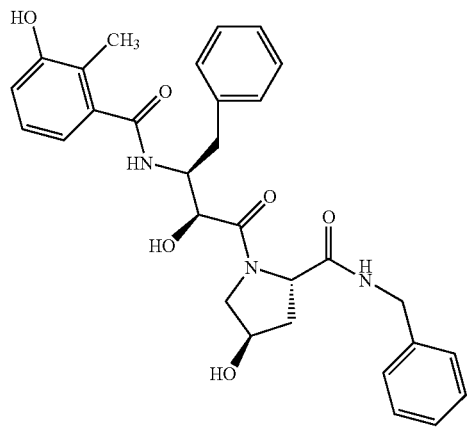

TABLE 2-continued
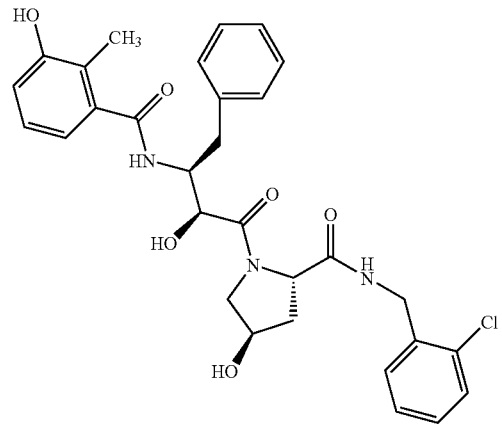
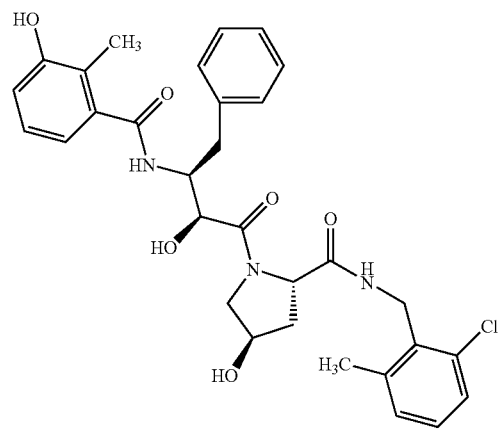
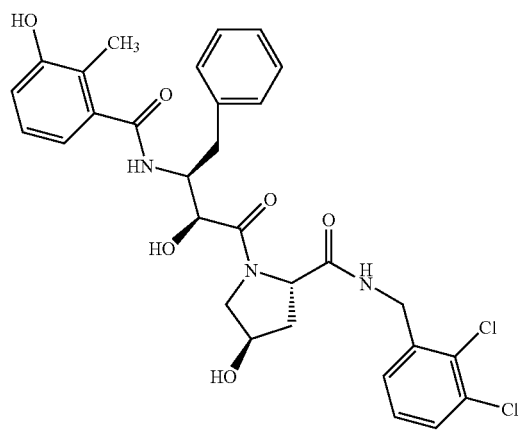

TABLE 2-continued
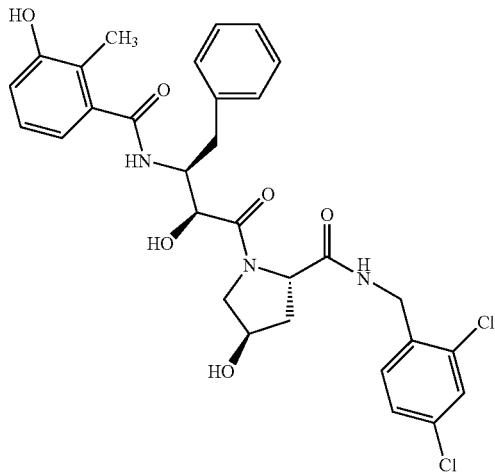
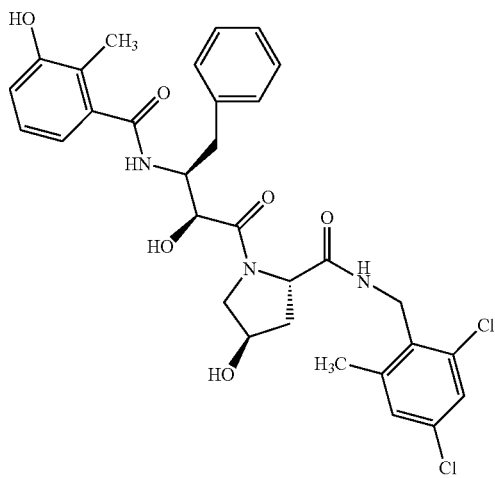
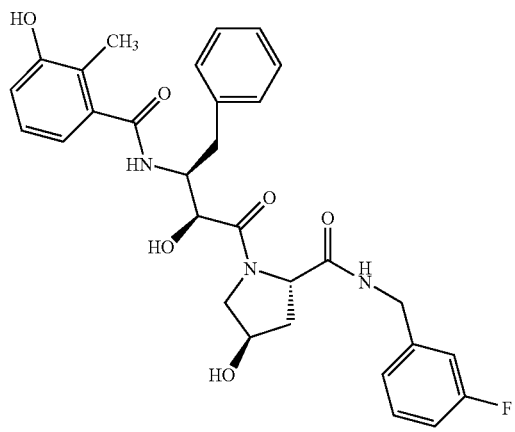

TABLE 2-continued
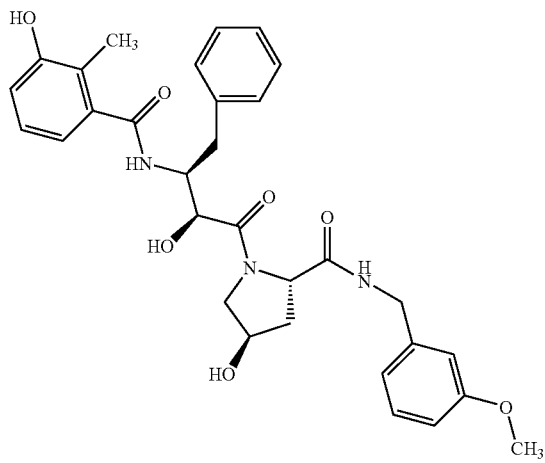
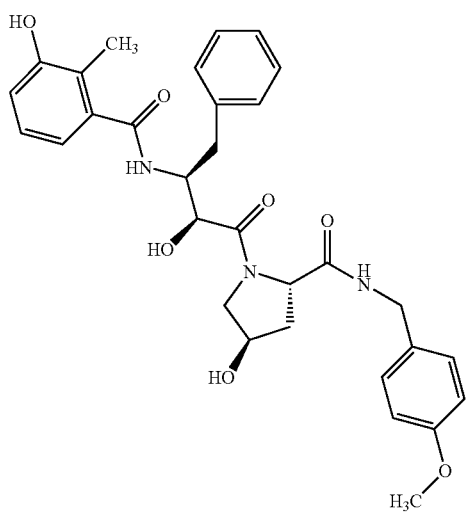
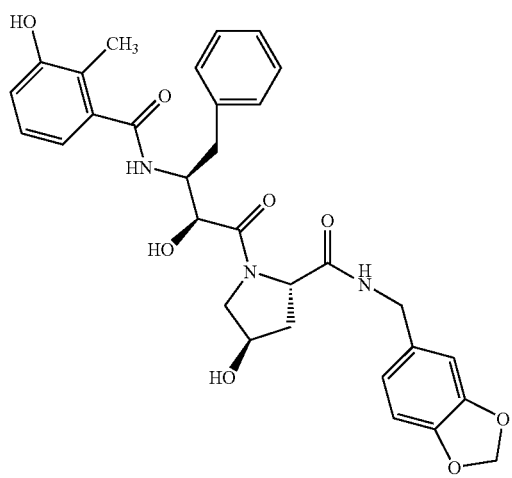

TABLE 2-continued
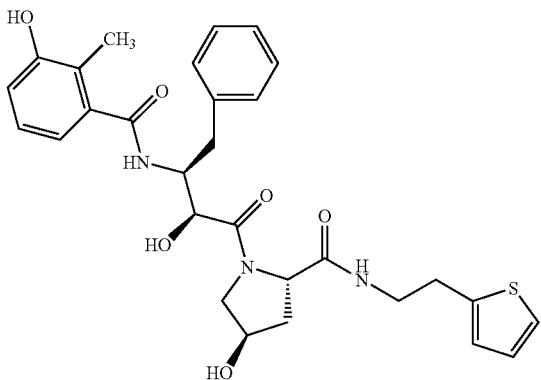
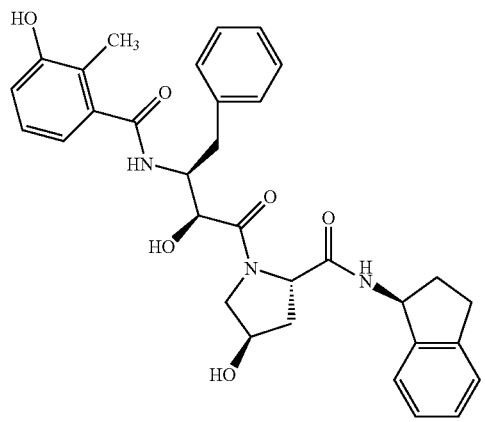
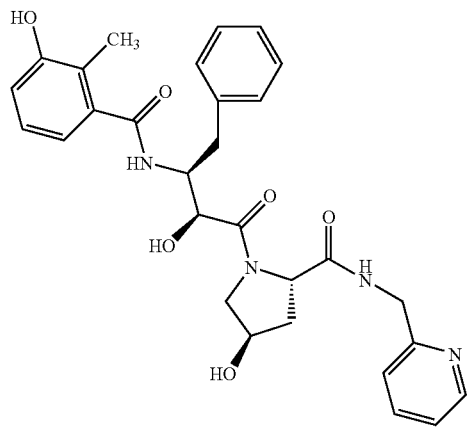

TABLE 2-continued
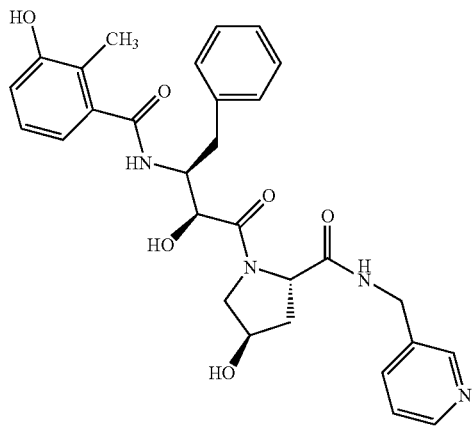
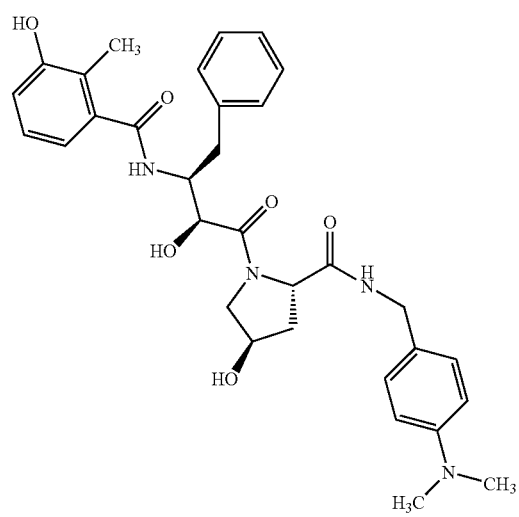
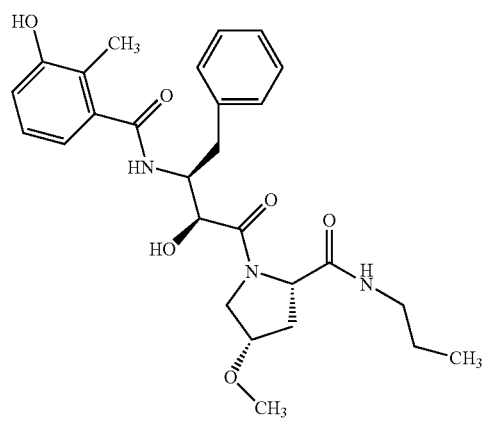

TABLE 2-continued
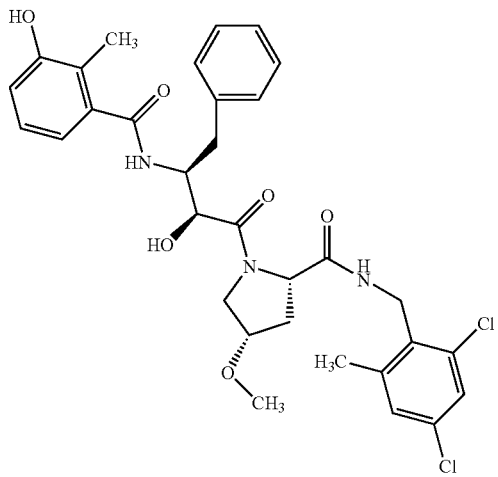
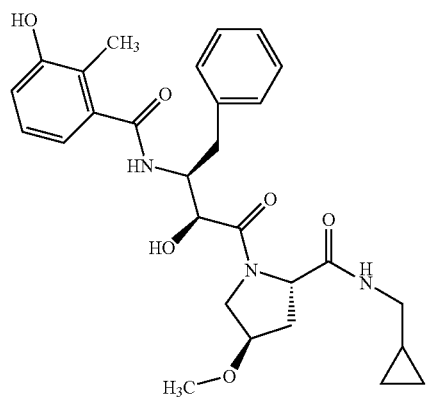
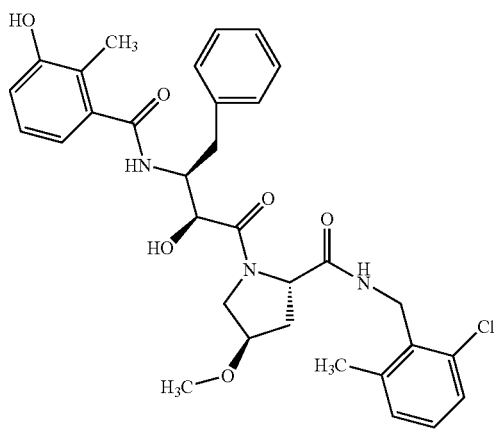

TABLE 2-continued
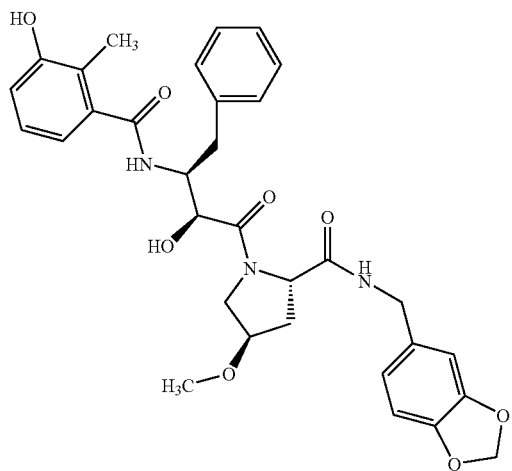
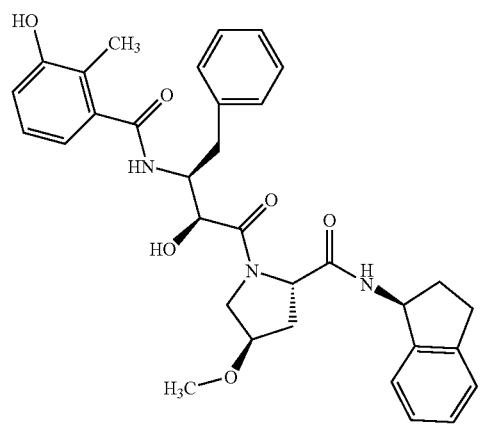
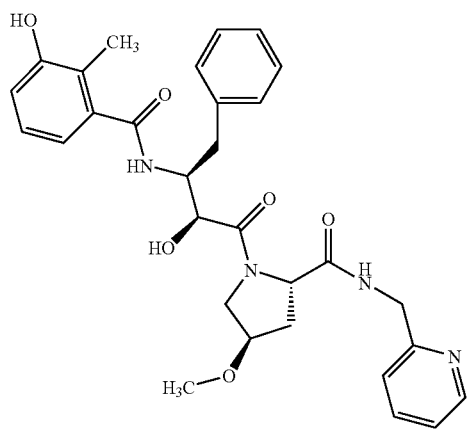

TABLE 2-continued
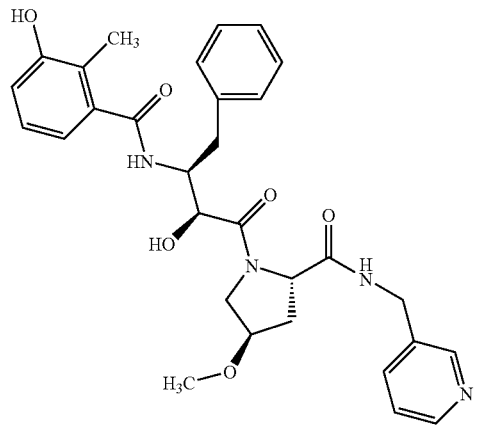
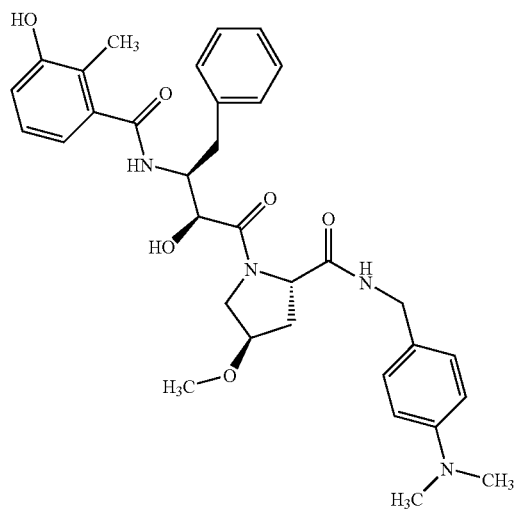
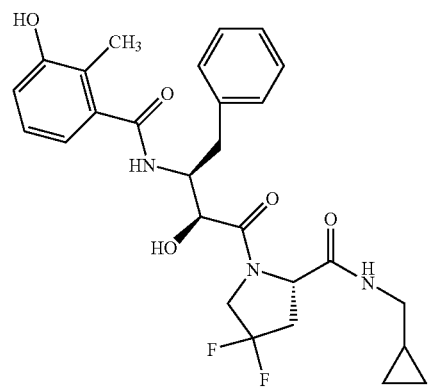

TABLE 2-continued
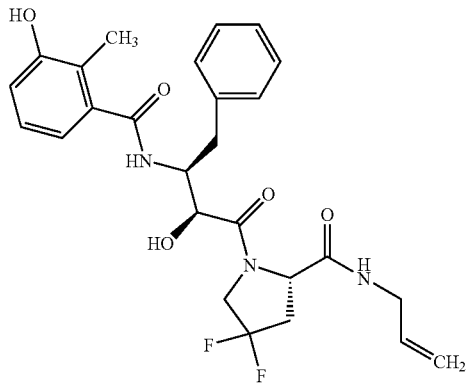
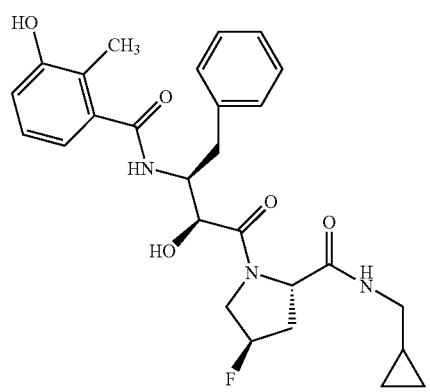
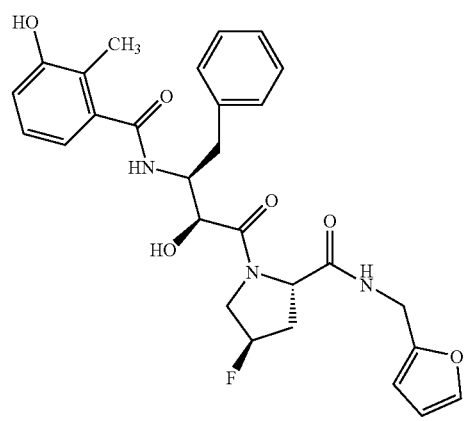
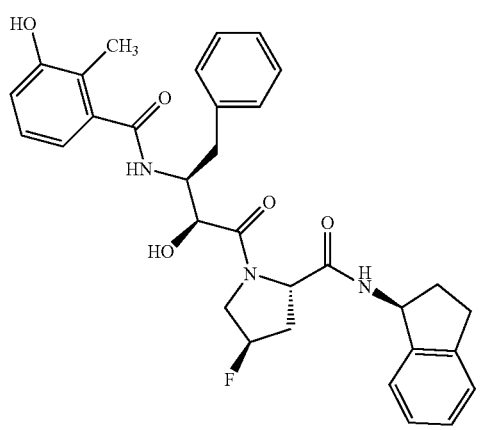

TABLE 2-continued
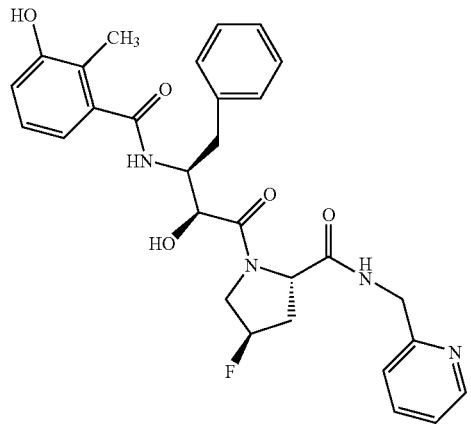
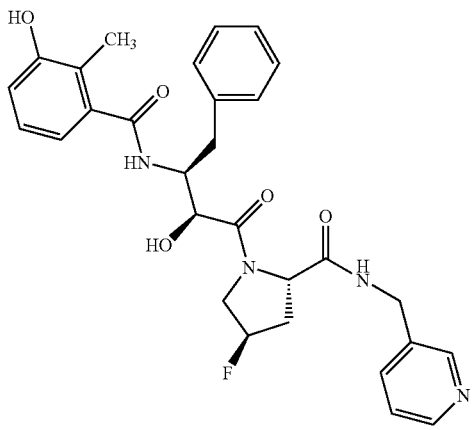
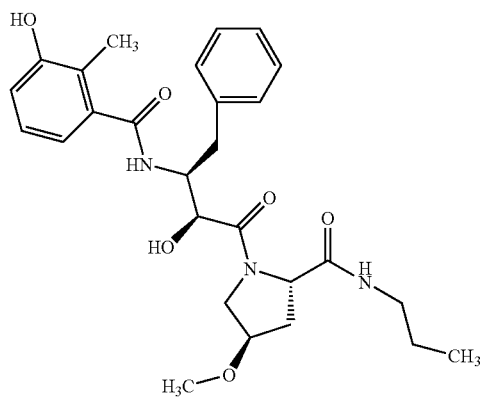

TABLE 2-continued
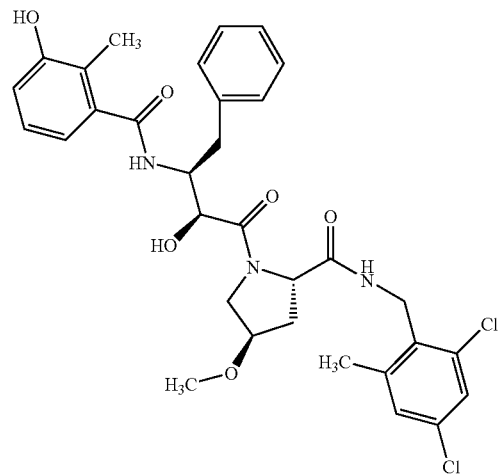
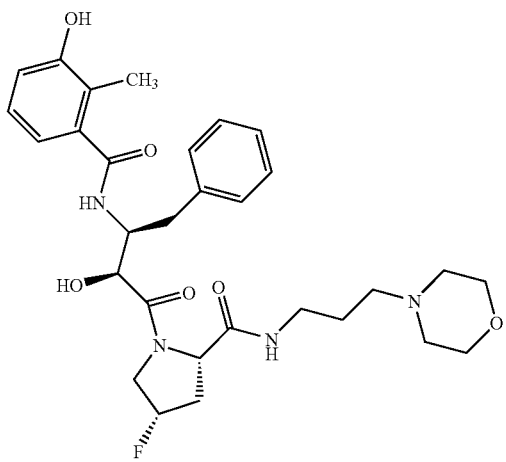
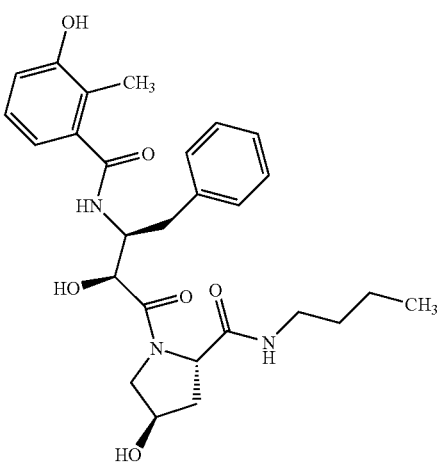

TABLE 2-continued
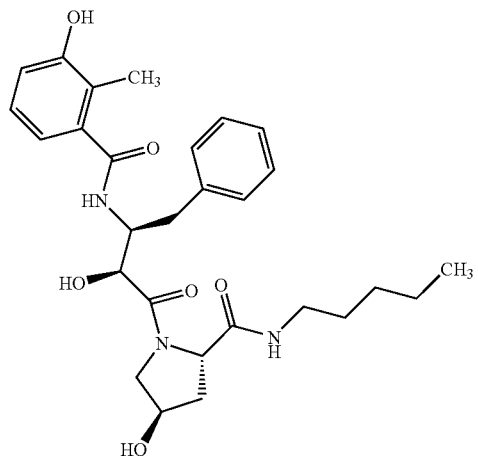
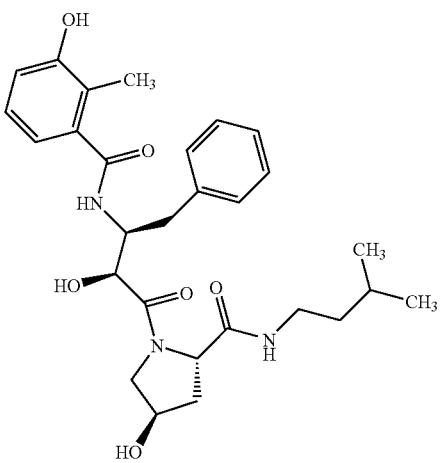
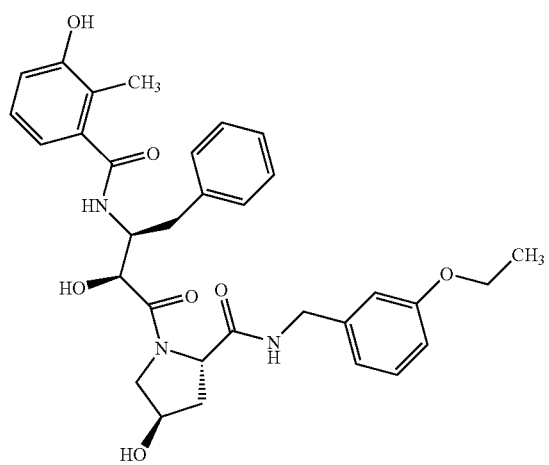

TABLE 2-continued
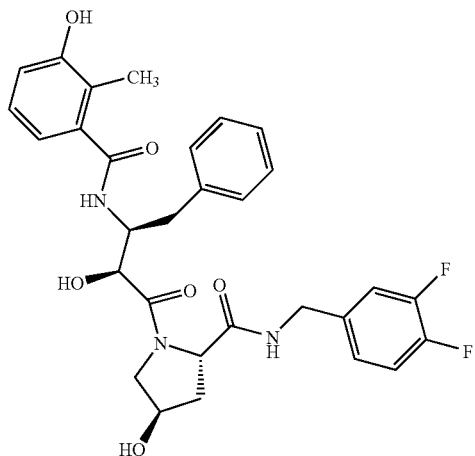
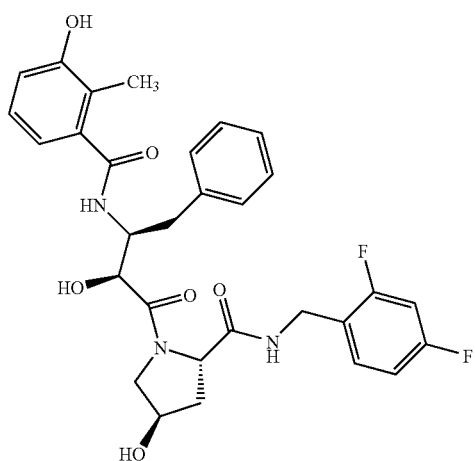
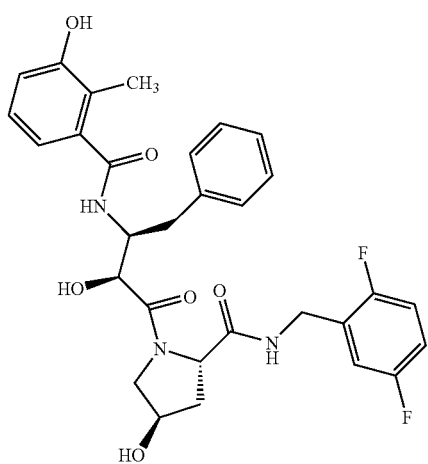

TABLE 2-continued
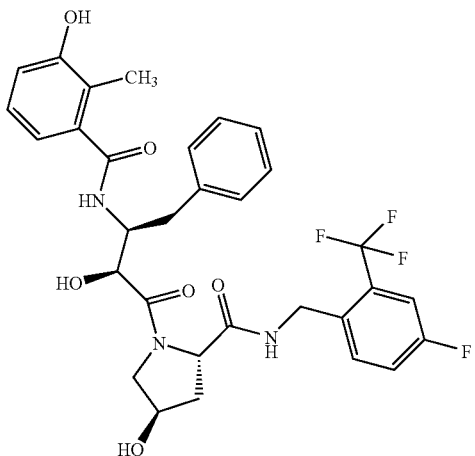
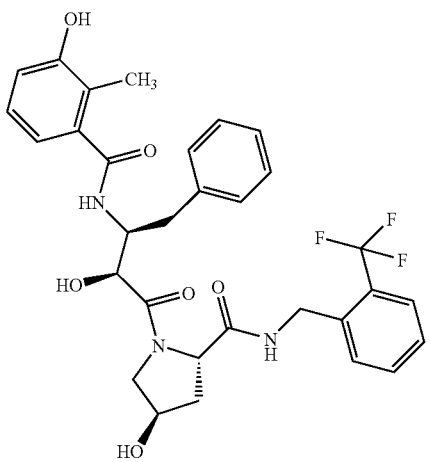
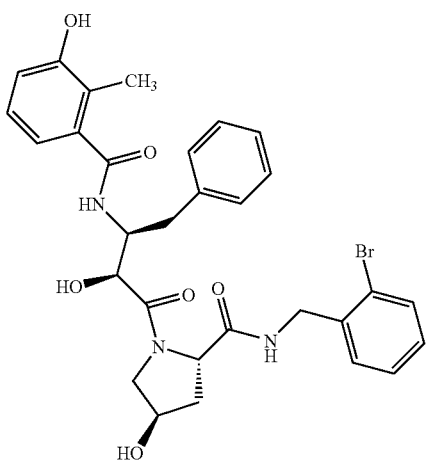

TABLE 2-continued
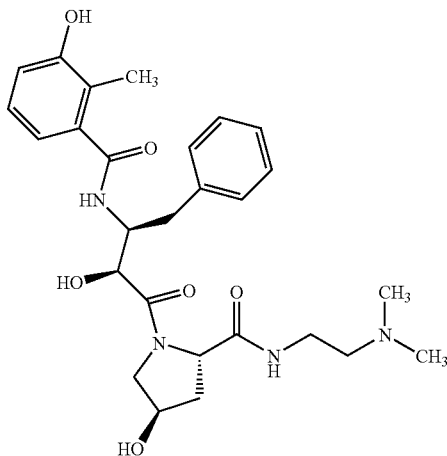
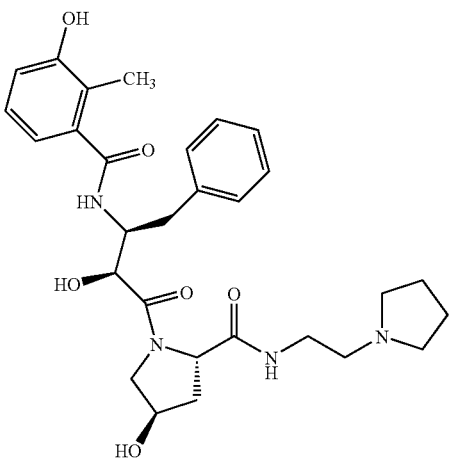
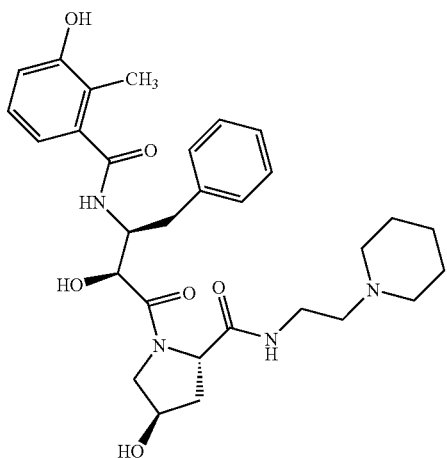

TABLE 2-continued
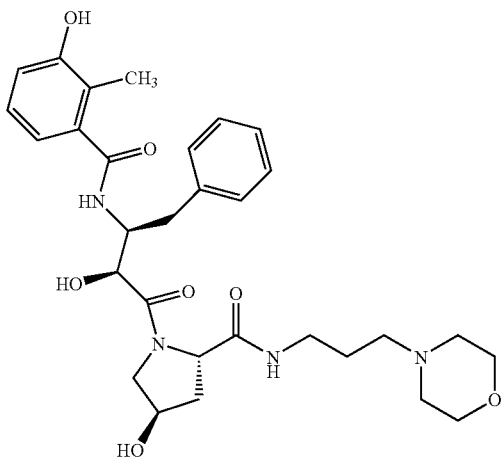
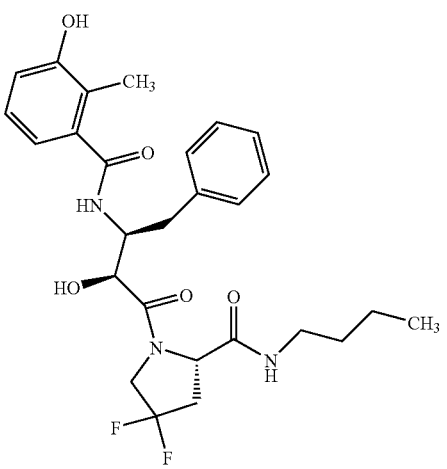
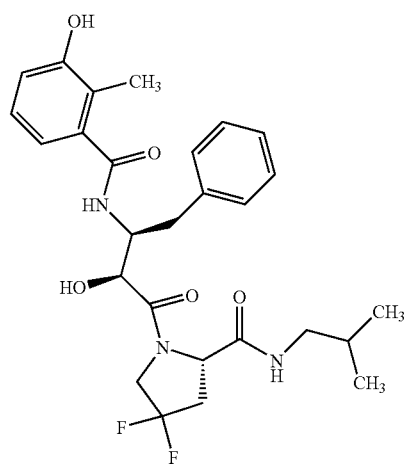

TABLE 2-continued
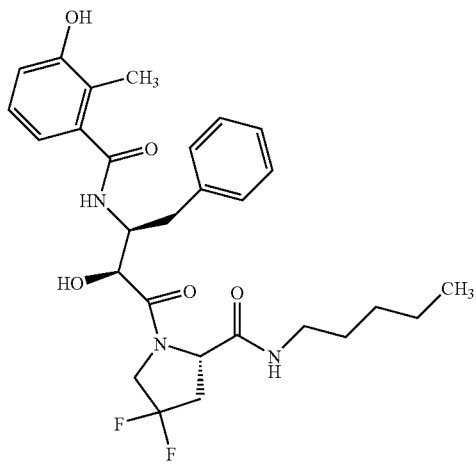
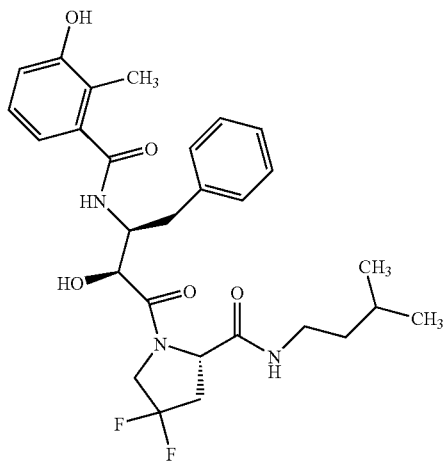
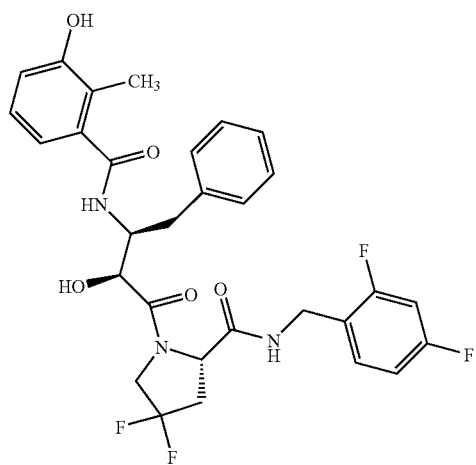

TABLE 2-continued
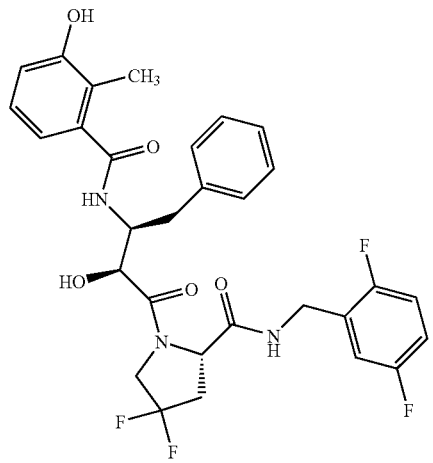
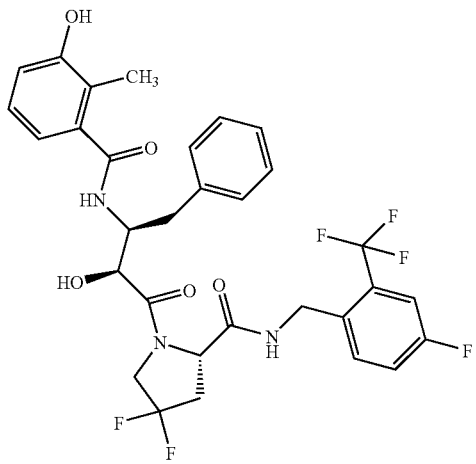
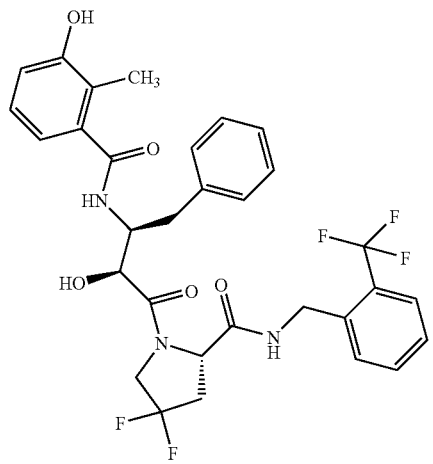

TABLE 2-continued
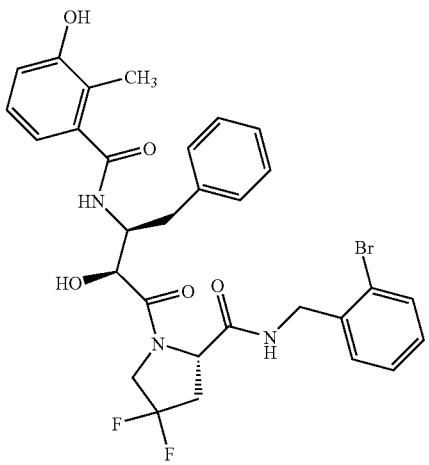
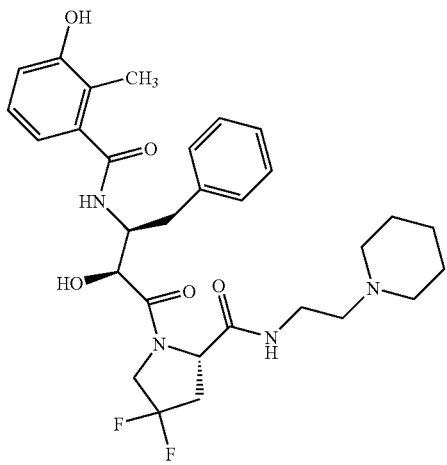
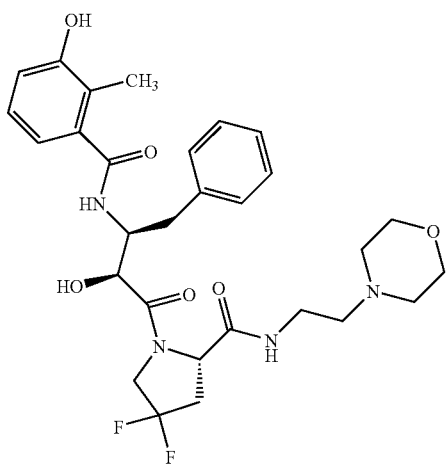

TABLE 2-continued
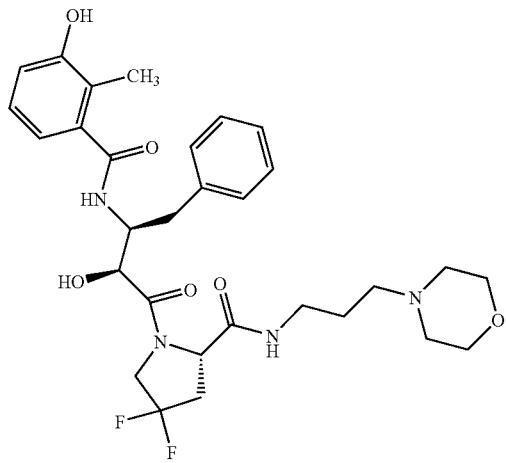
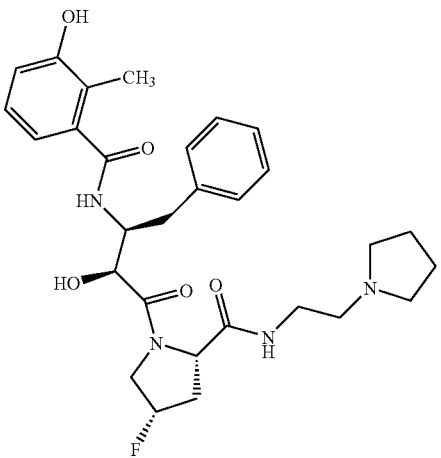
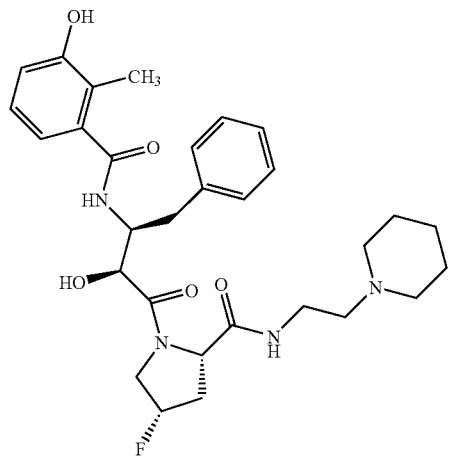

TABLE 2-continued
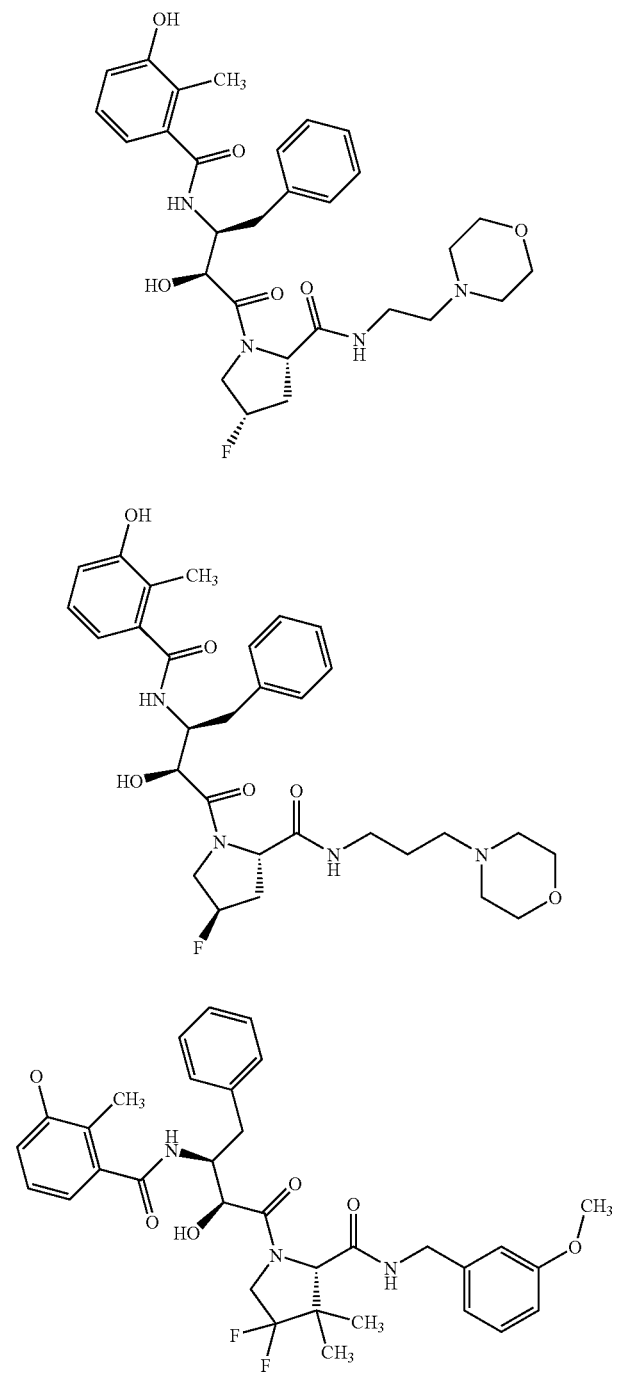

TABLE 2-continued
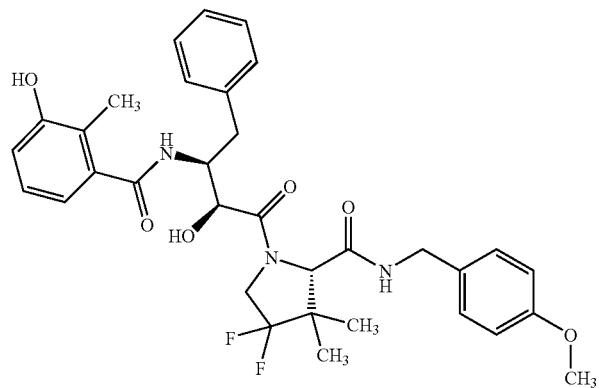
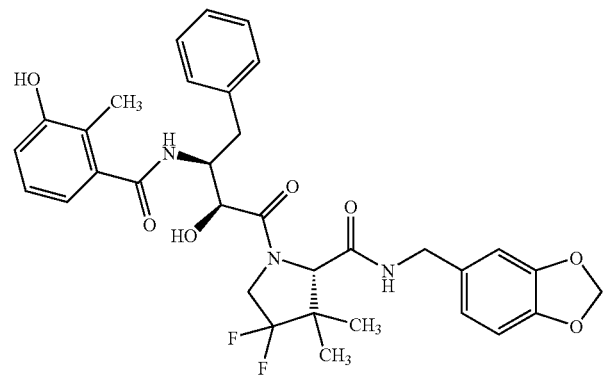
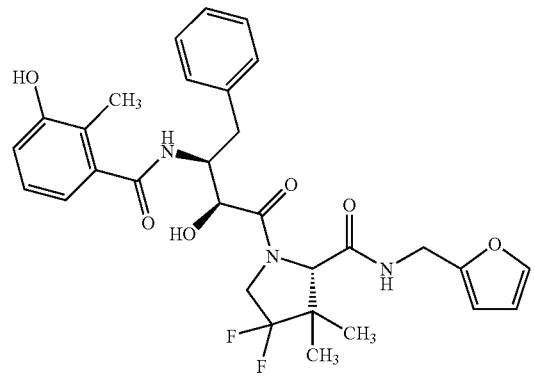
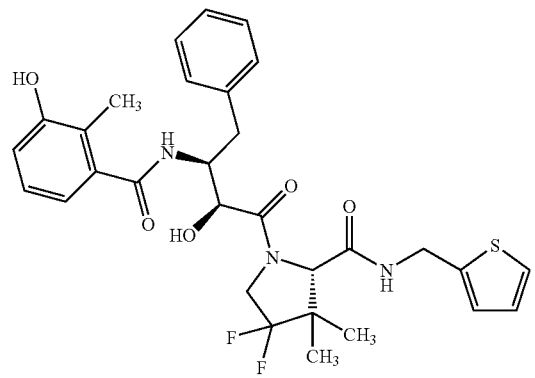

TABLE 2-continued
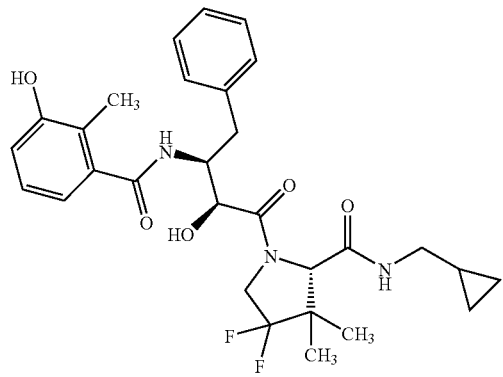
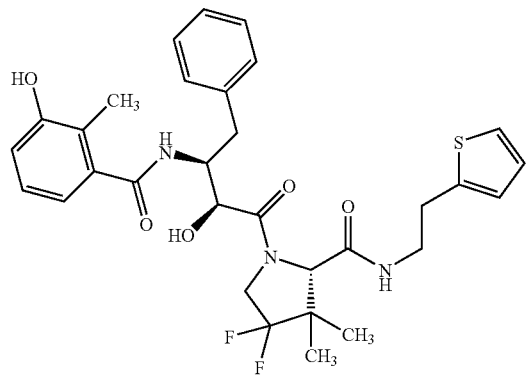
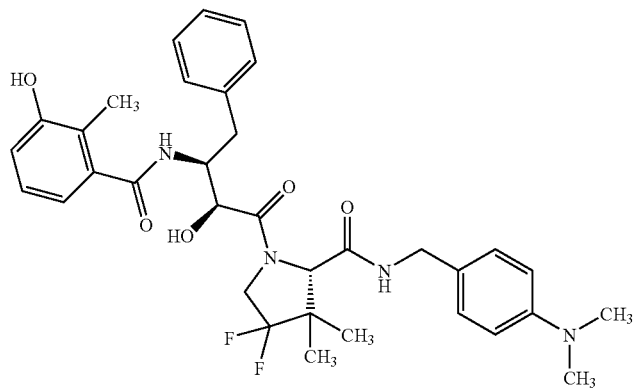
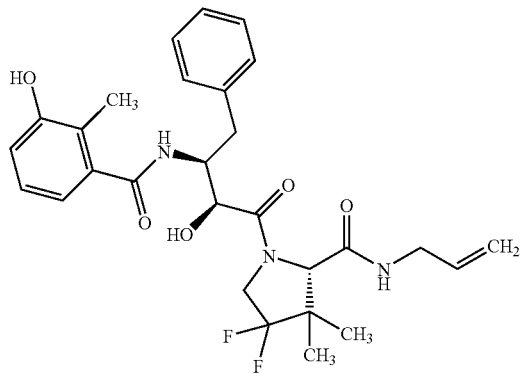

TABLE 2-continued
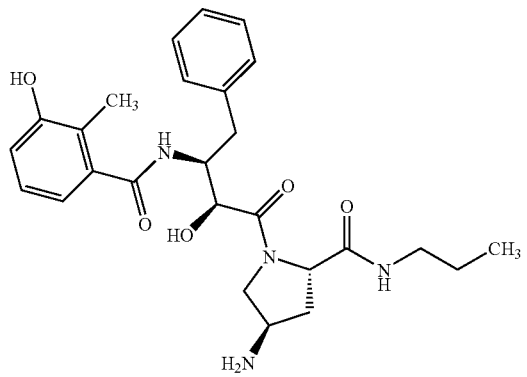
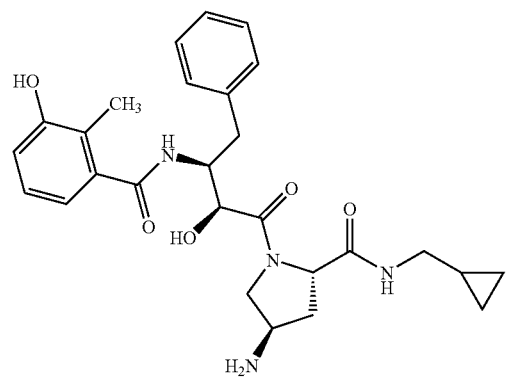
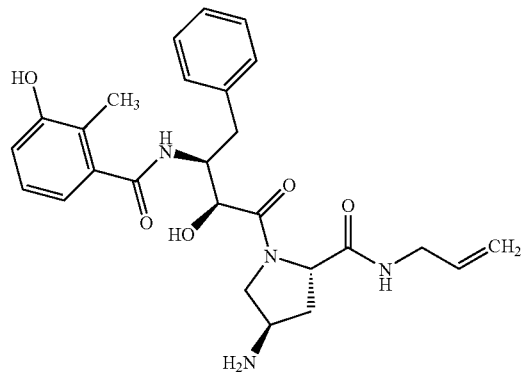
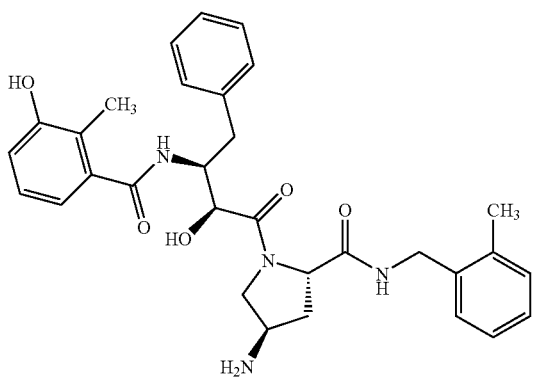

TABLE 2-continued
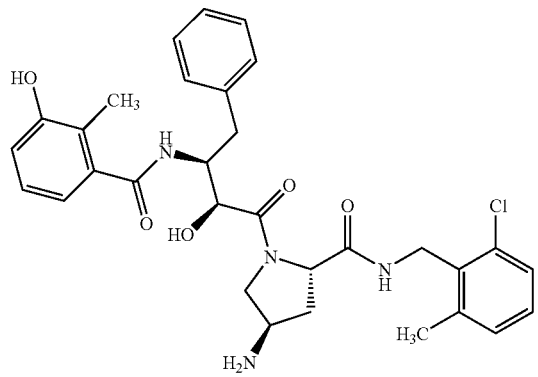
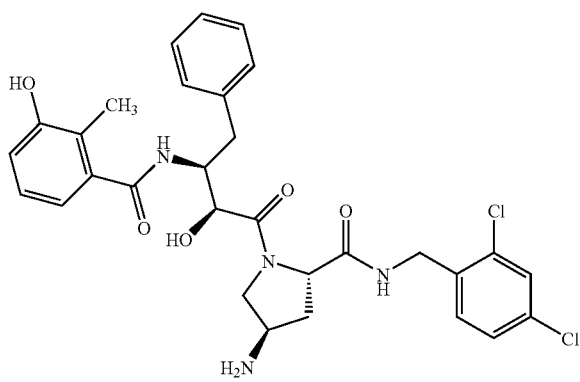
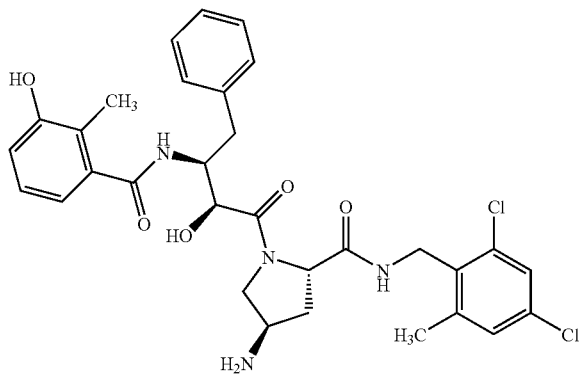
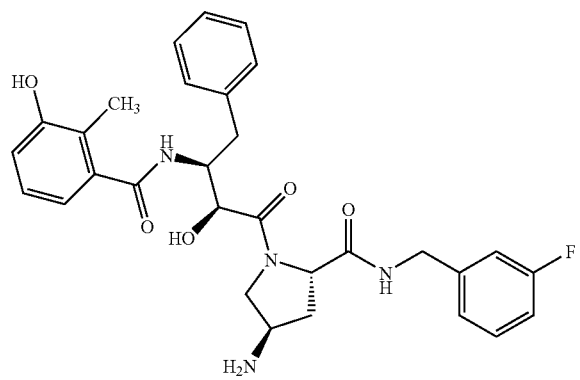

TABLE 2-continued
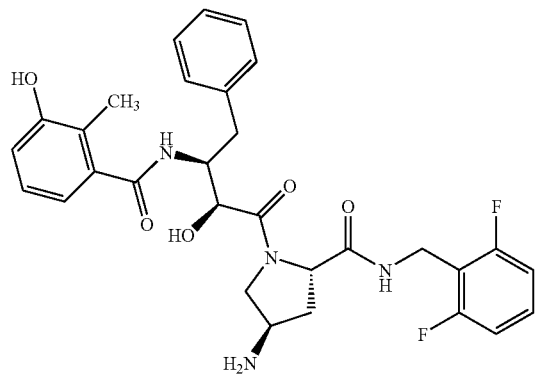
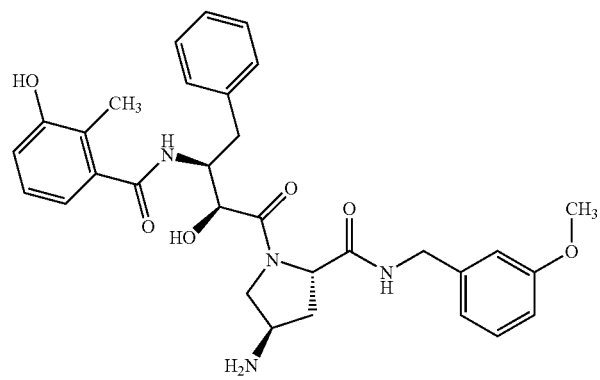
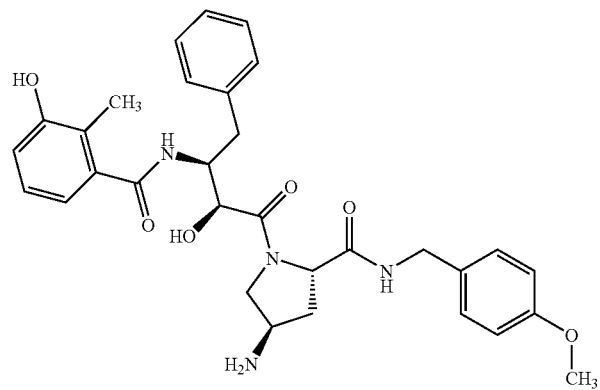
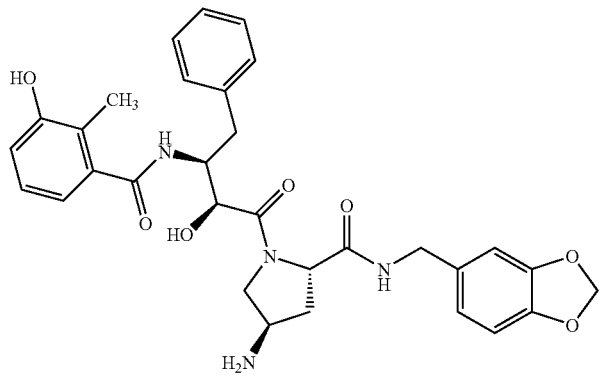

TABLE 2-continued
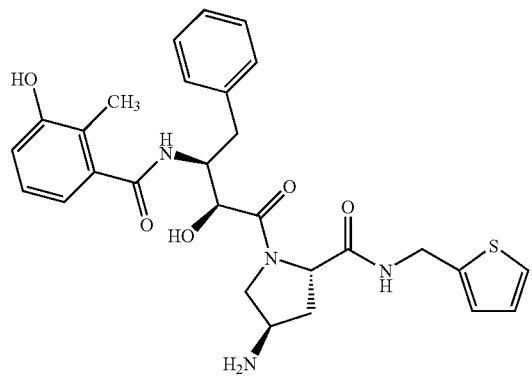
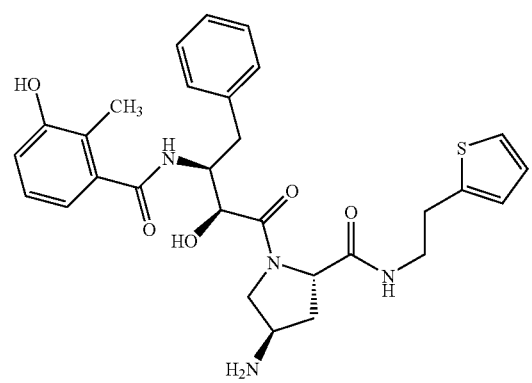
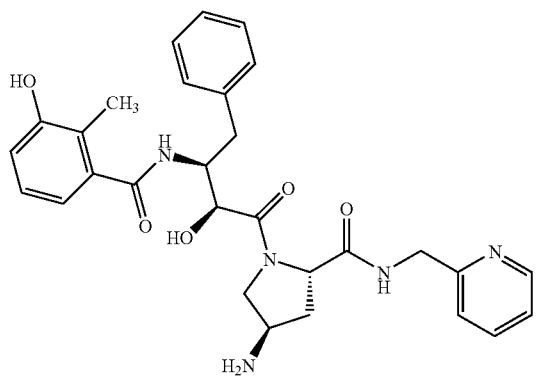
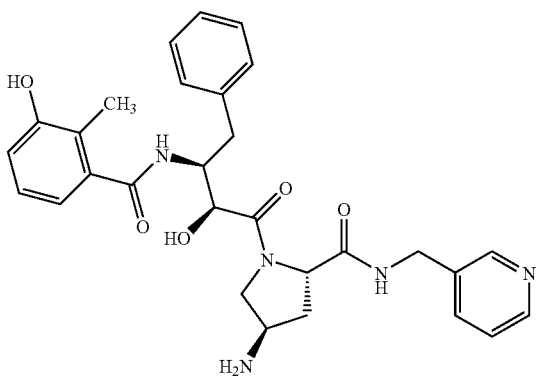

TABLE 2-continued
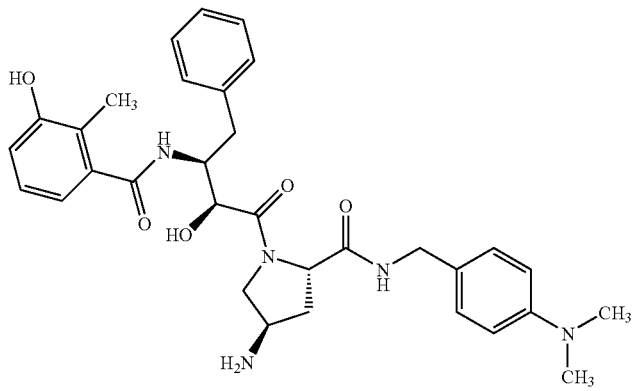
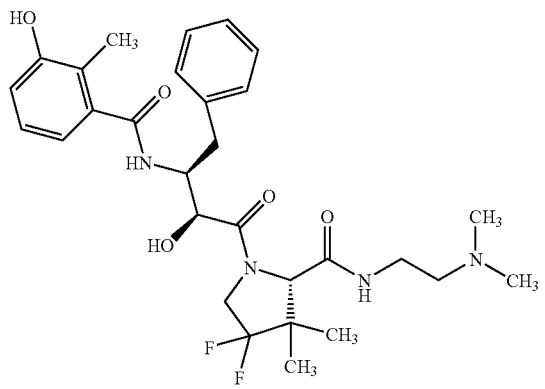
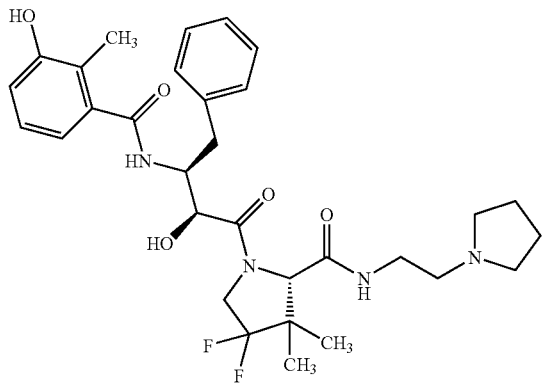
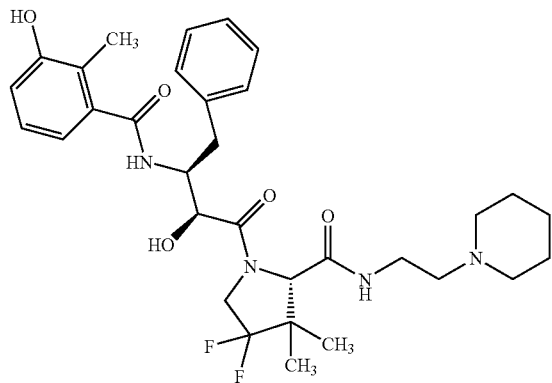

TABLE 2-continued
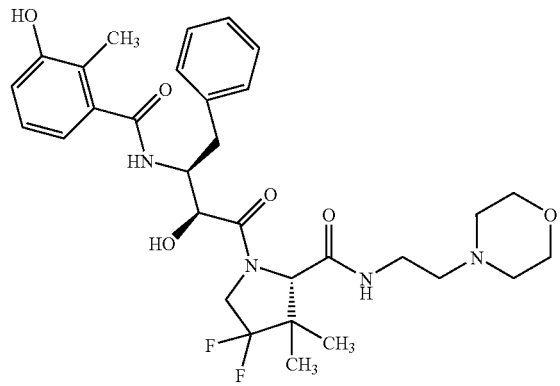
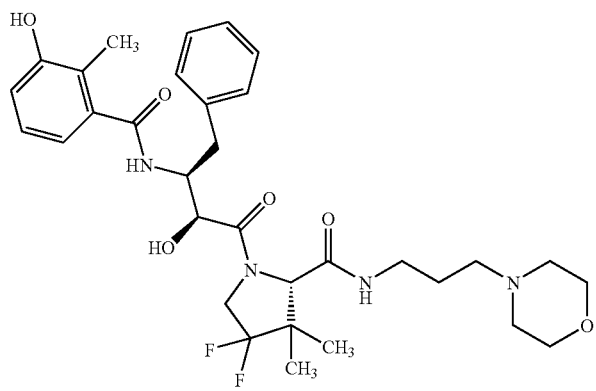
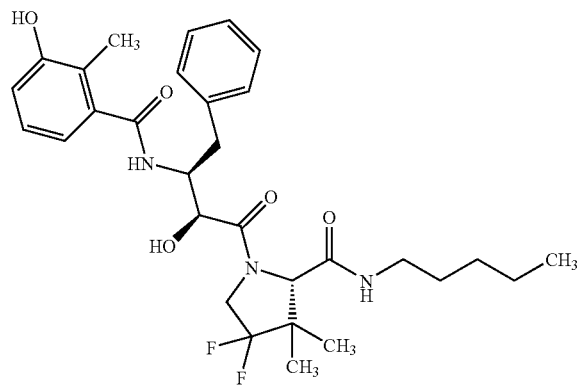
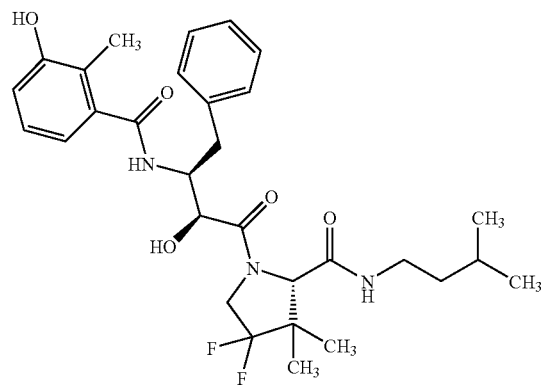

TABLE 2-continued
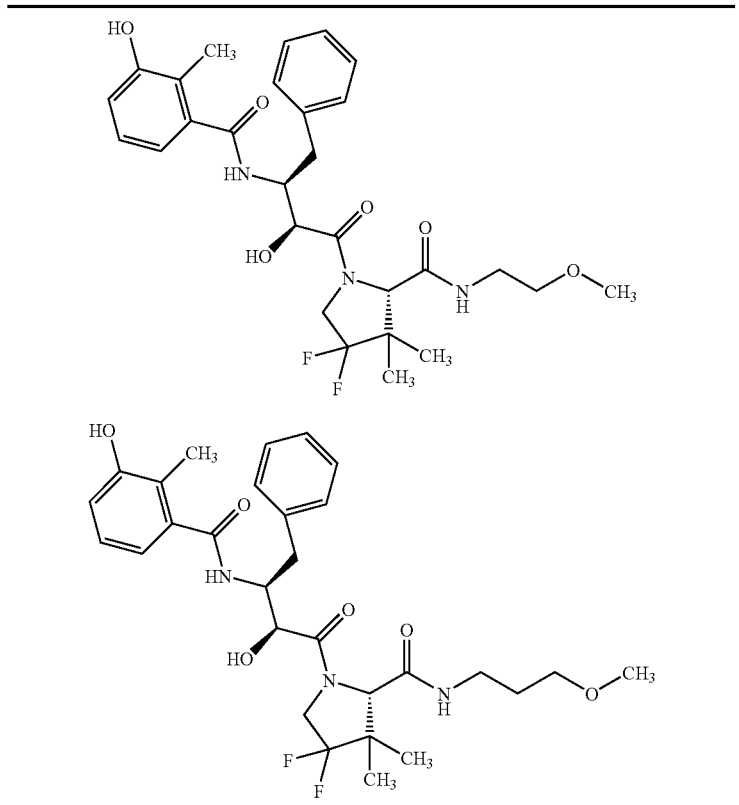
Scheme 3: Solid Phase Synthesis Of HIV Protease Inhibitors
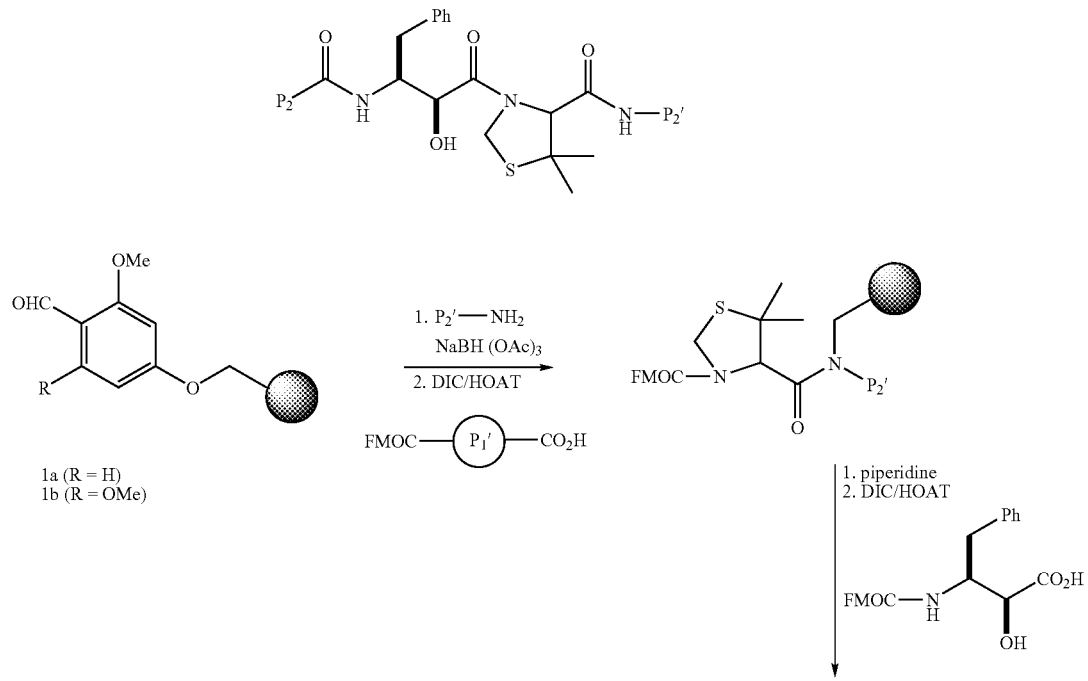

Scheme 3 Experimental

The solid phase combinatorial synthesis of HIV protease inhibitors was performed using the IRORI Directed Sorting Technology. Commercial 4-formyl-3-methoxyphenoxymethyl polystyrene resin 1a (PS-MB-CHO, Argonaut Technologies) or 4-formyl-3,5-dimethoxyphenoxymethyl polystyrene resin 1b (PL-FDMP resin, Polymer Laboratories) was loaded into individual Minikans.

Step A. Reductive Amination with $P_2'$ Amines

To separate flasks containing sorted MiniKans was added DCM (3 mL/MiniKan). The appropriate primary $P_2'$ amine (3 eq), sodium triacetoxyborohydride (5 eq), and acetic acid (3 eq) were added, and the mixtures were placed under argon, agitated with periodic venting at room temperature for 1–2 hours, and allowed to react overnight. For resin 1a, the filtrates were poured off and the MiniKans were washed with DCM, MeOH (2×), DCM (2×), EBt$_3$N/DCM (1:3, 3×), DCM (2×), MeOH (3×), and DCM (4×). For resin 1b, a washing sequence of DCM, MeOH (2×), DCM (2×), Et$_3$N/DCM (1:3, 3×), DCM (2×), DMF, 1M NaOH/DMF (1:5, 3×), DMF (3×), MeOH (3×), and DCM (3×) was used. The MiniKans were dried under vacuum and taken on in Step B.

Step B. Peptide Coupling with $P_1'$ Amino Acids

To separate flasks containing the sorted MiniKans was added DMF (3 mL/MiniKan). The appropriate FMOC-protected amino acid (2.5 eq) and 1-hydroxy-7-azabenzotriazole (HOAT) (3 eq) were added and mixed until dissolved, and 1,3-diisopropylcarbodiimide (DIC) (3 eq) was added. The containers were placed under argon and agitated at room temperature overnight. The filtrates were poured off, and the MiniKans were washed with DMF (3×), MeOH (3×), DCM (2×), and DMF (2×). The MiniKans were taken directly on to Step C.

Step C. FMOC Deprotection

A z A container of MiniKans in DMF and piperidine (25%) with a total reaction volume of 3 mL/MiniKan was agitated under argon at room temperature for 45 minutes. The filtrate was removed, and the reaction procedure was repeated. The MiniKans were filtered and washed with DMF (3×), MeOH (2×), DCM (3×), and DMF, and taken directly on to Step D.

Step D. Peptide Coupling with FMOC-APNS

FMOC-Allophenylnorstatine (APNS) (3 eq) was added to the flask of MiniKans in DMF (3 mL/MiniKan). After dissolution, HOAT (3.5 eq) and DIC (3.5 eq) were added. The mixture was placed under argon and agitated at room temperature overnight. The reaction was filtered and the MiniKans were washed with DMF (3×), MeOH (3×), DCM (3×), and DMF. FMOC deprotection was carried out as in Step C, and the MiniKans were washed with DMF (3×), MeOH (2×), DCM (3×), dried under vacuum and taken on to Step E or F.

Step E. Peptide Coupling with $P_2$ Acids

To separate flasks containing the sorted MiniKans in DMF (3 mL/MiniKan) was added the appropriate $P_2$ acid (3 eq), HOBT hydrate (4 eq), and (3-(dimethylamino)propyl) ethylcarbodiimide hydrochloride (EDAC) (3.5 eq). The reaction was agitated under argon at room temperature for 3 hours. After filtration, the MiniKans were washed with DMF (3×), MeOH (3×), and DCM (3×), dried under vacuum, and taken on to Step G.

Step F. Reaction with $P_2$ Isocyanates and Chloroformates

To separate flasks containing the sorted MiniKans in DCM (3 mL/MiniKan) was added the $P_2$ isocyanate (3 eq) or $P_2$ chloroformate (5 eq) and diisopropylethylamine (10 eq). The containers were agitated under argon at room temperature for 2–4 hours. After filtration, the MiniKans were washed with DCM (3×), MeOH (3×), and DCM (3×), dried under vacuum, and taken on to Step G.

Step G. Cleavage and Processing of the HIV Analogs

The individual MinKans were sorted into cleavage racks and a solution of 25%

TFA in DCM (3 mL/MinKan) was added. The racks were agitated for 1.5 hours. The individual filtrates and DCM rinses were collected, concentrated, and purified by HPLC to provide the final compounds.

TABLE 3

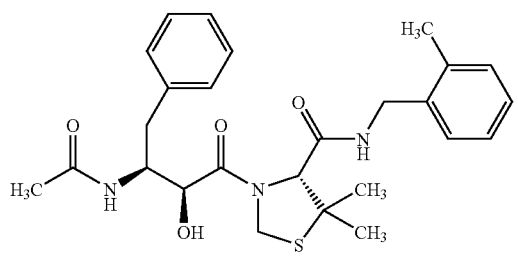

TABLE 3-continued
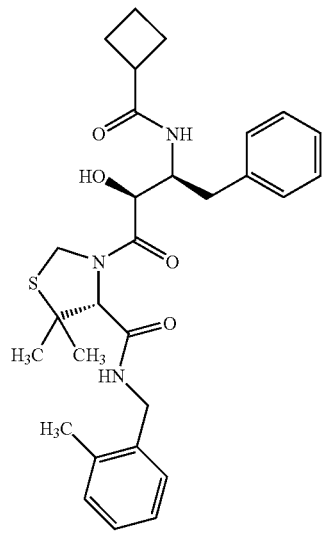
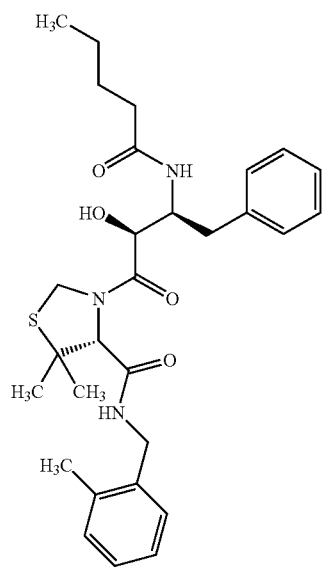

TABLE 3-continued
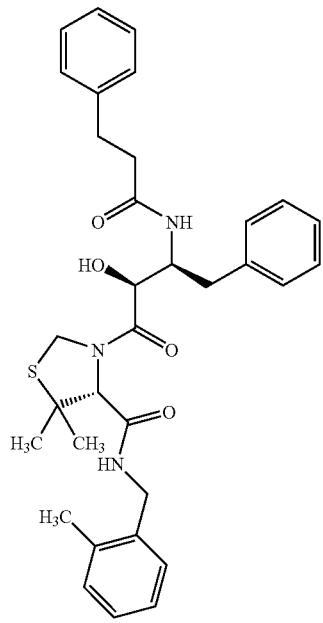
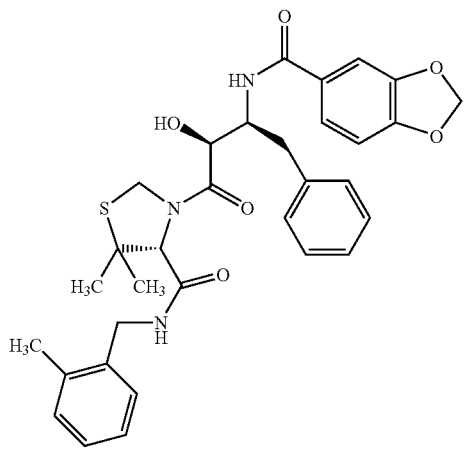
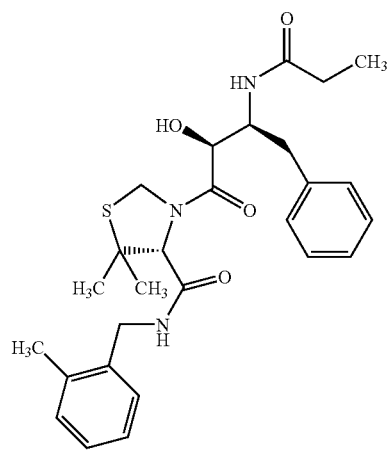

TABLE 3-continued
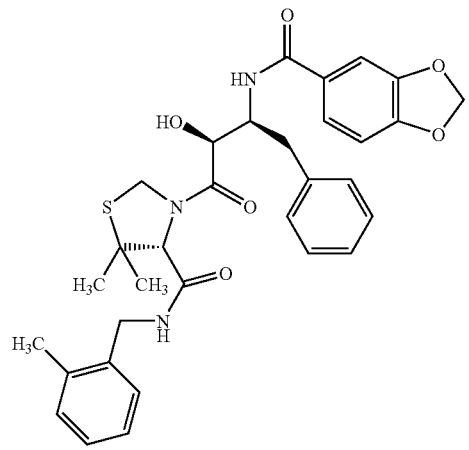
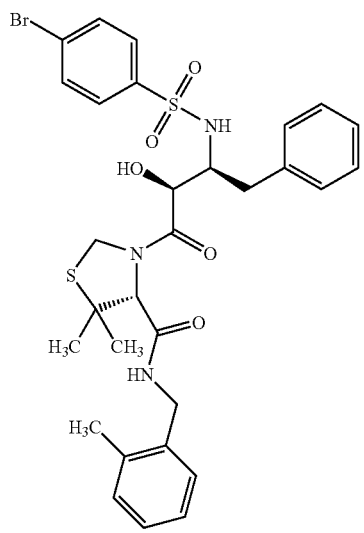
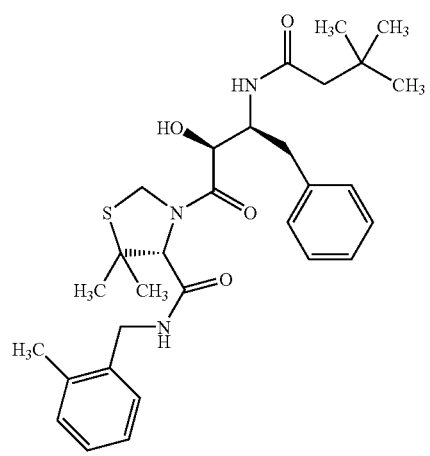

TABLE 3-continued
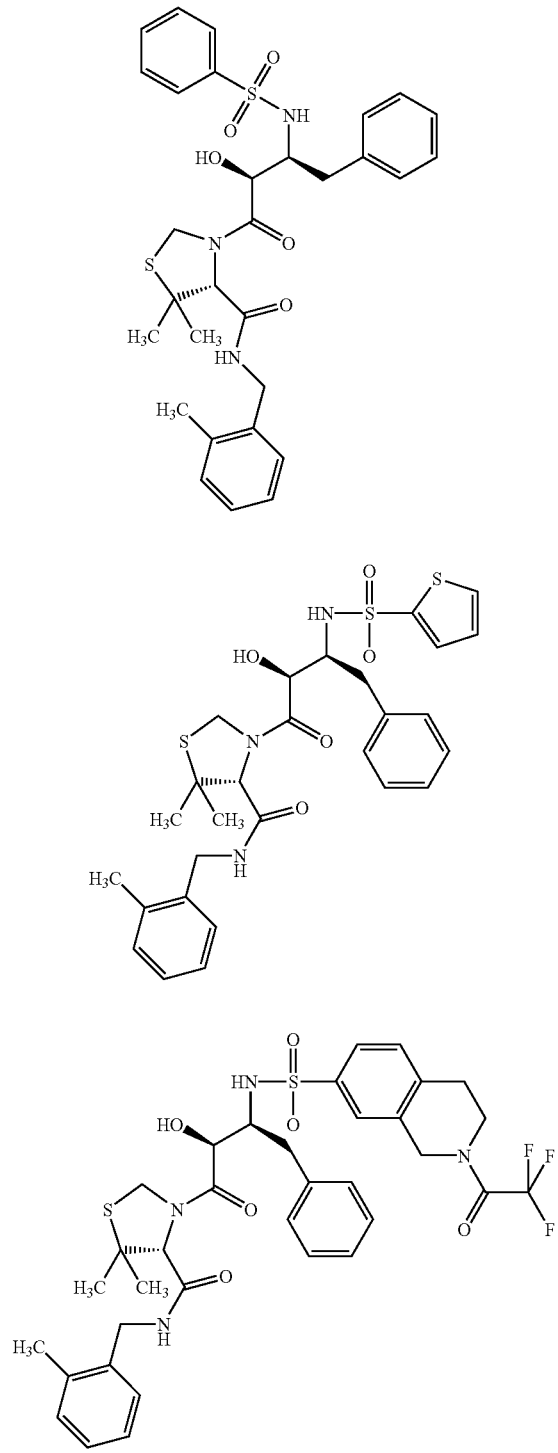

TABLE 3-continued
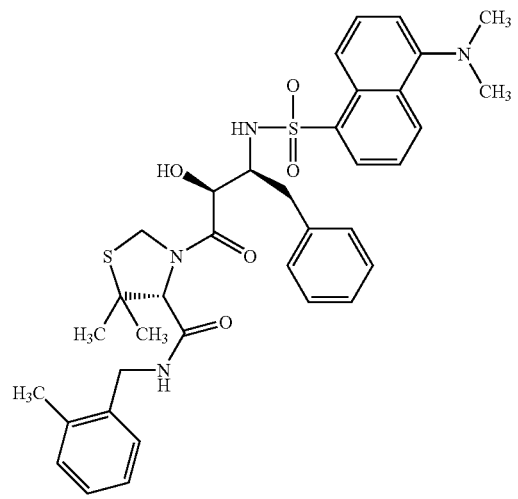
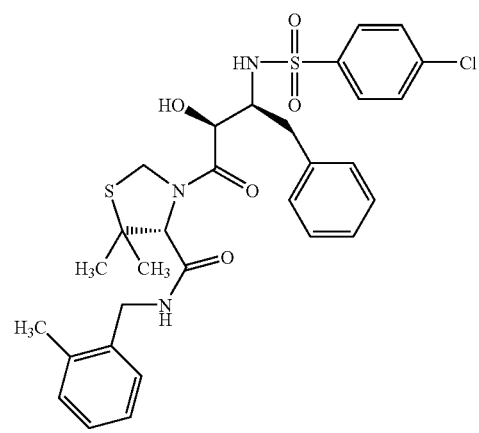
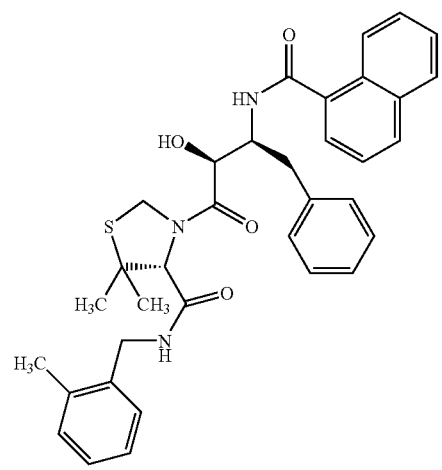

TABLE 3-continued
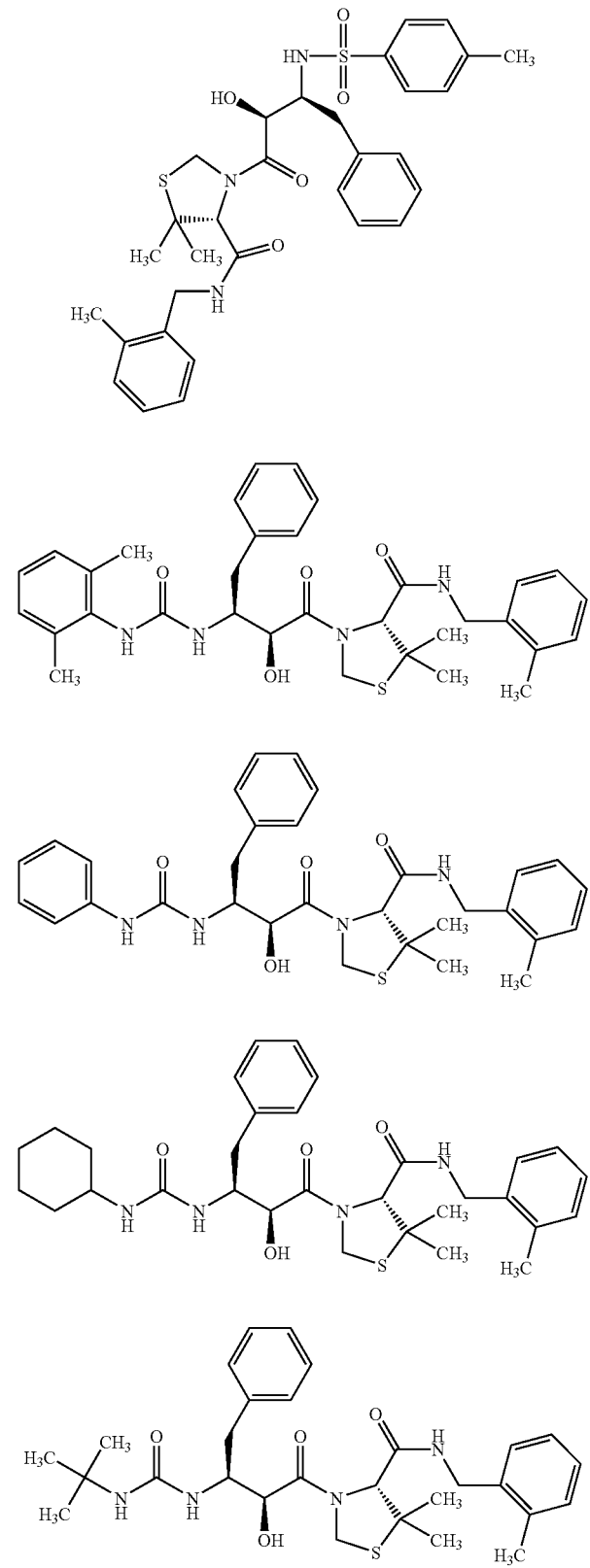

TABLE 3-continued
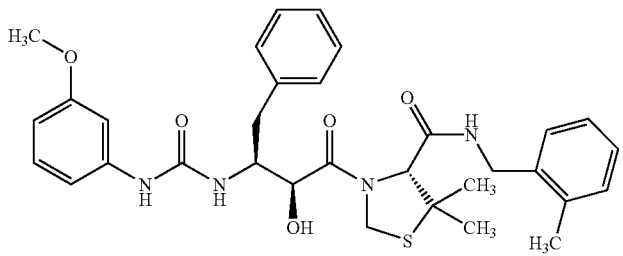
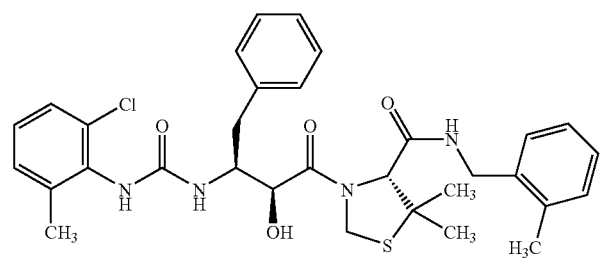
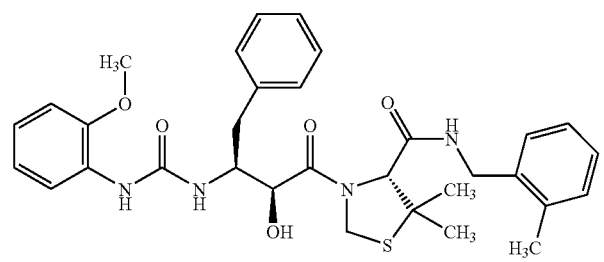
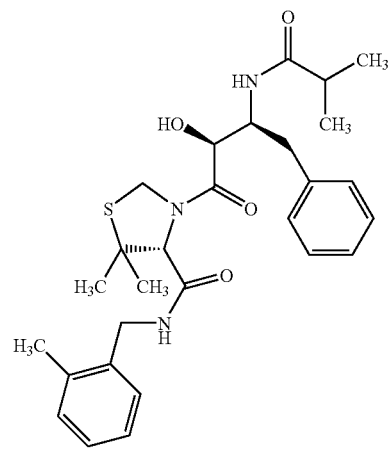
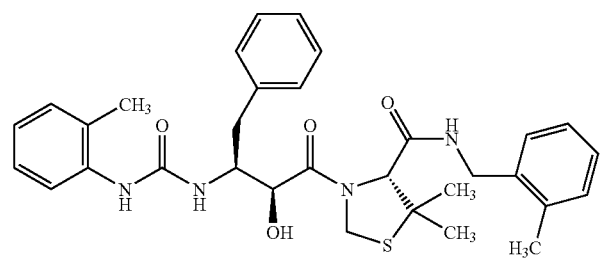

TABLE 3-continued
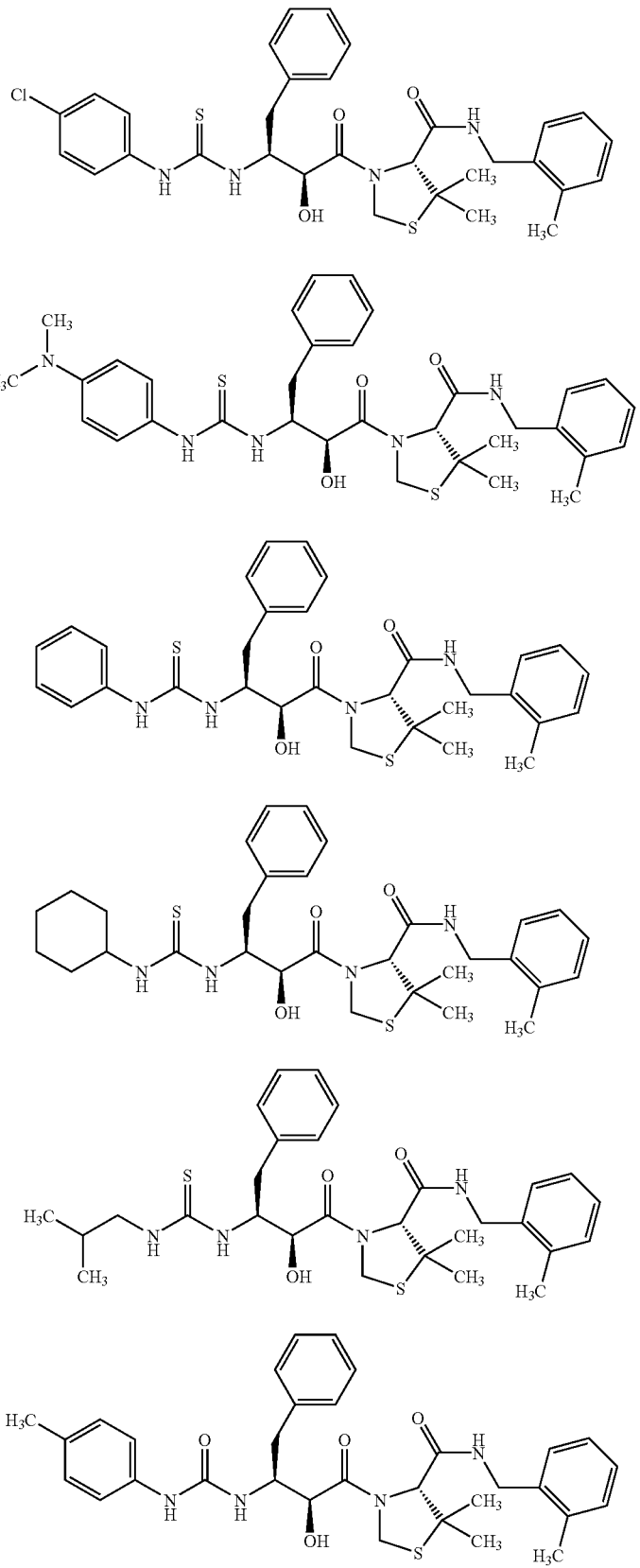

TABLE 3-continued
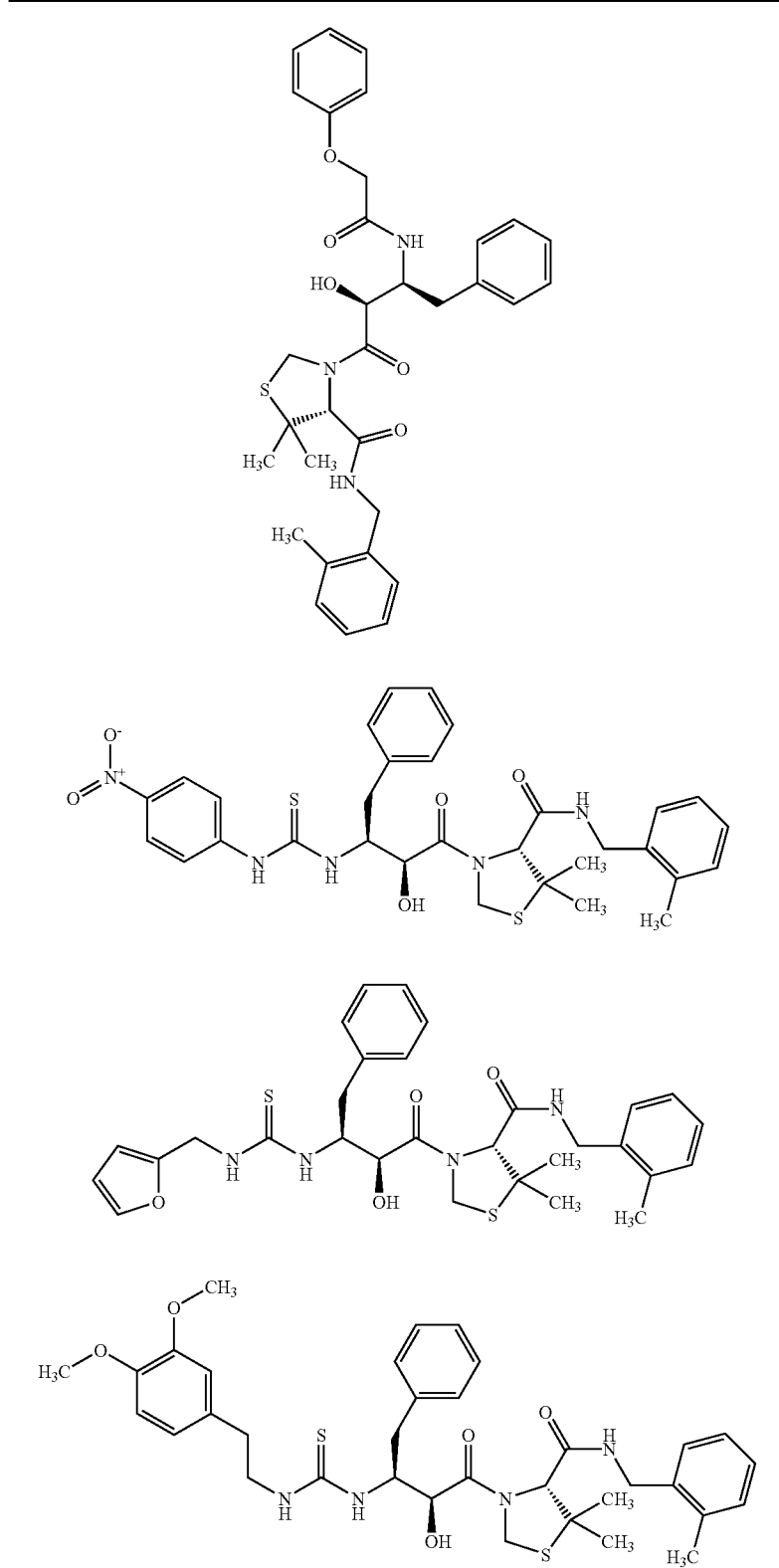

TABLE 3-continued
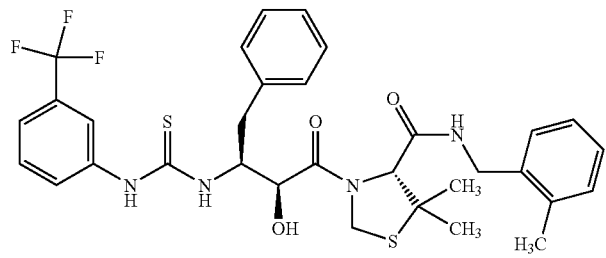
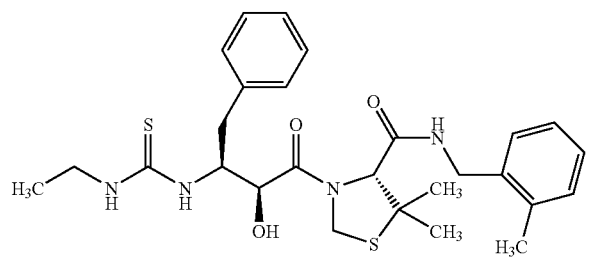
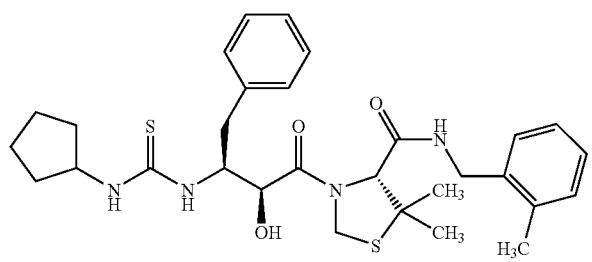
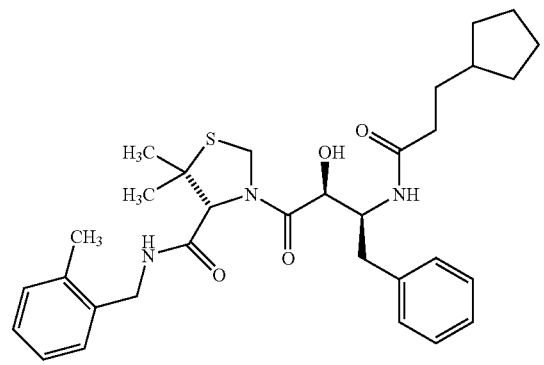
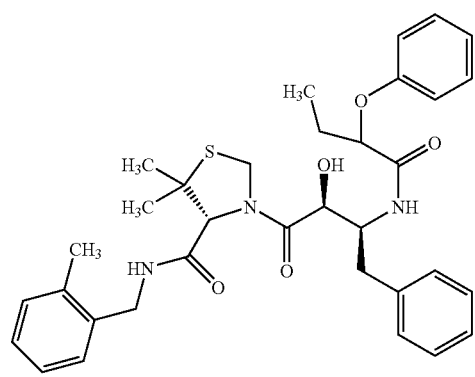

TABLE 3-continued
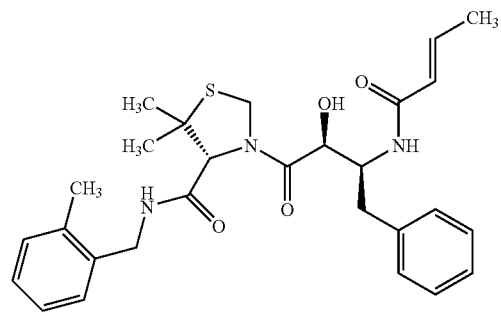
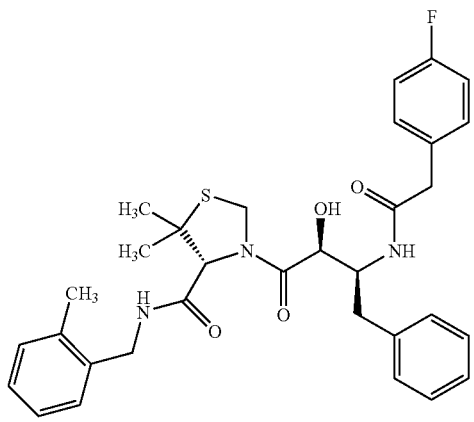
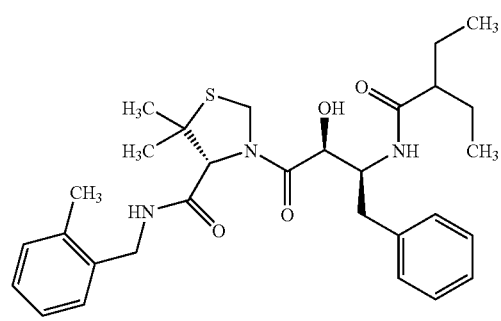
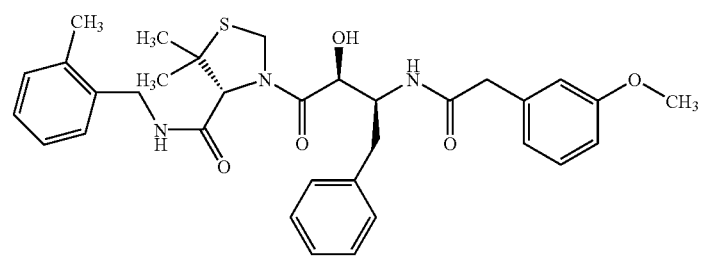

TABLE 3-continued
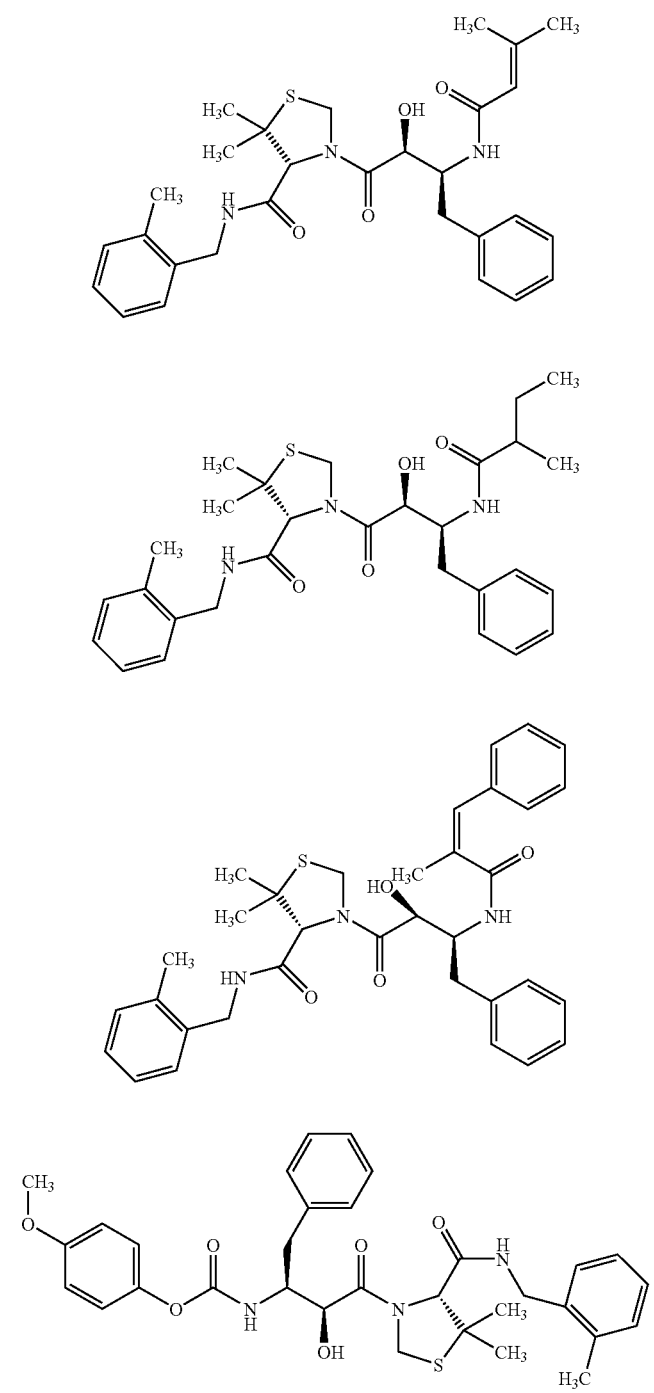

TABLE 3-continued
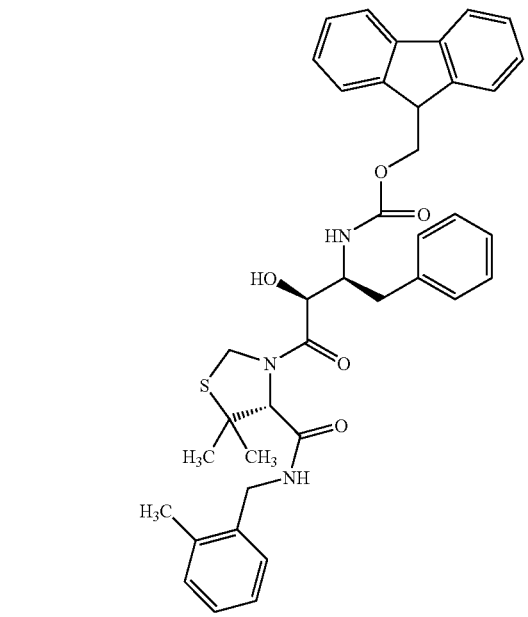
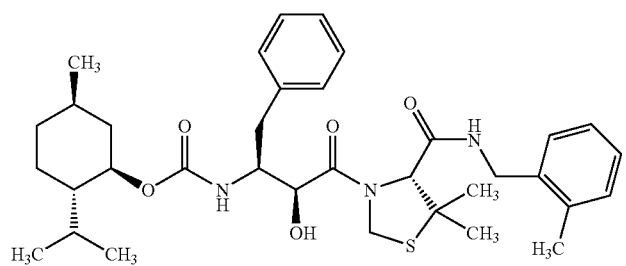
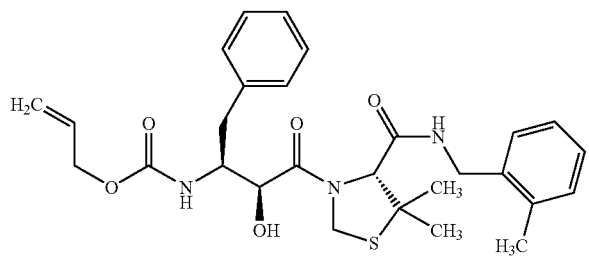
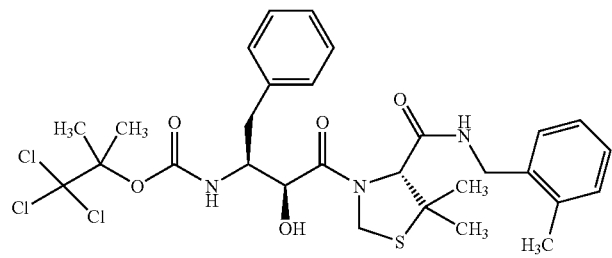

TABLE 3-continued
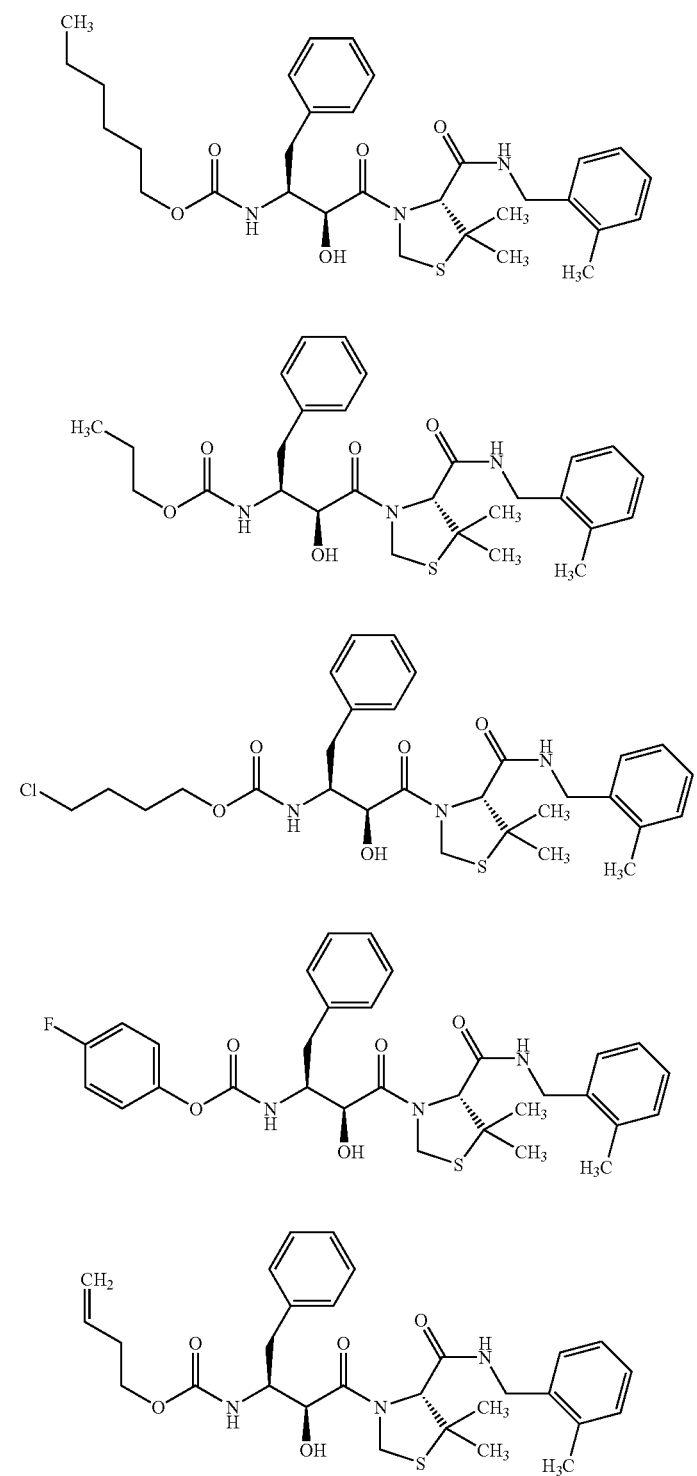

TABLE 3-continued
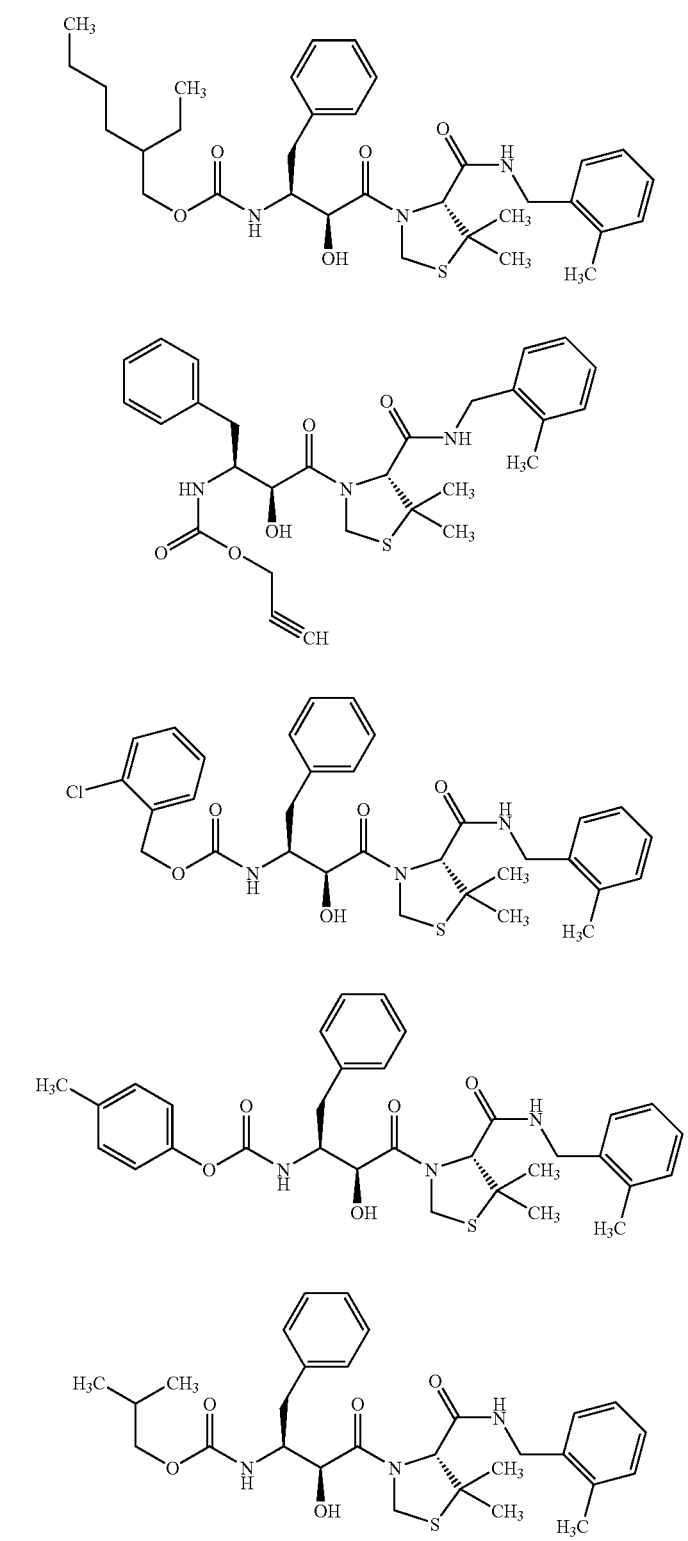

TABLE 3-continued
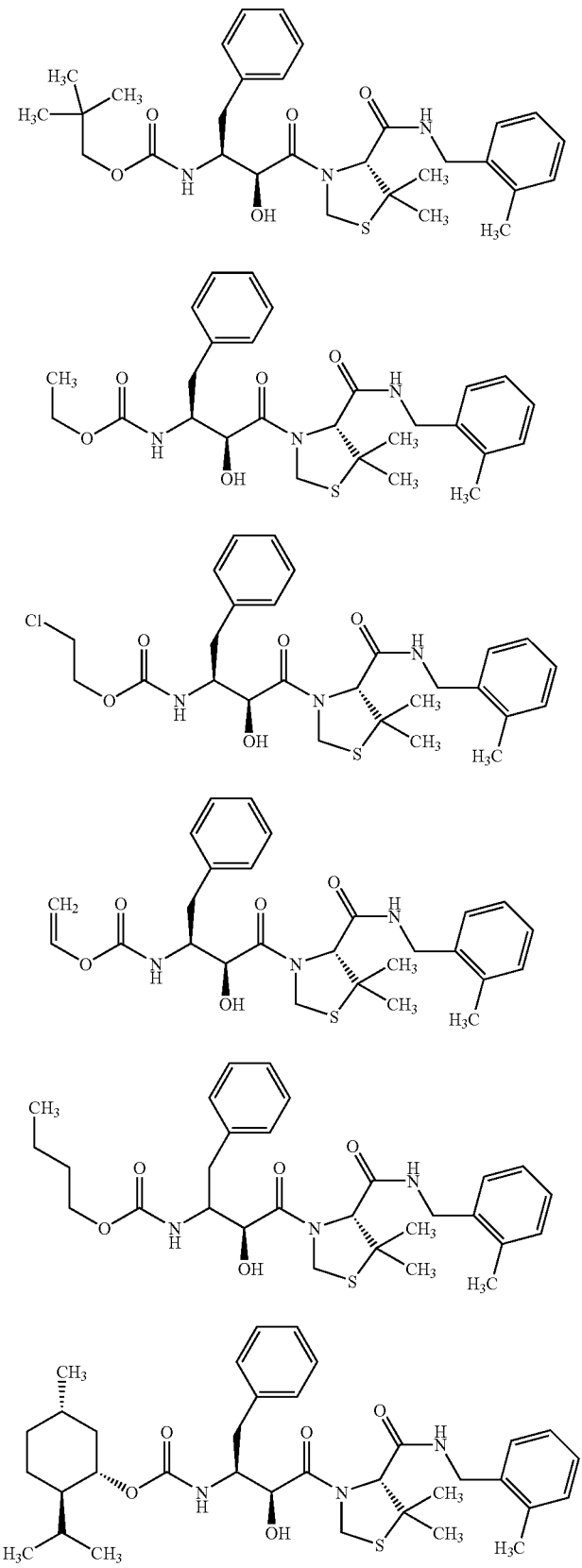

TABLE 3-continued
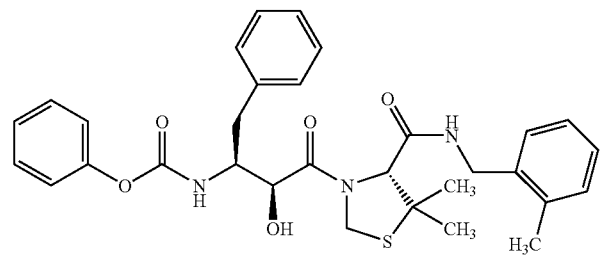
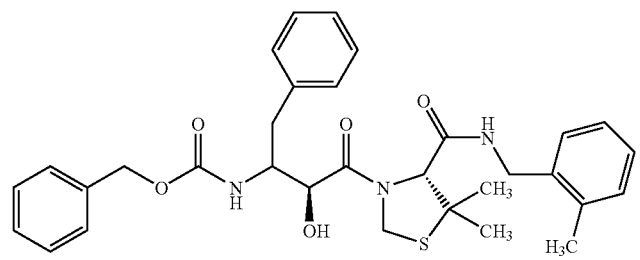
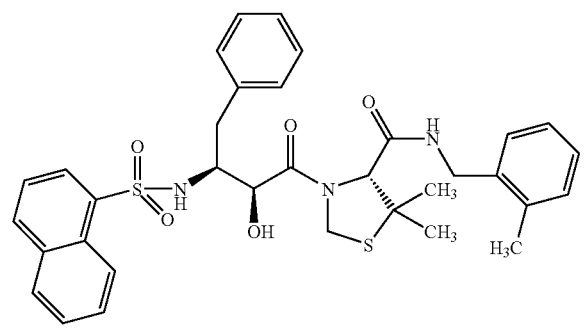
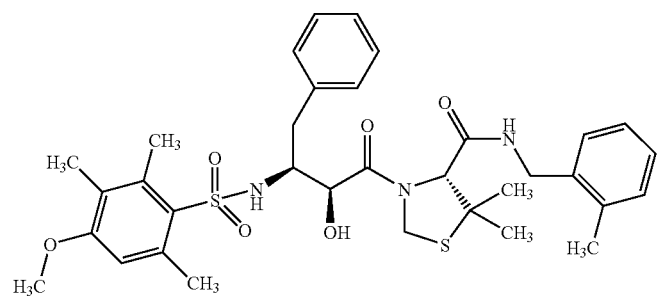
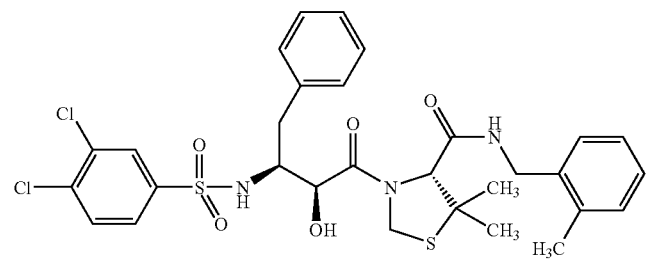

TABLE 3-continued
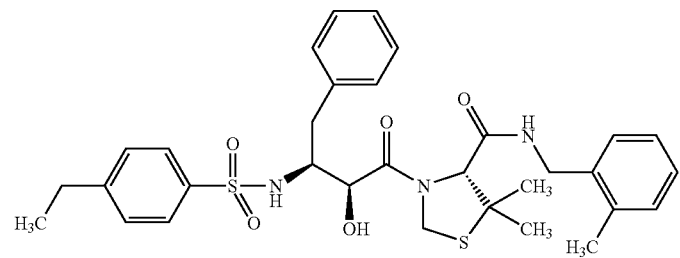
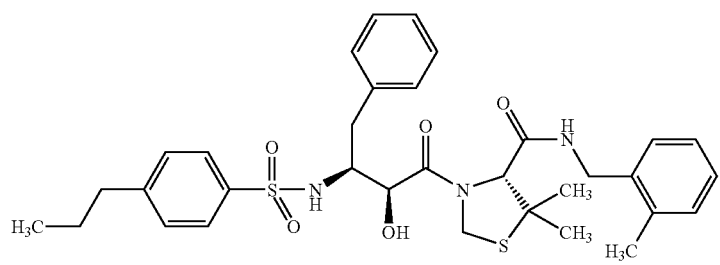
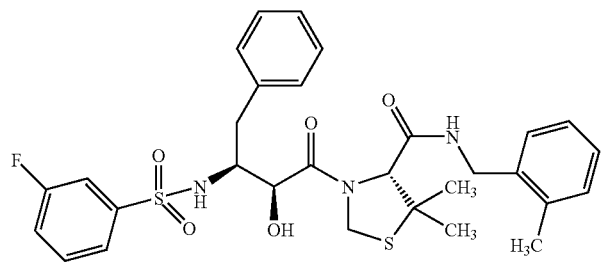
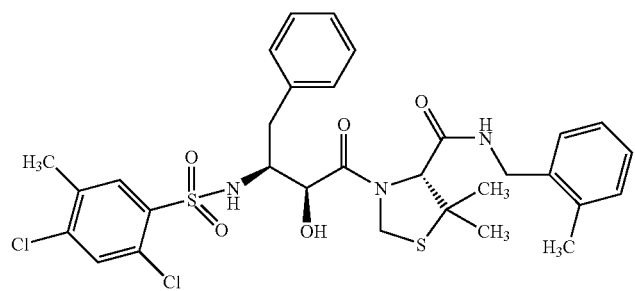
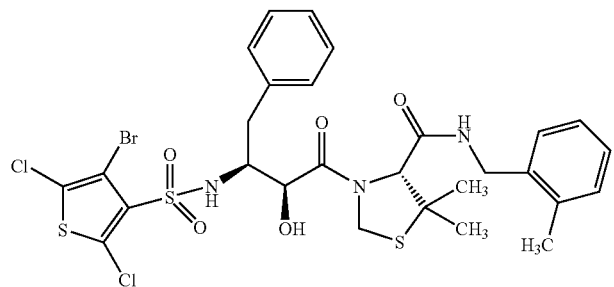

TABLE 3-continued
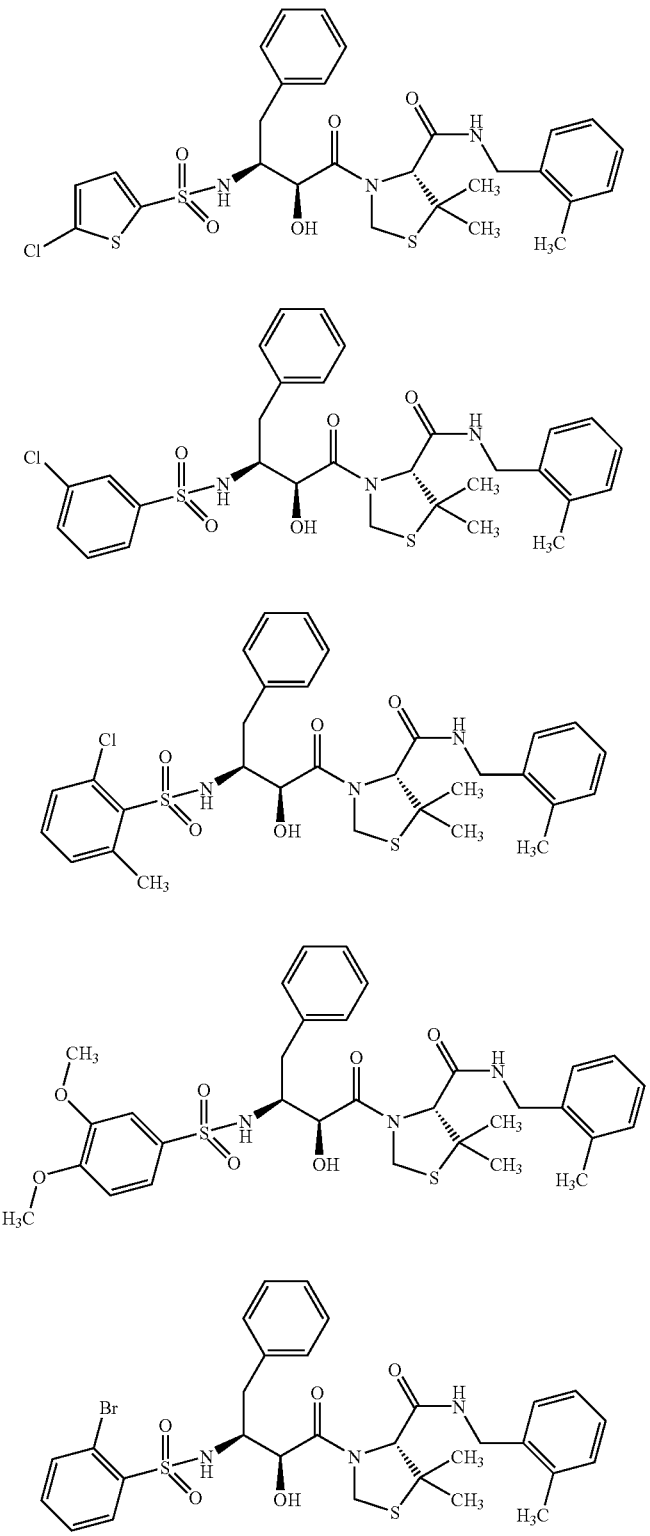

TABLE 3-continued
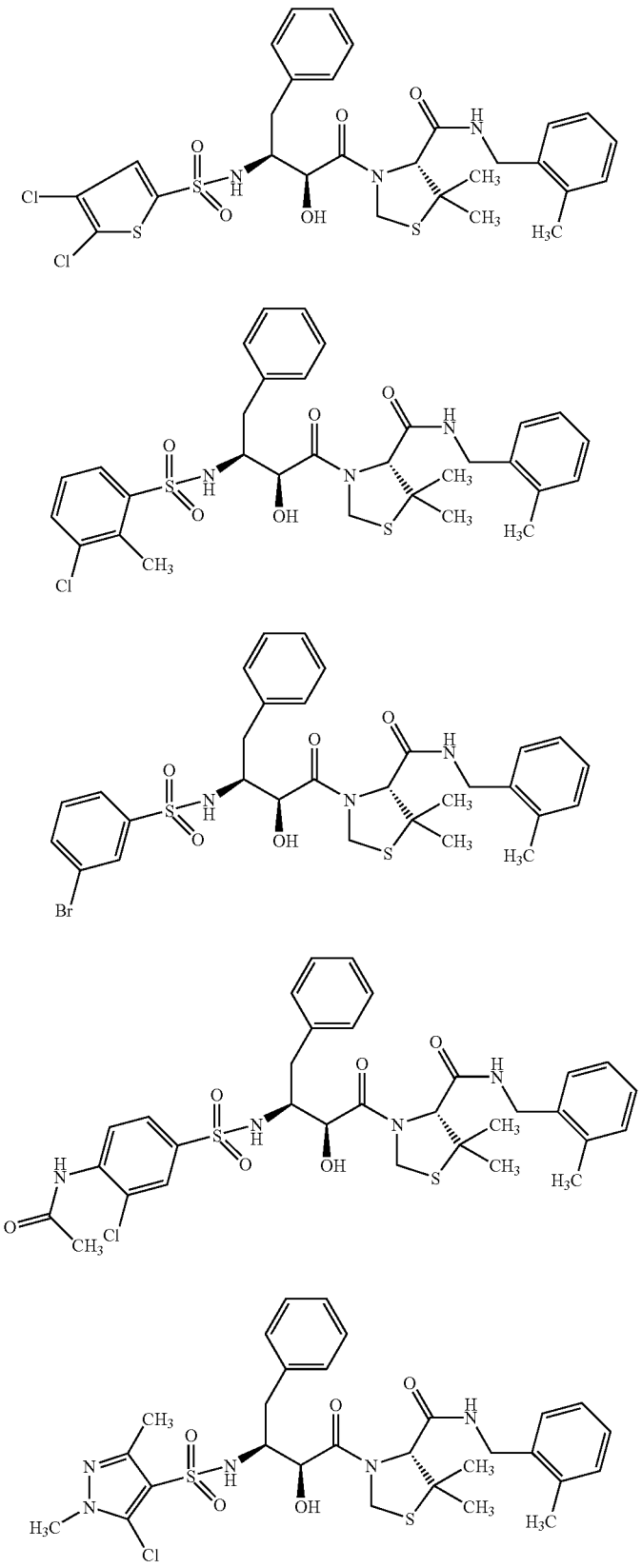

TABLE 3-continued
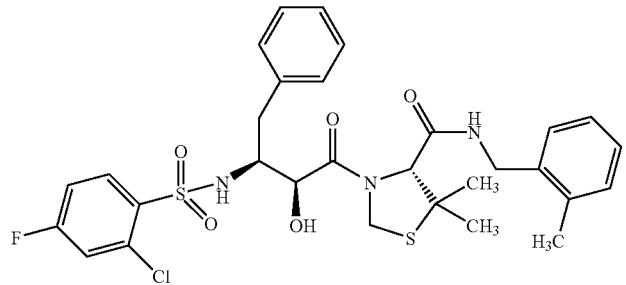
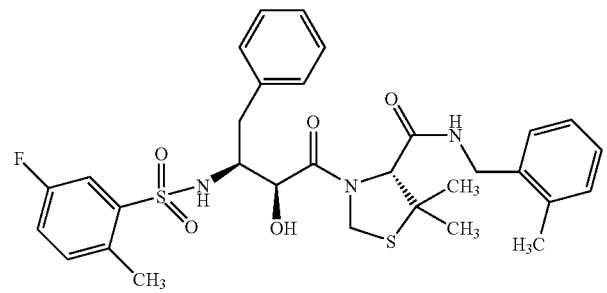
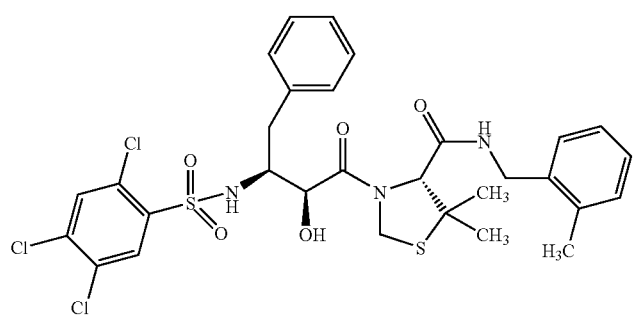
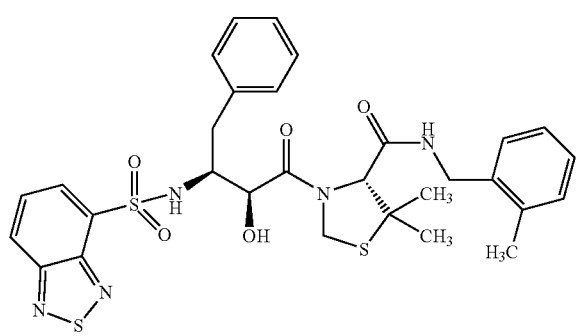
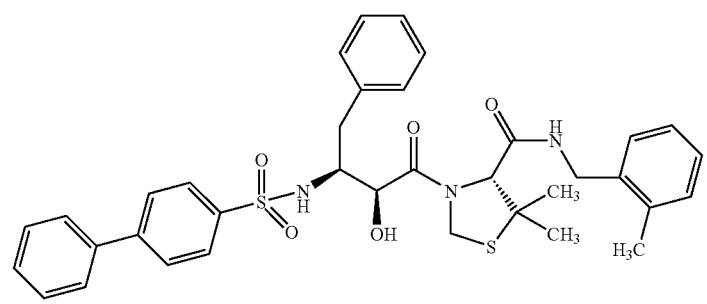

TABLE 3-continued
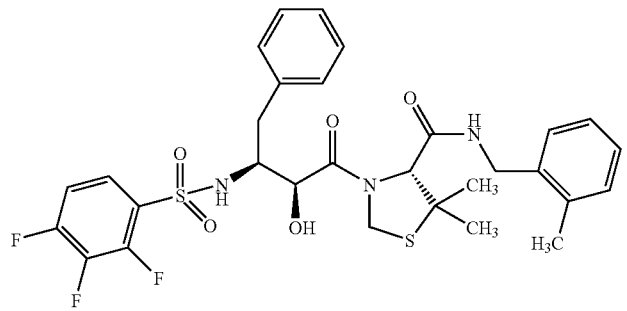
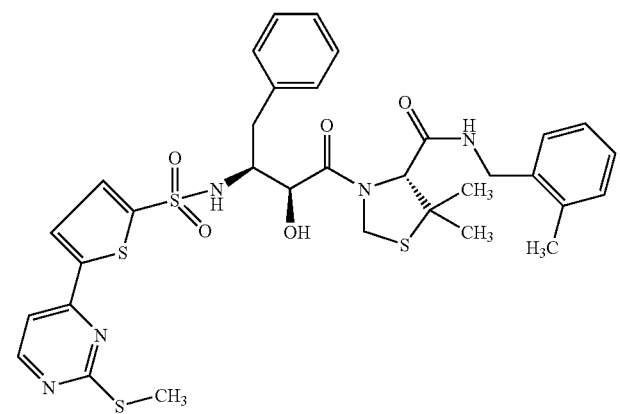
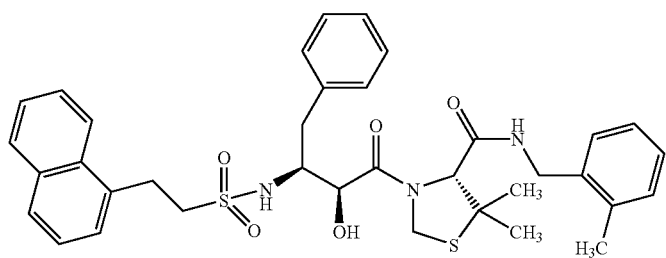
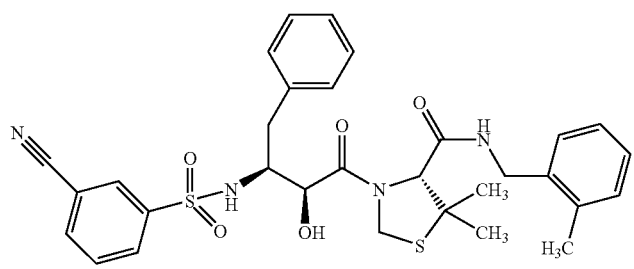
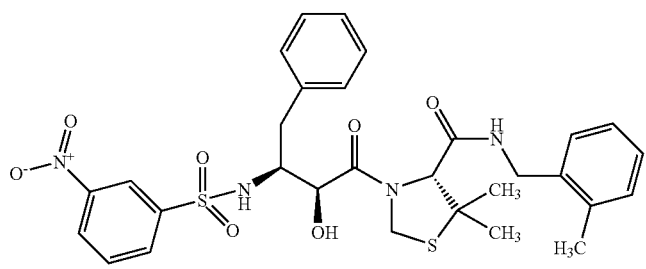

TABLE 3-continued
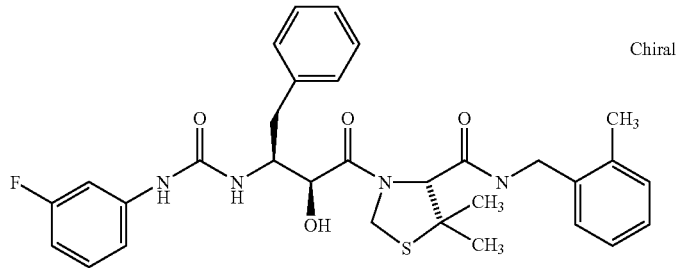
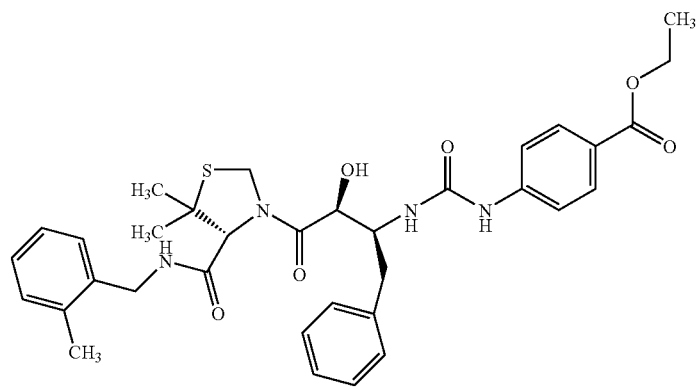
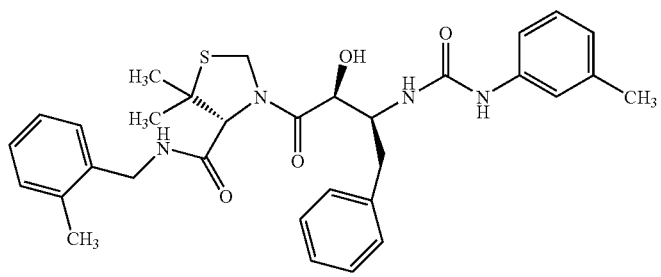
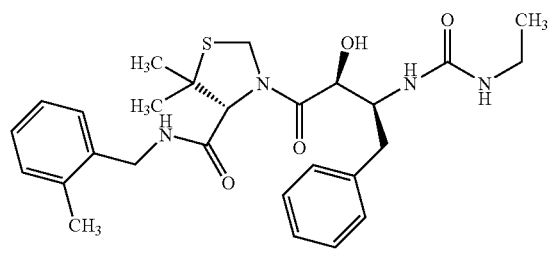
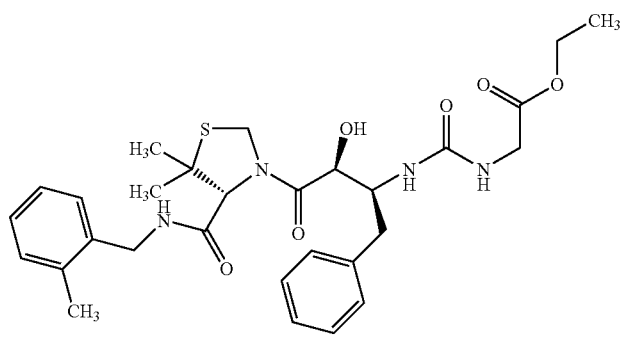

TABLE 3-continued
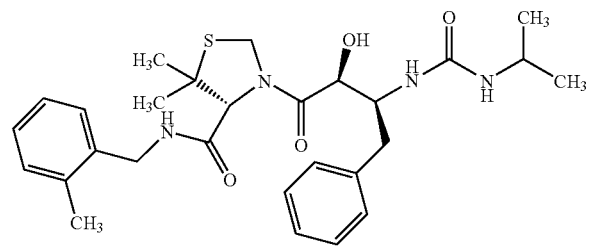
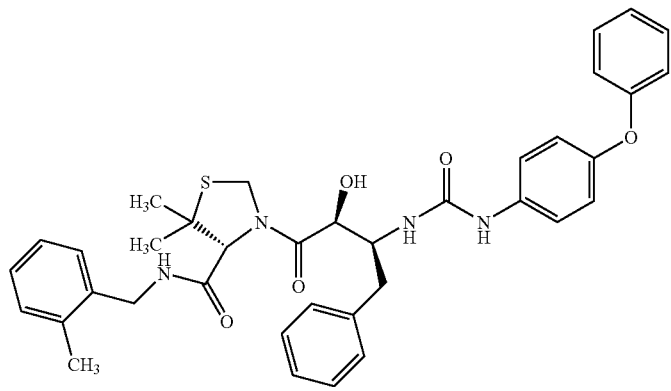
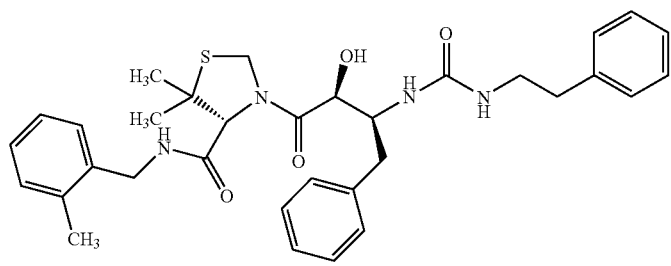
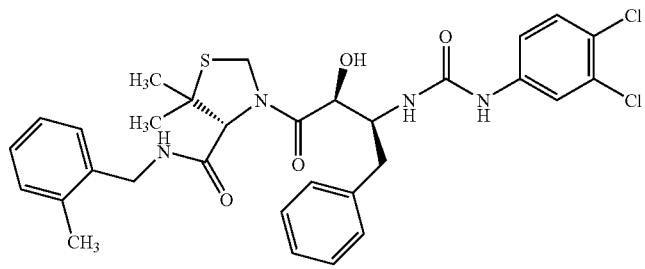
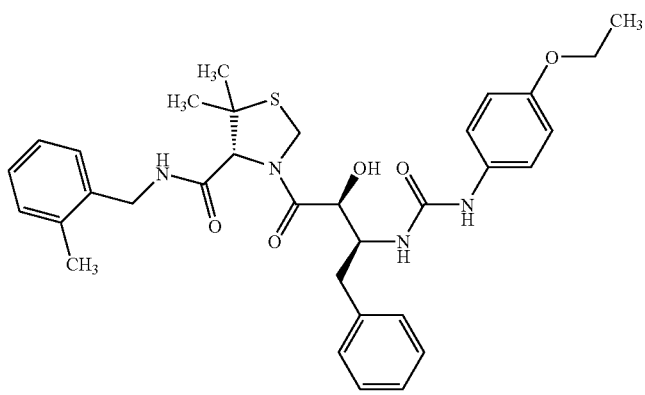

TABLE 3-continued
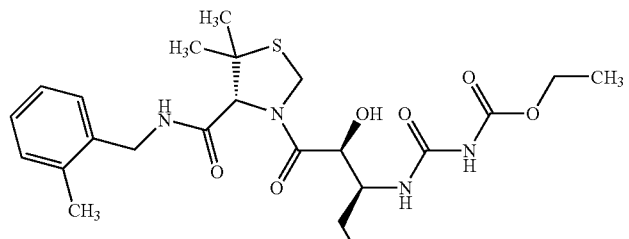
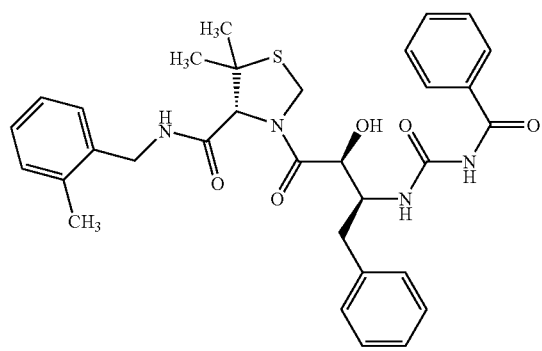
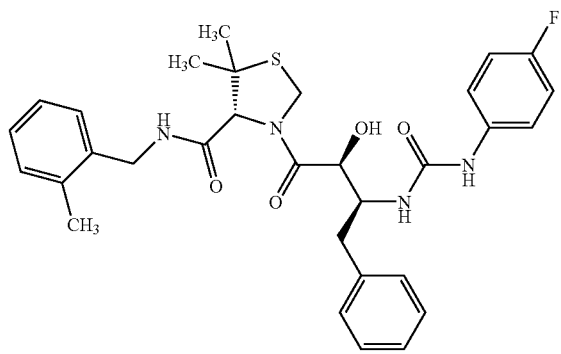
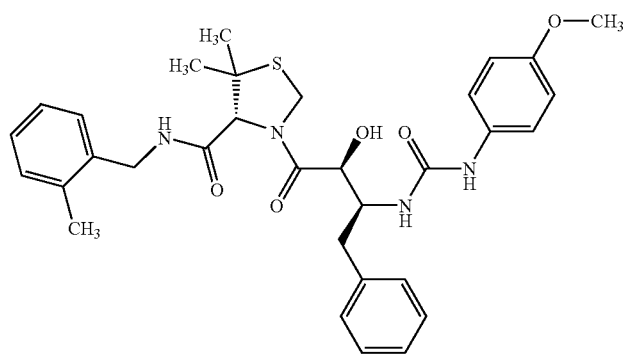

TABLE 3-continued
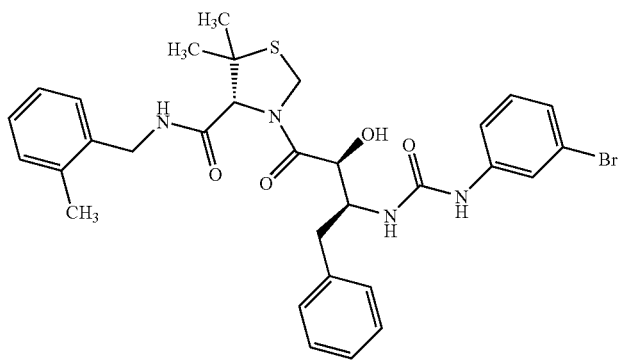
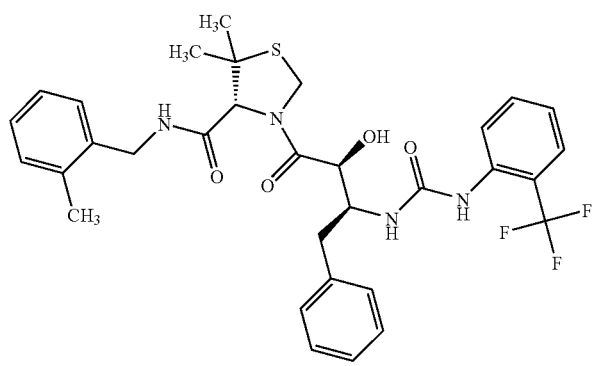
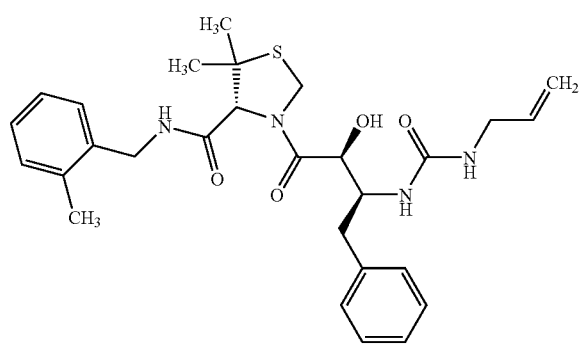
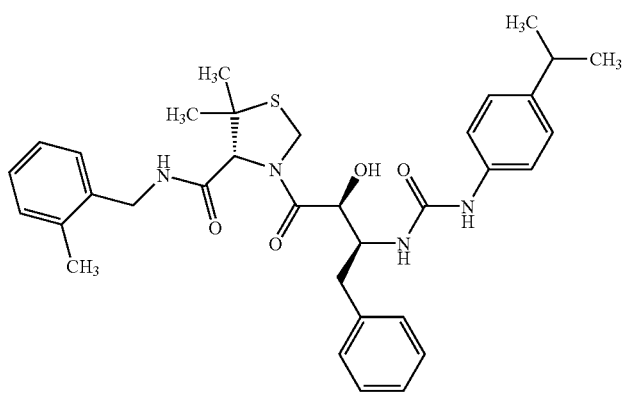

TABLE 3-continued
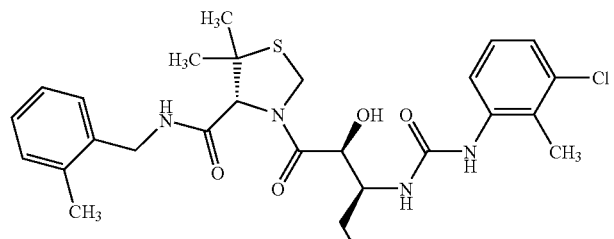
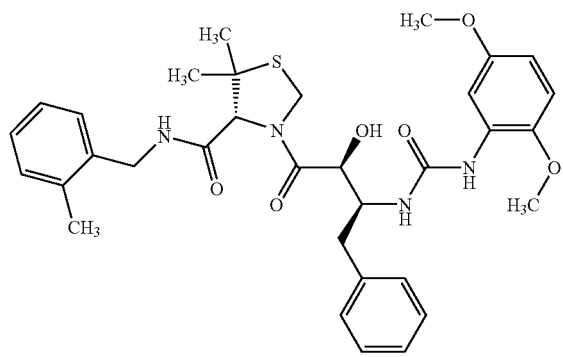
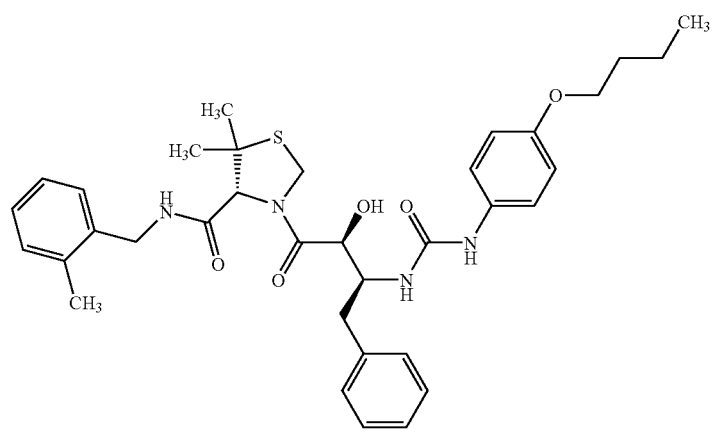
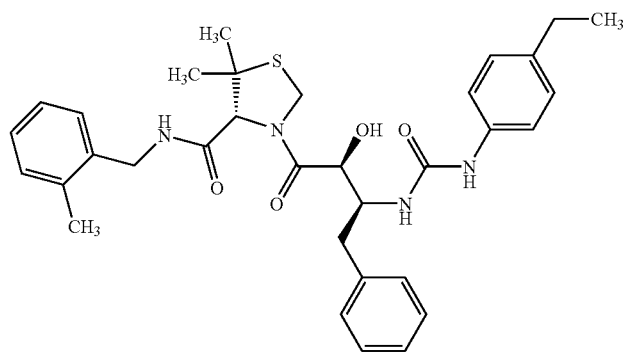

TABLE 3-continued
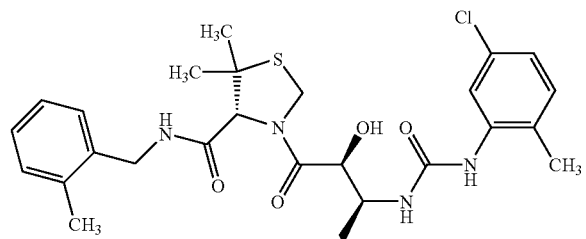
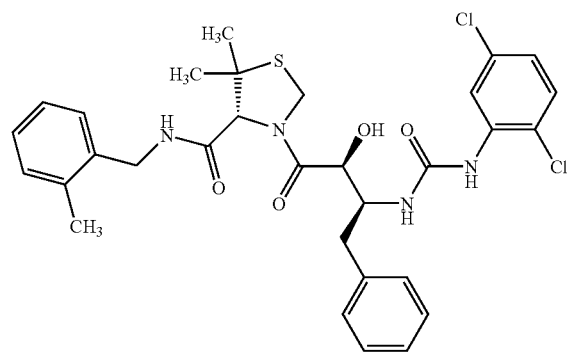
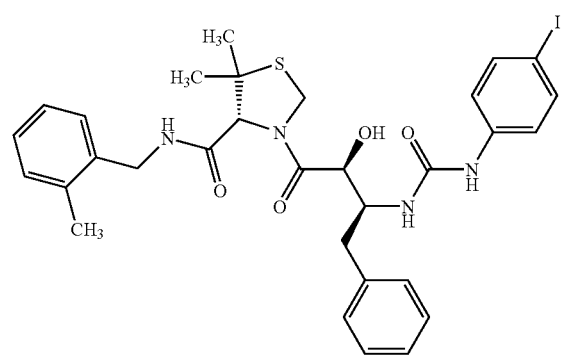
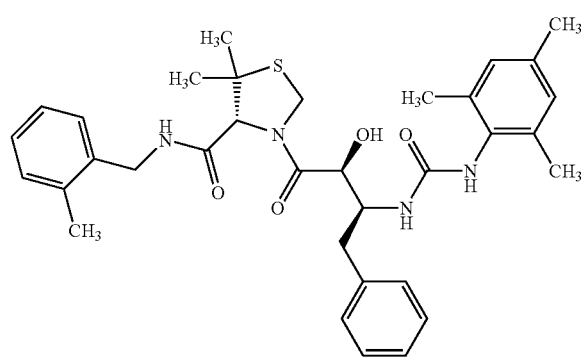

TABLE 3-continued
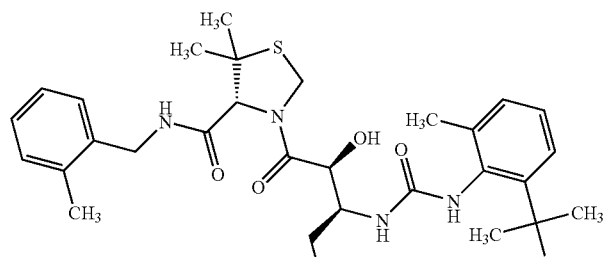
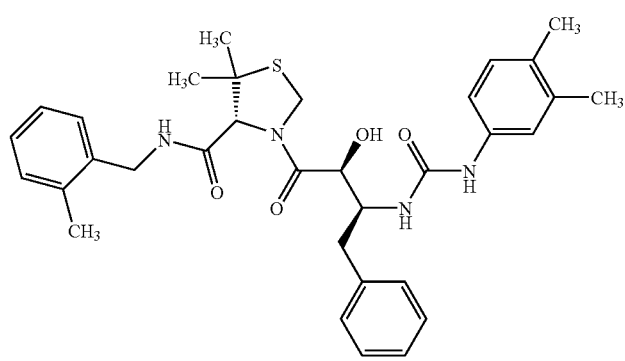
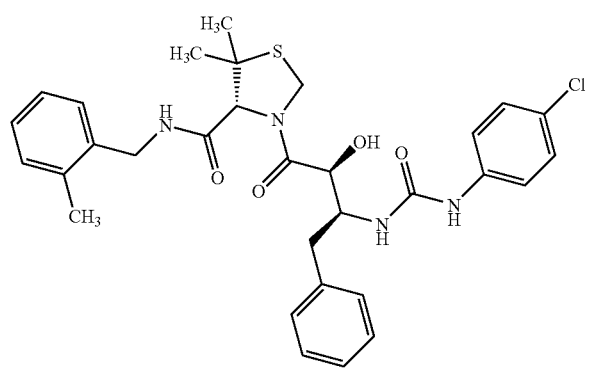
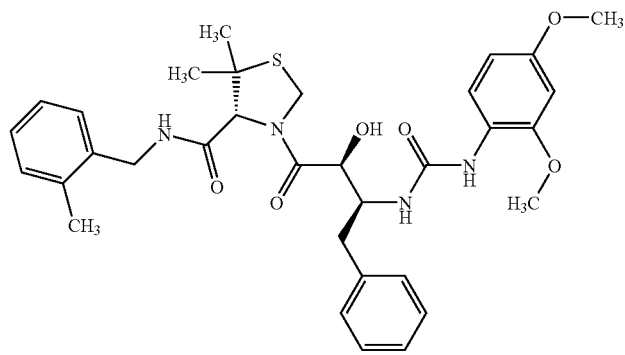

TABLE 3-continued
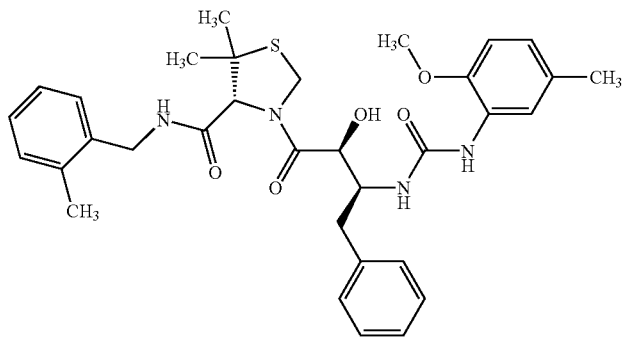
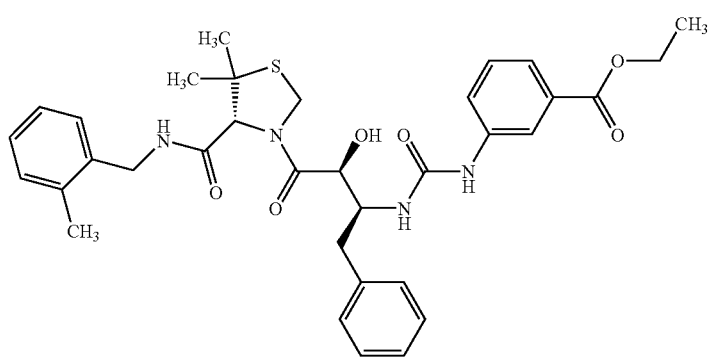
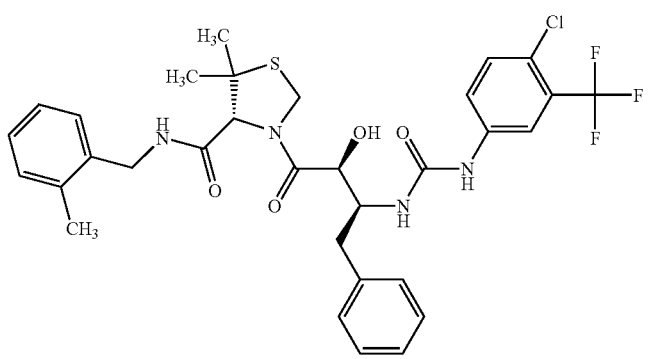
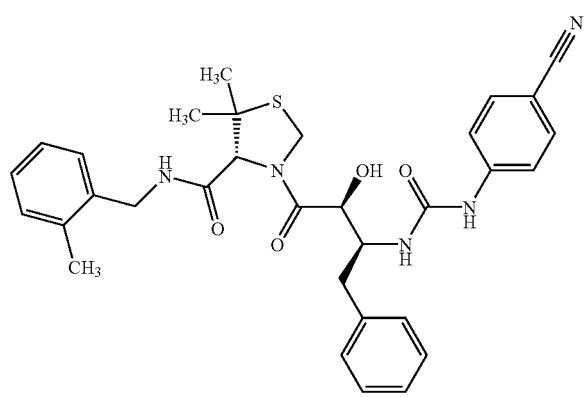

TABLE 3-continued
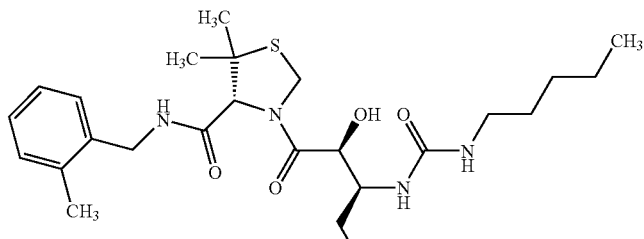
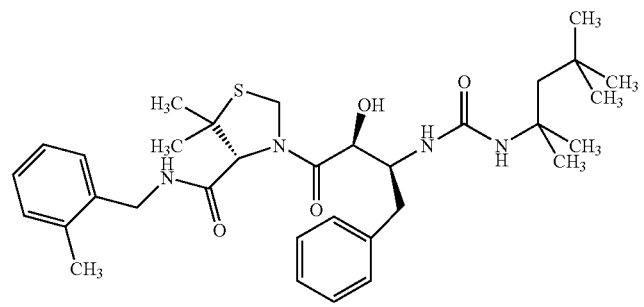
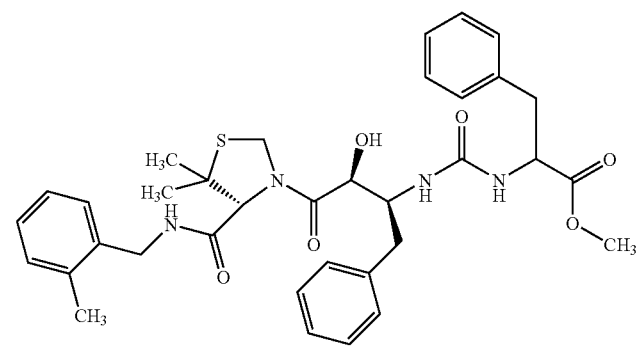
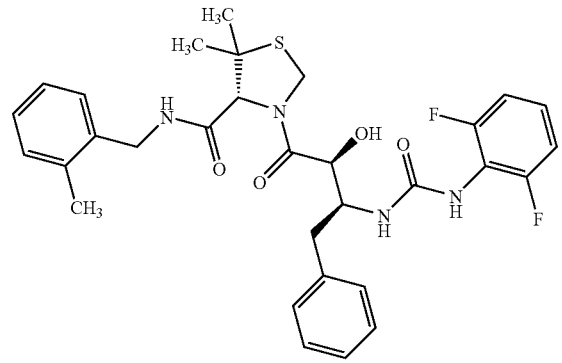

TABLE 3-continued
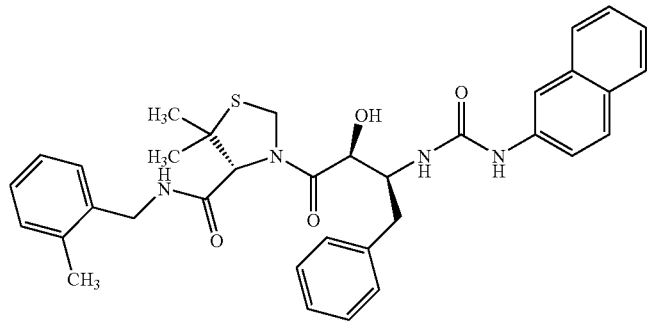
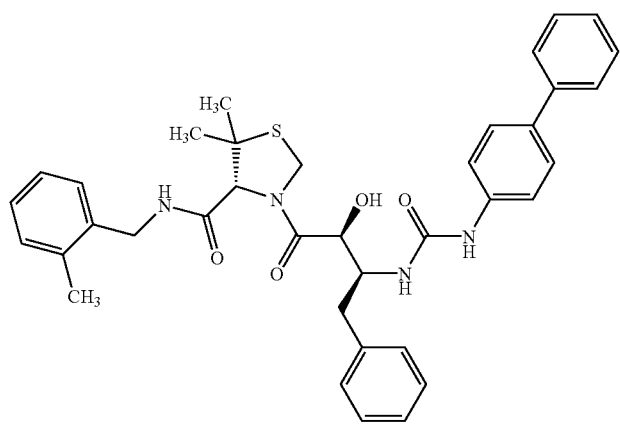
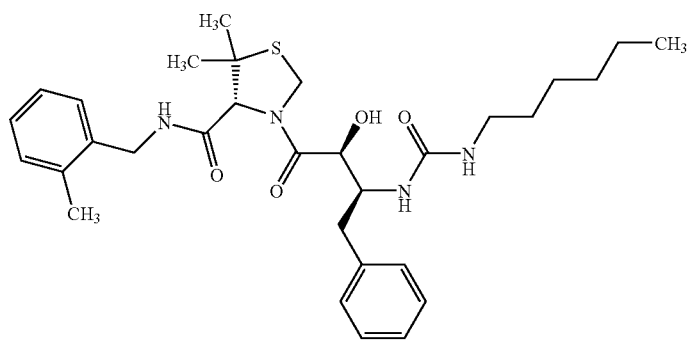
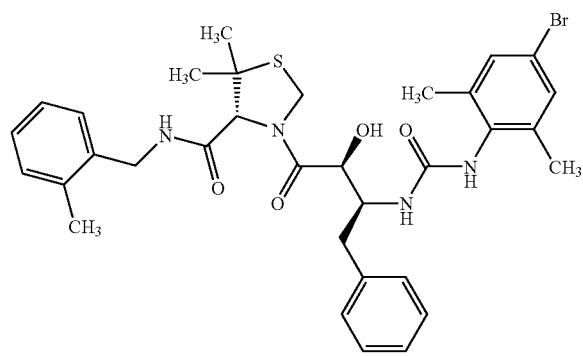

TABLE 3-continued
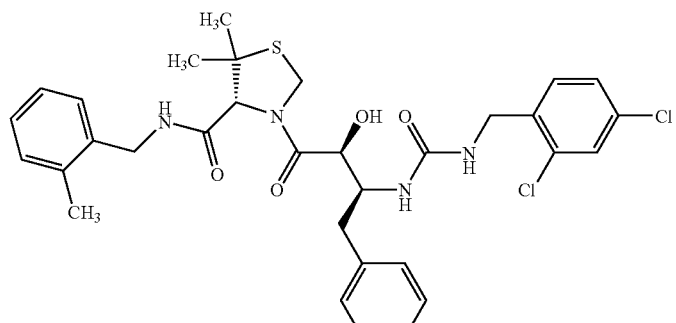
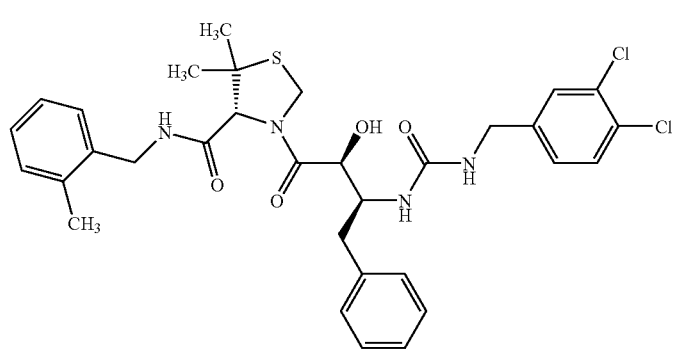
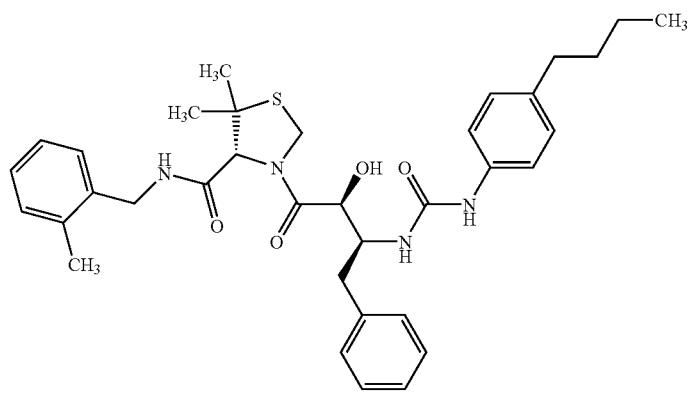
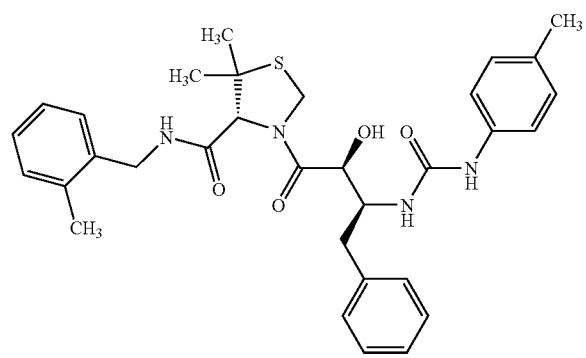

TABLE 3-continued
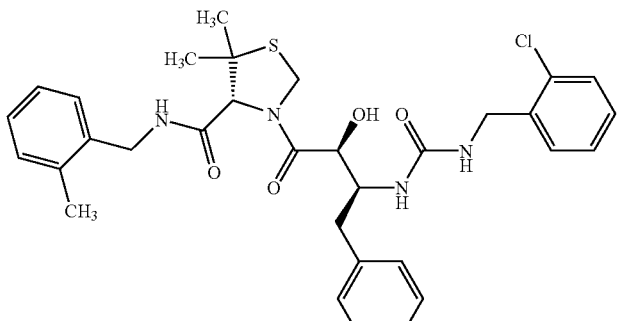
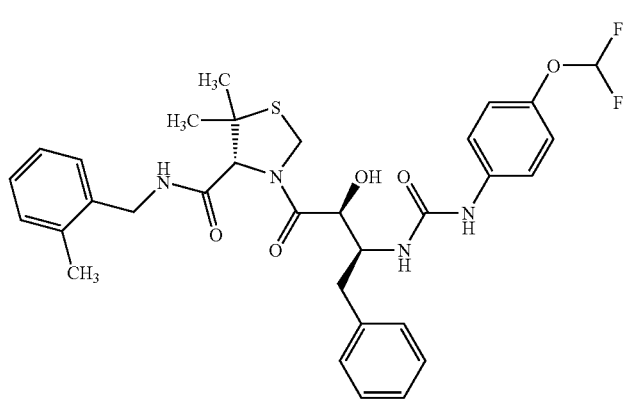
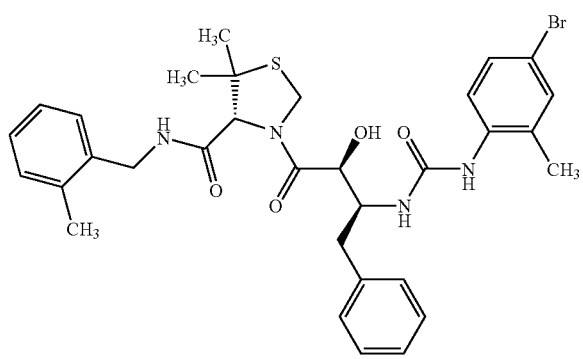
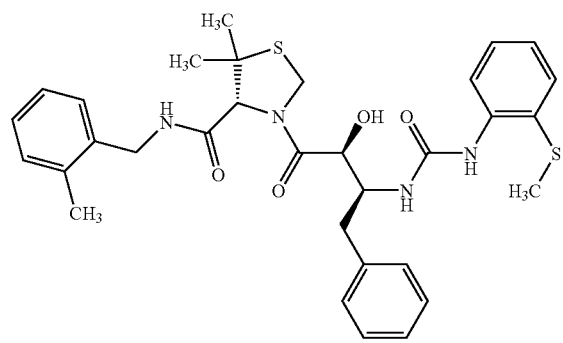

TABLE 3-continued
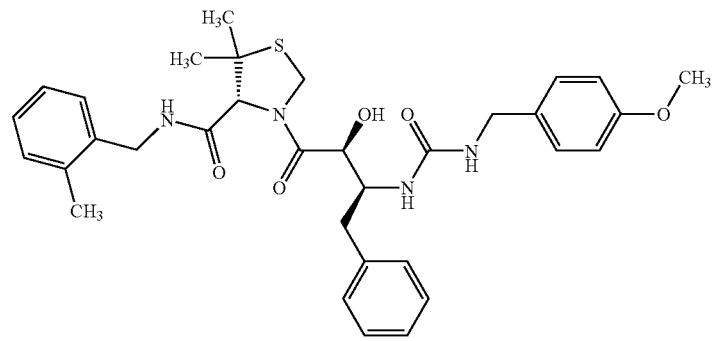
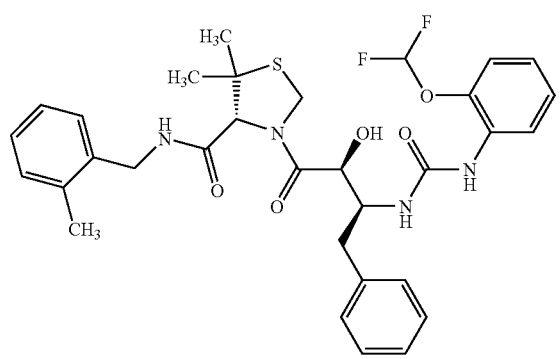
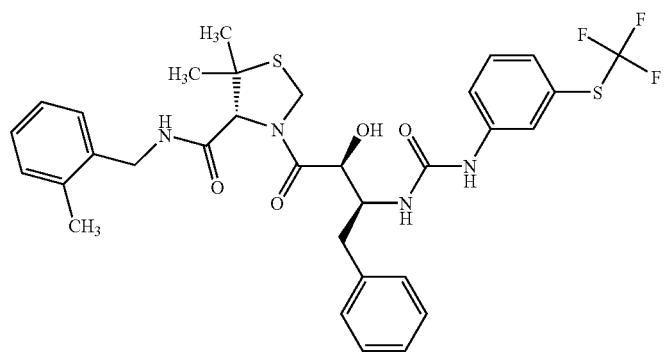
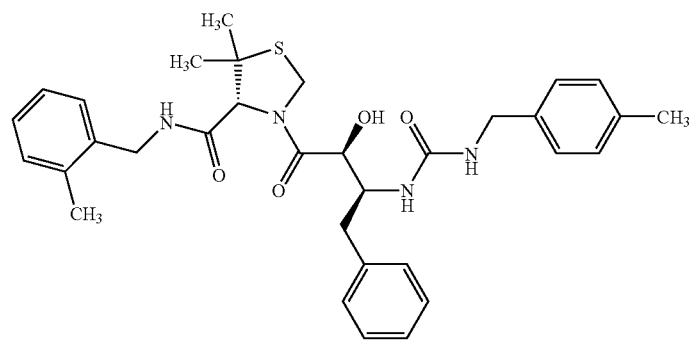

TABLE 3-continued
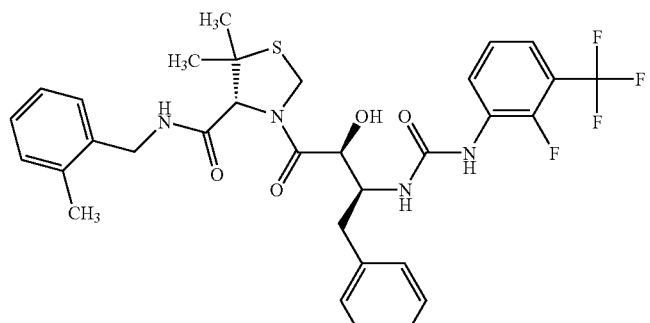
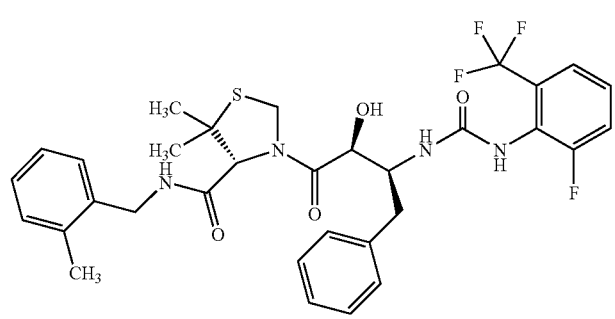
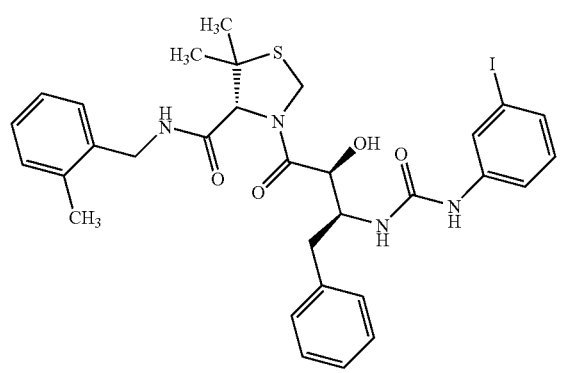
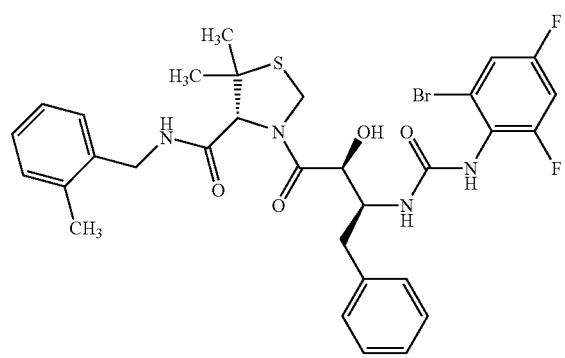

TABLE 3-continued
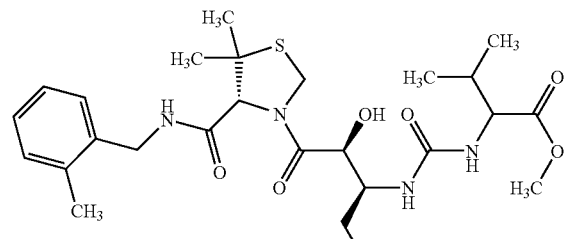
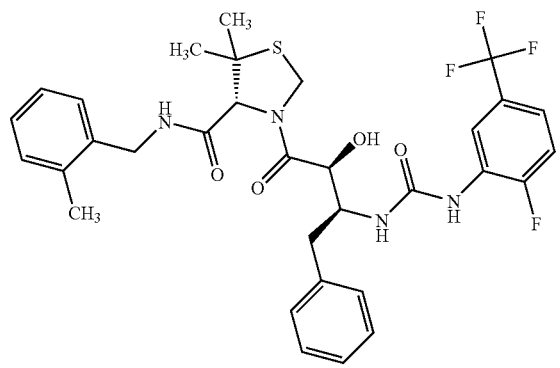
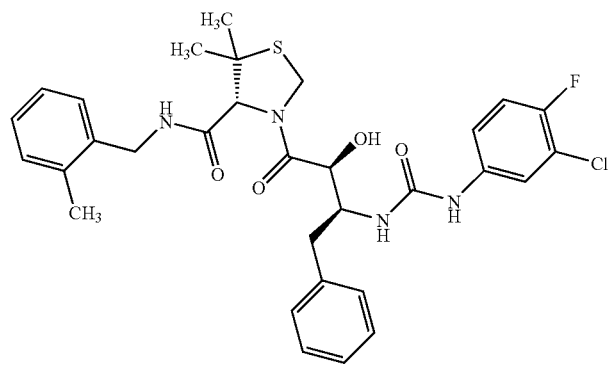
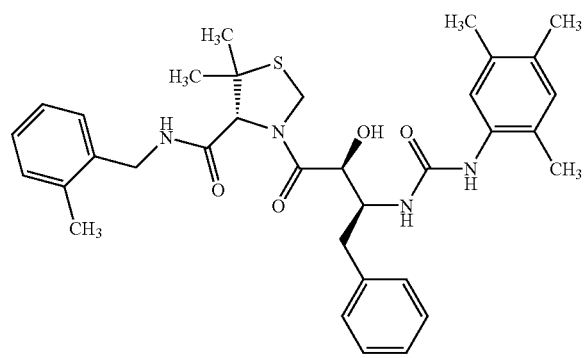

TABLE 3-continued
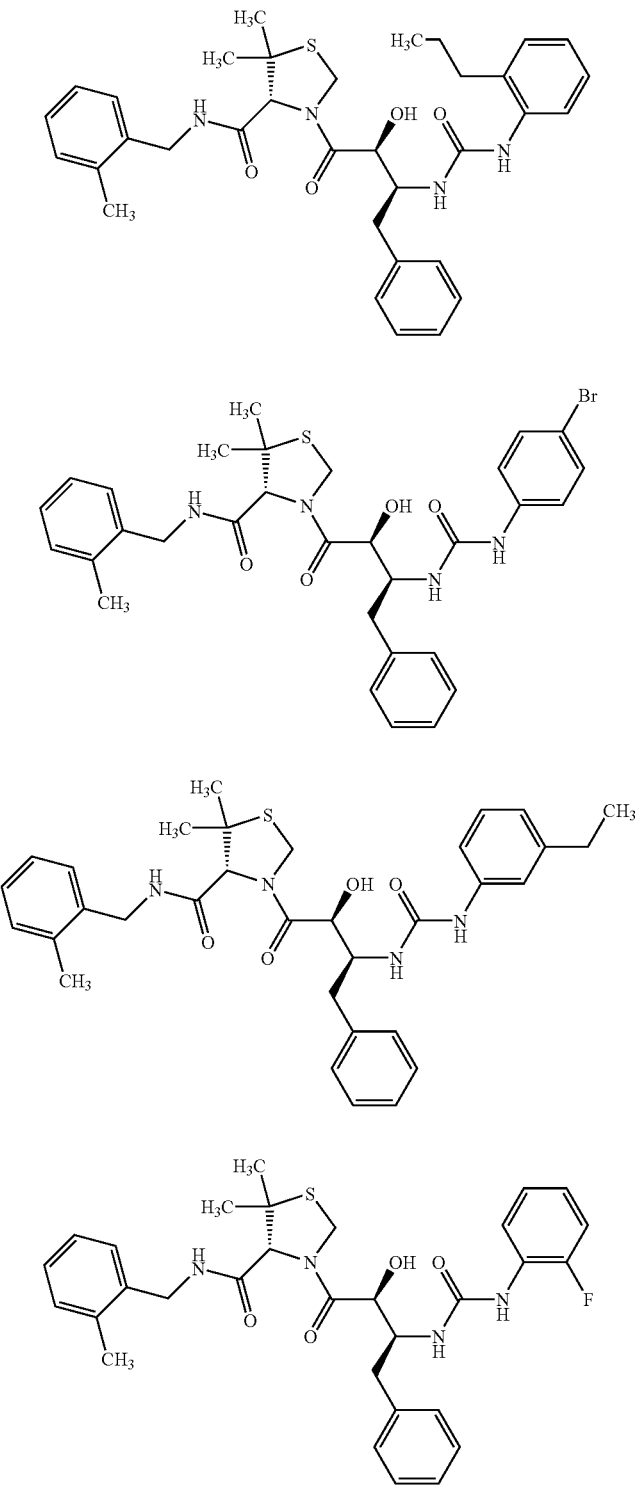

TABLE 3-continued
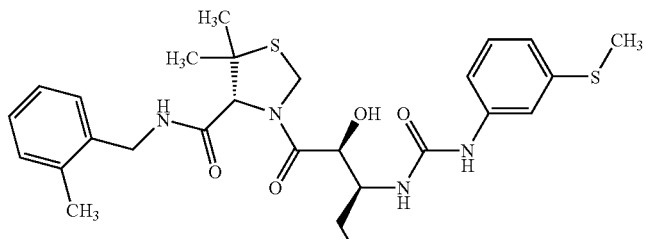
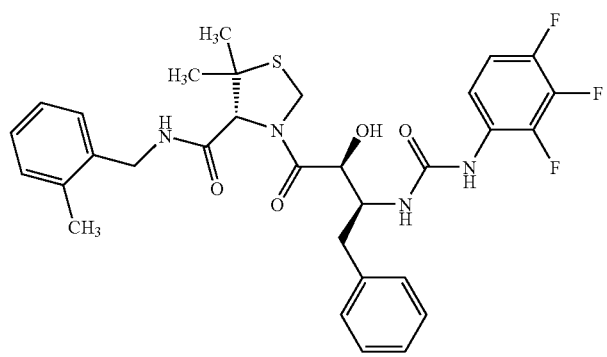
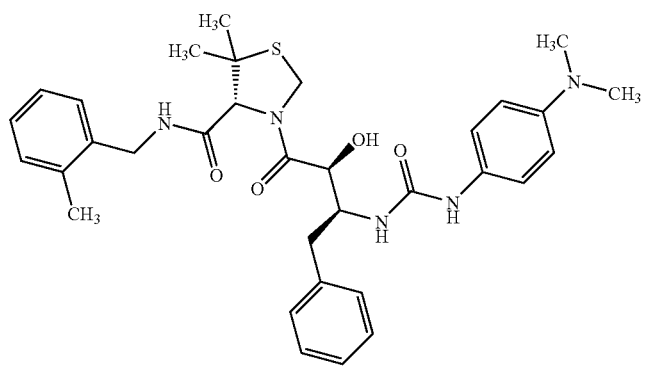
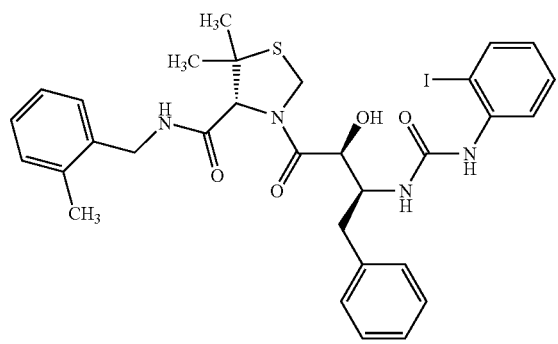

TABLE 3-continued
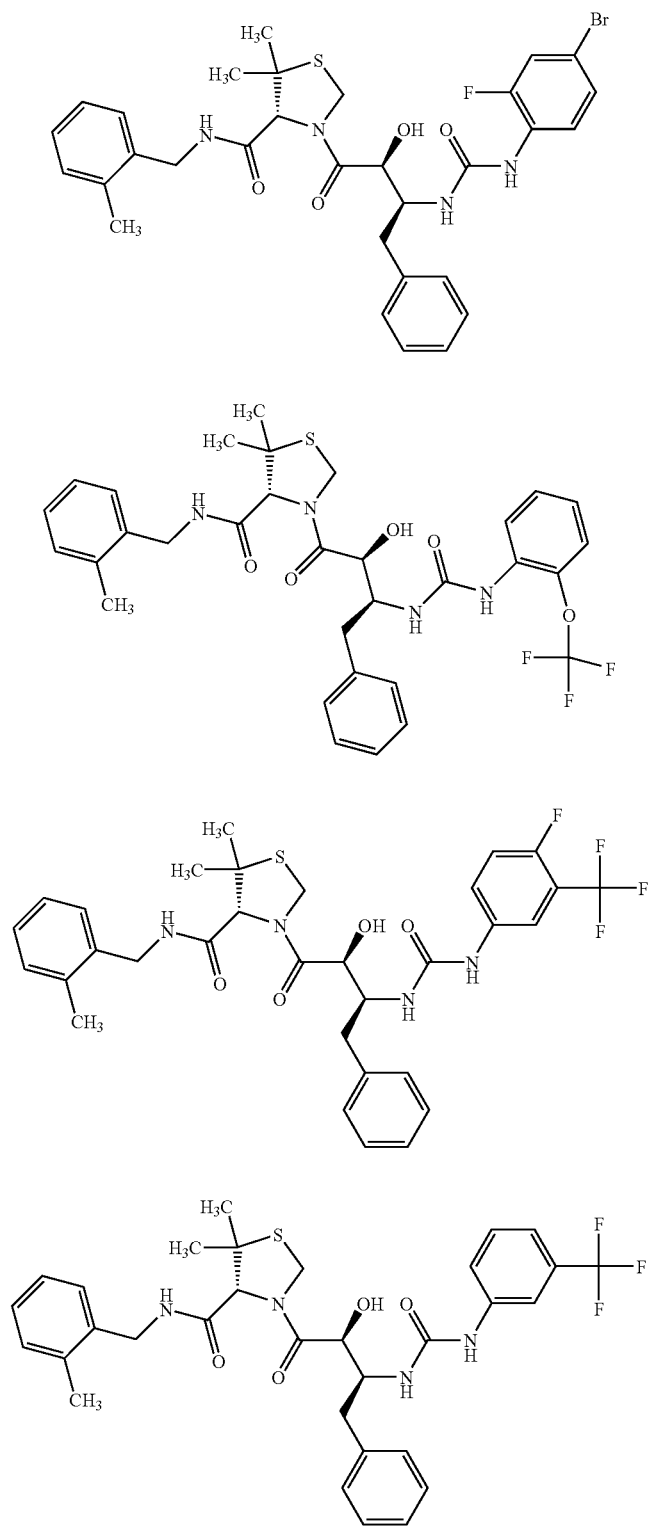

TABLE 3-continued
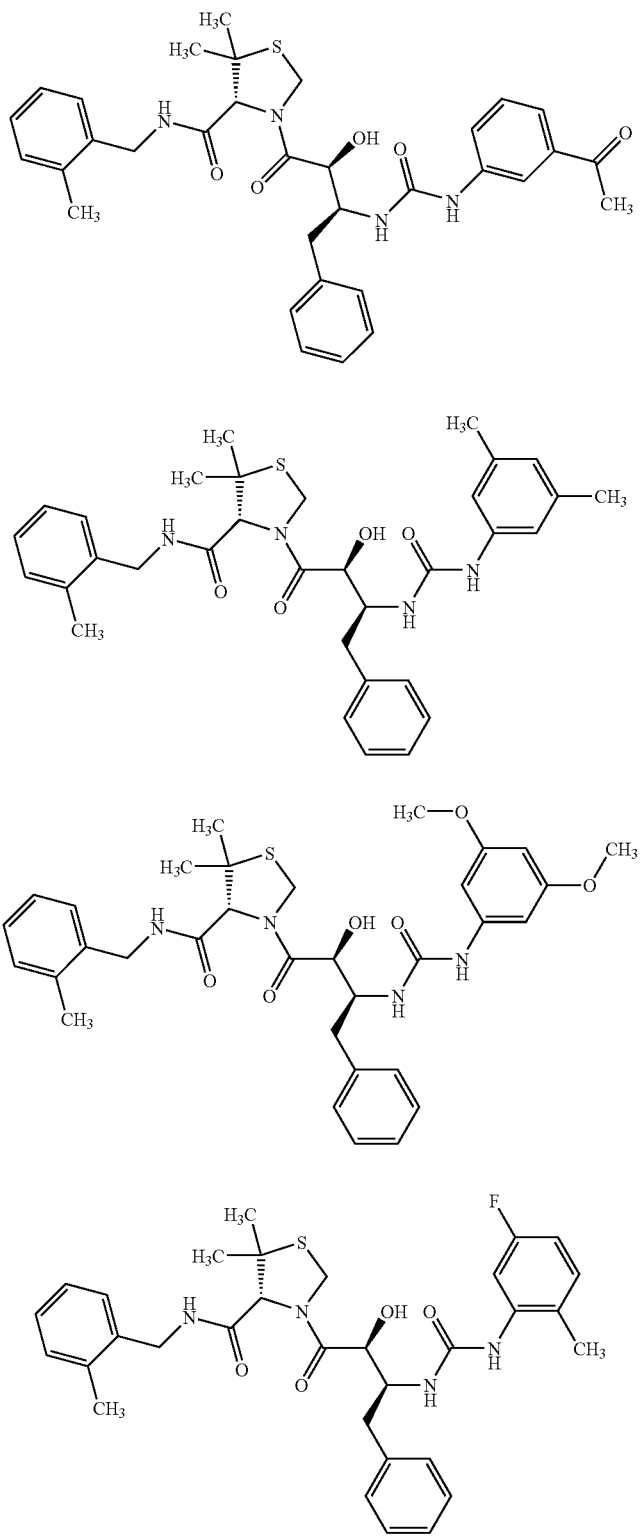

TABLE 3-continued
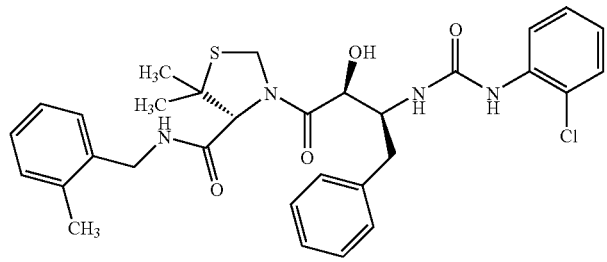
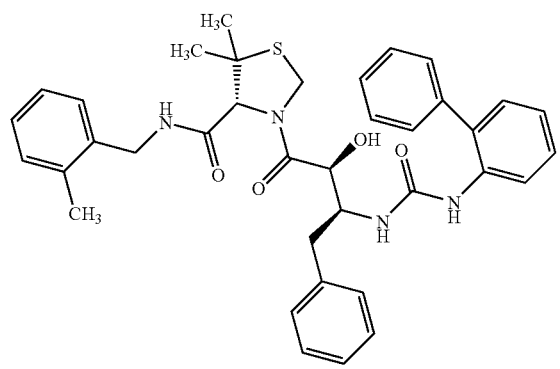
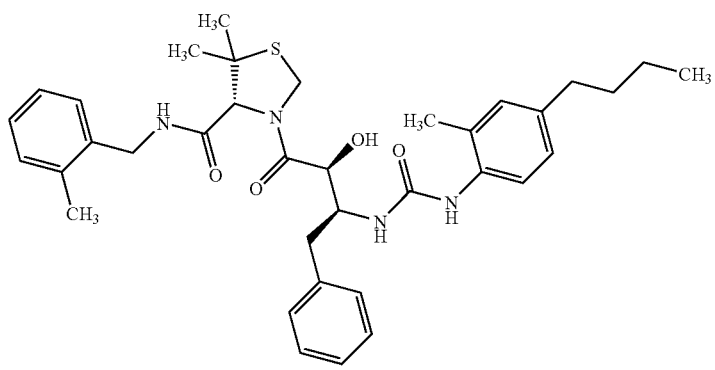
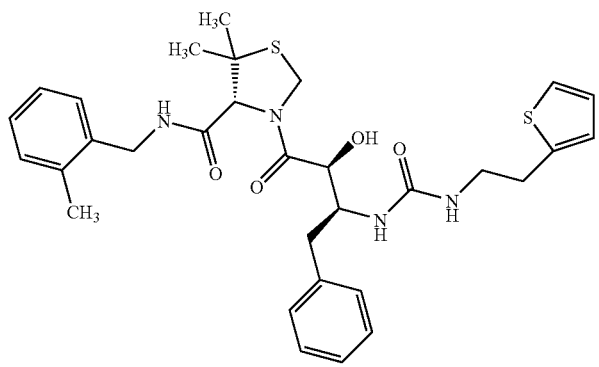

TABLE 3-continued
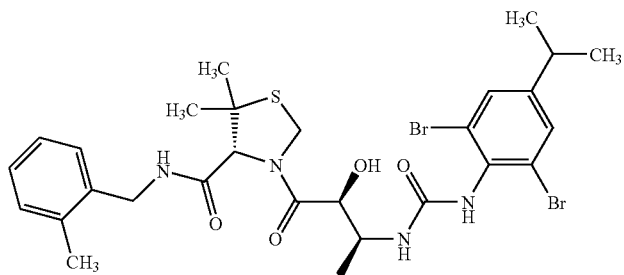
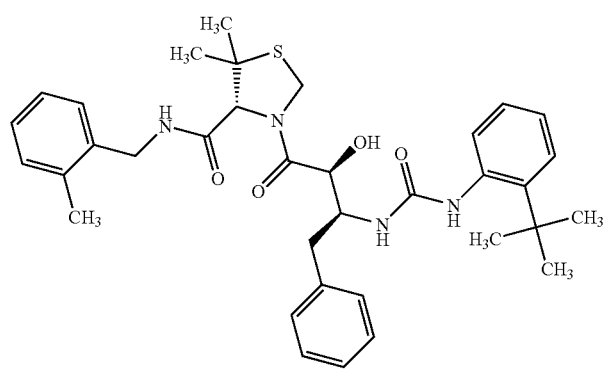
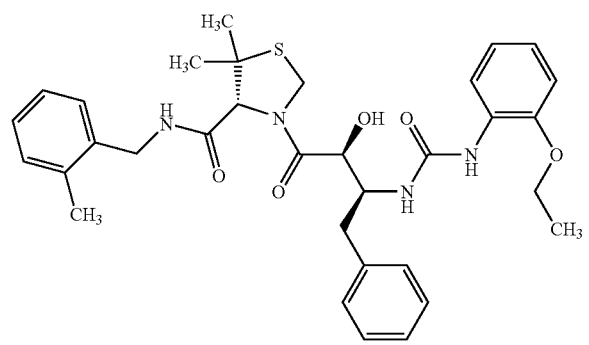
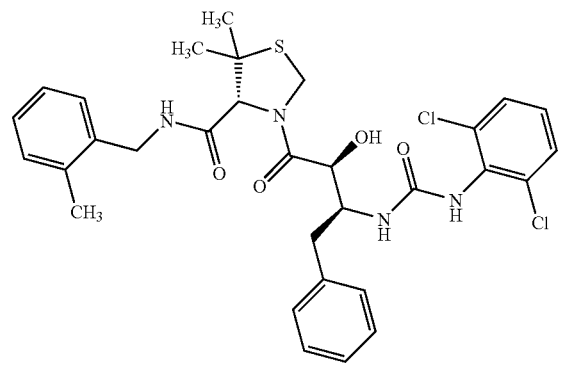

TABLE 3-continued
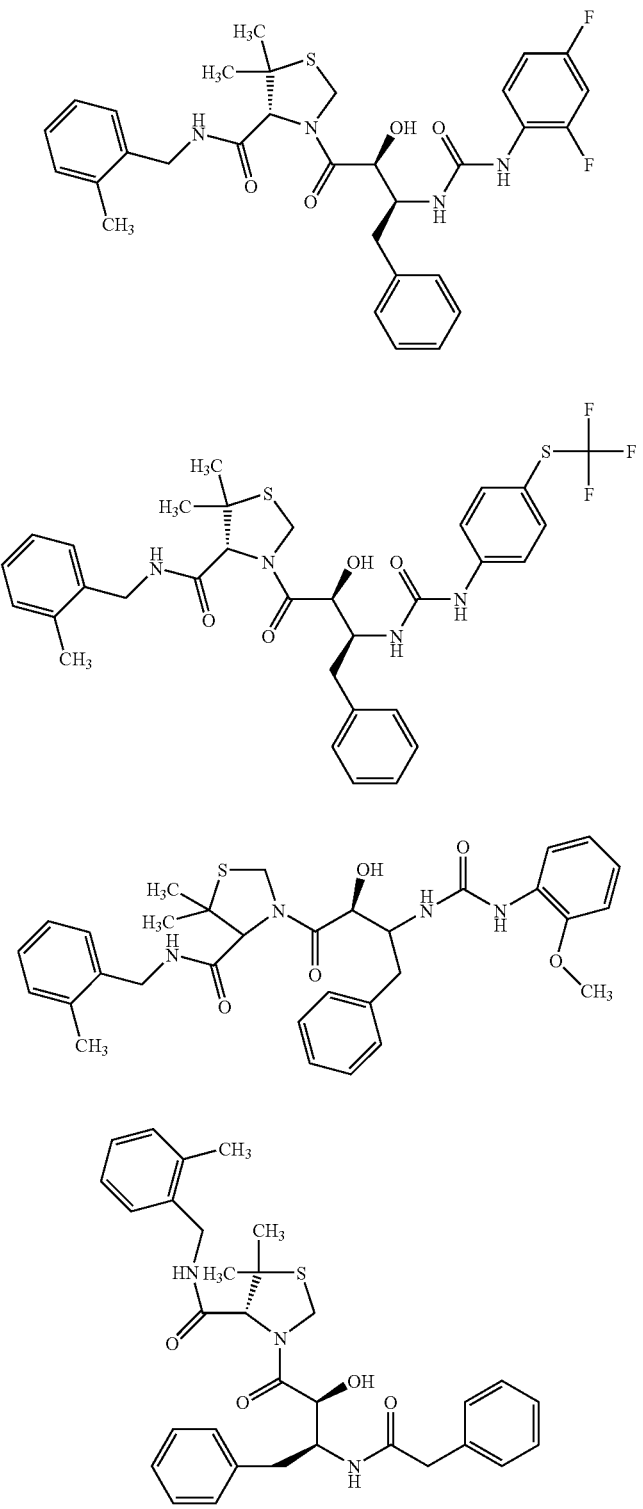

TABLE 3-continued
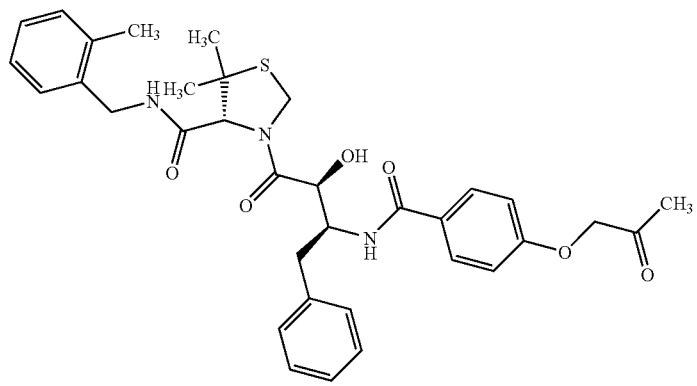
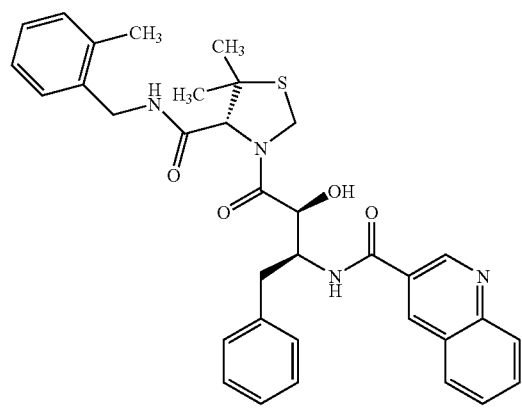
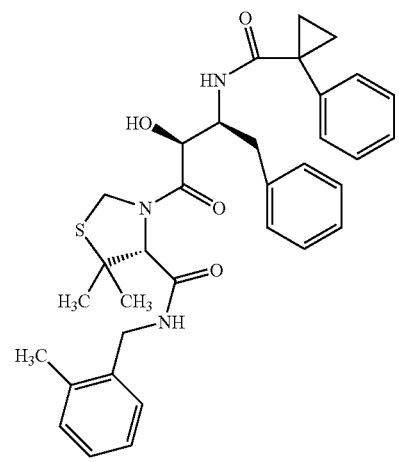

TABLE 3-continued
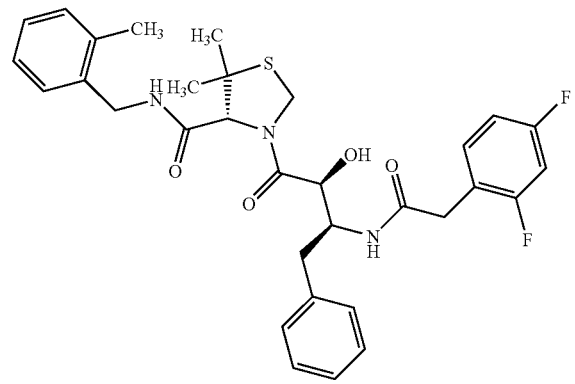
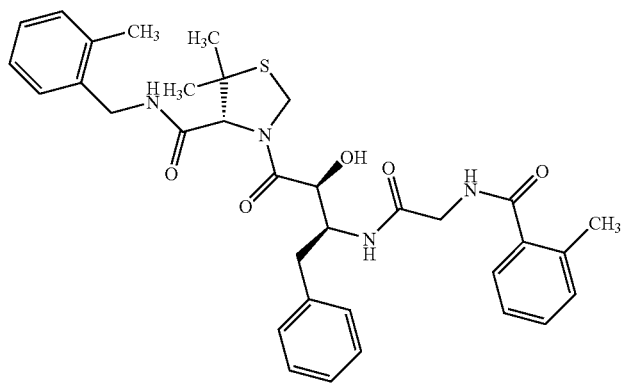
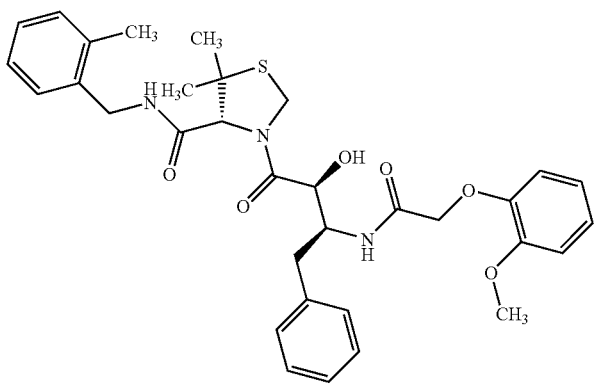
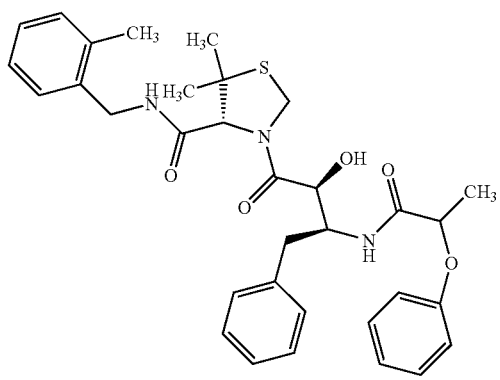

TABLE 3-continued
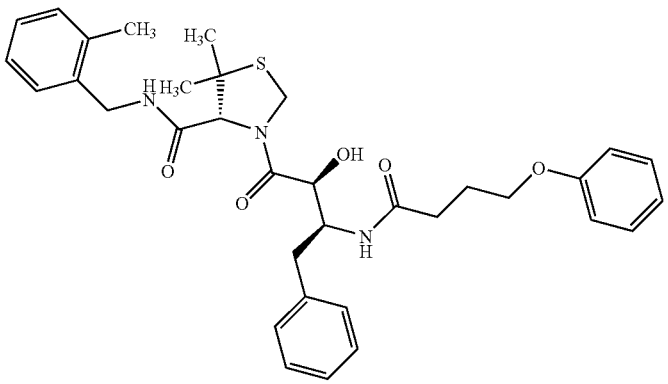
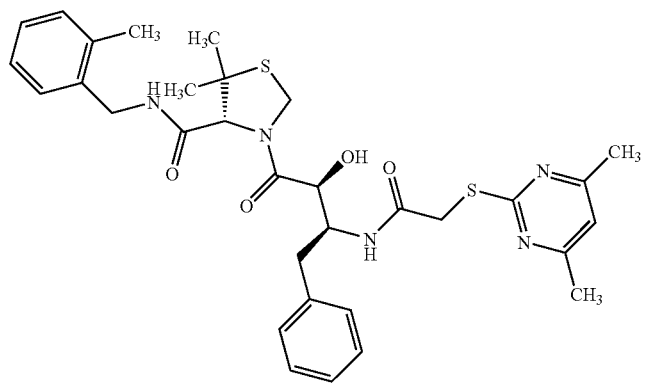
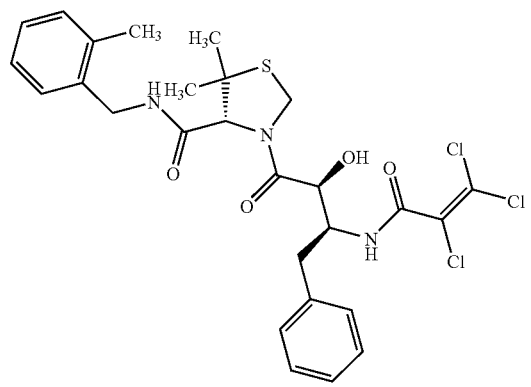
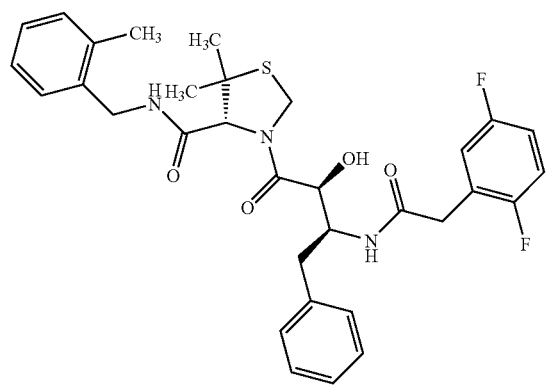

TABLE 3-continued
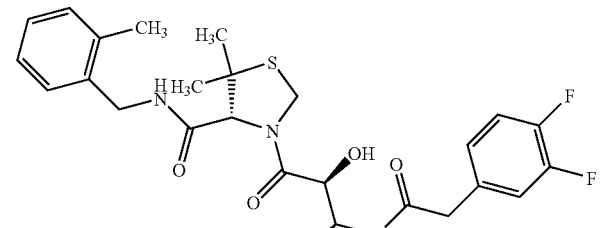
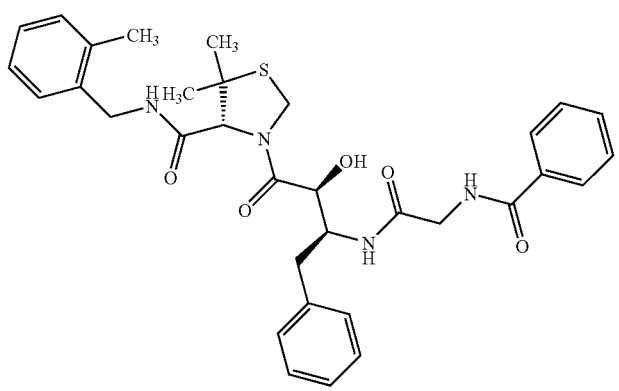
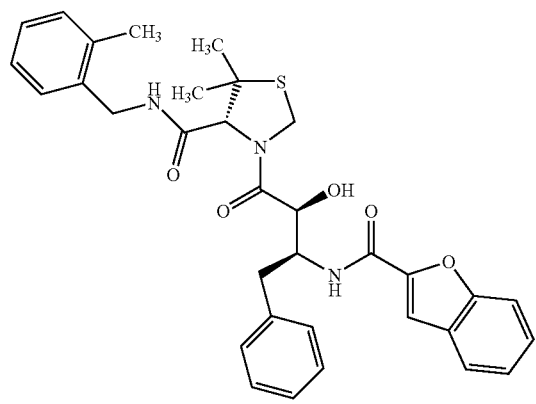
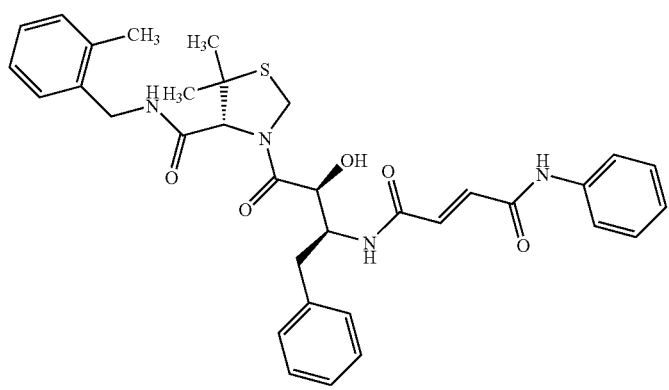

TABLE 3-continued
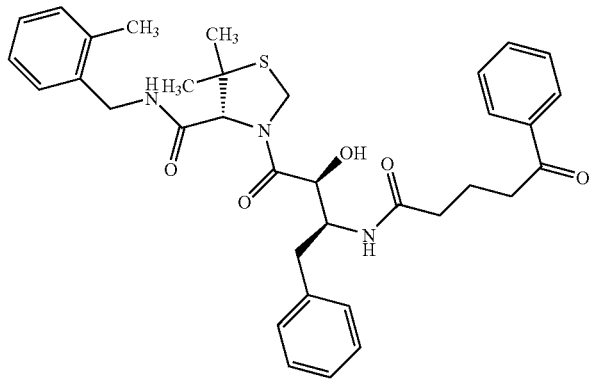
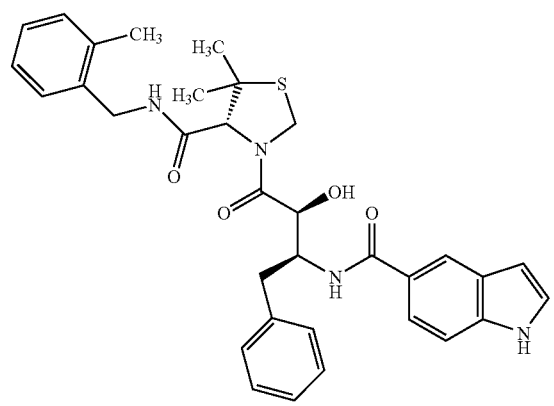
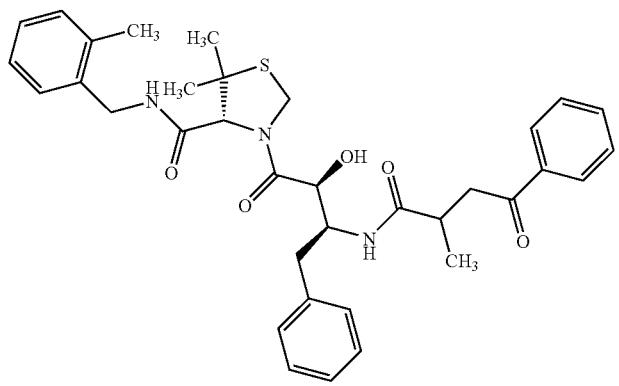
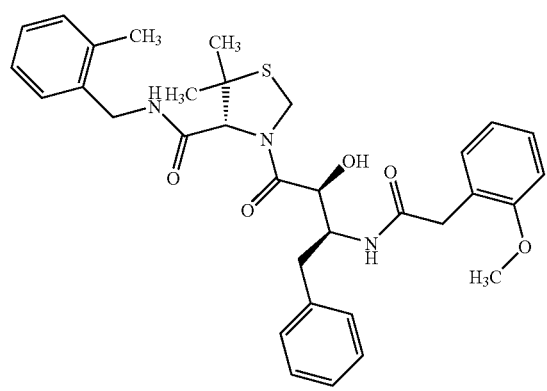

TABLE 3-continued
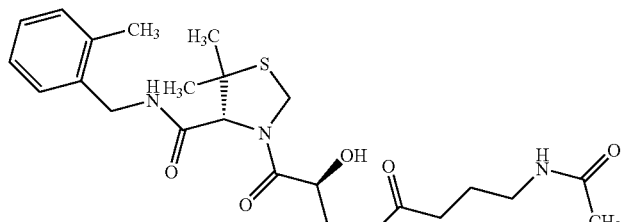
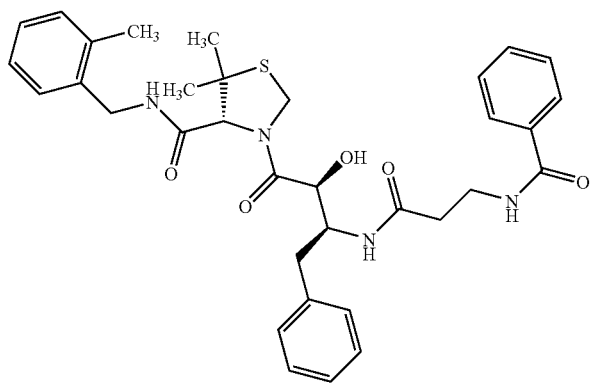
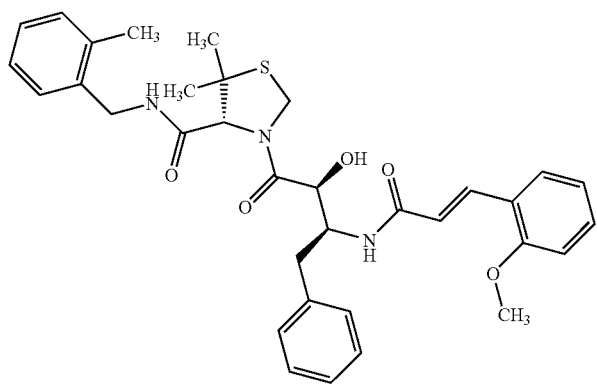
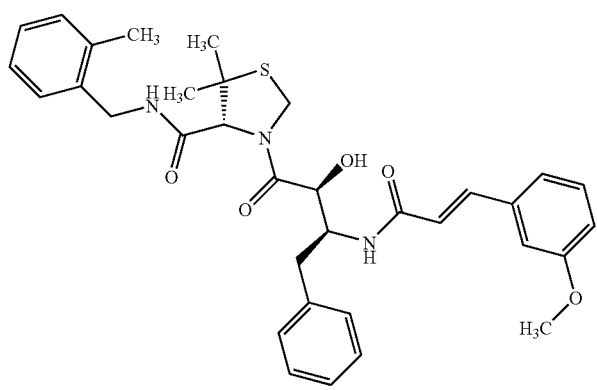

TABLE 3-continued
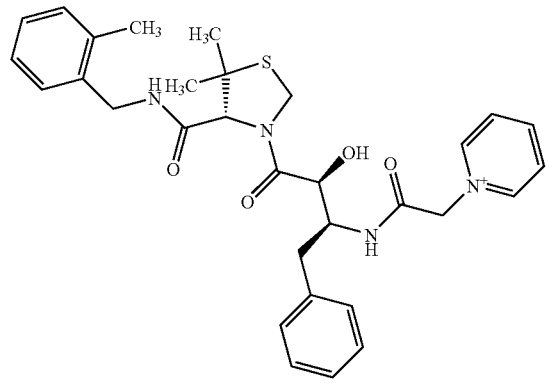
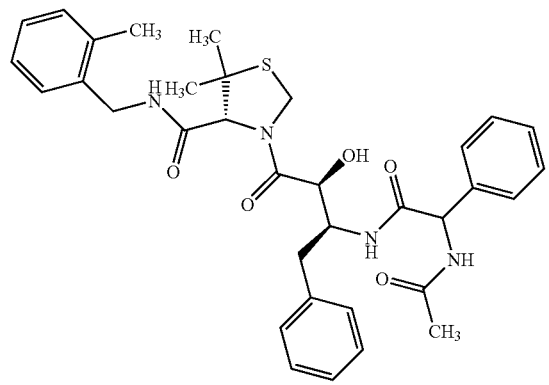
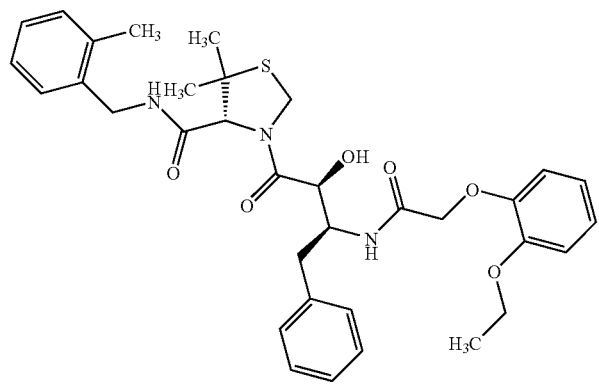
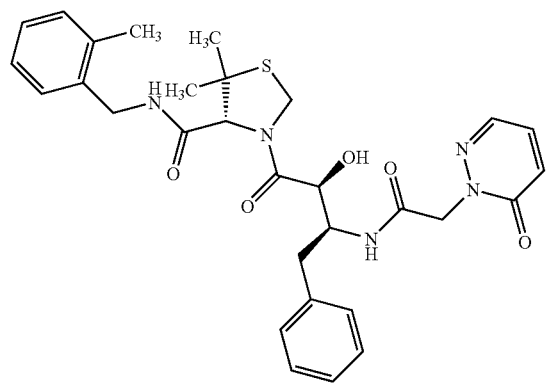

TABLE 3-continued
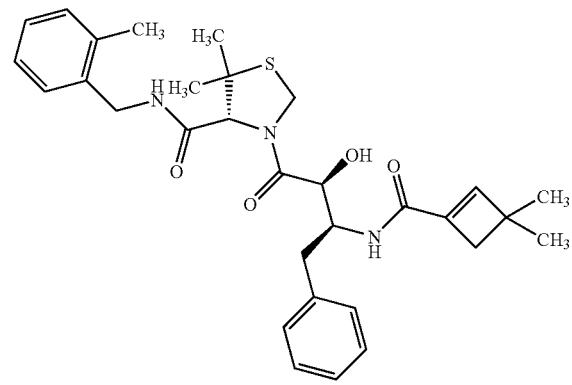
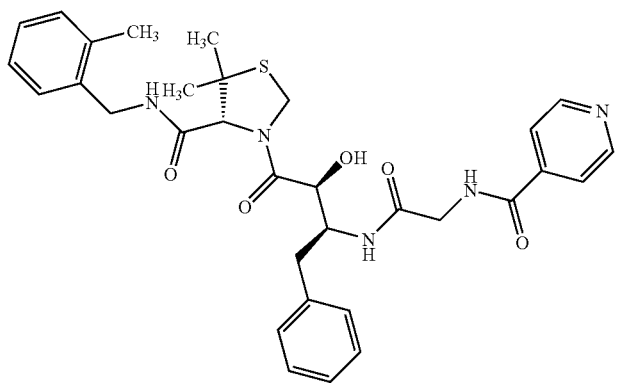
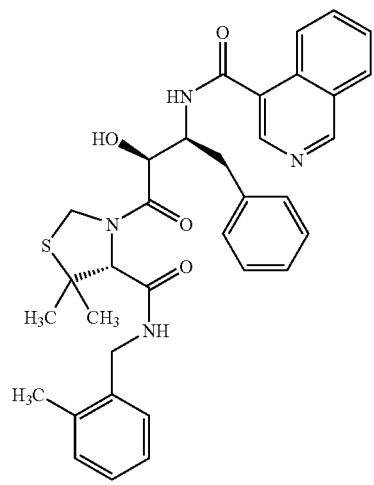

TABLE 3-continued
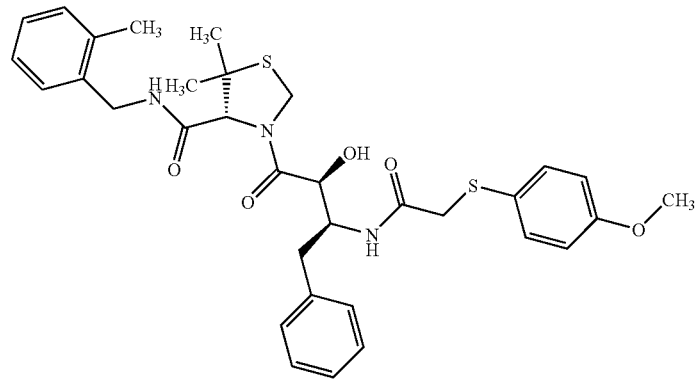
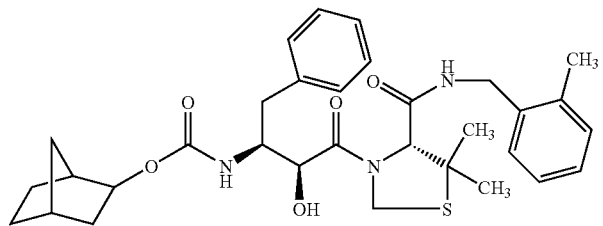
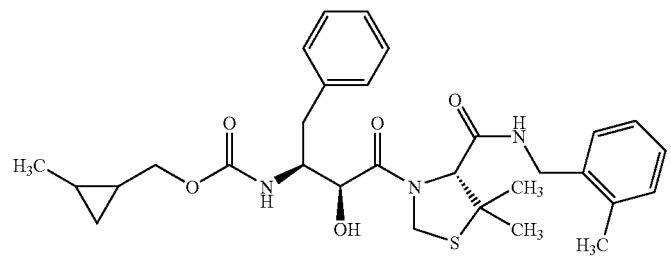
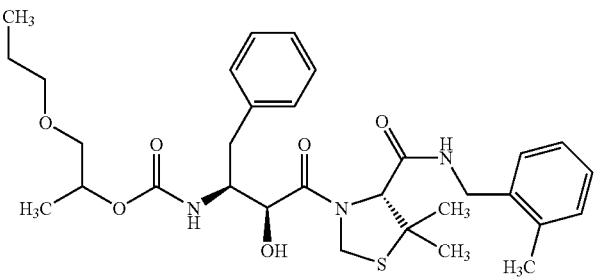
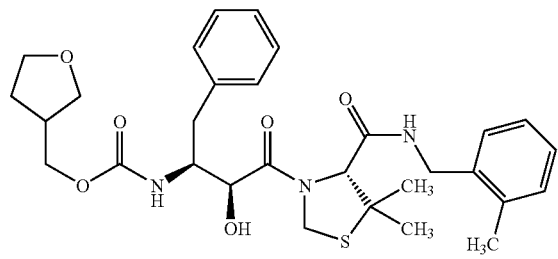

TABLE 3-continued
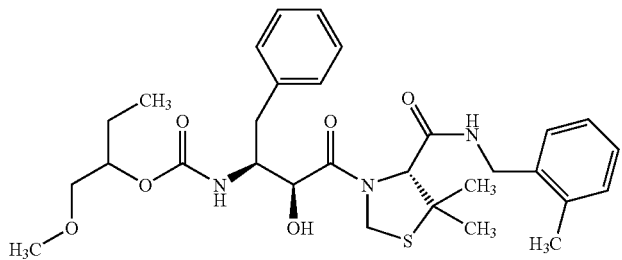
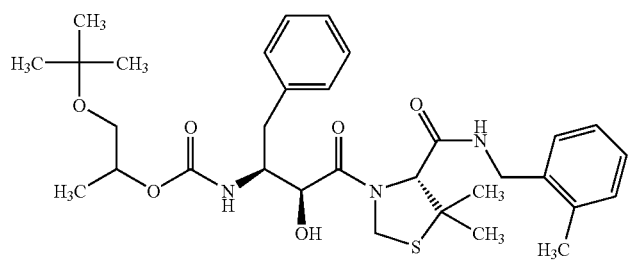
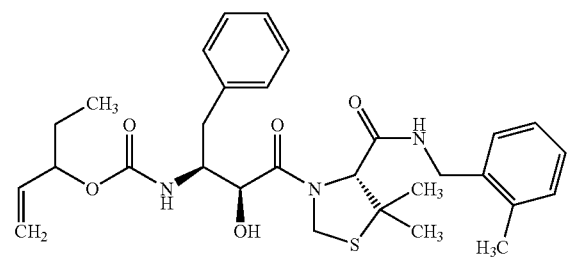
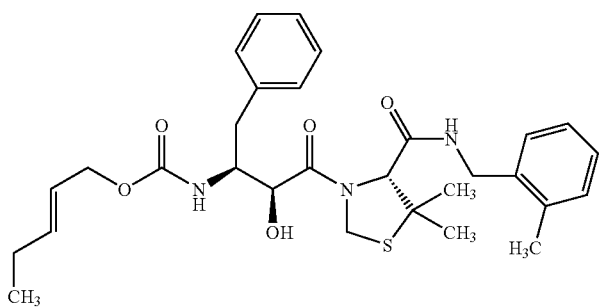
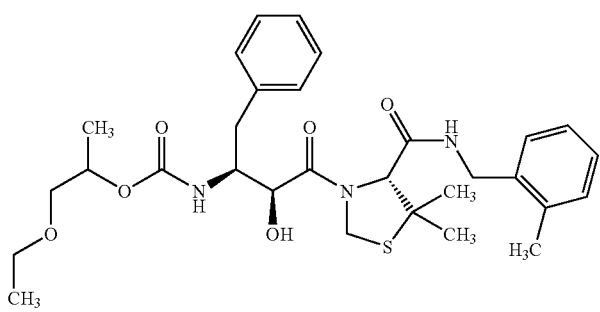

TABLE 3-continued
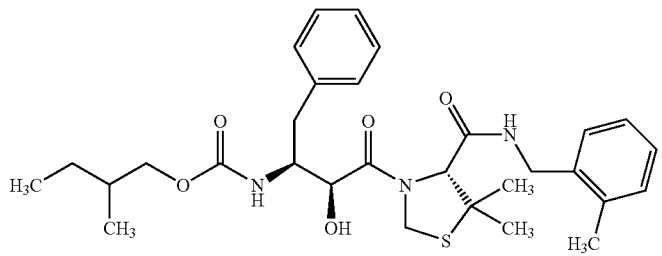
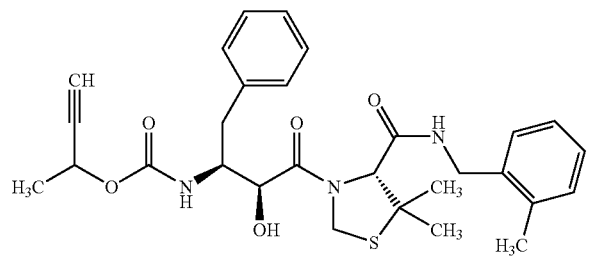
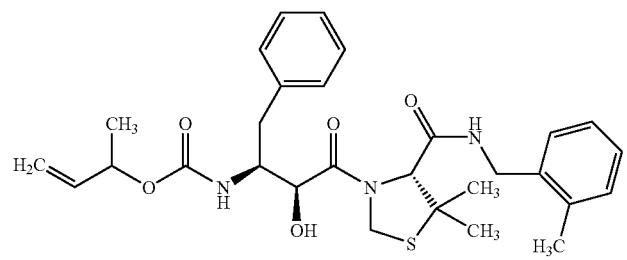
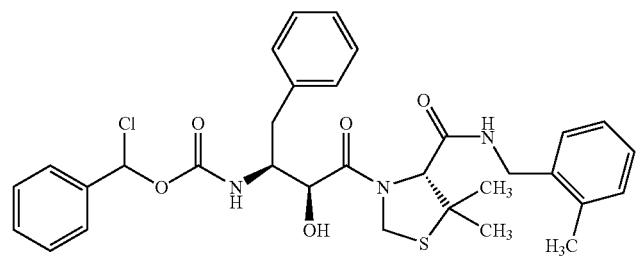
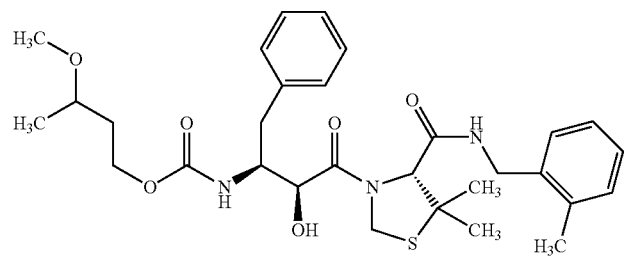

TABLE 3-continued
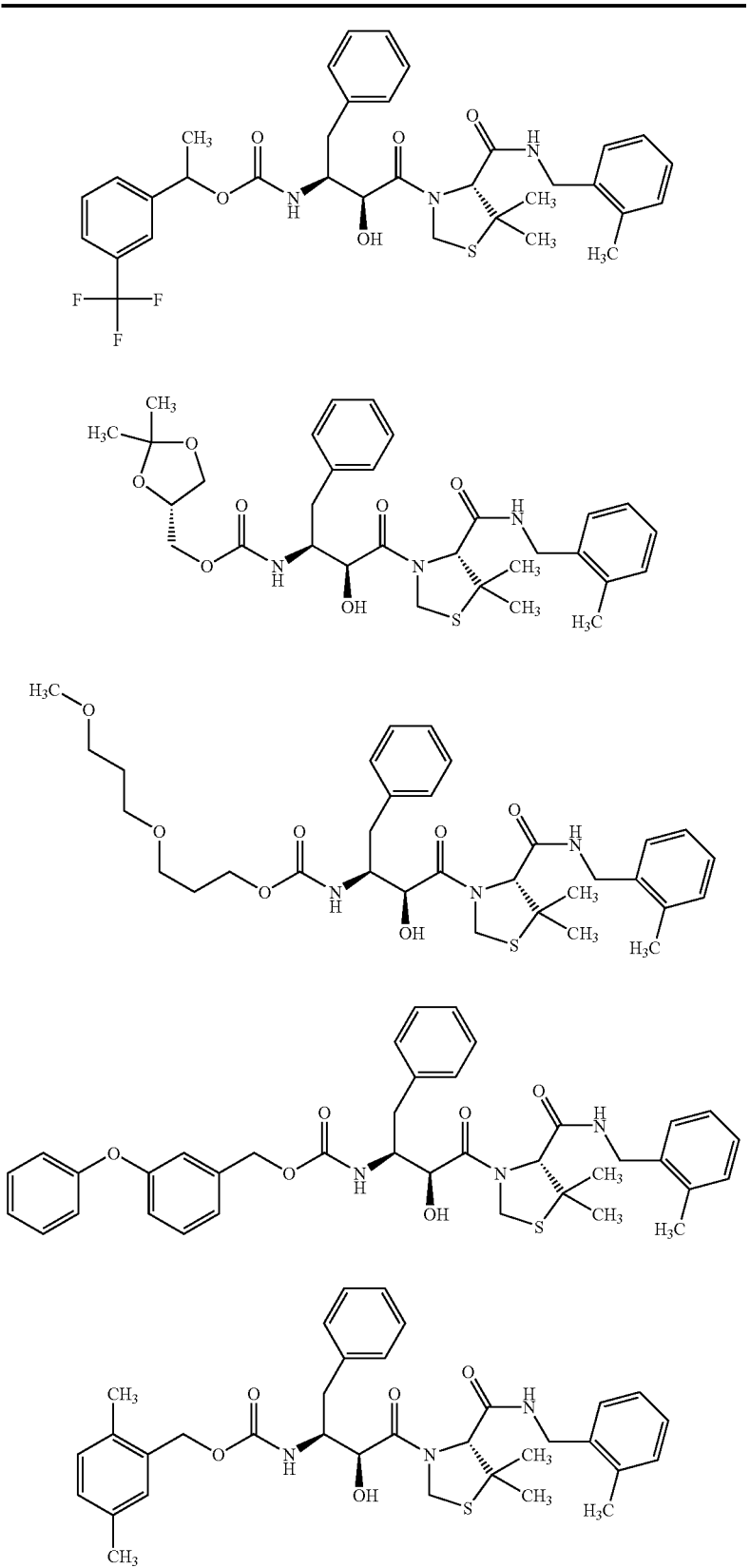

TABLE 3-continued
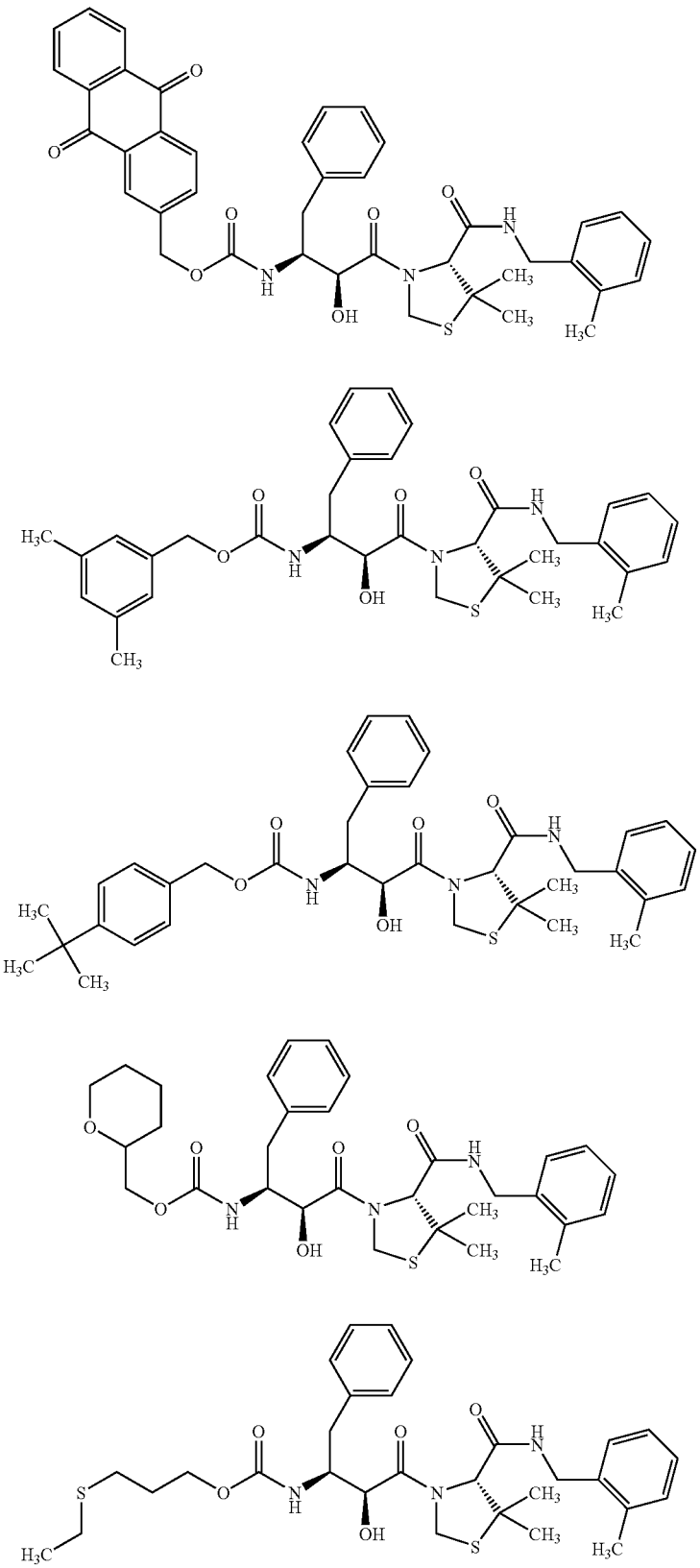

TABLE 3-continued
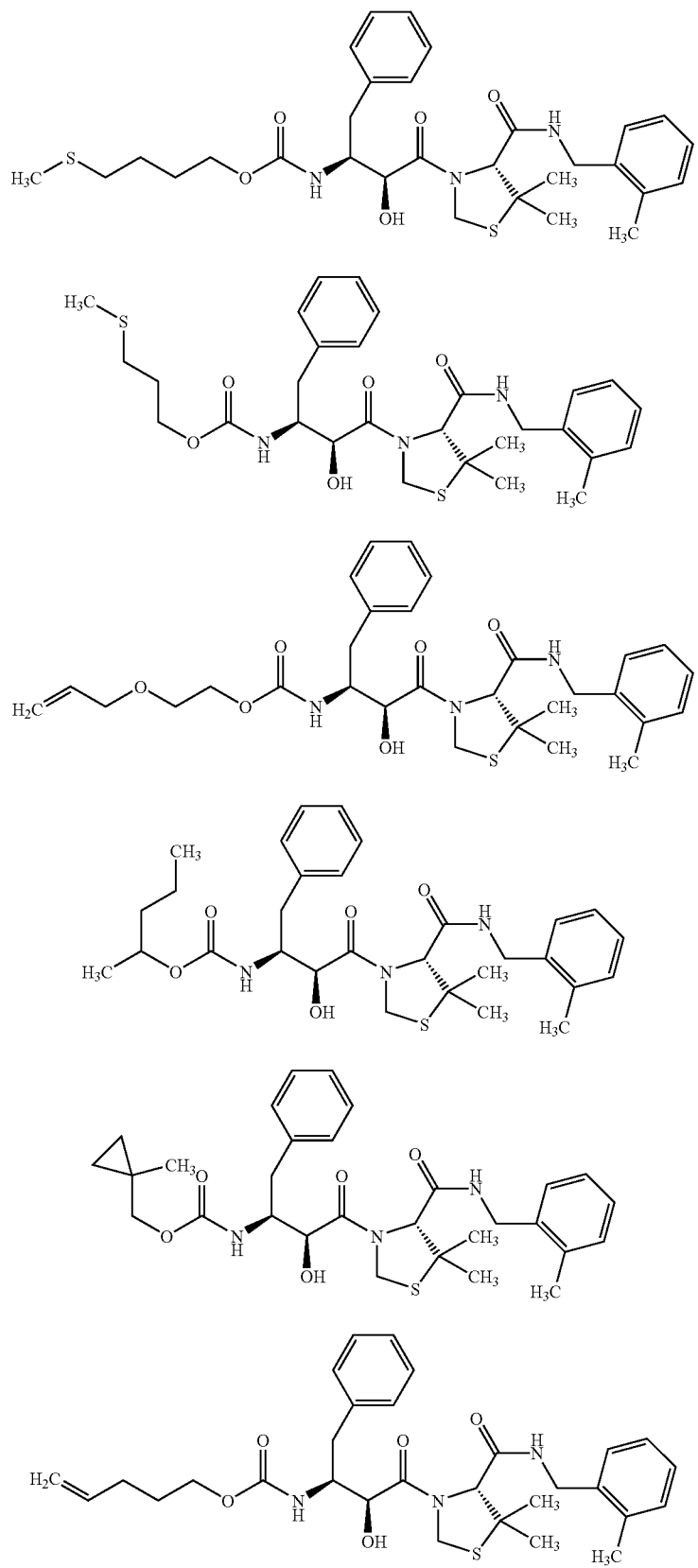

TABLE 3-continued
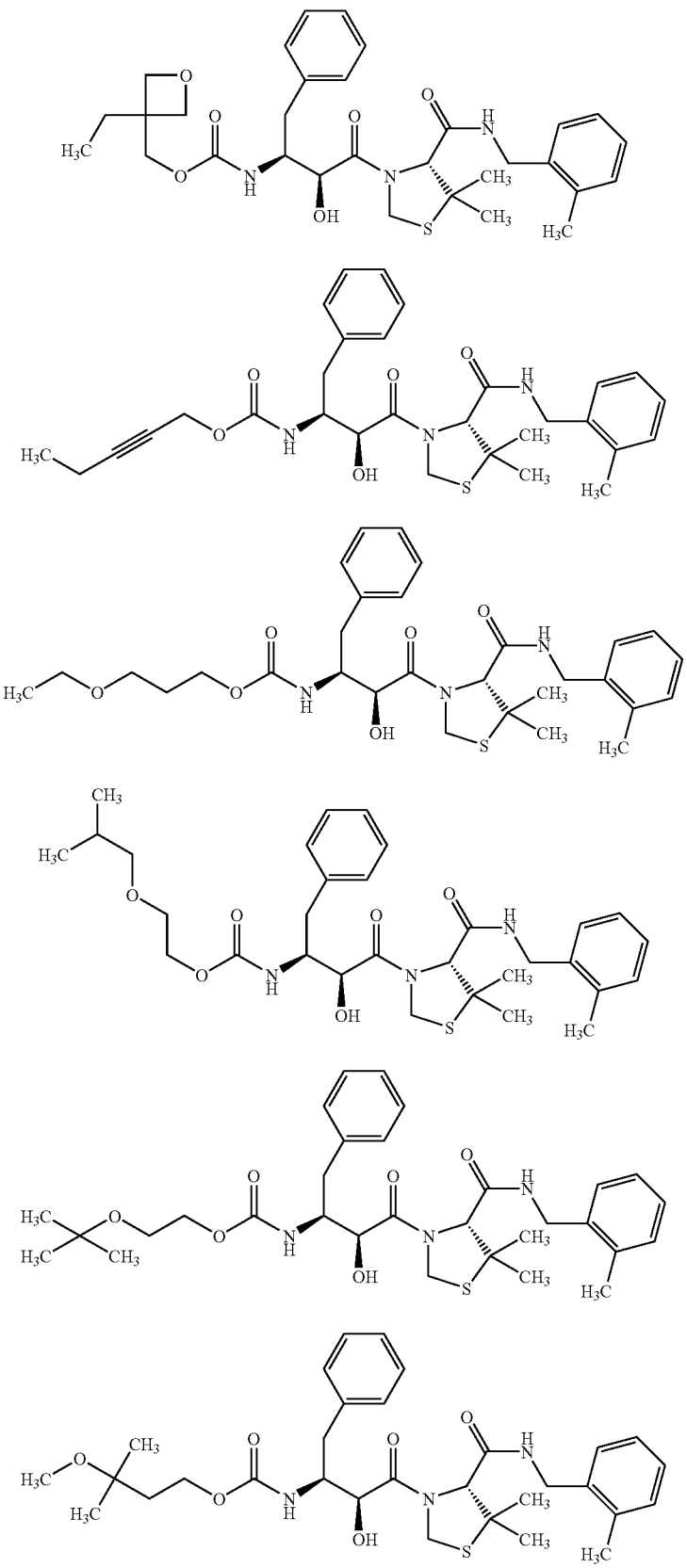

TABLE 3-continued
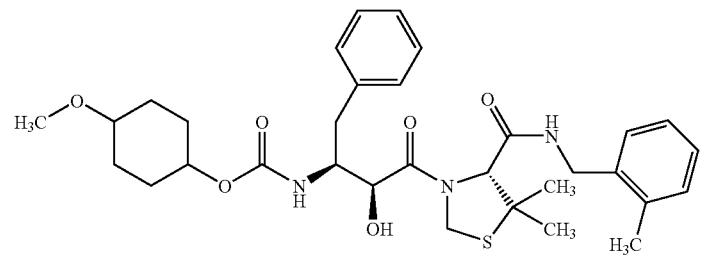
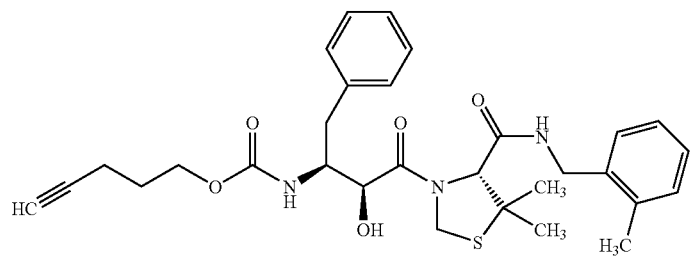
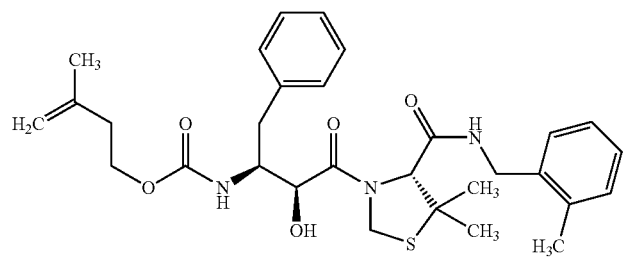
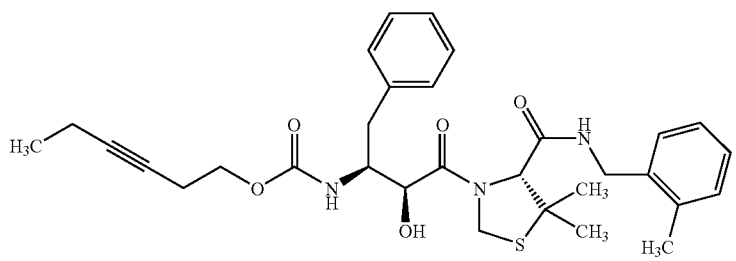
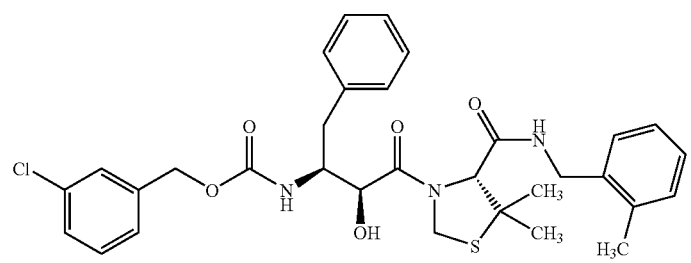
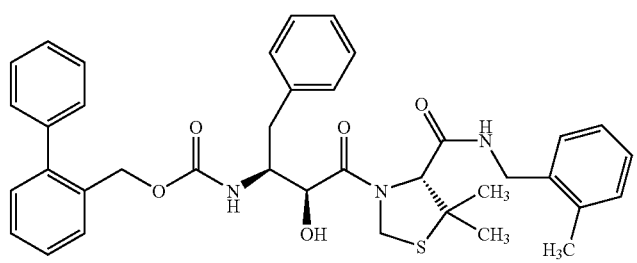

TABLE 3-continued
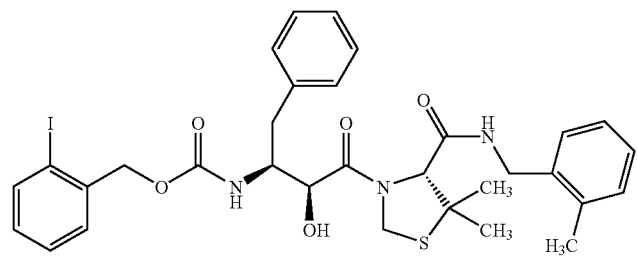
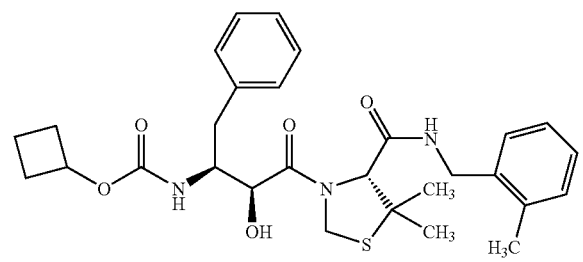
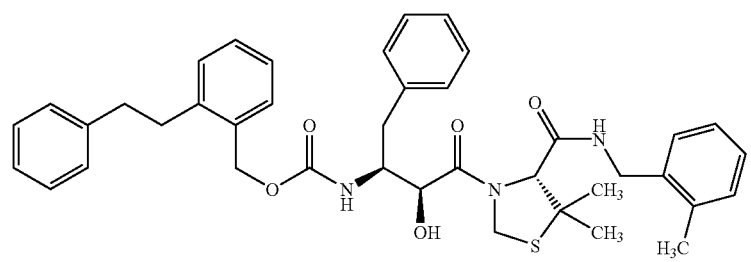
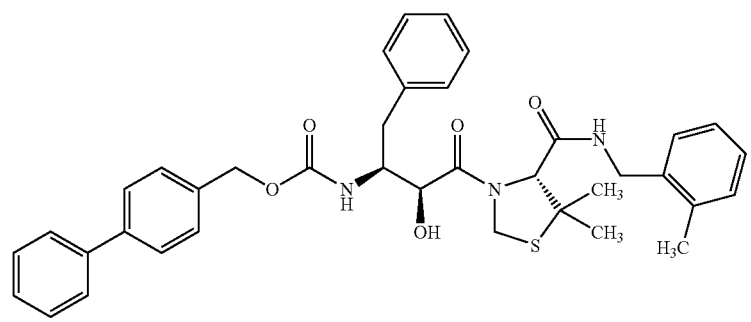
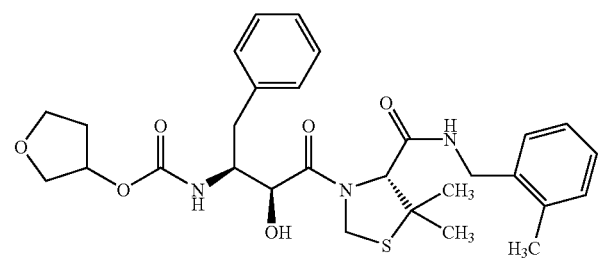

TABLE 3-continued

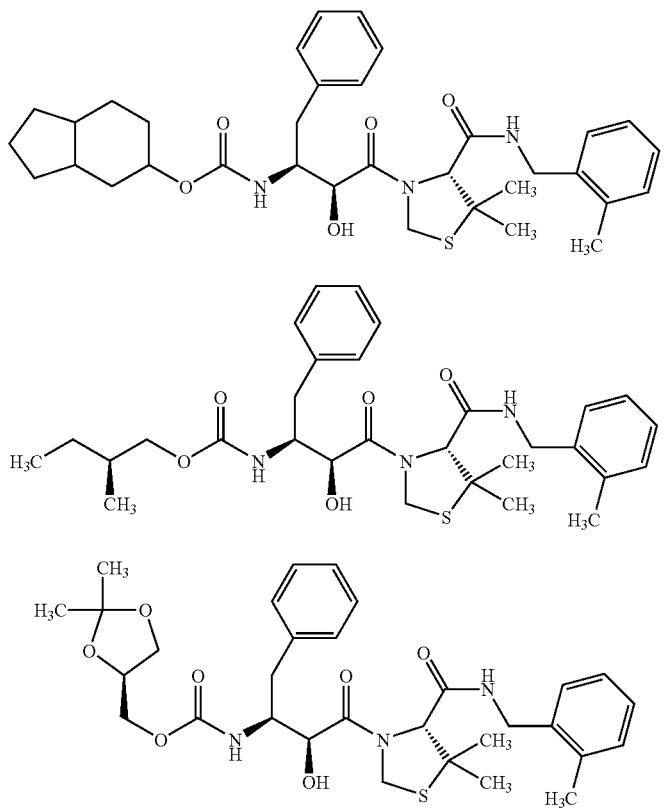

BIOLOGICAL EVALUATION

Cells and Virus

T-cell lines, CEM-SS, and MT-2, and viruses HIV-1 RF and HIV-1 NL4-3 (pNL4-3) were obtained from the National Institutes of Health (AIDS Research and Reference Reagent Program, Bethesda, Md.). HIV-1 NL4-3(I84V/L90M) was derived from a clinical isolate that exhibited the protease inhibitor-resistance associated substitutions I84V and L90M, by cloning of an reverse transcriptase-polymerase chain reaction amplified fragment into the unique Age I and Spe I restriction sites of pNL4-3.

Cytopathic Effect (CPE) Inhibition Assays

The ability of compounds to protect cells against HIV infection was measured by the MTT dye reduction method, essentially as described (See Pauwels, R. Balzarini, J. Baba, M. Snoeck, R. Schols, D. Herdewijn, P. Desmyter, J. and De Clercq, E. 1988, "Rapid and automated tetrazolium-based calorimetric assay for the detection of anti-HIV compounds, ". *J. Virol. Methods.*, 20: 309–321 and Weislow, O. S. Kiser, R. Fine, D. L. Bader, J. Shoemaker, R. H. and Boyd, M. R. 1989. "New soluble-formazan assay for HIV-1 cytopathic effects: application to high-flux screening of synthetic and natural products for AIDS-antiviral activity". *J. Natl. Cancer Inst.* 81:577–586). Subject cells were infected with test virus at an moi of 0.025 to 0.819 or mock infected with medium only and added at $2 \times 10^4$ cells per well into 96 well plates containing half-log dilutions of test compounds. Six days later, 50 µl of XTT (1 mg/ml XTT tetrazolium, 0.02 nM phenazine methosulfate) was added to the wells and the plate was reincubated for four hours. Viability, as determined by the amount of XTT formazan produced, was quantified spectrophotometrically by absorbance at 450 nm. Data from CPE assays were expressed as the percent of formazan produced in compound-treated cells compared to formazan produced in wells of uninfected, compound-free cells. The fifty percent effective concentration ($EC_{50}$) was calculated as the concentration of compound that effected an increase in the percentage of formazan production in infected, compound-treated cells to 50% of that produced by uninfected, compound-free cells. The 50% cytotoxicity concentration ($CC_{50}$) was calculated as the concentration of compound that decreased the percentage of formazan produced in uninfected, compound-treated cells to 50% of that produced in uninfected, compound-free cells. The therapeutic index was calculated by dividing the cytotoxicity ($CC_{50}$) by the antiviral activity ($EC_{50}$).

Susceptibility Assays

Compounds were tested in phenotypic susceptibility assays at Virologic, Inc., (See Petropoulos C. J., Parkin N. T., Limoli K. L., Lie Y. S., Wrin T., Huang W., Tian H., Smith D., Winslow G. A., Capon D J, Whitcomb J M. 2000, "A novel phenotypic drug susceptibility assay for human immunodeficiency virus type 1," *Antimicrob Agents Chemother* 44(4):920–928) or using the assay described here. MT-2 cells were infected with either HIV-1 NL4-3 or HIV-1 NL4-3(I84V/L90M) and incubated in the presence of serial 0.5 log dilutions of test compounds. Three days later, culture supernatants were collected and virus production, as determined by p24 ELISA, was assayed. Percent inhibition was calculated as p24 concentration in compound-treated samples as compared to infected, compound-free controls. Inhibition of viral replication is determined by measuring reduction in HIV p24 present in the culture supernatant, using a Beckman-Coulter p24 HIV-1 Ag EIA kit and following the supplied protocol. Absorbance is read on a MRX microplate reader (Dynex Technologies). The $EC_{50}$ was calculated as the concentration of compound that effected a decrease in the p24 production by infected, compound-treated cells to 50% of that produced by infected, compound-free cells.

HIV-1 Protease RET Assay

Ki's for the inhibitors of HIV-1 protease were determined using a resonance energy transfer (RET) assay. A mutant form of this enzyme (Q7S) is used for this assay because it is more stable against auto-proteolysis than the wild-type protein. This enzyme is first partially purified as inclusion bodies from cell lysate. It is then solublized in 8M urea and passed through a Q-Sepharose column (Pharmnacia) for further purification. To refold this protein, samples containing Q7S is dialyzed into 50 mM sodium phosphate pH 7.0, 50 mM NaCl, 10 mM DTT, and 10% glycerol.

The commercially available peptide substrate (Molecular Probes Cat. #H-2930) SEQ. ID NO: 1 RE(EDANS)SQNYPIVQK(DABCYL)R is used to assess activity and Ki's. This peptide is cleaved quantitatively by HIV-1 Pr at the Tyr-Pro bond. The EDANS fluorophore absorbs at 340 nm and emits at 490 nm. The reaction is carried out in a 96 well plate in a total volume of 100 μL and is run for 12 minutes at 37 C under steady-state conditions with 5 μM substrate and 2 nM active dimer enzyme concentration. The literature value Km for this substrate and enzyme is 103+/−8 μM (See Matayoshi, et al., "Novel Fluorogenic Substrates for Assaying Retroviral Proteases by Resonance Energy Transfer," *Science* 247, 954 (1990)). The buffer for this reaction is 0.1M sodium acetate pH 4.8, 1M NaCl, 1 mM EDTA, 5 mM dithiothreitol, 10% dimethyl sulfoxide and 1 mg/ml bovine serum albumin. Inhibition curves are fit using the Morrison tight binding equation.

| Example No. | Ave. $K_i$ (nM) | Ave CPE $EC_{50}$ (mM) | $EC_{50}$ or $IC_{50}$ (mM) |
|---|---|---|---|
| A1 | 0.21 | 0.029 | |
| A3 | 0.51 | 0.156 | |
| A4 | 2.2 | 0.27 | |
| A5 | 0.2 | 0.148 | |
| A6 | 0.23 | 0.036 | |
| A7 | 1.7 | 0.113 | |
| A8 | 1.4 | 0.451 | |
| A9 | 0.49 | 0.138 | 1.081 |
| A10 | <0.1 | 0.104 | 0.118* |
| A11 | 0.5 | 0.144 | |
| A12 | 5.5 | 0.127 | |
| A13 | 3.4 | 0.495 | 0.921* |
| A14 | 0.32 | 0.061 | 0.226* |
| A15 | <0.1 | 0.055 | 0.057* |
| A16 | 0.43 | 0.254 | |
| A17 | <0.1 | 0.024 | 0.049* |
| A18 | 0.3 | 0.027 | |
| A19 | 0.21 | 0.015 | |
| A20 | 0.16 | 0.035 | 0.219* |
| A21 | <0.1 | 0.049 | 0.655* |
| A22 | <0.1 | 0.138 | 0.318 |
| A23 | 2.6 | 0.017 | 0.048* |
| A24 | 0.52 | 0.466 | |
| A25 | 0.97 | 0.125 | |
| A26 | 0.6 | 0.168 | |
| A27 | <0.1 | 0.11 | |
| A28 | 3.4 | 0.327 | |

-continued

| Example No. | Ave. $K_i$ (nM) | Ave CPE $EC_{50}$ (mM) | $EC_{50}$ or $IC_{50}$ (mM) |
|---|---|---|---|
| A29 | 0.31 | 0.118 | |
| A30 | 10.9 | 0.586 | |
| A31 | 0.44 | 0.062 | |
| A32 | <0.1 | 0.012 | 0.055* |
| A33 | 5.1 | 0.749 | |
| A34 | 1.4 | 0.386 | |
| A35 | <0.1 | 0.016 | 0.041* |
| A36 | 0.78 | 0.343 | |
| A37 | 3.7 | 0.416 | |
| A38 | <0.1 | 0.038 | |
| A39 | <0.1 | 0.123 | 0.213 |
| A40 | <0.1 | 0.04 | 0.109 |
| A41 | 0.17 | 0.145 | 0.242 |
| A42 | <0.1 | 0.065 | 0.098 |
| A43 | 2.6 | 0.534 | |
| A44 | 1.4 | 0.478 | |
| A45 | <0.1 | 0.034 | 0.048 |
| A46 | 1.1 | 0.469 | |
| A47 | 0.27 | 0.196 | |
| A48 | <0.1 | 0.037 | 0.092 |
| A49 | 0.49 | 0.161 | |
| A50 | <0.1 | 0.024 | 0.125 |
| A51 | <0.1 | 0.159 | 0.05 |
| A52 | 0.51 | 0.456 | |
| A53 | <0.1 | 0.028 | 0.07 |
| A54 | 4.5 | 1.231 | |
| A55 | 0.21 | 0.054 | 0.798 |
| A56 | 0.27 | 0.042 | 0.378 |
| A57 | 5.6 | 1.531 | |
| A58 | 13% @ 64 nM | | |
| A59 | 0.19 | 0.417 | |
| A60 | 66.6 | | |
| A61 | 0.99 | 1.061 | |
| A62 | 9.6 | 2.261 | |
| A63 | 4.5 | 1.189 | |
| A65 | 0% @ 64 nM | | |
| B1 | 0.27 | 0.049 | 0.236* |
| B2 | 0.35 | 0.087 | |
| B3 | 2.5 | 0.905 | |
| B4 | 3 | 0.707 | |
| B5 | 1.2 | 0.314 | |
| B6 | 0.31 | 0.095 | 0.405* |
| B7 | <0.1 | 0.265 | 0.333* |
| B8 | 0.63 | 0.474 | |
| B9 | 1.1 | 0.452 | |
| B10 | 0.57 | 0.386 | |
| B11 | 0.86 | 0.567 | 2.015 |
| B12 | 9.9 | >1 | |
| B13 | 2 | 1.458 | |
| B14 | 2.7 | 1.661 | |
| B15 | 1.3 | 2.305 | |
| B16 | 2.6 | 1.566 | |
| B17 | 4.8 | | |
| B18 | 0.56 | 1.25 | |
| B19 | 1.4 | 1.595 | 1.298 |
| B20 | 2.1 | 1.563 | 2.084* |
| B21 | 0.91 | 0.109 | 0.547* |
| B22 | 12 | 0.246 | |
| B23 | 0.15 | 0.294 | |
| B24 | 8.3 | 0.512 | |
| B25 | 21 | >1 | |
| B26 | 2.1 | 0.348 | |
| B27 | 0.5 | 0.506 | |
| B28 | 4.2 | 0.731 | |
| B29 | 0.82 | 0.063 | |
| B30 | 0.21 | 0.443 | |
| B31 | 4.7 | >1 | |
| B32 | 0.48 | 0.433 | |
| B33 | <0.1 | 0.045 | 0.604* |
| B34 | 1.2 | 0.389 | |
| B35 | 11 | 0.564 | |
| B36 | <0.1 | 0.519 | |
| B37 | 7.4 | 0.529 | |
| B38 | 0.16 | 0.6 | |
| B39 | 1.9 | 0.372 | |
| B40 | 15.1 | >1 | |

| Example No. | Ave. $K_i$ (nM) | Ave CPE $EC_{50}$ (mM) | $EC_{50}$ or $IC_{50}$ (mM) |
|---|---|---|---|
| B41 | 0.11 | 0.268 | |
| B42 | 0.13 | 0.155 | |
| B43 | <0.1 | 0.375 | |
| B44 | 4.8 | 0.66 | |
| B45 | 1.1 | 0.572 | |
| B46 | 93 | | |
| B47 | 1.9 | 1.477 | |
| B48 | 0.83 | 1.478 | |
| B49 | 120 | | |
| B50 | 7.4 | | |
| B51 | 0.99 | >3.2 | |
| B52 | 120 | | |
| B54 | 2.3 | 1.659 | |
| B55 | 679 | | |
| B56 | 153 | | |
| B57 | 16% @ 64 nM | | |
| B58 | 240 | | |
| B59 | 2.1 | 1.815 | |
| B60 | 1.1 | >3.2 | |
| B61 | 16.9 | | |
| B62 | 4.2 | | |
| B63 | 7.8 | | |
| B64 | 0.53 | 1.603 | |
| B65 | 4.9 | 1.636 | |
| B66 | 5.2 | | |
| B67 | 11.4 | >3.2 | |
| B68 | 36 | | |
| B69 | 7.7 | | |
| B70 | 21 | | |
| B71 | 6.4 | | |
| B72 | 6.6 | | |
| B73 | 13 | | |
| B74 | 39 | | |
| B75 | 81 | | |
| B76 | 11.2 | | |
| B77 | <0.1 | 0.143 | 1.633 |
| B78 | 0.18 | 0.557 | |
| B79 | 0.78 | 0.53 | |
| B80 | 0.15 | 0.419 | 1.383 |
| B81 | 0.35 | 0.878 | |
| B82 | 0.19 | 1.286 | |
| B83 | <0.1 | 0.009 | 0.202 |
| B84 | <0.1 | 0.009 | 0.686 |
| B85 | 1.3 | 0.363 | |
| C1 | 0.38 | 0.627 | 0.427 |
| C3 | 0.16 | 0.486 | |
| C4 | 0.17 | 0.236 | 1.903 |
| C5 | 0.6 | 0.669 | 1.608 |
| C6 | 2.4 | 0.744 | 1.944 |
| C7 | 3 | 0.347 | |
| C8 | 1.5 | 0.152 | 1.419 |
| C9 | 6.3 | | |
| C10 | 1.5 | 1.289 | |
| C11 | 2.8 | 1.308 | |
| C12 | 2.7 | 1.768 | |
| C13 | 0.59 | 1.184 | |
| C14 | 2.5 | | |
| C15 | <0.1 | 0.025 | 0.057 |
| C16 | <0.1 | 0.019 | 0.201 |
| C17 | <0.1 | 0.115 | 0.186 |
| C18 | <0.1 | 0.148 | 0.618 |
| C19 | <0.1 | 0.055 | 0.084 |
| C20 | <0.1 | 0.035 | |
| C21 | <0.1 | 0.015 | 0.081 |
| C22 | <0.1 | 0.015 | 0.062 |
| C23 | <0.1 | 0.037 | 0.109 |
| C24 | <0.1 | 0.019 | 0.074 |
| C25 | <0.1 | 0.031 | 0.068 |
| C26 | <0.1 | 0.076 | 0.131 |
| C27 | 0.13 | 0.115 | 0.189 |
| C28 | 8.4 | | |
| C29 | 0.18 | 0.142 | 1.359 |
| C30 | <0.1 | 0.018 | 0.273 |
| C31 | 0.17 | 0.031 | 1.067 |
| C32 | <0.1 | 0.009 | 0.19 |
| C33 | 0.13 | 0.045 | 1.27 |
| C34 | <0.1 | 0.022 | 0.627 |
| C35 | <0.1 | 0.003 | 0.289 |
| C36 | <0.1 | 0.05 | 0.666 |
| C37 | 0.61 | 0.027 | 1.293 |
| C38 | <0.1 | 0.042 | 1.313 |
| C39 | <0.1 | 0.013 | 0.404 |
| C40 | 1.8 | 1.599 | |
| C40 | 0.82 | 0.174 | 1.796 |
| C41 | 1.3 | 1.433 | |
| C42 | 4 | 3.2 | |
| C43 | 21 | | |
| C44 | 14.8 | | |
| C45 | 3.6 | 1.575 | |
| C46 | <0.1 | 0.407 | |
| C47 | 1.4 | 1.382 | |
| C48 | <0.1 | 0.128 | |
| C49 | 150 | | |
| C50 | 7.9 | 0.997 | |
| D1 | <0.1 | 0.052 | 0.601 |
| D2 | <0.1 | 0.016 | |
| D3 | <.01 | 0.013 | |
| D4 | <0.1 | 0.009 | |
| D5 | <0.1 | 0.011 | |
| D6 | <0.1 | 0.018 | |

*$IC_{50}$ (mM) Data was determined at Virologic Inc against the 46I, 84V, 90M virus The following compounds have been prepared according to the procedures described herein and have demonstrated the noted activity:

| MOLSTRUCTURE | $K_i$ | $EC_{50}$ |
|---|---|---|
| 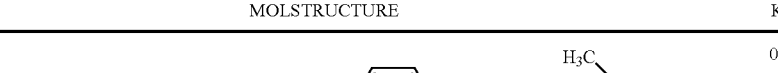 | 0.1 | 0.014 |

| MOLSTRUCTURE | $K_i$ | $EC_{50}$ |
|---|---|---|
| | | 10 |
| | 0.34 | 0.04 |
| | 422 | |
| | 468 | |
| | 152 | |

-continued
| MOLSTRUCTURE | $K_1$ | $EC_{50}$ |
|---|---|---|
| 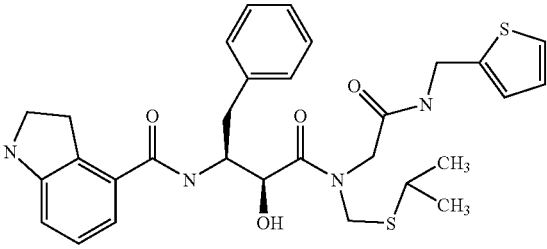 | 6.8 | |
| 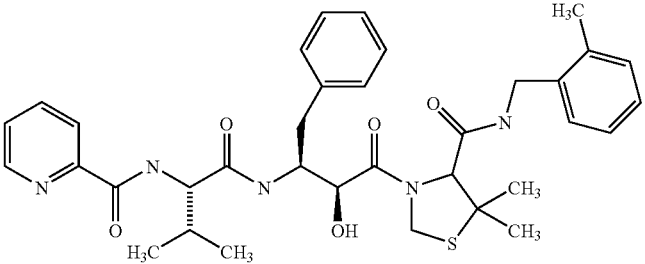 | 0.1 | 0.126 |
| 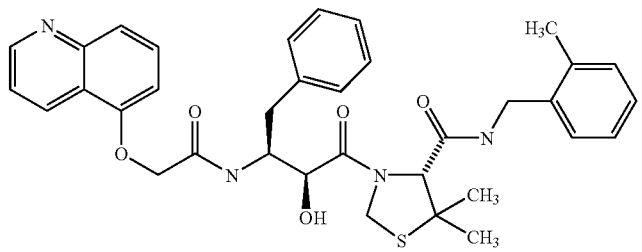 | 14.2 | |
| 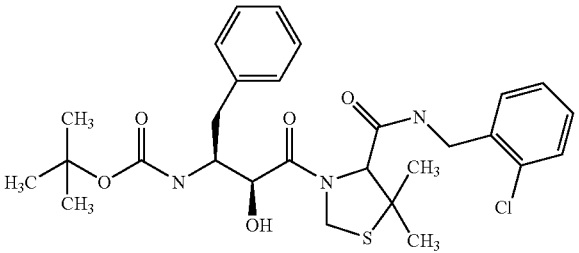 | 20 | |
| 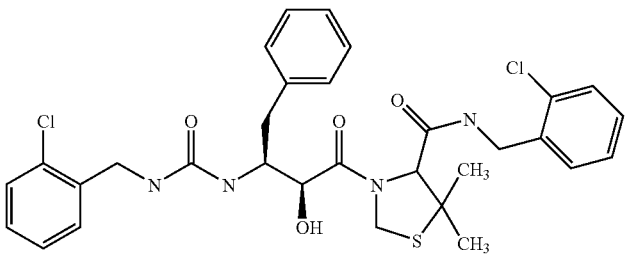 | 74 | |
| 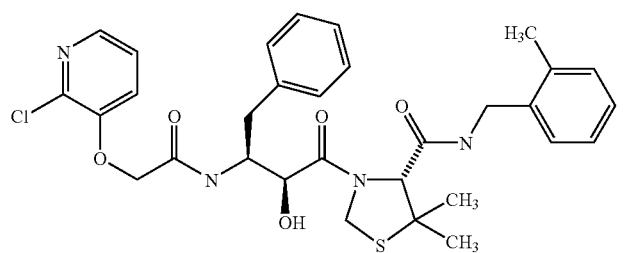 | 7.6 | |

| MOLSTRUCTURE | K₁ | EC₅₀ |
|---|---|---|
| (structure) | 0.1 | 0.027 |
| (structure) | 10 | |
| (structure) | 0.1 | 0.041 |
| (structure) | 148 | |
| (structure) | 368 | |

| MOLSTRUCTURE | K₁ | EC₅₀ |
|---|---|---|
| | 30 | |
| | 13.9 | |
| | 21 | |
| | 21 | |
| | 54 | |
| | 25 | |

-continued
| MOLSTRUCTURE | $K_1$ | $EC_{50}$ |
|---|---|---|
| 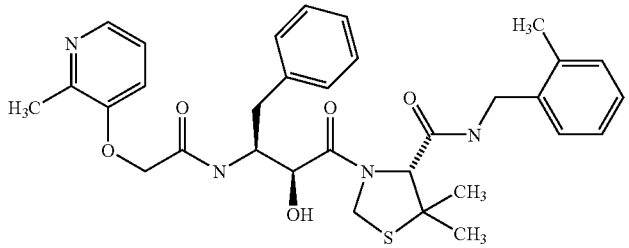 | 17 | |
| 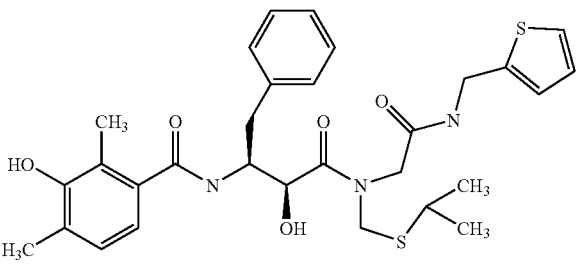 | 0.39 | 0.332 |
| 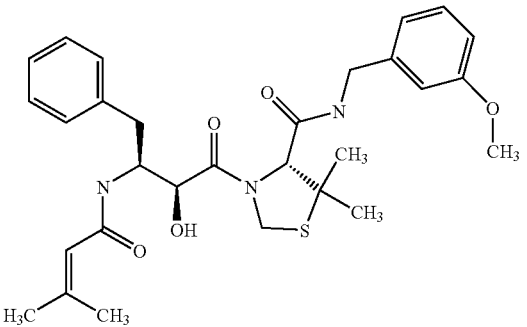 | 125 | |
| 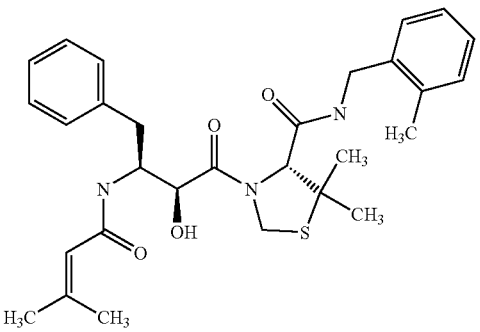 | 6.1 | |
| 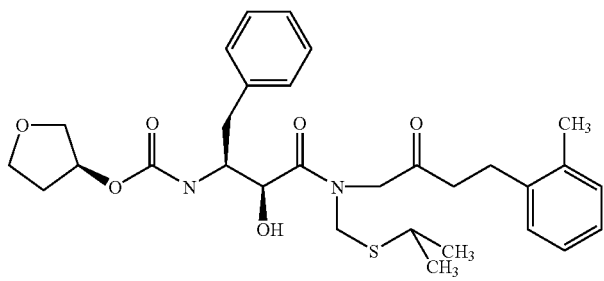 | 0.76 | 0.573 |

-continued
| MOLSTRUCTURE | $K_i$ | $EC_{50}$ |
|---|---|---|
| 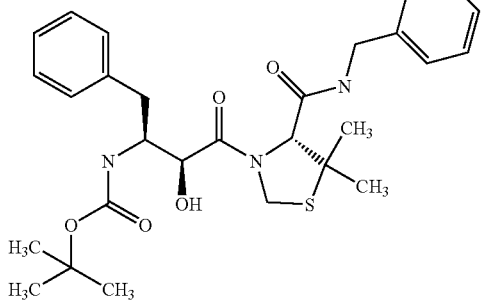 | 68 | |
| 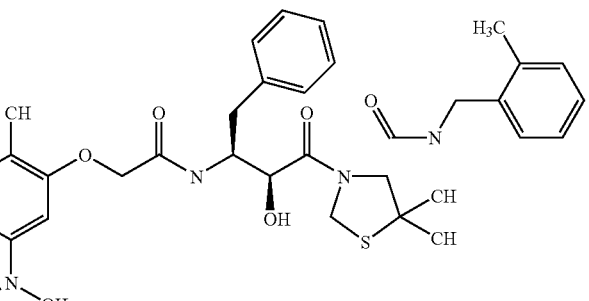 | 8.1 | |
| 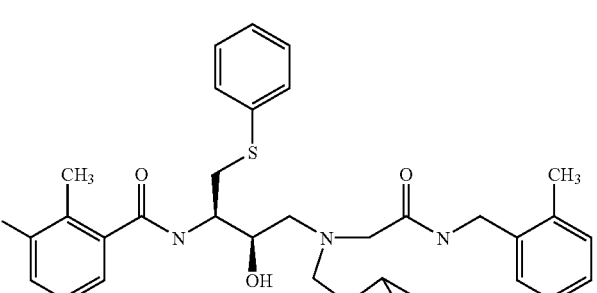 | 0.25 | 0.879 |
| 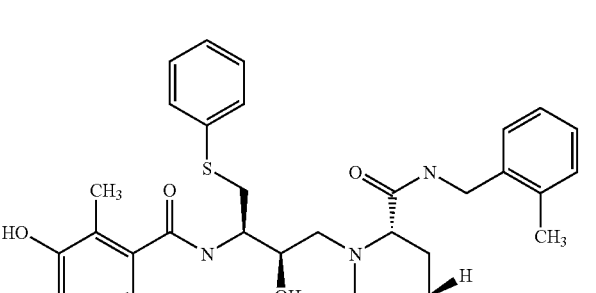 | 6.4 | 0.901 |

-continued
| MOLSTRUCTURE | $K_i$ | $EC_{50}$ |
|---|---|---|
| 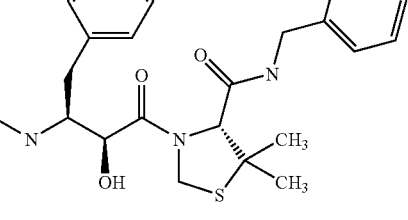 | 4.7 | 1 |
| 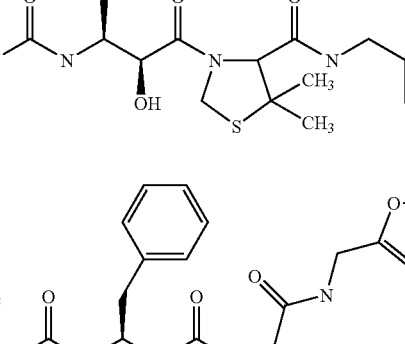 | 7.8 | |
| 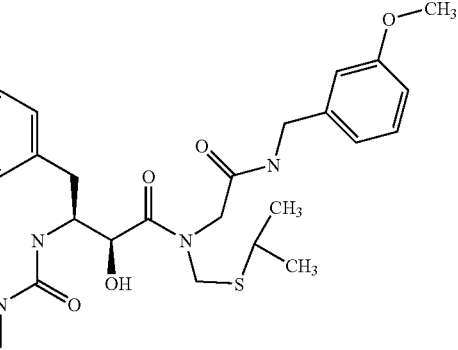 | 2 | 0.488 |
|  | 59 | |

| MOLSTRUCTURE | $K_i$ | $EC_{50}$ |
|---|---|---|
| | 3.8 | |
| | 109 | 0.672 |
| | 47 | |
| | 5 | |

-continued

| MOLSTRUCTURE | $K_i$ | $EC_{50}$ |
|---|---|---|
| | 11.9 | |
| | 0.78 | 1 |
| | 3.4 | |
| | 4.2 | 1 |
| | 4.4 | |

| MOLSTRUCTURE | $K_i$ | $EC_{50}$ |
|---|---|---|
| 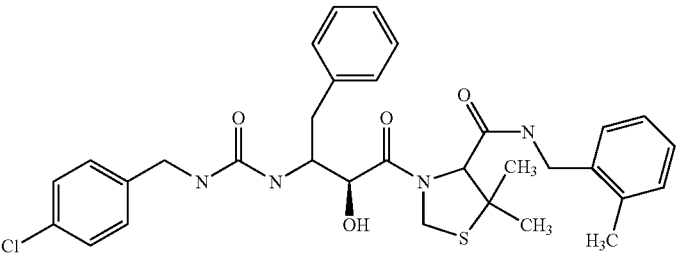 | 8.2 | |
| 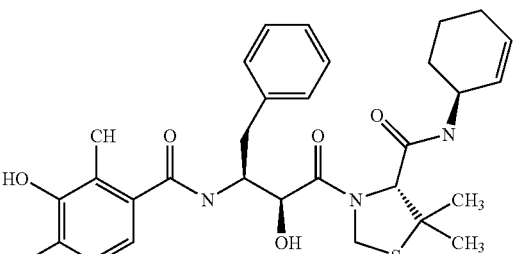 | 0.13 | 1.16 |
| 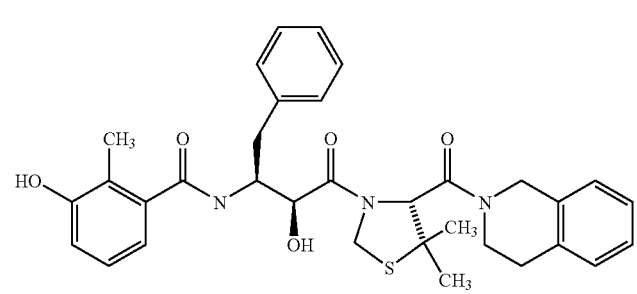 | 9 | 1.176 |
| 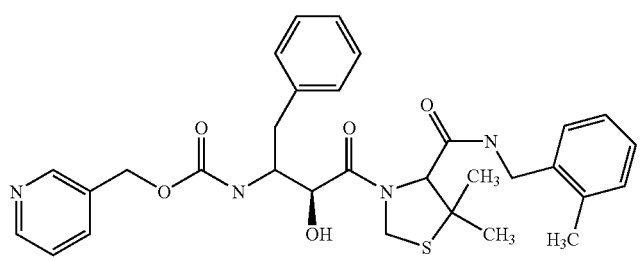 | 27 | |
| 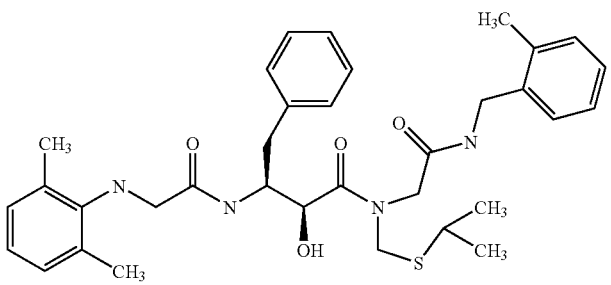 | 2.3 | 1.215 |

-continued
| MOLSTRUCTURE | $K_i$ | $EC_{50}$ |
|---|---|---|
| 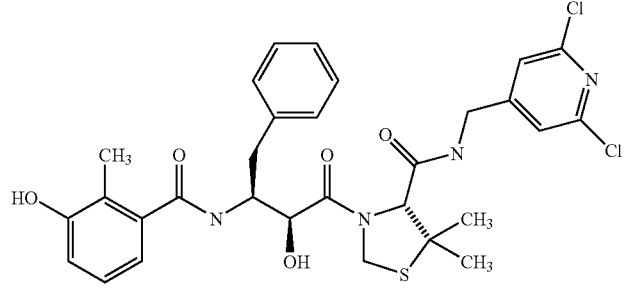 | 47 | |
| 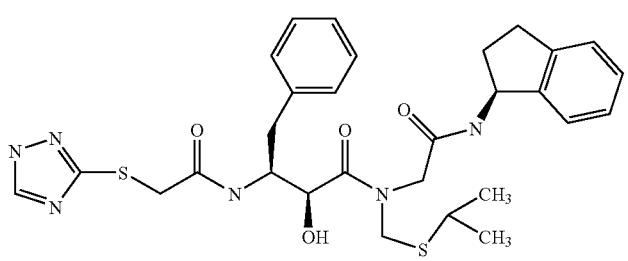 | 3.9 | 1.232 |
| 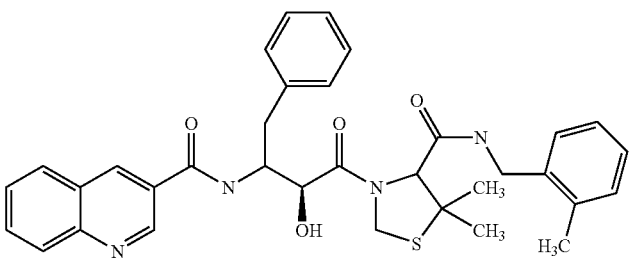 | 18.1 | |
| 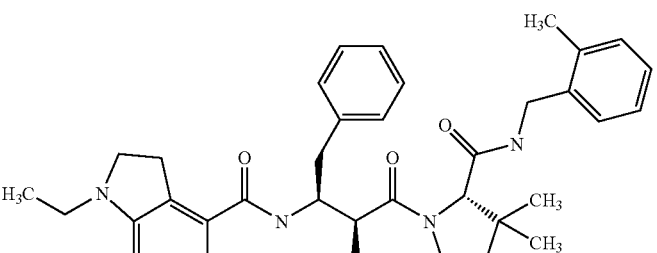 | 6.7 | 1.008 |
| 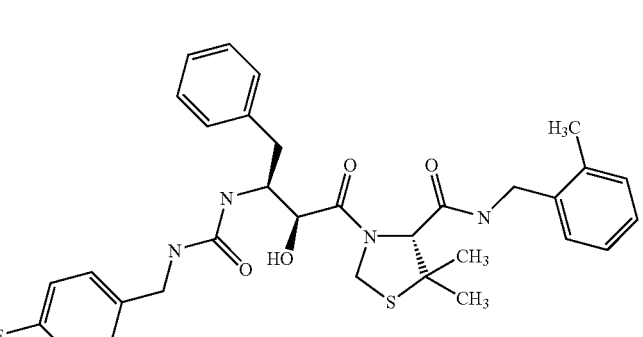 | 6 | |

| MOLSTRUCTURE | $K_i$ | $EC_{50}$ |
|---|---|---|
| 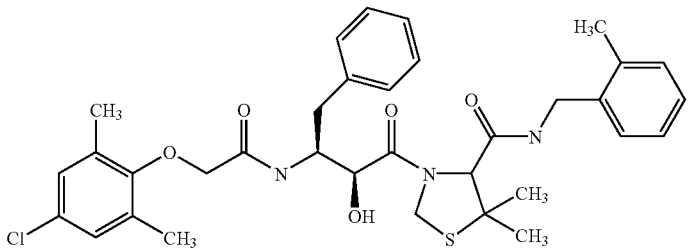 | 0.38 | 1.109 |
| 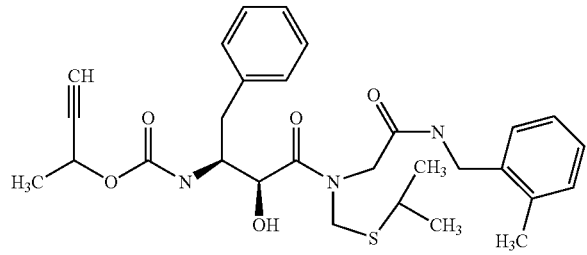 | 5.4 | |
| 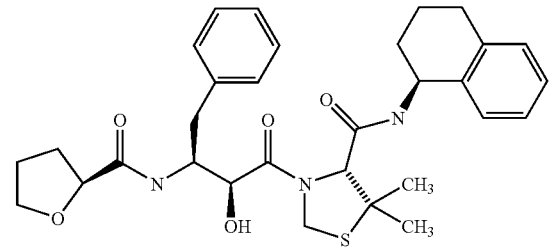 | 4.3 | 1.188 |
| 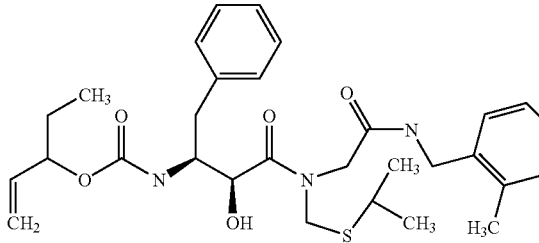 | 92 | |
| 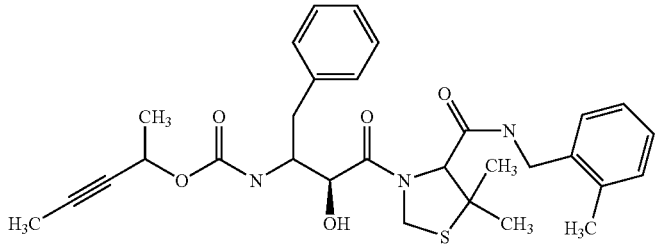 | 29 | |

-continued

| MOLSTRUCTURE | K₁ | EC₅₀ |
|---|---|---|
| | 26 | 1.23 |
| | 99 | |
| | 7.5 | 1.252 |
| | 6.1 | 1.281 |
| | 3 | 1.293 |

-continued

| MOLSTRUCTURE | $K_i$ | $EC_{50}$ |
|---|---|---|
| | 4.7 | |
| | 17.2 | 1.328 |
| | 4.8 | 1.35 |
| | 117 | |
| | 59 | |

| MOLSTRUCTURE | $K_i$ | $EC_{50}$ |
|---|---|---|
| | 0.44 | 1.431 |
| | 0.1 | 1.536 |
| | 6.9 | 1.551 |
| | 1.1 | 1.552 |
| | 45 | |

| MOLSTRUCTURE | $K_1$ | $EC_{50}$ |
|---|---|---|
| | 108 | |
| | 122 | |
| | 7.6 | |
| | 72 | |
| | 11.5 | |

-continued
| MOLSTRUCTURE | $K_i$ | $EC_{50}$ |
|---|---|---|
| 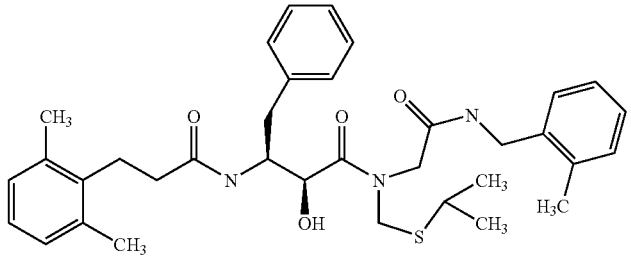 | 20 | |
| 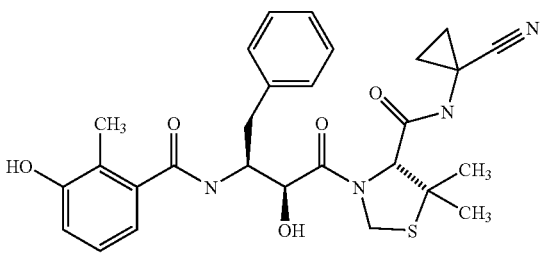 | 6.2 | |
| 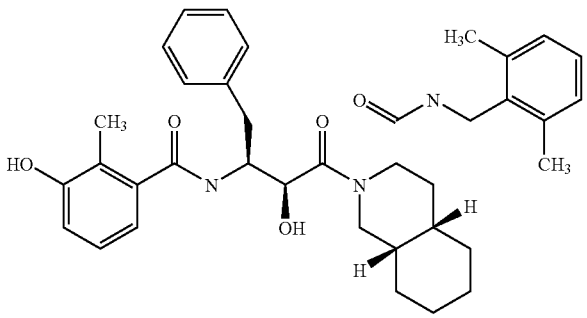 | 83 | |
| 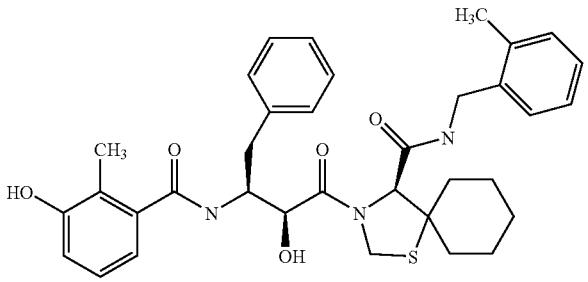 | 11 | |
| 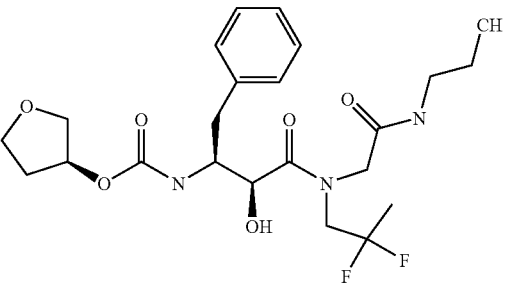 | 42 | |

-continued
| MOLSTRUCTURE | $K_i$ | $EC_{50}$ |
|---|---|---|
| 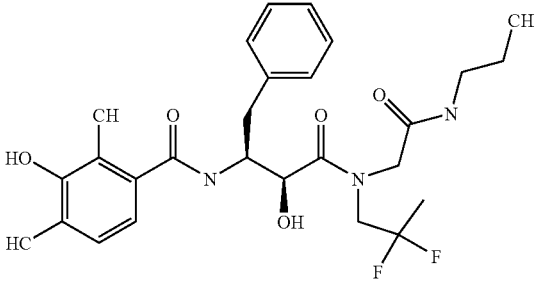 | 108 | |
| 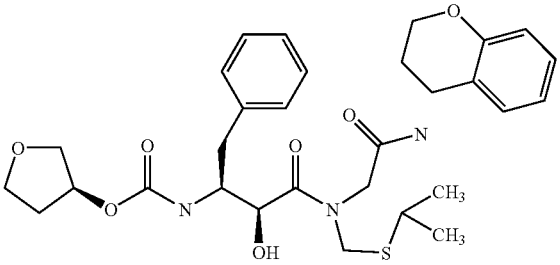 | 3.7 | 1.553 |
| 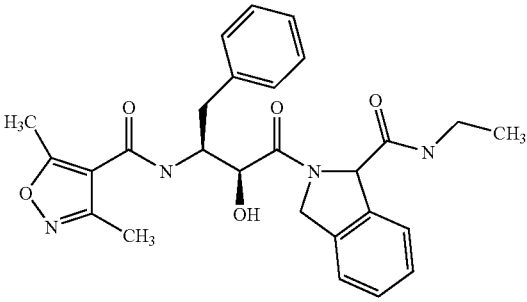 | 84 | |
| 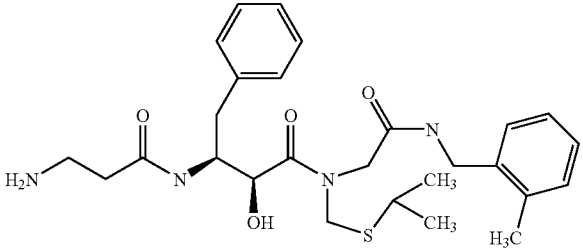 | 156 | |
| 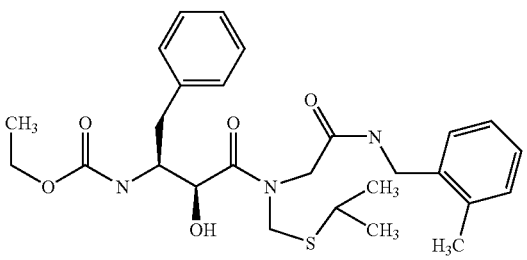 | 0.88 | 1.641 |

-continued

| MOLSTRUCTURE | K₁ | EC₅₀ |
|---|---|---|
| | 7.6 | 1.756 |
| | 0.32 | 1.884 |
| | 1.4 | 1.947 |
| | 7.4 | 1.957 |
| | 17.1 | 2.199 |

| MOLSTRUCTURE | $K_1$ | $EC_{50}$ |
|---|---|---|
| | 88 | |
| | 48 | |
| | 28 | 3.2 |
| | 0.89 | 1.564 |
| | 51 | |
| | 110 | |

-continued
| MOLSTRUCTURE | $K_1$ | $EC_{50}$ |
|---|---|---|
| 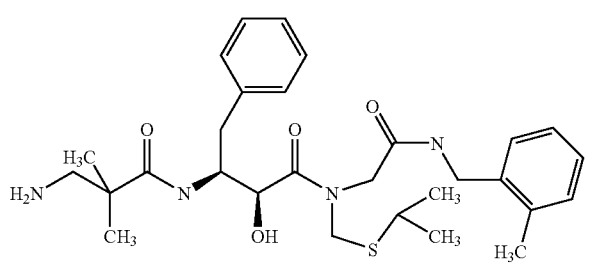 | 18.7 | |
| 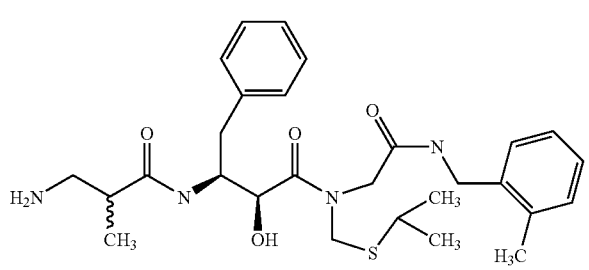 | 158 | |
| 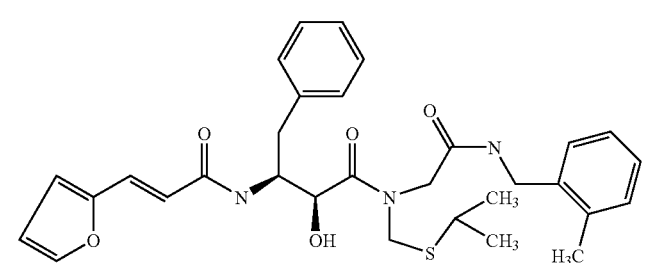 | 60 | |
| 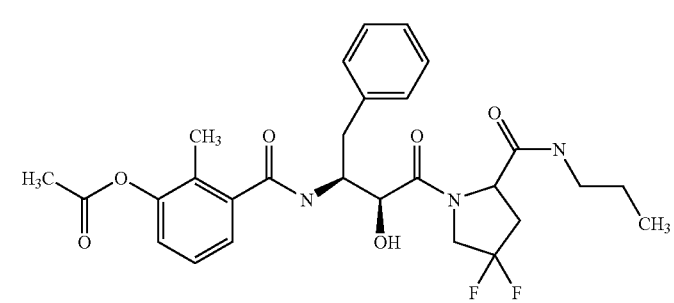 | 85 | |
| 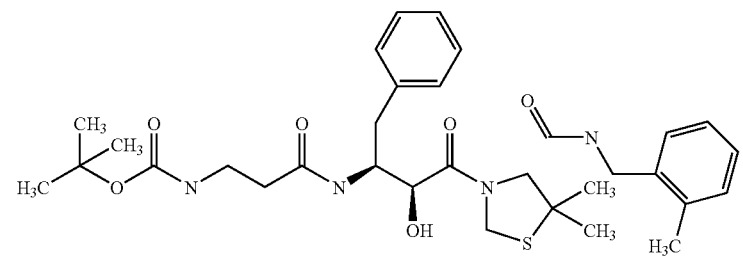 | 94 | |

-continued
| MOLSTRUCTURE | $K_i$ | $EC_{50}$ |
|---|---|---|
| 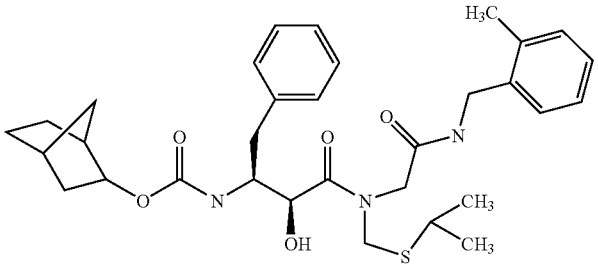 | 9.4 | 2.881 |
| 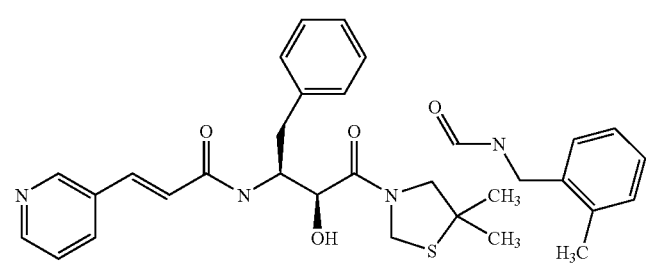 | 9.9 | |
| 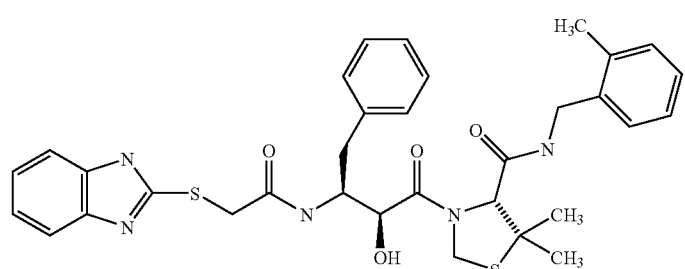 | 17.4 | 3.2 |
| 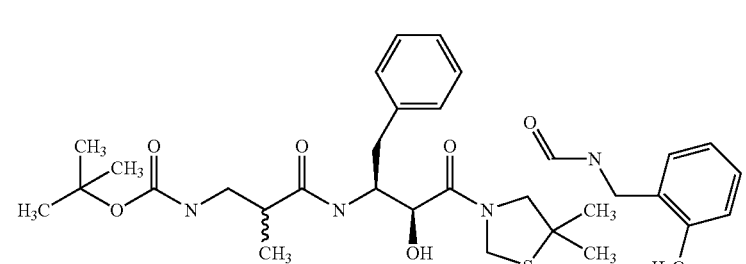 | 52 | |
| 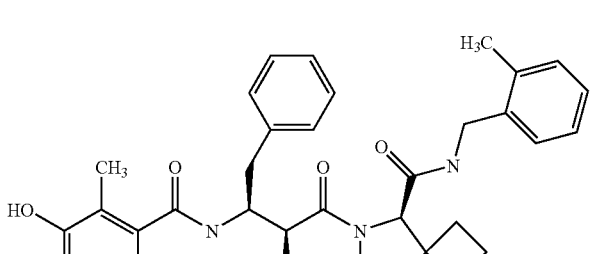 | 30 | |

| MOLSTRUCTURE | $K_1$ | $EC_{50}$ |
|---|---|---|
| | 17.3 | |
| | 53 | |
| | 3.2 | |
| | 12.6 | 3.2 |
| | 15.1 | 3.2 |

-continued
| MOLSTRUCTURE | $K_1$ | $EC_{50}$ |
|---|---|---|
| 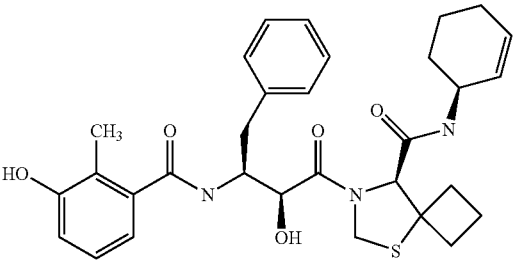 | 12.9 | |
| 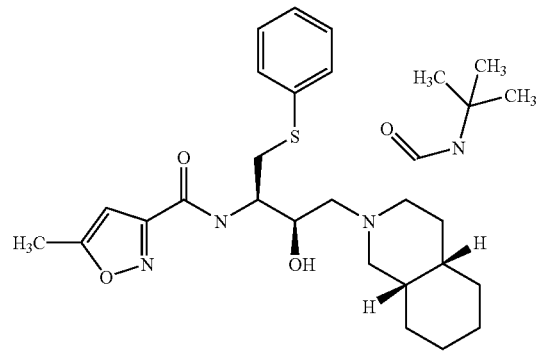 | 185 | 3.916 |
| 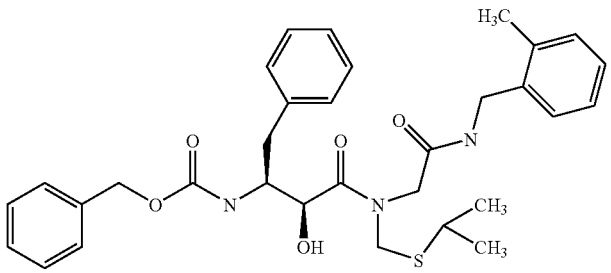 | 1.4 | 4.224 |
| 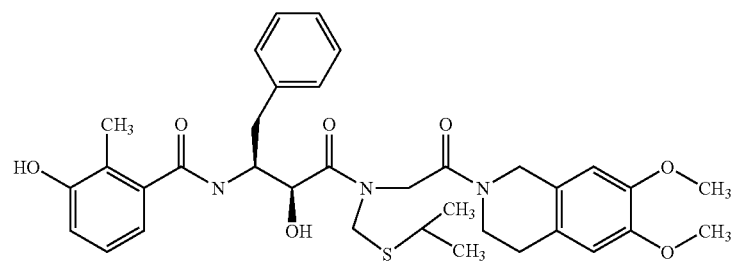 | 46 | 10 |
| 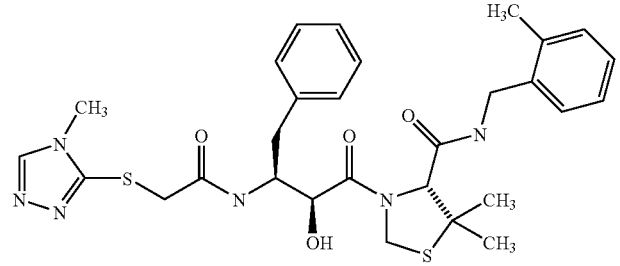 | 82 | 3.2 |

-continued
| MOLSTRUCTURE | $K_1$ | $EC_{50}$ |
|---|---|---|
| 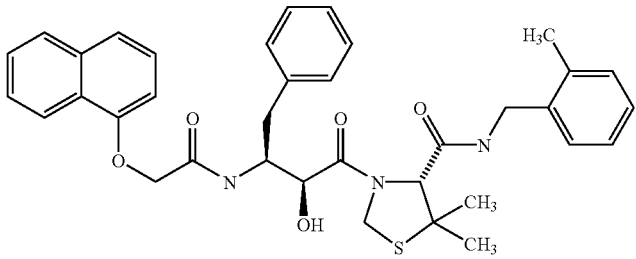 | 5.8 | 3.2 |
| 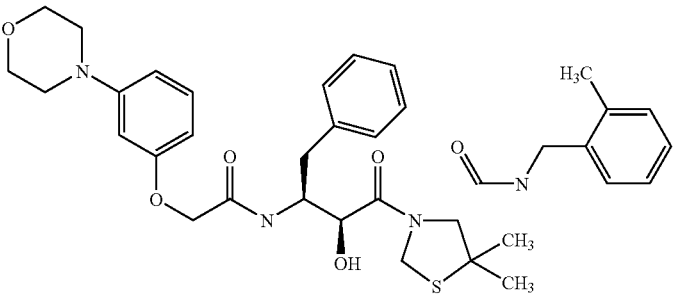 | 4.4 | 3.2 |
| 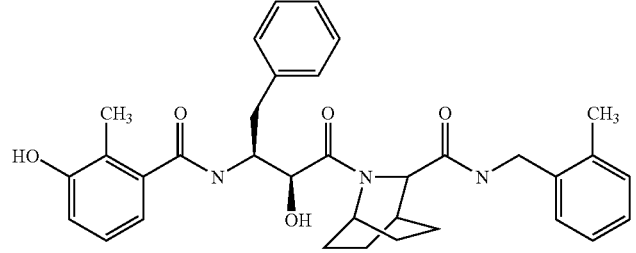 | 9.8 | 3.2 |
| 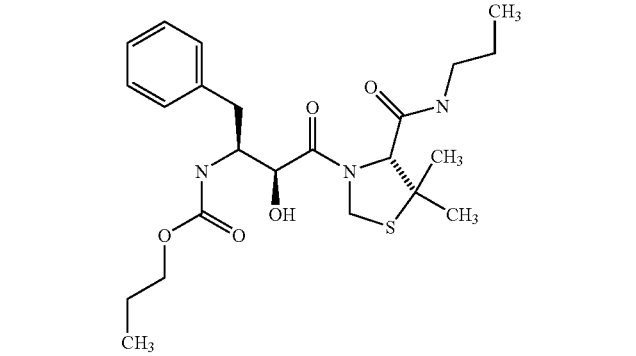 | 12.7 | 3.2 |
| 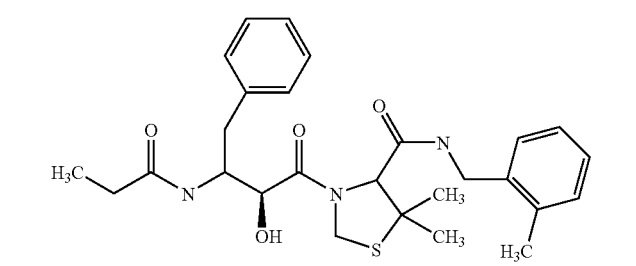 | 8.4 | 3.2 |

-continued

| MOLSTRUCTURE | $K_1$ | $EC_{50}$ |
|---|---|---|
| 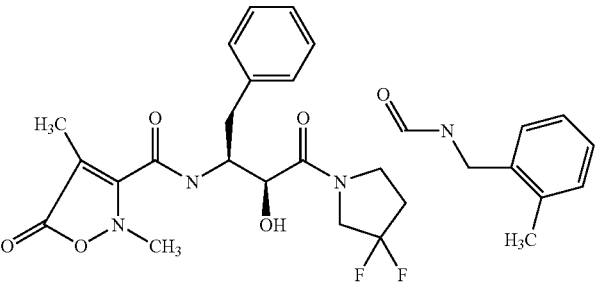 | 3.6 | 3.2 |
| 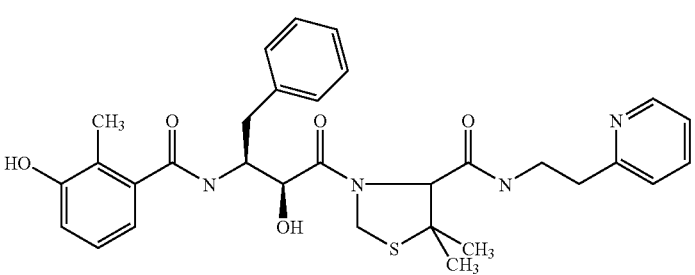 | 134 | |
| 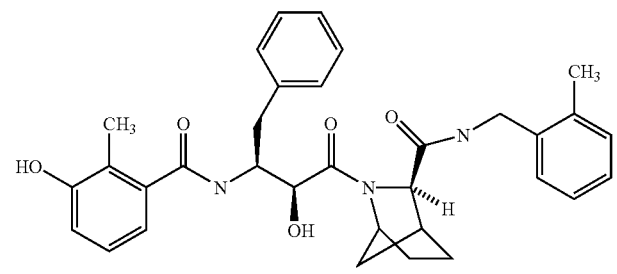 | 18.4 | 3.995 |
| 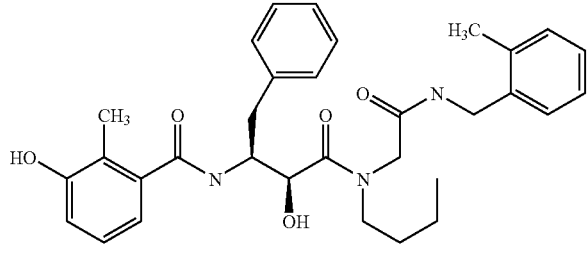 | 51.7 | 5.873 |

While the invention has been described in terms of preferred embodiments and specific examples, those skilled in the art will recognize that various changes and modifications can be made through routine experimentation without departing from the spirit and scope of the invention.

Thus, the invention should be understood as not being limited by the foregoing detailed description, but as being defined by the appended claims and their equivalents.

We claim:

1. A compound of the Formula I-A:

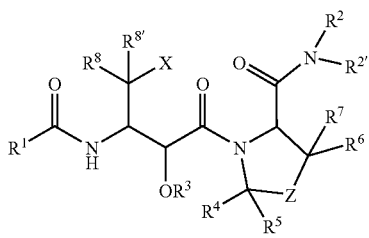

wherein:
$R^1$ is a 3-, 4-, or 7-membered mono-cyclic carbocyclic group;
$R^2$ is an aliphatic group, a carbocyclic group, a carbocyclic-aliphatic group, a heterocyclic group, or a heterocyclic-aliphatic group;
$R^{2'}$ is H or a $C_1$–$C_6$ alkyl group;
or $R^2$ and $R^{2'}$ taken together with the nitrogen atom to which they are attached form an unsubstituted or substituted heterocyclic ring;
X is

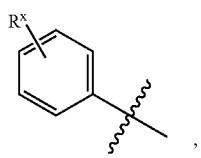

wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;
$R^8$ and $R^{8'}$ are each independently H, halo or a $C_1$–$C_4$ aliphatic group;
Z is $CH_2$, CHF, $CF_2$, CH(OH), CH(O—$R^Z$), CH(N—$R^Z R^{Z'}$),
CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;
$R^3$ is H or a $C_1$–$C_6$ aliphatic group;
$R^4$ and $R^5$ are independently selected from H, halo, a $C_1$–$C_6$ aliphatic group or a group having the formula C(O)$R^{4'}$, wherein $R^{4'}$ is an aliphatic, carbocyclic or heterocyclic group;
$R^6$ and $R^7$ are independently selected from H, halo or a $C_1$–$C_6$ aliphatic group;
wherein any of said aliphatic groups are unsubstituted or substituted by one or more suitable substituents and saturated, partially unsaturated or fully unsaturated; and
wherein any of said carbocyclic or heterocyclic groups are mono-, bi- or tri-cyclic saturated, partially unsaturated or fully unsaturated or unsubstituted or substituted by one or more suitable substituents;
provided that $R^2$ is not an aliphatic group, a phenyl group or a phenyl-substituted aliphatic group, when Z is CHF or $CH_2$; $R^{2'}$, $R^3$, $R^8$ and $R^{8'}$ are H or a $C_1$–$C_4$ alkyl group; $R^4$, $R^5$, $R^6$ and $R^7$ are H or a $C_1$–$C_6$ alkyl group; X is

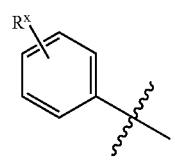

and $R^1$ is a substituted or unsubstituted 5- or 6-membered mono-cyclic carbocyclic group;
or a prodrug, pharmaceutically acceptable salt, or pharmaceutically acceptable solvate thereof.

2. A compound of the Formula I-D:

I-D

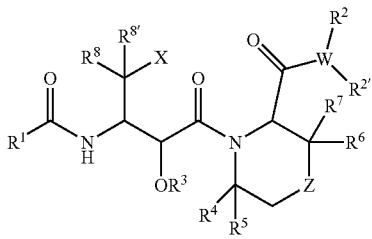

wherein:
$R^1$ is a carbocyclic group;
$R^2$ is an aliphatic group, a carbocyclic group, a carbocyclic-aliphatic group, a heterocyclic group, or a heterocyclic-aliphatic group;
W is N;
$R^{2'}$ is H or a $C_1$–$C_6$ alkyl group or $R^2$ and $R^{2'}$ taken together with the atom W to which they are attached form an unsubstituted or substituted carbocyclic or heterocyclic ring;
X is

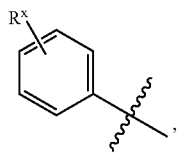

$R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;
$R^8$ and $R^{8'}$ are each independently H, halo or a $C_1$–$C_4$ aliphatic group;
Z is $CH_2$, $CF_2$, CHF, CH(OH), CH(O—$R^Z$), CH(N—$R^Z R^{Z'}$),
CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;
$R^3$ is H or a $C_1$–$C_6$ aliphatic group;
$R^4$ and $R^5$ are independently selected from H, halo, a $C_1$–$C_6$ aliphatic group or a group having the formula C(O)$R^{4'}$, wherein $R^{4'}$ is an aliphatic, carbocyclic or heterocyclic group;
$R^6$ and $R^7$ are independently selected from H, halo or a $C_1$–$C_6$ aliphatic group;
where any of said aliphatic groups are saturated, partially saturated or fully unsaturated and unsubstituted or substituted by one or more suitable substituents; and
where any of said carbocyclic or heterocyclic groups are unsubstituted or substituted by one or more suitable substituents; saturated, partially unsaturated or fully unsaturated; or mono-, bi- or tri-cyclic;
or a prodrug, pharmaceutically acceptable salt or solvate thereof.

3. A compound of the Formula I-E:

I-E

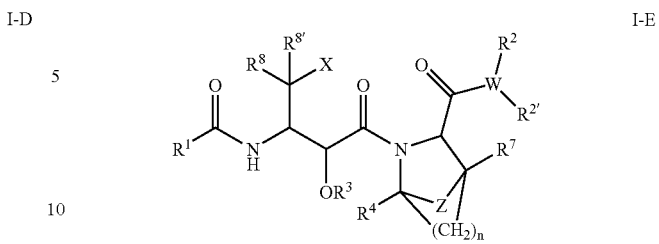

wherein:
$R^1$ is a carbocyclic group;
$R^2$ is an aliphatic group, a carbocyclic group, a carbocyclic-aliphatic group, a heterocyclic group, or a heterocyclic-aliphatic group;
W is N;
$R^{2'}$ is H or a $C_1$–$C_6$ alkyl group or $R^2$ and $R^{2'}$ taken together with the atom W to which they are attached form an unsubstituted or substituted heterocyclic ring;
X is

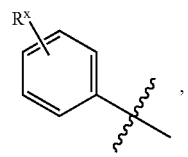

wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;
$R^8$ and $R^{8'}$ are each independently H, halo or a $C_1$–$C_4$ aliphatic group;
Z is $CH_2$, CHF, $CF_2$, CH(OH), CH(O—$R^Z$), CH(N—$R^Z R^{Z'}$),
CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;
n is 1 or 2;
$R^3$ is H or a $C_1$–$C_6$ aliphatic group;
$R^4$ is selected from H, halo, a $C_1$–$C_6$ aliphatic group or a group having the formula C(O)$R^{4'}$, wherein $R^{4'}$ is an aliphatic, carbocyclic or heterocyclic group;
$R^7$ is H, halo or a $C_1$–$C_6$ aliphatic group;
where any of said aliphatic groups are saturated, partially unsaturated or fully unsaturated and unsubstituted or substituted by one or more suitable substituents; and
where any of said carbocyclic or heterocyclic groups are unsubstituted or substituted by one or more suitable substituents, saturated, partially unsaturated or fully unsaturated or mono-, bi- or tri-cyclic;
or a prodrug, pharmaceutically acceptable salt or solvate thereof.

4. A compound of the Formula I-F:

I-F

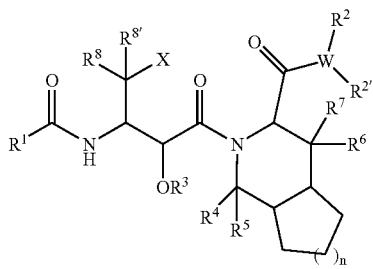

wherein:

R¹ is a carbocyclic group;

R² is an aliphatic group, a carbocyclic group, a carbocyclic-aliphatic group, a heterocyclic group, or a heterocyclic-aliphatic group;

W is N;

R²' is H or a $C_1$–$C_6$ alkyl group or R² and R²' taken together with the atom W to which they are attached form an unsubstituted or substituted heterocyclic ring;

X is

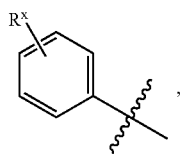

$R^x$ or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

n is 1 or 2;

R³ is H or a $C_1$–$C_6$ aliphatic group;

R⁴ and R⁵ are independently selected from H, halo, a $C_1$–$C_6$ aliphatic group or a group having the formula C(O)R⁴', wherein R⁴' is an aliphatic, carbocyclic or heterocyclic group;

R⁶ and R⁷ are independently selected from H, halo or a $C_1$–$C_6$ aliphatic group;

R⁸ and R⁸' are each independently H, halo or a $C_1$–$C_4$ aliphatic group;

where any of said aliphatic groups are saturated, partially unsaturated or fully unsaturated and unsubstituted or substituted by one or more suitable substituents; and where any of said carbocyclic or heterocyclic groups are unsubstituted or substituted by one or more suitable substituents; saturated, partially unsaturated or fully unsaturated; or mono-, bi- or tri-cyclic;

or a prodrug, pharmaceutically acceptable salt or solvate thereof.

5. A compound of the Formula I-G:

I-G

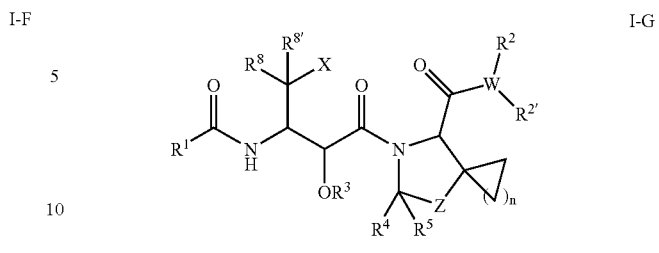

wherein:

R¹ is a carbocyclic group;

R² is an aliphatic group, a carbocyclic group, a carbocyclic-aliphatic group, a heterocyclic group, or a heterocyclic-aliphatic group;

W is N;

R²' is H or a $C_1$–$C_6$ alkyl group or R² and R²' taken together with the atom W to which they are attached form an unsubstituted or substituted heterocyclic ring;

X is

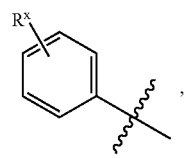

wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

R⁸ and R⁸' are each independently H, halo or a $C_1$–$C_4$ aliphatic group;

Z is $CH_2$, CHF, $CF_2$, CH(OH), CH(O—$R^Z$), CH(N—$R^Z R^{Z'}$), CH(S—$R^Z$), C(=O), or CH($R^Z$), where $R^Z$ is a $C_1$–$C_6$ aliphatic group or a carbocyclic or heterocyclic group and $R^{Z'}$ is H or a $C_1$–$C_6$ aliphatic group;

n is 1, 2, 3 or 4;

R³ is H or a $C_1$–$C_6$ aliphatic group;

R⁴ and R⁵ are independently selected from H, halo, a $C_1$–$C_6$ aliphatic group or a group having the formula C(O)R⁴', wherein R⁴' is an aliphatic, carbocyclic or heterocyclic group;

where any of said aliphatic groups are saturated, partially unsaturated or fully unsaturated and unsubstituted or substituted by one or more suitable substituents; and where any of said carbocyclic or heterocyclic groups are unsubstituted or substituted by one or more suitable substituents; saturated, partially unsaturated or fully unsaturated; or mono-, bi- or tri-cyclic;

or a prodrug, pharmaceutically acceptable salt or solvate thereof.

6. A compound of the Formula I-E':

I-E'

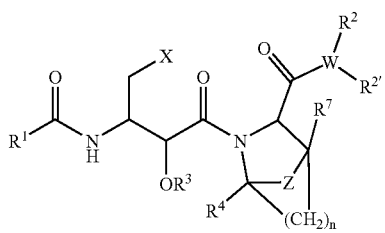

wherein

R$^1$ is a carbocyclic;

R$^2$ is an aliphatic group, a carbocyclic group, a carbocyclic-aliphatic group, a heterocyclic group, or a heterocyclic-aliphatic group;

W is N;

R$^{2'}$ is H or a C$_1$–C$_6$ alkyl group;

X is

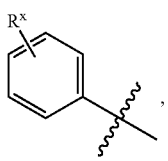

wherein R$^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

Z is CH$_2$, CHF, CF$_2$, or CH(R$^Z$), where R$^Z$ is a C$_1$–C$_6$ aliphatic group;

n is 1 or 2;

R$^3$ and R$^4$ are each H; and

R$^7$ is H;

wherein any of said aliphatic groups are saturated, partially unsaturated or fully unsaturated and unsubstituted or substituted by one or more suitable substituents; and wherein any of said carbocyclic or heterocyclic groups are unsubstituted or substituted by one or more suitable substituents; saturated, partially unsaturated or fully unsaturated; or mono-, bi- or tri-cyclic;

or a prodrug, pharmaceutically acceptable salt, or pharmaceutically acceptable solvate thereof.

7. The compound, prodrug, salt, or solvate according to claim 6, wherein:

R$^1$ is a carbocyclic group;

R$^2$ is an arylalkyl group;

R$^{2'}$ is H;

X is

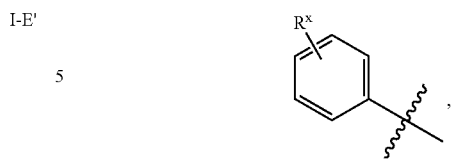

wherein R$^x$ is H; and

Z is CH$_2$;

wherein said carbocyclic group and arylalkyl group are unsubstituted or substituted with one or more substituents selected from methyl, halo, and hydroxy.

8. A compound of the Formula I-F':

I-F'

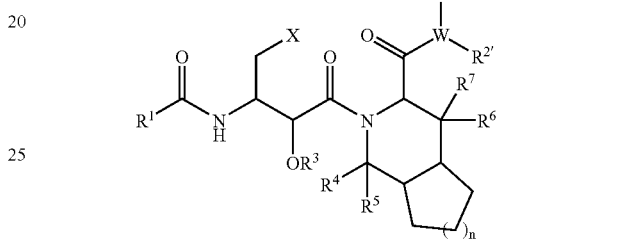

wherein:

R$^1$ is a carbocyclic group,

R$^2$ is an aliphatic group, a carbocyclic group, a carbocyclic-aliphatic group, a heterocyclic group, or a heterocyclic-aliphatic group;

W is N;

R$^{2'}$ is H or a C$_1$–C$_6$ alkyl group;

X is

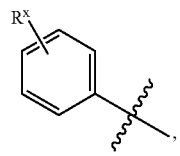

wherein R$^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;

n is 1 or 2;

R$^3$, R$^4$ and R$^5$ are each H; and

R$^6$ and R$^7$ and H;

wherein any of said aliphatic groups are saturated, partially unsaturated or fully unsaturated and unsubstituted or substituted by one or more suitable substituents; and wherein any of said carbocyclic or heterocyclic groups are unsubstituted or substituted by one or more suitable substituents; saturated, partially unsaturated or fully unsaturated; or mono-, bi- or tri-cyclic;

or a prodrug, pharmaceutically acceptable salt, or pharmaceutically acceptable solvate thereof.

9. The compound, prodrug, or salt, according to claim 8, wherein:
$R^1$ is a carbocyclic group;
$R^2$ is an arylalkyl group;
$R^{2'}$ is H; and
X is

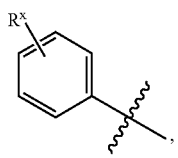

wherein $R^x$ is H;
wherein said carbocyclic group and arylalkyl group are unsubstituted or substituted with one or more substituents selected from methyl, halo, or hydroxy.

10. A compound of the Formula I-G':

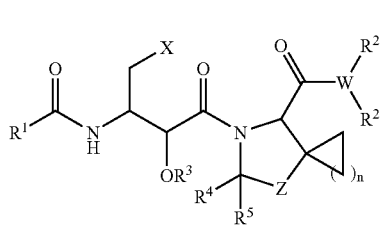

I-G' wherein:
$R^1$ is a carbocyclic group,
$R^2$ is an aliphatic group, a carbocyclic group, a carbocyclic-aliphatic group, a heterocyclic group, or a heterocyclic-aliphatic group;
W is N;
$R^{2'}$ is H or $C_1$–$C_6$ alkyl group;
X is

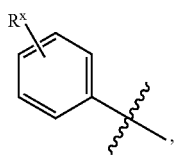

wherein $R^x$ is H or one or more substituents independently selected from alkyl, nitro, amino, cyano, halogen, haloalkyl, hydroxyl, alkoxy, alkylenedioxy, alkylcarbonyl, alkyloxycarbonyl, alkylcarbonyloxy, carboxyl, carbamoyl, formyl, alkylamino, dialkylamino, alkylaminocarbonyl, dialkylaminocarbonyl, alkylaminothiocarbonyl, dialkylaminothiocarbonyl, alkylsulfonyl, alkylsulfenyl, alkylcarbonylamino, alkylthiocarbonylamino, alkylsulfonyloxy, alkylsulfonylamino, mercapto, and alkylthio;
Z is $CH_2$, CHF, $CF_2$, or $CH(R^Z)$, where $R^Z$ is a $C_1$–$C_6$ aliphatic group;
n is 2, 3 or 4;
$R^3$, $R^4$ and $R^5$ are each H;
wherein any of said aliphatic groups are saturated, partially unsaturated or fully unsaturated and unsubstituted or substituted by one or more suitable substituents; and
wherein any of said carbocyclic or heterocyclic groups are unsubstituted or substituted by one or more suitable substituents; saturated, partially unsaturated or fully unsaturated; or mono-, bi- or tri-cyclic;
or a prodrug, pharmaceutically acceptable salt, or pharmaceutically acceptable solvate thereof.

11. The compound, prodrug, salt, or salt according to claim 10, wherein:
$R^1$ is a carbocyclic group;
$R^2$ is an arylalkyl group;
W is N;
$R^{2'}$ is H;
X is

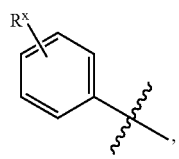

wherein $R^x$ is H; and
Z is $CH_2$;
wherein said carbocyclic group and arylalkyl group are unsubstituted or substituted with one or more substituents selected from methyl, halo, and hydroxy.

12. The compound, prodrug, salt, or solvate according to claim 10, wherein:
$R^1$ is a carbocyclic group;
$R^2$ is an arylalkyl group;
W is N;
$R^{2'}$ is H;
X is wherein $R^x$ is H; and
Z is $CF_2$;
wherein said carbocyclic group and arylalkyl group are unsubstituted or substituted with one or more substituents selected from methyl, halo, and hydroxy.

13. A compound selected from:

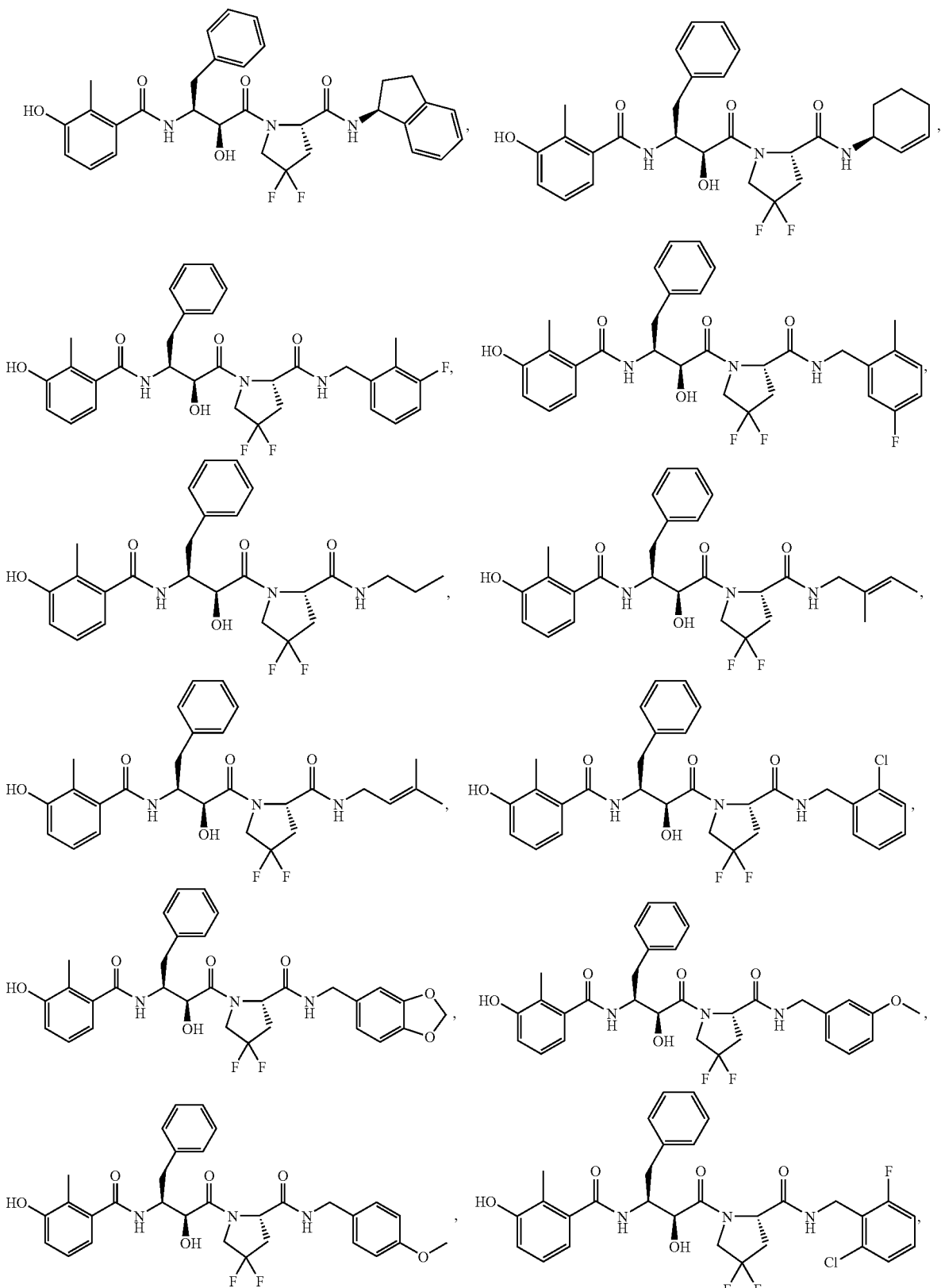

or a prodrug, pharmaceutically acceptable salt or solvate thereof.

14. A compound of the formula:

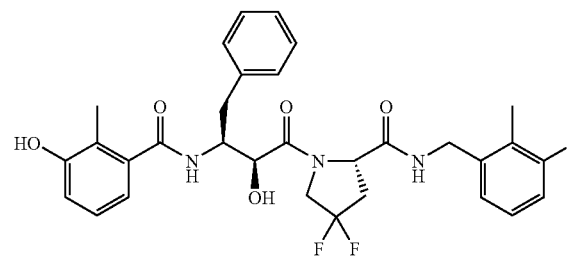

or a prodrug, pharmaceutically acceptable salt or solvate thereof.

15. A compound of the formula:

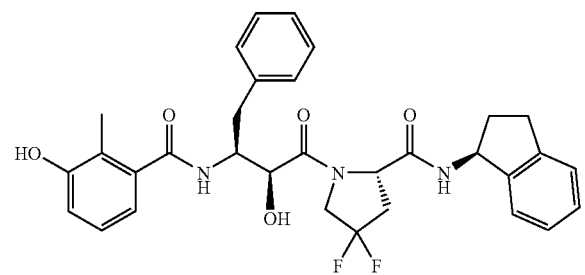

or a prodrug, pharmaceutically acceptable salt or solvate thereof.

16. A compound of the formula:

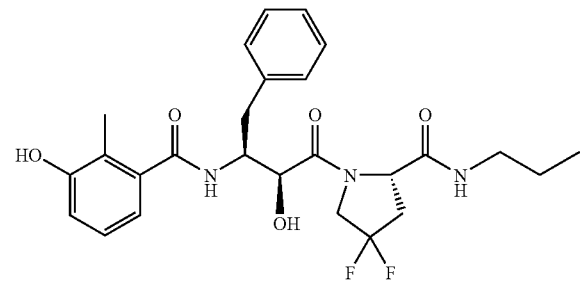

or a prodrug, pharmaceutically acceptable salt or solvate thereof.

17. A compound of the formula:

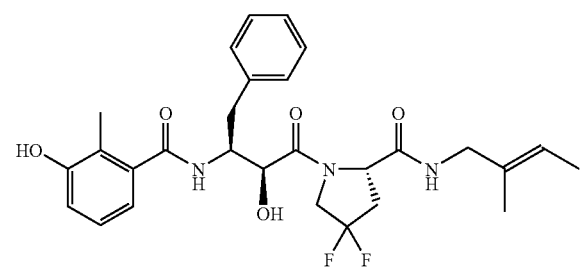

or a prodrug, pharmaceutically acceptable salt or solvate thereof.

18. A compound of the formula:

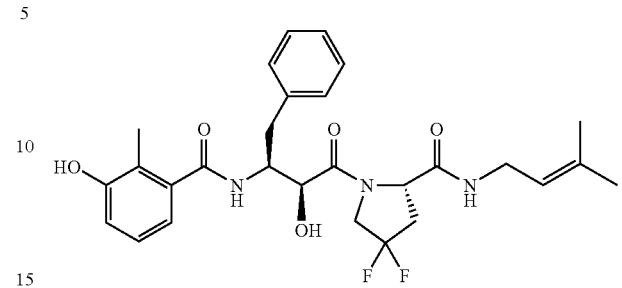

or a prodrug, pharmaceutically acceptable salt or solvate thereof.

19. A compound of the formula:

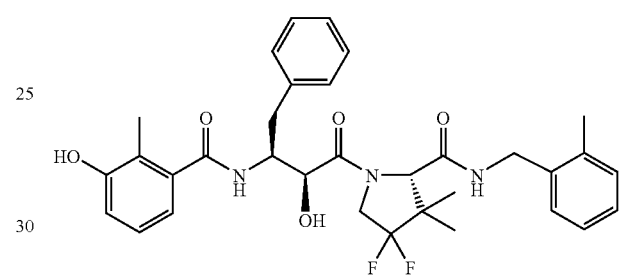

or a prodrug, pharmaceutically acceptable salt or solvate thereof.

20. A compound of the formula:

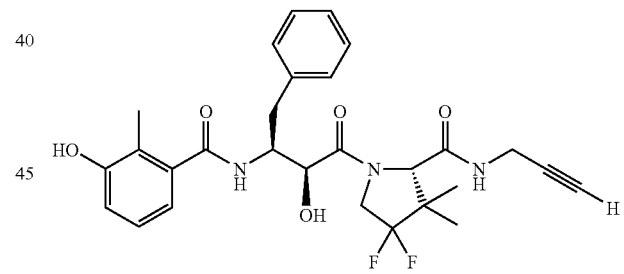

or a prodrug, pharmaceutically acceptable salt or solvate thereof.

21. A compound of the formula:

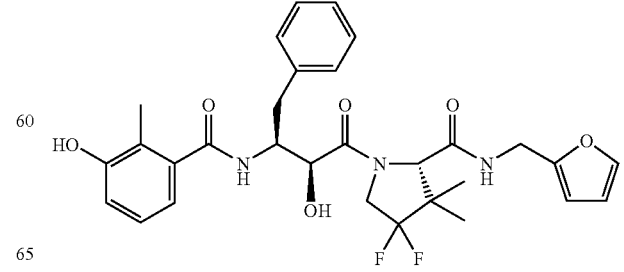

or a prodrug, pharmaceutically acceptable salt or solvate thereof.
22. A compound of the formula:
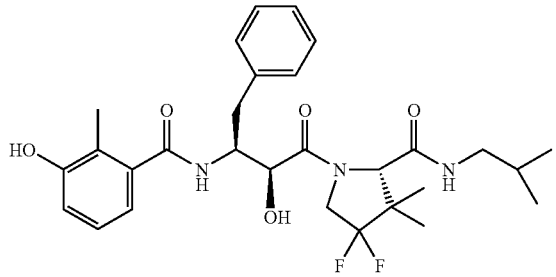
or a prodrug, pharmaceutically acceptable salt or solvate thereof.
23. A compound of the formula:
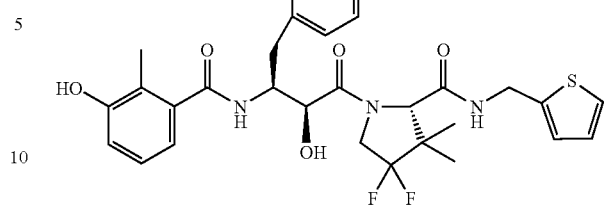
or a prodrug, pharmaceutically acceptable salt or solvate thereof.
24. A compound of the formula:
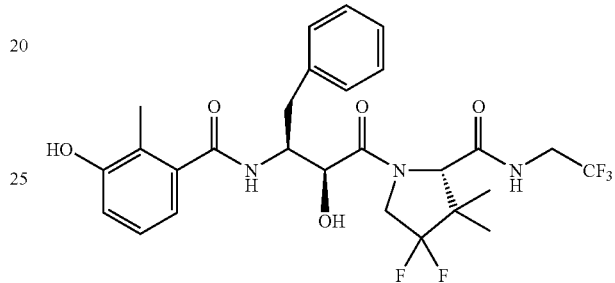
or a prodrug, pharmaceutically acceptable salt or solvate thereof.
* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Artificial

```
<220> FEATURE:
<223> OTHER INFORMATION: Synthetic peptide substrate for HIV protease
<220> FEATURE:
<221> NAME/KEY: BINDING
<222> LOCATION: (2)..(2)
<223> OTHER INFORMATION: EDANS, a fluorophore
<220> FEATURE:
<221> NAME/KEY: BINDING
<222> LOCATION: (11)..(11)
<223> OTHER INFORMATION: DABCYL, a non-fluorescent dye predominantly
      used as a fluorophore quencher

<400> SEQUENCE: 1

Arg Glu Ser Gln Asn Tyr Pro Ile Val Gln Lys Arg
1               5                   10
```